United States Patent
Dyckman et al.

(10) Patent No.: US 11,053,244 B1
(45) Date of Patent: Jul. 6, 2021

(54) 4-AZAINDOLE COMPOUNDS

(71) Applicant: BRISTOL-MYERS SQUIBB COMPANY, Princeton, NJ (US)

(72) Inventors: Alaric J. Dyckman, Lawrenceville, NJ (US); Dharmpal S. Dodd, Monmouth Junction, NJ (US); Christopher P. Mussari, Princeton, NJ (US); Trevor C. Sherwood, West Windsor, NJ (US); Brian K. Whiteley, Lebanon, NJ (US); John L. Gilmore, Yardley, PA (US); Sreekantha Ratna Kumar, Bangalore (IN); Laxman Pasunoori, Warangal (IN); Pitani Veera Venkata Srinivas, West Godawri (IN); Srinivasan Kunchithapatham Duraisamy, Hosur (IN); Subramanya Hegde, Bangalore (IN); Rushith Kumar Anumula, Secunderabad (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/910,101

(22) Filed: Jun. 24, 2020

Related U.S. Application Data

(63) Continuation of application No. 16/695,303, filed on Nov. 26, 2019, now Pat. No. 10,730,877, which is a continuation of application No. 16/222,145, filed on Dec. 17, 2018, now Pat. No. 10,544,143.

(60) Provisional application No. 62/599,875, filed on Dec. 18, 2017.

(51) Int. Cl.
| | |
|---|---|
| *C07D 471/04* | (2006.01) |
| *A61K 31/437* | (2006.01) |
| *C07D 491/107* | (2006.01) |
| *C07D 471/08* | (2006.01) |
| *A61P 25/00* | (2006.01) |
| *A61P 37/00* | (2006.01) |
| *A61P 19/02* | (2006.01) |
| *C07D 495/10* | (2006.01) |
| *C07D 519/00* | (2006.01) |
| *A61P 29/00* | (2006.01) |

(52) U.S. Cl.
CPC ........... *C07D 471/04* (2013.01); *A61P 19/02* (2018.01); *A61P 25/00* (2018.01); *A61P 29/00* (2018.01); *A61P 37/00* (2018.01); *C07D 471/08* (2013.01); *C07D 491/107* (2013.01); *C07D 495/10* (2013.01); *C07D 519/00* (2013.01)

(58) Field of Classification Search
CPC .. C07D 471/04; C07D 487/04; C07D 519/00; A61K 31/437; A61K 31/519; A61P 29/00; A61P 37/00

USPC .......... 546/113, 117; 544/280, 350; 514/300, 514/258.1, 250

See application file for complete search history.

(56) References Cited

U.S. PATENT DOCUMENTS

| | | | |
|---|---|---|---|
| 6,867,200 | B1 | 3/2005 | Allen et al. |
| 7,410,975 | B2 | 8/2008 | Lipford et al. |
| 8,138,187 | B2 | 3/2012 | Zemolka et al. |
| 8,354,400 | B2 | 1/2013 | Zheng et al. |
| 9,126,996 | B2 | 9/2015 | Lipford et al. |
| 9,241,991 | B2 | 1/2016 | Ji et al. |
| 9,353,115 | B2 | 5/2016 | Lipford et al. |
| 9,376,398 | B2 | 6/2016 | Hori et al. |
| 9,428,495 | B2 | 8/2016 | Carlson et al. |
| 9,643,967 | B2 | 5/2017 | Koul et al. |
| 10,544,143 | B2 * | 1/2020 | Dyckman .............. A61P 25/00 |
| 2006/0235037 | A1 | 10/2006 | Purandare et al. |
| 2010/0160314 | A1 | 6/2010 | Lipford et al. |
| 2011/0015219 | A1 | 1/2011 | Trawick et al. |
| 2011/0275631 | A1 | 11/2011 | Abeywardane et al. |
| 2013/0045986 | A1 | 2/2013 | Nagarathnam et al. |
| 2014/0066432 | A1 | 3/2014 | Howbert et al. |
| 2014/0088085 | A1 | 3/2014 | Burgess et al. |
| 2014/0242121 | A1 | 8/2014 | Lipford et al. |

FOREIGN PATENT DOCUMENTS

| | | | |
|---|---|---|---|
| EP | 2738172 A1 | | 6/2014 |
| WO | WO2006113458 A1 | | 10/2006 |
| WO | WO2007115306 A2 | | 10/2007 |

(Continued)

OTHER PUBLICATIONS

International Search Report Application No. PCT/US2018/065908, dated Feb. 15, 2019.

(Continued)

*Primary Examiner* — Charanjit Aulakh
(74) *Attorney, Agent, or Firm* — Gary Greenblatt

(57) ABSTRACT

Disclosed are compounds of Formula (I)

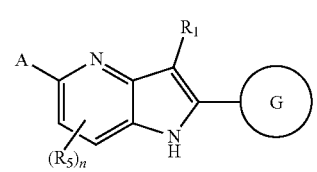

(I)

N-oxides, or salts thereof, wherein G, A, $R_1$, $R_5$, and n are defined herein. Also disclosed are methods of using such compounds as inhibitors of signaling through Toll-like receptor 7, or 8, or 9, and pharmaceutical compositions comprising such compounds. These compounds are useful in treating inflammatory and autoimmune diseases.

7 Claims, No Drawings

(56) References Cited

FOREIGN PATENT DOCUMENTS

| WO | WO2008065198 A1 | 6/2008 |
| WO | WO2008152471 A1 | 12/2008 |
| WO | WO2009030996 A1 | 3/2009 |
| WO | WO2010149769 A1 | 12/2010 |
| WO | WO2013010904 A1 | 1/2013 |
| WO | WO2013181579 A2 | 12/2013 |
| WO | WO2015088045 A1 | 6/2015 |
| WO | WO2016029077 A1 | 2/2016 |
| WO | WO2018026620 A1 | 2/2018 |
| WO | WO2018049089 A1 | 3/2018 |

OTHER PUBLICATIONS

Kawai, T., et al., "The Role of Pattern-Recognition Receptors in Innate Immunity: Update on Toll-like Receptors", Nature Immunol., 2011, 11, 373-384.

Lamphier, M. et al., "Novel Small Molecule Inhibitors of TLR7 and TLR9: Mechanism of Action and Efficacy in Vivo", Mol Pharmacol, 2014, 85:429-440.

Patra, Mahesh Chandra, et al. "Recent Progress in the Development of Toll-like Receptor (TLR) antagonists", Exp. Opin. On Therapeutic Patents, 2016, vol. 26, No. 6, 719-730.

Roy, et al., "Design and developmen of benzoxazole derivatives with toll-like receptor 9 antagonism", Eur J Med Chem, 2017, vol. 134, 334-347.

Sims, et al., "The IL-1 Family: Regulators of Immunity", Nature Rev. Immunol., 2010, 10, 89-102.

\* cited by examiner

4-AZAINDOLE COMPOUNDS

CROSS REFERENCE

This application is a continuation application of U.S. patent application Ser. No. 16/695,303, filed Nov. 26, 2019, which is a continuation application of U.S. Non-provisional application Ser. No. 16/222,145, filed Dec. 17, 2018, which claims priority to U.S. Provisional Application Ser. No. 62/599,875, filed Dec. 18, 2017, the contents of which are specifically incorporated fully herein by reference.

DESCRIPTION

The present invention generally relates to 4-azaindole compounds useful as inhibitors of signaling through Toll-like receptor 7, 8, or 9 (TLR7, TLR8, TLR9) or combinations thereof provided herein are 4-azaindole compounds, compositions comprising such compounds, and methods of their use. The invention further pertains to pharmaceutical compositions containing at least one compound according to the invention that are useful for the treatment of conditions related to TLR modulation, such as inflammatory and autoimmune diseases, and methods of inhibiting the activity of TLRs in a mammal.

Toll/IL-1 receptor family members are important regulators of inflammation and host resistance. The Toll-like receptor family recognizes molecular patterns derived from infectious organisms including bacteria, fungi, parasites, and viruses (reviewed in Kawai, T. et al., *Nature Immunol.*, 11:373-384 (2010)). Ligand binding to the receptor induces dimerization and recruitment of adaptor molecules to a conserved cytoplasmic motif in the receptor termed the Toll/IL-1 receptor (TIR) domain with the exception of TLR3, all TLRs recruit the adaptor molecule MyD88. The IL-1 receptor family also contains a cytoplasmic TIR motif and recruits MyD88 upon ligand binding (reviewed in Sims, J. E. et al., *Nature Rev. Immunol.*, 10:89-102 (2010)).

Toll-like receptors (TLRs) are a family of evolutionarily conserved, transmembrane innate immune receptors that participate in the first-line defense. As pattern recognition receptors, the TLRs protect against foreign molecules, activated by pathogen associated molecular patterns (PAMPs), or from damaged tissue, activated by danger associated molecular patterns (DAMPs). A total of 13 TLR family members have been identified, 10 in human, that span either the cell surface or the endosomal compartment. TLR7-9 are among the set that are endosomally located and respond to single-stranded RNA (TLR7 and TLR8) or unmethylated single-stranded DNA containing cytosine-phosphate-guanine (CpG) motifs (TLR9).

Activation of TLR7/8/9 can initiate a variety of inflammatory responses (cytokine production, B cell activation and IgG production, Type I interferon response). In the case of autoimmune disorders, the aberrant sustained activation of TLR7/8/9 leads to worsening of disease states. Whereas overexpression of TLR7 in mice has been shown to exacerbate autoimmune disease, knockout of TLR7 in mice was found to be protective against disease in lupus-prone MRL/lpr mice. Dual knockout of TLR7 and 9 showed further enhanced protection.

As numerous conditions may benefit by treatment involving modulation of cytokines, IFN production and B cell activity, it is immediately apparent that new compounds capable of modulating TLR7 and/or TLR8 and/or TLR9 and methods of using these compounds could provide substantial therapeutic benefits to a wide variety of patients.

The present invention relates to a new class of 4-azaindole compounds found to be effective inhibitors of signaling through TLR7/8/9. These compounds are provided to be useful as pharmaceuticals with desirable stability, bioavailability, therapeutic index, and toxicity values that are important to their drugability.

SUMMARY OF THE INVENTION

The present invention provides compounds of Formula (I) that are useful as inhibitors of signaling through Toll-like receptor 7, 8, or 9 and are useful for the treatment of proliferative diseases, allergic diseases, autoimmune diseases and inflammatory diseases, or stereoisomers, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Toll-like receptor 7, 8, or 9 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating a disease or disorder associated with Toll-like receptor 7, 8, or 9 activity, the method comprising administering to a mammal in need thereof, at least one of the compounds of Formula (I) or salts, solvates, and prodrugs thereof.

The present invention also provides processes and intermediates for making the compounds of Formula (I) including salts, solvates, and prodrugs thereof.

The present invention also provides at least one of the compounds of Formula (I) or salts, solvates, and prodrugs thereof, for use in therapy.

The present invention also provides the use of at least one of the compounds of Formula (I) or salts, solvates, and prodrugs thereof, for the manufacture of a medicament for the treatment of prophylaxis of Toll-like receptor 7, 8, or 9 related conditions, such as allergic disease, autoimmune diseases, inflammatory diseases, and proliferative diseases.

The compound of Formula (I) and compositions comprising the compounds of Formula (I) may be used in treating, preventing, or curing various Toll-like receptor 7, 8, or 9 related conditions. Pharmaceutical compositions comprising these compounds are useful for treating, preventing, or slowing the progression of diseases or disorders in a variety of therapeutic areas, such as allergic disease, autoimmune diseases, inflammatory diseases, and proliferative diseases.

These and other features of the invention will be set forth in expanded form as the disclosure continues.

DETAILED DESCRIPTION
The first aspect of the present invention provides at least one compound of Formula (I):
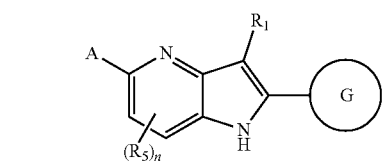
(I)
N-oxide, or a salt thereof, wherein:
G is:
(i)
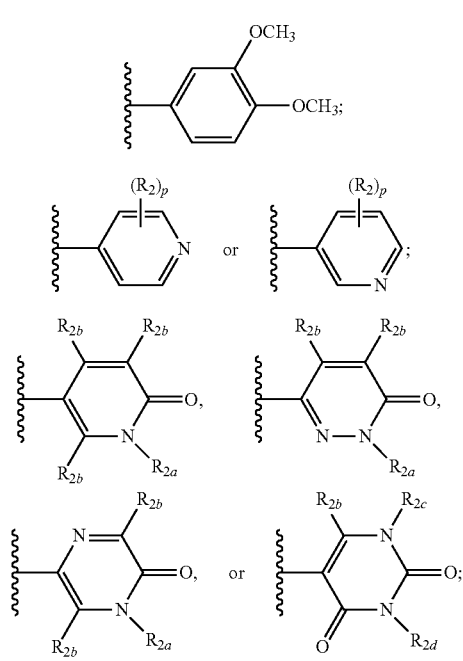
(ii)
(iii)
(iv) a 9-membered heterocyclic ring selected from:
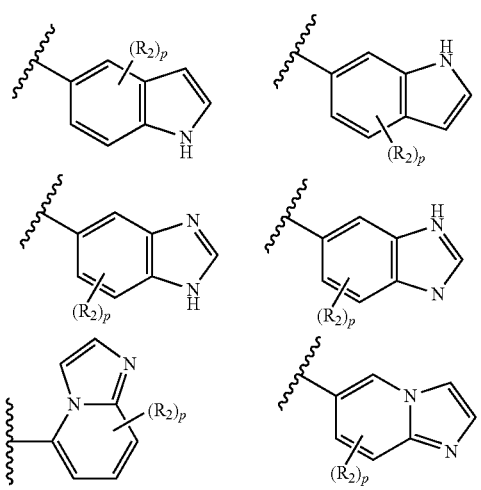
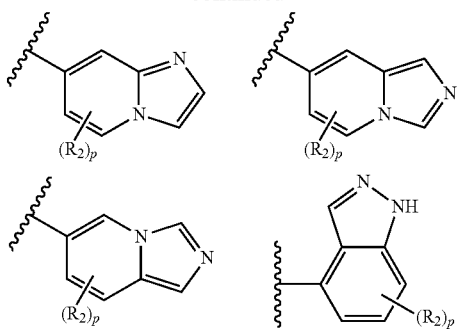
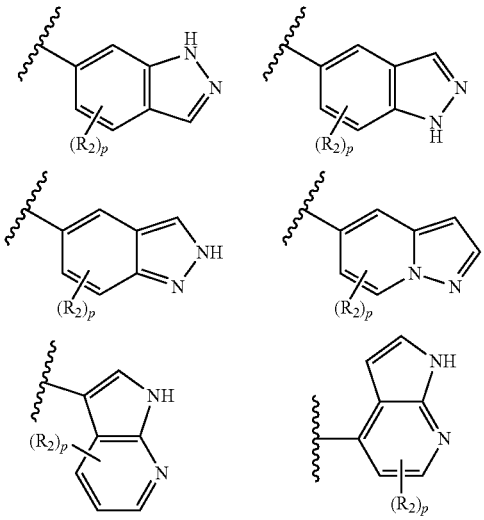
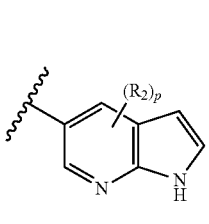
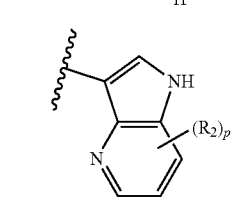
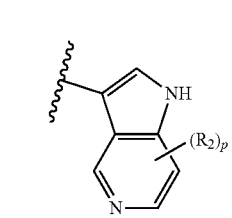
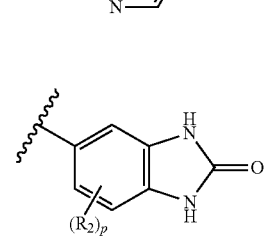

-continued
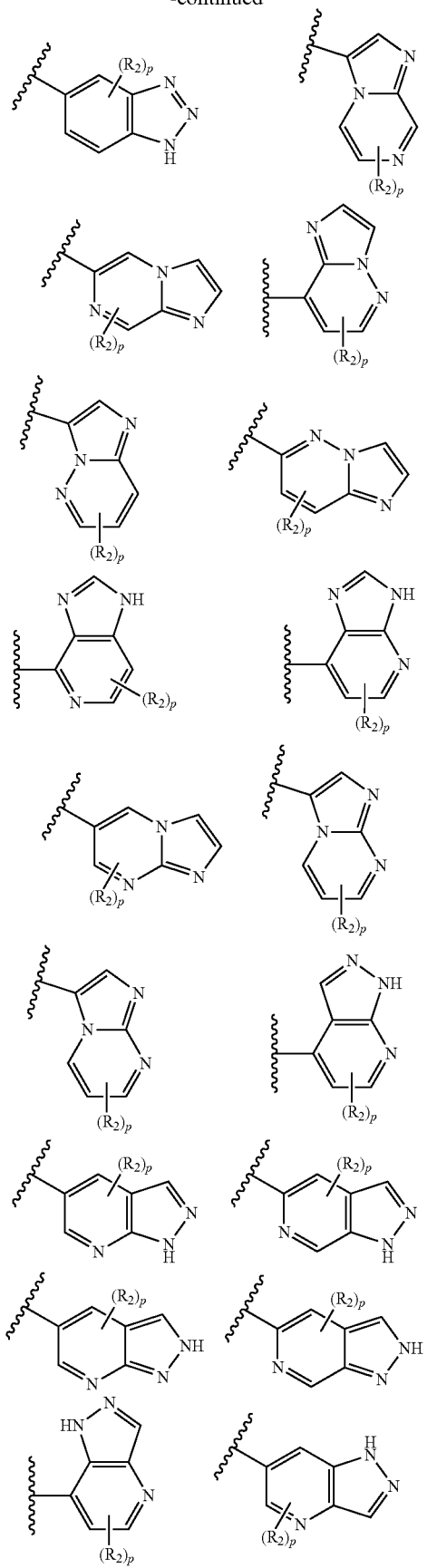
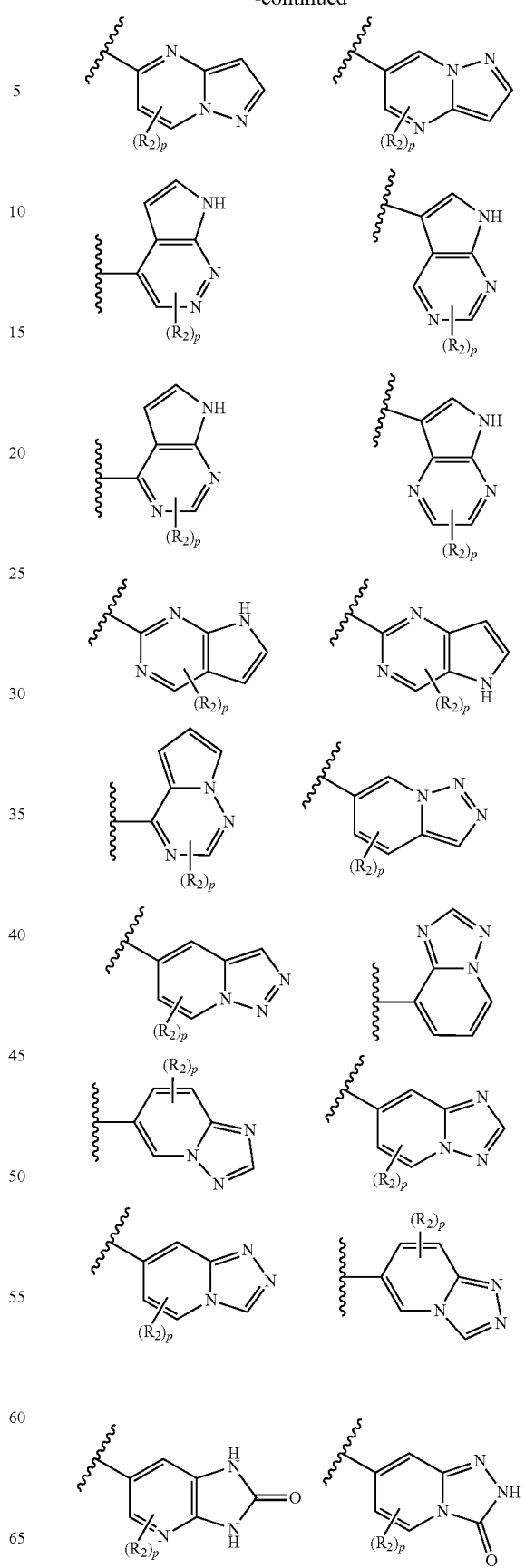

-continued
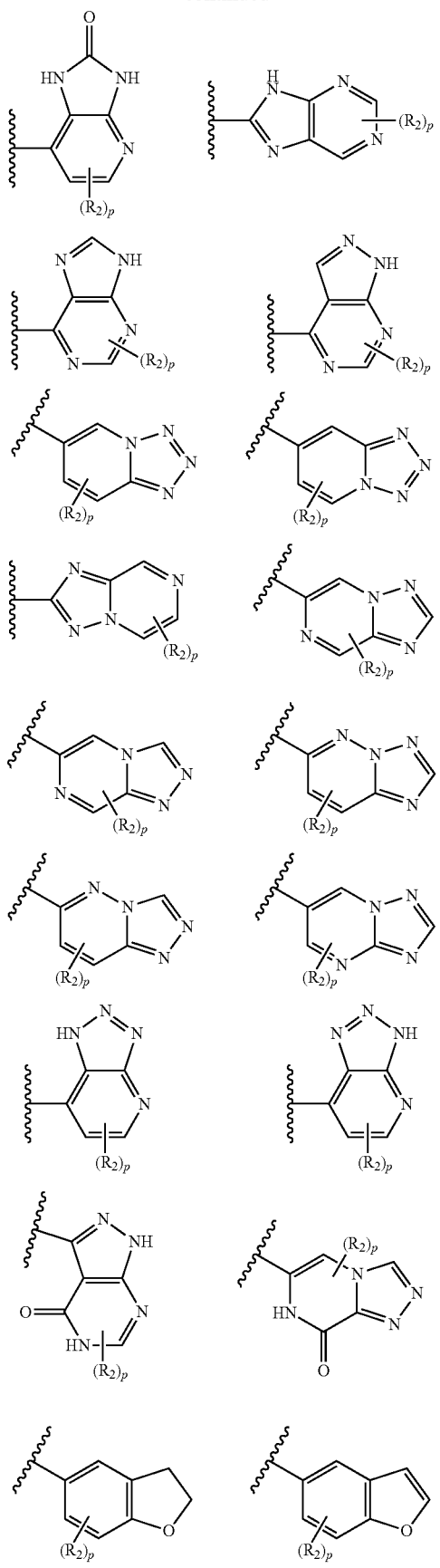
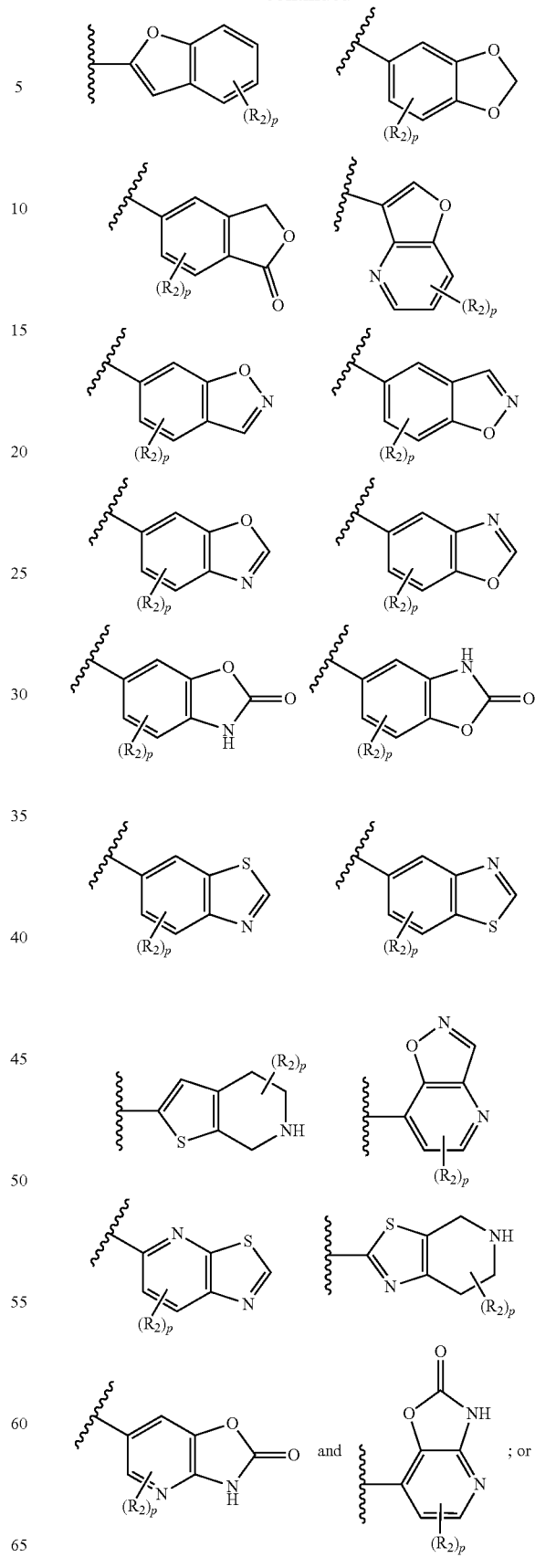
; or (v) 10-membered heterocyclic ring selected from:

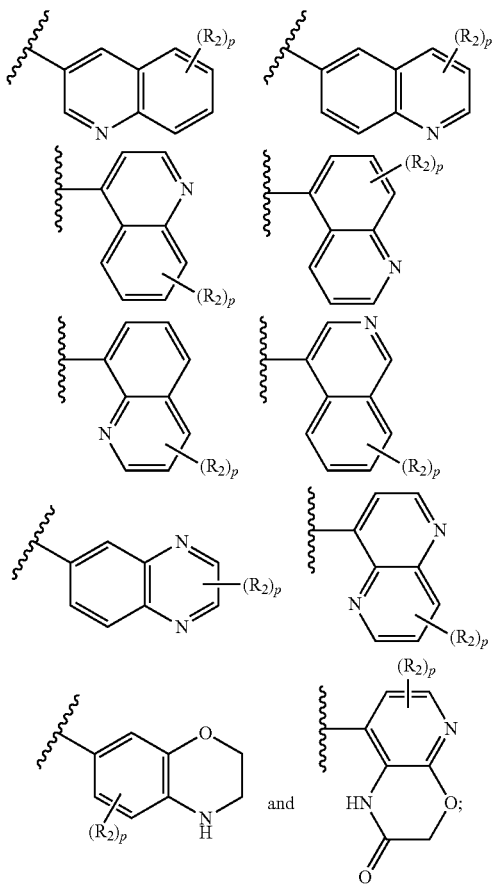

and

A is:
(i) —O-L$_1$-R$_6$;
(ii) —NR$_7$R$_8$;
(iii) -L$_2$-C(O)NR$_9$R$_{10}$;
(iv) —(CR$_x$R$_x$)$_{1-3}$R$_{11}$, C$_{1-3}$ aminoalkyl, —(CR$_x$R$_x$)$_{1-3}$NR$_x$C(O)R$_{11}$, —(CR$_x$R$_x$)$_{1-2}$NR$_x$C(O)(CH$_2$)$_{1-2}$(piperidinyl), —(CR$_x$R$_x$)$_{1-2}$NR$_x$C(O)O(CH$_2$)$_{1-2}$(piperidinyl), or —(CR$_x$R$_x$)$_{1-2}$NR$_x$C(O)(CH$_2$)$_{1-2}$NR$_x$R$_x$;
(v) —CR$_x$R$_{12}$R$_{13}$, wherein R$_{12}$ and R$_{13}$ together with the carbon atom to which they are attached form a cyclic group selected from azabicyclo[4.1.1]octanyl, azepanyl, azetidinyl, C$_{3-7}$ cycloalkyl, diazepanyl, azaspiro[3.3]heptanyl, diazaspiro[4.5]decanonyl, morpholinyl, octahydrocyclopenta[c]pyrrolyl, piperazinyl, piperidinyl, pyrrolidinyl, and quinuclidinyl, each substituted with zero to 4 R$_{12a}$;
(vi) —CR$_x$=CR$_x$(piperidinyl); or
(vii) an aromatic group selected from [1,2,4]triazolo[1,5-a]pyridinyl, imidazo[1,2-a]pyridinyl, imidazolyl, indazolyl, isoquinolinyl, oxadiazolyl, oxazolyl, phenyl, pyrazinyl, pyrazolo[3,4-b]pyridinyl, pyrazolyl, pyridazinyl, pyridinyl, pyrimidinyl, pyrrolyl, quinolinonyl, quinolinyl, quinoxalinyl, tetrahydro-[1,2,4]triazolo[1,5-a]pyrazinyl, tetrahydroimidazo[1,2-a]pyrazinyl, tetrahydroisoquinolinyl, tetrahydrothiazolo[5,4-c]pyridinyl, tetrahydrothieno[2,3-c]pyridinyl, thiadiazolyl, thiazolyl, thiooxadiazolyl, and triazolyl, each substituted with zero to 2 R$_{14a}$ and zero to 3 R$_{14b}$;
L$_1$ is bond, —(CR$_x$R$_x$)$_{1-2}$—, —(CR$_x$R$_x$)$_{1-2}$CR$_x$(OH)—, —(CR$_x$R$_x$)$_{1-2}$O—, —CR$_x$R$_x$C(O)—, —CR$_x$R$_x$C(O)NR$_x$(CR$_x$R$_x$)$_{0-4}$—, —CR$_x$R$_x$NR$_x$C(O)(CR$_x$R$_x$)$_{0-4}$—, or —CR$_x$R$_x$NR$_x$C(O)(CR$_x$R$_x$)$_{0-4}$—;
L$_2$ is a bond or —(CR$_x$R$_x$)$_{1-3}$—;
R$_1$ is H, Cl, —CN, C$_{1-4}$ alkyl, C$_{1-3}$ fluoroalkyl, C$_{1-3}$ hydroxyalkyl, C$_{1-3}$ hydroxyfluoroalkyl, —CR$_y$=CH$_2$, C$_{3-6}$ cycloalkyl, —CH$_2$(C$_{3-6}$ cycloalkyl), —C(O)O(C$_{1-3}$ alkyl), or tetrahydropyranyl;
each R$_2$ is independently halo, —CN, —OH, —NO$_2$, C$_{1-4}$ alkyl, C$_{1-2}$ fluoroalkyl, C$_{1-2}$ cyanoalkyl, C$_{1-3}$ hydroxyalkyl, C$_{1-3}$ aminoalkyl, —O(CH$_2$)$_{1-2}$OH, —(CH$_2$)$_{0-4}$O(C$_{1-4}$ alkyl), C$_{1-3}$ fluoroalkoxy, —(CH$_2$)$_{1-4}$O(C$_{1-3}$ alkyl), —O(CH$_2$)$_{1-2}$OC(O)(C$_{1-3}$ alkyl), —O(CH$_2$)$_{1-2}$NR$_x$R$_x$, —C(O)O(C$_{1-3}$ alkyl), —(CH$_2$)$_{0-2}$C(O)NR$_y$R$_y$, —C(O)NR$_x$(C$_{1-5}$ hydroxyalkyl), —C(O)NR$_x$(C$_{2-6}$ alkoxyalkyl), —C(O)NR$_x$(C$_{3-6}$ cycloalkyl), —NR$_y$R$_y$, —NR$_y$(C$_{1-3}$ fluoroalkyl), —NR$_y$(C$_{1-4}$ hydroxyalkyl), —NR$_x$CH$_2$(phenyl), —NR$_x$S(O)$_2$(C$_{3-6}$ cycloalkyl), —NR$_x$C(O)(C$_{1-3}$ alkyl), —NR$_x$CH$_2$(C$_{3-6}$ cycloalkyl), —(CH$_2$)$_{0-2}$S(O)$_2$(C$_{1-3}$ alkyl), —(CH$_2$)$_{0-2}$(C$_{3-6}$ cycloalkyl), —(CH$_2$)$_{0-2}$(phenyl), morpholinyl, dioxothiomorpholinyl, dimethyl pyrazolyl, methylpiperidinyl, methylpiperazinyl, amino-oxadiazolyl, imidazolyl, triazolyl, or —C(O)(thiazolyl);
R$_{2a}$ is C$_{1-6}$ alkyl, C$_{1-3}$ fluoroalkyl, C$_{1-6}$ hydroxyalkyl, C$_{1-3}$ aminoalkyl, —(CH$_2$)$_{0-4}$O(C$_{1-3}$ alkyl), C$_{3-6}$ cycloalkyl, —(CH$_2$)$_{1-3}$C(O)NR$_x$R$_x$, —CH$_2$(C$_{3-6}$ cycloalkyl), —CH$_2$(phenyl), tetrahydrofuranyl, tetrahydropyranyl, or phenyl;
each R$_{2b}$ is independently H, halo, —CN, —NR$_x$R$_x$, C$_{1-6}$ alkyl, C$_{1-3}$ fluoroalkyl, C$_{1-3}$ hydroxyalkyl, C$_{1-3}$ fluoroalkoxy, —(CH$_2$)$_{0-2}$O(C$_{1-3}$ alkyl), —(CH$_2$)$_{0-3}$C(O)NR$_x$R$_x$, —(CH$_2$)$_{1-3}$(C$_{3-6}$ cycloalkyl), —C(O)O(C$_{1-3}$ alkyl), —C(O)NR$_x$(C$_{1-3}$ alkyl), —CR$_x$=CR$_x$R$_x$, or —CR$_x$=CH(C$_{3-6}$ cycloalkyl);
R$_{2c}$ is R$_{2a}$ or R$_{2b}$;
R$_{2d}$ is R$_{2a}$ or R$_{2b}$; provided that one of R$_{2c}$ and R$_{2d}$ is R$_{2a}$, and the other of R$_{2c}$ and R$_2$ is R$_{2b}$;
each R$_5$ is independently F, Cl, —CN, C$_{1-3}$ alkyl, C$_{1-2}$ fluoroalkyl, or —OCH$_3$;
R$_6$ is:
(i) C$_{1-3}$ alkyl, —CR$_x$R$_x$C(O)NR$_x$(CR$_x$R$_x$)$_{1-3}$OH, —CR$_x$R$_x$C(O)NR$_x$(CR$_x$R$_x$)$_{1-2}$NR$_x$R$_x$, or —CR$_x$R$_x$C(O)NR$_x$(CR$_x$R$_x$)$_{1-2}$CHFCR$_x$R$_x$OH; or
(ii) azabicyclo[3.2.1]octanyl, azaspiro[5.5]undecanyl, azetidinyl, C$_{3-6}$ cycloalkyl, diazabicyclo[2.2.1]heptanyl, diazaspiro[3.5]nonanyl, morpholinyl, tetrahydrofuranyl, tetrahydropyranyl, octahydrocyclopenta[c]pyrrolyl, piperazinyl, piperidinyl, pyrrolidinyl, or quinuclidinyl, each substituted with zero to 3 R$_{6a}$;
each R$_{6a}$ is independently F, Cl, —OH, —CN, C$_{1-6}$ alkyl, C$_{1-4}$ fluoroalkyl, C$_{1-6}$ hydroxyalkyl, —(CH$_2$)$_{1-2}$O(C$_{1-3}$ alkyl), —NR$_y$R$_y$, —(CH$_2$)$_{1-2}$NR$_x$R$_x$, —(CR$_x$R$_x$)$_{1-2}$S(O)$_2$(C$_{1-3}$ alkyl), —(CR$_x$R$_x$)$_{1-2}$C(O)NR$_x$R$_x$, —C(O)(CR$_x$R$_x$)$_{1-2}$NR$_x$R$_x$, oxetanyl, tetrahydrofuranyl, tetrahydropyranyl, azetidinyl, pyrrolidinyl, piperidinyl, isobutylpiperidinyl, piperazinyl, or —O(piperidinyl);
R$_7$ is:
(i) R$_{7a}$, —CH$_2$R$_{7a}$, —(CH$_2$)$_{1-3}$NR$_y$R$_y$, —(CH$_2$)$_{1-3}$NR$_x$C(O)(CH$_2$)$_{1-2}$NR$_y$R$_y$, —C(O)R$_{7a}$, —C(O)CH(NH$_2$)R$_{7a}$, —C(O)(CH$_2$)$_{1-3}$NH$_2$, —C(O)CH(NH$_2$)(C$_{1-4}$ alkyl), —C(O)CH(NH$_2$)(CH$_2$)$_{1-2}$C(O)OH, —C(O)CH(NH$_2$)(CH$_2$)$_{2-4}$NH$_2$, or —C(O)CH(NH$_2$)(CH$_2$)$_{1-3}$C(O)NH$_2$; or
(ii) C$_{3-6}$ cycloalkyl substituted with one substituent selected from —NR$_x$(CH$_2$)$_{2-3}$NR$_y$R$_y$, —NR$_x$(methylpiperidinyl), —NR$_x$(CH$_2$)$_{2-3}$(morpholinyl), dimethylamino piperidinyl, and piperazinyl substituted with a substituent selected from C$_{1-4}$ alkyl, —C(O)CH$_3$, —(CH$_2$)$_{1-2}$OCH$_3$, —CH$_2$(methylphenyl), —(CH$_2$)$_{2-3}$(pyrrolidinyl), C$_{3-6}$ cycloalkyl, pyridinyl, and methylpiperidinyl;

R$_{7a}$ is azaspiro[3.5]nonanyl, C$_{3-6}$ cycloalkyl, diazaspiro[3.5]nonanyl, diazaspiro[5.5]undecanyl, diazepanonyl, diazepanyl, morpholinyl, phenyl, piperazinyl, piperidinyl, pyrrolidinonyl, pyrrolidinyl, or pyrrolyl, each substituted with zero to 1 substituent selected from C$_{1-3}$ alkyl, —NH$_2$, methylpiperidinyl, methylpyrrolidinyl, —OCH$_2$CH$_2$(pyrrolidinyl), and —OCH$_2$CH$_2$NHCH$_2$CH$_3$; and zero to 4 substituents selected from —CH$_3$;

R$_{7b}$ is:

(i) —OH, C$_{1-6}$ alkyl, C$_{1-4}$ fluoroalkyl, C$_{1-4}$ hydroxyalkyl, C$_{1-3}$ aminoalkyl, —(CH$_2$)$_{2-3}$C≡CH, —(CR$_x$R$_x$)$_{1-2}$O(C$_{1-2}$ alkyl), —(CH$_2$)$_{1-3}$S(O)$_2$(C$_{1-2}$ alkyl), —(CH$_2$)$_{0-3}$NR$_x$R$_y$, —(CH$_2$)$_{1-2}$C(O)NR$_x$R$_x$, —NR$_y$R$_y$, —NR$_x$(C$_{1-4}$ hydroxyalkyl), —NR$_y$(C$_{1-2}$ cyanoalkyl), —N(C$_{1-2}$ cyanoalkyl)$_2$, —NR$_x$(C$_{1-2}$ fluoroalkyl), —NR$_x$(C$_{2-4}$ hydroxyfluoroalkyl), —(CR$_x$R$_x$)$_{1-2}$C(O)NR$_x$R$_x$, —NR$_x$(CH$_2$)$_{1-2}$C(O)NR$_x$R$_x$, —N((CH$_2$)$_{0-2}$C(O)NR$_x$R$_x$)$_2$, —NR$_x$(CH$_2$)$_{1-2}$S(O)$_2$(C$_{1-2}$ alkyl), —NR$_x$(CH$_2$)$_{1-3}$NR$_x$R$_x$, —NR$_x$CH$_2$CH$_2$NR$_x$R$_x$, —NR$_x$C(O)(CH$_2$)$_{1-2}$NR$_x$R$_x$, —NR$_x$(CH$_2$CH$_2$S(O)$_2$CH$_3$), —(CH$_2$)$_{1-2}$NR$_x$C(O)(CH$_2$)$_{1-2}$NR$_x$R$_x$, —O(CH$_2$)$_{1-3}$NR$_x$R$_x$, —C(O)(CR$_x$R$_x$)$_{1-2}$NR$_y$R$_y$, —C(O)(CR$_x$R$_x$)$_{1-2}$NR$_y$(C$_{1-4}$ hydroxyalkyl), —C(O)(CR$_x$R$_x$)$_{1-2}$NR$_x$(CH$_2$CH$_2$OCH$_3$), —S(O)$_2$CH$_2$CH$_2$N(CH$_3$)$_2$, —(CH$_2$)$_{1-2}$R$_{7d}$, —NR$_x$R$_{7d}$, —NR$_x$(CH$_2$)$_{1-2}$R$_{7d}$), —NR$_{7d}$R$_{7d}$, —N((CH$_2$)$_{1-2}$R$_{7d}$)$_2$, —OR$_{7d}$, —C(O)R$_{7d}$, —C(O)(CR$_x$R$_x$)$_{1-2}$R$_{7d}$, or —C(O)(CR$_x$R$_x$)$_{1-2}$NR$_x$R$_{7d}$; or (ii) azepanyl, azetidinyl, C$_{3-6}$ cycloalkyl, diazepanyl, dioxotetrahydrothiopyranyl, dioxothiomorpholinyl, morpholinyl, oxaazaspiro[3.3]heptanyl, oxaazaspiro[4.3]octanyl, oxetanyl, piperazinonyl, piperazinyl, piperidinyl, pyridinyl, pyrimidinyl, pyrrolidinonyl, pyrrolidinyl, tetrahydrofuranyl, tetrahydroisoquinolinyl, tetrahydropyranyl, or thiadiazolyl, each substituted with zero to 1 R$_{8a}$ and zero to 3 R$_{8b}$;

each R$_{7c}$ is independently F, Cl, —CN, C$_{1-2}$ alkyl, —CF$_3$, or —CH$_2$CN;

R$_{7d}$ is azaspiro[3.5]nonanyl, azetidinyl, bicyclo[1.1.1]pentanyl, C$_{3-6}$ cycloalkyl, dioxothiaazaspiro[3.3]heptanyl, morpholinyl, oxaazaspiro[3.3]heptanyl, oxaazaspiro[4.3]octanyl, oxaazaspiro[4.4]nonyl, oxetanyl, phenyl, piperidinyl, pyrazolyl, pyrrolidinyl, tetrahydrofuranyl, tetrahydropyranyl, thiadiazolyl, or triazolyl, each substituted with zero to 2 substituents independently selected from F, —OH, C$_{1-3}$ alkyl, C$_{1-2}$ hydroxyalkyl, C$_{1-2}$ alkoxy, —NR$_x$R$_x$, —C(O)CH$_3$, —S(O)$_2$CH$_3$, methylpiperidinyl, methylpyrrolidinyl, tetramethylpiperidinyl, —OCH$_2$CH$_2$(pyrrolidinyl), and —OCH$_2$CH$_2$NHCH$_2$CH$_3$; and zero to 4 substituents selected from —CH$_3$;

R$_8$ is H or C$_{1-3}$ alkyl;

or R$_7$ and R$_8$ together with the nitrogen atom to which they are attached form a heterocyclic ring selected from azetidinyl, diazabicyclo[2.2.1]heptanyl, diazabicyclo[2.2.2]octanyl, diazabicyclo[3.1.1]heptanyl, diazabicyclo[3.2.1]octanyl, azaspiro[3.3]heptanyl, diazaspiro[2.5]octanyl, diazaspiro[3.3]heptanyl, diazepanonyl, diazepanyl, diazaspiro[3.5]nonanyl, diazaspiro[5.5]undecanyl, imidazolyl, imidazolidinonyl, octahydro-1H-pyrrolo[3,4-b]pyridinyl, oxadiazabicyclo[3.3.1]nonanyl, piperazinyl, piperazinonyl, piperidinyl, pyrrolidinonyl, pyrrolidinyl, and pyrrolyl, wherein said heterocyclic ring is substituted with zero to 1 R$_{7b}$ and zero to 2 R$_{7c}$;

R$_{8a}$ is —OH, C$_{1-6}$ alkyl, C$_{1-4}$ fluoroalkyl, C$_{1-4}$ hydroxyalkyl, —(CH$_2$)$_{1-2}$O(C$_{1-3}$ alkyl), C$_{1-2}$ alkoxy, —C(O)(C$_{1-3}$ alkyl), —C(O)O(C$_{1-2}$ alkyl), —(CH$_2$)$_{1-2}$(C$_{3-6}$ cycloalkyl), —(CH$_2$)$_{1-3}$(methyl phenyl), —(CH$_2$)$_{1-3}$(pyrrolidinyl), —(CH$_2$)$_{1-3}$(methylpyrazolyl), —(CH$_2$)$_{1-3}$(thiophenyl), —NR$_x$R$_x$, C$_{3-6}$ cycloalkyl, methylpiperidinyl, pyridinyl, or pyrimidinyl;

each R$_{8b}$ is independently F, Cl, —CN, C$_{1-3}$ alkyl, or —CF$_3$;

R$_9$ is C$_{1-6}$ alkyl, C$_{1-4}$ fluoroalkyl, C$_{1-6}$ hydroxyalkyl, C$_{1-6}$ hydroxy fluoroalkyl, C$_{1-3}$ aminoalkyl, —(CH$_2$)$_{1-2}$O(C$_{1-3}$ alkyl), —(CH$_2$)$_{1-3}$NR$_x$R$_x$, —(CH$_2$)$_{1-2}$C(O)NR$_x$R$_x$, —(CH$_2$)$_{1-3}$S(O)$_2$OH, —(CR$_x$R$_x$)$_{1-3}$NR$_x$S(O)$_2$(C$_{1-2}$ alkyl), or —(CH$_2$)$_{0-3}$R$_{9a}$;

R$_{9a}$ is C$_{3-7}$ cycloalkyl, furanyl, phenyl, piperazinyl, piperidinyl, pyrazolyl, pyridinyl, pyrrolidinyl, quinuclidinyl, thiazolyl, or octahydrocyclopenta[c]pyrrolyl, each substituted with zero to 3 substituents independently selected from F, Cl, —OH, C$_{1-4}$ alkyl, C$_{1-3}$ hydroxyalkyl, C$_{1-3}$ hydroxy fluoroalkyl, C$_{1-3}$ aminoalkyl, —NR$_y$R$_y$, oxetanyl, phenyl, piperazinyl, piperidinyl, and pyrrolidinyl;

R$_{10}$ is H, C$_{1-4}$ alkyl, —(CH$_2$)$_{1-3}$O(C$_{1-2}$ alkyl), or C$_{3-6}$ cycloalkyl;

or R$_9$ and R$_{10}$ together with the nitrogen atom to which they are attached form a heterocyclic ring selected from azabicyclo[3.1.1]heptanyl, azaspiro[5.5]undecanyl, diazabicyclo[2.2.1]heptanyl, diazabicyclo[3.1.1]heptanyl, diazabicyclo[3.2.0]heptanyl, diazaspiro[3.5]nonanyl, diazaspiro[4.4]nonanyl, diazaspiro[4.5]decanyl, diazepanyl, indolinyl, morpholinyl, octahydropyrrolo[3,4-c]pyrrolyl, piperazinonyl, piperazinyl, piperidinyl, and pyrrolidinyl, each substituted with zero to 3 R$_{10a}$;

each R$_{10a}$ is independently C$_{1-4}$ alkyl, C$_{1-4}$ hydroxyalkyl, —(CH$_2$)$_{1-3}$O(C$_{1-3}$ alkyl), —(CH$_2$)$_{1-3}$NR$_x$R$_x$, —(CH$_2$)$_{1-2}$C(O)NR$_x$R$_x$, —(CH$_2$)$_{1-2}$(methyltriazolyl), —CH$_2$CH$_2$(phenyl), —CH$_2$CH$_2$(morpholinyl), —C(O)(C$_{1-2}$ alkyl), —C(O)NR$_y$R$_y$, —C(O)CH$_2$NR$_y$R$_y$, —NR$_y$R$_y$, —NHC(O)(C$_{1-3}$ alkyl), —C(O)(furanyl), —O(piperidinyl), —C(O)CH$_2$(diethylcarbamoylpiperidinyl), methylpiperazinyl, piperidinyl, methylpiperidinyl, diethylcarbamoylpiperidinyl, isopropylpiperidinyl, pyridinyl, trifluoromethylpyridinyl, pyrimidinyl, or dihydrobenzo[d]imidazolonyl;

R$_{11}$ is azetidinyl, azaspiro[3.5]nonanyl, dioxidothiomorpholinyl, hexahydropyrrolo[3,4-c]pyrrolyl, morpholinyl, piperazinyl, piperidinyl, pyridinyl, or pyrrolidinyl, each substituted with zero to 3 substituents independently selected from halo, —CN, C$_{1-4}$ alkyl, C$_{1-3}$ aminoalkyl, —(CH$_2$)$_{1-2}$(methyloxetanyl), —(CH$_2$)$_{1-2}$(triazolyl), —(CH$_2$)$_{1-2}$(phenyl), —C(O)CH$_2$NR$_x$R$_x$, C$_{1-5}$ hydroxyalkyl, —(CH$_2$)$_{1-2}$C(O)NR$_x$R$_x$, —(CH$_2$)$_{1-2}$S(O)$_2$(C$_{1-3}$ alkyl), —(CH$_2$)$_{1-2}$S(O)(C$_{1-3}$ alkyl), oxetanyl, tetrahydrofuranyl, and tetrahydropyranyl;

each R$_{12a}$ is independently F, Cl, —OH, C$_{1-6}$ alkyl, C$_{1-4}$ fluoroalkyl, C$_{1-4}$ cyanoalkyl, C$_{1-6}$ hydroxyalkyl, —(CH$_2$)$_{1-2}$O(C$_{1-3}$ alkyl), —(CH$_2$)$_{1-2}$C(O)NR$_x$R$_x$, —(CH$_2$)$_{1-2}$S(O)$_2$(C$_{1-2}$ alkyl), —(CH$_2$)$_{1-2}$NR$_x$HS(O)$_2$(C$_{1-2}$ alkyl), —(CH$_2$)$_{1-2}$NR$_x$R$_x$, C$_{1-3}$ alkoxy, —NR$_y$R$_y$, —NR$_x$(C$_{1-4}$ fluoroalkyl), —NR$_x$(C$_{1-2}$ cyanoalkyl), —NR$_x$CH$_2$NR$_x$R$_x$, —NR$_x$(C$_{1-4}$ hydroxyalkyl), —NR$_x$(CR$_x$R$_x$CR$_x$R$_x$)O(C$_{1-3}$ alkyl), —NR$_x$(CH$_2$C(O)NR$_x$R$_x$), —NR$_x$(C$_{1-3}$ alkoxy), —NR$_x$CH$_2$CH$_2$S(O)$_2$(C$_{1-2}$ alkyl), —NR$_x$C(O)CH$_3$, —NR$_x$C(O)(C$_{1-2}$ fluoroalkyl), —NR$_x$C(O)CR$_x$R$_x$NR$_y$R$_y$, —NR$_x$C(O)CH$_2$NR$_y$R$_y$, —NR$_x$C(O)CH$_2$NR$_x$(C$_{1-4}$ hydroxyalkyl), —NR$_x$(CH$_2$)$_{1-2}$C(O)NR$_x$R$_x$, —NR$_x$S(O)$_2$(C$_{1-2}$ alkyl), —C(O)(C$_{1-5}$ alkyl), —C(O)(CH$_2$)$_{1-3}$O(C$_{1-2}$ alkyl), —C(O)(CR$_x$R$_x$)$_{1-2}$NR$_y$R$_y$, R$_{12b}$, —CR$_x$R$_x$R$_{12b}$, —C(O)R$_{12b}$, —C(O)

$CR_xR_xNR_xR_{12b}$, $-C(O)NR_xR_{12b}$, $-NR_xC(O)CR_xR_xR_{12b}$, $-NR_xR_{12b}$, $-NR_xCR_xR_xR_{12b}$, $-N(CH_2CN)R_{12b}$, $-NR_xC(O)CR_xR_xNR_xR_{12b}$, $-NR_xC(O)CR_xR_xNR_xCH_2R_{12b}$, $-NR_xCR_xR_xC(O)NR_xR_{12b}$, or $-OR_{12b}$; or two $R_{12a}$ and the carbon atom to which they are attached form C=O;

$R_{12b}$ is azetidinyl, bicyclo[1.1.1]pentanyl, $C_{3-6}$ cycloalkyl, diazabicyclo[2.2.1]heptanyl, dioxolanyl, dioxothiaazaspiro[3.3]heptanyl, dioxidotetrahydrothiopyranyl, dioxidothiomorpholinyl, imidazolyl, morpholinyl, octahydrocyclopenta[c]pyrrolyl, octahydropyrrolo[3,4-c]pyrrolyl, oxaazaspiro[3.3]heptanyl, oxaazaspiro[4.3]octanyl, oxaazaspiro[4.4]nonanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, Cl, $-OH$, $C_{1-4}$ alkyl, $C_{1-3}$ fluoroalkyl, $C_{1-3}$ hydroxyalkyl, $C_{1-3}$ aminoalkyl, $C_{1-4}$ alkoxy, $-(CH_2)_{1-2}O(C_{1-3}$ alkyl), $-NR_xR_x$, $-C(O)NR_xR_x$, and $-(CR_xR_x)_{0-1}S(O)_2(C_{1-3}$ alkyl);

each $R_{14a}$ is independently is:

(i) H, halo, $-OH$, $C_{1-6}$ alkyl, $C_{1-23}$ fluoroalkyl, $C_{1-4}$ hydroxyalkyl, $-(CH_2)_{0-2}O(C_{1-3}$ alkyl), $-CR_xR_xNR_yR_y$, $-CR_xR_xNR_x(C_{1-3}$ cyanoalkyl), $-CR_xR_xNR_x((CH_2)_{1-2}O(C_{1-2}$ alkyl)), $-CR_xR_xN((CH_2)_{1-2}OCH_3)_2$, $-CR_xR_xNR_x(CH_2C≡CR_x)$, $-CR_xR_xNR_x(CH_2)_{1-3}NR_xR_x$, $-(CR_xR_x)_{1-3}CR_xR_xNR_xR_x$, $-CR_x(NH_2)(CH_2)_{1-4}NR_xR_x$, $-CR_xR_xNR_x(CH_2)_{1-2}O(C_{1-3}$ alkyl), $-CR_xR_xNR_x(CH_2)_{1-2}O(CH_2)_{1-2}OH$, $-CR_xR_xNR_x(CH_2)_{1-3}S(O)_2OH$, $-CR_xR_xC(O)NR_xR_x$, $-NR_yR_y$, $-NR_x(CH_2)_{1-3}NR_xR_x$, $-NR_xC(O)(C_{1-3}$ alkyl), $-NR_xC(O)(C_{1-3}$ fluoroalkyl), $-NR_xC(O)O(C_{1-3}$ alkyl), $-NR_xC(O)(CH_2)_{1-3}NR_xR_x$, $-NR_xCH_2C(O)CH_2NR_xR_x$, $-C(O)(C_{1-3}$ alkyl), $-C(O)(CR_xR_x)_{1-3}OH$, $-C(O)CR_xR_xNR_xR_x$, $-C(O)NR_xR_x$, $-C(O)NR_x(C_{1-2}$ cyanoalkyl), $-C(O)NR_x(CR_xR_x)_{1-3}NR_xR_x$, $-C(O)N(CH_2CH_3)(CR_xR_x)_{1-3}NR_xR_x$, $-C(O)NR_x(CR_xR_x)_{1-2}C(O)NR_xR_x$, $-C(O)NR_x(CR_xR_x)_{1-3}NR_xC(O)(C_{1-2}$ alkyl), $-O(CR_xR_x)_{1-3}NR_xR_x$, $-S(O)_2NR_xR_x$, or $-C(O)(CR_xR_x)_{1-2}S(O)_2(C_{1-2}$ alkyl);

(ii) 8-azabicyclo[3.2.1]octanyl, azaspiro[3.5]nonanyl, azetidinyl, benzo[c][1,2,5]oxadiazolyl, cyclopentyl, cyclohexyl, diazepanyl, morpholinyl, phenyl, piperazinyl, piperidinyl, pyrazolyl, pyridinyl, pyrrolidinonyl, quinolinyl, quinuclidinyl, tetrahydroisoquinolinyl, tetrahydropyridinyl, or thiazolidinyl, each substituted with zero to 2 substituents independently selected from $C_{1-4}$ alkyl, $C_{1-2}$ fluoroalkyl, $C_{1-4}$ hydroxyalkyl, $-NR_xR_x$, $-(CH_2)_{1-2}NR_xR_x$, $-C(O)(C_{1-2}$ alkyl), $-C(O)CH_2NR_xR_x$, $-C(O)O(C_{1-3}$ alkyl), $-CH_2C(O)NR_xR_x$, $C_{3-6}$ cycloalkyl, $-CH_2(phenyl)$, $-CH_2(pyrrolyl)$, $-CH_2(morpholinyl)$, $-CH_2(methylpiperazinyl)$, $-CH_2(thiophenyl)$, methylpiperidinyl, isobutylpiperidinyl, and pyridinyl; or (iii) $-L_3-R_{14c}$;

each $R_{14b}$ is F, Cl, $-OH$, $-CH_3$, or $-OCH_3$;

$R_{14c}$ is adamantanyl, azepanyl, azetidinyl, $C_{3-7}$ cycloalkyl, diazepanyl, imidazolyl, indolyl, morpholinyl, octahydropyrrolo[3,4-c]pyrrolyl, phenyl, piperazinonyl, piperazinyl, piperidinyl, pyridinyl, pyrrolidinonyl, pyrrolidinyl, pyrrolyl, triazolyl, or tetrazolyl, each substituted with zero to 1 substituent selected from F, $-OH$, $C_{1-4}$ alkyl, $C_{1-3}$ hydroxyalkyl, $-NR_xR_y$, $-NR_xC(O)CH_3$, $-C(O)(C_{1-2}$ alkyl), $-C(O)NR_xR_x$, $-C(O)N(CH_2CH_3)_2$, $-C(O)(tetrahydrofuranyl)$, $-C(O)O(C_{1-2}$ alkyl), $-CH_2C(O)NR_xR_y$, morpholinyl, methylpiperidinyl, pyrazinyl, pyridinyl, and pyrrolidinyl;

$L_3$ is $-(CR_xR_x)_{1-3}-$, $-CH(NH_2)-$, $-CR_xR_xNR_x-$, $-C(O)-$, $-C(O)NR_x(CH_2)_{0-4}-$, $-NR_x-$, $-NR_xC(O)-$, $-NR_xCH_2-$, $-NR_xCH_2C(O)-$, or $-O(CH_2)_{0-2}-$;

$R_y$ is H, $C_{1-2}$ alkyl, or $C_{1-2}$ fluoroalkyl;
each $R_x$ is independently H or $-CH_3$;
each $R_y$ is independently H or $C_{1-6}$ alkyl;
n is zero, 1, or 2; and
p is zero, 1, 2, 3, or 4.

The second aspect of the present invention provides at least one compound of Formula (I), N-oxide, or a salt thereof, wherein:

G is defined in the first aspect;

A is:

(i) $-O-L_1-R_6$;
(ii) $-NR_7R_8$;
(iii) $-L_2-C(O)NR_9R_{10}$;
(iv) $-(CR_xR_x)_{1-3}R_{11}$, $C_{1-3}$ aminoalkyl, $-(CR_xR_x)_{1-3}NR_xC(O)R_{11}$, $-(CR_xR_x)_{1-2}NR_xC(O)(CH_2)_{1-2}(piperidinyl)$, $-(CR_xR_x)_{1-2}NR_xC(O)O(CH_2)_{1-2}(piperidinyl)$, or $-(CR_xR_x)_{1-2}NR_xC(O)(CH_2)_{1-2}NR_xR_x$;
(v) $-CR_xR_{12}R_{13}$, wherein $R_{12}$ and $R_{13}$ together with the carbon atom to which they are attached form a cyclic group selected from azabicyclo[4.1.1]octanyl, azepanyl, azetidinyl, $C_{3-7}$ cycloalkyl, diazepanyl, diazaspiro[4.5]decanonyl, morpholinyl, octahydrocyclopenta[c]pyrrolyl, piperazinyl, piperidinyl, pyrrolidinyl, and quinuclidinyl, each substituted with zero to 4 $R_{12a}$;
(vi) $-CR_x=CR_x(piperidinyl)$; or
(vii) an aromatic group selected from [1,2,4]triazolo[1,5-a]pyridinyl, imidazo[1,2-a]pyridinyl, imidazolyl, indazolyl, isoquinolinyl, oxadiazolyl, oxazolyl, phenyl, pyrazinyl, pyrazolo[3,4-b]pyridinyl, pyrazolyl, pyridazinyl, pyridinyl, pyrimidinyl, pyrrolyl, quinolinonyl, quinolinyl, quinoxalinyl, tetrahydro-[1,2,4]triazolo[1,5-a]pyrazinyl, tetrahydroimidazo[1,2-a]pyrazinyl, tetrahydroisoquinolinyl, tetrahydrothiazolo[5,4-c]pyridinyl, tetrahydrothieno[2,3-c]pyridinyl, thiadiazolyl, thiazolyl, thiooxadiazolyl, and triazolyl, each substituted with zero to 2 $R_{14a}$ and zero to 3 $R_{14b}$;

$L_1$ is bond, $-(CR_xR_x)_{1-2}-$, $-(CR_xR_x)_{1-2}CR_x(OH)-$, $-(CR_xR_x)_{1-2}O-$, $-CR_xR_xC(O)-$, $-CR_xR_xC(O)NR_x(CR_xR_x)_{0-4}-$, $-CR_xR_xNR_xC(O)(CR_xR_x)_{0-4}-$, or $-CR_xR_xNR_xC(O)(CR_xR_x)_{0-4}-$;

$L_2$ is a bond or $-(CR_xR_x)_{1-3}-$;

$R_1$ is H, Cl, $-CN$, $C_{1-4}$ alkyl, $C_{1-3}$ fluoroalkyl, $C_{1-3}$ hydroxyalkyl, $C_{1-3}$ hydroxy-fluoroalkyl, $-CR_y=CH_2$, $C_{3-6}$ cycloalkyl, $-CH_2(C_{3-6}$ cycloalkyl), $-C(O)O(C_{1-3}$ alkyl), or tetrahydropyranyl;

each $R_2$ is independently halo, $-CN$, $-OH$, $-NO_2$, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, $-O(CH_2)_{1-2}OH$, $-(CH_2)_{0-4}O(C_{1-4}$ alkyl), $C_{1-3}$ fluoroalkoxy, $-(CH_2)_{1-40}(C_{1-3}$ alkyl), $-O(CH_2)_{1-2}OC(O)(C_{1-3}$ alkyl), $-O(CH_2)_{1-2}NR_xR_x$, $-C(O)O(C_{1-3}$ alkyl), $-(CH_2)_{0-2}C(O)NR_yR_y$, $-C(O)NR_x(C_{1-5}$ hydroxyalkyl), $-C(O)NR_x(C_{2-6}$ alkoxyalkyl), $-C(O)NR_x(C_{3-6}$ cycloalkyl), $-NR_yR_y$, $-NR_y(C_{1-3}$ fluoroalkyl), $-NR_y(C_{1-4}$ hydroxyalkyl), $-NR_xCH_2(phenyl)$, $-NR_xS(O)_2(C_{3-6}$ cycloalkyl), $-NR_xC(O)(C_{1-3}$ alkyl), $-NR_xCH_2(C_{3-6}$ cycloalkyl), $-(CH_2)_{0-2}S(O)_2(C_{1-3}$ alkyl), $-(CH_2)_{0-2}(C_{3-6}$ cycloalkyl), $-(CH_2)_{0-2}(phenyl)$, morpholinyl, dioxothiomorpholinyl, dimethyl pyrazolyl, methylpiperidinyl, methylpiperazinyl, amino-oxadiazolyl, imidazolyl, triazolyl, or $-C(O)(thiazolyl)$;

$R_{2a}$ is $C_{1-6}$ alkyl, $C_{1-3}$ fluoroalkyl, $C_{1-6}$ hydroxyalkyl, $C_{1-3}$ aminoalkyl, $-(CH_2)_{0-4}O(C_{1-3}$ alkyl), $C_{3-6}$ cycloalkyl, —(CH$_2$)$_{1-3}$C(O)NR$_x$R$_x$, —CH$_2$(C$_{3-6}$ cycloalkyl), —CH$_2$ (phenyl), tetrahydrofuranyl, tetrahydropyranyl, or phenyl;

each R$_{2b}$ is independently H, halo, —CN, —NR$_x$R$_x$, C$_{1-6}$ alkyl, C$_{1-3}$ fluoroalkyl, C$_{1-3}$ hydroxyalkyl, C$_{1-3}$ fluoroalkoxy, —(CH$_2$)$_{0-2}$O(C$_{1-3}$ alkyl), —(CH$_2$)$_{0-3}$C(O)NR$_x$R$_x$, —(CH$_2$)$_{1-3}$(C$_{3-6}$ cycloalkyl), —C(O)O(C$_{1-3}$ alkyl), —C(O)NR$_x$(C$_{1-3}$ alkyl), —CR$_x$=CR$_x$R$_x$, or —CR$_x$=CH (C$_{3-6}$ cycloalkyl);

R$_{2c}$ is R$_{2a}$ or R$_{2b}$;

R$_{2d}$ is R$_{2a}$ or R$_{2b}$; provided that one of R$_{2c}$ and R$_{2d}$ is R$_{2a}$ and the other of R$_{2c}$ and R$_2$ is R$_{2b}$;

each R$_5$ is independently F, Cl, —CN, C$_{1-3}$ alkyl, C$_{1-2}$ fluoroalkyl, or —OCH$_3$;

R$_6$ is:
(i) —CR$_x$R$_x$C(O)NR$_x$(CR$_x$R$_x$)$_{1-3}$OH, —CR$_x$R$_x$C(O)NR$_x$ (CR$_x$R$_x$)$_{1-2}$NR$_x$R$_x$, or —CR$_x$R$_x$C(O)NR$_x$(CR$_x$R$_x$)$_{1-2}$CHFCR$_x$R$_x$OH; or
(ii) azabicyclo[3.2.1]octanyl, azaspiro[5.5]undecanyl, azetidinyl, C$_{3-6}$ cycloalkyl, diazabicyclo[2.2.1]heptanyl, diazaspiro[3.5]nonanyl, morpholinyl, tetrahydrofuranyl, tetrahydropyranyl, octahydrocyclopenta[c]pyrrolyl, piperazinyl, piperidinyl, pyrrolidinyl, or quinuclidinyl, each substituted with zero to 3 R$_{6a}$;

each R$_{6a}$ is independently F, Cl, —OH, —CN, C$_{1-6}$ alkyl, C$_{1-4}$ fluoroalkyl, C$_{1-6}$ hydroxyalkyl, —(CH$_2$)$_{1-2}$O(C$_{1-3}$ alkyl), —NR$_x$R$_x$, —(CH$_2$)$_{1-2}$NR$_x$R$_x$, —(CR$_x$R$_x$)$_{1-2}$S(O)$_2$(C$_{1-3}$ alkyl), —(CR$_x$R$_x$)$_{1-2}$C(O)NR$_x$R$_x$, —C(O)(CR$_x$R$_x$)$_{1-2}$NR$_x$R$_x$, oxetanyl, tetrahydrofuranyl, tetrahydropyranyl, azetidinyl, pyrrolidinyl, piperidinyl, isobutylpiperidinyl, piperazinyl, or —O(piperidinyl);

R$_7$ is:
(i) R$_a$, —CH$_2$R$_{7a}$, —C(O)R$_{7a}$, —C(O)CH(NH$_2$)R$_{7a}$, —C(O)(CH$_2$)$_{1-3}$NH$_2$, —C(O)CH(NH$_2$)(C$_{1-4}$ alkyl), —C(O)CH(NH$_2$)(CH$_2$)$_{1-2}$C(O)OH, —C(O)CH(NH$_2$) (CH$_2$)$_{2-4}$NH$_2$, or —C(O)CH(NH$_2$)(CH$_2$)$_{1-3}$C(O)NH$_2$; or
(ii) C$_{3-6}$ cycloalkyl substituted with one substituent selected from —NR$_x$(CH$_2$)$_{2-3}$NR$_y$R$_y$, —NR$_x$(methylpiperidinyl), —NR$_x$(CH$_2$)$_{2-3}$(morpholinyl), dimethylamino piperidinyl, and piperazinyl substituted with a substituent selected from C$_{1-4}$ alkyl, —C(O)CH$_3$, —(CH$_2$)$_{1-2}$OCH$_3$, —CH$_2$(methylphenyl), —(CH$_2$)$_{2-3}$(pyrrolidinyl), C$_{3-6}$ cycloalkyl, pyridinyl, and methylpiperidinyl;

R$_{7a}$ is azaspiro[3.5]nonanyl, C$_{3-6}$ cycloalkyl, diazaspiro[3.5]nonanyl, diazaspiro[5.5]undecanyl, diazepanonyl, diazepanyl, morpholinyl, phenyl, piperazinyl, piperidinyl, pyrrolidinonyl, pyrrolidinyl, or pyrrolyl, each substituted with zero to 1 substituent selected from C$_{1-3}$ alkyl, —NH$_2$, methylpiperidinyl, methylpyrrolidinyl, —OCH$_2$CH$_2$(pyrrolidinyl), and —OCH$_2$CH$_2$NHCH$_2$CH$_3$; and zero to 4 substituents selected from —CH$_3$;

R$_{7b}$ is:
(i) C$_{1-4}$ alkyl, C$_{1-3}$ hydroxyalkyl, —(CH$_2$)$_{2-3}$C≡CH, —(CH$_2$)$_{1-2}$O(C$_{1-2}$ alkyl), —(CH$_2$)$_{1-2}$S(O)$_2$(C$_{1-2}$ alkyl), —(CH$_2$)$_{0-3}$NR$_x$R$_y$, —CH$_2$C(O)NR$_x$R$_x$, —NR$_x$(C$_{1-4}$ hydroxyalkyl), —NR$_y$(C$_{1-2}$ cyanoalkyl), —NR$_x$(C$_{1-2}$ fluoroalkyl), —NR$_x$(C$_{2-4}$ hydroxyfluoroalkyl), —NR$_x$ (CH$_2$)$_{0-2}$C(O)NR$_x$R$_x$, —NR$_x$(CH$_2$)$_{1-3}$NR$_x$R$_x$, —NR$_x$CH$_2$CH$_2$NR$_x$R$_x$, —NR$_x$C(O)(CH$_2$)$_{1-2}$NR$_x$R$_x$, —O(CH$_2$)$_{1-3}$NR$_x$R$_x$, —C(O)CH$_2$NR$_x$R$_x$, —(CH$_2$)$_{1-2}$R$_{7d}$, —NHR$_{7d}$, —NH(CH$_2$)$_{1-2}$R$_{7d}$, or —OR$_{7d}$; or
(ii) azepanyl, azetidinyl, diazepanyl, dioxothiomorpholinyl, morpholinyl, oxaazaspiro[3.3]heptanyl, oxetanyl, piperazinonyl, piperazinyl, piperidinyl, pyridinyl, pyrrolidinonyl, pyrrolidinyl, or tetrahydroisoquinolinyl, each substituted with zero to 1 R$_{8a}$ and zero to 3 R$_{8b}$;

each R$_{7c}$ is independently F, Cl, —CN, C$_{1-2}$ alkyl, —CF$_3$, or —CH$_2$CN;

R$_{7d}$ is azaspiro[3.5]nonanyl, bicyclo[1.1.1]pentanyl, C$_{3-6}$ cycloalkyl, morpholinyl, oxetanyl, phenyl, piperidinyl, pyrazolyl, pyrrolidinyl, tetrahydrofuranyl, or tetrahydropyranyl, each substituted with zero to 1 substituent selected from C$_{1-3}$ alkyl, —NR$_x$R$_x$, —C(O)CH$_3$, methylpiperidinyl, methylpyrrolidinyl, tetramethylpiperidinyl, —OCH$_2$CH$_2$(pyrrolidinyl), and —OCH$_2$CH$_2$NHCH$_2$CH$_3$; and zero to 4 substituents selected from —CH$_3$;

R$_8$ is H or C$_{1-3}$ alkyl;

or R$_7$ and R$_8$ together with the nitrogen atom to which they are attached form a heterocyclic ring selected from azetidinyl, diazepanonyl, diazepanyl, diazaspiro[3.5]nonanyl, diazaspiro[5.5]undecanyl, imidazolyl, imidazolidinonyl, octahydro-1H-pyrrolo[3,4-b]pyridinyl, piperazinyl, piperidinyl, pyrrolidinonyl, pyrrolidinyl, and pyrrolyl, wherein said heterocyclic ring is substituted with zero to 1 R$_{7b}$ and zero to 2 R$_{7c}$;

R$_{8a}$ is —OH, C$_{1-6}$ alkyl, C$_{1-4}$ fluoroalkyl, C$_{1-4}$ hydroxyalkyl, —(CH$_2$)$_{1-2}$O(C$_{1-3}$ alkyl), —C(O)(C$_{1-3}$ alkyl), —(CH$_2$)$_{1-2}$ (C$_{3-6}$ cycloalkyl), —(CH$_2$)$_{1-3}$(methyl phenyl), —(CH$_2$)$_{1-3}$(pyrrolidinyl), —(CH$_2$)$_{1-3}$(methylpyrazolyl), —(CH$_2$)$_{1-3}$(thiophenyl), —NR$_x$R$_x$, C$_{3-6}$ cycloalkyl, methylpiperidinyl, pyridinyl, or pyrimidinyl;

each R$_{8b}$ is independently F, Cl, —CN, C$_{1-3}$ alkyl, or —CF$_3$;

R$_9$ is C$_{1-6}$ alkyl, C$_{1-6}$ hydroxyalkyl, C$_{1-6}$ hydroxy fluoroalkyl, C$_{1-3}$ aminoalkyl, —(CH$_2$)$_{1-2}$O(C$_{1-3}$ alkyl), —(CH$_2$)$_{1-3}$NR$_x$R$_x$, —(CH$_2$)$_{1-2}$C(O)NR$_x$R$_x$, —(CH$_2$)$_{1-3}$S (O)$_2$OH, —(CR$_x$R$_x$)$_{1-3}$NR$_x$S(O)$_2$(C$_{1-2}$ alkyl), or —(CH$_2$)$_{0-3}$R$_{9a}$;

R$_{9a}$ is C$_{3-7}$ cycloalkyl, furanyl, phenyl, piperazinyl, piperidinyl, pyrazolyl, pyridinyl, pyrrolidinyl, quinuclidinyl, thiazolyl, or octahydrocyclopenta[c]pyrrolyl, each substituted with zero to 3 substituents independently selected from F, Cl, —OH, C$_{1-4}$ alkyl, C$_{1-3}$ hydroxyalkyl, C$_{1-3}$ hydroxy fluoroalkyl, C$_{1-3}$ aminoalkyl, —NR$_y$R$_y$, oxetanyl, phenyl, piperazinyl, piperidinyl, and pyrrolidinyl;

R$_{10}$ is H, C$_{1-4}$ alkyl, —(CH$_2$)$_{1-3}$O(C$_{1-2}$ alkyl), or C$_{3-6}$ cycloalkyl;

or R$_9$ and R$_{10}$ together with the nitrogen atom to which they are attached form a heterocyclic ring selected from azabicyclo[3.1.1]heptanyl, azaspiro[5.5]undecanyl, diazabicyclo[2.2.1]heptanyl, diazabicyclo[3.1.1]heptanyl, diazabicyclo[3.2.0]heptanyl, diazaspiro[3.5]nonanyl, diazaspiro[4.4]nonanyl, diazaspiro[4.5]decanyl, diazepanyl, indolinyl, morpholinyl, octahydropyrrolo[3,4-c]pyrrolyl, piperazinonyl, piperazinyl, piperidinyl, and pyrrolidinyl, each substituted with zero to 3 R$_{10a}$;

each R$_{10a}$ is independently C$_{1-4}$ alkyl, C$_{1-4}$ hydroxyalkyl, —(CH$_2$)$_{1-3}$O(C$_{1-3}$ alkyl), —(CH$_2$)$_{1-3}$NR$_x$R$_x$, —(CH$_2$)$_{1-2}$C (O)NR$_x$R$_x$, —(CH$_2$)$_{1-2}$(methyltriazolyl), —CH$_2$CH$_2$(phenyl), —CH$_2$CH$_2$(morpholinyl), —C(O)(C$_{1-2}$ alkyl), —C(O)NR$_y$R$_y$, —C(O)CH$_2$NR$_y$R$_y$, —NR$_y$R$_y$, —NHC(O) (C$_{1-3}$ alkyl), —C(O)(furanyl), —O(piperidinyl), —C(O) CH$_2$(diethylcarbamoylpiperidinyl), methylpiperazinyl, piperidinyl, methylpiperidinyl, diethylcarbamoylpiperidinyl, isopropylpiperidinyl, pyridinyl, trifluoromethylpyridinyl, pyrimidinyl, or dihydrobenzo[d]imidazolonyl;

R$_{11}$ is azetidinyl, azaspiro[3.5]nonanyl, dioxidothiomorpholinyl, hexahydropyrrolo[3,4-c]pyrrolyl, morpholinyl, piperazinyl, piperidinyl, pyridinyl, or pyrrolidinyl, each substituted with zero to 3 substituents independently selected from halo, —CN, C$_{1-4}$ alkyl, C$_{1-3}$ aminoalkyl, —(CH$_2$)$_{1-2}$(phenyl), —C(O)CH$_2$NR$_x$R$_x$, C$_{1-5}$ hydroxyalkyl, —(CH$_2$)$_{1-2}$C(O)NR$_x$R$_x$, —(CH$_2$)$_{1-2}$S(O)$_2$(C$_{1-3}$ alkyl), —(CH$_2$)$_{1-2}$S(O)(C$_{1-3}$ alkyl), oxetanyl, tetrahydrofuranyl, and tetrahydropyranyl;

each R$_{12a}$ is independently F, Cl, —OH, C$_{1-6}$ alkyl, C$_{1-4}$ fluoroalkyl, C$_{1-4}$ cyanoalkyl, C$_{1-6}$ hydroxyalkyl, —(CH$_2$)$_{1-2}$O(C$_{1-3}$ alkyl), —(CH$_2$)$_{1-2}$C(O)NR$_x$R$_x$, —(CH$_2$)$_{1-2}$S(O)$_2$(C$_{1-2}$ alkyl), —(CH$_2$)$_{1-2}$NR$_x$HS(O)$_2$(C$_{1-2}$ alkyl), —(CH$_2$)$_{1-2}$NR$_x$R$_x$, C$_{1-3}$ alkoxy, —NR$_y$R$_y$, —NR$_x$(C$_{1-4}$ fluoroalkyl), —NR$_x$(C$_{1-2}$ cyanoalkyl), —NR$_x$CH$_2$NR$_x$R$_x$, —NR$_x$(C$_{1-4}$ hydroxyalkyl), —NR$_x$(CR$_x$R$_x$CR$_x$R$_x$)O(C$_{1-3}$ alkyl), —NR$_x$(CH$_2$C(O)NR$_x$R$_x$), —NR$_x$(C$_{1-3}$ alkoxy), —NR$_x$CH$_2$CH$_2$S(O)$_2$(C$_{1-2}$ alkyl), —NR$_x$C(O)CH$_3$, —NR$_x$C(O)(C$_{1-2}$ fluoroalkyl), —NR$_x$C(O)CR$_x$R$_x$NR$_x$R$_x$, —NR$_x$C(O)CH$_2$NR$_y$R$_y$, —NR$_x$C(O)CH$_2$NR$_x$(C$_{1-4}$ hydroxyalkyl), —NR$_x$(CH$_2$)$_{1-2}$C(O)NR$_x$R$_x$, —NR$_x$S(O)$_2$(C$_{1-2}$ alkyl), —C(O)(C$_{1-5}$ alkyl), —C(O)(CH$_2$)$_{1-3}$O(C$_{1-2}$ alkyl), —C(O)CR$_x$NRyRy, R$_{12b}$, —CR$_x$R$_x$R$_{12b}$, —C(O)R$_{12b}$, —C(O)CR$_x$R$_x$NR$_x$R$_{12b}$, —C(O)NR$_x$R$_{12b}$, —NR$_x$C(O)CR$_x$R$_x$R$_{12b}$, —NR$_x$R$_{12b}$, —NR$_x$CR$_x$R$_x$R$_{12b}$, —N(CH$_2$CN)R$_{12b}$, —NR$_x$C(O)CR$_x$R$_x$NR$_x$R$_{12b}$, —NR$_x$C(O)CR$_x$R$_x$NR$_x$CH$_2$R$_{12b}$, —NR$_x$CR$_x$R$_x$C(O)NR$_x$R$_{12b}$, or —OR$_{12b}$; or two R$_{12a}$ and the carbon atom to which they are attached form C=O;

R$_{12b}$ is azetidinyl, bicyclo[1.1.1]pentanyl, C$_{3-6}$ cycloalkyl, diazabicyclo[2.2.1]heptanyl, dioxolanyl, dioxidotetrahydrothiopyranyl, dioxidothiomorpholinyl, imidazolyl, morpholinyl, octahydrocyclopenta[c]pyrrolyl, octahydropyrrolo[3,4-c]pyrrolyl, oxaazaspiro[3.3]heptanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, Cl, —OH, C$_{1-4}$ alkyl, C$_{1-3}$ fluoroalkyl, C$_{1-3}$ hydroxyalkyl, C$_{1-4}$ aminoalkyl, C$_{1-4}$ alkoxy, —(CH$_2$)$_{1-2}$O(C$_{1-3}$ alkyl), —NR$_x$R$_x$, —C(O)NR$_x$R$_x$, and —(CR$_x$R$_x$)$_{0-1}$S(O)$_2$(C$_{1-3}$ alkyl);

each R$_{14a}$ is independently is:

(i) H, halo, —OH, C$_{1-6}$ alkyl, C$_{1-23}$ fluoroalkyl, C$_{1-4}$ hydroxyalkyl, —(CH$_2$)$_{0-2}$O(C$_{1-3}$ alkyl), —CR$_x$R$_x$NR$_y$R$_y$, —CR$_x$R$_x$NR$_x$(C$_{1-3}$ cyanoalkyl), —CR$_x$R$_x$NR$_x$((CH$_2$)$_{1-2}$O(C$_{1-2}$ alkyl)), —CR$_x$R$_x$N((CH$_2$)$_{1-2}$OCH$_3$)$_2$, —CR$_x$R$_x$NR$_x$(CH$_2$C≡CR$_x$), —CR$_x$R$_x$NR$_x$(CH$_2$)$_{1-3}$NR$_x$R$_x$, —(CR$_x$R$_x$)$_{1-3}$CR$_x$R$_x$NR$_x$R$_x$, —CR$_x$(NH$_2$)(CH$_2$)$_{1-4}$NR$_x$R$_x$, —CR$_x$R$_x$NR$_x$(CH$_2$)$_{1-2}$O(C$_{1-3}$ alkyl), —CR$_x$R$_x$NR$_x$(CH$_2$)$_{1-2}$O(CH$_2$)$_{1-2}$OH, —CR$_x$R$_x$NR$_x$(CH$_2$)$_{1-3}$S(O)$_2$OH, —CR$_x$R$_x$C(O)NR$_x$R$_x$, —NR$_x$R$_y$, —NR$_x$(CH$_2$)$_{1-3}$NR$_x$R$_x$, —NR$_x$C(O)(C$_{1-3}$ alkyl), —NR$_x$C(O)(C$_{1-3}$ fluoroalkyl), —NR$_x$C(O)O(C$_{1-3}$ alkyl), —NR$_x$C(O)(CH$_2$)$_{1-3}$NR$_x$R$_x$, —NR$_x$CH$_2$C(O)CH$_2$NR$_x$R$_x$, —C(O)(C$_{1-3}$ alkyl), —C(O)(CR$_x$R$_x$)$_{1-3}$OH, —C(O)CR$_x$R$_x$NR$_x$R$_x$, —C(O)NR$_x$R$_x$, —C(O)NR$_x$(C$_{1-2}$ cyanoalkyl), —C(O)NR$_x$(CR$_x$R$_x$)$_{1-3}$NR$_x$R$_x$, —C(O)N(CH$_2$CH$_3$)(CR$_x$R$_x$)$_{1-3}$NR$_x$R$_x$, —C(O)NR$_x$(CR$_x$R$_x$)$_{1-2}$C(O)NR$_x$R$_x$, —C(O)NR$_x$(CR$_x$R$_x$)$_{1-3}$NR$_x$C(O)(C$_{1-2}$ alkyl), —O(CR$_x$R$_x$)$_{1-3}$NR$_x$R$_x$, —S(O)$_2$NR$_x$R$_x$, or —C(O)(CR$_x$R$_x$)$_{1-2}$S(O)$_2$(C$_{1-2}$ alkyl);

(ii) 8-azabicyclo[3.2.1]octanyl, azaspiro[3.5]nonanyl, azetidinyl, benzo[c][1,2,5]oxadiazolyl, cyclopentyl, cyclohexyl, diazepanyl, morpholinyl, phenyl, piperazinyl, piperidinyl, pyrazolyl, pyridinyl, pyrrolidinonyl, quinolinyl, quinuclidinyl, tetrahydroisoquinolinyl, tetrahydropyridinyl, or thiazolidinyl, each substituted with zero to 2 substituents independently selected from C$_{1-4}$ alkyl, C$_{1-2}$ fluoroalkyl, C$_{1-4}$ hydroxyalkyl, —NR$_x$R$_x$, —(CH$_2$)$_{1-2}$NR$_x$R$_x$, —C(O)(C$_{1-2}$ alkyl), —C(O)CH$_2$NR$_x$R$_x$, —C(O)O(C$_{1-3}$ alkyl), —CH$_2$C(O)NR$_x$R$_x$, C$_{3-6}$ cycloalkyl, —CH$_2$(phenyl), —CH$_2$(pyrrolyl), —CH$_2$(morpholinyl), —CH$_2$(methylpiperazinyl), —CH$_2$(thiophenyl), methylpiperidinyl, isobutylpiperidinyl, and pyridinyl; or (iii) -L$_3$-R$_{14c}$;

each R$_{14b}$ is F, Cl, —OH, —CH$_3$, or —OCH$_3$;

R$_{14c}$ is adamantanyl, azepanyl, azetidinyl, C$_{3-7}$ cycloalkyl, diazepanyl, imidazolyl, indolyl, morpholinyl, octahydropyrrolo[3,4-c]pyrrolyl, phenyl, piperazinonyl, piperazinyl, piperidinyl, pyridinyl, pyrrolidinonyl, pyrrolidinyl, pyrrolyl, triazolyl, or tetrazolyl, each substituted with zero to 1 substituent selected from F, —OH, C$_{1-4}$ alkyl, C$_{1-3}$ hydroxyalkyl, —NR$_x$R$_y$, —NR$_x$C(O)CH$_3$, —C(O)(C$_{1-2}$ alkyl), —C(O)NR$_x$R$_x$, —C(O)N(CH$_2$CH$_3$)$_2$, —C(O)(tetrahydrofuranyl), —C(O)O(C$_{1-2}$ alkyl), —CH$_2$C(O)NR$_x$R$_y$, morpholinyl, methylpiperidinyl, pyrazinyl, pyridinyl, and pyrrolidinyl;

L$_3$ is —(CR$_x$R$_x$)$_{1-3}$—, —CH(NH$_2$)—, —CR$_x$R$_x$NR$_x$—, —C(O)—, —C(O)NR$_x$(CH$_2$)$_{0-4}$—, —NR$_x$—, —NR$_x$C(O)—, —NR$_x$CH$_2$—, —NR$_x$CH$_2$C(O)—, or —O(CH$_2$)$_{0-2}$—;

R$_v$ is H, C$_{1-2}$ alkyl, or C$_{1-2}$ fluoroalkyl;
each R$_x$ is independently H or —CH$_3$;
each R$_y$ is independently H or C$_{1-6}$ alkyl;
n is zero, 1, or 2; and
p is zero, 1, 2, 3, or 4.

The compounds of Formula (I) or salts thereof in which A is —CR$_x$R$_{12}$R$_{13}$; and R$_{12}$ and R$_{13}$ together with the carbon atom to which they are attached form a cyclic group and the cyclic group has one or more heteroatoms, the cyclic group is bonded to the indole ring by a carbon atom in the cyclic group.

One embodiment provides a compound of Formula (I) or a salt thereof wherein G is

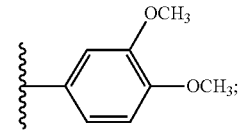 [SMILES: *c1ccc(OC)c(OC)c1]

and A, R$_1$, R$_5$, and n are defined in the first aspect or the second aspect.

One embodiment provides a compound of Formula (I) or a salt thereof wherein G is:

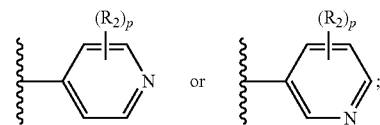

and A, R$_1$, R$_2$, R$_5$, n, and p are defined in the first aspect or the second aspect.

One embodiment provides a compound of Formula I) or a salt thereof wherein G is

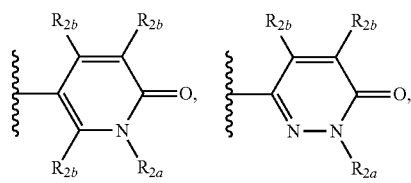

-continued

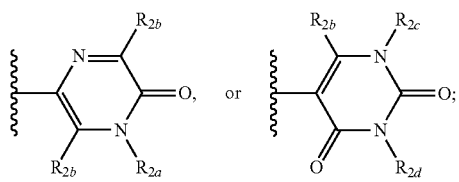

and A, $R_1$, $R_{2a}$, $R_{2b}$, $R_{2c}$, $R_{2d}$, $R_5$, n, and p are defined in the first aspect or the second aspect. Included in this embodiment are compounds in which $R_{2a}$ is $C_{1-4}$ alkyl, $C_{1-2}$ fluoroalkyl, $C_{1-4}$ hydroxyalkyl, —$(CH_2)_{1-30}CH_3$, $C_{3-6}$ cycloalkyl, —$CH_2C(O)NR_xR_x$, —$CH_2(C_{3-6}$ cycloalkyl), —$CH_2$(phenyl), tetrahydrofuranyl, or phenyl; and each $R_{2b}$ is independently H, F, Cl, —CN, —$NR_xR_x$, $C_{1-6}$ alkyl, $C_{1-2}$ fluoroalkyl, $C_{1-3}$ hydroxyalkyl, —$(CH_2)_{0-2}O(C_{1-2}$ alkyl), —$(CH_2)_{0-2}C(O)NR_xR_x$, —$(CH_2)_{1-3}$(cyclopropyl), —$C(O)O$ $(C_{1-2}$ alkyl), —$C(O)NR_x(C_{1-3}$ alkyl), —$CR_x$=$CH_2$, or —CH=CH($C_{3-6}$ cycloalkyl). Also included in this embodiment are compounds in which $R_{2a}$ is —$CH_3$; and each $R_{2b}$ is independently H, Cl, or —$CH_3$.

One embodiment provides a compound of Formula (I) or a salt thereof wherein G is a 9-membered heterocyclic ring selected from:

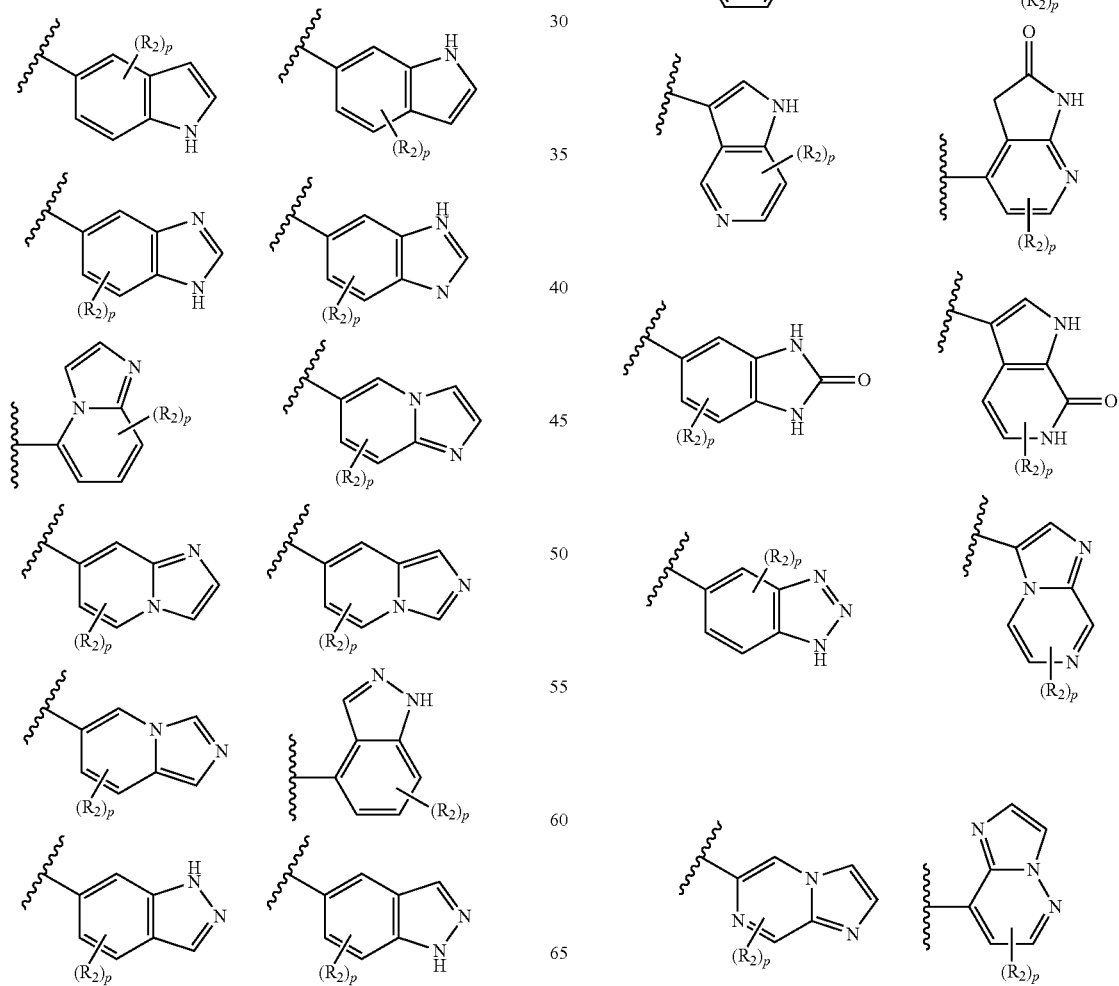

-continued
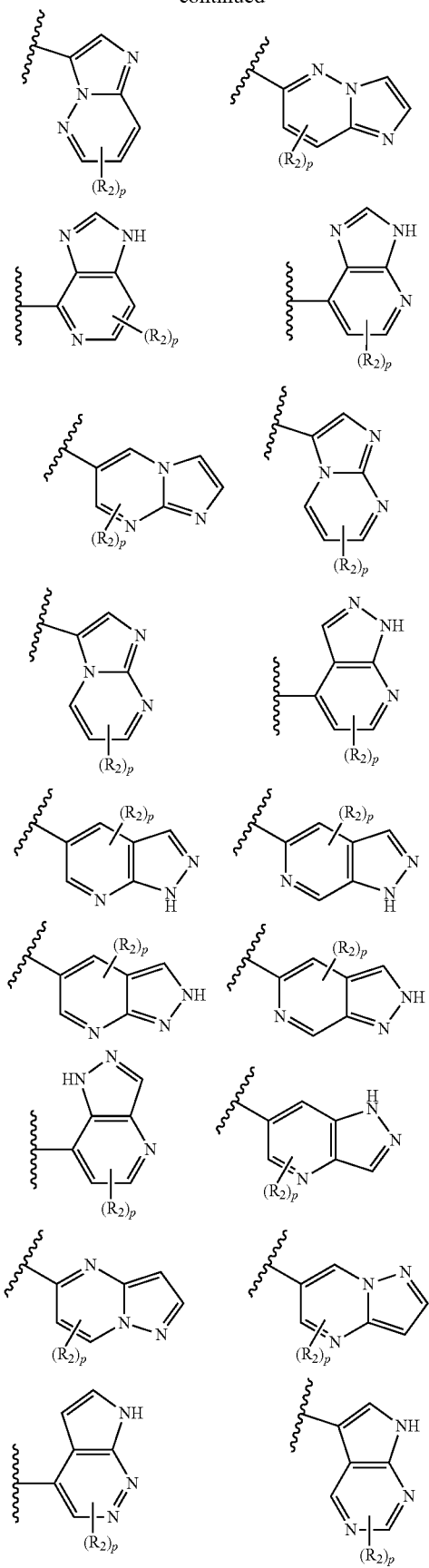
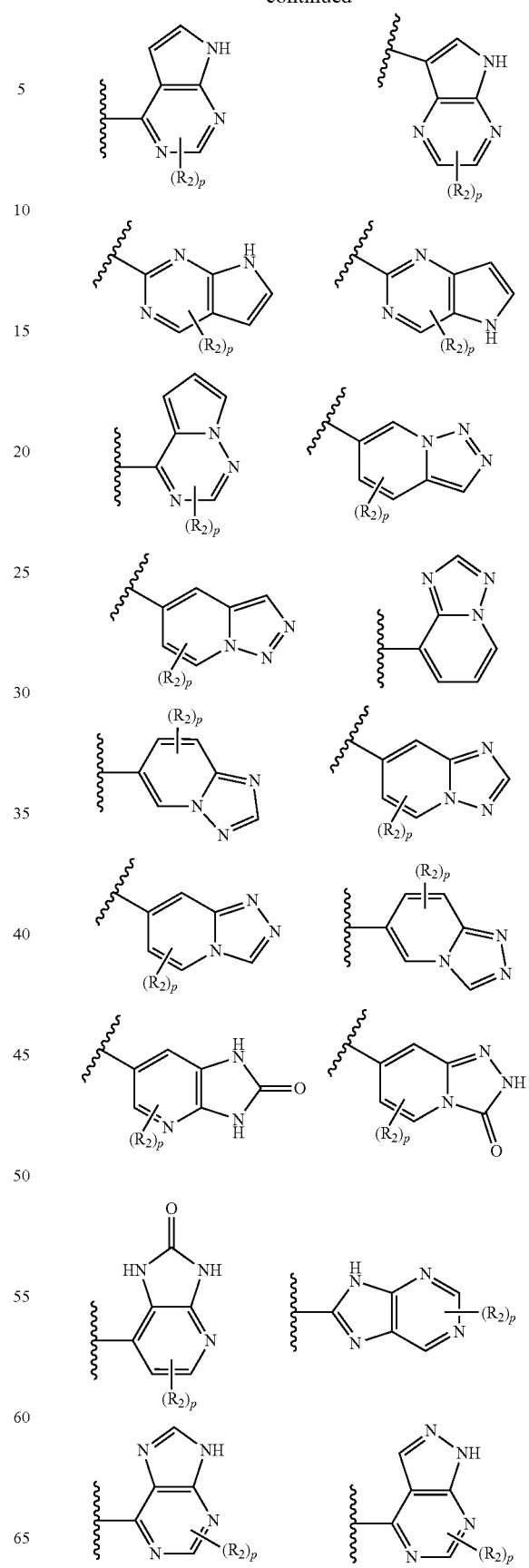

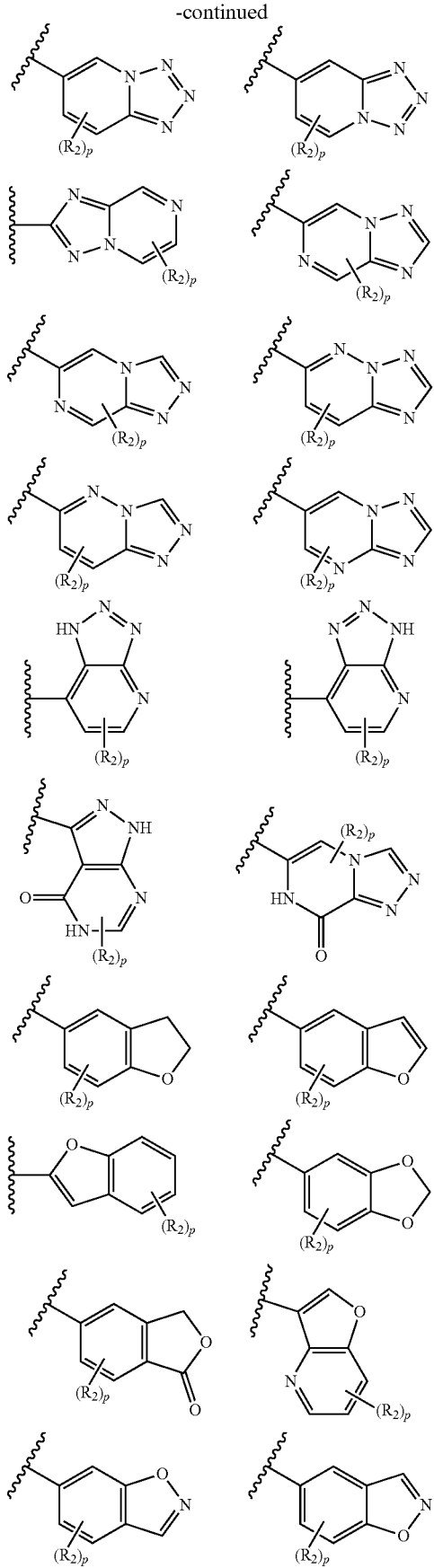
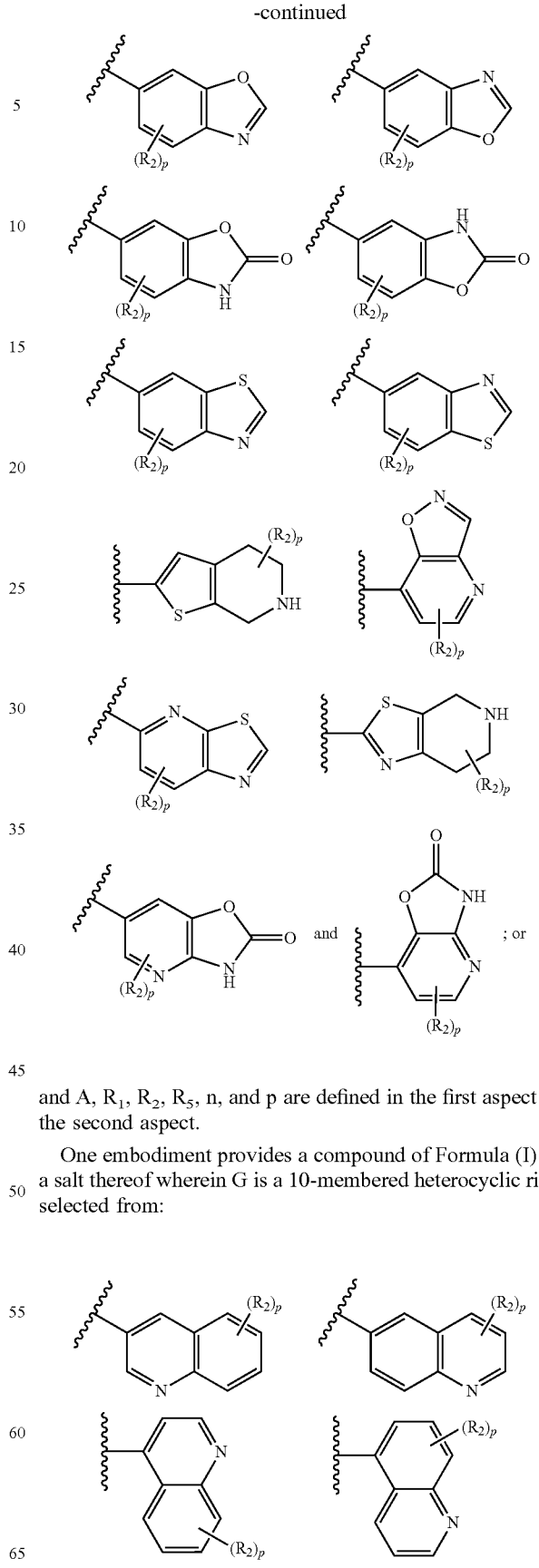
and A, $R_1$, $R_2$, $R_5$, n, and p are defined in the first aspect or the second aspect.
One embodiment provides a compound of Formula (I) or a salt thereof wherein G is a 10-membered heterocyclic ring selected from:

-continued

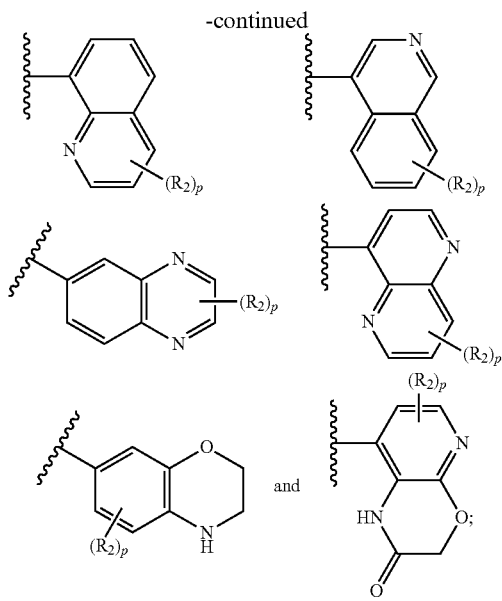

and A, R$_1$, R$_2$, R$_5$, n, and p are defined in the first aspect or the second aspect.

One embodiment provides a compound of Formula (I), N-oxide, or a salt thereof, wherein
A is:
(i) —O-L$_1$-R$_6$;
(ii) —NR$_7$R$_8$;
(iii) -L$_2$-C(O)NR$_9$R$_{10}$;
(iv) —(CR$_x$R$_x$)$_{1-2}$R$_{11}$, C$_{1-2}$ aminoalkyl, —(CR$_x$R$_x$)$_{1-2}$NR$_x$C(O)R$_{11}$, —CH$_2$NR$_x$C(O)(CH$_2$)$_{1-2}$(piperidinyl), —CH$_2$NR$_x$C(O)OCH$_2$(piperidinyl), or —CH$_2$NR$_x$C(O)(CH$_2$)$_{1-2}$NR$_x$R$_x$;
(v) —CR$_x$R$_{12}$R$_{13}$, wherein R$_{12}$ and R$_{13}$ together with the carbon atom to which they are attached form a cyclic group selected from azabicyclo[4.1.1]octanyl, azepanyl, azetidinyl, C$_{3-7}$ cycloalkyl, diazepanyl, azaspiro[3.3]heptanyl, diazaspiro[4.5]decanonyl, morpholinyl, octahydrocyclopenta[c]pyrrolyl, piperazinyl, piperidinyl, pyrrolidinyl, and quinuclidinyl, each substituted with zero to 3 R$_{12a}$;
(vi) —CR$_x$=CR$_x$(piperidinyl); or
(vii) an aromatic group selected from [1,2,4]triazolo[1,5-a]pyridinyl, imidazo[1,2-a]pyridinyl, imidazolyl, indazolyl, isoquinolinyl, oxadiazolyl, oxazolyl, phenyl, pyrazinyl, pyrazolo[3,4-b]pyridinyl, pyrazolyl, pyridazinyl, pyridinyl, pyrimidinyl, pyrrolyl, quinolinonyl, quinolinyl, quinoxalinyl, tetrahydro-[1,2,4]triazolo[1,5-a]pyrazinyl, tetrahydroimidazo[1,2-a]pyrazinyl, tetrahydroisoquinolinyl, tetrahydrothiazolo[5,4-c]pyridinyl, tetrahydrothieno[2,3-c]pyridinyl, thiadiazolyl, thiazolyl, thiooxadiazolyl, and triazolyl, each substituted with zero to 2 R$_{14a}$ and zero to 3 R$_{14b}$;
L$_1$ is bond, —(CR$_x$R$_x$)$_{1-2}$—, —CH$_2$C(O)—, —CH$_2$C(O)NR$_x$(CR$_x$R$_x$)$_{0-2}$—, —CH$_2$NR$_x$C(O)—, or —CH$_2$NR$_x$C(O)CH$_2$—;
L$_2$ is a bond or —(CR$_x$R$_x$)$_{1-2}$—;
R$_1$ is H, Cl, —CN, C$_{1-4}$ alkyl, C$_{1-2}$ fluoroalkyl, C$_{1-2}$ hydroxyalkyl, or —C(O)O(C$_{1-2}$ alkyl);
each R$_2$ is independently F, Cl, —CN, —OH, C$_{1-3}$ alkyl, C$_{1-2}$ fluoroalkyl, C$_{1-2}$ cyanoalkyl, C$_{1-3}$ hydroxyalkyl, C$_{1-2}$ aminoalkyl, —(CH$_2$)$_{0-2}$O(C$_{1-3}$ alkyl), C$_{3-6}$ cycloalkyl, —NR$_x$R$_x$, —(CH$_2$)$_{0-2}$C(O)NR$_x$R$_x$, —(CH$_2$)$_{0-2}$S(O)$_2$(C$_{1-3}$ alkyl), —CH$_2$(C$_{3-6}$ cycloalkyl), —CH$_2$(phenyl), or phenyl;
R$_{2a}$ is C$_{1-4}$ alkyl, C$_{1-2}$ fluoroalkyl, C$_{1-4}$ hydroxyalkyl, —(CH$_2$)$_{1-3}$OCH$_3$, C$_{3-6}$ cycloalkyl, —CH$_2$C(O)NR$_x$R$_x$, —CH$_2$(C$_{3-6}$ cycloalkyl), —CH$_2$(phenyl), tetrahydrofuranyl, or phenyl;
each R$_{2b}$ is independently H, F, Cl, —CN, —NR$_x$R$_x$, C$_{1-6}$ alkyl, C$_{1-2}$ fluoroalkyl, C$_{1-3}$ hydroxyalkyl, —(CH$_2$)$_{0-2}$O(C$_{1-2}$ alkyl), —(CH$_2$)$_{0-2}$C(O)NR$_x$R$_x$, —(CH$_2$)$_{1-3}$(cyclopropyl), —C(O)O(C$_{1-2}$ alkyl), —C(O)NR$_x$(C$_{1-3}$ alkyl), —CR$_x$=CH$_2$, or —CH=CH(C$_{3-6}$ cycloalkyl);
each R$_5$ is independently F, Cl, —CN, C$_{1-2}$ alkyl, or —OCH$_3$;
R$_6$ is:
(i) C$_{1-2}$ alkyl, —CH$_2$C(O)NHCH$_2$CR$_x$R$_x$OH, —CH$_2$C(O)NHCH$_2$CH$_2$CR$_x$R$_x$OH, —CH$_2$C(O)NHCH$_2$CH$_2$NR$_x$R$_x$, or —CH$_2$C(O)NHCH$_2$CHFCR$_x$R$_x$OH; or
(ii) azabicyclo[3.2.1]octanyl, azaspiro[5.5]undecanyl, azetidinyl, C$_{3-6}$ cycloalkyl, diazabicyclo[2.2.1]heptanyl, diazaspiro[3.5]nonanyl, morpholinyl, tetrahydropyranyl, octahydrocyclopenta[c]pyrrolyl, piperazinyl, piperidinyl, pyrrolidinyl, or quinuclidinyl, each substituted with zero to 3 R$_{6a}$;
each R$_{6a}$ is independently F, —OH, C$_{1-4}$ alkyl, C$_{1-4}$ fluoroalkyl, C$_{1-4}$ hydroxyalkyl, —(CH$_2$)$_{1-2}$OCH$_3$, —NR$_x$R$_x$, —N(C$_{2-3}$ alkyl)$_2$, —(CH$_2$)$_{1-2}$NR$_x$R$_x$, —(CH$_2$)$_{1-2}$S(O)$_2$(C$_{1-2}$ alkyl), —(CH$_2$)$_{1-2}$C(O)NR$_x$R$_x$, —C(O)CH$_2$NR$_x$R$_x$, oxetanyl, tetrahydrofuranyl, tetrahydropyranyl, piperidinyl, isobutylpiperidinyl, piperazinyl, or —O(piperidinyl);
R$_7$ is:
(i) R$_{7a}$, —CH$_2$R$_{7a}$, —(CH$_2$)$_{1-2}$NR$_x$R$_x$, —(CH$_2$)$_{1-2}$NR$_x$C(O)CH$_2$NR$_x$R$_x$, —C(O)R$_{7a}$, —C(O)CH(NH$_2$)R$_{7a}$, —C(O)(CH$_2$)$_{1-3}$NH$_2$, —C(O)CH(NH$_2$)(C$_{1-4}$ alkyl), —C(O)CH(NH$_2$)(CH$_2$)$_{1-2}$C(O)OH, —C(O)CH(NH$_2$)(CH$_2$)$_{2-4}$NH$_2$, or —C(O)CH(NH$_2$)(CH$_2$)$_{1-3}$C(O)NH$_2$; or
(ii) C$_{3-6}$ cycloalkyl substituted with one substituent selected from —NR$_x$(CH$_2$)$_{2-3}$NR$_x$R$_x$, —NH(CH$_2$)$_{2-3}$NHCH$_3$, —NH(methylpiperidinyl), —NH(CH$_2$)$_{2-3}$(morpholinyl), dimethylamino piperidinyl, and piperazinyl substituted with a substituent selected from C$_{1-4}$ alkyl, —C(O)CH$_3$, —(CH$_2$)$_{1-2}$OCH$_3$, —CH$_2$(methylphenyl), —(CH$_2$)$_{2-3}$(pyrrolidinyl), C$_{3-6}$ cycloalkyl, pyridinyl, and methylpiperidinyl;
R$_{7b}$ is:
(i) —OH, C$_{1-6}$ alkyl, C$_{1-4}$ fluoroalkyl, C$_{1-4}$ hydroxyalkyl, C$_{1-2}$ aminoalkyl, —(CH$_2$)$_{2-3}$C≡CH, —(CR$_x$R$_x$)$_{1-2}$O(C$_{1-2}$ alkyl), —(CH$_2$)$_{1-3}$S(O)$_2$(C$_{1-2}$ alkyl), —(CH$_2$)$_{0-3}$NR$_x$R$_y$, —(CH$_2$)$_{1-2}$C(O)NR$_x$R$_x$, —NR$_x$R$_y$, —NR$_x$(C$_{1-4}$ hydroxyalkyl), —NR$_y$(C$_{1-2}$ cyanoalkyl), —N(C$_{1-2}$ cyanoalkyl)$_2$, —NR$_x$(C$_{1-2}$ fluoroalkyl), —NR$_x$(C$_{2-4}$ hydroxyfluoroalkyl), —(CR$_x$R$_x$)$_{1-2}$C(O)NR$_x$R$_x$, —NR$_x$(CH$_2$)$_{1-2}$C(O)NR$_x$R$_x$, —N((CH$_2$)$_{1-2}$C(O)NR$_x$R$_x$)$_2$, —NR$_x$(CH$_2$)$_{1-2}$S(O)$_2$(C$_{1-2}$ alkyl), —NR$_x$(CH$_2$)$_{1-3}$NR$_x$R$_x$, —NR$_x$CH$_2$CH$_2$NR$_x$R$_x$, —NR$_x$C(O)(CH$_2$)$_{1-2}$NR$_x$R$_x$, —NR$_x$(CH$_2$CH$_2$S(O)$_2$CH$_3$), —(CH$_2$)$_{1-2}$NR$_x$C(O)(CH$_2$)$_{1-2}$NR$_x$R$_x$, —O(CH$_2$)$_{1-3}$NR$_x$R$_x$, —C(O)(CR$_x$R$_x$)$_{1-2}$NR$_y$R$_y$, —C(O)(CR$_x$R$_x$)$_{1-2}$NR$_y$(C$_{1-4}$ hydroxyalkyl), —C(O)(CR$_x$R$_x$)$_{1-2}$NR$_x$(CH$_2$CH$_2$OCH$_3$), —S(O)$_2$CH$_2$CH$_2$N(CH$_3$)$_2$, —(CH$_2$)$_{1-2}$R$_{7d}$, —NR$_x$R$_{7d}$, —NR$_x$(CH$_2$)$_{1-2}$R$_{7d}$), —NR$_{7d}$R$_{7d}$, —N((CH$_2$)$_{1-2}$R$_{7d}$)$_2$, —OR$_{7d}$, —C(O)R$_{7d}$, —C(O)(CR$_x$R$_x$)$_{1-2}$R$_{7d}$, or —C(O)(CR$_x$R$_x$)$_{1-2}$NR$_x$R$_{7d}$;
or
(ii) azepanyl, azetidinyl, C$_{3-6}$ cycloalkyl, diazepanyl, dioxotetrahydrothiopyranyl, dioxothiomorpholinyl, morpholinyl, oxaazaspiro[3.3]heptanyl, oxaazaspiro[4.3]octanyl, oxetanyl, piperazinonyl, piperazinyl, piperidinyl, pyridinyl, pyrimidinyl, pyrrolidinonyl, pyrrolidinyl, tetrahydrofuranyl, tetrahydroisoquinolinyl, tetrahydropyranyl, or thiadiazolyl, each substituted with zero to 1 $R_{8a}$ and zero to 3 $R_{8b}$;

each $R_{7c}$ is independently F, —$CH_3$ or —$CH_2CN$;

$R_{7d}$ is azaspiro[3.5]nonanyl, azetidinyl, bicyclo[1.1.1]pentanyl, $C_{3-6}$ cycloalkyl, dioxothiaazaspiro[3.3]heptanyl, morpholinyl, oxaazaspiro[3.3]heptanyl, oxaazaspiro[4.3]octanyl, oxaazaspiro[4.4]nonyl, oxetanyl, phenyl, piperidinyl, pyrazolyl, pyrrolidinyl, tetrahydrofuranyl, tetrahydropyranyl, thiadiazolyl, or triazolyl, each substituted with zero to 2 substituents independently selected from F, —OH, $C_{1-3}$ alkyl, $C_{1-2}$ hydroxyalkyl, $C_{1-2}$ alkoxy, —$NR_xR_x$, —$C(O)CH_3$, —$S(O)_2CH_3$, methylpiperidinyl, methylpyrrolidinyl, tetramethylpiperidinyl, —$OCH_2CH_2$(pyrrolidinyl), and —$OCH_2CH_2NHCH_2CH_3$; and zero to 4 substituents selected from —$CH_3$;

$R_8$ is H or $C_{1-2}$ alkyl;

or $R_7$ and $R_8$ together with the nitrogen atom to which they are attached form a heterocyclic ring selected from azetidinyl, diazabicyclo[2.2.1]heptanyl, diazabicyclo[2.2.2]octanyl, diazabicyclo[3.1.1]heptanyl, diazabicyclo[3.2.1]octanyl, azaspiro[3.3]heptanyl, diazaspiro[2.5]octanyl, diazaspiro[3.3]heptanyl, diazepanonyl, diazepanyl, diazaspiro[3.5]nonanyl, diazaspiro[5.5]undecanyl, imidazolyl, imidazolidinonyl, octahydro-1H-pyrrolo[3,4-b]pyridinyl, oxadiazabicyclo[3.3.1]nonanyl, piperazinyl, piperazinonyl, piperidinyl, pyrrolidinonyl, pyrrolidinyl, and pyrrolyl, wherein said heterocyclic ring is substituted with zero to 1 $R_{7b}$ and zero to 2 $R_{7c}$;

$R_{8a}$ is —OH, $C_{1-4}$ alkyl, $C_{1-3}$ fluoroalkyl, —$(CH_2)_{1-2}O(C_{1-2}$ alkyl), $C_{1-2}$ alkoxy, —$C(O)(C_{1-2}$ alkyl), —$C(O)O(C_{1-2}$ alkyl), —$CH_2(C_{3-6}$ cycloalkyl), —$(CH_2)_{1-2}$(methyl phenyl), —$(CH_2)_{1-3}$(pyrrolidinyl), —$(CH_2)_{1-2}$(methylpyrazolyl), —$(CH_2)_{1-2}$(thiophenyl), —$NR_xR_x$, $C_{3-6}$ cycloalkyl, methylpiperidinyl, or pyridinyl;

each $R_{8b}$ is independently F or —$CH_3$;

$R_9$ is $C_{1-3}$ alkyl, $C_{1-3}$ fluoroalkyl, $C_{1-5}$ hydroxyalkyl, $C_{2-5}$ hydroxy fluoroalkyl, $C_{1-2}$ aminoalkyl, —$(CH_2)_{1-2}O(C_{1-2}$ alkyl), —$(CH_2)_{1-3}N(CH_3)_2$, —$(CH_2)_{1-2}C(O)NH_2$, —$(CH_2)_{1-2}S(O)_2OH$, —$(CH_2)_{1-2}CR_xR_xNHS(O)_2CH_3$, or —$(CH_2)_{0-3}R_{9a}$;

$R_{9a}$ is $C_{5-7}$ cycloalkyl, furanyl, phenyl, piperazinyl, piperidinyl, pyridinyl, pyrrolidinyl, quinuclidinyl, thiazolyl, or octahydrocyclopenta[c]pyrrolyl, each substituted with zero to 2 substituents independently selected from —OH, $C_{1-3}$ alkyl, —$NR_xR_x$, oxetanyl, phenyl, piperazinyl, piperidinyl, and pyrrolidinyl;

$R_{10}$ is H, $C_{1-3}$ alkyl, —$(CH_2)_{1-2}O(C_{1-2}$ alkyl), or $C_{3-6}$ cycloalkyl;

or $R_9$ and $R_{10}$ together with the nitrogen atom to which they are attached form a heterocyclic ring selected from azabicyclo[3.1.1]heptanyl, azaspiro[5.5]undecanyl, diazabicyclo[2.2.1]heptanyl, diazabicyclo[3.1.1]heptanyl, diazabicyclo[3.2.0]heptanyl, diazaspiro[3.5]nonanyl, diazaspiro[4.4]nonanyl, diazaspiro[4.5]decanyl, diazepanyl, indolinyl, morpholinyl, octahydropyrrolo[3,4-c]pyrrolyl, piperazinonyl, piperazinyl, piperidinyl, and pyrrolidinyl, each substituted with zero to 3 $R_{10a}$;

each $R_{10a}$ is independently $C_{1-3}$ alkyl, $C_{1-3}$ hydroxyalkyl, —$(CH_2)_{1-2}O(C_{1-2}$ alkyl), —$(CH_2)_{1-2}NR_xR_x$, —$CH_2C(O)NR_xR_x$, —$CH_2$(methyltriazolyl), —$CH_2CH_2$(phenyl), —$CH_2CH_2$(morpholinyl), —$C(O)(C_{1-2}$ alkyl), —$C(O)NH_2$, —$C(O)N(C_{1-2}$ alkyl)$_2$, —$C(O)CH_2NR_xR_x$, —$NR_xR_x$, —$NHC(O)(C_{1-2}$ alkyl), —$C(O)$(furanyl), —O(piperidinyl), —$C(O)CH_2$(diethylcarbamoylpiperidinyl), methylpiperazinyl, piperidinyl, methylpiperidinyl, diethylcarbamoylpiperidinyl, isopropylpiperidinyl, pyridinyl, trifluoromethylpyridinyl, pyrimidinyl, or dihydrobenzo[d]imidazolonyl;

$R_{11}$ is azetidinyl, azaspiro[3.5]nonanyl, dioxidothiomorpholinyl, hexahydropyrrolo[3,4-c]pyrrolyl, morpholinyl, piperazinyl, piperidinyl, pyridinyl, or pyrrolidinyl, each substituted with zero to 3 substituents independently selected from F, Cl, —CN, $C_{1-3}$ alkyl, $C_{1-2}$ aminoalkyl, —$CH_2$(methyloxetanyl), —$CH_2$(triazolyl), —$CH_2$(phenyl), —$C(O)CH_2NR_xR_x$, —$CH_2CR_xR_xOH$, —$CH_2C(O)NR_xR_x$, —$CH_2CH_2S(O)_2(C_{1-3}$ alkyl), —$CH_2CH_2S(O)(C_{1-3}$ alkyl), oxetanyl, tetrahydrofuranyl, and tetrahydropyranyl;

each $R_{12a}$ is independently —OH, $C_{1-4}$ alkyl, $C_{1-3}$ fluoroalkyl, $C_{1-2}$ cyanoalkyl, $C_{1-4}$ hydroxyalkyl, —$(CH_2)_{1-2}O(C_{1-2}$ alkyl), —$CH_2C(O)NR_xR_x$, —$(CH_2)_{1-2}S(O)_2(C_{1-2}$ alkyl), —$(CH_2)_{1-2}NHS(O)_2(C_{1-2}$ alkyl), —$(CH_2)_{1-2}NR_xR_x$, $C_{1-2}$ alkoxy, —$NR_yR_y$, —$NR_x(C_{1-3}$ fluoroalkyl), —$NR_x(CH_2CR_xR_x)OCH_3)$, —$NR_x(C_{1-2}$ cyanoalkyl), —$NR_xCH_2NR_xR_x$, —$NR_x(C_{1-4}$ hydroxyalkyl), —$NR_x(CH_2C(O)NH_2)$, —$NR_x(OCH_3)$, —$NR_xCH_2CH_2S(O)_2(C_{1-2}$ alkyl), —$NR_x(CH_2CR_xR_x)OCH_3)$, —$NR_xC(O)CH_3$, —$NR_xC(O)(C_{1-4}$ fluoroalkyl), —$NR_xC(O)CR_xR$—$NR_xC(O)CH_2NR_yR_y$, —$NR_xC(O)CH_2NR_x(C_{1-4}$ hydroxyalkyl), —$NR_xCH_2C(O)NR_xR_x$, —$NR_xS(O)_2CH_3$, —$C(O)(C_{1-5}$ alkyl), —$C(O)CH_2O(C_{1-2}$ alkyl), —$C(O)CH_2CH_2O(C_{1-2}$ alkyl), —$C(O)(CH_2)_{1-2}NR_xR_x$, —$C(O)CHR_xNR_yR_y$, $R_{12b}$, —$CR_xR_xR_{12b}$, —$C(O)R_{12b}$, —$C(O)CH_2NR_xR_{12b}$, —$C(O)NR_xR_{12b}$, —$NR_xC(O)CR_xR_xR_{12b}$, —$NR_xR_{12b}$, —$NR_xCR_xR_xR_{12b}$, —$N(CH_2CN)R_{12b}$, —$NR_xC(O)CH_2NR_xR_{12b}$, —$NR_xC(O)CH_2NR_xCH_2R_{12b}$, —$NR_xCH_2C(O)NR_xR_{12b}$, or —$OR_{12b}$; or two $R_{12a}$ and the carbon atom to which they are attached form C=O;

$R_{12b}$ is azetidinyl, bicyclo[1.1.1]pentanyl, $C_{3-6}$ cycloalkyl, diazabicyclo[2.2.1]heptanyl, dioxolanyl, dioxothiaazaspiro[3.3]heptanyl, dioxidotetrahydrothiopyranyl, dioxidothiomorpholinyl, imidazolyl, morpholinyl, octahydrocyclopenta[c]pyrrolyl, octahydropyrrolo[3,4-c]pyrrolyl, oxaazaspiro[3.3]heptanyl, oxaazaspiro[4.3]octanyl, oxaazaspiro[4.4]nonanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, Cl, —OH, $C_{1-3}$ alkyl, $C_{1-2}$ hydroxyalkyl, $C_{1-2}$ alkoxy, —$(CH_2)_{1-2}O(C_{1-2}$ alkyl), —$NR_xR_x$, —$C(O)NR_xR_x$, —$S(O)_2(C_{1-2}$ alkyl), and —$CH_2S(O)_2(C_{1-2}$ alkyl);

each $R_{14a}$ is independently:
(i) H, F, Cl, —OH, $C_{1-5}$ alkyl, $C_{1-2}$ fluoroalkyl, $C_{1-2}$ hydroxyalkyl, —$(CH_2)_{0-2}OCH_3$, —$CHR_xNR_x(C_{1-5}$ alkyl), —$CHR_xNR_x(C_{1-2}$ cyanoalkyl), —$CHR_xNR_x((CH_2)_{1-2}OCH_3)$, —$CHR_xN((CH_2)_{1-2}OCH_3)_2$, —$CH_2NR_x(CH_2C\equiv CR_x)$, —$CH_2NR_xCH_2CH_2NR_xR_x$, —$(CH_2)_{1-3}CR_xR_xNR_xR_x$, —$CH(NH_2)(CH_2)_{3-4}NR_xR_x$, —$CH_2NR_x(CH_2)_{1-2}O(C_{1-3}$ alkyl), —$CH_2NR_x(CH_2)_{1-2}O(CH_2)_{1-2}OH$, —$CH_2NH(CH_2)_{1-2}S(O)_2OH$, —$CH_2C(O)NR_xR_x$, —$NR_xR_y$, —$NR_x(CH_2)_{2-3}NR_xR_x$, —$NR_xC(O)(C_{1-2}$ alkyl), —$NR_xC(O)(C_{1-2}$ fluoroalkyl), —$NR_xC(O)O(C_{1-3}$ alkyl), —$NR_xC(O)(CH_2)_{1-2}NR_xR_x$, —$NR_xCH_2C(O)CH_2NR_xR_x$, —$C(O)(C_{1-2}$ alkyl), —$C(O)CH_2CR_xR_xOH$, —$C(O)CH_2NR_xR_x$, —$C(O)NR_xR_x$, —$C(O)NR_x(CH_2CN)$, —$C(O)NR_x(CR_xR_x)_{2-3}NR_xR_x$, —$C(O)N(CH_2CH_3)(CR_xR_x)_{2-3}NR_xR_x$, —$C(O)NR_xCH_2C(O)NR_xR_x$, —$C(O)$ NR$_x$CH$_2$CH$_2$NR$_x$C(O)CH$_3$, —O(CR$_x$R$_x$)$_{2-3}$NR$_x$R$_x$, —S(O)$_2$NR$_x$R$_x$, or —C(O)CH$_2$S(O)$_2$(Cl-2 alkyl);

(ii) 8-azabicyclo[3.2.1]octanyl, azaspiro[3.5]nonanyl, azetidinyl, benzo[c][1,2,5]oxadiazolyl, cyclopentyl, cyclohexyl, diazepanyl, morpholinyl, phenyl, piperazinyl, piperidinyl, pyrazolyl, pyridinyl, pyrrolidinonyl, quinolinyl, quinuclidinyl, tetrahydroisoquinolinyl, tetrahydropyridinyl, or thiazolidinyl, each substituted with zero to 2 substituents independently selected from C$_{1-4}$ alkyl, C$_{1-2}$ fluoroalkyl, C$_{1-4}$ hydroxyalkyl, —NR$_x$R$_x$, —(CH$_2$)$_{1-2}$NR$_x$R$_x$, —C(O)(C$_{1-2}$ alkyl), —C(O)CH$_2$NR$_x$R$_x$, —C(O)O(C$_{1-3}$ alkyl), —CH$_2$C(O)NR$_x$R$_x$, C$_{3-6}$ cycloalkyl, —CH$_2$(phenyl), —CH$_2$(pyrrolyl), —CH$_2$(morpholinyl), —CH$_2$(methylpiperazinyl), —CH$_2$(thiophenyl), methylpiperidinyl, isobutylpiperidinyl, and pyridinyl; or (iii) -L$_3$-R$_{14c}$;

each R$_{14b}$ is F, —CH$_3$, or —OCH$_3$;

L$_3$ is —(CR$_x$R$_x$)$_{1-3}$—, —CH(NH$_2$)—, —CR$_x$R$_x$NH—, —C(O)—, —C(O)NR$_x$(CH$_2$)$_{0-4}$—, —NR$_x$—, —NR$_x$C(O)—, —NR$_x$CH$_2$—, —NR$_x$CH$_2$C(O)—, —O—, or —O(CH$_2$)$_{1-2}$—; and R$_{14c}$ is adamantanyl, azetidinyl, C$_{3-6}$ cycloalkyl, diazepanyl, imidazolyl, indolyl, morpholinyl, octahydropyrrolo[3,4-c]pyrrolyl, phenyl, piperazinonyl, piperazinyl, piperidinyl, pyridinyl, pyrrolidinonyl, pyrrolidinyl, or tetrazolyl, each substituted with zero to 1 substituent selected from F, —OH, C$_{1-4}$ alkyl, C$_{1-3}$ hydroxyalkyl, —NR$_x$R$_y$, —NR$_x$C(O)CH$_3$, —C(O)(C$_{1-2}$ alkyl), —C(O)NR$_x$R$_x$, —C(O)N(CH$_2$CH$_3$)$_2$, —C(O)(tetrahydrofuranyl), —C(O)O(C$_{1-2}$ alkyl), —CH$_2$C(O)NR$_x$R$_y$, morpholinyl, methylpiperidinyl, pyrazinyl, pyridinyl, and pyrrolidinyl;

and G, n, and p is defined in the first aspect or the second aspect.

One embodiment provides a compound of Formula (I), N-oxide, or a salt thereof, wherein:

A is:
(i) —O-L$_1$-R$_6$;
(ii) —NR$_7$R$_8$;
(iii) -L$_2$-C(O)NR$_9$R$_{10}$;
(iv) —CHR$_x$R$_{11}$, —CH$_2$CH$_2$R$_{11}$, —CH$_2$NH$_2$, —CH$_2$NHC(O)R$_{11}$, —CH$_2$NHC(O)CH$_2$CH$_2$(piperidinyl), —CH$_2$NHC(O)OCH$_2$(piperidinyl), or —CH$_2$NHC(O)CH$_2$N(CH$_3$)$_2$;
(v) —CHR$_{12}$R$_{13}$, wherein R$_{12}$ and R$_{13}$ together with the carbon atom to which they are attached form a cyclic group selected from azabicyclo[4.1.1]octanyl, azepanyl, azetidinyl, C$_{3-6}$ cycloalkyl, azaspiro[3.3]heptanyl, diazaspiro[4.5]decanonyl, morpholinyl, octahydrocyclopenta[c]pyrrolyl, piperidinyl, pyrrolidinyl, and quinuclidinyl, each substituted with zero to 3 R$_{12a}$;
(vi) —CH═CH(piperidinyl); or
(vii) an aromatic group selected from [1,2,4]triazolo[1,5-a]pyridinyl, imidazo[1,2-a]pyridinyl, imidazolyl, indazolyl, isoquinolinyl, oxadiazolyl, oxazolyl, phenyl, pyrazinyl, pyrazolo[3,4-b]pyridinyl, pyrazolyl, pyridazinyl, pyridinyl, pyrimidinyl, pyrrolyl, quinolinonyl, quinolinyl, quinoxalinyl, tetrahydro-[1,2,4]triazolo[1,5-a]pyrazinyl, tetrahydroimidazo[1,2-a]pyrazinyl, tetrahydroisoquinolinyl, tetrahydrothiazolo[5,4-c]pyridinyl, tetrahydrothieno[2,3-c]pyridinyl, thiadiazolyl, thiazolyl, thiooxadiazolyl, and triazolyl, each substituted with zero to 2 R$_{14a}$ and zero to 3 R$_{14b}$;

L$_1$ is bond, —CH$_2$—, —CH$_2$CH$_2$—, —CH$_2$C(O)—, —CH$_2$C(O)NH—, —CH$_2$C(O)N(CH$_3$)—, —CH$_2$C(O)NHCH$_2$—, or —CH$_2$C(O)NHCH$_2$CH$_2$—;

L$_2$ is a bond, —CH(CH$_3$)—, —C(CH$_3$)$_2$—, or —CH$_2$CH$_2$—;

each R$_5$ is independently F, Cl, —CN, C$_{1-2}$ alkyl, or —OCH$_3$;

R$_6$ is:
(i) —CH$_3$, —CH$_2$C(O)NHCH$_2$C(CH$_3$)$_2$OH, —CH$_2$C(O)NHCH$_2$CH$_2$C(CH$_3$)$_2$OH, —CH$_2$C(O)NHCH$_2$CH$_2$NH$_2$, or —CH$_2$C(O)NHCH$_2$CHFC(CH$_3$)$_2$OH; or
(ii) azabicyclo[3.2.1]octanyl, azaspiro[5.5]undecanyl, azetidinyl, cyclohexyl, diazabicyclo[2.2.1]heptanyl, diazaspiro[3.5]nonanyl, morpholinyl, octahydrocyclopenta[c]pyrrolyl, piperazinyl, piperidinyl, pyrrolidinyl, or quinuclidinyl, each substituted with zero to 2 R$_{6a}$;

each R$_{6a}$ is independently F, —OH, —CH$_3$, —CH$_2$CH$_2$CH$_3$, —C(CH$_3$)$_2$, —CH$_2$CH(CH$_3$)$_2$, —CH$_2$CH$_2$CH$_2$CF$_3$, —CH$_2$CH$_2$OH, —CH$_2$CH$_2$CH$_2$OH, —CH$_2$CH(CH$_3$)OH, —CH$_2$C(CH$_3$)$_2$OH, —CH$_2$CH$_2$OCH$_3$, —NH$_2$, —N(CH$_3$)$_2$, —N(CH$_2$CH$_3$)$_2$, —CH$_2$NH$_2$, —CH$_2$CH$_2$NH$_2$, —CH$_2$CH$_2$S(O)$_2$CH$_3$, —CH$_2$C(O)N(CH$_3$)$_2$, —C(O)CH$_2$N(CH$_3$)$_2$, oxetanyl, tetrahydropyranyl, piperidinyl, isobutylpiperidinyl, or —O(piperidinyl);

R$_7$ is:
(i) —CH$_2$CH$_2$NH$_2$, —CH$_2$CH$_2$NHC(O)CH$_2$N(CH$_3$)$_2$, —CH$_2$(isopropyl azaspiro[3.5]nonanyl), —CH$_2$(methylpyrrolidinyl), —C(O)(CH$_2$)$_{1-3}$NH$_2$, —C(O)CH(NH$_2$)CH$_2$CH$_2$CH$_3$, —C(O)CH(NH$_2$)CH$_2$CH(CH$_3$)$_2$, —C(O)CH(NH$_2$)CH(CH$_3$)CH$_2$CH$_3$, —C(O)CH(NH$_2$)CH$_2$CH$_2$C(O)OH, —C(O)CH(NH$_2$)(CH$_2$)$_{3-4}$NH$_2$, —C(O)CH(NH$_2$)(CH$_2$)$_{12}$C(O)NH$_2$, —C(O)CH(NH$_2$)(cyclohexyl), —C(O)CH(NH$_2$)(phenyl), —C(O)(aminocyclohexyl), —C(O)(morpholinyl), —C(O)(pyrrolidinyl), pentamethylpiperidinyl, methylpiperidinyl-piperidinyl, methylpyrrolidinyl-pyrrolidinyl, or phenyl substituted with —OCH$_2$CH$_2$(pyrrolidinyl) or —OCH$_2$CH$_2$NHCH$_2$CH$_3$; or
(ii) cyclohexyl substituted with —NR$_x$(CH$_2$)$_{2-3}$N(CH$_3$)$_2$, —NHCH$_2$CH$_2$NHCH$_3$, —NH(methylpiperidinyl), —NH(CH$_2$)$_{2-3}$(morpholinyl), dimethylamino piperidinyl, or piperazinyl substituted with —CH$_3$, —CH$_2$CH$_3$, —C(CH$_3$)$_3$, —CH$_2$CH(CH$_3$)$_2$, —C(O)CH$_3$, —CH$_2$CH$_2$OCH$_3$, —CH$_2$(methylphenyl), —(CH$_2$)$_{2-3}$(pyrrolidinyl), cyclopentyl, pyridinyl, or methylpiperidinyl;

R$_{7b}$ is:
(i) —OH, C$_{1-6}$ alkyl, C$_{3-4}$ fluoroalkyl, C$_{3-4}$ hydroxyalkyl, —CH$_2$CN, —CH$_2$CH$_2$CN, —CH$_2$CH$_2$CH$_2$C≡CH, —(CR$_x$R$_x$)$_{1-2}$OCH$_3$, —(CH$_2$)$_{2-3}$S(O)$_2$CH$_3$, —(CH$_2$)$_{1-2}$NR$_x$R$_x$, —(CH$_2$)$_{1-2}$C(O)NR$_x$R$_x$, —NR$_x$R$_y$, —NR$_x$(C$_{1-4}$ hydroxyalkyl), —NH(CH$_2$CH$_2$OCH$_3$), —NR$_y$(C$_{1-2}$ cyanoalkyl), —N(CH$_2$CH$_2$CN)$_2$, —NR$_x$(C$_{1-2}$ fluoroalkyl), —NR$_x$(C$_{2-4}$ hydroxyfluoroalkyl), —(CH$_2$)$_{1-2}$C(O)NR$_x$R$_x$, —NR$_x$(CH$_2$)$_{1-2}$C(O)NR$_x$R$_x$, —N((CH$_2$)$_{1-2}$C(O)NR$_x$R$_x$)$_2$, —NR$_x$(CH$_2$)$_{1-2}$S(O)$_2$(C$_{1-2}$ alkyl), —NR$_x$(CH$_2$)$_{1-3}$NR$_x$R$_x$, —NR$_x$CH$_2$CH$_2$N(CH$_3$)$_2$, —NR$_x$C(O)(CH$_2$)$_{1-2}$NR$_x$R$_x$, —NR$_x$(CH$_2$CH$_2$S(O)$_2$CH$_3$), —OCH$_2$CH$_2$N(CH$_3$)$_2$, —C(O)(CR$_x$R$_x$)$_{1-2}$NR$_y$R$_y$, —C(O)(CR$_x$R$_x$)$_{1-2}$NR$_y$(C$_{1-4}$ hydroxyalkyl), —C(O)(CR$_x$R$_x$)$_{1-2}$NR$_x$(CH$_2$CH$_2$OCH$_3$), —S(O)$_2$CH$_2$CH$_2$N(CH$_3$)$_2$, —(CH$_2$)$_{1-2}$R$_{7d}$, —NR$_x$R$_{7d}$, —NR$_x$(CH$_2$)$_{1-2}$R$_{7d}$), —NR$_{7d}$R$_{7d}$, —N((CH$_2$)$_{1-2}$R$_{7d}$)$_2$, —OR$_{7d}$, —C(O)R$_{7d}$, —C(O)(CR$_x$R$_x$)$_{1-2}$R$_{7d}$, or —C(O)(CR$_x$R$_x$)$_{1-2}$NR$_x$R$_{7d}$; or
(ii) azepanyl, azetidinyl, cyclobutyl, cyclohexyl, diazepanyl, dioxotetrahydrothiopyranyl, dioxothiomorpholinyl, morpholinyl, oxaazaspiro[3.3]heptanyl, oxaazaspiro[4.3]octanyl, oxetanyl, piperazinonyl, piperazinyl, piperidinyl, pyridinyl, pyrimidinyl, pyrrolidinonyl, pyrrolidinyl, tetrahydrofuranyl, tetrahydroisoquinolinyl, tetrahydropyranyl, or thiadiazolyl, each substituted with zero to 1 $R_{8a}$ and zero to 3 $R_{8b}$;

each $R_{7c}$ is independently —$CH_3$ or —$CH_2CN$;

$R_{7d}$ is azaspiro[3.5]nonanyl, azetidinyl, bicyclo[1.1.1]pentanyl, $C_{3-6}$ cycloalkyl, dioxothiaazaspiro[3.3]heptanyl, morpholinyl, oxaazaspiro[3.3]heptanyl, oxaazaspiro[4.3]octanyl, oxaazaspiro[4.4]nonyl, oxetanyl, phenyl, piperidinyl, pyrazolyl, pyrrolidinyl, tetrahydrofuranyl, tetrahydropyranyl, thiadiazolyl, or triazolyl, each substituted with zero to 2 substituents selected from F, —OH, $C_{1-3}$ alkyl, —$CH_2OH$, —$OCH_3$, —$NR_xR_x$, —$C(O)CH_3$, —$S(O)_2CH_3$, methylpiperidinyl, methylpyrrolidinyl, tetramethylpiperidinyl, —$OCH_2CH_2$(pyrrolidinyl), and —$OCH_2CH_2NHCH_2CH_3$; and zero to 4 substituents selected from —$CH_3$;

$R_8$ is H, —$CH_3$ or —$CH_2CH_3$;

or $R_7$ and $R_8$ together with the nitrogen atom to which they are attached form a heterocyclic ring selected from azetidinyl, diazabicyclo[2.2.1]heptanyl, diazabicyclo[2.2.2]octanyl, diazabicyclo[3.1.1]heptanyl, diazabicyclo[3.2.1]octanyl, azaspiro[3.3]heptanyl, diazaspiro[2.5]octanyl, diazaspiro[3.3]heptanyl, diazepanonyl, diazepanyl, diazaspiro[3.5]nonanyl, diazaspiro[5.5]undecanyl, imidazolidinonyl, octahydro-1H-pyrrolo[3,4-b]pyridinyl, oxadiazabicyclo[3.3.1]nonanyl, piperazinyl, piperazinonyl, piperidinyl, pyrrolidinonyl, and pyrrolidinyl, wherein said heterocyclic ring is substituted with zero to 1 $R_{7b}$ and zero to 2 $R_{7c}$;

$R_{8a}$ is —OH, —$CH_3$, —$CH_2CH_3$, —$CH(CH_3)_2$, —$C(CH_3)_3$, —$CH_2CH(CH_3)_2$, —$CH_2CH_2OCH_3$, —$CH_2CH_2CF_3$, —$OCH_3$, —$C(O)CH_3$, —$C(O)OCH_3$, —$CH_2$(cyclopropyl), —$CH_2$(methyl phenyl), —$(CH_2)_{2-3}$(pyrrolidinyl), —$CH_2$(methylpyrazolyl), —$CH_2$(thiophenyl), —$NR_xR_x$, cyclopentyl, methylpiperidinyl, or pyridinyl;

$R_{8a}$ is —OH, —$CH_3$, —$CH_2CH_3$, —$CH(CH_3)_2$, —$C(CH_3)_3$, —$CH_2CH(CH_3)_2$, —$CH_2CH_2OCH_3$, —$CH_2CH_2CF_3$, —$OCH_3$, —$C(O)CH_3$, —$C(O)OCH_3$, —$CH_2$(cyclopropyl), —$CH_2$(methyl phenyl), —$(CH_2)_{2-3}$(pyrrolidinyl), —$CH_2$(methylpyrazolyl), —$CH_2$(thiophenyl), —$NR_xR_x$, cyclopentyl, methylpiperidinyl, or pyridinyl;

each $R_{8b}$ is —$CH_3$;

$R_9$ is —$CH_3$, —$CH_2CH_2CF_3$, —$CH_2CH_2OH$, —$CH_2C(CH_3)_2OH$, —$CH_2C(CH_3)_2CH_2OH$, —$CH_2CHFC(CH_3)_2OH$, —$CH_2CH_2C(CH_3)_2OH$, —$CH(CH_2OH)_2$, —$CH_2CH_2OCH_3$, —$CH_2CH_2NH_2$, —$CH_2CH_2N(CH_3)_2$, —$CH_2CH_2CH_2N(CH_3)_2$, —$CH_2CH_2C(O)NH_2$, —$CH_2S(O)_2OH$, —$CH_2CH_2C(CH_3)_2NHS(O)_2CH_3$, or —$(CH_2)_{0-3}R_{9a}$;

$R_{9a}$ is cyclohexyl, cycloheptyl, furanyl, phenyl, piperazinyl, piperidinyl, pyrazolyl, pyridinyl, pyrrolidinyl, quinuclidinyl, thiazolyl, or octahydrocyclopenta[c]pyrrolyl, each substituted with zero to 2 substituents independently selected from —OH, $C_{1-3}$ alkyl, —$NH_2$, —$N(CH_3)_2$, oxetanyl, phenyl, piperazinyl, piperidinyl, and pyrrolidinyl;

$R_{10}$ is H, —$CH_3$, —$CH_2CH_3$, —$CH_2CH_2OCH_3$, or cyclopropyl;

or $R_9$ and $R_{10}$ together with the nitrogen atom to which they are attached form a heterocyclic ring selected from azabicyclo[3.1.1]heptanyl, azaspiro[5.5]undecanyl, diazabicyclo[2.2.1]heptanyl, diazabicyclo[3.1.1]heptanyl, diazabicyclo[3.2.0]heptanyl, diazaspiro[3.5]nonanyl, diazaspiro[4.4]nonanyl, diazaspiro[4.5]decanyl, diazepanyl, indolinyl, morpholinyl, octahydropyrrolo[3,4-c]pyrrolyl, piperazinonyl, piperazinyl, piperidinyl, and pyrrolidinyl, each substituted with zero to 2 $R_{10a}$;

each $R_{10a}$ is independently —$CH_3$, —$CH_2CH_3$, —$CH(CH_3)_2$, —$CH_2OH$, —$CH_2CH_2OH$, —$CH_2OCH_3$, —$CH_2CH_2OCH_3$, —$CH_2NH_2$, —$CH_2CH_2NH_2$, —$CH_2CH_2NH(CH_3)$, —$CH_2C(O)NH(CH_3)$, —$CH_2C(O)N(CH_3)_2$, —$CH_2$(methyltriazolyl), —$CH_2CH_2$(phenyl), —$CH_2CH_2$(morpholinyl), —$C(O)CH_3$, —$C(O)NH_2$, —$C(O)N(CH_2CH_3)_2$, —$C(O)CH_2NH(CH_3)$, —$C(O)CH_2N(CH_3)_2$, —$NH_2$, —$N(CH_3)_2$, —$NHC(O)CH_3$, —$C(O)$(furanyl), —O(piperidinyl), —$C(O)CH_2$(diethylcarbamoylpiperidinyl), methylpiperazinyl, piperidinyl, methylpiperidinyl, diethylcarbamoylpiperidinyl, isopropylpiperidinyl, pyridinyl, trifluoromethylpyridinyl, pyrimidinyl, or dihydrobenzo[d]imidazolonyl;

$R_{11}$ is azetidinyl, azaspiro[3.5]nonanyl, dioxidothiomorpholinyl, hexahydropyrrolo[3,4-c]pyrrolyl, morpholinyl, piperazinyl, piperidinyl, or pyrrolidinyl, each substituted with zero to 2 substituents independently selected from F, —$CH_3$, —$CH(CH_3)_2$, —$CH_2CN$, —$CH_2$(methyloxetanyl), —$CH_2$(triazolyl), —$CH_2$(phenyl), —$C(O)CH_2N(CH_3)_2$, —$CH_2C(CH_3)_2OH$, —$CH_2C(O)N(CH_3)_2$, —$CH_2CH_2S(O)_2CH_3$, —$CH_2CH_2S(O)CH_3$, oxetanyl, and tetrahydropyranyl;

each $R_{12a}$ is independently —OH, —$CH_3$, —$CH_2CH_3$, —$CH(CH_3)_2$, —$CH_2CH(CH_3)_2$, —$CF_3$, —$CH_2CF_3$, —$CH_2CH_2CF_3$, —$CH_2CN$, —$CH_2C(CH_3)_2OH$, —$CH_2CH_2OCH_3$, —$CH_2C(O)NH(CH_3)$, —$CH_2C(O)N(CH_3)_2$, —$CH_2C(O)NH_2$, —$CH_2CH_2S(O)_2CH_3$, —$CH_2CH_2NHS(O)_2CH_3$, —$CH_2NR_xR_x$, —$CH_2CH_2NH(CH_3)$, —$OCH_3$, —$NR_xR_y$, —$NR_x(C_{2-4}$ fluoroalkyl), —$NR_x(CH_2CR_xR_xH_2OCH_3)$, —$NH(CH_2CN)$, —$N(CH_3)CH_2N(CH_3)_2$, —$NH(CH_2C(CH_3)_2OH)$, —$NR_x(CH_2C(O)NH_2)$, —$N(CH_3)(OCH_3)$, —$NR_xCH_2CH_2S(O)_2CH_3$, —$NHC(O)CH_3$, —$NHC(O)CH_2CF_3$, —$NHC(O)CHR_xNH(CH_3)$, —$NR_xC(O)CH_2N(CH_3)_2$, —$NHC(O)CH_2N(CH_3)(CH_2CH_3)$, —$NHC(O)CH_2N(CH_2CH_3)_2$, —$NHC(O)CH_2NH(CH_2C(CH_3)_2OH)$, —$NHCH_2C(O)NR_x(CH_3)$, —$NHS(O)_2CH_3$, —$C(O)C(CH_3)_3$, —$C(O)CH(CH_2CH_3)_2$, —$C(O)CH_2OCH_3$, —$C(O)CH_2CH_2OCH_3$, —$C(O)CH_2NH(CH_3)$, —$C(O)CH_2N(CH_3)_2$, —$C(O)CH_2CH_2N(CH_3)_2$, —$C(O)CH(CH_3)NH(CH_3)$, —$C(O)CH_2N(CH_3)(CH_2CH_3)$, —$C(O)CH_2N(CH_2CH_3)_2$, $R_{12b}$, —$CH_2R_{12b}$, —$C(O)R_{2b}$, —$C(O)CH_2R_{12b}$, —$C(O)CH_2NHR_{12b}$, —$C(O)NR_xR_{12b}$, —$NR_xC(O)CH_2R_{12b}$, —$NR_yR_{12b}$, —$NR_xCH_2R_{12b}$, —$N(CH_2CN)R_{12b}$, —$NHC(O)CH_2NR_xR_{12b}$, —$NHC(O)CH_2NR_xCH_2R_{12b}$, —$NHCH_2C(O)NHR_{12b}$, or —$OR_{12b}$;

or two $R_{12a}$ and the carbon atom to which they are attached form C=O;

$R_{12b}$ is azetidinyl, bicyclo[1.1.1]pentanyl, cyclopropyl, diazabicyclo[2.2.1]heptanyl, dioxolanyl, dioxothiaazaspiro[3.3]heptanyl, dioxidotetrahydrothiopyranyl, dioxidothiomorpholinyl, imidazolyl, morpholinyl, octahydrocyclopenta[c]pyrrolyl, octahydropyrrolo[3,4-c]pyrrolyl, oxaazaspiro[3.3]heptanyl, oxaazaspiro[4.3]octanyl, oxaazaspiro[4.4]nonanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, —OH, —$CH_3$, —$CH(CH_3)_2$, —$CH_2OH$, —$OCH_3$, —$CH_2CH_2OCH_3$, —$NR_xR_x$, —$C(O)NH_2$, —$C(O)N(CH_3)_2$, —$S(O)_2CH_3$, and —$CH_2S(O)_2CH_3$;

each $R_{14a}$ is independently:

(i) H, F, Cl, —OH, —$CH_3$, —$CH(CH_3)_2$, —$CH(CH_3)(CH_2CH_3)$, —$CH_2CH_2CH_2C(CH_3)_2$, —$CF_3$,

—CH$_2$CF$_3$, —CH$_2$OH, —OCH$_3$, —CH$_2$CH$_2$OCH$_3$, —CHR$_x$NR$_x$(CH$_3$), —CH$_2$N(CH$_3$)(CH(CH$_3$)$_2$), —CH$_2$NH(CH$_2$C(CH$_3$)$_3$), —CH$_2$NH(CH$_2$CN), —CH$_2$N(CH$_3$)(CH$_2$CH$_2$OCH$_3$), —CH$_2$N(CH$_2$CH$_2$OCH$_3$)$_2$, —CH$_2$NR$_x$(CH$_2$C≡CH), —CH$_2$NHCH$_2$CH$_2$N(CH$_3$)$_2$, —CH$_2$CH$_2$NR$_x$(CH$_3$), —CH$_2$CR$_x$(CH$_3$)NH$_2$, —CH$_2$CH$_2$CH$_2$N(CH$_3$)$_2$, —CH$_2$CH$_2$CH$_2$CH$_2$NH$_2$, —CH(NH$_2$)(CH$_2$)$_{3\text{-}4}$NH$_2$, —CH$_2$NHCH$_2$CH$_2$O(C$_{1\text{-}3}$ alkyl), —CH$_2$NHCH$_2$CH$_2$OCH$_2$CH$_2$OH, —CH$_2$NHCH$_2$CH$_2$S(O)$_2$OH, —CH$_2$C(O)NR$_x$(CH$_3$), —NR$_x$R$_x$, —NH(CH(CH$_3$)$_2$), —NHCH$_2$CH$_2$NH(CH$_3$), —NHCH$_2$CH$_2$CH$_2$N(CH$_3$)$_2$, —NHC(O)CH$_3$, —NHC(O)CF$_3$, —NHC(O)OC(CH$_3$)$_3$, —NHC(O)CH$_2$N(CH$_3$)$_2$, —NHC(O)CH$_2$CH$_2$N(CH$_3$)$_2$, —NHCH$_2$C(O)CH$_2$NH(CH$_3$), —C(O)CH$_3$, —C(O)CH$_2$CH(CH$_3$)OH, —C(O)CH$_2$NR$_x$(CH$_3$), —C(O)NR$_x$R$_x$, —C(O)NH(CH$_2$CN), —C(O)NHCH$_2$CH$_2$CH$_2$NR$_x$R$_x$, —C(O)NHCH$_2$CH(CH$_3$)CH$_2$NH$_2$, —C(O)NHCH$_2$C(O)NH$_2$, —C(O)N(CH$_3$)CH$_2$CH$_2$CH$_2$N(CH$_3$)$_2$, —C(O)N(CH$_2$CH$_3$)CH$_2$CH$_2$N(CH$_3$)$_2$, —OCH$_2$CH$_2$CH$_2$N(CH$_3$)$_2$, —C(O)NHCH$_2$CH$_2$NHC(O)CH$_3$, —S(O)$_2$NH$_2$, or —C(O)CH$_2$S(O)$_2$CH$_3$;

(ii) 8-azabicyclo[3.2.1]octanyl, azaspiro[3.5]nonanyl, azetidinyl, benzo[c][1,2,5]oxadiazolyl, cyclopentyl, cyclohexyl, diazepanyl, morpholinyl, phenyl, piperazinyl, piperidinyl, pyrazolyl, pyridinyl, pyrrolidinonyl, quinolinyl, quinuclidinyl, tetrahydroisoquinolinyl, tetrahydropyridinyl, or thiazolidinyl, each substituted with zero to 2 substituents independently selected from —CH$_3$, —CH(CH$_3$)$_2$, —CH$_2$CH(CH$_3$)$_2$, —CF$_3$, —CH$_2$CH$_2$CF$_3$, —CH$_2$CH$_2$OH, —CH$_2$CH$_2$CH(CH$_3$)OH, —NH$_2$, —CH$_2$N(CH$_3$)$_2$, —CH$_2$CH$_2$NH(CH$_3$), —C(O)CH$_3$, —C(O)CH$_2$NH(CH$_3$), —C(O)CH$_2$N(CH$_3$)$_2$, —C(O)O(C(CH$_3$)$_3$), —CH$_2$C(O)NR$_x$(CH$_3$), cyclobutyl, cyclopentyl, —CH$_2$(phenyl), —CH$_2$(pyrrolyl), —CH$_2$(morpholinyl), —CH$_2$(methylpiperazinyl), —CH$_2$(thiophenyl), methylpiperidinyl, isobutylpiperidinyl, and pyridinyl; or (iii) -L$_3$-R$_{14c}$;

each R$_{14b}$ is —CH$_3$;

L$_3$ is —(CH$_2$)$_{1\text{-}3}$—, —CH(CH$_3$)—, —CH(NH$_2$)—, —CH$_2$NH—, —C(O)—, —C(O)NH(CH$_2$)$_{0\text{-}4}$—, —C(O)N(CH$_3$)CH$_2$CH$_2$—, —NH—, —NHC(O)—, —NHCH$_2$—, —NHCH$_2$C(O)—, —O—, or —OCH$_2$CH$_2$—;

R$_{14c}$ is adamantanyl, azetidinyl, cyclopropyl, cyclohexyl, diazepanyl, imidazolyl, indolyl, morpholinyl, octahydropyrrolo[3,4-c]pyrrolyl, phenyl, piperazinonyl, piperazinyl, piperidinyl, pyridinyl, pyrrolidinonyl, pyrrolidinyl, or tetrazolyl, each substituted with zero to 1 substituent selected from —OH, —CH$_3$, —CH(CH$_3$)$_2$, —CH$_2$CH(CH$_3$)$_2$, —C(CH$_3$)$_2$OH, —NH$_2$, —N(CH$_3$)$_2$, —NH(C(CH$_3$)$_2$), —NHC(O)CH$_3$, —C(O)CH$_3$, —C(O)NH$_2$, —C(O)N(CH$_2$CH$_3$)$_2$, —C(O)(tetrahydrofuranyl), —C(O)OCH$_2$CH$_3$, —CH$_2$C(O)NH(CH(CH$_3$)$_2$, morpholinyl, methylpiperidinyl, pyrazinyl, pyridinyl, and pyrrolidinyl;

n is zero or 1; and p is zero, 1, 2, or 3.

One embodiment provides a compound of Formula (I), or a salt thereof, wherein:

G is:

(i)

(ii)


(iii)

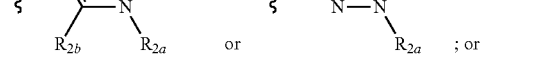

; or

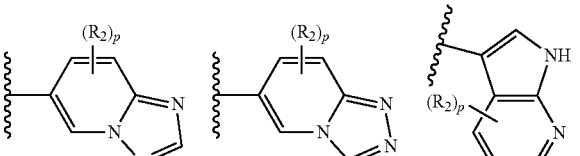

(iv)

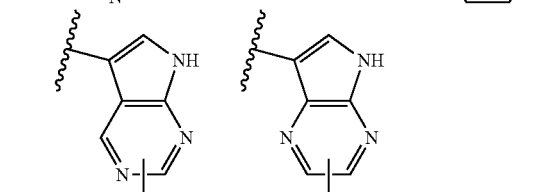

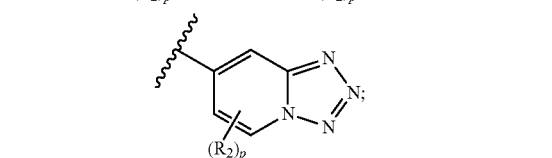

A is:
(i) —OR$_6$ or —O(CR$_x$R$_x$)$_{1\text{-}2}$—R$_6$;
(ii) —NR$_7$R$_8$;
(iii) —C(O)NR$_9$R$_{10}$;
(vi) —CH$_2$CH$_2$Rn;
(v) —CHR$_{12}$R$_{13}$, wherein R$_{12}$ and R$_{13}$ together with the carbon atom to which they are attached form a cyclic group selected from azetidinyl, C$_{3\text{-}6}$ cycloalkyl, morpholinyl, or piperidinyl, each substituted with zero to 3 R$_{12a}$; or
(vi) an aromatic group selected from pyrazolyl substituted with zero to 1 R$_{14a}$; R$_1$ is —CH$_3$ or —CH(CH$_3$)$_2$;

each R$_2$ is independently Cl, —CH$_3$, —CH$_2$CH$_3$, —CH$_2$OH, —CH$_2$CH$_2$OH, —CH$_2$CN, —OCH$_3$, —CH$_2$OCH$_3$, or —CH$_2$CH$_2$S(O)$_2$CH$_3$;

R$_6$ is:
(a) —CH$_3$; or
(b) azetidinyl, cyclohexyl, or piperidinyl, each substituted with zero to 2 R$_{6a}$;

each R<sub>6a</sub> is independently —CH₃, —CH₂CH₂CH₃, —C(CH₃)₂, —CH₂C(CH₃)₂OH, —N(CH₃)₂, —N(CH₂CH₂CH₃)₂, —CH₂CH₂S(O)₂CH₃, —CH₂C(O)N(CH₃)₂, or tetrahydropyranyl;

R₇ and R₈ together with the nitrogen atom to which they are attached form a heterocyclic ring selected from azetidinyl, diazepanyl, diazaspiro[3.5]nonanyl, piperazinonyl, piperazinyl, piperidinyl, and pyrrolidinyl, wherein said heterocyclic ring is substituted with zero to 1 R$_{7b}$, and zero to 2 R$_{7c}$;

R$_{7b}$ is:
(a) —NR$_x$R$_x$, C$_{1-6}$ alkyl, C$_{2-3}$ fluoroalkyl, C$_{1-4}$ hydroxyalkyl, C$_{1-2}$ cyanoalkyl, —CHR$_x$CH₂OCH₃, —CH₂C(O)NR$_x$R$_x$, —CH₂CH₂C(O)NR$_x$R$_x$, —(CH₂)$_{2-3}$S(O)₂CH₃, —CH₂CH₂NHS(O)₂CH₃, —NR$_x$R$_x$, —N(CH₃)(CH₂CH₃), —N(CH₂CH₃)₂, —NH(CH₂CN), —N(CH₂CN)₂, —NR$_x$CH₂C(O)N(CH₃)₂, —NR$_x$C(O)CH₂N(CH₃)₂, —NH(CH₂CH₂S(O)₂CH₃), —N(CH₂C(O)N(CH₃)₂)₂, —S(O)₂CH₂CH₂N(CH₃)₂, —C(O)CH₂CH₂N(CH₃)₂, —C(O)CH₂N(CH₃)₂, —C(O)CH₂NH(CH(CH₃)₂), —C(O)CH₂NH(CH₂CH₂OCH₃), —C(O)CH₂NH(CH₂CH₂OH), —CH₂(cyclopropyl), —CH₂(methyloxetanyl), —CH₂(tetrahydrofuranyl), —CH₂(methyltriazolyl), —CH₂CH₂(morpholinyl), —NR$_x$(cyclobutyl), —NR$_x$(oxetanyl), —NR$_x$(pyrimidinyl), —NR$_x$(tetrahydropyranyl), —NHCH₂(methylsulfonylcyclopropyl), —NHCH₂(methyloxetanyl), —NHCH₂(methoxypyrimidinyl), —C(O)CH₂NH(cyclobutyl), —N(CH₂(dimethoxypyrimidinyl))₂, —N(CH₂(methoxypyrimidinyl))₂, —N(CH₂(triazolyl))₂, —N(CH₂(methyltriazolyl))₂, —N(CH₃)CH₂(cyclopropyl), —N(CH₃)CH₂(methylpyrazolyl), —N(CH₃)CH₂(pyrimidinyl), —N(CH₃)CH₂(methylpyrimidinyl), —N(CH₃)CH₂(dimethoxypyrimidinyl), —N(CH₃)CH₂(methoxypyrimidinyl), —N(CH₃)CH₂(thiadiazolyl), —N(CH₃)CH₂(methyltriazolyl), —NH(CH₂(methylpyrimidinyl))₂, —NH(CH₂(thiadiazolyl), —C(O)CH₂(azetidinyl), —C(O)CH₂(morpholinyl), —C(O)CH₂(hydroxypiperidinyl), —C(O)CH₂(pyrrolidinyl), or —C(O)CH₂NHCH₂(cyclopropyl); or
(b) cyclobutyl, cyclohexyl, dioxothiomorpholinyl, oxetanyl, piperazinyl, piperidinyl, tetrahydrofuranyl, or tetrahydropyranyl, each substituted with zero to 1 R$_{8a}$ and zero to 3 R$_{8b}$;

each R$_{7c}$ is independently —CH₃ or —CH₂CN;

R$_{8a}$ is —OH, —CH₃, —CH₂CH₃, —CH(CH₃)₂, —C(CH₃)₃, —CH₂CH(CH₃)₂, —CH₂CH₂OCH₃, —CH₂CH₂CF₃, —C(O)CH₃, —C(O)OCH₃, —CH₂(cyclopropyl), —CH₂(methyl phenyl), —(CH₂)$_{2-3}$(pyrrolidinyl), —CH₂(methylpyrazolyl), —CH₂(thiophenyl), —NR$_x$R$_x$, cyclopentyl, methylpiperidinyl, or pyridinyl;

each R$_{8b}$ is —CH₃;

R₉ is —CH₂CH₂CF₃ or —CH₂CH₂N(CH₃)₂;

R₁₀ is H or C$_{1-2}$ alkyl;

or R₉ and R₁₀ together with the nitrogen atom to which they are attached form a heterocyclic ring selected piperidinyl substituted with —C(O)CH₃ or —CH(CH₃)₂;

R₁₁ is azetidinyl or piperidinyl, each substituted with zero to 1 substituent selected from —CH₂(triazolyl), —CH₂(methyloxetanyl), —C(O)CH₂N(CH₃)₂, —CH₂C(CH₃)₂OH, —CH₂C(O)N(CH₃)₂, —CH₂CH₂S(O)₂CH₃, and oxetanyl;

each R$_{12a}$ is independently —OH, —CH₃, —CH₂CH₃, —CH(CH₃)₂, —CH₂CH(CH₃)₂, —CH₂CN, —CH₂C(CH₃)₂OH, —CH₂C(O)NH(CH₃), —CH₂C(O)N(CH₃)₂, —CH₂C(O)NH₂, —C(CH₃)₂CH₂C(O)N(CH₃)₂, —CH₂CH₂S(O)₂CH₃, —NR$_x$R$_y$, —NR$_x$(CH₂CHF₂), —N(R$_x$)(CH₂CH₂CF₃), —NR$_x$(CH₂CH₂OCH₃), —NR$_x$(C$_{1-2}$ cyanoalkyl), —NR$_x$(CH₂CH₂OH), —N(CH₂CH₂OH)(CH₂C(O)N(CH₃)₂), —N(CH₂CH₂OH)(CH₂CH₂S(O)₂CH₃), —N(CH₂CH₂S(O)₂CH₃)₂, —NR$_x$(CH₂CH₂OCH₃), —NR$_x$CH₂CR$_x$R$_x$S(O)₂CH₃, —NR$_x$CH₂CH₂S(O)₂CF₃, —NR$_x$CH₂CH₂S(O)₂NH₂, —NR$_x$C(O)CH₃, —NR$_x$C(O)CH₂N(CH₃)₂, —NR$_x$(CR$_x$R$_x$C(O)NR$_x$R$_x$), —NHCH₂C(O)NR$_x$(C(CH₃)₃), —NR$_x$(CR$_x$R$_x$C(O)CH₂NR$_x$R$_x$), —NH(CH₂C(O)N(CH₃)CH₂CH₂OCH₃), —N(CH₂CH₃)₂, —N(CH₂CH₃)(CH₂C(O)N(CH₃)₂), —N(CH₂CH₃)(CH₂CH₂S(O)₂CH₃), —N(CH₂CN)₂, —N(CH₂CN)(CH₂C(O)N(CH₃)₂), —N(CH₂CN)(CH₂CH₂S(O)₂CH₃), —N(CH₂C(O)NR$_x$R$_x$)₂, —N(CH₂(methyloxetanyl))₂, —C(O)CH₂N(CH₃)₂, —C(O)CH₂CH₂N(CH₃)₂, R$_{2b}$, —CH₂R$_{12b}$, —NR$_x$R$_{12b}$, —N(cyclopropyl)R$_{2b}$, —NR$_x$CHR$_x$R$_{12b}$, —NHC(O)R$_{12b}$, —NHCR$_x$R$_x$C(O)R$_{2b}$, —N(CH₂CH₃)(CH₂R$_{12b}$), —N(CH₂CH₂OH)R$_{12b}$, —N(CH₂CH₂OH)(CH₂R$_{12b}$), —N(CH₂CN)R$_{2b}$, —N(CH₂CN)(CH₂R$_{12b}$), or —N(CH₂(methyloxetanyl))₂; or two R$_{12a}$ and the carbon atom to which they are attached form C=O;

R$_{12b}$ is azaspiro[3.5]nonanyl, azetidinyl, cyclopropyl, cyclopentyl, dioxotetrahydrothiofuranyl, dioxidotetrahydrothiopyranyl, dioxothiaazaspiro[3.3]heptanyl, morpholinyl, oxaazaspiro[3.3]heptanyl, oxazolyl, oxetanyl, phenyl, piperazinonyl, piperidinyl, pyrazinyl, pyridinyl, pyrimidinyl, pyrrolidinyl, pyrrolidinonyl, tetrahydrofuranyl, tetrahydropyranyl, or triazolyl, each substituted with zero to 4 substituents independently selected from F, —CN, —CH₃, —CH(CH₃)₂, —CH₂CH(CH₃)₂, —CH₂OH, —CH₂CH₂OH, C$_{1-2}$ cyanoalkyl, —OCH₃, —CH₂C(O)NH(CH₃), —C(O)NR$_x$R$_x$, —S(O)₂CH₃, —S(O)₂CH₃, and —CH₂S(O)₂CH₃; and R$_{14a}$ is piperidinyl or —CH₂CH₂(morpholinyl);

and R₅ and n are defined in the first aspect or the second aspect.

One embodiment provides a compound of Formula (I), N-oxide, or a salt thereof, wherein:

G is:

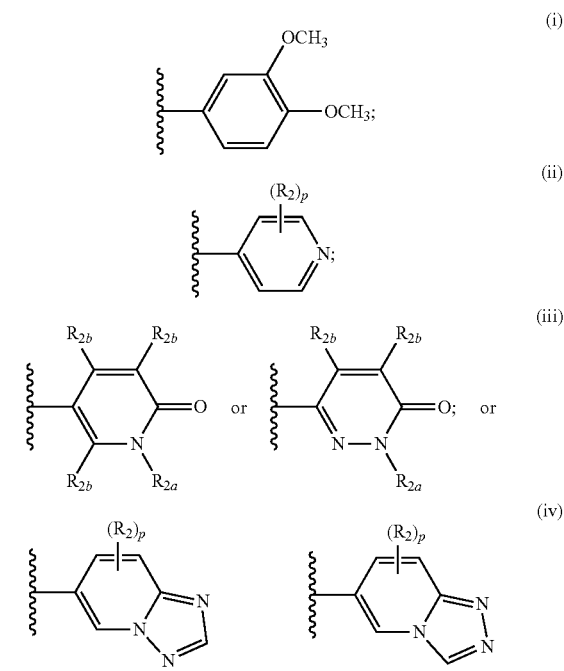

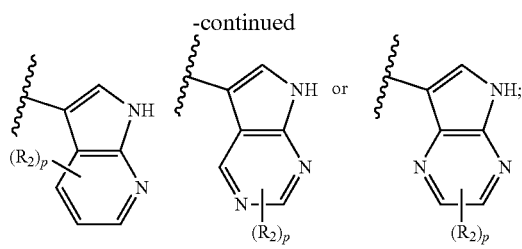

A is:
(i) —OR$_6$ or —O(CR$_x$R$_x$)$_{1-2}$—R$_6$;
(ii) —NR$_7$R$_8$;
(iii) —C(O)NR$_9$R$_{10}$;
(vi) —CH$_2$CH$_2$Rn;
(v) —CHR$_{12}$R$_{13}$, wherein R$_{12}$ and R$_{13}$ together with the carbon atom to which they are attached form a cyclic group selected from azetidinyl, C$_{3-6}$ cycloalkyl, morpholinyl, or piperidinyl, each substituted with zero to 3 R$_{12a}$; or
(vi) an aromatic group selected from pyrazolyl substituted with zero to 1 R$_{14a}$;
R$_1$ is —CH(CH$_3$)$_2$;
each R$_2$ is independently Cl, —CH$_3$, —CH$_2$CH$_3$, —CH$_2$OH, —CH$_2$CH$_2$OH, —OCH$_3$, —CH$_2$OCH$_3$, or —CH$_2$CH$_2$S(O)$_2$CH$_3$;
R$_6$ is:
(a) —CH$_3$; or
(b) azetidinyl, cyclohexyl, or piperidinyl, each substituted with zero to 2 R$_{6a}$;
each R$_{6a}$ is independently —CH$_3$, —CH$_2$CH$_2$CH$_3$, —C(CH$_3$)$_2$, —CH$_2$C(CH$_3$)$_2$OH, —N(CH$_3$)$_2$, —N(CH$_2$CHCH)$_2$, —CH$_2$CH$_2$S(O)$_2$CH$_3$, —CH$_2$C(O)N(CH$_3$)$_2$, or tetrahydropyranyl;
R$_7$ and R$_8$ together with the nitrogen atom to which they are attached form a heterocyclic ring selected from azetidinyl, diazepanyl, diazaspiro[3.5]nonanyl, piperazinonyl, piperazinyl, piperidinyl, and pyrrolidinyl, wherein said heterocyclic ring is substituted with zero to 1 R$_{7b}$, and zero to 2 R$_{7c}$;
R$_{7b}$ is:
(a) —NR$_x$R$_x$, C$_{1-6}$ alkyl, C$_{2-3}$ fluoroalkyl, C$_{1-4}$ hydroxyalkyl, C$_{1-2}$ cyanoalkyl, —CHR$_x$CH$_2$OCH$_3$, —CH$_2$C(O)NR$_x$R$_x$, —CH$_2$CH$_2$C(O)NR$_x$R$_x$, —(CH$_2$)$_{2-3}$S(O)$_2$CH$_3$, —CH$_2$CH$_2$NHS(O)$_2$CH$_3$, —NR$_x$R$_x$, —N(CH$_3$)(CH$_2$CH$_3$), —N(CH$_2$CH$_3$)$_2$, —NH(CH$_2$CN), —N(CH$_2$CN)$_2$, —NR$_x$CH$_2$C(O)N(CH$_3$)$_2$, —NR$_x$C(O)CH$_2$N(CH$_3$)$_2$, —NH(CH$_2$CH$_2$S(O)$_2$CH$_3$), —N(CH$_2$C(O)N(CH$_3$)$_2$)$_2$, —S(O)$_2$CH$_2$CH$_2$N(CH$_3$)$_2$, —C(O)CH$_2$CH$_2$N(CH$_3$)$_2$, —C(O)CH$_2$N(CH$_3$)$_2$, —C(O)CH$_2$NH(CH(CH$_3$)$_2$), —C(O)CH$_2$NH(CH$_2$CH$_2$OCH$_3$), —C(O)CH$_2$NH(CH$_2$CH$_2$OH), —CH$_2$(cyclopropyl), —CH$_2$(methyloxetanyl), —CH$_2$(tetrahydrofuranyl), —CH$_2$(methyltriazolyl), —CH$_2$CH$_2$(morpholinyl), —NR$_x$(cyclobutyl), —NR$_x$(oxetanyl), —NR$_x$(pyrimidinyl), —NR$_x$(tetrahydropyranyl), —NHCH$_2$(methylsulfonylcyclopropyl), —NHCH$_2$(methyloxetanyl), —NHCH$_2$(methoxypyrimidinyl), —C(O)CH$_2$NH(cyclobutyl), —N(CH$_2$(dimethoxypyrimidinyl))$_2$, —N(CH$_2$(methoxypyrimidinyl))$_2$, —N(CH$_2$(triazolyl))$_2$, —N(CH$_2$(methyltriazolyl))$_2$, —N(CH$_3$)CH$_2$(cyclopropyl), —N(CH$_3$)CH$_2$(methylpyrazolyl), —N(CH$_3$)CH$_2$(pyrimidinyl), —N(CH$_3$)CH$_2$(methylpyrimidinyl), —N(CH$_3$)CH$_2$(dimethoxypyrimidinyl), —N(CH$_3$)CH$_2$(methoxypyrimidinyl), —N(CH$_3$)CH$_2$(thiadiazolyl), —N(CH$_3$)CH$_2$(methyltriazolyl), —NH(CH$_2$(methylpyrimidinyl))$_2$, —NH(CH$_2$(thiadiazolyl), —C(O)CH$_2$(azetidinyl), —C(O)CH$_2$(morpholinyl), —C(O)CH$_2$(hydroxypiperidinyl), —C(O)CH$_2$(pyrrolidinyl), or —C(O)CH$_2$NHCH$_2$(cyclopropyl); or (b) cyclobutyl, cyclohexyl, dioxothiomorpholinyl, oxetanyl, piperazinyl, piperidinyl, tetrahydrofuranyl, or tetrahydropyranyl, each substituted with zero to 1 R$_{8a}$ and zero to 3 R$_{8b}$;
each R$_{7c}$ is independently —CH$_3$ or —CH$_2$CN;
R$_{8a}$ is —OH, —CH$_3$, —CH$_2$CH$_3$, —CH(CH$_3$)$_2$, —C(CH$_3$)$_3$, —CH$_2$CH(CH$_3$)$_2$, —CH$_2$CH$_2$OCH$_3$, —CH$_2$CH$_2$CF$_3$, —C(O)CH$_3$, —C(O)OCH$_3$, —CH$_2$(cyclopropyl), —CH$_2$(methyl phenyl), —(CH$_2$)$_{2-3}$(pyrrolidinyl), —CH$_2$(methylpyrazolyl), —CH$_2$(thiophenyl), —NR$_x$R$_x$, cyclopentyl, methylpiperidinyl, or pyridinyl;
each R$_{8b}$ is —CH$_3$;
R$_9$ is —CH$_2$CH$_2$CF$_3$ or —CH$_2$CH$_2$N(CH$_3$)$_2$;
R$_{10}$ is H or C$_{1-2}$ alkyl;
or R$_9$ and R$_{10}$ together with the nitrogen atom to which they are attached form a heterocyclic ring selected piperidinyl substituted with —C(O)CH$_3$ or —CH(CH$_3$)$_2$;
R$_{11}$ is azetidinyl or piperidinyl, each substituted with zero to 1 substituent selected from —CH$_2$(triazolyl), —CH$_2$(methyloxetanyl), —C(O)CH$_2$N(CH$_3$)$_2$, —CH$_2$C(CH$_3$)$_2$OH, —CH$_2$C(O)N(CH$_3$)$_2$, —CH$_2$CH$_2$S(O)$_2$CH$_3$, and oxetanyl;
each R$_{12a}$ is independently —OH, —CH$_3$, —CH$_2$CH$_3$, —CH(CH$_3$)$_2$, —CH$_2$CH(CH$_3$)$_2$, —CH$_2$CN, —CH$_2$C(CH$_3$)$_2$OH, —CH$_2$C(O)NH(CH$_3$), —CH$_2$C(O)N(CH$_3$)$_2$, —CH$_2$C(O)NH$_2$, —C(CH$_3$)$_2$CH$_2$C(O)N(CH$_3$)$_2$, —CH$_2$CH$_2$S(O)$_2$CH$_3$, —NR$_x$R$_y$, —NR$_x$(CH$_2$CHF$_2$), —N(R$_x$)(CH$_2$CH$_2$CF$_3$), —NR$_x$(CH$_2$CH$_2$OCH$_3$), —NR$_x$(C$_{1-2}$ cyanoalkyl), —NR$_x$(CH$_2$CH$_2$OH), —N(CH$_2$CH$_2$OH)(CH$_2$C(O)N(CH$_3$)$_2$), —N(CH$_2$CH$_2$OH)(CH$_2$CH$_2$S(O)$_2$CH$_3$), —N(CH$_2$CH$_2$S(O)$_2$CH$_3$)$_2$, —NR$_x$(CH$_2$CH$_2$OCH$_3$), —NR$_x$CH$_2$CR$_x$R$_x$S(O)$_2$CH$_3$, —NR$_x$CH$_2$CH$_2$S(O)$_2$CF$_3$, —NR$_x$CH$_2$CH$_2$S(O)$_2$NH$_2$, —NR$_x$C(O)CH$_3$, —NR$_x$C(O)CH$_2$N(CH$_3$)$_2$, —NR$_x$(CR$_x$R$_x$C(O)NR$_x$R$_x$), —NHCH$_2$C(O)NR$_x$(C(CH$_3$)$_3$), —NR$_x$(CR$_x$R$_x$C(O)CH$_2$NR$_x$R$_x$), —NH(CH$_2$C(O)N(CH$_3$)CH$_2$CH$_2$OCH$_3$), —N(CH$_2$CH$_3$)$_2$, —N(CH$_2$CH$_3$)(CH$_2$C(O)N(CH$_3$)$_2$), —N(CH$_2$CH$_3$)(CH$_2$CH$_2$S(O)$_2$CH$_3$), —N(CH$_2$CN)$_2$, —N(CH$_2$CN)(CH$_2$C(O)N(CH$_3$)$_2$), —N(CH$_2$CN)(CH$_2$CH$_2$S(O)$_2$CH$_3$), —N(CH$_2$C(O)NR$_x$R$_x$)$_2$, —N(CH$_2$(methyloxetanyl))$_2$, —C(O)CH$_2$N(CH$_3$)$_2$, —C(O)CH$_2$N(CH$_3$)$_2$, R$_{2b}$, —CH$_2$R$_{12b}$, —NR$_x$R$_{12b}$, —N(cyclopropyl)R$_{2b}$, —NR$_x$CHR$_x$R$_{12b}$, —NHC(O)R$_{12b}$, —NHCR$_x$R$_x$C(O)R$_{12b}$, —N(CH$_2$CH$_3$)(CH$_2$R$_{12b}$), —N(CH$_2$CH$_2$OH)R$_{12b}$, —N(CH$_2$CH$_2$OH)(CH$_2$R$_{12b}$), —N(CH$_2$CN)R$_{2b}$, —N(CH$_2$CN)(CH$_2$R$_{12b}$), or —N(CH$_2$(methyloxetanyl))$_2$; or two R$_{12a}$ and the carbon atom to which they are attached form C═O;
R$_{12b}$ is azaspiro[3.5]nonanyl, azetidinyl, cyclopropyl, cyclopentyl, dioxotetrahydrothiofuranyl, dioxidotetrahydrothiopyranyl, dioxothiaazaspiro[3.3]heptanyl, morpholinyl, oxaazaspiro[3.3]heptanyl, oxazolyl, oxetanyl, phenyl, piperazinonyl, piperidinyl, pyrazinyl, pyridinyl, pyrimidinyl, pyrrolidinyl, pyrrolidinonyl, tetrahydrofuranyl, tetrahydropyranyl, or triazolyl, each substituted with zero to 4 substituents independently selected from F, —CN, —CH$_3$, —CH(CH$_3$)$_2$, —CH$_2$CH(CH$_3$)$_2$, —CH$_2$OH, —CH$_2$CH$_2$OH, C$_{1-2}$ cyanoalkyl, —OCH$_3$, —CH$_2$C(O)NH(CH$_3$), —C(O)NR$_x$R$_x$, —S(O)$_2$CH$_3$, and —CH$_2$S(O)$_2$CH$_3$;
R$_{14a}$ is piperidinyl or —CH$_2$CH$_2$(morpholinyl);
and G, n, R$_5$, and p are defined in the first aspect or the second aspect One embodiment provides a compound of Formula (I) or a salt thereof wherein G is:

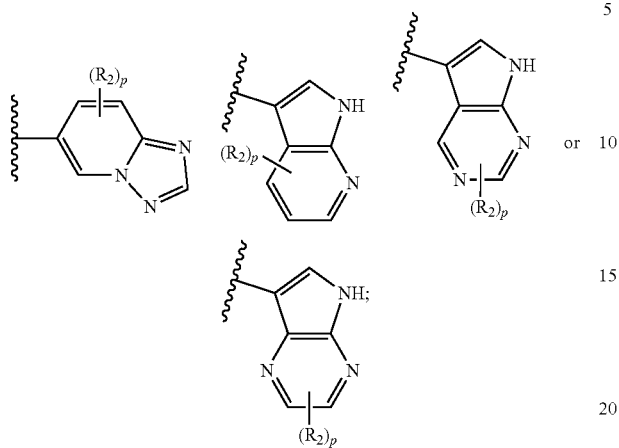

A is —NR$_7$R$_8$; and R$_1$, R$_2$, R$_5$, n, and p are defined in the first aspect or the second aspect.

One embodiment provides a compound of Formula (I) or a salt thereof wherein G is:

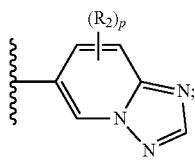

R$_1$ is —CH(CH$_3$)$_2$; A is piperazinyl; and R$_1$, R$_2$, R$_5$, n, and p are defined in the first aspect or the second aspect.

One embodiment provides a compound of Formula (I) or a salt thereof wherein G is

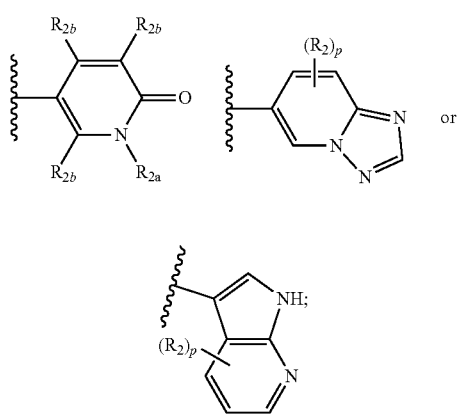

A is —CR$_x$R$_{12}$R$_{13}$, wherein R$_{12}$ and R$_{13}$ together with the carbon atom to which they are attached form a cyclic group selected from azetidinyl, C$_{4-6}$ cycloalkyl, or piperidinyl, each substituted with zero to 4 R$_{12a}$; and R$_1$, R$_2$, R$_{2a}$, R$_{2b}$, R$_5$, R$_{12a}$, n, and p are defined in the first aspect or the second aspect.

One embodiment provides a compound of Formula (I) or a salt thereof wherein G is

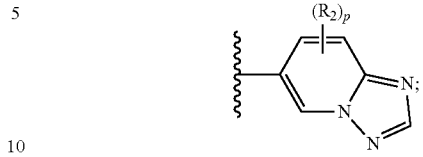

A is —CR$_x$R$_{12}$R$_{13}$, wherein R$_{12}$ and R$_{13}$ together with the carbon atom to which they are attached form a cyclic group selected from cyclopentyl and cyclohexyl, each substituted with zero to 1 R$_{12a}$; R$_1$ is —CH(CH$_3$)$_2$; R$_{12a}$ is —NR$_y$R$_y$, —NR$_x$(C$_{1-3}$ fluoroalkyl), —NR$_x$(CH$_2$CH$_2$O(C$_{1-3}$ alkyl)), —NR$_x$(C$_{1-2}$ cyanoalkyl), —NR$_x$CH$_2$NR$_x$R$_x$, —NR$_x$(C$_{1-4}$ hydroxyalkyl), —NR$_x$(CH$_2$C(O)NR$_x$R$_x$), —CR$_x$R$_x$R$_{12b}$, —NR$_x$R$_{12b}$, or —NR$_x$CR$_x$R$_x$R$_{12b}$; R$_{12b}$ is cyclopropyl, cyclopentyl, dioxotetrahydrothiofuranyl, dioxidotetrahydrothiopyranyl, morpholinyl, oxaazaspiro[3.3]heptanyl, oxazolyl, oxetanyl, phenyl, piperidinyl, pyrazinyl, pyridinyl, pyrimidinyl, pyrrolidinyl, pyrrolidinonyl, tetrahydrofuranyl, tetrahydropyranyl, or triazolyl, each substituted with zero to 4 substituents independently selected from F, —CN, —CH$_3$, —CH(CH$_3$)$_2$, —CH$_2$CH(CH$_3$)$_2$, —CH$_2$OH, —CH$_2$CH$_2$OH, C$_{1-2}$ cyanoalkyl, —OCH$_3$, —CH$_2$C(O)NH(CH$_3$), —C(O)NR$_x$R$_x$, —S(O)$_2$CH$_3$, and —CH$_2$S(O)$_2$CH$_3$; and R$_2$, R$_5$, n, and p are defined in the first aspect or the second aspect.

One embodiment provides a compound of Formula (I) or a salt thereof, wherein R$_1$ is H, Cl, —CN, C$_{1-4}$ alkyl, C$_{1-2}$ fluoroalkyl, C$_{1-2}$ hydroxyalkyl, or —C(O)O(C$_{1-2}$ alkyl); and G, A, R$_5$, and n are defined in the first aspect or the second aspect. Included in this embodiment are compounds in which R$_1$ is —CH$_3$, —CH$_2$CH$_3$, —CH(CH$_3$)$_2$, —CH$_2$CHF$_2$, or —CH$_2$CF$_3$. Also included in this embodiment are compounds in which R$_1$ is —CH$_3$ or —CH(CH$_3$)$_2$. Additionally, included in this embodiment are compounds in which R$_1$ is —CH(CH$_3$)$_2$.

One embodiment provides a compound of Formula (I) or a salt thereof, wherein each R$_2$ is independently F, Cl, —CN, —OH, C$_{1-3}$ alkyl, C$_{1-2}$ fluoroalkyl, C$_{1-2}$ cyanoalkyl, C$_{1-3}$ hydroxyalkyl, C$_{1-2}$ aminoalkyl, —(CH$_2$)$_{0-2}$O(C$_{1-3}$ alkyl), C$_{3-6}$ cycloalkyl, —NR$_x$R$_x$, —(CH$_2$)$_{0-2}$C(O)NR$_x$R$_x$, —(CH$_2$)$_{0-2}$S(O)$_2$(C$_{1-3}$ alkyl), —CH$_2$(C$_{3-6}$ cycloalkyl), —CH$_2$(phenyl), or phenyl; and G, A, R$_1$, R$_5$, R$_x$, and n are defined in the first aspect or the second aspect. Included in this embodiment are compounds in which each R$_2$ is independently Cl, —CH$_3$, —CH$_2$CH$_3$, —CH$_2$OH, —CH$_2$CH$_2$OH, —CH$_2$CN, —OCH$_3$, —CH$_2$OCH$_3$, or —CH$_2$CH$_2$S(O)$_2$CH$_3$. Also, included in this embodiment are compounds in which each R$_2$ is independently Cl, —CH$_3$, —CH$_2$CH$_3$, —CH$_2$OH, —CH$_2$CH$_2$OH, —OCH$_3$, —CH$_2$OCH$_3$, or —CH$_2$CH$_2$S(O)$_2$CH$_3$.

One embodiment provides a compound of Formula (I) or a salt thereof wherein A is —O-L$_1$-R$_6$; and G, R$_1$, R$_5$, R$_6$, R$_x$, L$_1$, and n are defined in the first aspect or the second aspect. Included in this embodiment are compounds in which L$_1$ is bond, —(CR$_x$R$_x$)$_{1-2}$—, —CH$_2$C(O)—, —CH$_2$C(O)NR$_x$(CR$_x$R$_x$)$_{0-2}$—, —CH$_2$NR$_x$C(O)—, or —CH$_2$NR$_x$C(O)CH$_2$—; and each R$_{6a}$ is independently F, —OH, C$_{1-4}$ alkyl, C$_{1-4}$ fluoroalkyl, C$_{1-4}$ hydroxyalkyl, —(CH$_2$)$_{1-2}$OCH$_3$, —NR$_x$R$_x$, —N(C$_{2-3}$ alkyl)$_2$, —(CH$_2$)$_{1-2}$NR$_x$R$_x$, —(CH$_2$)$_{1-2}$S(O)$_2$(C$_{1-2}$ alkyl), —(CH$_2$)$_{1-2}$C(O)NR$_x$R$_x$, —C(O)CH$_2$NR$_x$R$_x$, oxetanyl, tetrahydrofuranyl, tetrahydropyranyl, piperidinyl, isobutylpiperidinyl, piperazinyl, or —O(piperidinyl). Also included in this embodiment are compounds in which each $R_{6a}$ is independently F, —OH, $C_{1-4}$ alkyl, $C_{1-4}$ fluoroalkyl, $C_{1-4}$ hydroxyalkyl, —(CH$_2$)$_{1-2}$OCH$_3$, —NR$_x$R$_x$, —(CH$_2$)$_{1-2}$NR$_x$R$_x$, —(CH$_2$)$_{1-2}$S(O)$_2$(C$_{1-2}$ alkyl), —(CH$_2$)$_{1-2}$C(O)NR$_x$R$_x$, —C(O)CH$_2$NR$_x$R$_x$, oxetanyl, tetrahydrofuranyl, tetrahydropyranyl, piperidinyl, isobutylpiperidinyl, piperazinyl, or —O(piperidinyl).

One embodiment provides a compound of Formula (I) or a salt thereof wherein A is —O-L$_1$-R$_6$; L$_1$ is bond, —(CR$_x$R$_x$)$_{1-2}$—, —CH$_2$C(O)—, —CH$_2$C(O)NR$_x$(CR$_x$R$_x$)$_{0-2}$—, —CH$_2$NR$_x$C(O)—, or —CH$_2$NR$_x$C(O)CH$_2$—; R$_6$ is: (i) $C_{1-2}$ alkyl, —CH$_2$C(O)NHCH$_2$CR$_x$R$_x$OH, —CH$_2$C(O)NHCH$_2$CH$_2$CR$_x$R$_x$OH, —CH$_2$C(O)NHCH$_2$CH$_2$NR$_x$R$_x$, or —CH$_2$C(O)NHCH$_2$CHFCR$_x$R$_x$OH; or (ii) azabicyclo[3.2.1]octanyl, azaspiro[5.5]undecanyl, azetidinyl, $C_{3-6}$ cycloalkyl, diazabicyclo[2.2.1]heptanyl, diazaspiro[3.5]nonanyl, morpholinyl, tetrahydropyranyl, octahydrocyclopenta[c]pyrrolyl, piperazinyl, piperidinyl, pyrrolidinyl, or quinuclidinyl, each substituted with zero to 3 $R_{6a}$; and each $R_{6a}$ is independently F, —OH, $C_{1-4}$ alkyl, $C_{1-4}$ fluoroalkyl, $C_{1-4}$ hydroxyalkyl, —(CH$_2$)$_{1-2}$OCH$_3$, —NR$_x$R$_x$, —N(C$_{2-3}$ alkyl)$_2$, —(CH$_2$)$_{1-2}$NR$_x$R$_x$, —(CH$_2$)$_{1-2}$S(O)$_2$(C$_{1-2}$ alkyl), —(CH$_2$)$_{0-2}$C(O)NR$_x$R$_x$, —C(O)CH$_2$NR$_x$R$_x$, oxetanyl, tetrahydrofuranyl, tetrahydropyranyl, piperidinyl, isobutylpiperidinyl, piperazinyl, or —O(piperidinyl). Also included in this embodiment are compounds in which each $R_{6a}$ is independently F, —OH, $C_{1-4}$ alkyl, $C_{1-4}$ fluoroalkyl, $C_{1-4}$ hydroxyalkyl, —(CH$_2$)$_{1-2}$OCH$_3$, —NR$_x$R$_x$, —(CH$_2$)$_{1-2}$NR$_x$R$_x$, —(CH$_2$)$_{1-2}$S(O)$_2$(C$_{1-2}$ alkyl), —(CH$_2$)$_{1-2}$C(O)NR$_x$R$_x$, —C(O)CH$_2$NR$_x$R$_x$, oxetanyl, tetrahydrofuranyl, tetrahydropyranyl, piperidinyl, isobutylpiperidinyl, piperazinyl, or —O(piperidinyl); and G, R$_1$, R$_5$, R$_x$, and n are defined in the first aspect or the second aspect.

One embodiment provides a compound of Formula (I) or a salt thereof wherein A is —NR$_7$R$_8$; and G, R$_1$, R$_5$, R$_7$, R$_8$, R$_x$, R$_y$, n, and p are defined in the first aspect or the second aspect. Included in this embodiment are compounds in which R$_7$ is: (i) —CH$_2$CH$_2$NH$_2$, —CH$_2$CH$_2$NHC(O)CH$_2$N(CH$_3$)$_2$, —CH$_2$(isopropyl azaspiro[3.5]nonanyl), —CH$_2$(methylpyrrolidinyl), —C(O)(CH$_2$)$_{1-3}$NH$_2$, —C(O)CH(NH$_2$)CH$_2$CH$_2$CH$_3$, —C(O)CH(NH$_2$)CH$_2$CH(CH$_3$)$_2$, —C(O)CH(NH$_2$)CH(CH$_3$)CH$_2$CH$_3$, —C(O)CH(NH$_2$)CH$_2$CH$_2$C(O)OH, —C(O)CH(NH$_2$)(CH$_2$)$_{3-4}$NH$_2$, —C(O)CH(NH$_2$)(CH$_2$)$_{1-2}$C(O)NH$_2$, —C(O)CH(NH$_2$)(cyclohexyl), —C(O)CH(NH$_2$)(phenyl), —C(O)(aminocyclohexyl), —C(O)(morpholinyl), —C(O)(pyrrolidinyl), pentamethylpiperidinyl, methylpiperidinyl-piperidinyl, methylpyrrolidinyl-pyrrolidinyl, or phenyl substituted with —OCH$_2$CH$_2$(pyrrolidinyl) or —OCH$_2$CH$_2$NHCH$_2$CH$_3$; or (ii) cyclohexyl substituted with —NR$_x$(CH$_2$)$_{2-3}$N(CH$_3$)$_2$, —NHCH$_2$CH$_2$NHCH$_3$, —NH(methylpiperidinyl), —NH(CH$_2$)$_{2-3}$(morpholinyl), dimethylamino piperidinyl, or piperazinyl substituted with —CH$_3$, —CH$_2$CH$_3$, —C(CH$_3$)$_3$, —CH$_2$CH(CH$_3$)$_2$, —C(O)CH$_3$, —CH$_2$CH$_2$OCH$_3$, —CH$_2$(methylphenyl), —(CH$_2$)$_{2-3}$(pyrrolidinyl), cyclopentyl, pyridinyl, or methylpiperidinyl; R$_{7b}$ is: (i) —OH, $C_{1-6}$ alkyl, $C_{3-4}$ fluoroalkyl, $C_{3-4}$ hydroxyalkyl, —CH$_2$CN, —CH$_2$CH$_2$CN, —CH$_2$CH$_2$CH$_2$C≡CH, —(CR$_x$R$_x$)$_{1-2}$OCH$_3$, —(CH$_2$)$_{2-3}$S(O)$_2$CH$_3$, —(CH$_2$)$_{1-2}$NR$_x$R$_x$, —(CH$_2$)$_{1-2}$C(O)NR$_x$R$_x$, —NR$_y$R$_y$, —NR$_x$(C$_{1-4}$ hydroxyalkyl), —NH(CH$_2$CH$_2$OCH$_3$), —NR$_y$(C$_{1-2}$ cyanoalkyl), —N(CH$_2$CH$_2$CN)$_2$, —NR$_x$(C$_{1-2}$ fluoroalkyl), —NR$_x$(C$_{2-4}$ hydroxyfluoroalkyl), —(CH$_2$)$_{1-2}$C(O)NR$_x$R$_x$, —NR$_x$(CH$_2$)$_{1-2}$C(O)NR$_x$R$_x$, —N((CH$_2$)$_{1-2}$C(O)NR$_x$R$_x$)$_2$, —NR$_x$(CH$_2$)$_{1-2}$S(O)$_2$(C$_{1-2}$ alkyl), —NR$_x$(CH$_2$)$_{1-3}$NR$_x$R$_x$, —NR$_x$CH$_2$CH$_2$N(CH$_3$)$_2$, —NR$_x$C(O)(CH$_2$)$_{1-2}$NR$_x$R$_x$, —NR$_x$(CH$_2$CH$_2$S(O)$_2$CH$_3$), —OCH$_2$CH$_2$N(CH$_3$)$_2$, —C(O)(CR$_x$R$_x$)$_{1-2}$NR$_y$R$_y$, —C(O)(CR$_x$R$_x$)$_{1-2}$NR$_y$(C$_{1-4}$ hydroxyalkyl), —C(O)(CR$_x$R$_x$)$_{1-2}$NR$_x$(CH$_2$CH$_2$OCH$_3$), —S(O)$_2$CH$_2$CH$_2$N(CH$_3$)$_2$, —(CH$_2$)$_{1-2}$R$_{7d}$, —NR$_x$R$_{7d}$, —NR$_x$(CH$_2$)$_{1-2}$R$_{7d}$, —NR$_{7d}$R$_{7d}$, —N((CH$_2$)$_{1-2}$R$_{7d}$)$_2$, —OR$_{7d}$, —C(O)R$_{7d}$, —C(O)(CR$_x$R$_x$)$_{1-2}$R$_{7d}$, or —C(O)(CR$_x$R$_x$)$_{1-2}$NR$_x$R$_{7d}$; or (ii) azepanyl, azetidinyl, cyclobutyl, cyclohexyl, diazepanyl, dioxotetrahydrothiopyranyl, dioxothiomorpholinyl, morpholinyl, oxaazaspiro[3.3]heptanyl, oxaazaspiro[4.3]octanyl, oxetanyl, piperazinonyl, piperazinyl, piperidinyl, pyridinyl, pyrimidinyl, pyrrolidinonyl, pyrrolidinyl, tetrahydrofuranyl, tetrahydroisoquinolinyl, tetrahydropyranyl, or thiadiazolyl, each substituted with zero to 1 $R_{8a}$ and zero to 3 $R_{8b}$; R$_{7d}$ is azaspiro[3.5]nonanyl, azetidinyl, bicyclo[1.1.1]pentanyl, $C_{3-6}$ cycloalkyl, dioxothiaazaspiro[3.3]heptanyl, morpholinyl, oxaazaspiro[3.3]heptanyl, oxaazaspiro[4.3]octanyl, oxaazaspiro[4.4]nonyl, oxetanyl, phenyl, piperidinyl, pyrazolyl, pyrrolidinyl, tetrahydrofuranyl, tetrahydropyranyl, thiadiazolyl, or triazolyl, each substituted with zero to 2 substituents selected from F, —OH, $C_{1-3}$ alkyl, —CH$_2$OH, —OCH$_3$, —NR$_x$R$_x$, —C(O)CH$_3$, —S(O)$_2$CH$_3$, methylpiperidinyl, methylpyrrolidinyl, tetramethylpiperidinyl, —OCH$_2$CH$_2$(pyrrolidinyl), and —OCH$_2$CH$_2$NHCH$_2$CH$_3$; and zero to 4 substituents selected from —CH$_3$; R$_8$ is H, —CH$_3$ or —CH$_2$CH$_3$; R$_{8a}$ is —OH, $C_{1-4}$ alkyl, $C_{1-3}$ fluoroalkyl, —(CH$_2$)$_{1-2}$O(C$_{1-2}$ alkyl), $C_{1-2}$ alkoxy, —C(O)(C$_{1-2}$ alkyl), —C(O)O(C$_{1-2}$ alkyl), —CH$_2$(C$_{3-6}$ cycloalkyl), —(CH$_2$)$_{1-2}$(methyl phenyl), —(CH$_2$)$_{1-3}$(pyrrolidinyl), —(CH$_2$)$_{1-2}$(methylpyrazolyl), —(CH$_2$)$_{1-2}$(thiophenyl), —NR$_x$R$_x$, $C_{3-6}$ cycloalkyl, methylpiperidinyl, or pyridinyl; and each R$_{8b}$ is independently F or —CH$_3$.

One embodiment provides a compound of Formula (I) or a salt thereof wherein A is —NR$_7$R$_8$; and G, R$_1$, R$_5$, R$_7$, R$_8$, R$_x$, and n are defined in the first aspect or the second aspect. Included in this embodiment are compounds in which R$_7$ is: (i) R$_{7a}$, —CH$_2$R$_{7a}$, —C(O)R$_{7a}$, —C(O)CH(NH$_2$)R$_{7a}$, —C(O)(CH$_2$)$_{1-3}$NH$_2$, —C(O)CH(NH$_2$)(C$_{1-4}$ alkyl), —C(O)CH(NH$_2$)(CH$_2$)$_{1-2}$C(O)OH, —C(O)CH(NH$_2$)(CH$_2$)$_{2-4}$NH$_2$, or —C(O)CH(NH$_2$)(CH$_2$)$_{1-3}$C(O)NH$_2$; or (ii) $C_{3-6}$ cycloalkyl substituted with one substituent selected from —NR$_x$(CH$_2$)$_{2-3}$NR$_x$R$_x$, —NH(CH$_2$)$_{2-3}$NHCH$_3$, —NH(methylpiperidinyl), —NH(CH$_2$)$_{2-3}$(morpholinyl), dimethylamino piperidinyl, and piperazinyl substituted with a substituent selected from $C_{1-4}$ alkyl, —C(O)CH$_3$, —(CH$_2$)$_{1-2}$OCH$_3$, —CH$_2$(methylphenyl), —(CH$_2$)$_{2-3}$(pyrrolidinyl), $C_{3-6}$ cycloalkyl, pyridinyl, and methylpiperidinyl; R$_{7b}$ is: (i) $C_{1-4}$ alkyl, $C_{1-3}$ hydroxyalkyl, —(CH$_2$)$_{2-3}$C≡CH, —(CH$_2$)$_{0-3}$NR$_x$R$_x$, —NR$_x$(CH$_2$)$_{1-3}$NR$_x$R$_x$, —N(CH$_3$)CH$_2$CH$_2$NH$_2$, —O(CH$_2$)$_{1-3}$NR$_x$R$_x$, —(CH$_2$)$_{1-2}$R$_{7d}$, —NHR$_{7d}$, —NH(CH$_2$)$_{1-2}$R$_{7d}$, or —OR$_{7d}$; or (ii) azepanyl, diazepanyl, morpholinyl, piperazinyl, piperidinyl, pyridinyl, pyrrolidinonyl, pyrrolidinyl, or tetrahydroisoquinolinyl, each substituted with zero to 1 $R_{8a}$ and zero to 3 $R_{8b}$; R$_{7d}$ is azaspiro[3.5]nonanyl, $C_{3-6}$ cycloalkyl, morpholinyl, phenyl, piperidinyl, or pyrrolidinyl, each substituted with zero to 1 substituent selected from $C_{1-3}$ alkyl, —NH$_2$, methylpiperidinyl, methylpyrrolidinyl, —OCH$_2$CH$_2$(pyrrolidinyl), —OCH$_2$CH$_2$NHCH$_2$CH$_3$; and zero to 4 substituents selected from —CH$_3$; and R$_8$ is H or $C_{1-2}$ alkyl; R$_{8a}$ is —OH, $C_{1-4}$ alkyl, $C_{1-3}$ fluoroalkyl, —(CH$_2$)$_{1-2}$O(C$_{1-2}$ alkyl), —C(O)(C$_{1-2}$ alkyl), —CH$_2$(C$_{3-6}$ cycloalkyl), —(CH$_2$)$_{1-2}$(methyl phenyl), —(CH$_2$)$_{1-3}$(pyrrolidinyl), —(CH$_2$)$_{1-2}$(methylpyrazolyl), —(CH$_2$)$_{1-2}$(thiophenyl), —NR$_x$R$_x$, $C_{3-6}$ cycloalkyl, methylpiperidinyl, or pyridinyl; and each R$_{8b}$ is independently F or —CH$_3$.

One embodiment provides a compound of Formula (I) or a salt thereof wherein A is —NR$_7$R$_8$; and G, R$_1$, R$_5$, R$_7$, R$_8$, $R_x$, $R_y$, and n are defined in the first aspect or the second aspect. Included in this embodiment are compounds in which $R_7$ and $R_8$ together with the nitrogen atom to which they are attached form a heterocyclic ring selected azetidinyl, diazabicyclo[2.2.1]heptanyl, diazabicyclo[2.2.2]octanyl, diazabicyclo[3.1.1]heptanyl, diazabicyclo[3.2.1]octanyl, azaspiro[3.3]heptanyl, diazaspiro[2.5]octanyl, diazaspiro[3.3]heptanyl, diazepanonyl, diazepanyl, diazaspiro[3.5]nonanyl, diazaspiro[5.5]undecanyl, imidazolyl, imidazolidinonyl, octahydro-1H-pyrrolo[3,4-b]pyridinyl, oxadiazabicyclo[3.3.1]nonanyl, piperazinyl, piperazinonyl, piperidinyl, pyrrolidinonyl, pyrrolidinyl, and pyrrolyl, wherein said heterocyclic ring is substituted with zero to 1 $R_{7b}$ and zero to 2 $R_{7c}$; $R_{7b}$ is: (i) —OH, $C_{1-6}$ alkyl, $C_{1-4}$ fluoroalkyl, $C_{1-4}$ hydroxyalkyl, $C_{1-2}$ aminoalkyl, —(CH$_2$)$_{2-3}$C≡CH, —(CR$_x$R$_x$)$_{1-2}$O(C$_{1-2}$ alkyl), —(CH$_2$)$_{1-3}$S(O)$_2$(C$_{1-2}$ alkyl), —(CH$_2$)$_{0-3}$NR$_x$R$_y$, —(CH$_2$)$_{1-2}$C(O)NR$_x$R$_x$, —NR$_y$R$_y$, —NR$_x$(C$_{1-4}$ hydroxyalkyl), —NR$_y$(C$_{1-2}$ cyanoalkyl), —N(C$_{1-2}$ cyanoalkyl)$_2$, —NR$_x$(C$_{1-2}$ fluoroalkyl), —NR$_x$(C$_{2-4}$ hydroxyfluoroalkyl), —(CR$_x$R$_x$)$_{1-2}$C(O)NR$_x$R$_x$, —NR$_x$(CH$_2$)$_{1-2}$C(O)NR$_x$R$_x$, —N((CH$_2$)$_{0-2}$C(O)NR$_x$R$_x$)$_2$, —NR$_x$(CH$_2$)$_{1-2}$S(O)$_2$(C$_{1-2}$ alkyl), —NR$_x$(CH$_2$)$_{1-3}$NR$_x$R$_x$, —NR$_x$CH$_2$CH$_2$NR$_x$R$_x$, —NR$_x$C(O)(CH$_2$)$_{1-2}$NR$_x$R$_x$, —NR$_x$(CH$_2$CH$_2$S(O)$_2$CH$_3$), —(CH$_2$)$_{1-2}$NR$_x$C(O)(CH$_2$)$_{1-2}$NR$_x$R$_x$, —O(CH$_2$)$_{1-3}$NR$_x$R$_x$, —C(O)(CR$_x$R$_x$)$_{1-2}$NR$_y$R$_y$, —C(O)(CR$_x$R$_x$)$_{1-2}$NR$_y$(C$_{1-4}$ hydroxyalkyl), —C(O)(CR$_x$R$_x$)$_{1-2}$NR$_x$(CH$_2$CH$_2$OCH$_3$), —S(O)$_2$CH$_2$CH$_2$N(CH$_3$)$_2$, —(CH$_2$)$_{1-2}$R$_{7d}$, —NR$_x$R$_{7d}$, —NR$_x$(CH$_2$)$_{1-2}$R$_{7d}$), —NR$_{7d}$R$_{7d}$, —N((CH$_2$)$_{1-2}$R$_{7d}$)$_2$, —OR$_{7d}$, —C(O)R$_{7d}$, —C(O)(CR$_x$R$_x$)$_{1-2}$R$_{7d}$, or —C(O)(CR$_x$R$_x$)$_{1-2}$NR$_x$R$_{7d}$; or (ii) azepanyl, azetidinyl, $C_{3-6}$ cycloalkyl, diazepanyl, dioxotetrahydrothiopyranyl, dioxothiomorpholinyl, morpholinyl, oxaazaspiro[3.3]heptanyl, oxaazaspiro[4.3]octanyl, oxetanyl, piperazinonyl, piperazinyl, piperidinyl, pyridinyl, pyrimidinyl, pyrrolidinonyl, pyrrolidinyl, tetrahydrofuranyl, tetrahydroisoquinolinyl, tetrahydropyranyl, or thiadiazolyl, each substituted with zero to 1 $R_{8a}$ and zero to 3 $R_{8b}$; each $R_{7c}$ is independently F, —CH$_3$ or —CH$_2$CN; $R_{7d}$ is azaspiro[3.5]nonanyl, azetidinyl, bicyclo[1.1.1]pentanyl, $C_{3-6}$ cycloalkyl, dioxothiaazaspiro[3.3]heptanyl, morpholinyl, oxaazaspiro[3.3]heptanyl, oxaazaspiro[4.3]octanyl, oxaazaspiro[4.4]nonyl, oxetanyl, phenyl, piperidinyl, pyrazolyl, pyrrolidinyl, tetrahydrofuranyl, tetrahydropyranyl, thiadiazolyl, or triazolyl, each substituted with zero to 2 substituents independently selected from F, —OH, $C_{1-3}$ alkyl, $C_{1-2}$ hydroxyalkyl, $C_{1-2}$ alkoxy, —NR$_x$R$_x$, —C(O)CH$_3$, —S(O)$_2$CH$_3$, methylpiperidinyl, methylpyrrolidinyl, tetramethylpiperidinyl, —OCH$_2$CH$_2$(pyrrolidinyl), and —OCH$_2$CH$_2$NHCH$_2$CH$_3$; and zero to 4 substituents selected from —CH$_3$; $R_{8a}$ is —OH, $C_{1-4}$ alkyl, $C_{1-3}$ fluoroalkyl, —(CH$_2$)$_{1-2}$O(C$_{1-2}$ alkyl), $C_{1-2}$ alkoxy, —C(O)(C$_{1-2}$ alkyl), —C(O)O(C$_{1-2}$ alkyl), —CH$_2$(C$_{3-6}$ cycloalkyl), —(CH$_2$)$_{1-2}$(methyl phenyl), —(CH$_2$)$_{1-3}$(pyrrolidinyl), —(CH$_2$)$_{1-2}$(methylpyrazolyl), —(CH$_2$)$_{1-2}$(thiophenyl), —NR$_x$R$_x$, $C_{3-6}$ cycloalkyl, methylpiperidinyl, or pyridinyl; and each $R_{8b}$ is independently F or —CH$_3$.

One embodiment provides a compound of Formula (I) or a salt thereof wherein A is —NR$_7$R$_8$; and G, $R_1$, $R_5$, $R_7$, $R_8$, and n are defined in the first aspect or the second aspect. Included in this embodiment are compounds in which $R_7$ and $R_8$ together with the nitrogen atom to which they are attached form a heterocyclic ring selected from azetidinyl, diazepanonyl, diazepanyl, diazaspiro[3.5]nonanyl, diazaspiro[5.5]undecanyl, imidazolyl, imidazolidinonyl, octahydro-1H-pyrrolo[3,4-b]pyridinyl, piperazinyl, piperidinyl, pyrrolidinonyl, pyrrolidinyl, and pyrrolyl, wherein said heterocyclic ring is substituted with zero to 1 $R_{7b}$ and zero to 2 $R_{7c}$; $R_{7b}$ is: (i) $C_{1-4}$ alkyl, $C_{1-3}$ hydroxyalkyl, —(CH$_2$)$_{2-3}$C≡CH, —(CH$_2$)$_{0-3}$NR$_x$R$_x$, —NR$_x$(CH$_2$)$_{1-3}$NR$_x$R$_x$, —N(CH$_3$)CH$_2$CH$_2$NH$_2$, —O(CH$_2$)$_{1-3}$NR$_x$R$_x$, —(CH$_2$)$_{1-2}$R$_{7d}$, —NHR$_{7d}$, —NH(CH$_2$)$_{1-2}$R$_{7d}$, or —OR$_{7d}$; or (ii) azepanyl, diazepanyl, morpholinyl, piperazinyl, piperidinyl, pyridinyl, pyrrolidinonyl, pyrrolidinyl, or tetrahydroisoquinolinyl, each substituted with zero to 1 $R_{8a}$ and zero to 3 $R_{8b}$; each $R_{7c}$ is independently F, —CH$_3$ or —CH$_2$CN; $R_{8a}$ is —OH, $C_{1-4}$ alkyl, $C_{1-3}$ fluoroalkyl, —(CH$_2$)$_{1-2}$O(C$_{1-2}$ alkyl), —C(O)(C$_{1-2}$ alkyl), —CH$_2$(C$_{3-6}$ cycloalkyl), —(CH$_2$)$_{1-2}$(methyl phenyl), —(CH$_2$)$_{1-3}$(pyrrolidinyl), —(CH$_2$)$_{1-2}$(methylpyrazolyl), —(CH$_2$)$_{1-2}$(thiophenyl), —NR$_x$R$_x$, $C_{3-6}$ cycloalkyl, methylpiperidinyl, or pyridinyl; and each $R_{8b}$ is independently F or —CH$_3$.

One embodiment provides a compound of Formula (I) or a salt thereof wherein A is —(CR$_x$R$_x$)$_{1-3}$R$_{11}$, —(CR$_x$R$_x$)$_{1-3}$NR$_x$C(O)R$_{11}$, or —(CR$_x$R$_x$)$_{1-2}$NR$_x$C(O)(CH$_2$)$_{1-2}$NR$_x$R$_x$; and G, $R_1$, $R_5$, $R_{11}$, $R_x$, and n are defined in the first aspect or the second aspect. Included in this embodiment are compounds in which $R_{11}$ is azetidinyl, azaspiro[3.5]nonanyl, dioxidothiomorpholinyl, hexahydropyrrolo[3,4-c]pyrrolyl, morpholinyl, piperazinyl, piperidinyl, pyridinyl, or pyrrolidinyl, each substituted with zero to 3 substituents independently selected from F, Cl, —CN, $C_{1-3}$ alkyl, $C_{1-2}$ aminoalkyl, —CH$_2$(methyloxetanyl), —CH$_2$(triazolyl), —CH$_2$(phenyl), —C(O)CH$_2$NR$_x$R$_x$, —CH$_2$CR$_x$R$_x$OH, —CH$_2$C(O)NR$_x$R$_x$, —CH$_2$CH$_2$S(O)$_2$(C$_{1-3}$ alkyl), —CH$_2$CH$_2$S(O)(C$_{1-3}$ alkyl), oxetanyl, tetrahydrofuranyl, and tetrahydropyranyl. Also included in this embodiment are compounds in which $R_{11}$ is azetidinyl, azaspiro[3.5]nonanyl, dioxidothiomorpholinyl, hexahydropyrrolo[3,4-c]pyrrolyl, morpholinyl, piperazinyl, piperidinyl, pyridinyl, or pyrrolidinyl, each substituted with zero to 3 substituents independently selected from F, Cl, —CN, $C_{1-3}$ alkyl, $C_{1-2}$ aminoalkyl, —CH$_2$(phenyl), —C(O)CH$_2$NR$_x$R$_x$, —CH$_2$CR$_x$R$_x$OH, —CH$_2$C(O)NR$_x$R$_x$, —CH$_2$CH$_2$S(O)$_2$(C$_{1-3}$ alkyl), —CH$_2$CH$_2$S(O)(C$_{1-3}$ alkyl), oxetanyl, tetrahydrofuranyl, and tetrahydropyranyl.

One embodiment provides a compound of Formula (I) or a salt thereof wherein A is —CR$_x$R$_{12}$R$_{13}$, wherein $R_{12}$ and $R_{13}$ together with the carbon atom to which they are attached form a cyclic group selected from azabicyclo[4.1.1]octanyl, azepanyl, azetidinyl, $C_{3-7}$ cycloalkyl, diazepanyl, azaspiro[3.3]heptanyl, diazaspiro[4.5]decanonyl, morpholinyl, octahydrocyclopenta[c]pyrrolyl, piperazinyl, piperidinyl, pyrrolidinyl, and quinuclidinyl, each substituted with zero to 4 $R_{12a}$; and G, $R_1$, $R_5$, $R_{12}$, $R_{13}$, $R_x$, $R_y$, and n are defined in the first aspect or the second aspect. Included in this embodiment are compounds in which $R_{12}$ and $R_{13}$ together with the carbon atom to which they are attached form a cyclic group selected from azabicyclo[4.1.1]octanyl, azepanyl, azetidinyl, $C_{3-7}$ cycloalkyl, diazepanyl, diazaspiro[4.5]decanonyl, morpholinyl, octahydrocyclopenta[c]pyrrolyl, piperazinyl, piperidinyl, pyrrolidinyl, and quinuclidinyl, each substituted with zero to 4 $R_{12a}$. Also included in this embodiment are compounds in which each $R_{12a}$ is independently —OH, $C_{1-4}$ alkyl, $C_{1-3}$ fluoroalkyl, $C_{1-2}$ cyanoalkyl, $C_{1-4}$ hydroxyalkyl, —(CH$_2$)$_{1-2}$O(C$_{1-2}$ alkyl), —CH$_2$C(O)NR$_x$R$_x$, —(CH$_2$)$_{1-2}$S(O)$_2$(C$_{1-2}$ alkyl), —(CH$_2$)$_{1-2}$NHS(O)$_2$(C$_{1-2}$ alkyl), —(CH$_2$)$_{1-2}$NR$_x$R$_x$, $C_{1-2}$ alkoxy, —NR$_y$R$_y$, —NR$_x$(C$_{1-3}$ fluoroalkyl), —NR$_x$(CH$_2$CH$_2$O(C$_{1-2}$ alkyl)), —NR$_x$(C$_{1-2}$ cyanoalkyl), —NR$_x$CH$_2$NR$_x$R$_x$, —NR$_x$(C$_{1-4}$ hydroxyalkyl), —NR$_x$(CH$_2$C(O)NH$_2$), —NR$_x$(OCH$_3$), —NR$_x$CH$_2$CH$_2$S(O)$_2$(C$_{1-2}$ alkyl), —NR$_x$C(O)CH$_3$, —NR$_x$C(O)(C$_{1-2}$ fluoroalkyl), —NR$_x$C(O)CR$_x$R$_x$NR$_x$R$_x$, —NR$_x$C(O)CH$_2$NR$_y$R$_y$, —NR$_x$C(O)CH$_2$NR$_x$(C$_{1-4}$ hydroxyalkyl), —NR$_x$CH$_2$C(O)

NR$_x$R$_x$, —NR$_x$S(O)$_2$CH$_3$, —C(O)(C$_{1-5}$ alkyl), —C(O)CH$_2$O(C$_{1-2}$ alkyl), —C(O)CH$_2$CH$_2$O(C$_{1-2}$ alkyl), —C(O)(CH$_2$)$_{1-2}$NR$_x$R$_x$, —C(O)CHR$_x$NR$_x$R$_y$, R$_{12b}$, —CR$_x$R$_x$R$_{12b}$, —C(O)R$_{12b}$, —C(O)CH$_2$NR$_x$R$_{12b}$, —C(O)NR$_x$R$_{12b}$, —NR$_x$C(O)CR$_x$R$_x$R$_{12b}$, —NR$_x$R$_{12b}$, —NR$_x$CR$_x$R$_x$R$_{12b}$, —NR$_x$C(O)CH$_2$NR$_x$R$_{12b}$, —NR$_x$C(O)CH$_2$NR$_x$CH$_2$R$_{12b}$, —NR$_x$CH$_2$C(O)NR$_x$R$_{12b}$, or —OR$_{12b}$; and R$_{12b}$ is azetidinyl, bicyclo[1.1.1]pentanyl, C$_{3-6}$ cycloalkyl, diazabicyclo[2.2.1]heptanyl, dioxolanyl, dioxothiaazaspiro[3.3]heptanyl, dioxidotetrahydrothiopyranyl, dioxidothiomorpholinyl, imidazolyl, morpholinyl, octahydrocyclopenta[c]pyrrolyl, octahydropyrrolo[3,4-c]pyrrolyl, oxaazaspiro[3.3]heptanyl, oxaazaspiro[4.3]octanyl, oxaazaspiro[4.4]nonanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, Cl, —OH, C$_{1-3}$ alkyl, C$_{1-2}$ hydroxyalkyl, C$_{1-2}$ alkoxy, —(CH$_2$)$_{1-2}$O(C$_{1-2}$ alkyl), —NR$_x$R$_x$, —C(O)NR$_x$R$_x$, and —CH$_2$S(O)$_2$(C$_{1-2}$ alkyl).

One embodiment provides a compound of Formula (I) or a salt thereof wherein A is an aromatic group selected from [1,2,4]triazolo[1,5-a]pyridinyl, imidazo[1,2-a]pyridinyl, imidazolyl, indazolyl, isoquinolinyl, oxadiazolyl, oxazolyl, phenyl, pyrazinyl, pyrazolo[3,4-b]pyridinyl, pyrazolyl, pyridazinyl, pyridinyl, pyrimidinyl, pyrrolyl, quinolinonyl, quinolinyl, quinoxalinyl, tetrahydro-[1,2,4]triazolo[1,5-a]pyrazinyl, tetrahydroimidazo[1,2-a]pyrazinyl, tetrahydroisoquinolinyl, tetrahydrothiazolo[5,4-c]pyridinyl, tetrahydrothieno[2,3-c]pyridinyl, thiadiazolyl, thiazolyl, thiooxadiazolyl, and triazolyl, each substituted with zero to 2 R$_{14a}$ and zero to 3 R$_{14b}$; and G, R$_1$, R$_5$, R$_{14a}$, R$_{14b}$, R$_x$, R$_y$, and n are defined in the first aspect. Included in this embodiment are compounds in which each R$_{14a}$ is independently: (i) H, F, Cl, —OH, C$_{1-5}$ alkyl, C$_{1-2}$ fluoroalkyl, C$_{1-2}$ hydroxyalkyl, —(CH$_2$)$_{0-2}$OCH$_3$, —CHR$_x$NR$_x$(C$_{1-5}$ alkyl), —CHR$_x$NR$_x$(C$_{1-2}$ cyanoalkyl), —CHR$_x$NR$_x$((CH$_2$)$_{1-2}$OCH$_3$), —CHR$_x$N((CH$_2$)$_{1-2}$OCH$_3$)$_2$, —CH$_2$NR$_x$(CH$_2$C≡CR$_x$), —CH$_2$NR$_x$CH$_2$CH$_2$NR$_x$R$_x$, —(CH$_2$)$_{1-3}$CR$_x$R$_x$NR$_x$R$_x$, —CH(NH$_2$)(CH$_2$)$_{3-4}$NR$_x$R$_x$, —CH$_2$NR$_x$(CH$_2$)$_{1-2}$O(C$_{1-3}$ alkyl), —CH$_2$NR$_x$(CH$_2$)$_{1-2}$O(CH$_2$)$_{1-2}$OH, —CH$_2$NH(CH$_2$)$_{1-2}$S(O)$_2$OH, —CH$_2$C(O)NR$_x$R$_x$, —NR$_x$R$_y$, —NR$_x$(CH$_2$)$_{2-3}$NR$_x$R$_x$, —NR$_x$C(O)(C$_{1-2}$ alkyl), —NR$_x$C(O)(C$_{1-2}$ fluoroalkyl), —NR$_x$C(O)O(C$_{1-3}$ alkyl), —NR$_x$C(O)(CH$_2$)$_{1-2}$NR$_x$R$_x$, —NR$_x$CH$_2$C(O) CH$_2$NR$_x$R$_x$, —C(O)(C$_{1-2}$ alkyl), —C(O)CH$_2$CR$_x$R$_x$OH, —C(O)CH$_2$NR$_x$R$_x$, —C(O)NR$_x$R$_x$, —C(O)NR$_x$(CH$_2$CN), —C(O)NR$_x$(CR$_x$R$_x$)$_{2-3}$NR$_x$R$_x$, —C(O)N(CH$_2$CH$_3$)(CR$_x$R$_x$)$_{2-3}$NR$_x$R$_x$, —C(O)NR$_x$CH$_2$C(O)NR$_x$R$_x$, —C(O)NR$_x$CH$_2$CH$_2$NR$_x$C(O)CH$_3$, —O(CR$_x$R$_x$)$_{2-3}$NR$_x$R$_x$, —S(O)$_2$NR$_x$R$_x$, or —C(O)CH$_2$S(O)$_2$(C$_{1-2}$ alkyl); (ii) 8-azabicyclo[3.2.1]octanyl, azaspiro[3.5]nonanyl, azetidinyl, benzo[c][1,2,5]oxadiazolyl, cyclopentyl, cyclohexyl, diazepanyl, morpholinyl, phenyl, piperazinyl, piperidinyl, pyrazolyl, pyridinyl, pyrrolidinonyl, quinolinyl, quinuclidinyl, tetrahydroisoquinolinyl, tetrahydropyridinyl, or thiazolidinyl, each substituted with zero to 2 substituents independently selected from C$_{1-4}$ alkyl, C$_{1-2}$ fluoroalkyl, C$_{1-4}$ hydroxyalkyl, —NR$_x$R$_x$, —(CH$_2$)$_{1-2}$NR$_x$R$_x$, —C(O)(C$_{1-2}$ alkyl), —C(O)CH$_2$NR$_x$R$_x$, —C(O)O(C$_{1-3}$ alkyl), —CH$_2$C(O)NR$_x$R$_x$, C$_{3-6}$ cycloalkyl, —CH$_2$(phenyl), —CH$_2$(pyrrolyl), —CH$_2$(morpholinyl), —CH$_2$(methylpiperazinyl), —CH$_2$(thiophenyl), methylpiperidinyl, isobutylpiperidinyl, and pyridinyl; or (iii) -L$_3$-R$_{14c}$; each R$_{14b}$ is F, —CH$_3$, or —OCH$_3$; and R$_{14}$ is adamantanyl, azepanyl, azetidinyl, C$_{3-7}$ cycloalkyl, diazepanyl, imidazolyl, indolyl, morpholinyl, octahydropyrrolo[3,4-c]pyrrolyl, phenyl, piperazinonyl, piperazinyl, piperidinyl, pyridinyl, pyrrolidinonyl, pyrrolidinyl, pyrrolyl, triazolyl, or tetrazolyl, each substituted with zero to 1 substituent selected from F, —OH, C$_{1-4}$ alkyl, C$_{1-3}$ hydroxyalkyl, —NR$_x$R$_y$, —NR$_x$C(O)CH$_3$, —C(O)(C$_{1-2}$ alkyl), —C(O)NR$_x$R$_x$, —C(O)N(CH$_2$CH$_3$)$_2$, —C(O)(tetrahydrofuranyl), —C(O)O(C$_{1-2}$ alkyl), —CH$_2$C(O)NR$_x$R$_y$, morpholinyl, methylpiperidinyl, pyrazinyl, pyridinyl, and pyrrolidinyl.

One embodiment provides a compound of Formula (I), N-oxide, or a salt thereof, wherein said compound has the structure:

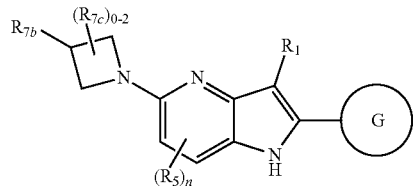

wherein G, R$_1$, R$_2$, R$_5$, R$_{7b}$, R$_{7c}$, n, and p are defined in the first aspect or the second aspect. Included in this embodiment are compounds in which G is

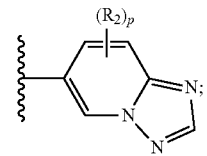

and R$_1$ is —CH(CH$_3$)$_2$. Also included in this embodiment are compounds in which n is zero.

One embodiment provides a compound of Formula (I), N-oxide, or a salt thereof, wherein said compound has the structure:

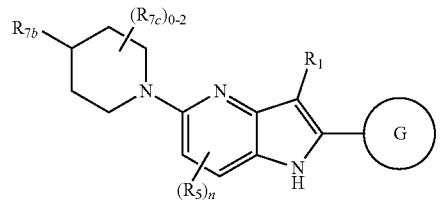

wherein G, R$_1$, R$_2$, R$_5$, R$_{7b}$, R$_{7c}$, n, and p are defined in the first aspect or the second aspect. Included in this embodiment are compounds in which G is

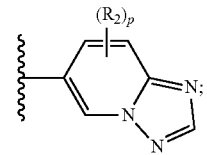

and R$_1$ is —CH(CH$_3$)$_2$. Also included in this embodiment are compounds in which n is zero.

One embodiment provides a compound of Formula (I), N-oxide, or a salt thereof, wherein said compound has the structure:

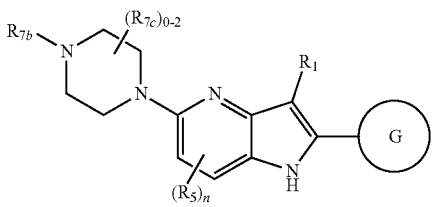

wherein G, $R_1$, $R_2$, $R_5$, $R_{7b}$, $R_{7c}$, n, and p are defined in the first aspect or the second aspect. Included in this embodiment are compounds in which G is

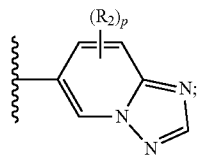

and $R_1$ is —CH(CH$_3$)$_2$. Also included in this embodiment are compounds in which n is zero.

One embodiment provides a compound of Formula (I), N-oxide, or a salt thereof, wherein said compound has the structure:

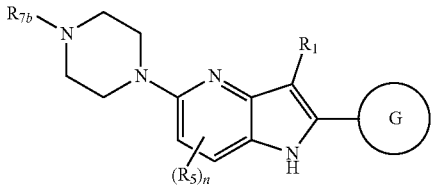

wherein $R_{7b}$ is —C(O)(CR$_x$R$_x$)$_{1-2}$NR$_y$R$_y$, —C(O)(CR$_x$R$_x$)$_{1-2}$NR$_y$(C$_{1-4}$ hydroxyalkyl), or —C(O)(CR$_x$R$_x$)$_{1-2}$NR$_x$(CH$_2$CH$_2$CH$_3$); and G, $R_1$, $R_2$, $R_5$, $R_x$, $R_y$, n, and p are defined in the first aspect or the second aspect. Included in this embodiment are compounds in which G is

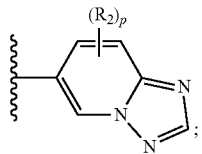

$R_1$ is —CH(CH$_3$)$_2$; and n is zero. Also included in this embodiment are compounds in which $R_{7b}$ is —C(O)(CR$_x$R$_x$)$_{1-2}$NR$_y$R$_y$. Additionally, included in this embodiment are compounds in which G is

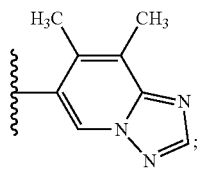 [SMILES: *c1cn2ncnc2c(C)c1C]

$R_1$ is —CH(CH$_3$)$_2$; $R_{7b}$ is —C(O)CH$_2$N(CH$_3$)$_2$ or —C(O)CH$_2$CH$_2$N(CH$_3$)$_2$ or and n is zero.

One embodiment provides a compound of Formula (I), N-oxide, or a salt thereof, wherein said compound has the structure:

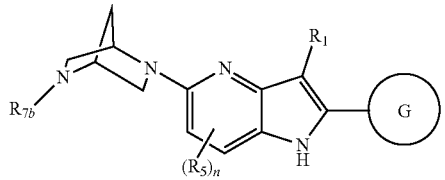

wherein G, $R_1$, $R_2$, $R_5$, $R_{7b}$, n, and p are defined in the first aspect or the second aspect. Included in this embodiment are compounds in which G is

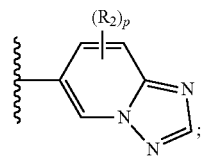

and $R_1$ is —CH(CH$_3$)$_2$. Also included in this embodiment are compounds in which n is zero.

One embodiment provides a compound of Formula (I), N-oxide, or a salt thereof, wherein said compound has the structure:

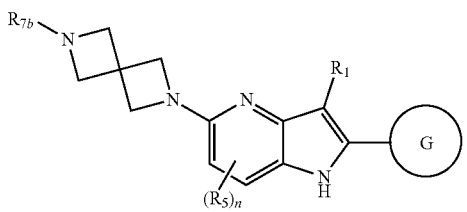

wherein G, $R_1$, $R_2$, $R_5$, $R_{7b}$, n, and p are defined in the first aspect or the second aspect. Included in this embodiment are compounds in which G is

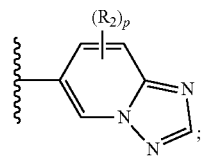

and $R_1$ is —CH(CH$_3$)$_2$. Also included in this embodiment are compounds in which compounds in which G is

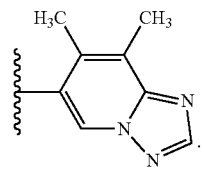 [SMILES: *c1cn2ncnc2c(C)c1C]

Additionally, included in this embodiment are compounds in which n is zero.

One embodiment provides a compound of Formula (I), N-oxide, or a salt thereof, wherein said compound has the structure:

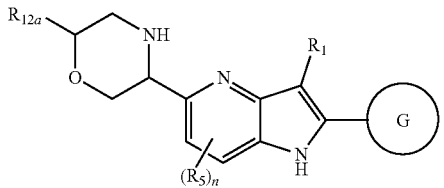

wherein G, $R_1$, $R_2$, $R_5$, $R_{12a}$, n, and p are defined in the first aspect or the second aspect. Included in this embodiment are compounds in which G is

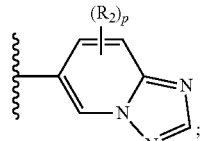

and $R_1$ is —CH(CH$_3$)$_2$. Also included in this embodiment are compounds in which n is zero.

One embodiment provides a compound of Formula (I), N-oxide, or a salt thereof, wherein said compound has the structure:

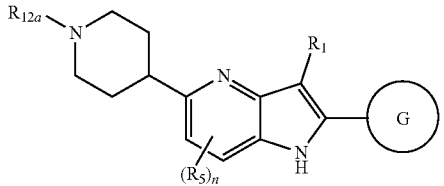

wherein G, $R_1$, $R_2$, $R_5$, $R_{12a}$, n, and p are defined in the first aspect or the second aspect. Included in this embodiment are compounds in which G is

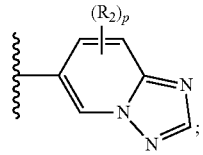

and $R_1$ is —CH(CH$_3$)$_2$. Also included in this embodiment are compounds in which n is zero.

One embodiment provides a compound of Formula (I), N-oxide, or a salt thereof, wherein said compound has the structure:

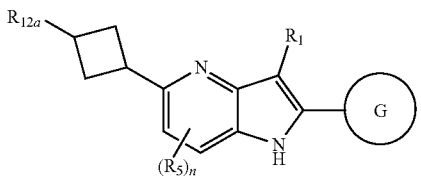

wherein G, $R_1$, $R_2$, $R_5$, $R_{12a}$, n, and p are defined in the first aspect or the second aspect. Included in this embodiment are compounds in which G is

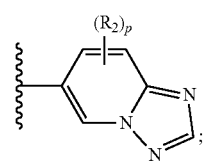

and $R_1$ is —CH(CH$_3$)$_2$. Also included in this embodiment are compounds in which n is zero.

One embodiment provides a compound of Formula (I), N-oxide, or a salt thereof, wherein said compound has the structure:

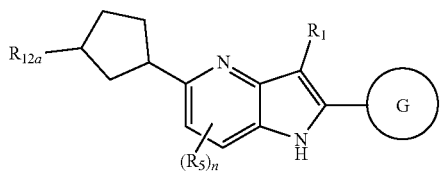

wherein G, $R_1$, $R_2$, $R_5$, $R_{12a}$, n, and p are defined in the first aspect or the second aspect. Included in this embodiment are compounds in which G is

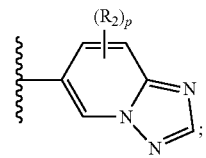

and $R_1$ is —CH(CH$_3$)$_2$. Also included in this embodiment are compounds in which compounds in which G is

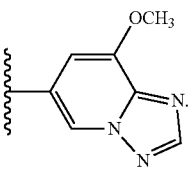

Additionally, included in this embodiment are compounds in which n is zero.

One embodiment provides a compound of Formula (I), N-oxide, or a salt thereof, wherein said compound has the structure:

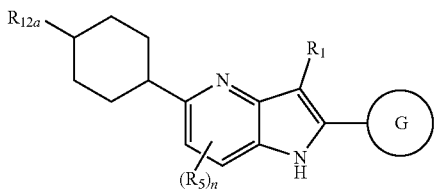

wherein G, $R_1$, $R_2$, $R_5$, $R_{12a}$, n, and p are defined in the first aspect or the second aspect. Included in this embodiment are compounds in which G is

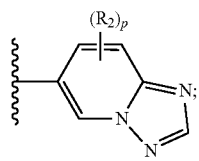

and $R_1$ is —CH(CH$_3$)$_2$. Also included in this embodiment are compounds in which compounds in which G is

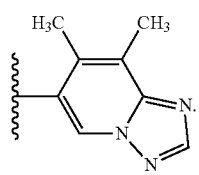 [SMILES: *c1cn2ncnc2c(C)c1C]

Additionally, included in this embodiment are compounds in which n is zero.

One embodiment provides a compound of Formula (I), N-oxide, or a salt thereof, wherein said compound has the structure:

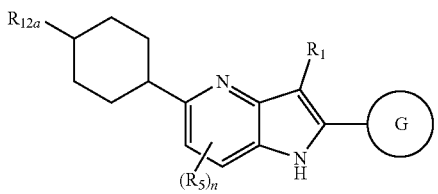

wherein $R_{12a}$ is —NR$_x$CR$_x$R$_x$R$_{12b}$; $R_{12b}$ is $C_{3-6}$ cycloalkyl, each substituted with —S(O)$_2$(C$_{1-2}$ alkyl) or —CH$_2$S(O)$_2$(C$_{1-2}$ alkyl); and G, $R_1$, $R_2$, $R_5$, $R_x$, n, and p are defined in the first aspect or the second aspect. Included in this embodiment are compounds in which G is

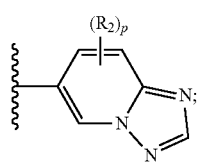

and $R_1$ is —CH(CH$_3$)$_2$. Also included in this embodiment are compounds in which compounds in which G is

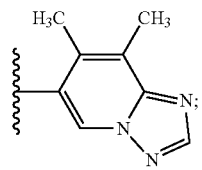

$R_1$ is —CH(CH$_3$)$_2$; $R_{12b}$ is cyclopropyl substituted with —S(O)$_2$(C$_{1-2}$ alkyl) or —CH$_2$S(O)$_2$(C$_{1-2}$ alkyl); and n is zero.

One embodiment provides a compound of Formula (I), N-oxide, or a salt thereof, wherein:

G is

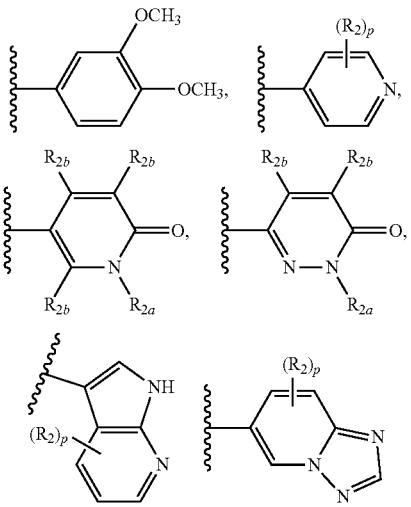

or

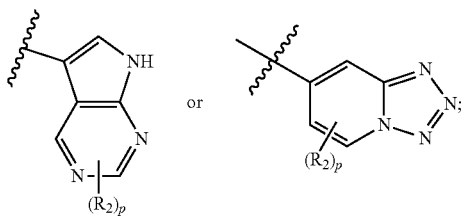

$R_1$ is —CH(CH$_3$)$_2$; each $R_2$ is independently Cl, —CH$_3$, —CH$_2$CH$_3$, —CH$_2$OH, —CH$_2$CH$_2$OH, —CH$_2$CN, —OCH$_3$, —CH$_2$OCH$_3$, or —CH$_2$CH$_2$S(O)$_2$CH$_3$; and A is —CR$_x$R$_{12}$R$_{13}$, wherein $R_{12}$ and $R_{13}$ together with the carbon atom to which they are attached form a cyclic group selected from azaspiro[3.3]heptanyl, $C_{4-6}$ cycloalkyl,

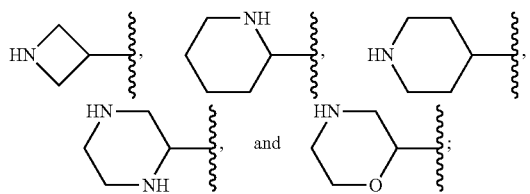

each substituted with zero to 2 $R_{12a}$; and $R_{2a}$, $R_{2b}$, $R_5$, $R_{12a}$, n, and p are defined in the first aspect or the second aspect.

One embodiment provides a compound of Formula (I) or a salt thereof wherein:

G is

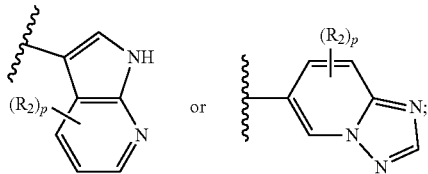

$R_1$ is —CH(CH$_3$)$_2$; each $R_2$ is independently —CH$_3$ or —OCH$_3$; A is —CH$_2$CH$_2$R$_{11}$; and R$_1$ is azetidinyl or piperidinyl, each substituted with zero to 2 substituents independently selected from —CH$_2$(methyloxetanyl), —CH$_2$(triazolyl), —C(O)CH$_2$N(CH$_3$)$_2$, —CH$_2$C(CH$_3$)$_2$OH, —CH$_2$C(O)N(CH$_3$)$_2$, —CH$_2$CH$_2$S(O)$_2$CH$_3$, and oxetanyl; and R$_5$, n, and p are defined in the first aspect or the second aspect.

One embodiment provides a compound of Formula (I) or a salt thereof wherein:

G is

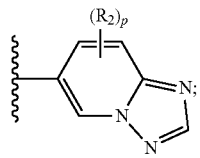

A is —C(O)NR$_9$R$_{10}$; R$_1$ is —CH(CH$_3$)$_2$; each R$_2$ is —OCH$_3$; R$_9$ is —CH$_2$CH$_2$CF$_3$, —CH$_2$CH$_2$N(CH$_3$)$_2$, or —(CH$_2$)$_{0-3}$R$_{9a}$; R$_{9a}$ is piperidinyl substituted with —CH(CH$_3$)$_2$; R$_{10}$ is H, —CH$_3$, or —CH$_2$CH$_3$; or R$_9$ and R$_{10}$ together with the nitrogen atom to which they are attached form a heterocyclic ring selected from piperazinyl substituted with —C(O)CH$_3$; and R$_5$, n, and p are defined in the first aspect or the second aspect.

One embodiment provides a compound of Formula(I) or a salt thereof wherein:

G is

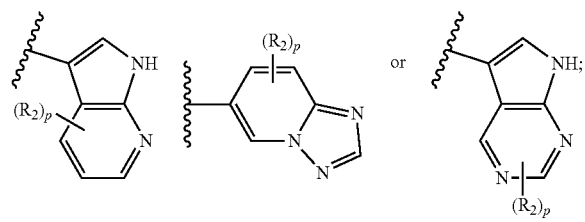

A is —NR$_7$R$_8$; R$_1$ is —CH(CH$_3$)$_2$; each R$_2$ is independently —CH$_3$, —CH$_2$OH, or —OCH$_3$; R$_7$ and R$_8$ together with the nitrogen atom to which they are attached form a heterocyclic ring selected from azetidinyl, diazabicyclo[2.2.1]heptanyl, diazabicyclo[2.2.2]octanyl, diazabicyclo[3.1.1]heptanyl, diazabicyclo[3.2.1]octanyl, azaspiro[3.3]heptanyl, diazaspiro[2.5]octanyl, diazaspiro[3.3]heptanyl, diazepanyl, diazaspiro[3.5]nonanyl, oxadiazabicyclo[3.3.1]nonanyl, piperazinyl, piperazinonyl, piperidinyl, and pyrrolidinyl, wherein said heterocyclic ring is substituted with zero to 1 R$_{7b}$ and zero to 2 R$_{7c}$; R$_{7b}$ is: (i) —OH, C$_{1-6}$ alkyl, C$_{3-4}$ fluoroalkyl, C$_{3-4}$ hydroxyalkyl, —CH$_2$CN, —CH$_2$CH$_2$CN, —(CR$_x$R$_x$)$_{1-2}$OCH$_3$, —(CH$_2$)$_{2-3}$S(O)$_2$CH$_3$, —(CH$_2$)$_{2-3}$NHS(O)$_2$CH$_3$, —(CH$_2$)$_{1-2}$NR$_x$R$_x$, —(CH$_2$)$_{1-2}$C(O)NR$_x$R$_x$, —NR$_y$R$_y$, —NR$_x$(C$_{1-4}$ hydroxyalkyl), —NH(CH$_2$CH$_2$OCH$_3$), —N(CH$_2$CH$_2$CN)$_2$, —(CH$_2$)$_{1-2}$C(O)NR$_x$R$_x$, —N((CH$_2$)$_{1-2}$C(O)NR$_x$R$_x$)$_2$, —NR$_x$C(O)(CH$_2$)$_{1-2}$NR$_x$R$_x$, —NR$_x$(CH$_2$CH$_2$S(O)$_2$CH$_3$), —C(O)(CR$_x$R$_x$)$_{1-2}$NR$_y$R$_y$, —C(O)(CR$_x$R$_x$)$_{1-2}$NR$_x$(CH$_2$CH$_2$OCH$_3$), —NR$_x$R$_{7d}$, —NR$_x$(CH$_2$)$_{1-2}$R$_{7d}$), —NR$_{7d}$R$_{7d}$, —N((CH$_2$)$_{1-2}$R$_{7d}$)$_2$, —C(O)R$_{7d}$, or —C(O)(CR$_x$R$_x$)$_{1-2}$R$_{7d}$; or (ii) azetidinyl, cyclobutyl, cyclohexyl, dioxotetrahydrothiopyranyl, dioxothiomorpholinyl, morpholinyl, oxaazaspiro[4.3]octanyl, oxetanyl, piperazinyl, piperidinyl, pyrimidinyl, tetrahydrofuranyl, tetrahydropyranyl, or thiadiazolyl, each substituted with zero to 1 R$_{8a}$ and zero to 3 R$_{8b}$; each R$_{7c}$ is independently —CH$_3$ or —CH$_2$CN; each R$_{7d}$ is independently azetidinyl, C$_{3-6}$ cycloalkyl, dioxothiaazaspiro[3.3]heptanyl, morpholinyl, oxaazaspiro[3.3]heptanyl, oxaazaspiro[4.3]octanyl, oxaazaspiro[4.4]nonyl, oxetanyl, piperidinyl, pyrimidinyl, pyrazolyl, pyrrolidinyl, tetrahydropyranyl, thiadiazolyl, or triazolyl, each substituted with zero to 2 substituents selected from F, —OH, C$_{1-3}$ alkyl, —CH$_2$OH, —OCH$_3$, —NR$_x$R$_x$, and —S(O)$_2$CH$_3$; R$_{8a}$ is —OH, —CH$_3$, —OCH$_3$, —C(O)CH$_3$, or —C(O)OCH$_3$; each R$_{8b}$ is —CH$_3$; and R$_2$, R$_x$, R$_y$, R$_5$, n, and p are defined in the first aspect or the second aspect.

One embodiment provides a compound of Formula (I) or a salt thereof wherein:

G is

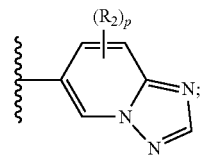

A is —O-L$_1$-R$_6$; L$_1$ is bond or —CH$_2$—; R$_1$ is —CH(CH$_3$)$_2$; each R$_2$ is independently —CH$_3$ or —OCH$_3$; R$_6$ is: (i) —CH$_3$; or (ii) azetidinyl, cyclohexyl, or piperidinyl, each substituted with zero to 2 R$_{6a}$; each R$_{6a}$ is independently —CH$_3$, —CH$_2$CH$_2$CH$_3$, —C(CH$_3$)$_2$, —CH$_2$C(CH$_3$)$_2$OH, —N(CH$_3$)$_2$, —N(CH$_2$CH$_2$CH$_3$)$_2$, —CH$_2$CH$_2$S(O)$_2$CH$_3$, —CH$_2$C(O)N(CH$_3$)$_2$, or tetrahydropyranyl; and R$_5$, n, and p are defined in the first aspect or the second aspect.

One embodiment provides a compound of Formula (I) or a salt thereof wherein:

G is

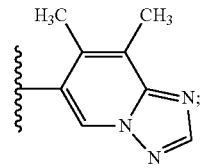

R$_1$ is —CH(CH$_3$)$_2$; A is —CHR$_{12}$R$_{13}$, wherein R$_{12}$ and R$_{13}$ together with the carbon atom to which they are attached form a cyclohexyl group; R$_1$ is —CH(CH$_3$)$_2$; and n is zero.

One embodiment provides a compound of Formula (I) or a salt thereof wherein:

G is

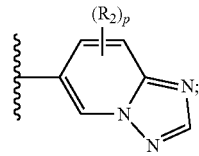

$R_1$ is —CH(CH$_3$)$_2$; each $R_2$ is independently —CH$_3$ or —OCH$_3$; A is —CHR$_{12}$R$_{13}$, wherein $R_{12}$ and $R_{13}$ together with the carbon atom to which they are attached form a C$_{4-6}$ cyclohexyl group substituted with $R_{12a}$;

$R_{12a}$ is:

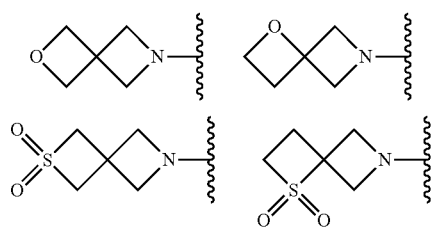

p is 1 or 2; and n is zero or 1. Included in this embodiment are compounds in which $R_{12}$ and $R_{13}$ together with the carbon atom to which they are attached form a cyclohexyl group substituted with $R_{12a}$.

One embodiment provides a compound of Formula (I) or a salt thereof wherein A is:

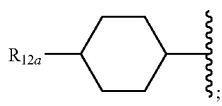

and G, $R_1$, $R_2$, $R_5$, $R_{12a}$, n, and p are defined in the first aspect.

Included in this embodiment are compounds in which G is

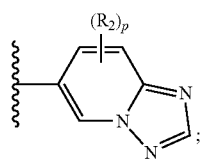

$R_1$ is —CH(CH$_3$)$_2$; and n is zero. Also included in this embodiment are compounds in which G is

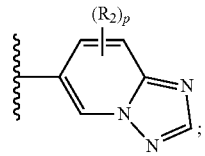

$R_1$ is —CH(CH$_3$)$_2$; $R_{12a}$ is:

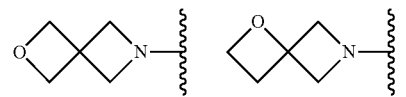

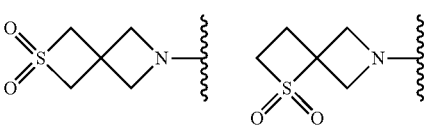

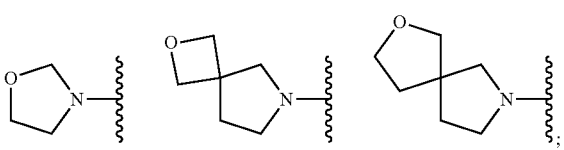

and n is zero.

One embodiment provides a compound of Formula (I) or a salt thereof wherein compound is:

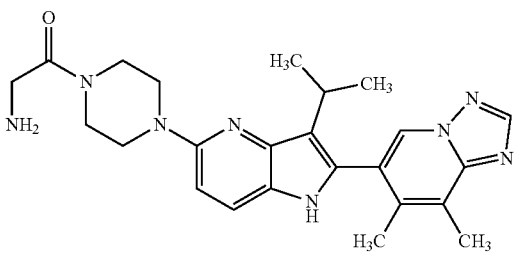

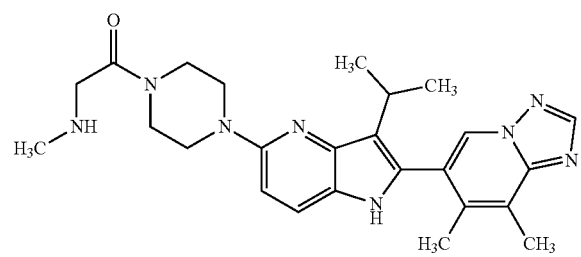

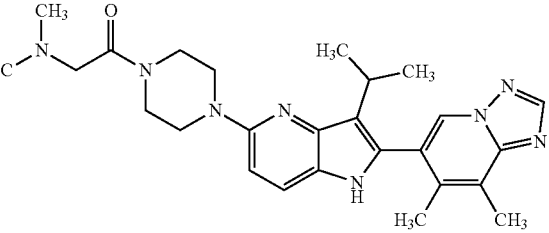

-continued
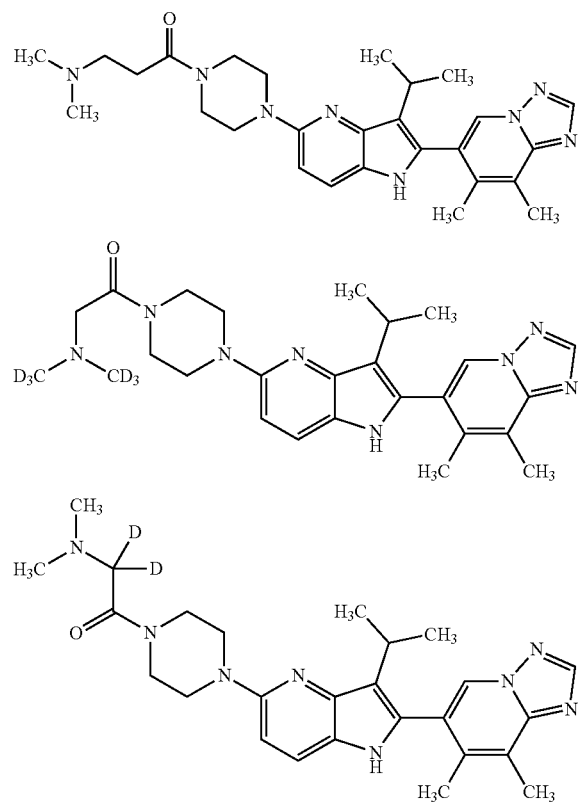
or
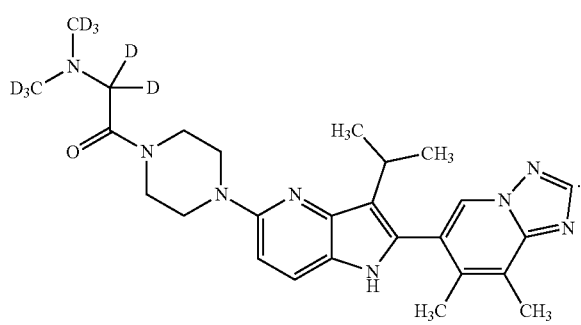
One embodiment provides a compound of Formula (I) or a salt thereof wherein compound is:
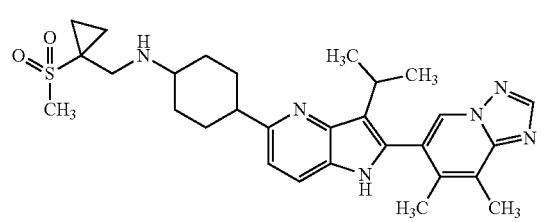
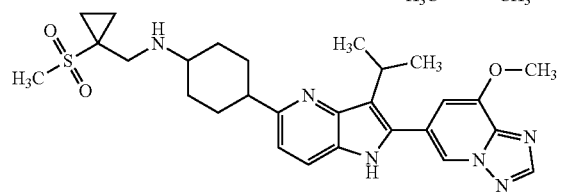
-continued
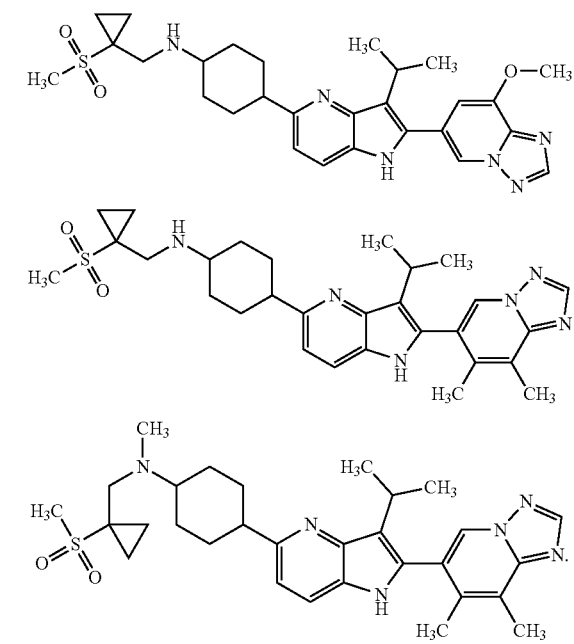
One embodiment provides a compound of Formula (I) or a salt thereof wherein compound is:
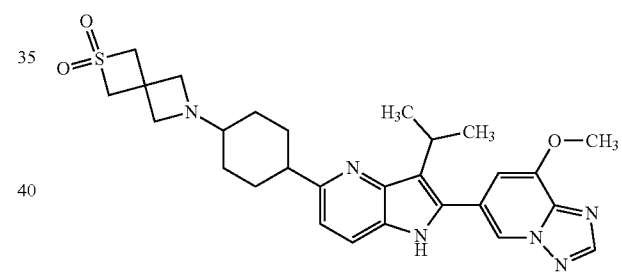
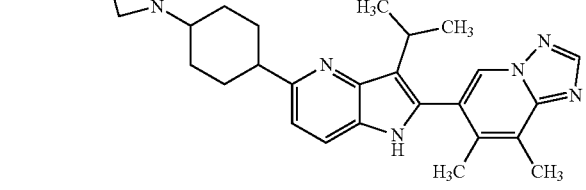

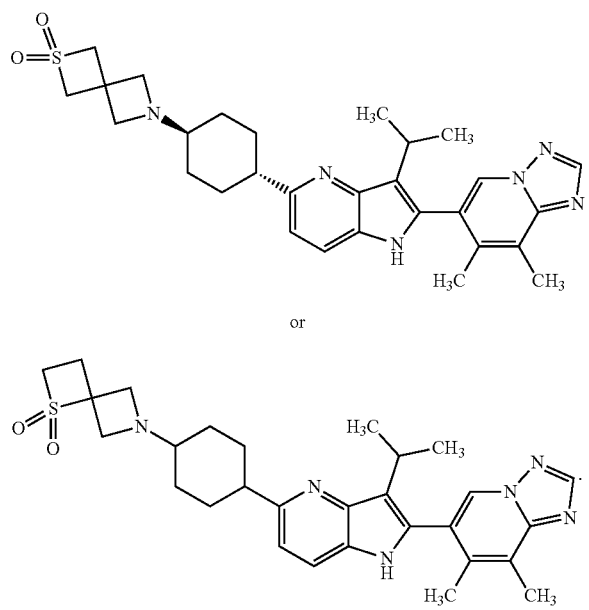

or

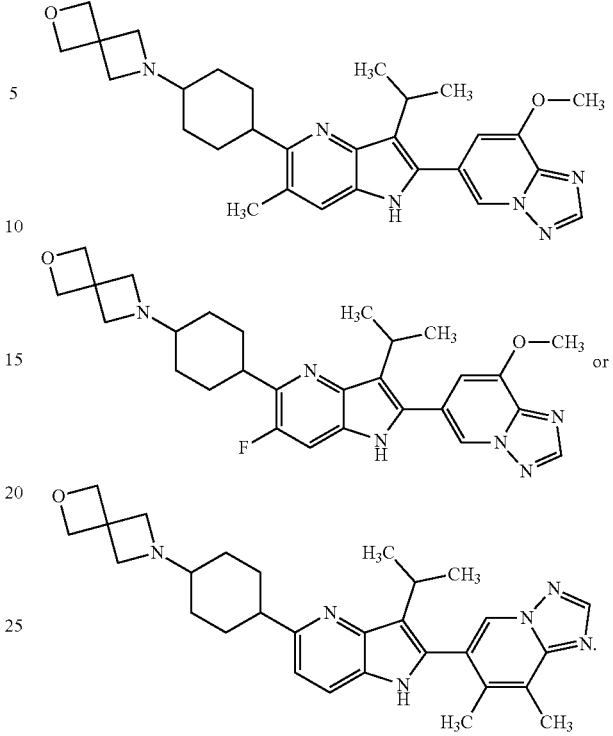

One embodiment provides a compound of Formula (I) or a salt thereof wherein said compound is:

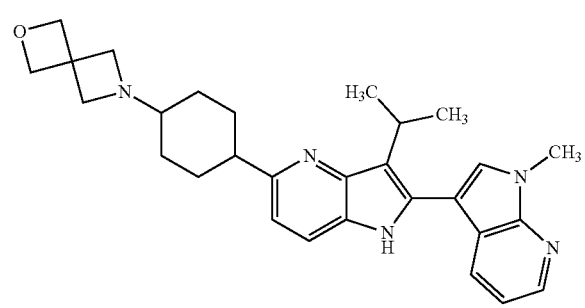

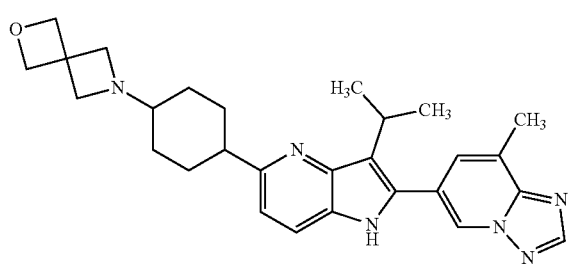

One embodiment provides a compound of Formula (I), N-oxide, or a salt thereof wherein said compound is selected from Examples 1 to 1078.

One embodiment provides a compound of Formula (I), N-oxide, or a salt thereof wherein said compound is selected from Examples 1 to 736.

One embodiment provides a compound of Formula (I), N-oxide, or a salt thereof wherein said compound is selected from Examples 737 to 1078.

The present invention may be embodied in other specific forms without departing from the spirit or essential attributes thereof. The invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.
The term "amino" refers to the group —NH$_2$.
The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "cyanoalkyl" includes both branched and straight-chain saturated alkyl groups substituted with one or more cyano groups. For example, "cyanoalkyl" includes —CH$_2$CN, —CH$_2$CH$_2$CN, and $C_{1-4}$ cyanoalkyl.

The term "aminoalkyl" includes both branched and straight-chain saturated alkyl groups substituted with one or more amine groups. For example, "aminoalkyl" includes —CH$_2$NH$_2$, —CH$_2$CH$_2$NH$_2$, and $C_{1-4}$ aminoalkyl.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and $C_{1-4}$ hydroxyalkyl.

The term "hydroxy-fluoroalkyl" includes both branched and straight-chain saturated alkyl groups substituted with one or more hydroxyl groups and one or more fluorine atoms. For example, "hydroxy-fluoroalkyl" includes —CHFCH$_2$OH, —CH$_2$CHFC(CH$_3$)$_2$OH, and $C_{1-4}$ hydroxy-fluoroalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_3$-$C_6$ cycloalkyl" denotes cycloalkyl groups with three to six carbon atoms.

The term "alkoxy," as used herein, refers to an alkyl group attached to the parent molecular moiety through an oxygen atom, for example, methoxy group (—OCH$_3$). For example, "$C_{1-3}$ alkoxy" denotes alkoxy groups with one to three carbon atoms.

The term "alkoxyalkyl," as used herein, refers to an alkoxy group attached through its oxygen atom to an alkyl group, which is attached to the parent molecular moiety, for example, methoxymethyl group (—CH$_2$OCH$_3$). For example, "$C_{2-4}$ alkoxyalkyl" denotes alkoxyalkyl groups with two to four carbon atoms, such as —CH$_2$OCH$_3$, —CH$_2$CH$_2$OCH$_3$, —CH$_2$OCH$_2$CH$_3$, and —CH$_2$CH$_2$OCH$_2$CH$_3$.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to TLR7/8/9, or effective to treat or prevent autoimmune and/or inflammatory disease states, such as SLE, IBD, multiple sclerosis (MS), and Sjögren's syndrome, and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease.

The compounds of the invention inhibit signaling through Toll-like receptor 7, or 8, or 9 (TLR7, TLR8, TLR9) or combinations thereof. Accordingly, compounds of Formula (I) have utility in treating conditions associated with the inhibition of signaling through one or more of TLR7, TLR8, or TLR9. Such conditions include TLR7, TLR8, or TLR9 receptor associated diseases in which cytokine levels are modulated as a consequence of intracellular signaling.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of TLR7, TLR8, or TLR9, compounds of Formula (I) are useful in treating TLR7, TLR8, or TLR9 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosus, lupus nephritis, cutaneous lupus, psoriasis; auto-inflammatory diseases including Cryopyrin-Associated Periodic Syndromes (CAPS), TNF Receptor Associated Periodic Syndrome (TRAPS), Familial Mediterranean Fever (FMF), adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovascularization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovascularization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Included in this embodiment are methods of treatment in which the condition is selected from lupus including lupus nephritis and systemic lupus erythematosus (SLE), Crohn's disease, ulcerative colitis, allograft rejection, rheumatoid arthritis, psoriasis, ankylosing spondylitis, psoriatic arthritis, and pemphigus vulgaris. Also included are methods of treatment in which the condition is selected from ischemia reperfusion injury, including cerebral ischemia reperfusions injury arising from stroke and cardiac ischemia reperfusion injury arising from myocardial infarction. Another method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the TLR7, TLR8, or TLR9 inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional TLR7/8/9 associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

The present invention thus provides methods for treating such conditions, comprising administering to a subject in need thereof a therapeutically-effective amount of at least one compound of Formula (I) or a salt thereof "Therapeutically effective amount" is intended to include an amount of a compound of the present invention that is effective when administered alone or in combination to inhibit autoimmune disease or chronic inflammatory disease.

The methods of treating TLR7, TLR8, or TLR9 associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit TLR7, TLR8, or TLR9 and/or treat diseases associated with TLR7, TLR8, or TLR9.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating TLR7/8/9 receptor-associated conditions, including IL-1 family receptor-mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Remington's Pharmaceutical Sciences, 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parenterally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride solution, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and (c) a package insert stating that the pharmaceutical composition can be used for the treatment of an inflammatory disorder and/or an autoimmune disease (as defined previously). In another embodiment, the package insert states that the pharmaceutical composition can be used in combination (as defined previously) with a second therapeutic agent to treat an inflammatory disorder and/or an autoimmune disease. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). In one embodiment, the package insert specifically recites the indications for which the pharmaceutical composition has been approved. The package insert may be made of any material on which a person can read information contained therein or thereon. For example, the package insert is a printable material (e.g., paper, plastic, cardboard, foil, adhesive-backed paper or plastic, etc.) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

Abbreviations

Ac acetyl
ACN acetonitrile
AcOH acetic acid
anhyd. anhydrous
aq. aqueous
Bn benzyl
Bu butyl
Boc tert-butoxycarbonyl
CV Column Volumes
DCE dichloroethane
DCM dichloromethane
DMAP dimethylaminopyridine
DMF dimethylformamide
DMSO dimethylsulfoxide
EtOAc ethyl acetate
Et ethyl
EtOH ethanol
H or $H_2$ hydrogen
h, hr or hrs hour(s)
hex hexane
i iso
IPA isopropyl alcohol
HCl hydrochloric acid
HPLC high pressure liquid chromatography
LC liquid chromatography
M molar
mM millimolar
Me methyl
MeOH methanol
MHz megahertz
min. minute(s)
mins minute(s)
$M^{+1}$ $(M+H)^+$
MS mass spectrometry
n or N normal
NBS n-bromosuccinimide
nm nanometer
nM nanomolar
NMP N-methylpyrrolidine
Pd/C palladium on carbon
Ph phenyl
$PPh_3$ triphenylphosphine
Pr propyl
PSI pounds per square inch
Ret Time retention time
sat. saturated
SFC supercritical fluid chromatography
TBAF tetrabutylammonium fluoride
TEA triethylamine
TFA trifluoroacetic acid
THF tetrahydrofuran
T3P 2,4,6-tripropyl-1,3,5,2,4,6-trioxatriphosphorinane-2,4,6-trioxide
$2^{nd}$ Generation RuPhos Precatalyst: chloro(2-dicyclohexylphosphino-2',6'-diisopropoxy-1,1'-biphenyl)[2-(2'-amino-1,1'-biphenyl)]palladium(II)
$2^{nd}$ Generation Xphos precatalyst: chloro(2-dicyclohexylphosphino-2',4',6'-triisopropyl-1,1'-biphenyl)[2-(2'-amino-1,1'-biphenyl)]palladium(II)
Analytical and Preparative HPLC Conditions:
QC-ACN-AA-XB: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

QC-ACN-TFA-XB: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Method A1: L3 Acquity: Column: (LCMS) UPLC BEH C18, 2.1×50 mm, 1.7 µm particles; Mobile Phase: (A) water; (B) acetonitrile; Buffer: 0.05% TFA; Gradient Range: 2%-98% B (0 to 1 min) 98% B (to 1.5 min) 98%-2% B (to 1.6 min); Gradient Time: 1.6 min; Flow Rate: 0.8 mL/min; Analysis Time: 2.2 min; Detection: Detector 1: UV at 220 nm; Detector 2: MS (ESI$^+$).

Method B1: L2 Aquity(4); Column: (LCMS) UPLC BEH C18, 2.1×50 mm, 1.7 µm particles; Mobile Phase: (A) water; (B) acetonitrile; Buffer: 0.05% TFA; Gradient Range: 2%-98% B (0 to 1 min) 98% B (to 1.5 min) 98%-2% B (to 1.5 min); Gradient Time: 1.8 min; Flow Rate: 0.8 mL/min; Analysis Time: 2.2 min; Detection: Detector 1: UV at 220 nm; Detector 2: MS (ESI$^+$).

Method D1 SCP: Column: Waters Acquity UPLC BEH C18, 2.1×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.11 mL/min; Detection: UV at 220 nm.

Method D2 SCP: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 10-50% B over 20 minutes, then a 5 minute hold at 100% B; Flow: 20 mL/min. Detection: UV at 220 nm.

Method D3 SCP: Column: XBridge C18, 19×200 mm, 5 µm particles; Mobile Phase A: 5:95 acetonitrile:water with 0.1% trifluoroacetic acid; Mobile Phase B: 95:5 acetonitrile:water with 0.1% trifluoroacetic acid; Gradient: 6-46% B over 20 minutes, then a 4 minute hold at 100% B; Flow: 20 mL/min. Detection: UV at 220 nm.

Method E1 iPAC: Column: Waters Xbridge C18 4.6×50 mm 5 µm particles; Mobile Phase A: 5:95 acetonitrile:water with 10 mM ammonium acetate; Mobile Phase B: 95:5 acetonitrile:water with 10 mM ammonium acetate. Temperature: 50° C.; Gradient: 0-100% B over 1 minute; Flow: 4 mL/min; Detection: UV at 220 nm.

Method F1 iPAC: Column: Waters Acquity BEH C18 2.1×50 mm 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 2.20 minutes; Flow: 0.800 mL/min; Detection: UV at 220 nm.

Method G1: Column: Symmetry C8, (250×4.6 mm), 5 µm particles; Mobile Phase A: 1:1 acetonitrile:TFE with 10 mM ammonium acetate; Mobile Phase B: 1:1 acetonitrile:TFE with 10 mM ammonium acetate; Temperature: 50° C.; Gradient: 0-100% B over 25 minutes, then a 0.75 minute hold at 100% B; Flow: 1.0 mL/min; Detection: UV at 220 nm.

Method H1 (SFC): Column: Luxcellulose-4 (250×4.6 mm), 5 µm particles; % $CO_2$: 50%, % Cosolvent: 50% of 0.4% isopropyl amine in methanol; Temperature 30° C.; Flow: 120 g/min; Detection: UV at 230 nm.

(A): Column-Ascentis Express C18 (50×2.1 mm-2.7 μm) Mphase A: 10 mM $NH_4COOH$ in water: ACN (98:02); Mphase B: 10 mM $NH_4COOH$ in water: ACN (02:98), Gradient: 0-100% B over 3 minutes, Flow=1 mL/min.

(D): Kinetex XB-C18 (75×3 mm) 2.6 micron; Solvent A: 10 mM ammonium formate in water:acetonitrile (98:02); Mobile Phase B: 10 mM ammonium formate in water: acetonitrile (02:98); Temperature: 50° C.; Gradient: 0-100% B over 3 minutes; Flow rate: 1.1 mL/min; Detection: UV at 220 nm.

(E): Column: Ascentis Express C18 (50×2.1) mm, 2.7 m; Mobile Phase A: 5:95 acetonitrile:water with 10 mM $NH_{40}Ac$; Mobile Phase B: 95:5 acetonitrile:water with 10 mM $NH_{40}Ac$; Temperature: 50° C.; Gradient: 0-100% B over 3 minutes; Flow: 1.1 mL/min.

(F): Column: Ascentis Express C18 (50×2.1) mm, 2.7 m; Mobile Phase A: 5:95 acetonitrile:water with 0.1% TFA; Mobile Phase B: 95:5 acetonitrile:water with 0.1% TFA; Temperature: 50° C.; Gradient: 0-100% B over 3 minutes; Flow: 1.1 mL/min. (G): Column: Waters Acquity UPLC BEH C18 (2.1×50 mm), 1.7 micron; Solvent A=100% water with 0.05% TFA; Solvent B=100% acetonitrile with 0.05% TFA; gradient=2-98% B over 1 minute, then a 0.5-minute hold at 98% B; Flow rate: 0.8 mL/min; Detection: UV at 220 nm.

(H): Column: Acentis Express C18 (50×2.1 mm) 1.7 m, Acentis C8 $NH_4COOH$ 5 min. M, Mobile Phase A: 10 mM ammonium formate: ACN (98:2), Mobile Phase B: 10 mM ammonium formate: ACN (2:98), gradient: 20%-100% B (0-4 min); 100% B (4-4.6 min); Flow: 1 mL/min (I) Column: Sunfire C18 (4.6×150) mm, 3.5 m; Mobile Phase A: 5:95 acetonitrile:water with 0.05% TFA; Mobile Phase B: 95:5 acetonitrile:water with 0.05% TFA; Temperature: 50° C.; Gradient: 10-100% B over 12 minutes; Flow: 1 mL/min.

(J) Column: Sunfire C18 (4.6×150) mm, 3.5 m; Mobile Phase A: 5:95 acetonitrile:water with 0.05% TFA; Mobile Phase B: 95:5 acetonitrile:water with 0.05% TFA.

(K) Waters Acquity SDS Mobile Phase: A: water B: ACN; 5%-95% B in 1 min; Gradient Range: 50%-98% B (0-0.5 min); 98% B (0.5 min-1 min); 98%-2% B (1-1.1 min); Run time: 1.2 min; Flow Rate: 0.7 mL/min; Analysis Time: 1.7 min; Detection: Detector 1: UV at 220 nm; Detector 2: MS $(ES^+)$.

(L) Acquity UPLC BEH C18 (3.0×50 mm) 1.7 μm. Buffer: 5 mM ammonium acetate Mobile phase A: Buffer: ACN (95:5); Mobile phase B: Buffer:ACN (5:95) Method: % B: 0 min—20%: 1.1 min—90%: 1.7 min—90%. Run time: 2.25 min; Flow Rate: 0.7 mL/min; Detection: Detector 1: UV at 220 nm; Detector 2: MS $(ES^+)$.

(M): Kinetex SBC18 (4.6×50 mm) 5 micron; Solvent A: 10 mM ammonium formate in water:acetonitrile (98:02); Mobile Phase B: 10 mM ammonium formate in water: acetonitrile (02:98); Temperature: 50° C.; Gradient: 30-100% B (0-4 min), 100% B (4-4.6 min), 100-30% B (4.6-4.7 min), 30% B (4.7-5.0 min); Flow rate: 1.5 mL/min; Detection: UV at 220 nm.

(N): Column-Ascentis Express C18 (50×2.1 mm 2.7 μm) Mphase A: 10 mM $NH_4COOH$ in water: ACN (98:02); Mphase B: 10 mM $NH_4COOH$ in water: ACN (02:98), Gradient: 0-100% B (0-1.7 minutes); 100% B (1.7-3.4 minutes). Flow=1 mL/min.

(O) Waters Acquity SDS Column BEH C18 (2.1×50 mm) 1.7 μm. Phase A: buffer in water; Mphase B: buffer in ACN, Gradient: 20-98% B (0-1.25 minutes); 98% B (1.25-1.70 minutes); 98%-2% B (1.70-1.75 minutes); Flow=0.8 mL/min.

(P): Column: XBridge BEH XP C18 (50×2.1) mm, 2.5 m; Mobile Phase A: 5:95 acetonitrile:water with 10 mM $NH_{40}Ac$; Mobile Phase B: 95:5 acetonitrile:water with 10 mM $NH_{40}Ac$; Temperature: 50° C.; Gradient: 0-100% B over 3 minutes; Flow: 1.1 mL/min.

(Q): Column: XBridge BEH XP C18 (50×2.1) mm, 2.5 m; Mobile Phase A: 5:95 acetonitrile:water with 0.1% TFA; Mobile Phase B: 95:5 acetonitrile:water with 0.1% TFA; Temperature: 50° C.; Gradient: 0-100% B over 3 minutes; Flow: 1.1 mL/min.

(R): Column-ZORBAX SB-C18 (50×4.6 mm-5.0 μm) Mphase A: 10 mM $NH_4COOH$ in water:ACN (98:02) Mphase B: 10 mM $NH_4COOH$ in water:ACN (02:98). Gradient: 0 min—30%, 4.0 min—100%, 4.6 min—100%, 4.7 min—30%. Flow\min. 1.5 mL.

(TS): Column: Waters Acquity UPLC BEH C18 (2.1×50 mm), 1.7 micron; Solvent A=100% water with 0.05% TFA; Solvent B=100% acetonitrile with 0.05% TFA; gradient=2-98% B over 1 minute, then a 0.5 minute hold at 98% B; Flow rate: 0.8 mL/min; Detection: UV at 254 nm.

(DDS) Aquity: Column: (LCMS) UPLC BEH C18, 3.0× 50 mm, 1.7 μm particles; Mobile Phase: (A) 10 mM $NH_{40}Ac$: acetonitrile (95:5) Phase B) 10 mM $NH_{40}Ac$: acetonitrile (5:95): Method:% B: 0 min—20:2 min—100:2.3 min—1001.8 min; Flow Rate: 0.7 mL/min; Detection: Detector 1: UV at 220 nm; Detector 2: MS $(ESI^+)$.

(DDS2) Aquity: Column: (LCMS) UPLC BEH C18, 3.2×50 mm, 1.7 μm particles; Buffer: 10 mM Ammonium Acetate Mobile Phase A: Buffer: ACN (95:5) Mobile Phase B: Buffer:ACN (5:95); Method % B: 0 min—20%: 2 min—100%: 2.2 min—100%; Flow rate=0.7 mL/min, Detection: Detector 1: UV at 220 nm; Detector 2: MS $(ESI^+)$.

Example 1

1-(2-(7,8-dimethyl-[1,2,4]triazolo[1,5-a]pyridin-6-yl)-3-isopropyl-1H-pyrrolo[3,2-b]pyridin-5-yl)-N-(tetrahydro-2H-pyran-4-yl)azetidin-3-amine

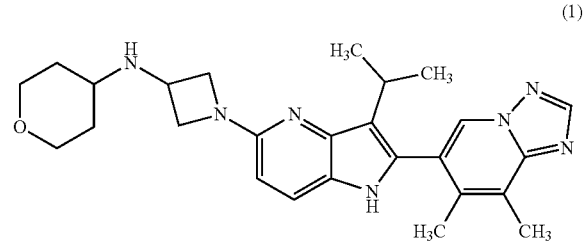 [SMILES: Cc1c(-c2[nH]c3ccc(N4CC(NC5CCOCC5)C4)nc3c2C(C)C)cn2ncnc2c1C]

(1)

Intermediate 1A: 2-bromo-5-hydrazinylpyridine

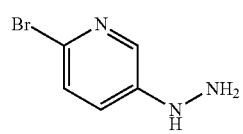

(1A)

A solution of 6-bromopyridin-3-amine (10.0 g, 57.8 mmol) in 6 M aqueous HCl (111 mL) was cooled to 0° C. A solution of sodium nitrite (3.99 g, 57.8 mmol) in water (148 mL), precooled to 0° C., was added over 5 min and the reaction mixture was stirred for 45 minutes at 0° C. Tin(II) chloride dihydrate (32.6 g, 144 mmol) was suspended in 6 M aqueous HCl (111 mL), precooled to 0° C., and was added to the reaction mixture over 5 min. The reaction mixture was stirred for 60 min more at 0° C. Upon completion, the reaction was quenched via addition of 40% w/w solution of KOH in water until the solution was basic as judged by pH paper. The mixture was diluted with water and DCM. The organic layer was separated and the aqueous layer was extracted with DCM. The combined organic layers were dried over sodium sulfate, filtered, and concentrated to afford 2-bromo-5-hydrazinylpyridine (8.08 g, 43.0 mmol, 74.3% yield). LCMS retention time 0.41 min [A1]. MS (E$^+$) m/z: 190.1 [(M+2)+H$^+$]. $^1$H NMR (499 MHz, CHLOROFORM-d) δ 7.98 (d, J=3.0 Hz, 1H), 7.28 (app d, J=8.5 Hz, 1H), 7.10 (dd, J=8.7, 3.0 Hz, 1H), 5.25 (br app s, 1H), 3.62 (br app s, 2H).

Intermediate 1B: 5-bromo-3-isopropyl-1H-pyrrolo[3,2-b]pyridine

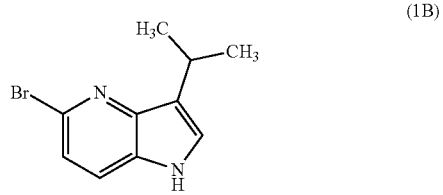

(1B)

2-bromo-5-hydrazinylpyridine (8.08 g, 43.0 mmol) was suspended in 5% v/v H$_2$SO$_4$ in water (215 mL) to form a chunky suspension. 3-Methylbutanal (5.19 mL, 47.3 mmol) was added and the suspension was stirred for 20 min at room temperature, then heated with a reflux condenser at 110° C. for 20 hours. Upon completion, the mixture was cooled in an ice bath. The reaction was quenched via the addition of 40% w/w solution of KOH in water until the pH was basic as judged by pH paper. Water and DCM were added until all solids had dissolved. The organic layer was separated and the aqueous layer was extracted twice with DCM. The combined organics were dried over sodium sulfate, filtered, and concentrated to afford a crude orange solid which was purified on silica gel column chromatography (Hex/EtOAc 0-50%) to afford 5-bromo-3-isopropyl-1H-pyrrolo[3,2-b]pyridine (6.19 g, 25.9 mmol, 60% yield). LCMS retention time 0.90 min [A1]. MS (E$^+$) m/z: 239.1 (M+H). $^1$H NMR (499 MHz, CHLOROFORM-d) δ 8.71-8.43 (m, 1H), 7.48 (d, J=8.4 Hz, 1H), 7.22-7.17 (m, 2H), 3.37 (spt, J=6.8 Hz, 1H), 1.35 (d, J=6.8 Hz, 6H).

Intermediate 1C: tert-butyl 5-bromo-3-isopropyl-1H-pyrrolo[3,2-b]pyridine-1-carboxylate

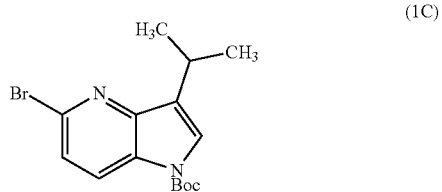

(1C)

To a solution of 5-bromo-3-isopropyl-1H-pyrrolo[3,2-b]pyridine (5.0 g, 20.9 mmol) in THF (84 mL) were added Et$_3$N (4.37 mL, 31.4 mmol) and DMAP (0.255 g, 2.09 mmol). The mixture was cooled to 0° C. BOC-anhydride 30% in toluene (16.73 g, 23.0 mmol) was added in a single portion and the reaction mixture was stirred for 1 hour. Another aliquot of BOC-anhydride 30% in toluene (2.0 g, 2.75 mmol) was added and the reaction mixture was stirred for 10 min. Upon completion, the reaction mixture was concentrated and the crude material was purified on silica gel column chromatography (Hex/EtOAc 0-40%) to afford tert-butyl 5-bromo-3-isopropyl-1H-pyrrolo[3,2-b]pyridine-1-carboxylate (6.98 g, 20.6 mmol, 98% yield). LCMS retention time 1.14 min [TS]. MS (E$^+$) m/z: 339.1 (M+H).

Intermediate 1D: tert-butyl 5-(3-((tert-butoxycarbonyl)amino)azetidin-1-yl)-3-isopropyl-1H-pyrrolo[3,2-b]pyridine-1-carboxylate

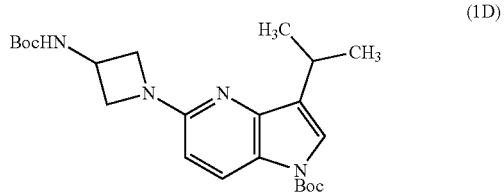 [SMILES: CC(C)c1cn(C(=O)OC(C)(C)C)c2ccc(N3CC(NC(=O)OC(C)(C)C)C3)nc12]

(1D)

A suspension of tert-butyl 5-bromo-3-isopropyl-1H-pyrrolo[3,2-b]pyridine-1-carboxylate (1.05 g, 3.10 mmol), tert-butyl azetidin-3-ylcarbamate (0.693 g, 4.02 mmol), RuPhos 2$^{nd}$ Generation precatalyst (0.120 g, 0.155 mmol), and Cs$_2$CO$_3$ (3.03 g, 9.29 mmol) was made in 1,4-dioxane (21 mL). The suspension was degassed with nitrogen for 5 min, sealed, and placed in a heating block at 130° C. for 4 h and 20 min. Upon completion, the reaction mixture was filtered, concentrated and purified using silica gel column chromatography (Hex/EtOAc 0-50%) to afford tert-butyl 5-(3-((tert-butoxycarbonyl)amino)azetidin-1-yl)-3-isopropyl-1H-pyrrolo[3,2-b]pyridine-1-carboxylate (970 mg, 2.253 mmol, 72.8% yield). LCMS retention time 0.86 min [TS]. MS (E$^+$) m/z: 431.2 (M+H). $^1$H NMR (499 MHz, CHLOROFORM-d) δ 8.19-7.98 (m, 1H), 7.45-7.29 (m, 1H), 6.26 (d, J=8.8 Hz, 1H), 5.07-4.88 (m, 1H), 4.68-4.51 (m, 1H), 4.35 (br t, J=7.6 Hz, 2H), 3.78 (dd, J=8.6, 5.4 Hz, 2H), 3.24-3.15 (m, 1H), 1.65 (s, 9H), 1.46 (s, 9H), 1.35 (d, J=7.0 Hz, 6H).

Intermediate 1E: tert-butyl 5-(3-((tert-butoxycarbonyl)amino)azetidin-1-yl)-3-isopropyl-2-(4,4,5,5-tetramethyl-1,3,2-dioxaborolan-2-yl)-1H-pyrrolo[3,2-b]pyridine-1-carboxylate

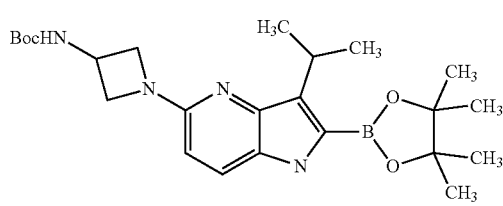

A solution containing tert-butyl 5-(3-((tert-butoxycarbonyl)amino)azetidin-1-yl)-3-isopropyl-1H-pyrrolo[3,2-b]pyridine-1-carboxylate (802 mg, 1.86 mmol) and 2-isopropoxy-4,4,5,5-tetramethyl-1,3,2-dioxaborolane (0.49 mL, 2.42 mmol) in dry THF (9.3 mL), under a nitrogen atmosphere was cooled to −78° C. and treated with LDA (2M in THF) (2.33 mL, 4.66 mmol). The mixture was warmed to −30° C. over 30 min and stirred at −30° C. for 30 min, then allowed to warm slowly to 0° C. The reaction mixture was treated with saturated aqueous ammonium chloride solution, water, and DCM. The organic layer was dried over sodium sulfate, filtered and concentrated. The crude material was purified on silica gel column chromatography (Hex/EtOAc 0-50%) to afford tert-butyl 5-(3-((tert-butoxycarbonyl)amino)azetidin-1-yl)-3-isopropyl-2-(4,4,5,5-tetramethyl-1,3,2-dioxaborolan-2-yl)-1H-pyrrolo[3,2-b]pyridine-1-carboxylate (830 mg, 1.49 mmol, 80% yield). LCMS retention time 1.05 min [TS]. MS (E$^+$) m/z: 557.7 (M+H). $^1$H NMR (499 MHz, CHLOROFORM-d) δ 7.84 (d, J=8.8 Hz, 1H), 6.21 (d, J=8.8 Hz, 1H), 5.05-4.86 (m, 1H), 4.70-4.53 (m, 1H), 4.34 (br t, J=7.5 Hz, 2H), 3.77 (dd, J=8.5, 5.3 Hz, 2H), 3.29-3.14 (m, 1H), 1.64 (s, 9H), 1.46 (s, 9H), 1.44-1.41 (m, 18H).

Intermediate 1F: (1-(3-isopropyl-2-(4,4,5,5-tetramethyl-1,3,2-dioxaborolan-2-yl)-1H-pyrrolo[3,2-b]pyridin-5-yl)azetidin-3-yl)carbamate

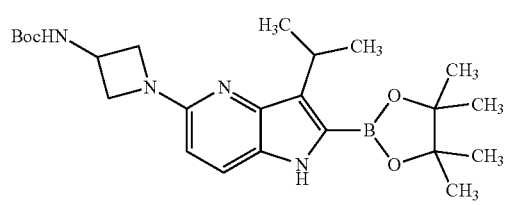

tert-butyl 5-(3-((tert-butoxycarbonyl)amino)azetidin-1-yl)-3-isopropyl-2-(4,4,5,5-tetramethyl-1,3,2-dioxaborolan-2-yl)-1H-pyrrolo[3,2-b]pyridine-1-carboxylate (830 mg, 1.49 mmol) was heated neat under nitrogen atmosphere with slow stirring at 165° C. for 100 min. Upon completion, the material was dissolved in DCM and concentrated to obtain tert-butyl (1-(3-isopropyl-2-(4,4,5,5-tetramethyl-1,3,2-dioxaborolan-2-yl)-1H-pyrrolo[3,2-b]pyridin-5-yl)azetidin-3-yl)carbamate as an off-white foam. LCMS retention time 0.92 min [TS]. MS (E$^+$) m/z: 457.7 (M+H). $^1$H NMR (499 MHz, CHLOROFORM-d) δ 8.06 (br s, 1H), 7.42 (d, J=8.8 Hz, 1H), 6.29 (d, J=8.7 Hz, 1H), 5.07-4.85 (m, 1H), 4.66-4.54 (m, 1H), 4.39-4.29 (m, 2H), 3.77 (dd, J=8.7, 5.5 Hz, 2H), 3.68-3.59 (m, 1H), 1.48 (d, J=7.0 Hz, 6H), 1.46 (s, 9H), 1.34 (s, 12H).

Intermediate 1G: tert-butyl(1-(2-(7,8-dimethyl-[1,2,4]triazolo[1,5-a]pyridin-6-yl)-3-isopropyl-1H-pyrrolo[3,2-b]pyridin-5-yl)azetidin-3-yl)carbamate

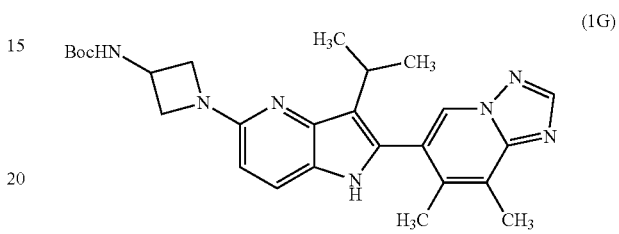

To a suspension of tert-butyl (1-(3-isopropyl-2-(4,4,5,5-tetramethyl-1,3,2-dioxaborolan-2-yl)-1H-pyrrolo[3,2-b]pyridin-5-yl)azetidin-3-yl)carbamate (227 mg, 0.497 mmol), 6-bromo-7,8-dimethyl-[1,2,4]triazolo[1,5-a]pyridine (124 mg, 0.547 mmol), and 2$^{nd}$ Generation XPhos precatalyst (19.6 mg, 0.025 mmol) in dioxane (3.3 mL) was added 2M aqueous potassium phosphate tribasic (0.75 mL, 1.49 mmol). The biphasic mixture was degassed with nitrogen for 10 min. The vial was sealed and stirred at 70° C. for 2 hours. Upon completion, the reaction mixture was cooled to room temperature and concentrated. The crude material was taken up in DCM and purified by silica gel column chromatography (0-100% Hex/EtOAc) to afford tert-butyl (1-(2-(7,8-dimethyl-[1,2,4]triazolo[1,5-a]pyridin-6-yl)-3-isopropyl-1H-pyrrolo[3,2-b]pyridin-5-yl) azetidin-3-yl)carbamate (170 mg, 0.357 mmol, 72% yield). LCMS retention time 0.77 min [TS]. MS (E$^+$) m/z: 476.6 (M+H).

Example 1

To a suspension of tert-butyl (1-(2-(7,8-dimethyl-[1,2,4]triazolo[1,5-a]pyridin-6-yl)-3-isopropyl-1H-pyrrolo[3,2-b]pyridin-5-yl)azetidin-3-yl)carbamate (170 mg, 0.357 mmol) in DCM (14 mL) at room temperature was added TFA (3.6 mL). The reaction mixture was stirred at room temperature for 30 minutes. Upon completion, the reaction mixture was concentrated. The crude material was taken up in DMF (3.6 mL) and Et$_3$N (0.15 mL, 1.07 mmol), tetrahydro-4H-pyran-4-one (71.5 mg, 0.714 mmol), and sodium triacetoxyborohydride (151 mg, 0.714 mmol) were added sequentially. After stirring for 3 hours, additional DMF (3.6 mL) and Et$_3$N (0.15 mL, 1.07 mmol), tetrahydro-4H-pyran-4-one (71.5 mg, 0.714 mmol), and sodium triacetoxyborohydride (151 mg, 0.714 mmol) were added sequentially. After stirring for 2 hours more at room temperature, the reaction was quenched by the addition of water, aqueous K$_2$HPO$_4$ 1.5M dibasic solution and DCM. The organic layer was separated, dried over sodium sulfate, concentrated and the crude material was purified by SFC chromatography using the following conditions: CHIRAL IC 25×3.0 cm ID, 5 μm column; 85.0 mL/min flow rate; 60/40 CO$_2$/methanol with 0.1% diethylamine mobile phase; 260 nm detector wavelength to obtain 1-(2-(7,8-dimethyl-[1,2,4]triazolo[1,5-a]pyridin-6-yl)-3-isopropyl-1H-pyrrolo[3,2-b]pyridin-5-yl)-N-(tetrahydro-2H-pyran-4-yl)azetidin-3-amine (95 mg, 0.203 mmol, 57% yield). LCMS retention time 0.53 min [TS]. MS (E⁺) m/z: 460.7 (M+H). ¹H NMR (499 MHz, DMSO-d₆) δ 10.80 (s, 1H), 8.75 (s, 1H), 8.46 (s, 1H), 7.50 (d, J=8.7 Hz, 1H), 6.27 (d, J=8.7 Hz, 1H), 4.11 (t, J=7.3 Hz, 2H), 3.86-3.73 (m, 3H), 3.57 (t, J=6.8 Hz, 2H), 3.32-3.25 (m, 3H), 2.84-2.75 (m, 1H), 2.58 (s, 3H), 2.15 (s, 3H), 1.75-1.66 (m, 2H), 1.36 (br d, J=6.8 Hz, 6H), 1.31-1.21 (m, 2H).

Example 2

6-(3-isopropyl-5-(piperazin-1-yl)-1H-pyrrolo[3,2-b]pyridin-2-yl)-7,8-dimethyl-[1,2,4]triazolo[1,5-a]pyridine

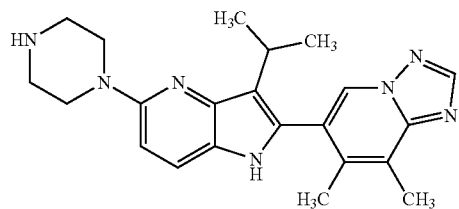

(2)

Intermediate 2A: tert-butyl 5-(4-(tert-butoxycarbonyl)piperazin-1-yl)-3-isopropyl-1H-pyrrolo[3,2-b]pyridine-1-carboxylate

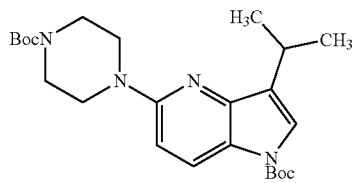

(2A)

A suspension of tert-butyl 5-bromo-3-isopropyl-1H-pyrrolo[3,2-b]pyridine-1-carboxylate (2.0 g, 5.90 mmol), tert-butyl piperazine-1-carboxylate (1.32 g, 7.07 mmol), 2$^{nd}$ generation RuPhos precatalyst (0.114 g, 0.147 mmol), and Cs₂CO₃ (4.80 g, 14.7 mmol) in 1,4-dioxane (20 mL) in a reaction vial with a pressure-relief septum-lined cap and stir bar was degassed with nitrogen gas for 5 minutes. The reaction vial was sealed and placed in a heating block with stirring at 100° C. for 3 hours. An identical reaction following the same protocol was set up in parallel, and the two reactions were combined for workup and purification. Upon completion, the combined reactions were filtered and concentrated. The crude material was purified by silica gel column chromatography on a Teledyne Isco instrument eluting with Hex/EtOAc 0-60% to give tert-butyl 5-(4-(tert-butoxycarbonyl) piperazin-1-yl)-3-isopropyl-1H-pyrrolo[3,2-b]pyridine-1-carboxylate (4.64 g total) as an off-white foam. LCMS retention time 1.13 [TS]. MS (E⁺) 445.3 (M+H). ¹H NMR (499 MHz, CHLOROFORM-d) δ 8.13 (br s, 1H), 7.39 (br s, 1H), 6.65 (br d, J=9.0 Hz, 1H), 3.64-3.57 (m, 4H), 3.57-3.50 (m, 4H), 3.28-3.14 (m, 1H), 1.65 (s, 9H), 1.49 (s, 9H), 1.36 (d, J=6.9 Hz, 6H).

Intermediate 2B: tert-butyl 5-(4-(tert-butoxycarbonyl)piperazin-1-yl)-3-isopropyl-2-(4,4,5,5-tetramethyl-1,3,2-dioxaborolan-2-yl)-1H-pyrrolo[3,2-b]pyridine-1-carboxylate

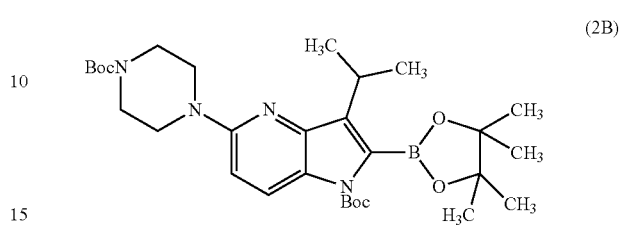

(2B)

A solution containing tert-butyl 5-(4-(tert-butoxycarbonyl)piperazin-1-yl)-3-isopropyl-1H-pyrrolo[3,2-b]pyridine-1-carboxylate (4.64 g, 10.4 mmol) and 2-isopropoxy-4,4,5,5-tetramethyl-1,3,2-dioxaborolane (3.19 mL, 15.66 mmol) in dry THF (52 mL), under a nitrogen atmosphere was cooled in a dry ice/acetone bath to −78° C. and treated with LDA (2M in THF, 10.4 mL, 20.8 mmol). The mixture was allowed to warm to 0° C. over the course of 5 hours. Upon completion, the reaction was quenched by the addition of saturated aqueous NH₄Cl solution, water, and EtOAc. The organic layer was separated, dried over magnesium sulfate, filtered and concentrated. The crude material was purified by silica gel column chromatography eluting with Hex/EtOAc 0-50% to give tert-butyl 5-(4-(tert-butoxycarbonyl)piperazin-1-yl)-3-isopropyl-2-(4,4,5,5-tetramethyl-1,3,2-dioxaborolan-2-yl)-1H-pyrrolo[3,2-b]pyridine-1-carboxylate (5.29 g, 9.27 mmol, 89% yield). LCMS retention time 1.23 [TS]. MS (E⁺) m/z: 571.2. ¹H NMR (499 MHz, CHLOROFORM-d) δ 7.86 (d, J=9.1 Hz, 1H), 6.59 (d, J=9.1 Hz, 1H), 3.62-3.55 (m, 4H), 3.55-3.49 (m, 4H), 3.20 (spt, J=7.0 Hz, 1H), 1.64 (s, 9H), 1.49 (s, 9H), 1.44 (d, J=6.9 Hz, 6H), 1.42 (s, 12H).

Intermediate 2C: tert-butyl 4-(3-isopropyl-2-(4,4,5,5-tetramethyl-1,3,2-dioxaborolan-2-yl)-1H-pyrrolo[3,2-b]pyridin-5-yl)piperazine-1-carboxylate

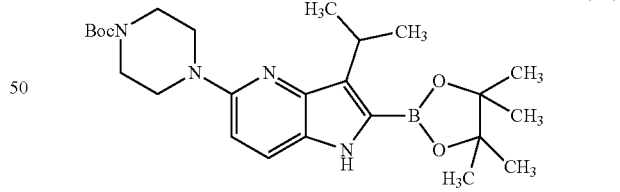

(2C)

tert-Butyl 5-(4-(tert-butoxycarbonyl)piperazin-1-yl)-3-isopropyl-2-(4,4,5,5-tetramethyl-1,3,2-dioxaborolan-2-yl)-1H-pyrrolo[3,2-b]pyridine-1-carboxylate (5.29 g, 9.27 mmol) was heated neat at 170° C. under a nitrogen atmosphere with stirring for 6 hours. The reaction mixture was cooled to room temperature and remained at room temperature for 3 days. The reaction mixture was then reheated to 170° C. under a nitrogen atmosphere with stirring for another 4 hours. Upon completion, the material was dissolved in DCM and concentrated to afford tert-butyl 4-(3-isopropyl-2-(4,4,5,5-tetramethyl-1,3,2-dioxaborolan-2-yl)-1H-pyrrolo[3,2-b]pyridin-5-yl)piperazine-1-carboxylate (4.02 g, 8.55 mmol, 92% yield) as a light brown foam. The material was carried forward without additional purification. Observed significant conversion to boronic acid on LCMS, although NMR indicated that the product was purely the compound. Boronic acid LCMS retention time 0.74 [TS]. Boronic acid MS (E$^+$) m/z: 389.1 (M+H). Product characterization: LCMS retention time 0.93 [TS]. MS (E$^+$) m/z: 471.2 (M+H). $^1$H NMR (499 MHz, CHLOROFORM-d) δ 8.07 (s, 1H), 7.46 (d, J=8.9 Hz, 1H), 6.69 (d, J=9.1 Hz, 1H), 3.68-3.55 (m, 5H), 3.55-3.47 (m, 4H), 1.51-1.48 (m, 15H), 1.34 (s, 12H).

Intermediate 2D: tert-butyl 4-(2-(7,8-dimethyl-[1,2,4]triazolo[1,5-a]pyridin-6-yl)-3-isopropyl-1H-pyrrolo[3,2-b]pyridin-5-yl)piperazine-1-carboxylate

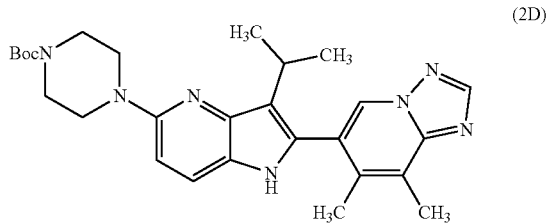 [SMILES: Cc1c(-c2[nH]c3ccc(N4CCN(C(=O)OC(C)(C)C)CC4)nc3c2C(C)C)cn2ncnc2c1C]

(2D)

To a mixture of tert-butyl 4-(3-isopropyl-2-(4,4,5,5-tetramethyl-1,3,2-dioxaborolan-2-yl)-1H-pyrrolo[3,2-b]pyridin-5-yl)piperazine-1-carboxylate (2.5 g, 5.31 mmol), 6-bromo-7,8-dimethyl-[1,2,4]triazolo[1,5-a]pyridine (1.44 g, 6.38 mmol), and 2$^{nd}$ generation XPhos precatalyst (0.209 g, 0.266 mmol) in 1,4-dioxane (27 mL) was added aqueous K$_3$PO$_4$ solution (2M, 7.97 mL, 15.9 mmol). The biphasic mixture was degassed with nitrogen gas for 10 min. The reaction vessel was sealed, a line of nitrogen gas was affixed, and the reaction mixture was stirred at 70° C. for 3 hours. Upon completion, the reaction mixture was cooled to room temperature and diluted with EtOAc and water. The layers were separated, and the aqueous layer was extracted with EtOAc. The combined organic layer was dried over MgSO$_4$ and concentrated to afford a crude brown oil. This material was by silica gel column chromatography on a Teledyne Isco instrument eluting with 0-100% Hex/EtOAc to afford tert-butyl 4-(2-(7,8-dimethyl-[1,2,4]triazolo[1,5-a]pyridin-6-yl)-3-isopropyl-1H-pyrrolo[3,2-b]pyridin-5-yl)piperazine-1-carboxylate (2.31 g, 4.72 mmol, 89% yield). LCMS retention time 0.77 [TS]. MS (E$^+$) m/z: 490.2 (M+H). $^1$H NMR (499 MHz, DMSO-d$_6$) δ 10.89 (s, 1H), 8.77 (s, 1H), 8.47 (s, 1H), 7.56 (d, J=8.9 Hz, 1H), 6.77 (d, J=8.9 Hz, 1H), 3.54-3.40 (m, 8H), 2.79 (spt, J=6.8 Hz, 1H), 2.58 (s, 3H), 2.16 (s, 3H), 1.43 (s, 9H), 1.38 (d, J=6.9 Hz, 6H).

Example 2

To a suspension of tert-butyl 4-(2-(7,8-dimethyl-[1,2,4]triazolo[1,5-a]pyridin-6-yl)-3-isopropyl-1H-pyrrolo[3,2-b]pyridin-5-yl)piperazine-1-carboxylate (223 mg, 0.455 mmol) in DCM (5 mL) at room temperature was added TFA (1 mL). The reaction mixture was stirred at room temperature for 90 min and then concentrated to afford crude 6-(3-isopropyl-5-(piperazin-1-yl)-1H-pyrrolo[3,2-b]pyridin-2-yl)-7,8-dimethyl-[1,2,4]triazolo[1,5-a]pyridine. A portion (10%) of this material was purified using preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 5% B, 5-45% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation to afford 6-(3-isopropyl-5-(piperazin-1-yl)-1H-pyrrolo[3,2-b]pyridin-2-yl)-7,8-dimethyl-[1,2,4]triazolo[1,5-a]pyridine (15.9 mg, 0.040 mmol). LCMS retention time 0.77 min [QC-ACN-TFA-XB]. MS (E$^+$) m/z: 390.3 (M+H). $^1$H NMR (500 MHz, DMSO-d$_6$) δ 10.70 (s, 1H), 8.69 (s, 1H), 8.42 (s, 1H), 7.53 (d, J=8.8 Hz, 1H), 6.71 (d, J=8.9 Hz, 1H), 3.46-3.36 (m, 4H), 2.94-2.85 (m, 4H), 2.85-2.77 (m, 1H), 2.59 (s, 3H), 2.17 (s, 3H), 1.37 (br d, J=6.6 Hz, 6H).

Example 3

1-(4-(2-(7,8-dimethyl-[1,2,4]triazolo[1,5-a]pyridin-6-yl)-3-isopropyl-1H-pyrrolo[3,2-b]pyridin-5-yl)piperazin-1-yl)-2-(dimethylamino)ethan-1-one

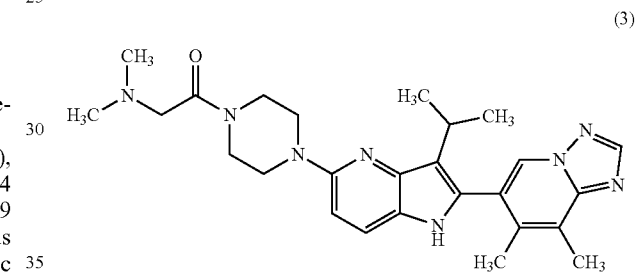

(3)

A solution of 6-(3-isopropyl-5-(piperazin-1-yl)-1H-pyrrolo[3,2-b]pyridin-2-yl)-7,8-dimethyl-[1,2,4]triazolo[1,5-a]pyridine, TFA (18.9 mg, 0.0376 mmol) in methanol was converted to the HCl salt form by adding 1 mL of 4N HCl in dioxane and concentrating to dryness. The material was taken up in methanol a second time, 1 mL of 4N HCl in dioxane was added, and the material was concentrated to dryness. The material was then suspended in DMF (1 mL) and dimethylglycine (28 mg, 0.272 mmol), Et$_3$N (0.10 mL, 0.717 mmol) and T3P 50% in DMF (0.110 mL, 0.188 mmol) were added. The reaction mixture was stirred for 1 hour at room temperature. Upon completion, the reaction was quenched by addition of water, aqueous K$_2$HPO$_4$ 1.5M solution, and DCM. The organic layer was separated, concentrated, taken up in methanol and purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0 minute hold at 13% B, 13-53% B over 20 minutes, then a 4 minute hold at 100% B; Flow Rate: 20 mL/min; Column Temperature: 25° C. Fraction collection was triggered by MS and UV signals. Fractions containing the product were combined and dried via centrifugal evaporation to afford 1-(4-(2-(7,8-dimethyl-[1,2,4]triazolo[1,5-a]pyridin-6-yl)-3-isopropyl-1H-pyrrolo[3,2-b]pyridin-5-yl)piperazin-1-yl)-2-(dimethylamino)ethan-1-one (12.8 mg, 0.026 mmol, 69.4% yield). LCMS retention time 0.86 min [QC-ACN-TFA-XB]. MS (E$^+$) m/z: 475.3 (M+H). $^1$H NMR (500 MHz, DMSO-d$_6$) δ 10.87 (s, 1H), 8.70 (s, 1H), 8.44 (s, 1H), 7.57 (d, J=8.9 Hz, 1H), 6.78 (d, J=8.9 Hz, 1H), 3.16 (s, 2H), 2.84-2.73 (m, 1H), 2.56 (s, 3H), 2.14 (s, 3H), 1.35 (br d, J=6.7 Hz, 6H).

Example 4

4-(2-(7,8-dimethyl-[1,2,4]triazolo[1,5-a]pyridin-6-yl)-3-isopropyl-1H-pyrrolo[3,2-b]pyridin-5-yl)-N-((1-(methylsulfonyl)cyclopropyl)methyl)cyclohexan-1-amine (4)

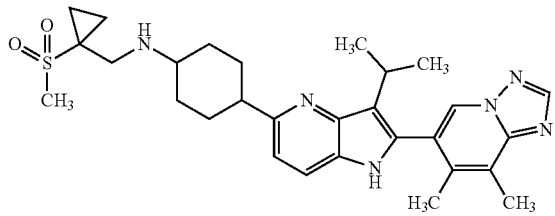

Intermediate 4A: tert-butyl 3-isopropyl-5-(1,4-dioxaspiro[4.5]dec-7-en-8-yl)-1H-pyrrolo[3,2-b]pyridine-1-carboxylate (4A)

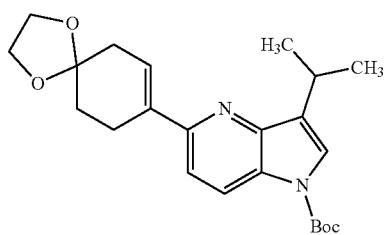

To a solution of tert-butyl 5-bromo-3-isopropyl-1H-pyrrolo[3,2-b]pyridine-1-carboxylate (19.00 g, 56.0 mmol), 4,4,5,5-tetramethyl-2-(1,4-dioxaspiro[4.5]dec-7-en-8-yl)-1,3,2-dioxaborolane (16.40 g, 61.6 mmol) and 2 M aqueous potassium phosphate tribasic (84 mL, 168 mmol) in TH (300 mL) was added PdCl$_2$(dppf)-CH$_2$Cl$_2$ adduct (1.372 g, 1.680 mmol). The bi-phasic mixture was degassed with nitrogen gas for 10 minutes and the sealed vial was stirred at 70° C. for 2 hours. The reaction mixture was cooled to room temperature and diluted with ethyl acetate and water. The mixture was transferred to a separatory funnel and the layers were separated. The combined organics were washed with saturated sodium sulfate, filtered and concentrated to dryness. Further purification was done by silica gel chromatography, which afforded tert-butyl 3-isopropyl-5-(1,4-dioxaspiro[4.5]dec-7-en-8-yl)-1H-pyrrolo[3,2-b]pyridine-1-carboxylate (18.00 g, 45.0 mmol, 86% yield) as a light yellow solid. LCMS retention time 1.09 min [A1]. MS m/z: 399.5 (M+H).

Intermediate 4B: tert-butyl 3-isopropyl-5-(1,4-dioxaspiro[4.5]decan-8-yl)-1H-pyrrolo[3,2-b]pyridine-1-carboxylate (4B)

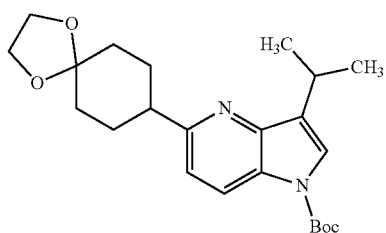

To tert-butyl 3-isopropyl-5-(1,4-dioxaspiro[4.5]dec-7-en-8-yl)-1H-pyrrolo[3,2-b]pyridine-1-carboxylate (18.00 g, 45.0 mmol) in a Parr bottle were added MeOH (15 mL) and 10% w/w Pd/C (1.490 g, 1.400 mmol). The vessel was placed on the Parr high pressure hydrogenation apparatus and pump/purged three times with nitrogen gas. After evacuation, the vessel was back-filled with hydrogen gas to approximately 40 psi and the reaction mixture was allowed to shake for 2 hours. The vessel was diluted with MeOH (200 mL) and ethyl acetate (200 mL) and the contents was filtered through tightly packed Celite. Upon concentration, collected 3-isopropyl-5-(1,4-dioxaspiro[4.5]decan-8-yl)-1H-indole (19.00 g, 47.0 mmol, 100% yield) as a dark oil. LCMS retention time 0.95 min [A1]. MS m/z: 401.6 (M+H).

Intermediate 4C: 3-isopropyl-5-(1,4-dioxaspiro[4.5]decan-8-yl)-2-(4,4,5,5-tetramethyl-1,3,2-dioxaborolan-2-yl)-1H-pyrrolo[3,2-b]pyridine (4C)

A solution containing tert-butyl 3-isopropyl-5-(1,4-dioxaspiro[4.5]decan-8-yl)-1H-pyrrolo[3,2-b]pyridine-1-carboxylate (1.600 g, 3.99 mmol) and 2-isopropoxy-4,4,5,5-tetramethyl-1,3,2-dioxaborolane (1.467 mL, 7.19 mmol) in dry THF (9.99 mL), under a nitrogen atmosphere was cooled in a dry-ice/acetone bath at −78° C. After stirring at −78° C. for 20 minutes, LDA (2 M in THF) (5.99 mL, 11.98 mmol) was added. The mixture was stirred at −78° C. for 30 min and allowed to warm to −30° C. over 1 hour and stirred at −30° C. for 30 minutes. The reaction mixture was treated with 1.5 M aqueous KH$_2$PO$_4$ solution. Water and ethyl acetate were added and the mixture was transferred to a separatory funnel. The layers were separated and the combined organics were washed with brine, dried over anhydrous sodium sulfate, filtered and concentrated. The crude product was further purified by silica gel chromatography, which afforded tert-butyl 3-isopropyl-5-(1,4-dioxaspiro[4.5]decan-8-yl)-2-(4,4,5,5-tetramethyl-1,3,2-dioxaborolan-2- yl)-1H-pyrrolo[3,2-b]pyridine-1-carboxylate (1.7 g, 3.22 mmol, 81% yield). LCMS retention time 1.00 min [A1]. MS m/z: 527.3 (M+H).

tert-Butyl 3-isopropyl-5-(1,4-dioxaspiro[4.5]decan-8-yl)-2-(4,4,5,5-tetramethyl-1,3,2-dioxaborolan-2-yl)-1H-pyrrolo[3,2-b]pyridine-1-carboxylate (1.7 g, 3.22 mmol) was added to a tall vial and the vial was capped. The vial was pump/purged three times with nitrogen gas and set to heat at 165° C. under a nitrogen atmosphere for 1.5 hours. The reaction mixture was cooled to room temperature and 3-isopropyl-5-(1,4-dioxaspiro[4.5]decan-8-yl)-2-(4,4,5,5-tetramethyl-1,3,2-dioxaborolan-2-yl)-1H-pyrrolo[3,2-b]pyridine (1.4 g, 3.28 mmol, 100% yield) was obtained and used as such. LCMS retention time 0.61 min [A1]. MS m/z: 345.8 (M+H) (observed the mass of the corresponding boronic acid).

Intermediate 4D: 4-(2-(7,8-dimethyl-[1,2,4]triazolo[1,5-a]pyridin-6-yl)-3-isopropyl-1H-pyrrolo[3,2-b]pyridin-5-yl)cyclohexan-1-one

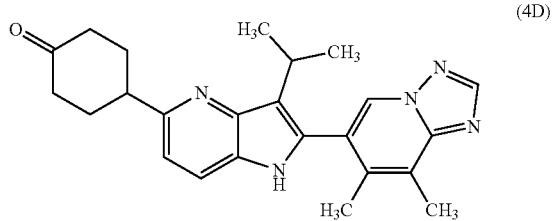 [SMILES: Cc1c(-c2[nH]c3ccc(C4CCC(=O)CC4)nc3c2C(C)C)cn2ncnc2c1C]

(4D)

In a 40 mL reaction vial were added 3-isopropyl-5-(1,4-dioxaspiro[4.5]decan-8-yl)-2-(4,4,5,5-tetramethyl-1,3,2-dioxaborolan-2-yl)-1H-pyrrolo[3,2-b]pyridine (0.500 g, 1.173 mmol), 1,1'-bis(di-tert-butylphosphino)ferrocene palladium dichloride (0.023 g, 0.035 mmol), 6-bromo-7,8-dimethyl-[1,2,4]triazolo[1,5-a]pyridine (0.265 g, 1.173 mmol) and THF (20 mL). The reaction vial was sealed and pump/purged three times with nitrogen gas. To this was added 2 M aqueous potassium phosphate tribasic (1.759 mL, 3.52 mmol) and the reaction mixture was heated to 65° C. for 1 hour. Following cooling to room temperature, the mixture was diluted with ethyl acetate and washed with water, then brine and dried over anhydrous sodium sulfate. The solids were filtered and the filtrate was concentrated. The residue was further purified by silica gel chromatography. Following concentration of the fractions, 6-(3-isopropyl-5-(1,4-dioxaspiro[4.5]decan-8-yl)-1H-pyrrolo[3,2-b]pyridin-2-yl)-7,8-dimethyl-[1,2,4]triazolo[1,5-a]pyridine was collected as a tan solid. To this intermediate was added DCM (0.5 mL), TFA (5 mL) and water (0.02 mL). The reaction vial was capped and stirred at room temperature for 4 hours, then concentrated under a stream of nitrogen. To this was added 1.5 M potassium phosphate solution, water and DCM. The mixture was poured into a separatory funnel and the layers were separated. The organics were washed with brine, dried over anhydrous sodium sulfate, filtered and concentrated to afford 4-(2-(7,8-dimethyl-[1,2,4]triazolo[1,5-a]pyridin-6-yl)-3-isopropyl-1H-pyrrolo[3,2-b]pyridin-5-yl)cyclohexan-1-one (0.22 g, 0.548 mmol, 47% yield). LCMS retention time 0.61 min [A1]. MS m/z: 402.2 (M+H).

Example 4

4-(2-(7,8-dimethyl-[1,2,4]triazolo[1,5-a]pyridin-6-yl)-3-isopropyl-1H-pyrrolo[3,2-b] pyridin-5-yl)cyclohexan-1-one (0.500 g, 1.245 mmol), (1-(methylsulfonyl)cyclopropyl)methanamine hydrochloride (0.347 g, 1.868 mmol) and TEA (0.694 mL, 4.98 mmol) were mixed in DCM (5 mL). The reaction vial was capped and the reaction mixture stirred under nitrogen overnight at room temperature. The volatiles were removed under a stream of nitrogen and the residue was placed under a nitrogen atmosphere and diluted with MeOH (5 mL). This was cooled to −78° C. and lithium borohydride (0.081 g, 3.74 mmol) was added. The reaction mixture was allowed to warm to room temperature in the dry ice bath overnight. The reaction was quenched via addition of 1.5M K$_2$HPO$_4$. Ethyl acetate was added and the mixture was extracted three times. The organics were washed with saturated NaCl solution, dried over sodium sulfate, filtered and concentrated. The material was further purified by silica gel chromatography and then SFC. The major and first eluting isolate was collected to afford 4-(2-(7,8-dimethyl-[1,2,4]triazolo[1,5-a]pyridin-6-yl)-3-isopropyl-1H-pyrrolo[3,2-b]pyridin-5-yl)-N-((1-(methylsulfonyl)cyclopropyl)methyl)cyclohexan-1-amine (0.300 g, 0.555 mmol, 45% yield) as an off-white solid. HPLC retention time 1.44 min [Method C]. MS m/z: 535.4 (M+H). HPLC retention time 0.845 min [Method D]. $^1$H NMR (499 MHz, DMSO-d$_6$) δ 11.14-11.02 (m, 1H), 8.80 (s, 1H), 8.49 (s, 1H), 7.66-7.55 (m, 1H), 7.07-6.94 (m, 1H), 3.41-3.29 (m, 2H), 3.17 (d, J=2.9 Hz, 1H), 3.14-3.12 (m, 1H), 3.14 (s, 1H), 3.02 (br d, J=7.0 Hz, 2H), 2.96-2.84 (m, 1H), 2.71 (tt, J=12.0, 3.5 Hz, 1H), 2.45 (br d, J=2.0 Hz, 1H), 2.18 (s, 3H), 2.08-1.99 (m, 2H), 1.94 (br d, J=11.8 Hz, 2H), 1.89-1.76 (m, 1H), 1.75-1.56 (m, 2H), 1.40 (d, J=6.8 Hz, 6H), 1.29-1.13 (m, 5H), 1.08-0.94 (m, 2H).

Example 5

2-(3,4-dimethoxyphenyl)-5-(1'-isobutyl-[1,4'-bipiperidin]-4-yl)-3-methyl-1H-pyrrolo[3,2-b]pyridine

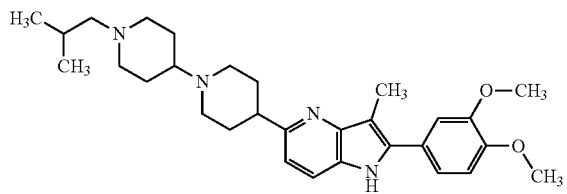

(5)

Intermediates 5A-1 and 5A-1: 5-bromo-2-(3,4-dimethoxyphenyl)-3-methyl-1H-pyrrolo[3,2-b]pyridine and 5-bromo-3-(3,4-dimethoxyphenyl)-2-methyl-1H-pyrrolo[3,2-b]pyridine

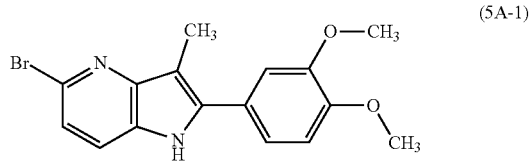

(5A-1)

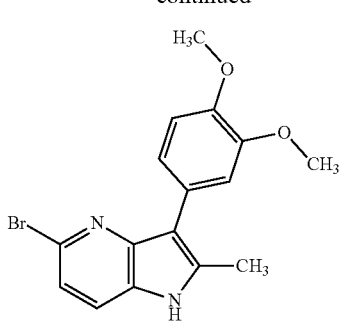

(5A-2)

To a mixture of 6-bromo-2-iodopyridin-3-amine (100 mg, 0.34 mmol), 1,2-dimethoxy-4-(prop-1-yn-1-yl)benzene (74 mg, 0.42 mmol), lithium chloride (18 mg, 0.42 mmol), sodium carbonate (180 mg, 1.68 mmol) and Pd(dppf)Cl$_2$ (12.5 mg, 0.017 mmol) in a screw cap vial was added DMF (2 mL). The vial was fitted with a Teflon-lined septum cap. The system was evacuated under vacuum (via a needle from a nitrogen/vacuum manifold line) and backfilled with nitrogen gas. The procedure was repeated three times. The needle was removed and the vial was heated at 100° C. for 16 h. LCMS analysis shows formation of two isomers, in approximately 3:1 ratio. $^1$H NMR analysis suggested the major product to be 5-bromo-2-(3,4-dimethoxyphenyl)-3-methyl-1H-pyrrolo[3,2-b]pyridine (5A-1). The reaction mixture was diluted with EtOAc (50 mL), poured into a separatory funnel and washed with 10% aqueous LiCl solution (2×10 mL) and saturated aqueous NaCl solution (10 mL), dried (Na$_2$SO$_4$), filtered and the filtrate was concentrated. The crude product was dissolved in a small amount of DCM and purified on a silica gel column chromatography with a 15 min gradient from 0%-100% DCM/EtOAc to afford 5-bromo-2-(3,4-dimethoxyphenyl)-3-methyl-1H-pyrrolo[3,2-b]pyridine (Intermediate 5A-1) that was contaminated with Intermediate 5A-2, 5-bromo-3-(3,4-dimethoxyphenyl)-2-methyl-1H-pyrrolo[3,2-b] pyridine, m/z (303, M+1), 80 mg (67%).

Intermediate 5B: tert-butyl 4-(2-(3,4-dimethoxyphenyl)-3-methyl-H-pyrrolo[3,2-b]pyridin-5-yl)-3,6-dihydropyridine-1(2H)-carboxylate

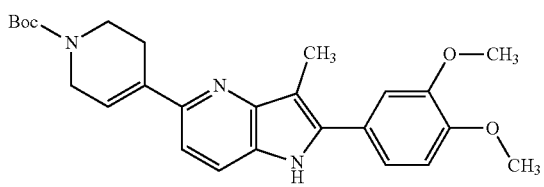

(5B)

To a mixture containing 5-bromo-2-(3,4-dimethoxyphenyl)-3-methyl-1H-pyrrolo[3,2-b]pyridine (Intermediate 5A-1) and Intermediate 5A-2 (100 mg, 0.29 mmol), tert-butyl 4-(4,4,5,5-tetramethyl-1,3,2-dioxaborolan-2-yl)-5,6-dihydropyridine-1(2H)-carboxylate (111 mg, 0.36 mmol), and Pd(dppf)Cl$_2$ (10.5 mg, 0.014 mmol) in a screw cap vial was added THF (2.5 mL) followed by 3M aqueous solution of tripotassium phosphate (0.10 mL, 0.3 mmol). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 75° C. for 3 h. The reaction mixture was cooled to room temperature and treated with saturated aqueous NaCl solution (5 mL) and extracted with ethyl acetate (3×10 mL). The extracts were combined, dried (Na$_2$SO$_4$), filtered and concentrated. The crude product was dissolved in a small amount of DCM and purified on silica gel column chromatography eluting with a 10 min gradient from 5%-100% DCM/EtOAc. No separation was observed. A mixture of tert-butyl 4-(2-(3,4-dimethoxyphenyl)-3-methyl-1H-pyrrolo[3,2-b]pyridin-5-yl)-5,6-dihydropyridine-1(2H)-carboxylate (Intermediate 5B) and the regioisomer tert-butyl 4-(3-(3,4-dimethoxyphenyl)-2-methyl-1H-pyrrolo[3,2-b]pyridin-5-yl)-5,6-dihydropyridine-1(2H)-carboxylate was isolated (100 mg, 77% yield), m/z (550, M+1) and was used as such in subsequent step.

Intermediate 5C: tert-butyl 4-(2-(3,4-dimethoxyphenyl)-3-methyl-H-pyrrolo[3,2-b]pyridin-5-yl)piperidine-1-carboxylate

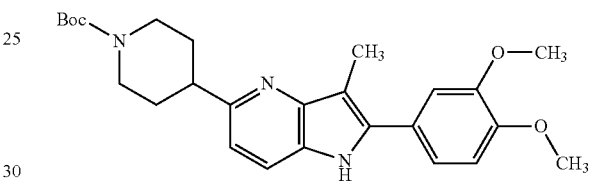

(5C)

A mixture of tert-butyl 4-(2-(3,4-dimethoxyphenyl)-3-methyl-1H-pyrrolo[3,2-b]pyridin-5-yl)-5,6-dihydropyridine-1(2H)-carboxylate (Intermediate 5B) and regioisomer tert-butyl 4-(3-(3,4-dimethoxyphenyl)-2-methyl-1H-pyrrolo [3,2-b]pyridin-5-yl)-5,6-dihydropyridine-1(2H)-carboxylate (95 mg, 0.21 mmol) was dissolved in MeOH (5 mL) and transferred to a Parr bottle. The mixture was purged with nitrogen. Pearlman's Catalyst (25 mg, 0.036 mmol) was added and the bottle was pressurized with hydrogen gas (50 psi) and shaken for 22 h. The reaction mixture was filtered through a pad of Celite and the filtrate was concentrated. The resulting residue was dissolved in a small amount of DCM and charged to a silica gel column, which was eluted over a 10 min gradient with 1%-5% MeOH/DCM to afford a mixture of tert-butyl 4-(2-(3,4-dimethoxyphenyl)-3-methyl-1H-pyrrolo[3,2-b]pyridin-5-yl)-5,6-dihydropyridine-1(2H)-carboxylate (Intermediate 5C) and the regioisomer tert-butyl 4-(3-(3,4-dimethoxyphenyl)-2-methyl-1H-pyrrolo[3,2-b]pyridin-5-yl)-5,6-dihydropyridine-1(2H)-carboxylate (82 mg, 80%), m/z (452, M+H).

Intermediate 5D: 2-(3,4-dimethoxyphenyl)-3-methyl-5-(piperidin-4-yl)-1H-pyrrolo[3,2-b]pyridine

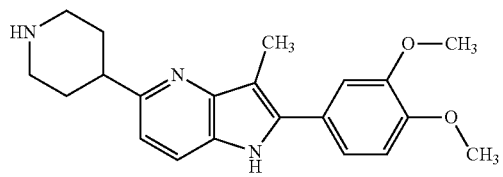

(5D)

The mixture of isomers (tert-butyl 4-(2-(3,4-dimethoxyphenyl)-3-methyl-1H-pyrrolo[3,2-b]pyridin-5-yl)piperidine-1-carboxylate (Intermediate 5C) and tert-butyl 4-(3-(3,4-dimethoxyphenyl)-2-methyl-1H-pyrrolo[3,2-b]pyridin-5-yl)piperidine-1-carboxylate (80 mg, 0.18 mmol) were suspended in 4 N HCl in dioxane (4 mL, 16.00 mmol), stirred for 30 min, and concentrated to dryness. The resulting residue was suspended in diethyl ether (1 mL) and the solids were filtered and dried to give a mixture of 2-(3,4-dimethoxyphenyl)-3-methyl-5-(piperidin-4-yl)-1H-pyrrolo[3,2-b]pyridine (Intermediate 5D) and 3-(3,4-dimethoxyphenyl)-2-methyl-5-(piperidin-4-yl)-1H-pyrrolo[3,2-b]pyridine as bis HCl salts (50 mg, 65%), m/z (352, M+H).

Example 5

To a solution containing a mixture of 3-(3,4-dimethoxyphenyl)-2-methyl-5-(piperidin-4-yl)-1H-pyrrolo[2,3-c]pyridine 2 HCl (Intermediate 5D) and 2-(3,4-dimethoxyphenyl)-3-methyl-5-(piperidin-4-yl)-1H-pyrrolo[3,2-b]pyridine, 2 HCl (30 mg, 0.07 mmol) in DMF (1 mL) was added 1-isobutylpiperidin-4-one (55 mg, 0.35 mmol) followed by the addition of sodium triacetoxyborohydride (75 mg, 0.35 mmol) and a drop of acetic acid. The reaction mixture was stirred and treated with aqueous 1 N NaOH solution (1 mL). The mixture was extracted with ethyl acetate (3×2 mL). The extracts were combined and washed with 10% aqueous LiCl solution (2×2 mL) and concentrated. The residue was suspended in DMF (2 mL), filtered through a 0.45 micron nylon syringe filter. The crude material was purified via preparative LC/MS with the following conditions: Column: Waters XBridge C18, 19×250 mm, 5 µm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-40% B over 25 minutes, then a 5-minute hold at 100% B; Flow: 20 mL/min. Fractions containing the product were combined and dried via centrifugal evaporation to afford 2-(3,4-dimethoxyphenyl)-5-(1'-isobutyl-[1,4'-bipiperidin]-4-yl)-3-methyl-1H-pyrrolo[3,2-b]pyridine, 3 TFA (25 mg, 0.03 mmol, 42%), m/z (491, M+H). Retention time, 1.3 min using LCMS Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm. $^1$H NMR (500 MHz, DMSO-$d_6$) δ 8.31-8.17 (m, 1H), 7.35 (br m, 2H), 7.33-7.28 (m, 1H), 7.18 (br d, J=8.1 Hz, 1H), 3.88 (s, 3H), 3.86 (m, 3H), 2.55 (m, 3H), 0.98 (d, J=6 Hz, 6H).

Example 6

N-(2-(dimethylamino)ethyl)-N-ethyl-3-isopropyl-2-(8-methoxy-[1,2,4]triazolo[1,5-a]pyridin-6-yl)-6-methyl-1H-pyrrolo[3,2-b]pyridine-5-carboxamide (6)

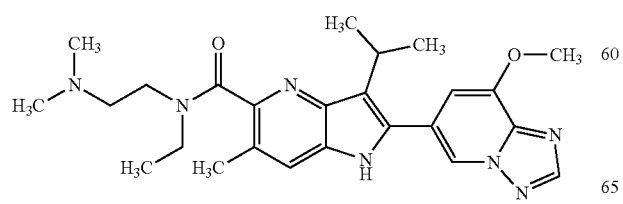

Intermediate 6A:
6-bromo-2-iodo-5-methylpyridin-3-amine (6A)

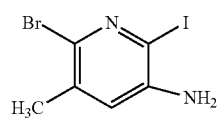

To a solution of 6-bromo-5-methylpyridin-3-amine (10 g, 53.5 mmol) in DMF (150 mL) was added NIS (12.03 g, 53.5 mmol). The resulting reaction mixture was stirred at room temperature for 12 h. The reaction mass was diluted with DCM (100 mL), washed with sodium thiosulfate solution (100 mL), the organic layer was dried over sodium sulfate, filtered and concentrated to get crude compound. The crude material was purified by combiflash using 120 g silica column, the compound was eluted with 22% EtOAc in petroleum ether, the fractions was collected and concentrated to afford 6-bromo-2-iodo-5-methylpyridin-3-amine (16 g, 51.1 mmol, 96% yield) as a pale yellow solid. LCMS retention time 2.14 min [I]. MS m/z: 314.1 (M+2H).

Intermediate 6B: (E)-6-bromo-2-(2-ethoxyvinyl)-5-methylpyridin-3-amine (6B)

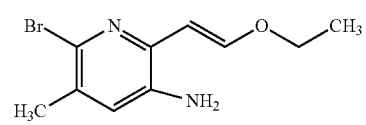

To a solution of 6-bromo-2-iodo-5-methylpyridin-3-amine (16 g, 51.1 mmol), and (E)-2-(2-ethoxyvinyl)-4,4,5,5-tetramethyl-1,3,2-dioxaborolane (15.19 g, 77 mmol) in THF (350 mL) was added sodium hydroxide (6.14 g, 153 mmol). The mixture was degassed for 10 min with nitrogen, tetrakis(triphenylphosphine)palladium (1.182 g, 1.023 mmol) was added, and the mixture was further degassed for 5 min. The resulting mixture was stirred at 80° C. for 16 h. The reaction mass was filtered through Celite, extracted with EtOAc (100 mL) and washed with water (2×100 mL), dried over sodium sulfate, filtered and concentrated to get crude compound. The crude compound was purified by combiflash using 120 g silica column, compound was eluted with 22% EtOAc in petroleum ether, the fractions were collected, concentrated to afford (E)-6-bromo-2-(2-ethoxyvinyl)-5-methylpyridin-3-amine (7 g, 27.2 mmol, 53.2% yield) as a brown solid. LCMS retention time 2.41 min [D]. MS m/z: 259.1 (M+2H).

Intermediate 6C: 5-bromo-6-methyl-1H-pyrrolo[3,2-b]pyridine (6C)

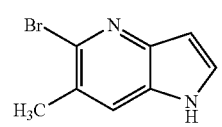

To a solution of (E)-6-bromo-2-(2-ethoxyvinyl)-5-methylpyridin-3-amine (7.0 g, 27.2 mmol) in methanol (300 mL) was added hydrochloric acid (8.27 mL, 272 mmol). The reaction mixture was heated at 85° C. for 16 h. The reaction mass was concentrated to afford 5-bromo-6-methyl-1H-pyrrolo[3,2-b]pyridine (5.1 g, 24.16 mmol, 89% yield) as a brown solid. LCMS retention time 1.19 min [R]. MS m/z: 213.1 (M+2H).

Intermediate 6D: Methyl 6-methyl-H-pyrrolo[3,2-b]pyridine-5-carboxylate

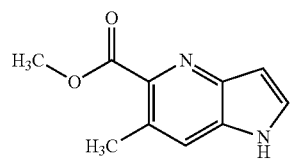

(6D)

To a solution of 5-bromo-6-methyl-1H-pyrrolo[3,2-b]pyridine (2.0 g, 9.48 mmol) in methanol (70 mL) and DMF (70 mL) were added DPPF (1.576 g, 2.84 mmol) and Pd(OAc)$_2$ (0.425 g, 1.895 mmol). The reaction mixture was degassed for 10 min with nitrogen and TEA (2.64 mL, 18.95 mmol) was added. The mixture was stirred at 90° C. in presence of CO with 8 kg pressure for 12 h. The reaction mass was concentrated, the residue was dissolved in DCM (100 mL), washed with water (2×100 mL), dried over sodium sulfate, filtered and concentrated to get crude compound. The crude compound was purified by silica gel column chromatography, the compound was eluted with 70% ethyl acetate in petroleum ether, the fractions were collected and concentrated to afford methyl 6-methyl-1H-pyrrolo[3,2-b]pyridine-5-carboxylate (1.1 g, 5.71 mmol, 60.3% yield) as a pale yellow solid product. LCMS retention time 0.80 min [R].

Intermediate 6E: Methyl 3-bromo-6-methyl-1H-pyrrolo[3,2-b]pyridine-5-carboxylate

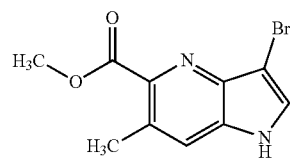

(6E)

To a solution of methyl 6-methyl-H-pyrrolo [3,2-b]pyridine-5-carboxylate (1.0 g, 5.26 mmol) in DMF (30 mL) was added dropwise NBS (0.936 g, 5.26 mmol) in DMF (15.00 mL). The resulting mixture was stirred at room temperature for 15 min. The reaction mass was poured into ice water (100 mL) and extracted with ethyl acetate (3×100 mL). The combined organic layer was dried over sodium sulfate, filtered and concentrated to afford methyl 3-bromo-6-methyl-1H-pyrrolo [3,2-b]pyridine-5-carboxylate (1.2 g, 4.24 mmol, 81% yield) as a brown solid. LCMS retention time 1.17 min [R]. MS m/z: 269.1 (M+2H).

Intermediate 6F: 1-tert-butyl 5-methyl 3-bromo-6-methyl-1H-pyrrolo[3,2-b]pyridine-1,5-dicarboxylate

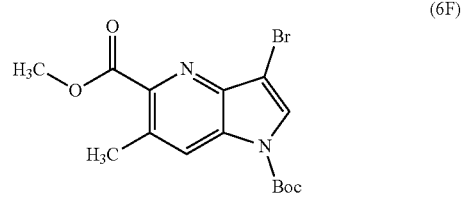 [SMILES: COC(=O)c1nc2c(Br)cn(C(=O)OC(C)(C)C)c2cc1C]

(6F)

To a solution of methyl 3-bromo-6-methyl-1H-pyrrolo[3,2-b]pyridine-5-carboxylate (1.2 g, 4.46 mmol) in THF (10 mL) were added BOC$_2$O (1.139 mL, 4.91 mmol), TEA (1.243 mL, 8.92 mmol) and DMAP (0.109 g, 0.892 mmol) at room temperature. The reaction mixture was stirred at the same temperature for 0.5 h. The reaction mass was quenched with water (50 mL), extracted with ethyl acetate (3×50 mL), combined organic layers was dried over sodium sulfate, filtered and concentrated to get crude compound. The crude compound was purified by silica gel column chromatography by eluting with 9% EtOAc in petroleum ether, the fractions was collected and concentrated to afford 1-tert-butyl 5-methyl 3-bromo-6-methyl-1H-pyrrolo[3,2-b] pyridine-1,5-dicarboxylate (1.3 g, 3.49 mmol, 78% yield) as a white solid. LCMS retention time 3.15 min [R]. MS m/z: 371.1 (M+H).

Intermediate 6G: 1-tert-butyl 5-methyl 6-methyl-3-(prop-1-en-2-yl)-1H-pyrrolo[3,2-b]pyridine-1,5-dicarboxylate

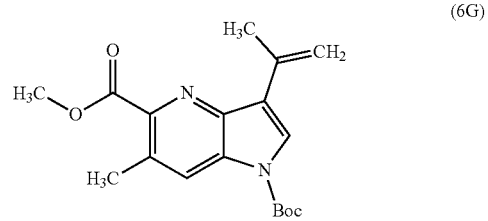 [SMILES: C=C(C)c1cn(C(=O)OC(C)(C)C)c2cc(C)c(C(=O)OC)nc12]

(6G)

To a solution of 1-tert-butyl 5-methyl 3-bromo-6-methyl-1H-pyrrolo[3,2-b]pyridine-1,5-dicarboxylate (1.3 g, 3.52 mmol) in THF (25 mL) and water (4 mL) was added potassium phosphate, tribasic (1.840 g, 10.56 mmol). The mixture was degassed for 10 minutes with nitrogen, XPhos Pd G2 (0.083 g, 0.106 mmol) was added, and the mixture was further degassed for 5 min. Next, 4,4,5,5-tetramethyl-2-(prop-1-en-2-yl)-1,3,2-dioxaborolane (0.769 g, 4.58 mmol) was added and the mixture was stirred at 70° C. for 12 h. The reaction mass was filtered through Celite, extracted with EtOAc (100 mL), washed with water (2×100 mL), dried over sodium sulfate and concentrated to get crude compound. The crude compound was purified by silica gel column chromatography. The compound was eluted with 6% EtOAc in petroleum ether, and the fractions were collected and concentrated to afford 1-tert-butyl 5-methyl 6-methyl-3-(prop-1-en-2-yl)-1H-pyrrolo [3,2-b]pyridine-1,5-dicarboxylate (1.1 g, 3.26 mmol, 93% yield) as a pale yellow solid. LCMS retention time 3.08 min [R]. MS m/z: 331.1 (M+H).

Intermediate 6H: 1-tert-butyl 5-methyl 3-isopropyl-6-methyl-1H-pyrrolo[3,2-b] pyridine-1,5-dicarboxylate

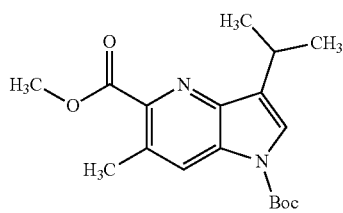

(6H)

To a solution of 1-tert-butyl 5-methyl 6-methyl-3-(prop-1-en-2-yl)-1H-pyrrolo[3,2-b]pyridine-1,5-dicarboxylate (1.1 g, 3.33 mmol) in methanol (20 mL) was added Pd/C (0.6 g, 0.564 mmol). The slurry was stirred at room temperature under a hydrogen bladder for 3 h. The suspension was filtered through Celite bed, the filtrate was collected and concentrated to afford 1-tert-butyl 5-methyl 3-isopropyl-6-methyl-1H-pyrrolo[3,2-b]pyridine-1,5-dicarboxylate (0.65 g, 1.869 mmol, 56% yield) as an off-white solid. LCMS retention time 3.7 min [R]. MS m/z: 333.1 (M+H).

Intermediate 6I: 1-tert-butyl 5-methyl 2-bromo-3-isopropyl-6-methyl-1H-pyrrolo[3,2-b]pyridine-1,5-dicarboxylate

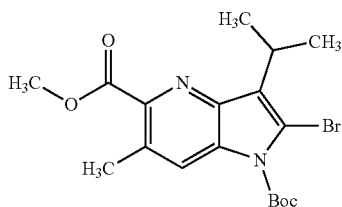

(6I)

To a solution of 1-tert-butyl 5-methyl 3-isopropyl-6-methyl-H-pyrrolo[3,2-b]pyridine-1,5-dicarboxylate (0.55 g, 1.655 mmol) in DCE (20 mL) was added NBS (0.442 g, 2.482 mmol) portion-wise. The resulting mixture was stirred at room temperature for 16 h. The reaction mixture was diluted with water (50 mL), extracted with DCM (2×50 mL), combined organic layers was dried over sodium sulfate, filtered and concentrated to get crude compound. The crude compound was purified by silica gel column chromatography, the compound was eluted with 5% EtOAc/petroleum ether, the fractions were collected and concentrated to afford 1-tert-butyl 5-methyl 2-bromo-3-isopropyl-6-methyl-1H-pyrrolo[3,2-b]pyridine-1,5-dicarboxylate (0.4 g, 0.807 mmol, 49% yield) as a yellow oil. LCMS retention time 4.12 min [D]. MS m/z: 411.1 (M+H).

Intermediate 6J: 1-tert-butyl 5-methyl 3-isopropyl-2-(8-methoxy-[1,2,4]triazolo[1,5-a]pyridin-6-yl)-6-methyl-1H-pyrrolo[3,2-b]pyridine-1,5-dicarboxylate

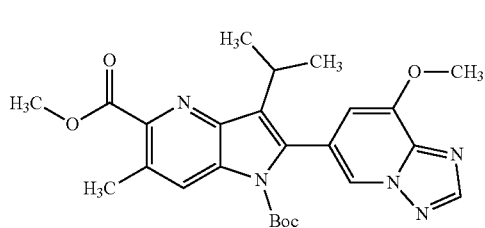

(6J)

A solution of 1-tert-butyl 5-methyl 2-bromo-3-isopropyl-6-methyl-1H-pyrrolo[3,2-b]pyridine-1,5-dicarboxylate (0.2 g, 0.486 mmol), 8-methoxy-6-(4,4,5,5-tetramethyl-1,3,2-dioxaborolan-2-yl)-[1,2,4]triazolo[1,5-a]pyridine (0.147 g, 0.535 mmol) and potassium phosphate tribasic (0.254 g, 1.459 mmol) in dioxane (10 mL) and water (1 mL) solvent mixture was degassed with $N_2$ for 10 min. Next, $PdCl_2$ (dppf)-$CH_2Cl_2$ adduct (0.040 g, 0.049 mmol) was added and the mixture was degassed again for 5 min. The resulting mixture was stirred at 80° C. for 3 h. The reaction mixture was extracted with ethyl acetate (20 mL), washed with water (2×10 mL), brine (50 mL), dried over sodium sulfate, and concentrated to get crude product. The crude product was purified by silica gel column chromatography, the compound was eluted with 22% ethyl acetate in petroleum ether, the fractions were collected and concentrated to afford 1-tert-butyl 5-methyl 3-isopropyl-2-(8-methoxy-[1,2,4]triazolo[1,5-a]pyridin-6-yl)-6-methyl-1H-pyrrolo[3,2-b] pyridine-1,5-dicarboxylate (0.2 g, 0.396 mmol, 81% yield) as a brown solid. LCMS retention time 2.96 min [R]. MS m/z: 480.1 (M+H).

Intermediate 6K: Methyl 3-isopropyl-2-(8-methoxy-[1,2,4]triazolo[1,5-a]pyridin-6-yl)-6-methyl-1H-pyrrolo[3,2-b]pyridine-5-carboxylate

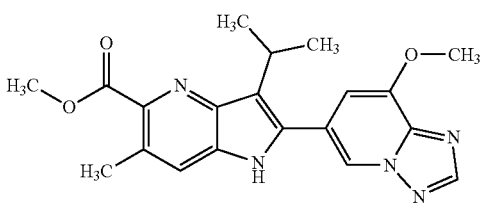

(6K)

To a solution of 1-tert-butyl 5-methyl 3-isopropyl-2-(8-methoxy-[1,2,4]triazolo [1,5-a]pyridin-6-yl)-6-methyl-1H-pyrrolo[3,2-b]pyridine-1,5-dicarboxylate (0.2 g, 0.417 mmol) in DCM (2 mL) was added 4 M hydrochloric acid in dioxane (0.209 mL, 0.834 mmol) drop wise. The reaction mixture was stirred at room temperature for 1 h. The solvent was removed under vacuum and the solids were washed with diethyl ether to afford methyl 3-isopropyl-2-(8-methoxy-[1,2,4]triazolo[1,5-a]pyridin-6-yl)-6-methyl-1H-pyrrolo[3,2-b]pyridine-5-carboxylate (0.15 g, 0.376 mmol, 95% yield) as a yellow solid. LCMS retention time 1.91 min [R]. MS m/z: 380.1 (M+H).

97

Intermediate 6L: 3-isopropyl-2-(8-methoxy-[1,2,4]triazolo[1,5-a]pyridin-6-yl)-6-methyl-1H-pyrrolo[3,2-b]pyridine-5-carboxylicacid

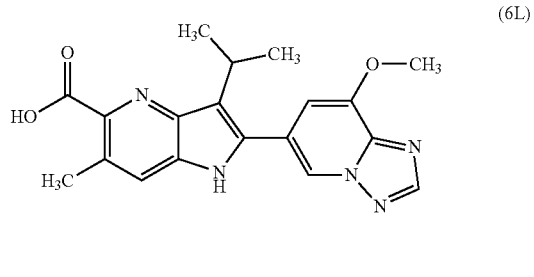 [SMILES: COc1cc(-c2[nH]c3cc(C)c(C(=O)O)nc3c2C(C)C)cn2ncnc12]

(6L)

To a solution of methyl 3-isopropyl-2-(8-methoxy-[1,2,4]triazolo[1,5-a]pyridin-6-yl)-6-methyl-1H-pyrrolo[3,2-b]pyridine-5-carboxylate (0.15 g, 0.395 mmol) in methanol (2 mL), THF (2 mL) and water (1 mL) solvent mixture was added lithium hydroxide (0.095 g, 3.95 mmol). The resulting mixture was stirred at room temperature for 5 h. The volatiles were removed under vacuum, diluted with water (5 mL) and neutralized with 1.5 N HCl. The aqueous layer was extracted with DCM (3×50 mL). The combined organic layer was dried over sodium sulfate, filtered and concentrated to afford 3-isopropyl-2-(8-methoxy-[1,2,4]triazolo[1,5-a]pyridin-6-yl)-6-methyl-1H-pyrrolo[3,2-b]pyridine-5-carboxylic acid (0.1 g, 0.235 mmol, 59.5% yield) as a yellow solid. LCMS retention time 0.98 min [R]. MS m/z: 366.1 (M+H).

Example 6

To a solution of 3-isopropyl-2-(8-methoxy-[1,2,4]triazolo[1,5-a]pyridin-6-yl)-6-methyl-1H-pyrrolo[3,2-b]pyridine-5-carboxylic acid (0.02 g, 0.055 mmol) in DMF (2 mL) were added N1-ethyl-N2,N2-dimethylethane-1,2-diamine (6.36 mg, 0.055 mmol), TEA (0.015 mL, 0.109 mmol) and 1-[bis(dimethylamino)methylene]-1H-1,2,3-triazolo[4,5-b]pyridinium 3-oxid hexafluorophosphate (HATU) (0.023 g, 0.060 mmol) at room temperature. Next, the mixture was stirred at same temperature for 3 h. The reaction mixture was diluted with EtOAc (20 mL) and washed with water (2×20 mL), dried over sodium sulfate, and concentrated to get crude product. The crude product was purified via preparative LC/MS using method D2, the fractions containing the product were combined and dried via centrifugal evaporation to afford N-(2-(dimethylamino)ethyl)-N-ethyl-3-isopropyl-2-(8-methoxy-[1,2,4]triazolo[1,5-a]pyridin-6-yl)-6-methyl-1H-pyrrolo[3,2-b] pyridine-5-carboxamide (7.8 mg, 0.017 mmol, 31% yield) as a pale yellow solid. LCMS retention time 1.30 min [E]. MS m/z: 464.1 (M+H). $^1$H NMR (400 MHz, DMSO-$d_6$) δ ppm 11.49-11.45 (m, 1H), 8.66 (s, 1H), 8.52 (d, J=1.2 Hz, 1H), 7.62 (s, 1H), 7.21 (s, 1H), 4.08 (d, J=1.0 Hz, 3H), 3.90 (s, 1H), 3.63 (t, J=7.1 Hz, 2H), 3.56-3.50 (m, 1H), 3.19-3.07 (m, 3H), 2.72 (br. s., 2H), 2.40 (br. s., 4H), 2.32 (s, 3H), 1.97-1.89 (m, 3H), 1.55-1.47 (m, 6H).

98

Examples 7, 8, and 9

3-(3-isopropyl-2-(8-methoxy-[1,2,4]triazolo[1,5-a]pyridin-6-yl)-1H-pyrrolo[3,2-b]pyridin-5-yl)cyclopentan-1-one

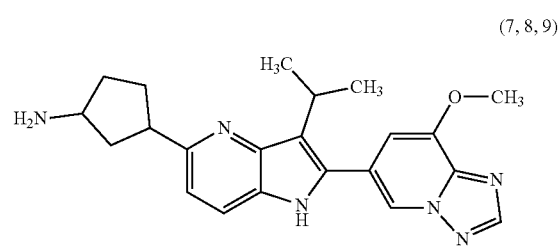 [SMILES: COc1cc(-c2[nH]c3ccc(C4CCC(N)C4)nc3c2C(C)C)cn2ncnc12]

(7, 8, 9)

Intermediate 7A: 3-bromocyclopent-2-en-1-one

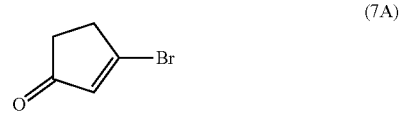

(7A)

To a stirred solution of triphenylphosphine (23.53 g, 90 mmol) in DCM (350 mL), was added bromine (4.62 mL, 90 mmol) at 0° C. The reaction mixture was stirred at same temperature for 15 min. Next, TEA (13.64 mL, 98 mmol) and cyclopentane-1,3-dione (8 g, 82 mmol) in DCM (350 mL) were added. The mixture was stirred at room temperature for 16 h. The reaction mass was concentrated, purified by silica gel column chromatography, the fractions were collected and concentrated to afford 3-bromocyclopent-2-en-1-one (8.9 g, 55.3 mmol, 68% yield) as an oil. $^1$H NMR (400 MHz, DMSO-$d_6$) δ ppm 6.57 (s, 1H), 2.99 (m, 2H), 2.52 (m, 2H).

Intermediate 7B: 3-(4,4,5,5-tetramethyl-1,3,2-dioxaborolan-2-yl)cyclopent-2-en-1-one

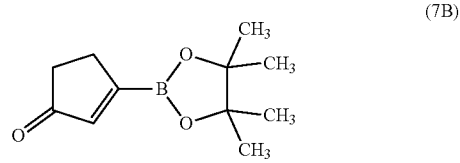

(7B)

To a stirred solution of 3-bromocyclopent-2-en-1-one (10 g, 62.1 mmol) in 1,4-dioxane (250 mL) were added bis(pinacolato)diboron (18.93 g, 74.5 mmol) and potassium acetate (12.19 g, 124 mmol). The reaction mixture was degassed with N$_2$ for 10 min, PdCl$_2$(dppf)-CH$_2$Cl$_2$ adduct (3.55 g, 4.35 mmol) was added, and the reaction mixture was stirred at 100° C. for 16 h. The reaction mass was diluted with EtOAc, filtered through Celite, washed with EtOAc, the filtrate was collected and concentrated to get crude product. The crude product was purified by ISCO using silica gel column chromatography, the fractions was collected and concentrated to afford 3-(4,4,5,5-tetramethyl-1, 3,2-dioxaborolan-2-yl)cyclopent-2-en-1-one (10.9 g, 52.4 mmol, 84% yield) as a white solid. $^1$H NMR (400 MHz, DMSO-$d_6$) δ ppm 6.43 (s, 1H), 2.66 (m, 2H), 2.26 (m, 2H), 1.18 (s, 9H).

Intermediate 7C: tert-butyl 5-bromo-3-isopropyl-1H-pyrrolo[3,2-b]pyridine-1-carboxylate

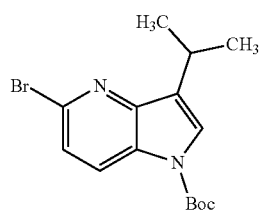
(7C)

To a stirred solution of 5-bromo-3-isopropyl-1H-pyrrolo[3,2-b]pyridine (5 g, 20.91 mmol) in THF (100 mL) were added DIPEA (41.8 mmol) and Boc-anhydride (7.28 mL, 31.4 mmol) at room temperature. The reaction mixture was stirred at the same temperature for 3 h. The reaction mass was extracted with ethyl acetate and washed with water, brine, dried over sodium sulfate and concentrated to get crude compound. The crude compound was purified by silica gel column chromatography, the fractions were collected and concentrated to afford tert-butyl 5-bromo-3-isopropyl-1H-pyrrolo[3,2-b]pyridine-1-carboxylate (6.5 g, 19.16 mmol, 92% yield) as an off-white solid. LCMS retention time 2.03 min [L]. MS m/z: 341 (M+H).

Intermediate 7D: tert-butyl 3-isopropyl-5-(3-oxocyclopent-1-en-1-yl)-1H-pyrrolo[3,2-b]pyridine-1-carboxylate

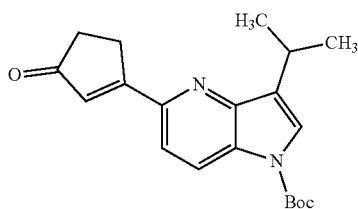
(7D)

To a stirred solution of tert-butyl 5-bromo-3-isopropyl-1H-pyrrolo[3,2-b]pyridine-1-carboxylate (16 g, 47.2 mmol) in dioxane (400 mL) were added 3-(4,4,5,5-tetramethyl-1,3,2-dioxaborolan-2-yl)cyclopent-2-en-1-one (14.72 g, 70.7 mmol) and potassium phosphate tribasic (20.02 g, 94 mmol). The reaction mixture was degassed with nitrogen for 10 min, and then PdCl$_2$(dppf)-CH$_2$Cl$_2$ adduct (3.85 g, 4.72 mmol) was added. The reaction mixture was stirred at 100° C. for 16 h. The reaction mass was filtered through a Celite bed, washed with EtOAc and concentrated to get crude product. The crude product was purified by silica gel column chromatography, the fractions were collected and concentrated to afford tert-butyl 3-isopropyl-5-(3-oxocyclopent-1-en-1-yl)-1H-pyrrolo[3,2-b]pyridine-1-carboxylate (15 g, 44.1 mmol, 93% yield) as a brown solid. LCMS retention time 1.76 min [L]. MS m/z: 341.6 (M+H).

Intermediate 7E: tert-butyl 5-(3-hydroxycyclopentyl)-3-isopropyl-1H-pyrrolo[3,2-b]pyridine-1-carboxylate

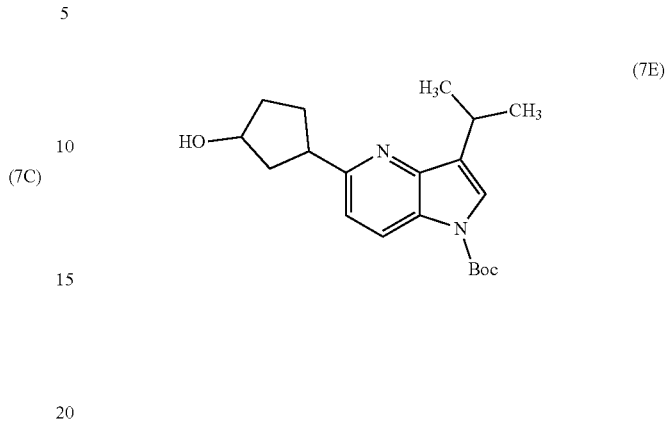
(7E)

To a stirred solution of tert-butyl 3-isopropyl-5-(3-oxocyclopent-1-en-1-yl)-1H-pyrrolo[3,2-b]pyridine-1-carboxylate (10 g, 29.4 mmol) in MeOH (20 mL) at 0° C. were added nickel(II) chloride hexahydrate (0.698 g, 2.94 mmol) and NaBH$_4$ (4.45 g, 118 mmol). The reaction mixture was stirred at room temperature for 10 min. The reaction was quenched with NH$_4$Cl solution. The reaction mixture was concentrated to remove methanol, the residue was extracted with EtOAc, washed with water, dried over sodium sulfate and concentrated to afford tert-butyl 5-(3-hydroxycyclopentyl)-3-isopropyl-1H-pyrrolo[3,2-b]pyridine-1-carboxylate (10 g, 29.0 mmol, 99% yield) as a brown solid. LCMS retention time 1.71 min [L]. MS m/z: 345.6 (M+H).

Intermediate 7F: tert-butyl 3-isopropyl-5-(3-oxocyclopentyl)-1H-pyrrolo[3,2-b]pyridine-1-carboxylate

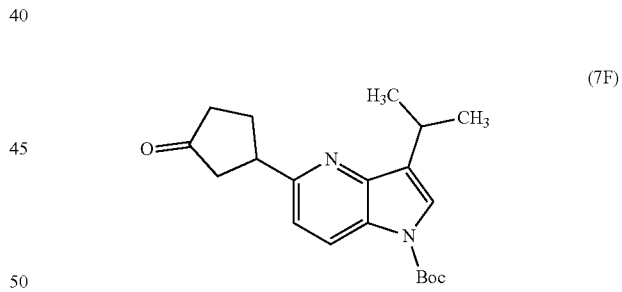
(7F)

To a stirred solution of tert-butyl 5-(3-hydroxycyclopentyl)-3-isopropyl-1H-pyrrolo[3,2-b]pyridine-1-carboxylate (1 g, 2.90 mmol) in DCM (25 mL) was added Dess-Martin periodinane (6.16 g, 14.52 mmol) at 0° C. The reaction mixture was stirred at room temperature for 16 h. The reaction mass was diluted with aqueous NaHCO$_3$ solution, the solids were filtered, the aqueous layer was extracted with DCM, the organic layer was dried over sodium sulfate and concentrated to get crude product. The crude product was purified by silica gel column chromatography, the fractions was collected and concentrated to afford tert-butyl 3-isopropyl-5-(3-oxocyclopentyl)-1H-pyrrolo[3,2-b]pyridine-1-carboxylate (380 mg, 1.110 mmol, 38% yield) as an off-white solid. LCMS retention time 1.75 min [L]. MS m/z: 343.6 (M+H).

Intermediate 7G: 3-isopropyl-5-(1,4-dioxaspiro[4.4]nonan-7-yl)-1H-pyrrolo[3,2-b]pyridine

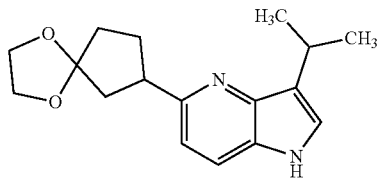

(7G)

To a stirred solution of tert-butyl 3-isopropyl-5-(3-oxo-cyclopentyl)-1H-pyrrolo[3,2-b] pyridine-1-carboxylate (2.8 g, 8.18 mmol) in toluene (40 mL) were added ethylene glycol (0.692 mL, 12.26 mmol) and p-toluenesulfonic acid (0.282 g, 1.635 mmol) at room temperature. Next, the mixture was stirred at 130° C. for 16 h. The reaction mass was concentrated, diluted with EtOAc, and washed with saturated NaHCO₃, dried over sodium sulfate and concentrated to get crude material. The crude material was purified by silica gel column chromatography, the fractions were collected and concentrated to afford 3-isopropyl-5-(1,4-dioxaspiro[4.4]nonan-7-yl)-1H-pyrrolo[3,2-b] pyridine (2.8 g, 7.24 mmol, 89% yield) as an off-white solid. LCMS retention time 1.18 min [L]. MS m/z: 287.5 (M+H).

Intermediate 7H: tert-butyl 3-isopropyl-5-(1,4-dioxaspiro[4.4]nonan-7-yl)-1H-pyrrolo[3,2-b]pyridine-1-carboxylate

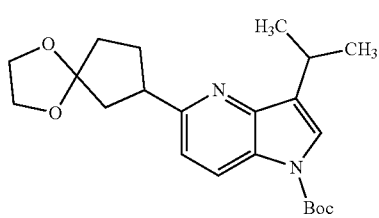

(7H)

To a stirred solution of 3-isopropyl-5-(1,4-dioxaspiro[4.4]nonan-7-yl)-1H-pyrrolo[3,2-b]pyridine (2.2 g, 7.68 mmol) in THF (30 mL), were added Boc-anhydride (2.68 mL, 11.52 mmol), DIPEA (2.68 mL, 15.36 mmol) and DMAP (0.939 g, 7.68 mmol) at room temperature. The reaction mixture was stirred at room temperature for 3 h. The reaction was quenched with water. The reaction mixture was extracted with EtOAc, dried over sodium sulfate and concentrated to get crude material. The crude material was purified by ISCO using silica gel column chromatography, the fractions were collected and concentrated to afford tert-butyl 3-isopropyl-5-(1,4-dioxaspiro[4.4]nonan-7-yl)-1H-pyrrolo[3,2-b]pyridine-1-carboxylate (2.8 g, 7.24 mmol, 94% yield) as a white foam. LCMS retention time 1.96 min [L]. MS m/z: 387.6 (M+H).

Intermediate 7I: tert-butyl 3-isopropyl-5-(1,4-dioxaspiro[4.4]nonan-7-yl)-2-(4,4,5,5-tetramethyl-1,3,2-dioxaborolan-2-yl)-1H-pyrrolo[3,2-b]pyridine-1-carboxylate

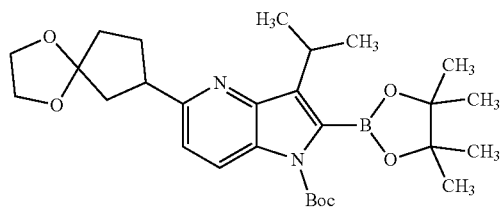

(7I)

To a stirred solution of tert-butyl 3-isopropyl-5-(1,4-dioxaspiro[4.4]nonan-7-yl)-1H-pyrrolo [3,2-b]pyridine-1-carboxylate (2.8 g, 7.24 mmol) in THF (20 mL) was added LDA (10.87 mL, 21.73 mmol) at −78° C. The reaction mixture was stirred at the same temperature for 2 h, and then 2-isopropoxy-4,4,5,5-tetramethyl-1,3,2-dioxaborolane (3.00 mL, 14.49 mmol) was added slowly. The reaction mixture was brought to room temperature and stirred at room temperature for 1 h. The reaction was quenched with water. The reaction mixture was extracted with EtOAc, dried over sodium sulfate and concentrated to get crude compound. The crude compound was purified by silica gel column chromatography, the fractions were collected and concentrated to afford tert-butyl 3-isopropyl-5-(1,4-dioxaspiro[4.4]nonan-7-yl)-2-(4,4,5,5-tetramethyl-1,3,2-dioxaborolan-2-yl)-1H-pyrrolo[3,2-b]pyridine-1-carboxylate (2.9 g, 5.66 mmol, 78% yield) as an off-white solid. LCMS retention time 2.29 min [L]. MS m/z: 513.7 [M+H]⁺.

Intermediate 7J: tert-butyl 3-isopropyl-2-(8-methoxy-[1,2,4]triazolo[1,5-a]pyridin-6-yl)-5-(1,4-dioxaspiro[4.4]nonan-7-yl)-1H-pyrrolo[3,2-b]pyridine-1-carboxylate

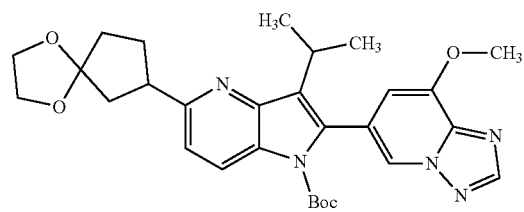

(7J)

To a stirred solution of tert-butyl 3-isopropyl-5-(1,4-dioxaspiro[4.4]nonan-7-yl)-2-(4,4,5,5-tetramethyl-1,3,2-dioxaborolan-2-yl)-1H-pyrrolo[3,2-b]pyridine-1-carboxylate (3 g, 5.85 mmol) in dioxane (100 mL) and water (2 mL) were added 6-bromo-8-methoxy-[1,2,4]triazolo[1,5-a]pyridine (1.602 g, 7.03 mmol) and potassium phosphate tribasic (3.73 g, 17.56 mmol). The reaction mixture was degassed with N₂ for 10 minutes and PdCl₂(dppf)-CH₂Cl₂ adduct (0.478 g, 0.585 mmol) was added. The mixture was stirred at 100° C. for 16 h. The reaction mass diluted with EtOAc, filtered, and the filtrate was concentrated to get crude product. The crude product was purified by silica gel column chromatography, the fractions were collected and concentrated to afford tert-butyl 3-isopropyl-2-(8-methoxy-[1,2,4]triazolo[1,5-a]pyridin-6-yl)-5-(1,4-dioxaspiro[4.4]nonan-7-yl)-1H-pyrrolo[3,2-b]pyridine-1-carboxylate (2.9 g, 5.43 mmol, 93% yield) as an off-white solid. LCMS retention time 1.62 min [L]. MS m/z: 534.7 [M+H]+.

Intermediate 7K: 3-(3-isopropyl-2-(8-methoxy-[1,2,4]triazolo[1,5-a]pyridin-6-yl)-1H-pyrrolo[3,2-b]pyridin-5-yl)cyclopentan-1-one (7K)

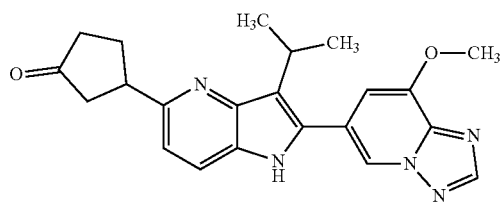

To a stirred solution of tert-butyl 3-isopropyl-2-(8-methoxy-[1,2,4]triazolo[1,5-a]pyridin-6-yl)-5-(1,4-dioxaspiro[4.4]nonan-7-yl)-1H-pyrrolo[3,2-b]pyridine-1-carboxylate (2.9 g, 5.43 mmol) in DCM (20 mL) was added TFA (2.093 mL, 27.2 mmol) at room temperature. The reaction mixture was stirred at the same temperature for 16 h. The reaction mixture was concentrated, extracted with EtOAc, washed with water, dried over sodium sulfate and concentrated to afford 3-(3-isopropyl-2-(8-methoxy-[1,2,4]triazolo[1,5-a]pyridin-6-yl)-1H-pyrrolo[3,2-b]pyridin-5-yl)cyclopentan-1-one (2.1 g, 5.43 mmol, 93% yield) as a gummy solid. LCMS retention time 1.14 min [L]. MS m/z: 390.6 [M+H]+.

Examples 7, 8, and 9

To a stirred solution of 3-(3-isopropyl-2-(8-methoxy-[1,2,4]triazolo[1,5-a]pyridin-6-yl)-1H-pyrrolo[3,2-b]pyridin-5-yl)cyclopentan-1-one (2.5 g, 6.42 mmol) in THF (3 mL), DMF (3 mL) were added ammonium acetate (4.95 g, 64.2 mmol), ammonium chloride (3.43 g, 64.2 mmol) and acetic acid (0.367 mL, 6.42 mmol) at room temperature. The reaction mixture was stirred at the same temperature for 16 h, then was added NaCNBH3 (1.210 g, 19.26 mmol) and stirred another 2h at room temperature. The reaction mass was concentrated to get crude compound. The crude compound was purified by Prep HPLC to separate the isomers. After Prep HPLC purifications, the fractions were collected, concentrated and lyophilized to isolate three isomers/mixtures.

Example 7: Isomer 1: diastereomer mixture, LCMS retention time 1.79 min [E]. MS m/z: 391.4 (M+H).

Example 8: Isomer 2: homochiral, LCMS retention time 1.78 min [E]. MS m/z: 391.2 (M+H).

Example 9: Isomer 3: diastereomer mixture, LCMS retention time 1.56 min [E]. MS m/z: 391.3 (M+H).

Example 10

2-((3-(3-isopropyl-2-(8-methoxy-[1,2,4]triazolo[1,5-a]pyridin-6-yl)-1H-pyrrolo[3,2-b]pyridin-5-yl)cyclopentyl)amino)-N-methylacetamide (10)

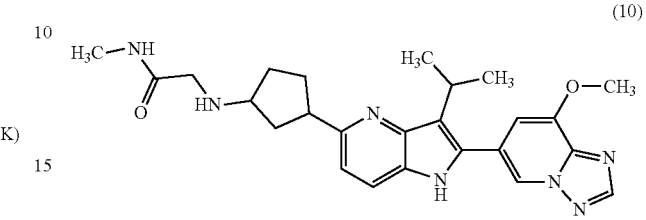

To a stirred solution of 3-(3-isopropyl-2-(8-methoxy-[1,2,4]triazolo[1,5-a]pyridin-6-yl)-1H-pyrrolo[3,2-b]pyridin-5-yl)cyclopentan-1-amine (20 mg, 0.051 mmol) (Example 9) in DMF (2 mL) were added TEA (0.021 mL, 0.154 mmol) and 2-chloro-N-methylacetamide (6.61 mg, 0.061 mmol) at room temperature. The reaction mixture was stirred at the same temperature for 16 h. The crude material was purified via preparative LC/MS using method D2, the fractions containing the product were combined and dried via centrifugal evaporation to afford 2-((3-(3-isopropyl-2-(8-methoxy-[1,2,4]triazolo[1,5-a]pyridin-6-yl)-1H-pyrrolo[3,2-b]pyridin-5-yl)cyclopentyl)amino)-N-methylacetamide (3 mg). LCMS retention time 1.29 min [E]. MS m/z: 462.3 (M+H). $^1$H NMR (400 MHz, DMSO-d$_6$) δ ppm 11.30 (s, 1H), 8.63 (d, J=1.0 Hz, 1H), 8.53 (s, 1H), 7.64 (d, J=8.3 Hz, 1H), 7.20 (d, J=1.0 Hz, 1H), 7.04 (d, J=8.6 Hz, 1H), 4.09 (s, 3H), 3.17-3.11 (m, 4H), 2.90 (s, 1H), 2.63 (d, J=4.9 Hz, 3H), 2.32-2.23 (m, 1H), 2.00 (q, J=7.4 Hz, 2H), 1.94-1.81 (m, 3H), 1.74-1.61 (m, 2H), 1.61-1.50 (m, 6H).

Example 11

6-(6-fluoro-3-isopropyl-5-(piperidin-4-yl)-1H-pyrrolo[3,2-b]pyridin-2-yl)-8-methyl-[1,2,4]triazolo[1,5-a]pyridine (11)

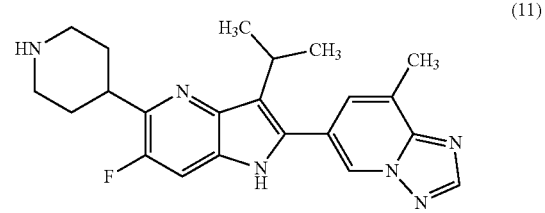 [SMILES: Cc1cc(-c2[nH]c3cc(F)c(C4CCNCC4)nc3c2C(C)C)cn2ncnc12]

Intermediate 11A: 6-bromo-5-fluoropyridin-3-amine (11A)

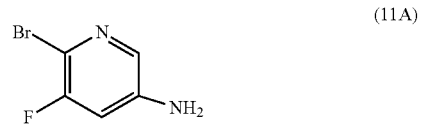

To a solution of 5-fluoropyridin-3-amine (4.5 g, 40.1 mmol) in DMF (80 mL) was added NBS (7.14 g, 40.1 mmol) portion wise at 0° C. The reaction mixture was stirred at room temperature for 20 min. The mixture was then partitioned between EtOAc (300 mL) and water (300 mL), both the layers were separated, the organic layer was washed with saturated NaHCO$_3$, brine, dried over sodium sulfate, filtered and concentrated to get crude compound. The crude compound was purified by silica gel column chromatography, the compound was eluted with 52% ethyl acetate\hexane, the fractions were collected and concentrated to afford 6-bromo-5-fluoropyridin-3-amine (4.7 g, 24.61 mmol, 61% yield) as a brown solid. LCMS retention time 0.98 min [R]. MS m/z: 193.1 (M+2H).

Intermediate 11B: tert-butyl 5-amino-3-fluoro-5',6'-dihydro-[2,4'-bipyridine]-1'(2'H)-carboxylate

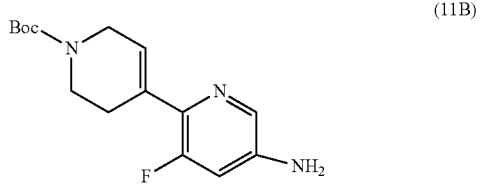 [SMILES: CC(C)(C)OC(=O)N1CC=C(c2ncc(N)cc2F)CC1]

(11B)

tert-butyl 5-amino-3-fluoro-5',6'-dihydro-[2,4'-bipyridine]-1'(2'H)-carboxylate (6.5 g, 22.16 mmol, 94% yield) was prepared according to the general procedure described in Intermediate 5B using 6-bromo-5-fluoropyridin-3-amine (4.5 g, 23.56 mmol) as the starting intermediate. LCMS retention time 1.94 min [R]. MS m/z: 293.1 (M+H).

Intermediate 11C: Tert-butyl 4-(5-amino-3-fluoropyridin-2-yl)piperidine-1-carboxylate

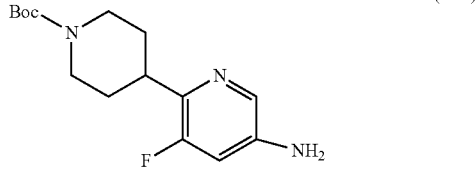

(11C)

A solution of tert-butyl 5-amino-3-fluoro-5',6'-dihydro-[2, 4'-bipyridine]-1'(2'H)-carboxylate (6.5 g, 22.16 mmol) and ethyl acetate (150 mL) was purged with nitrogen (N$_2$). Next, Pd/C (3.30 g, 3.10 mmol) was added and the reaction mixture was again purged with N$_2$ three times. Hydrogen gas (H$_2$) was introduced via a balloon to the mixture. The reaction mixture was stirred at room temperature for 12 h. The suspension was filtered through Celite bed, the filtrate was collected and concentrated to afford tert-butyl 4-(5-amino-3-fluoropyridin-2-yl)piperidine-1-carboxylate (5.8 g, 19.64 mmol, 89% yield) as a yellow oil. LCMS retention time 1.68 min [R]. MS m/z: 296.1 (M+H).

Intermediate 11D: tert-butyl 4-(5-amino-3-fluoro-6-iodopyridin-2-yl)piperidine-1-carboxylate

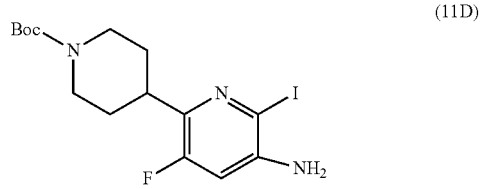 [SMILES: CC(C)(C)OC(=O)N1CCC(c2nc(I)c(N)cc2F)CC1]

(11D)

To a solution of tert-butyl 4-(5-amino-3-fluoropyridin-2-yl) piperidine-1-carboxylate (5.6 g, 18.96 mmol) in DMF (120 mL) was added NIS (4.27 g, 18.96 mmol) portion wise. The mixture was stirred for 2 h at room temperature. The reaction mass was diluted into water (200 mL) and extracted with ethyl acetate (3×200 mL). The organic extracts were combined, dried over sodium sulfate, filtered and concentrated to get crude compound. The crude compound was purified by combiflash using silica gel column chromatography, the compound was eluted with 25% ethyl acetate/petroleum ether, the fractions was collected and concentrated to afford tert-butyl 4-(5-amino-3-fluoro-6-iodopyridin-2-yl) piperidine-1-carboxylate (5.8 g, 13.77 mmol, 73% yield) as a brown solid. LCMS retention time 2.46 min [R]. MS m/z: 322.1 (M+H).

Intermediate 11E: tert-butyl 4-(3-fluoro-6-iodo-5-((3-methylbut-2-en-1-yl)amino) pyridin-2-yl)piperidine-1-carboxylate

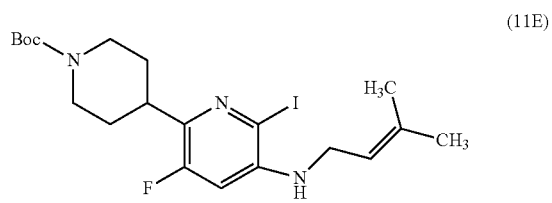 [SMILES: CC(C)=CCNc1cc(F)c(C2CCN(C(=O)OC(C)(C)C)CC2)nc1I]

(11E)

To a solution of tert-butyl 4-(5-amino-3-fluoro-6-iodopyridin-2-yl)piperidine-1-carboxylate (3.0 g, 7.12 mmol) and 3-methylbut-2-enal (2.72 mL, 28.5 mmol) in MeOH (50 mL) was added acetic acid (1 mL, 17.47 mmol). The resulting light yellow solution was stirred at room temperature for 6 h. Next, sodium cyanoborohydride (2.238 g, 35.6 mmol) was added at 0° C. and the reaction mixture was stirred at room temperature for 2 h. The reaction mass was concentrated to remove methanol, diluted with water (100 mL) and extracted with ethyl acetate (3×100 mL). The combined organic extracts were dried over sodium sulfate, filtered and concentrated to get crude compound. The crude compound was purified by silica gel column chromatography. The compound was eluted with 28% ethyl acetate/petroleum ether, the fractions were collected and concentrated to afford tert-butyl 4-(3-fluoro-6-iodo-5-((3-methylbut-2-en-1-yl)amino) pyridin-2-yl)piperidine-1-carboxylate (1.7 g, 3.35 mmol, 47% yield) as a pale yellow oil. LCMS retention time 3.39 min [R]. MS m/z: 490.1 (M+H).

107

Intermediate 11F: 4-(6-fluoro-3-isopropyl-1H-pyrrolo[3,2-b]pyridin-5-yl)piperidine-1-carboxylate

(11F)

A solution of tert-butyl 4-(3-fluoro-6-iodo-5-((3-methylbut-2-en-1-yl)amino) pyridin-2-yl)piperidine-1-carboxylate (1.6 g, 3.27 mmol), potassium carbonate (0.497 g, 3.60 mmol) and tetrabutylammonium bromide (3.16 g, 9.81 mmol) in DMF (20 mL) was degassed for 10 minutes with nitrogen, and Pd(OAc)$_2$ (0.073 g, 0.327 mmol) was added. The reaction mixture was further degassed for 5 min. The reaction mixture was stirred at 80° C. for 14 h. The reaction mixture was diluted with ethyl acetate (200 mL). The reaction mixture was washed with water (2×100 mL), brine (100 mL), dried over sodium sulfate, and concentrated to get crude product. The crude product was purified by silica gel column chromatography, the compound was eluted with 65% ethyl acetate/petroleum ether, the fractions were collected, and concentrated to afford tert-butyl 4-(6-fluoro-3-isopropyl-1H-pyrrolo[3,2-b]pyridin-5-yl) piperidine-1-carboxylate (0.5 g, 1.383 mmol, 42% yield) as a pale yellow oil. LCMS retention time 3.80 min [R]. MS m/z: 362.1 (M+H).

Intermediate 11G: tert-butyl 5-(1-(tert-butoxycarbonyl)piperidin-4-yl)-6-fluoro-3-isopropyl-1H-pyrrolo[3,2-b]pyridine-1-carboxylate

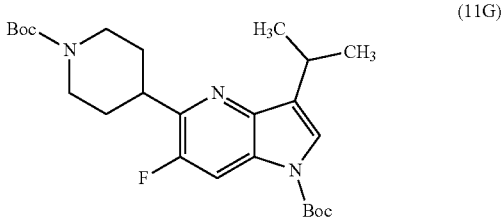 [SMILES: CC(C)c1cn(C(=O)OC(C)(C)C)c2cc(F)c(C3CCN(C(=O)OC(C)(C)C)CC3)nc12]

(11G)

To a solution of tert-butyl 4-(6-fluoro-3-isopropyl-1H-pyrrolo[3,2-b]pyridin-5-yl) piperidine-1-carboxylate (0.3 g, 0.830 mmol) in THF (2 mL) were added TEA (0.231 mL, 1.660 mmol), BOC$_2$O (0.212 mL, 0.913 mmol), and DMAP (0.020 g, 0.166 mmol) at room temperature. The reaction mixture was stirred at room temperature for 1 h. The reaction mixture was diluted with water (100 mL) and extracted with ethyl acetate (3×100 mL). The combined organic layers were dried over sodium sulfate, filtered, and concentrated to get crude compound. The crude compound was purified by silica gel column chromatography by eluting with 9% EtOAc: petroleum ether, the fractions were collected and concentrated to afford t-butyl 5-(1-(tert-butoxycarbonyl)piperidin-4-yl)-6-fluoro-3-isopropyl-1H-pyrrolo[3,2-b]pyridine-1-carboxylate (0.33 g, 0.715 mmol, 86% yield) as a white solid. LCMS retention time 3.92 min [R]. MS m/z: 462.1 (M+H).

108

Intermediate 11H: tert-butyl 2-bromo-5-(1-(tert-butoxycarbonyl)piperidin-4-yl)-6-fluoro-3-isopropyl-1H-pyrrolo[3,2-b]pyridine-1-carboxylate

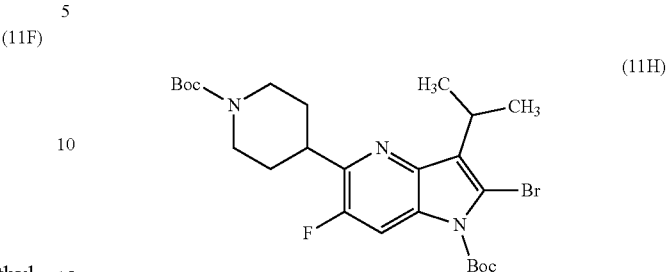

(11H)

tert-butyl 2-bromo-5-(1-(tert-butoxycarbonyl)piperidin-4-yl)-6-fluoro-3-isopropyl-1H-pyrrolo [3,2-b]pyridine-1-carboxylate (0.6 g, 0.766 mmol, 58.9% yield) was prepared according to the general procedure described in Intermediate 61 using tert-butyl 5-(1-(tert-butoxycarbonyl)piperidin-4-yl)-6-fluoro-3-isopropyl-1H-pyrrolo[3,2-b]pyridine-1-carboxylate (0.6 g, 1.300 mmol) as the starting intermediate. LCMS retention time 4.32 min [D]. MS m/z: 541.1 (M+H).

Intermediate 11I: tert-butyl 5-(1-(tert-butoxycarbonyl)piperidin-4-yl)-6-fluoro-3-isopropyl-2-(8-methyl-[1,2,4]triazolo[1,5-a]pyridin-6-yl)-1H-pyrrolo[3,2-b]pyridine-1-carboxylate

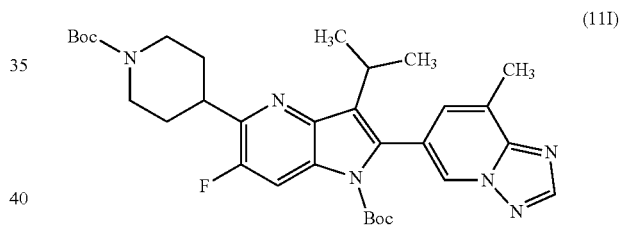

(11I)

tert-butyl 5-(1-(tert-butoxycarbonyl)piperidin-4-yl)-6-fluoro-3-isopropyl-2-(8-methyl-[1,2,4] triazolo[1,5-a]pyridin-6-yl)-1H-pyrrolo[3,2-b]pyridine-1-carboxylate (0.25 g, 0.359 mmol, 64% yield) was prepared according to the general procedure described in Intermediate 7J using tert-butyl 2-bromo-5-(1-(tert-butoxycarbonyl) piperidin-4-yl)-6-fluoro-3-isopropyl-1H-pyrrolo[3,2-b]pyridine-1-carboxylate (0.3 g, 0.555 mmol) as the starting material. LCMS retention time 4.16 min [R]. MS m/z: 593.1 (M+H).

Example 11

To a solution of tert-butyl 5-(1-(tert-butoxycarbonyl)piperidin-4-yl)-6-fluoro-3-isopropyl-2-(8-methyl-[1,2,4]triazolo[1,5-a]pyridin-6-yl)-1H-pyrrolo[3,2-b]pyridine-1-carboxylate (0.25 g, 0.422 mmol) in DCM (2 mL) was added 4 M hydrochloric acid in dioxane (2 mL, 8.00 mmol) drop-wise. The reaction mixture was stirred at room temperature for 1 h. The reaction mass was concentrated to get crude product. The crude product was purified via preparative LC/MS using method D2, the fractions containing the product were combined and dried via centrifugal evaporation to afford 6-(6-fluoro-3-isopropyl-5-(piperidin-4-yl)-1H-pyrrolo[3,2-b]pyridin-2-yl)-8-methyl-[1,2,4]triazolo [1,5-a]pyridine (11.3 mg, 0.029 mmol, 7% yield) as a pale yellow solid. LCMS retention time 1.26 min [E]. MS m/z: 393.1 (M+H). $^1$H NMR (400 MHz, DMSO-d$_6$) δ ppm 11.45 (br. s., 1H), 8.85 (s, 1H), 8.54 (s, 1H), 7.62 (s, 1H), 7.53 (d, J=11.0 Hz, 1H), 3.89 (s, 1H), 3.18-3.13 (m, 2H), 2.82-2.72 (m, 2H), 2.63 (s, 3H), 2.06 (s, 2H), 1.83-1.76 (m, 2H), 1.53 (d, J=6.8 Hz, 6H).

Example 39

4-(1-(2-(7,8-dimethyl-[1,2,4]triazolo[1,5-a]pyridin-6-yl)-3-isopropyl-1H-pyrrolo[3,2-b]pyridin-5-yl)azetidin-3-yl)morpholine

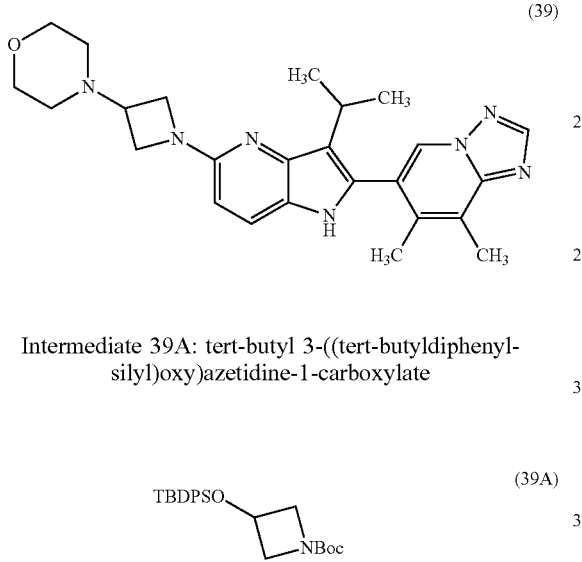

(39)

Intermediate 39A: tert-butyl 3-((tert-butyldiphenylsilyl)oxy)azetidine-1-carboxylate

(39A)

tert-Butyl 3-hydroxyazetidine-1-carboxylate (2.05 g, 11.8 mmol) was dissolved in DCM (40 mL), and imidazole (1.61 g, 23.7 mmol) and tert-butylchlorodiphenylsilane (3.58 g, 13.0 mmol) were added sequentially. The reaction mixture was stirred for 17 hours at room temperature. Upon completion, the reaction was quenched by the addition of water and DCM. The layers were separated, and the aqueous layer was extracted with DCM. The combined organic layer was dried over sodium sulfate, filtered, and concentrated to afford a clear oil. This material was purified by silica gel column chromatography on a Teledyne Isco instrument eluting with Hex/EtOAc 0-15% to afford tert-butyl 3-((tert-butyldiphenylsilyl) oxy)azetidine-1-carboxylate (11.8 mmol). LCMS retention time 1.22 [TS]. MS (E+) m/z: 823.4 (2M+H). $^1$H NMR (499 MHz, CHLOROFORM-d) δ 7.63-7.57 (m, 4H), 7.46-7.41 (m, 2H), 7.41-7.35 (m, 4H), 4.52 (tt, J=6.6, 4.7 Hz, 1H), 3.97-3.90 (m, 2H), 3.89-3.83 (m, 2H), 1.42 (s, 9H), 1.06 (s, 9H).

Intermediate 39B: 3-((tert-butyldiphenylsilyl)oxy)azetidine

(39B)

Intermediate 39A (11.8 mmol)) was dissolved in DCM (20 mL), cooled to 0° C., and precooled 0° C. TFA (20 mL) was added. When the reaction was completed as judged by LCMS analysis, the reaction mixture was concentrated, redissolved in DCM, and made basic by the addition of 1 M aqueous NaOH solution. The aqueous layer was extracted with DCM, and the combined organics were dried over sodium sulfate, filtered, and concentrated to afford 3-((tert-butyldiphenylsilyl)oxy)azetidine (11.8 mmol). LCMS retention time 0.84 [TS]. MS (E$^+$) m/z: 312.2 (M+1). $^1$H NMR (499 MHz, CHLOROFORM-d) δ 7.64-7.59 (m, 4H), 7.44-7.40 (m, 2H), 7.39-7.34 (m, 4H), 4.62 (quin, J=6.5 Hz, 1H), 3.70-3.61 (m, 2H), 3.55-3.47 (m, 2H), 1.05 (s, 9H).

Intermediate 39C: tert-butyl 5-(3-((tert-butyldiphenylsilyl)oxy)azetidin-1-yl)-3-isopropyl-1H-pyrrolo[3,2-b]pyridine-1-carboxylate

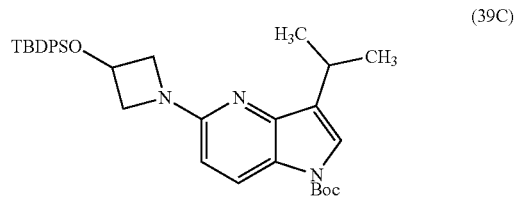

(39C)

tert-Butyl 5-bromo-3-isopropyl-1H-pyrrolo[3,2-b]pyridine-1-carboxylate(1 g, 2.95 mmol), 3-((tert-butyldiphenylsilyl)oxy)azetidine (1.19 g, 3.83 mmol), 2$^{nd}$ generation RuPhos precatalyst (0.114 g, 0.147 mmol), and Cs$_2$CO$_3$ (2.88 g, 8.84 mmol) were suspended in 1,4-dioxane (20 mL) in a reaction vial with a pressure-relief septum-lined cap and a stir bar. The suspension was degassed with nitrogen gas for 10 minutes and then sealed and placed in a heating block with stirring at 130° C. for 45 minutes. Upon completion, the reaction mixture was cooled to room temperature, filtered, concentrated and purified by silica gel column chromatography on a Teledyne Isco instrument eluting with Hex/EtOAc 0-30% to afford tert-butyl 5-(3-((tert-butyldiphenylsilyl)oxy)azetidin-1-yl)-3-isopropyl-1H-pyrrolo[3,2-b]pyridine-1-carboxylate (1.42 g, 2.49 mmol, 85% yield). LCMS retention time 1.09 [TS]. MS (E$^+$) m/z: 570.4 (M+H). $^1$H NMR (499 MHz, CHLOROFORM-d) δ 8.06 (br s, 1H), 7.69-7.63 (m, 4H), 7.47-7.33 (m, 7H), 6.23 (d, J=8.8 Hz, 1H), 4.79-4.71 (m, 1H), 4.14 (dd, J=8.6, 6.5 Hz, 2H), 3.95 (dd, J=8.7, 5.0 Hz, 2H), 3.25-3.15 (m, 1H), 1.64 (s, 9H), 1.36 (d, J=6.8 Hz, 6H), 1.07 (s, 9H).

Intermediate 39D: tert-butyl 5-(3-((tert-butyldiphenylsilyl)oxy)azetidin-1-yl)-3-isopropyl-2-(4,4,5,5-tetramethyl-1,3,2-dioxaborolan-2-yl)-1H-pyrrolo[3,2-b]pyridine-1-carboxylate

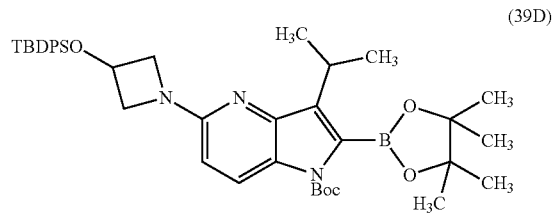

(39D)

A solution containing tert-butyl 5-(3-((tert-butyldiphenyl-silyl)oxy)azetidin-1-yl)-3-isopropyl-1H-pyrrolo[3,2-b]pyridine-1-carboxylate (1.42 g, 2.49 mmol) and 2-isopropoxy-4,4,5,5-tetramethyl-1,3,2-dioxaborolane (0.661 mL, 3.24 mmol) in dry THF (12.5 mL), under a nitrogen atmosphere was cooled in a dry ice/acetone bath to −78° C. and treated with LDA (2M in THF, 1.87 mL, 3.74 mmol). The mixture was allowed to warm to −30° C. over 30 min and stirred at −30° C. for 30 min. Upon completion, the reaction was quenched by the addition of saturated aqueous NH₄Cl solution, water, and DCM. The organic layer was separated, dried over sodium sulfate, filtered and concentrated. The crude material was purified by silica gel column chromatography on a Teledyne Isco instrument loading in hexanes and eluting with Hex/EtOAc 0-40% to afford tert-butyl 5-(3-((tert-butyldiphenylsilyl)oxy)azetidin-1-yl)-3-isopropyl-2-(4,4,5,5-tetramethyl-1,3,2-dioxaborolan-2-yl)-1H-pyrrolo[3,2-b]pyridine-1-carboxylate (1.64 g, 2.36 mmol, 95% yield). LCMS retention time 1.14 [TS]. MS (E+) m/z: 696.5 (M+H).

Intermediate 39E: 5-(3-((tert-butyldiphenylsilyl)oxy)azetidin-1-yl)-3-isopropyl-2-(4,4,5,5-tetramethyl-1,3,2-dioxaborolan-2-yl)-1H-pyrrolo[3,2-b]pyridine

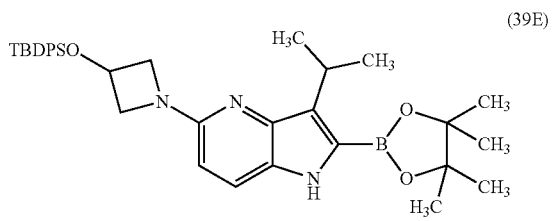

(39E)

tert-Butyl 5-(3-((tert-butyldiphenylsilyl)oxy)azetidin-1-yl)-3-isopropyl-2-(4,4,5,5-tetramethyl-1,3,2-dioxaborolan-2-yl)-1H-pyrrolo[3,2-b]pyridine-1-carboxylate (1.64 g, 2.36 mmol) was heated neat at 165° C. in a vial with a pressure-relief septum-lined cap and a stir bar under an atmosphere of nitrogen with a line of nitrogen gas. The reaction mixture was heated for a two hours, sat at room temperature overnight, and then was heated for another hour for a total of three hours of neat heating at 165° C. Upon completion, the reaction mixture was dissolved in DCM and concentrated to obtain 5-(3-((tert-butyldiphenylsilyl) oxy)azetidin-1-yl)-3-isopropyl-2-(4,4,5,5-tetramethyl-1,3,2-dioxaborolan-2-yl)-1H-pyrrolo[3,2-b]pyridine (1.40 g, 2.35 mmol, 100% yield) as a light brown foam. Note: observed partial conversion to the corresponding boronic acid on LCMS, although NMR indicated that the product was purely the compound. Boronic acid LCMS retention time 0.98 [TS]. Boronic acid MS (E+) m/z: 514.1 (M+H). Product characterization: LCMS retention time 1.07 [TS]. MS (E+) m/z: 596.1 (M+H). ¹H NMR (499 MHz, CHLOROFORM-d) δ 8.04 (s, 1H), 7.69-7.63 (m, 4H), 7.46-7.37 (m, 7H), 6.27 (d, J=8.8 Hz, 1H), 4.80-4.70 (m, 1H), 4.13 (dd, J=8.7, 6.4 Hz, 2H), 3.95 (dd, J=8.7, 5.2 Hz, 2H), 3.64 (spt, J=7.0 Hz, 1H), 1.50 (d, J=7.0 Hz, 6H), 1.35 (s, 12H), 1.07 (s, 9H).

Intermediate 39F: 6-(5-(3-((tert-butyldiphenylsilyl)oxy)azetidin-1-yl)-3-isopropyl-1H-pyrrolo[3,2-b]pyridin-2-yl)-7,8-dimethyl-[1,2,4]triazolo[1,5-a]pyridine

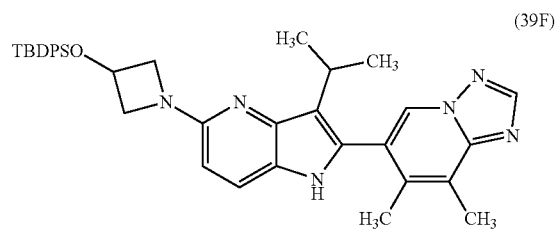

(39F)

To a mixture of 5-(3-((tert-butyldiphenylsilyl)oxy)azetidin-1-yl)-3-isopropyl-2-(4,4,5,5-tetramethyl-1,3,2-dioxaborolan-2-yl)-1H-pyrrolo[3,2-b]pyridine (500 mg, 0.839 mmol), 6-bromo-7,8-dimethyl-[1,2,4]triazolo[1,5-a]pyridine (209 mg, 0.923 mmol), and 2$^{nd}$ generation XPhos precatalyst (33.0 mg, 0.042 mmol) in 1,4-dioxane (6 mL) was added aqueous K₃PO₄ (2M, 1.26 mL, 2.52 mmol). The biphasic mixture was degassed with nitrogen gas for 10 min. The reaction vial was sealed with a pressure-relief septum-lined cap and stirred at 70° C. for 1.5 hours. Upon completion, the reaction mixture was cooled to room temperature, concentrated, and suspended in DCM for purification by silica gel column chromatography on a Teledyne Isco instrument eluting with Hex/EtOAc 0-100% to afford 6-(5-(3-((tert-butyldiphenylsilyl)oxy)azetidin-1-yl)-3-isopropyl-1H-pyrrolo[3,2-b]pyridin-2-yl)-7,8-dimethyl-[1,2,4]triazolo[1,5-a]pyridine (355 mg, 0.577 mmol, 68.8% yield). LCMS retention time 0.99 [TS]. MS (E+) m/z: 615.2 (M+H).

Intermediate 39G: 1-(2-(7,8-dimethyl-[1,2,4]triazolo[1,5-a]pyridin-6-yl)-3-isopropyl-1H-pyrrolo[3,2-b]pyridin-5-yl)azetidin-3-ol

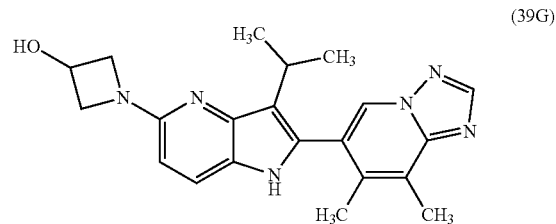 [SMILES: Cc1c(-c2[nH]c3ccc(N4CC(O)C4)nc3c2C(C)C)cn2ncnc2c1C]

(39G)

To a stirred solution of 6-(5-(3-((tert-butyldiphenylsilyl)oxy)azetidin-1-yl)-3-isopropyl-1H-pyrrolo[3,2-b]pyridin-2-yl)-7,8-dimethyl-[1,2,4]triazolo[1,5-a]pyridine (355 mg, 0.577 mmol) in THF (3.8 mL) was added TBAF (0.69 mL, 0.69 mmol). The reaction mixture was stirred at room temperature for 1 hour. Upon completion, the reaction mixture was concentrated directly, taken up in DCM, and purified by silica gel column chromatography on a Teledyne Isco instrument eluting with 0-100% Hex/EtOAc to afford 1-(2-(7,8-dimethyl-[1,2,4]triazolo[1,5-a]pyridin-6-yl)-3-isopropyl-1H-pyrrolo[3,2-b]pyridin-5-yl)azetidin-3-ol (195 mg, 0.518 mmol, 90% yield). LCMS retention time 0.59 [TS]. MS (E⁺) m/z: 377.1 (M+H).

Intermediate 39H: 1-(2-(7,8-dimethyl-[1,2,4]triazolo[1,5-a]pyridin-6-yl)-3-isopropyl-1H-pyrrolo[3,2-b]pyridin-yl)azetidin-3-yl methanesulfonate

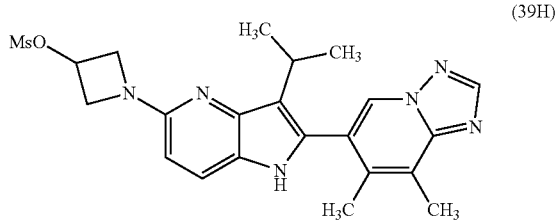 [SMILES: Cc1c(-c2[nH]c3ccc(N4CC(OS(C)(=O)=O)C4)nc3c2C(C)C)cn2ncnc2c1C]

(39H)

To a stirred solution of 1-(2-(7,8-dimethyl-[1,2,4]triazolo[1,5-a]pyridin-6-yl)-3-isopropyl-1H-pyrrolo[3,2-b]pyridin-5-yl)azetidin-3-ol (190 mg, 0.505 mmol) in THF (10 mL) at 25° C. was added Et$_3$N (176 μL, 1.26 mmol) and MsCl (43.3 μL, 0.555 mmol) sequentially. The reaction mixture was stirred for 2 hours at room temperature, and then another aliquot each of Et$_3$N (176 μl, 1.26 mmol) and MsCl (43.3 μl, 0.555 mmol) were added. Upon addition of these aliquots, the reaction reached completion quickly. The reaction was quenched by the addition of water and DCM. The layers were separated, and the aqueous layer was extracted with DCM. The combined organic layer was dried over sodium sulfate, filtered, and concentrated to afford 1-(2-(7,8-dimethyl-[1,2,4]triazolo[1,5-a]pyridin-6-yl)-3-isopropyl-1H-pyrrolo[3,2-b]pyridin-5-yl)azetidin-3-yl methanesulfonate (219 mg, 0.482 mmol, 95% yield. LCMS retention time 0.64 [TS]. MS (E+) m/z: 455.1 (M+H). $^1$H NMR (499 MHz, CHLOROFORM-d) δ 8.55 (br s, 1H), 8.35 (s, 1H), 8.28 (s, 1H), 7.56 (d, J=8.7 Hz, 1H), 6.32 (d, J=8.7 Hz, 1H), 5.42 (tt, J=6.4, 4.5 Hz, 1H), 4.47-4.40 (m, 2H), 4.19 (dd, J=10.3, 4.6 Hz, 2H), 3.08 (s, 3H), 2.87 (spt, J=6.9 Hz, 1H), 2.56 (s, 3H), 2.12 (s, 3H), 1.39 (d, J=6.8 Hz, 6H).

Example 39

A solution of 1-(2-(7,8-dimethyl-[1,2,4]triazolo[1,5-a]pyridin-6-yl)-3-isopropyl-1H-pyrrolo[3,2-b]pyridin-5-yl)azetidin-3-yl methanesulfonate (22 mg, 0.048 mmol), Et$_3$N (0.034 mL, 0.242 mmol) and morpholine (0.013 mL, 0.145 mmol) in DMF (1 mL) was heated to 80° C. with stirring for 2.5 hours and the reaction was cooled to room temperature. Another aliquot of morpholine (0.050 mL, 0.574 mmol) was added, and the reaction was heated to 100° C. for 20 hours. Upon completion, the reaction was diluted with DMF and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 19-59% B over 20 minutes, then a 4-minute hold at 100% B; Flow: 20 mL/min. The fractions containing the product were combined and dried via centrifugal evaporation to give 4-(1-(2-(7,8-dimethyl-[1,2,4]triazolo[1,5-a]pyridin-6-yl)-3-isopropyl-1H-pyrrolo[3,2-b]pyridin-5-yl)azetidin-3-yl)morpholine (5.3 mg, 0.011 mmol, 23% yield). LCMS retention time 0.77 [QC-ACN-TFA-XB]. MS (E+) m/z: 446.1 (M+H). $^1$H NMR (500 MHz, DMSO-d$_6$) δ 10.85 (s, 1H), 8.76 (s, 1H), 8.47 (s, 1H), 7.52 (d, J=8.6 Hz, 1H), 6.28 (d, J=8.7 Hz, 1H), 3.99 (br t, J=7.2 Hz, 2H), 3.73 (br t, J=6.4 Hz, 2H), 3.64-3.54 (m, 4H), 3.27-3.18 (m, 1H), 2.80 (dt, J=13.7, 6.9 Hz, 1H), 2.58 (s, 3H), 2.35 (br s, 4H), 2.15 (s, 3H), 1.35 (br d, J=6.4 Hz, 6H).

Example 96

6-(3-isopropyl-5-(4-methylpiperazin-1-yl)-1H-pyrrolo[3,2-b]pyridin-2-yl)-7,8-dimethyl-[1,2,4]triazolo[1,5-a]pyridine

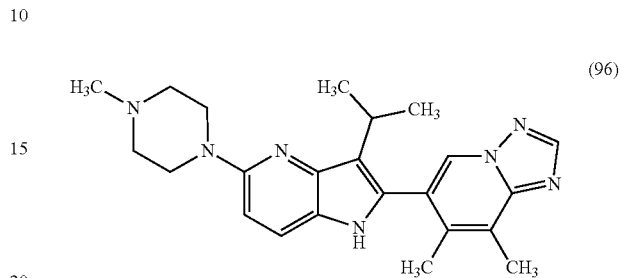

(96)

6-(3-isopropyl-5-(piperazin-1-yl)-1H-pyrrolo[3,2-b]pyridin-2-yl)-7,8-dimethyl-[1,2,4]triazolo[1,5-a]pyridine, TFA (18.93 mg, 0.0376 mmol) and Et$_3$N (0.1 mL, 0.717 mmol) were mixed in DMF (1 mL) at room temperature. Formaldehyde (37 wt % in water, 25 μL, 0.336 mmol) was added to the reaction vial followed by sodium triacetoxyborohydride (36 mg, 0.170 mmol). After 1 hour, the reaction was quenched by the addition of water, aqueous 1.5 M K$_2$HPO$_4$ solution, and DCM. The organic layer was separated, concentrated, taken up in methanol and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 15% B, 15-55% B over 19 minutes, then a 5-minute hold at 100% B; Flow Rate: 20 mL/min; Column Temperature: 25 C. Fraction collection was triggered by UV signals. The fractions containing the product were combined and dried via centrifugal evaporation to afford 6-(3-isopropyl-5-(4-methylpiperazin-1-yl)-1H-pyrrolo[3,2-b]pyridin-2-yl)-7,8-dimethyl-[1,2,4]triazolo[1,5-a]pyridine (13.9 mg, 0.033 mmol, 88% yield). LCMS retention time 1.31 min [QC-ACN-AA-XB]. MS (E$^+$) m/z: 404.3 (M+H). Select NMR peaks: $^1$H NMR (500 MHz, DMSO-d$_6$) δ 10.91 (s, 1H), 8.71 (s, 1H), 8.45 (s, 1H), 7.59 (d, J=8.9 Hz, 1H), 6.80 (d, J=8.9 Hz, 1H), 2.84-2.73 (m, 1H), 2.59 (br s, 3H), 2.57 (s, 3H), 2.14 (s, 3H), 1.35 (br d, J=6.7 Hz, 6H).

Example 105

1-(4-(2-(7,8-dimethyl-[1,2,4]triazolo[1,5-a]pyridin-6-yl)-3-isopropyl-1H-pyrrolo[3,2-b]pyridin-5-yl)piperazin-1-yl)-2-methylpropan-2-ol

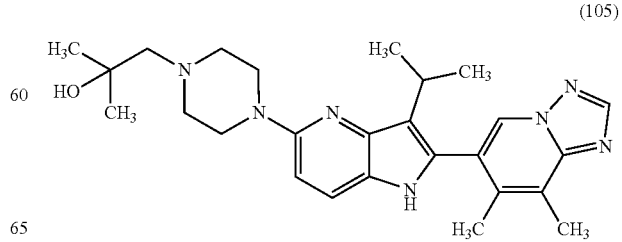

(105)

6-(3-isopropyl-5-(piperazin-1-yl)-1H-pyrrolo[3,2-b]pyridin-2-yl)-7,8-dimethyl-[1,2,4]triazolo[1,5-a]pyridine, TFA (18.93 mg, 0.0376 mmol) and potassium carbonate (27 mg, 0.195 mmol) were mixed in ethanol (1 mL). 2,2-dimethyloxirane (24 mg, 0.333 mmol) was added to the reaction mixture. The reaction vessel was sealed and heated to 80° C. with stirring for 3 hours. Upon completion, the reaction mixture was cooled to room temperature, filtered, concentrated, taken up in DMSO and purified via preparative LC/MS with the following conditions: Column: XBridge C18, 200 mm×19 mm, 5-m particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 27% B, 27-67% B over 20 minutes, then a 4-minute hold at 100% B; Flow Rate: 20 mL/min; Column Temperature: 25 C. Fraction collection was triggered by MS and UV signals. The fractions containing the product were combined and dried via centrifugal evaporation to afford 1-(4-(2-(7,8-dimethyl-[1,2,4]triazolo[1,5-a]pyridin-6-yl)-3-isopropyl-1H-pyrrolo[3,2-b]pyridin-5-yl)piperazin-1-yl)-2-methylpropan-2-ol (9.9 mg, 0.021 mmol, 57.0% yield). LCMS retention time 1.92 [QC-ACN-AA-XB]. MS (E+) m/z: 461.9 (M+H). $^1$H NMR (500 MHz, DMSO-$d_6$) δ 10.81 (s, 1H), 8.72 (s, 1H), 8.45 (s, 1H), 7.53 (d, J=8.9 Hz, 1H), 6.72 (d, J=8.9 Hz, 1H), 3.54-3.38 (m, 4H), 2.82-2.72 (m, 1H), 2.66 (br s, 4H), 2.57 (s, 3H), 2.26 (s, 2H), 2.16 (s, 3H), 1.36 (br d, J=6.7 Hz, 6H), 1.12 (s, 6H).

Example 164

1-(2-(7,8-dimethyl-[1,2,4]triazolo[1,5-a]pyridin-6-yl)-3-isopropyl-1H-pyrrolo[3,2-b]pyridin-5-yl)-N-(oxetan-3-yl)pyrrolidin-3-amine

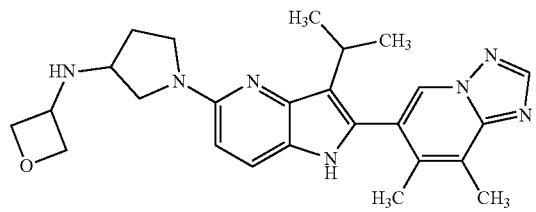

(164)

Intermediate 164A: 5-bromo-3-isopropyl-2-(4,4,5,5-tetramethyl-1,3,2-dioxaborolan-2-yl)-1H-pyrrolo[3,2-b]pyridine

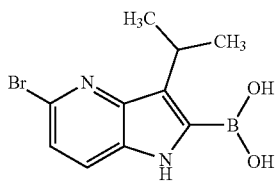

(164A)

A solution containing tert-butyl 5-bromo-3-isopropyl-1H-pyrrolo[3,2-b]pyridine-1-carboxylate (3.00 g, 8.84 mmol) and 2-isopropoxy-4,4,5,5-tetramethyl-1,3,2-dioxaborolane (2.71 mL, 13.27 mmol) in dry THF (30 mL) under a nitrogen atmosphere was cooled in a dry ice/acetone bath at −78° C. and treated with LDA (2M in TIF) (5.53 mL, 11.05 mmol). The mixture was stirred at −78° C. for 30 minutes and allowed to warm to −30° C. over 1 hour and stirred at −30° C. for 30 minutes. The reaction was treated with 1.5 M aqueous $KH_2PO_4$ solution, water, and DCM. The layers were separated and the organic layer was dried over anhydrous sodium sulfate, filtered and concentrated. The crude product was purified by silica gel chromatography to afford tert-butyl 5-bromo-3-isopropyl-2-(4,4,5,5-tetramethyl-1,3,2-dioxaborolan-2-yl)-1H-pyrrolo[3,2-b]pyridine-1-carboxylate. LCMS retention time 1.32 min [Method A]. MS m/z: 465.1 (M+H). This material was transferred to a 40 mL tall vial, which was capped and flushed with nitrogen gas. The reaction mixture was stirred and heated at 160° C. for 1.5 hours and 5-bromo-3-isopropyl-2-(4,4,5,5-tetramethyl-1,3,2-dioxaborolan-2-yl)-1H-pyrrolo[3,2-b]pyridine (2.1 g, 5.75 mmol, 65% yield) was obtained as a yellow solid. Note: material converted to the free boronic acid on LCMS and was observed as such: LCMS retention time 0.85 min [Method A]. MS m/z: 282.9/284.9 (M+H/(M+2)+H).

Intermediate 164B: tert-butyl 5-bromo-2-(7,8-dimethyl-[1,2,4]triazolo[1,5-a]pyridin-6-yl)-3-isopropyl-1H-pyrrolo[3,2-b]pyridine-1-carboxylate

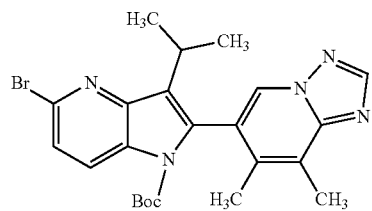

(164B)

In a 40 mL reaction vial was added 5-bromo-3-isopropyl-2-(4,4,5,5-tetramethyl-1,3,2-dioxaborolan-2-yl)-1H-pyrrolo[3,2-b]pyridine (1.500 g, 4.11 mmol), 6-bromo-7,8-dimethyl-[1,2,4]triazolo[1,5-a]pyridine (1.14 g, 4.90 mmol), and 2nd generation XPhos precatalyst (0.162 g, 0.205 mmol) and THF (20 mL). The reaction vial was sealed and pump/purged three times with nitrogen gas. Potassium phosphate, tribasic (6.16 mL, 12.33 mmol) was added and the reaction mixture was heated to 65° C. for 1 hour. The mixture was diluted with ethyl acetate and washed with water, then brine and dried over anhydrous sodium sulfate. The solids were filtered off and the filtrate was concentrated. To this was added THF (20 mL), a crystal of DMAP and BOC-anhydride (0.954 mL, 4.11 mmol). The reaction mixture was stirred for 18 hours and was concentrated under a stream of nitrogen gas. The residue was purified by silica gel chromatography to afford tert-butyl 5-bromo-2-(7,8-dimethyl-[1,2,4]triazolo[1,5-a]pyridin-6-yl)-3-isopropyl-1H-pyrrolo[3,2-b] pyridine-1-carboxylate (2.1 g, 5.75 mmol, 65% yield) as a tan solid. LCMS retention time 1.22 min [Method A]. MS m/z: 486.2 (M+H).

117

Intermediate 164C: 1-(2-(7,8-dimethyl-[1,2,4]triazolo[1,5-a]pyridin-6-yl)-3-isopropyl-1H-pyrrolo[3,2-b]pyridin-5-yl)pyrrolidin-3-one

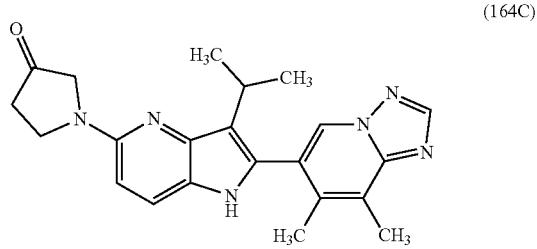 [SMILES: Cc1c(-c2[nH]c3ccc(N4CCC(=O)C4)nc3c2C(C)C)cn2ncnc2c1C]

(164C)

In a 1 dram vial was added tert-butyl 5-bromo-2-(7,8-dimethyl-[1,2,4]triazolo[1,5-a] pyridin-6-yl)-3-isopropyl-1H-pyrrolo[3,2-b]pyridine-1-carboxylate (0.150 g, 0.310 mmol), 2nd generation RuPhos precatalyst (0.024 g, 0.031 mmol), 1,4-dioxa-7-azaspiro[4.4]nonane (0.060 g, 0.464 mmol) and cesium carbonate (0.303 g, 0.929 mmol). The reaction vial was capped with a Teflon-lined cap and pump/purged two times with nitrogen gas. To this, under nitrogen, was added dioxane (2 mL) and the reaction vial was pump/purged three times and was set to heat at 100° C. for 18 hours. The reaction mixture was diluted with ethyl acetate and filtered through Celite. The filtrate was concentrated and purified by silica gel chromatography to afford tert-butyl 2-(7,8-dimethyl-[1,2,4]triazolo[1,5-a]pyridin-6-yl)-3-isopropyl-5-(1,4-dioxa-7-azaspiro[4.4]nonan-7-yl)-1H-pyrrolo[3,2-b]pyridine-1-carboxylate as a tan oil. LCMS retention time 1.06 min [Method A]. MS m/z: 533.4 (M+H). To this was added TFA (2 mL) and 1 drop of water and the reaction mixture was stirred for 6 hours, then was concentrated under a stream of nitrogen gas. The residue was diluted with 1.5M $K_2HPO_4$ solution and DCM. The mixture was transferred to a separatory funnel and the layers were separated. The organics were dried over anhydrous sodium sulfate, filtered and concentrated to afford 1-(2-(7,8-dimethyl-[1,2,4]triazolo[1,5-a]pyridin-6-yl)-3-isopropyl-1H-pyrrolo[3,2-b]pyridin-5-yl)pyrrolidin-3-one (50 mg, 0.206 mmol, 42% yield) as a brownish solid. LCMS retention time 0.79 min [Method A]. MS m/z: 389.3 (M+H).

Example 164

In a 1 dram vial was added 1-(2-(7,8-dimethyl-[1,2,4]triazolo[1,5-a]pyridin-6-yl)-3-isopropyl-1H-pyrrolo[3,2-b]pyridin-5-yl)pyrrolidin-3-one (0.025 g, 0.064 mmol), DCM (1 mL) and oxetan-3-amine (0.014 g, 0.193 mmol). The reaction mixture was stirred for 4 hours at 25° C., then sodium triacetoxyborohydride (0.041 g, 0.193 mmol) was added. The reaction mixture was stirred for 12 hours at the same temperature. The sample was concentrated, diluted with DMF, filtered and was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 24 minutes, then a 5-minute hold at 100% B; Flow: 20 mL/min. Fractions containing the product were combined and dried via centrifugal evaporation to afford 1-(2-(7,8-dimethyl-[1,2,4]triazolo[1,5-a]pyridin-6-yl)-3-isopropyl-1H-pyrrolo[3,2-b]pyridin-5-yl)-N-(oxetan-3-yl)pyrrolidin-3-amine as a racemic mixture (6.7 mg, 0.0150 mmol, 23% yield), m/z (446.4, M+H). Retention time, 1.450 min using LCMS Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM.

Example 368

2-((4-(2-(7,8-dimethyl-[1,2,4]triazolo[1,5-a]pyridin-6-yl)-3-isopropyl-1H-pyrrolo[3,2-b]pyridin-5-yl)cyclohexyl)(methyl)amino)-N,N-dimethylacetamide

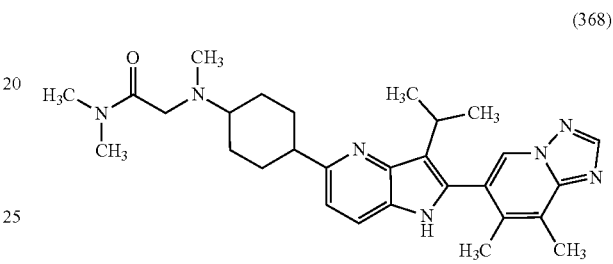

(368)

Intermediate 368A: 4-(2-(7,8-dimethyl-[1,2,4]triazolo[1,5-a]pyridin-6-yl)-3-isopropyl-1H-pyrrolo[3,2-b]pyridin-5-yl)-N-methylcyclohexanamine

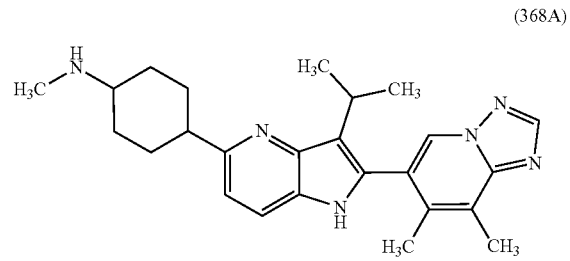 [SMILES: CNC1CCC(c2ccc3[nH]c(-c4cn5ncnc5c(C)c4C)c(C(C)C)c3n2)CC1]

(368A)

4-(2-(7,8-dimethyl-[1,2,4]triazolo[1,5-a]pyridin-6-yl)-3-isopropyl-1H-pyrrolo[3,2-b] pyridin-5-yl)cyclohexan-1-one (0.015 g, 0.037 mmol) and methylamine in THF (0.093 mL, 0.187 mmol) were mixed in DMF (1 mL) and AcOH (6.42 μL, 0.112 mmol). To this was added sodium triacetoxyborohydride (0.040 g, 0.187 mmol). The reaction mixture was stirred for 12 hours. The reaction was quenched via addition of 1.5M $K_2HPO_4$. Ethyl acetate was added and the mixture was extracted three times (3×50 mL). The organics were combined, washed with saturated NaCl solution, dried over anhydrous sodium sulfate, filtered and concentrated to obtain Intermediate 368A. Intermediate 368A was separated into cis/trans isomers according to the conditions below. Alternatively, crude Intermediate 368A could be carried forward as a cis/trans mixture for further derivatization and subsequent separation to afford the individual derivatized isomers.

Example 367 (Isomer 1) and Example 369 (Isomer 2)

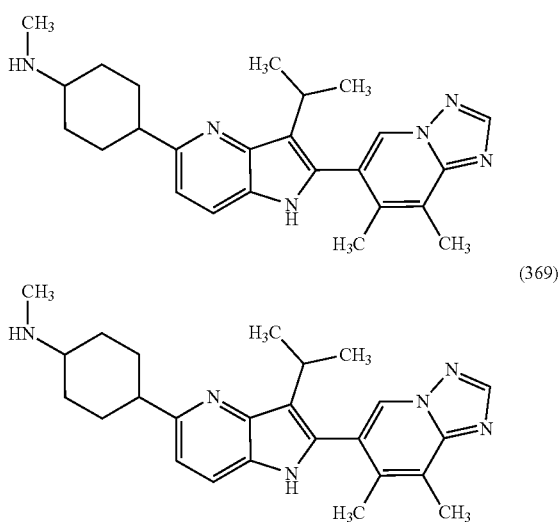

(367)

(369)

Intermediate 368A was purified and separated into the cis and trans isomers via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 4-minute hold at 100% B; Flow: 20 mL/min. Fractions containing the individual isomers were dried via centrifugal evaporation to afford the following:

Example 367: Isomer 1: 4-(2-(7,8-dimethyl-[1,2,4]triazolo[1,5-a]pyridin-6-yl)-3-isopropyl-1H-pyrrolo[3,2-b]pyridin-5-yl)-N-methylcyclohexanamine (4.3 mg, 0.00970 mmol, 26% yield), m/z (417.2, M+H). Retention time, 1.204 min [Method C]. $^1$H NMR (500 MHz, DMSO-$d_6$) δ 11.16-10.99 (m, 1H), 8.79 (s, 1H), 8.48 (s, 1H), 7.62 (d, J=8.2 Hz, 1H), 7.07 (d, J=8.2 Hz, 1H), 3.18 (s, 1H), 2.90 (br s, 2H), 2.71 (br s, 1H), 2.60 (s, 2H), 2.55 (s, 1H), 2.32 (s, 2H), 2.18 (s, 2H), 2.06 (br d, J=14.3 Hz, 1H), 1.86 (br s, 2H), 1.81-1.72 (m, 1H), 1.65 (br s, 2H), 1.56-1.47 (m, 1H), 1.40 (br d, J=6.7 Hz, 4H), 1.24 (s, 3H), 1.00 (d, J=6.4 Hz, 1H), 0.86 (br t, J=6.7 Hz, 1H).

Example 369: Isomer 2: 4-(2-(7,8-dimethyl-[1,2,4]triazolo[1,5-a]pyridin-6-yl)-3-isopropyl-1H-pyrrolo[3,2-b]pyridin-5-yl)-N-methylcyclohexanamine (2.4 mg, 0.00576 mmol, 11% yield), m/z (417.2, M+H). Retention time, 1.323 min [Method C]. $^1$H NMR (500 MHz, DMSO-$d_6$) δ 11.19-11.01 (m, 1H), 8.78 (s, 1H), 8.48 (s, 1H), 7.60 (d, J=8.2 Hz, 1H), 7.01 (br d, J=8.5 Hz, 1H), 2.96-2.83 (m, 1H), 2.72 (br t, J=11.9 Hz, 1H), 2.60 (s, 3H), 2.39 (s, 3H), 2.18 (s, 2H), 2.11-1.92 (m, 4H), 1.83 (br s, 3H), 1.75-1.58 (m, 2H), 1.40 (br d, J=6.7 Hz, 6H), 1.34-1.20 (m, 2H).

Example 368

To a 1 dram vial was added Intermediate 368a, 4-(2-(7,8-dimethyl-[1,2,4]triazolo[1,5-a]pyridin-6-yl)-3-isopropyl-1H-pyrrolo[3,2-b]pyridin-5-yl)-N-methylcyclohexanamine (0.020 g, 0.048 mmol), DCM (1 mL) and DBU (0.025 mL, 0.164 mmol). The material went into solution and 2-chloro-N,N-dimethylacetamide (0.018 g, 0.144 mmol) was added. The reaction mixture was stirred at 25° C. for 18 hours. The mixture was then concentrated under a steam of nitrogen gas, was diluted with 90:10:0.1 acetonitrile:water:TFA, filtered and was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 24 minutes, then a 5-minute hold at 100% B; Flow: 20 mL/min. Fractions containing the product were combined and dried via centrifugal evaporation to afford 2-((4-(2-(7,8-dimethyl-[1,2,4]triazolo[1,5-a]pyridin-6-yl)-3-isopropyl-1H-pyrrolo[3,2-b]pyridin-5-yl)cyclohexyl)(methyl)amino)-N,N-dimethylacetamide as a single cyclohexyl isomer (0.9 mg, 0.00160 mmol, 3.3% yield), m/z (502.3, M+H). Retention time, 1.249 min using LCMS Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM. $^1$H NMR (500 MHz, DMSO-$d_6$) δ 11.23-11.03 (m, 1H), 8.81 (s, 1H), 8.49 (s, 1H), 7.67-7.50 (m, 1H), 7.00 (d, J=8.3 Hz, 1H), 3.06 (s, 2H), 2.93-2.79 (m, 4H), 2.77-2.66 (m, 2H), 2.60 (s, 4H), 2.23 (s, 3H), 2.18 (s, 3H), 1.99 (br d, J=12.6 Hz, 2H), 1.89 (br s, 2H), 1.66 (br d, J=11.9 Hz, 3H), 1.50-1.35 (m, 9H).

Example 424 and Example 430

N-(4-(2-(7,8-dimethyl-[1,2,4]triazolo[1,5-a]pyridin-6-yl)-3-isopropyl-1H-pyrrolo[3,2-b]pyridin-5-yl)cyclohexyl)-N-methyloxetan-3-amine

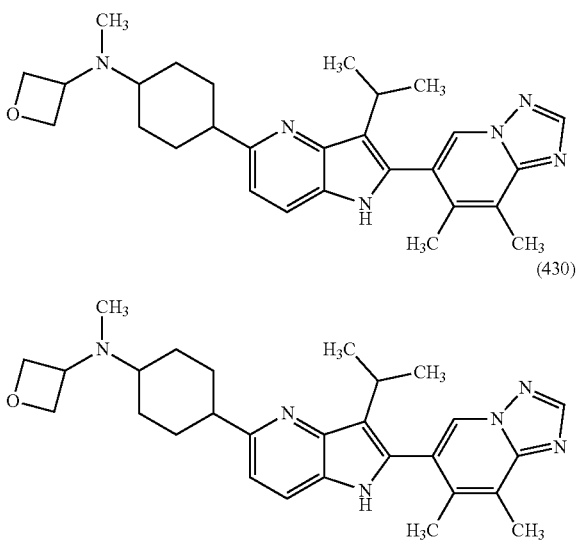

(424)

(430)

Intermediate 368A, 4-(2-(7,8-dimethyl-[1,2,4]triazolo[1,5-a]pyridin-6-yl)-3-isopropyl-1H-pyrrolo[3,2-b]pyridin-5-yl)-N-methylcyclohexanamine (0.025 g, 0.060 mmol) and oxetan-3-one (8.65 mg, 0.120 mmol) were mixed in DCM (1 mL). To this was added AcOH (0.344 μL, 6.00 μmol) and sodium triacetoxyborohydride (0.038 g, 0.180 mmol). The mixture was stirred for 2 hours at 25° C. then was quenched via addition of 1.5M $K_2HPO_4$ solution. Additional DCM was added and the contents were transferred to a separatory funnel and the layers were separated. The combined organics were washed with a saturated NaCl solution, dried over anhydrous sodium sulfate, filtered, concentrated and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 24 minutes, then a 5-minute hold at 100% B; Flow: 20 mL/min. Fractions containing the products were combined and dried via centrifugal evaporation to afford the following resolved products:

Example 424: Isomer 1: N-(4-(2-(7,8-dimethyl-[1,2,4]triazolo[1,5-a]pyridin-6-yl)-3-isopropyl-1h-pyrrolo[3,2-b]pyridin-5-yl)cyclohexyl)-N-methyloxetan-3-amine (2.5 mg, 0.00519 mmol, 7% yield), m/z (473.2, M+H). Retention time, 1.384 min [Method C]. $^1$H NMR (500 MHz, DMSO-$d_6$) δ 11.08 (s, 1H), 8.78 (s, 1H), 8.48 (s, 1H), 7.60 (br d, J=8.2 Hz, 1H), 7.00 (br d, J=8.2 Hz, 1H), 4.52 (br d, J=6.7 Hz, 4H), 4.04-3.90 (m, 1H), 3.18 (br s, 2H), 2.95-2.84 (m, 1H), 2.68 (br s, 1H), 2.60 (s, 3H), 2.45-2.32 (m, 1H), 2.18 (s, 6H), 1.97 (br d, J=11.3 Hz, 2H), 1.75 (br d, J=11.6 Hz, 2H), 1.64 (br d, J=12.8 Hz, 2H), 1.40 (br d, J=6.7 Hz, 8H).

Example 430: Isomer 2: N-(4-(2-(7,8-dimethyl-[1,2,4]triazolo[1,5-a]pyridin-6-yl)-3-isopropyl-1H-pyrrolo[3,2-b]pyridin-5-yl)cyclohexyl)-N-methyloxetan-3-amine (6.8 mg, 0.0140 mmol, 18% yield), m/z (473.3, M+H). Retention time, 1.537 min [Method C]. $^1$H NMR (500 MHz, DMSO-$d_6$) δ 11.10 (s, 1H), 8.82 (s, 1H), 7.96 (s, 1H), 7.63 (d, J=8.2 Hz, 1H), 7.08 (d, J=8.2 Hz, 1H), 4.48 (quin, J=6.3 Hz, 4H), 3.95-3.81 (m, 1H), 3.10 (br s, 1H), 2.90 (s, 2H), 2.61 (s, 2H), 2.41-2.16 (m, 6H), 2.07 (s, 3H), 1.90 (br s, 2H), 1.74 (br s, 3H), 1.45 (br d, J=7.0 Hz, 7H).

Example 438

6-((1r,4r)-(4-(2-(7,8-dimethyl-[1,2,4]triazolo[1,5-a]pyridin-6-yl)-3-isopropyl-1H-pyrrolo[3,2-b]pyridin-5-yl)cyclohexyl)-2-thia-6-azaspiro[3.3]heptane 2,2-dioxide

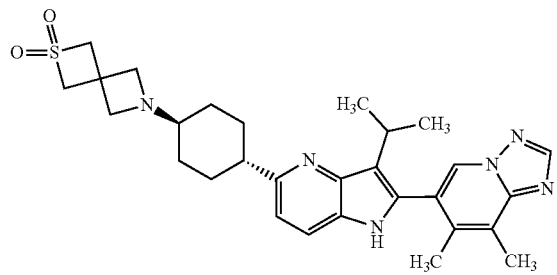

(438)

Intermediate 438A: 2-thia-6-azaspiro[3.3]heptane 2,2-dioxide hydrochloride

(438A)

Intermediate 438B: 6-tosyl-2-oxa-6-azaspiro[3.3]heptane

(438B)

To a solution of EtOH (500 mL) and 3-bromo-2,2-bis(bromomethyl)propan-1-ol (14.00 g, 43.1 mmol) was added 4-methylbenzenesulfonamide (16.23 g, 95 mmol) at 25° C. and the reaction mixture was refluxed for 20 h. The solvent was removed by evaporation and to this was added 100 mL of an 8% NaOH solution. The suspension was stirred for another 2 hours, filtered and the yellow filter cake was rinsed with water and dried overnight through air to give 6-tosyl-2-oxa-6-azaspiro[3.3]heptane (9.05 g, 35.7 mmol, 83% yield) as a light yellow solid. LCMS retention time 0.72 min [Method A]. MS m/z: 254.3 (M+H).

Intermediate 438C: (3-(bromomethyl)-1-tosylazetidin-3-yl) methanol

(438C)

To a suspension of 6-tosyl-2-oxa-6-azaspiro[3.3]heptane (10.50 g, 41.5 mmol) in diethyl ether (300 mL) at 0° C. was added a solution of hydrobromic acid in acetic acid (7.16 mL, 43.5 mmol) in 20 mL of ether, dropwise. The resulting solution was stirred at 0° C. for 2 hours, then 1N NaOH was added to pH=8. The phases were separated and the aqueous phase was extracted with ethyl acetate (3×150 mL). The combined organics were dried over anhydrous sodium sulfate, filtered, and concentrated in vacuo to afford the (3-(bromomethyl)-1-tosylazetidin-3-yl)methanol (13.5 g, 36.4 mmol, 88% yield) as a solid. LCMS retention time 0.80 min [Method A]. MS m/z: 336.2 (M+H)

Intermediate 438D: 3,3-bis(bromomethyl)-1-tosylazetidine

(438D)

In a 500 mL round bottom flask (3-(bromomethyl)-1-tosylazetidin-3-yl) methanol (14.44 g, 38.9 mmol) was dissolved in DCM (250 mL) and carbon tetrabromide (21.93 g, 66.1 mmol) was added. The solution was cooled in an ice bath and triphenylphosphine (17.34 g, 66.1 mmol) was added in one portion. The resulting mixture was stirred at 0° C. for 2 hours, then warmed to 25° C. and stirred for 4 hours. Diethyl ether (200 mL) was added and the resulting yellow precipitate was filtered and discarded. The filtrate was concentrated under reduced pressure and purified by silica gel chromatography to afford 3,3-bis(bromomethyl)-1-tosylazetidine (11 g, 27.7 mmol, 71.2% yield) as a white solid. LCMS retention time 0.99 min [Method A]. MS m/z: 398.1 (M+H)

Intermediate 438E:
6-tosyl-2-thia-6-azaspiro[3.3]heptane

(438E)

To a solution of 3,3-bis(bromomethyl)-1-tosylazetidine (36.0 g, 91 mmol) in a mixture of acetonitrile (30 mL) and water (5 mL) was added sodium sulfide nonahydrate (43.5 g, 181 mmol) and the reaction mixture was stirred at 50° C. for 4 hours. This was concentrated under reduced pressure and diluted with EtOAc (100 mL) and 1N NaOH solution (30 mL). The phases were separated and the aqueous phase was extracted with EtOAc (2×100 mL). The combined organics were washed with brine, dried over anhydrous sodium sulfate, filtered, and concentrated to give 6-tosyl-2-thia-6-azaspiro[3.3]heptane (21.2 g, 79 mmol, 87% yield) as a yellow solid. LCMS retention time 0.9 min [Method A]. MS m/z: 270.2 (M+H).

Intermediate 438F:
6-tosyl-2-thia-6-azaspiro[3.3]heptane 2,2-dioxide

(438F)

To a 100 mL round bottom flask was added 6-tosyl-2-thia-6-azaspiro[3.3]heptane (3.50 g, 12.99 mmol) and DCM (50 mL). The mixture was cooled to 0° C. and mCPBA (8.74 g, 39.0 mmol) was added. The reaction mixture was warmed to 25° C. and stirred for 4 hours. The mixture was concentrated, diluted with MeOH (50 mL) and stirred for 30 minutes. The suspension was filtered and the solid was washed with additional MeOH and dried through air to afford 6-tosyl-2-thia-6-azaspiro[3.3]heptane 2,2-dioxide (3.5 g, 11.61 mmol, 90% yield) as a white solid. LCMS retention time 0.72 min [Method A]. MS m/z: 302.2 (M+H)

Intermediate 438A: 2-thia-6-azaspiro[3.3]heptane 2,2-dioxide hydrochloride

(438A)

In a 250 mL round bottom flask was dissolved 6-tosyl-2-thia-6-azaspiro[3.3]heptane 2,2-dioxide (0.750 g, 2.489 mmol) in MeOH (30 mL). Fresh magnesium (0.907 g, 37.3 mmol) was added and the reaction was heated at 50° C. for 16 hours with vigorous stirring. The reaction mixture was then concentrated to near dryness and the resulting greyish material was suspended in diethyl ether (100 mL). Sodium sulfate decahydrate (8.02 g, 24.89 mmol) was added and the slurry was stirred for 1 hour, then filtered, dried over anhydrous sodium sulfate and filtered. The white solid was dissolved in DCM (2 mL) and 4M HCl/dioxane (5 mL) was added. A white solid precipitated out and the suspension was allowed to sit for 30 minutes, then concentrated. Diethyl ether was added and the suspension was stirred for 30 minutes. The solid was filtered through a frit and washed with diethyl ether to afford 2-thia-6-azaspiro[3.3]heptane 2,2-dioxide HCl (0.250 g, 1.361 mmol, 54.7% yield) as a white solid.

Example 438

4-(2-(7,8-dimethyl-[1,2,4]triazolo[1,5-a]pyridin-6-yl)-3-isopropyl-1H-pyrrolo[3,2-b] pyridin-5-yl)cyclohexan-1-one (Intermediate 4D, 0.755 g, 1.880 mmol), 2-thia-6-azaspiro [3.3]heptane 2,2-dioxide hydrochloride (0.518 g, 2.82 mmol) and DBU (0.567 mL, 3.76 mmol) were mixed in DCM (6 mL) with acetic acid (1.076 µl, 0.019 mmol). The reaction vial was capped. The reaction mixture was stirred overnight at 25° C. The volatiles were removed under a stream of nitrogen gas and the residue was diluted with MeOH (1 mL). The reaction mixture was cooled to −78° C. and lithium borohydride (2M in TF) (2.82 mL, 5.64 mmol) was added drop-wise over 10 minutes. The mixture was stirred at the same temperature for 1 hour, and then the reaction was quenched by addition of 1.5 M aqueous $K_2HPO_4$. DCM was added and the mixture was transferred to a separatory funnel and the layers were separated. The aqueous layer was extracted with DCM (3×50 mL) and the combined organics were washed with a saturated sodium chloride solution, dried over anhydrous sodium sulfate, filtered and concentrated to afford 1.4 g of crude material. The crude material was purified by preparative SFC using the following conditions: Sample preparation: 1.4 g/36 mL MeOH:DCM(4:1), 38.88 mg/mL; Column: Cellulose-4 (3×25 cm, 5 µm, #121391); temperature=35° C.; flow rate: 200 mL/min; BPR pressure: 100 bars; mobile Phase: $CO_2$/MeOH:MeCN (1:1) w 0.1% $NH_{40}H$ (45/55); separation program: Stack injection; Injection: 3.5 mL with cycle time: 4.2 mins; throughput: 1.9 g/hr; Detector Wavelength: 220 nm. The fractions containing the product were concentrated and further purified using the following procedure: Approximately 900 mg of the white solid from SFC purification was dissolved in a boiling mixture of ethyl acetate:methanol (4:1). The flask was capped and maintained at room temperature for 48 hours. A white solid was filtered off and washed with ethyl acetate, followed by MeOH. The solid was dried and collected to afford 6-((1r,4r)-(4-(2-(7,8-dimethyl-[1,2,4]triazolo[1,5-a]pyridin-6-yl)-3-isopropyl-1H-pyrrolo[3,2-b]pyridin-5-yl)cyclohexyl)-2-thia-6-azaspiro [3.3]heptane 2,2-dioxide (0.57 g, 1.070 mmol, 56.9% yield) as a white solid. LCMS retention time 0.56 min [Method A]. MS m/z: 533.5 (M+H).

Exploration of reductive amination conditions in the preparation of Example 438:

| Reducing Agent | Solvent | Temp. | *cis:trans:**alcohol ratio |
|---|---|---|---|
| $NaBH_4$ | DMF | 25° C. | 8:1:0 |
| $NaBH_4$ | DCM | 25° C. | 8:1:0 |
| $NaBH_4$ | MeOH | −78° C. | No Reaction |

-continued

| Reducing Agent | Solvent | Temp. | *cis:trans:**alcohol ratio |
|---|---|---|---|
| LiBH₄ | MeOH | −78° C. | 1:3:1 |
| LiBH₄ | ***DCM/MeOH | 25° C./−78° C. | 1:6:1 |

*Approximate ratios were obtained via HPLC.
**Alcohol ratio refers to the ketone reduction to the alcohol.
***Iminium was pre-generated in DCM at 25° C., The reduction was performed at −78° C. in MeOH.

Alternate Synthesis of Example 438

Intermediate 1A: 2-bromo-5-hydrazinylpyridine

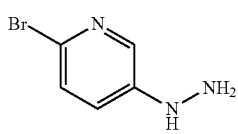

(1A)

To a solution of 6-bromopyridin-3-amine (50 g, 289 mmol) in HBr in 47% water (570 mL) at 0° C. in a 5 L multi-neck round bottom flask, was added dropwise a solution of sodium nitrite (19.94 g, 289 mmol) in water (312.5 mL). After 1 hour at 0° C., a solution of tin (II) chloride dihydrate (157 g, 694 mmol) in HBr, 47% in water (345 mL) is slowly added at 0° C. After this addition was complete, the reaction mixture was allowed to stir for 1 hour at 0° C. The solid was collected by filtration and dried for 30 minutes through air and then washed with diethyl ether (500 mL). Following drying to remove the diethyl ether, 2-bromo-5-hydrazineylpyridine dihydrobromide (65 g, 186 mmol, 64.3% yield) was collected as a solid. LCMS retention time 0.68 min [DDS]. MS m/z: 188.1 (M+H).

Intermediate 1B: 5-bromo-3-isopropyl-1H-pyrrolo[3,2-b]pyridine

(1B)

Isovaleraldehyde (23.70 mL, 220 mmol) was added to a solution of 2-bromo-5-hydrazineylpyridine dihydrobromide (70 g, 200 mmol) in sulfuric acid (70 mL, 1313 mmol) in water (630 mL) and the reaction mixture was stirred for 30 minutes at room temperature. The reaction mixture was heated to 110° C. and stirred for 18 hours. The reaction mixture was diluted with ethyl acetate (2000 mL) and washed with water (200 mL). The separated organic layer was dried over anhydrous sodium sulfate, filtered and concentrated under reduce pressure to afford 5-bromo-3-isopropyl-1H-pyrrolo[3,2-b]pyridine (200 mmol) as brown liquid. Material carried forward without additional purification. LCMS retention time 1.64 min [DDS]. MS m/z: 241.1 (M+H).

Intermediate 1C: tert-butyl 5-bromo-3-isopropyl-1H-pyrrolo[3,2-b]pyridine-1-carboxylate

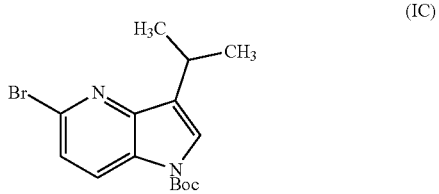

(IC)

To a solution of 5-bromo-3-isopropyl-1H-pyrrolo[3,2-b]pyridine (55 g, 193 mmol) in THF (550 mL) at 0° C. was added TEA (42.4 mL, 304 mmol) over 10 minutes followed by the addition of DMAP (2.360 g, 19.32 mmol). At 0° C., BOC-anhydride 30% in toluene (16.73 g, 23.0 mmol) was added in a single portion and the reaction mixture was stirred for 1 hour. Another aliquot of Boc-anhydride (67.3 mL, 290 mmol) was added and the reaction mixture was stirred for 18 hours at 25° C. Upon completion, the reaction mixture was concentrated in vacuo and the crude material was purified on silica gel chromatography to afford tert-butyl 5-bromo-3-isopropyl-1H-pyrrolo[3,2-b]pyridine-1-carboxylate (37 g, 104 mmol, 53.6% yield). LCMS retention time 1.59 min [DDS]. MS m/z: 339.0 (M+H). ¹H NMR (400 MHz, DMSO-d₆) δ 8.22 (d, J=8.5 Hz, 1H), 7.71 (s, 1H), 7.52 (d, J=8.5 Hz, 1H), 3.27-3.08 (m, 1H), 1.63 (s, 9H), 1.32 (d, J=7.0 Hz, 6H).

Intermediate 4A: tert-butyl 3-isopropyl-5-(1,4-dioxaspiro[4.5]dec-7-en-8-yl)-1H-pyrrolo[3,2-b]pyridine-1-carboxylate

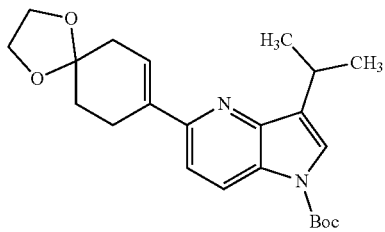

(4A)

To a 1000 mL sealed tube was added tert-butyl 5-bromo-3-isopropyl-1H-pyrrolo[3,2-b]pyridine-1-carboxylate (42 g, 124 mmol) and 4,4,5,5-tetramethyl-2-(1,4-dioxaspiro[4.5]dec-7-en-8-yl)-1,3,2-dioxaborolane (34.6 g, 130 mmol) in a mixture of tetrahydrofuran (360 mL) and water (42 mL). To this was added potassium phosphate tribasic (52.6 g, 248 mmol) and 2d generation X-Phos precatalyst (3.90 g, 4.95 mmol). The bi-phasic mixture was degassed with nitrogen gas for 10 minutes and the sealed vial was stirred at 70° C. for 12 hours. The reaction mixture was cooled to room temperature and diluted with ethyl acetate and water. The mixture was transferred to a separatory funnel and the layers were separated. The combined organics were washed with saturated sodium chloride, dried over anhydrous sodium sulfate, filtered and concentrated to dryness. Further purification was done by silica gel chromatography to afford tert-butyl 3-isopropyl-5-(1,4-dioxaspiro[4.5]dec-7-en-8-yl)-1H-pyrrolo[3,2-b]pyridine-1-carboxylate (39.00 g, 98.0 mmol, 79% yield) LCMS retention time 2.53 min [DDS2]. MS m/z: 399.5 (M+H). ¹H NMR (400 MHz, DMSO-d₆) δ 9.08 (d, J=9.0 Hz, 1H), 8.48 (s, 1H), 8.41 (d, J=9.0 Hz, 1H), 7.50-7.40 (m, 1H), 7.24-7.14 (m, 1H), 4.82 (s, 2H), 4.75 (s, 2H), 4.20 (s, 3H), 3.69-3.59 (m, 1H), 3.36-3.29 (m, 1H), 3.17-3.01 (m, 2H), 2.74 (s, 1H), 2.48 (s, 1H), 2.25 (d, J=7.0 Hz, 3H), 2.08 (s, 9H).

Intermediate 4B: tert-butyl 3-isopropyl-5-(1,4-dioxaspiro[4.5]decan-8-yl)-1H-pyrrolo[3,2-b]pyridine-1-carboxylate

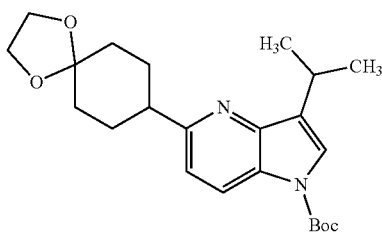

(4B)

To tert-butyl 3-isopropyl-5-(1,4-dioxaspiro[4.5]dec-7-en-8-yl)-1H-pyrrolo[3,2-b]pyridine-1-carboxylate (80 g, 201 mmol) in ethyl acetate (800 mL) was added 10% w/w Pd—C (29.9 g, 28.1 mmol). The flask was placed under vacuum and pump/purged with nitrogen gas. After evacuation, the vessel was back-filled with hydrogen gas via a hydrogen filled bladder and the reaction mixture was allowed to stir for 2-3 hours. The vessel was diluted with ethyl acetate and the contents was filtered through tightly packed Celite. Upon concentration, the crude material was purified by silica gel chromatography to afford tert-butyl 3-isopropyl-5-(1,4-dioxaspiro[4.5]decan-8-yl)-1H-pyrrolo[3,2-b]pyridine-1-carboxylate (67.00 g, 167.0 mmol, 83% yield) as a yellow oil. LCMS retention time 1.86 min [DDS2]. MS m/z: 401.4 (M+H). ¹H NMR (400 MHz, DMSO-d₆) δ 8.22-8.08 (m, 1H), 7.58-7.52 (m, 1H), 7.21-7.13 (m, 1H), 4.01 (d, J=7.0 Hz, 1H), 3.89-3.86 (m, 2H), 3.84 (s, 2H), 2.25-2.18 (m, 2H), 2.18-2.10 (m, 2H), 1.89-1.72 (m, 6H), 1.60 (s, 3H), 1.59-1.53 (m, 1H), 1.32 (d, J=7.0 Hz, 4H), 1.23-1.18 (m, 1H), 1.16-1.13 (m, 1H), 1.18-1.13 (m, 2H), 1.16-1.12 (m, 2H)

Intermediate 4E: tert-butyl 3-isopropyl-5-(1,4-dioxaspiro[4.5]decan-8-yl)-2-(4,4,5,5-tetramethyl-1,3,2-dioxaborolan-2-yl)-1H-pyrrolo[3,2-b]pyridine-1-carboxylate

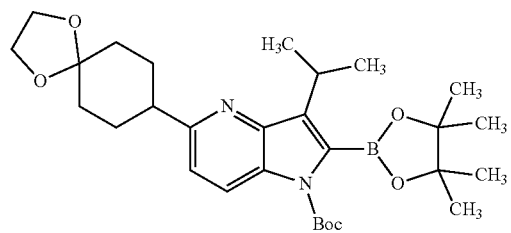

(4E)

In 1 L round bottom flask was added tert-butyl 3-isopropyl-5-(1,4-dioxaspiro[4.5]decan-8-yl)-1H-pyrrolo[3,2-b]pyridine-1-carboxylate (45 g, 112 mmol) in tetrahydrofuran (675 mL) under a nitrogen atmosphere. The reaction mixture was cooled in a dry ice/acetone bath to −78° C. To this was added slowly LDA (112 mL, 225 mmol) and the mixture was stirred at −78° C. for 45-50 min. 2-isopropoxy-4,4,5,5-tetramethyl-1,3,2-dioxaborolane (34.5 mL, 169 mmol) was added and the reaction mixture was stirred at the same temperature for 1-2 hours. The reaction was quenched with saturated aqueous KH₂PO₄ solution at the same temperature, then water and ethyl acetate were added and the mixture was transferred to a separatory funnel. The layers were separated and the combined organics were washed with brine, dried over anhydrous sodium sulfate, filtered and concentrated. The crude product was further purified by silica gel chromatography to afford tert-butyl 3-isopropyl-5-(1,4-dioxaspiro[4.5]decan-8-yl)-2-(4,4,5,5-tetramethyl-1,3,2-dioxaborolan-2-yl)-1H-pyrrolo[3,2-b]pyridine-1-carboxylate (35.0 g, 66.5 mmol, 60% yield). LCMS retention time 2.05 min [DDS2]. MS m/z: 527.5 (M+H).

Intermediate 4C: 3-isopropyl-5-(1,4-dioxaspiro[4.5]decan-8-yl)-2-(4,4,5,5-tetramethyl-1,3,2-dioxaborolan-2-yl)-1H-pyrrolo[3,2-b]pyridine

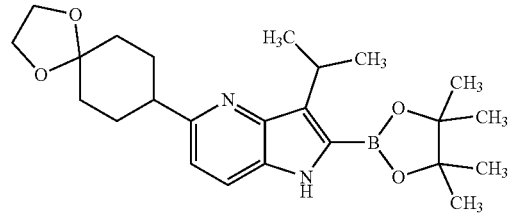

(4C)

tert-Butyl 3-isopropyl-5-(1,4-dioxaspiro[4.5]decan-8-yl)-2-(4,4,5,5-tetramethyl-1,3,2-dioxaborolan-2-yl)-1H-pyrrolo[3,2-b]pyridine-1-carboxylate (35 g, 66.5 mmol) was added to a 500 mL round bottom flask. The reaction mixture was pump/purged three times with nitrogen gas and set to heat at 150° C. under a nitrogen atmosphere for 7-8 hours. The reaction mixture was cooled to room temperature, then 200 mL petroleum ether was added and distilled completely. The solid was washed with ether and dried for 1-2 hours to afford 3-isopropyl-5-(1,4-dioxaspiro[4.5]decan-8-yl)-2-(4,4,5,5-tetramethyl-1,3,2-dioxaborolan-2-yl)-1H-pyrrolo[3,2-b]pyridine (23.0 g, 54.0 mmol, 81% yield) as a yellow solid. LCMS retention time 1.47 min [DDS2]. MS m/z: 427.5 (M+H). ¹H NMR (499 MHz, CHLOROFORM-d) δ 8.25 (br s, 1H), 7.52 (d, J=8.6 Hz, 1H), 7.05 (d, J=8.6 Hz, 1H), 4.03 (t, J=2.6 Hz, 4H), 3.83-3.71 (m, 1H), 2.98-2.86 (m, 1H), 2.13-1.90 (m, 6H), 1.79 (br s, 2H), 1.56 (d, J=6.9 Hz, 6H), 1.39 (s, 12H).

Intermediate 4F: 6-(3-isopropyl-5-(1,4-dioxaspiro[4.5]decan-8-yl)-1H-pyrrolo[3,2-b]pyridin-2-yl)-7,8-dimethyl-[1,2,4]triazolo[1,5-a]pyridine

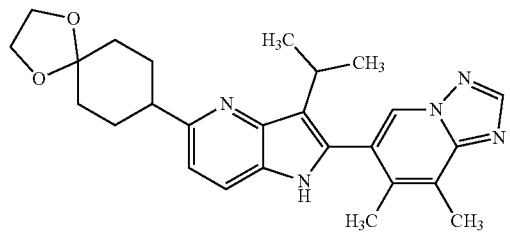

(4F)

In a 1 L sealed tube, 3-isopropyl-5-(1,4-dioxaspiro[4.5]decan-8-yl)-2-(4,4,5,5-tetramethyl-1,3,2-dioxaborolan-2-yl)-1H-pyrrolo[3,2-b]pyridine (22.5 g, 52.8 mmol), and 6-bromo-7,8-dimethyl-[1,2,4]triazolo[1,5-a]pyridine (11.93 g, 52.8 mmol) were dissolved in tetrahydrofuran (225 mL) and water (22.5 mL). Potassium phosphate tribasic (33.6 g, 158 mmol) was added, then the mixture was purged with nitrogen gas for 5 minutes. 1,1'-bis(di-tert-butylphosphino)ferrocene palladium dichloride (1.720 g, 2.64 mmol) was added and the reaction mixture was heated to 70° C. for 2-3 hours. Following cooling to room temperature, the mixture was diluted with ethyl acetate and washed with water, then brine and dried over anhydrous sodium sulfate. The solids were filtered and the filtrate was concentrated. The residue was further purified by silica gel chromatography to afford 6-(3-isopropyl-5-(1,4-dioxaspiro[4.5]decan-8-yl)-1H-pyrrolo[3,2-b]pyridin-2-yl)-7,8-dimethyl-[1,2,4]triazolo[1,5-a]pyridine (19.0 g, 42.6 mmol, 81% yield) as an off-white solid. LCMS retention time 1.70 min [DDS2]. MS m/z: 446.6 (M+H). $^1$H NMR (300 MHz, DMSO-$d_6$) δ 11.04 (s, 1H), 8.80 (s, 1H), 8.48 (s, 1H), 7.60 (d, J=8.6 Hz, 1H), 7.01 (d, J=8.6 Hz, 1H), 3.91 (t, J=2.8 Hz, 4H), 3.09-3.08 (m, 1H), 2.97-2.74 (m, 2H), 2.60 (s, 3H), 2.18 (s, 3H), 1.97-1.77 (m, 5H), 1.75-1.58 (m, 2H), 1.41 (d, J=6.9 Hz, 6H) Intermediate 4D: 4-(2-(7,8-dimethyl-[1,2,4]triazolo[1,5-a]pyridin-6-yl)-3-isopropyl-1H-pyrrolo[3,2-b]pyridin-5-yl)cyclohexan-1-one

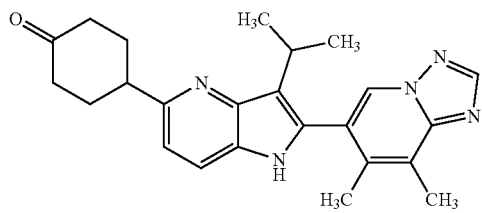

(4D)

In a 1 L sealed tube, 6-(3-isopropyl-5-(1,4-dioxaspiro[4.5]decan-8-yl)-1H-pyrrolo[3,2-b]pyridin-2-yl)-7,8-dimethyl-[1,2,4]triazolo[1,5-a]pyridine (36 g, 81 mmol) was mixed in tetrahydrofuran (660 mL). Next, HCl (101 mL, 1212 mmol) was added and the mixture was stirred at room temperature for 18 hours. To the reaction mixture was added saturated potassium phosphate solution to pH=8 and ethyl acetate (500 mL×2). The mixture was poured into a separatory funnel and the layers were separated. The organics were washed with brine, dried over anhydrous sodium sulfate, filtered and concentrated. The crude material was treated with petroleum ether (200 mL) and stirred for 15 minutes. The filter cake was washed with additional petroleum ether and dried to afford 4-(2-(7,8-dimethyl-[1,2,4]triazolo[1,5-a]pyridin-6-yl)-3-isopropyl-1H-pyrrolo[3,2-b]pyridin-5-yl)cyclohexan-1-one (30.0 g, 74.8 mmol, 92% yield) as an off-white solid. LCMS retention time 1.53 min [DDS2]. MS m/z: 402.4 (M+H). $^1$H NMR (400 MHz, DMSO-$d_6$) δ 11.12-10.98 (m, 1H), 8.78 (s, 1H), 8.47 (s, 1H), 7.58 (d, J=8.5 Hz, 1H), 6.98 (d, J=8.5 Hz, 1H), 4.31 (s, 4H), 2.97-2.81 (m, 1H), 2.59 (s, 2H), 2.17 (s, 3H), 2.13-2.00 (m, 1H), 1.97-1.76 (m, 4H), 1.72-1.53 (m, 2H), 1.39 (d, J=6.5 Hz, 3H), 1.18-0.98 (m, 2H)

Example 438

To a 2 L round bottom flask was added 4-(2-(7,8-dimethyl-[1,2,4]triazolo[1,5-a]pyridin-6-yl)-3-isopropyl-1H-pyrrolo[3,2-b]pyridin-5-yl)cyclohexan-1-one (29 g, 72.2 mmol), 2-thia-6-azaspiro[3.3]heptane 2,2-dioxide hydrochloride (19.90 g, 108 mmol), DCM (435 mL) and acetic acid (0.413 mL, 7.22 mmol). To this was added DBU (32.7 mL, 217 mmol) and the reaction mixture was stirred for 18 hours at room temperature. The volatiles were removed under reduced pressure and the resulting residue was dissolved in methanol (435 mL). The mixture was cooled to −78° C. and to this was added lithium borohydride (54.2 mL, 217 mmol) via syringe over 30-40 minutes. The reaction was stirred at −78° C. for 2 hours. The reaction mixture was allowed to warm to room temperature and was quenched with a saturated potassium phosphate solution. This was diluted with water (150 mL), extracted with ethyl acetate (300 mL×3), dried over anhydrous sodium sulfate, filtered and concentrated. The crude material was taken into 100 mL of IPA and stirred for 30-40 minutes at 50° C. The mixture was cooled to room temperature, filtered, and washed with 20 mL of IPA to give an off-white solid containing 90% of the trans product. Further purification was performed by preparative SFC using the following conditions: Sample preparation: 18 g of crude material; Column: Lux Cellulose-4 (250×4.6) mm 5 μm; temperature=30° C.; BPR pressure: 100 bar; mobile Phase: 0.2% NH$_{40}$H in ACN:MeOH (1:1); Injection: 10 mL; Detector Wavelength: 220 nm. The fractions containing product were concentrated and further purified using the following procedure: This material was then trapped with (methanol, THF, acetonitrile) and the solid was taken into 30% aqueous IPA 60 mL (18 mL water: 48 mL IPA), then heated to 70° C. for 1 hour. The mixture was brought to room temperature, filtered, washed with IPA (20 mL) and dried for 10-12 hours to afford 6-((r,4r)-(4-(2-(7,8-dimethyl-[1,2,4]triazolo[1,5-a]pyridin-6-yl)-3-isopropyl-1H-pyrrolo[3,2-b]pyridin-5-yl)cyclohexyl)-2-thia-6-azaspiro[3.3]heptane 2,2-dioxide (16.0 g, mmol, 41.4% yield)) as a white solid. LCMS retention time 1.31 min [DDS2]. MS m/z: 533.4 (M+H). $^1$H NMR (499 MHz, DMSO-$d_6$) δ 11.16-11.02 (m, 1H), 8.80 (s, 1H), 8.48 (s, 1H), 7.59 (d, J=8.2 Hz, 1H), 6.99 (d, J=8.5 Hz, 1H), 4.32 (s, 4H), 4.10 (q, J=5.2 Hz, 1H), 3.17 (d, J=5.2 Hz, 3H), 2.88 (quin, J=6.9 Hz, 1H), 2.74-2.56 (m, 4H), 2.17 (s, 3H), 2.13-1.99 (m, 1H), 1.98-1.88 (m, 2H), 1.84 (br d, J=10.7 Hz, 2H), 1.71-1.55 (m, 2H), 1.40 (d, J=6.9 Hz, 6H), 1.19-0.97 (m, 2H).

Alternate synthesis of Intermediate 438A: 2-thia-6-azaspiro[3.3]heptane 2,2-dioxide hydrochloride

Intermediate 438B:
6-tosyl-2-oxa-6-azaspiro[3.3]heptane

(438A)

(438B)

KOH (276 g, 4926 mmol) was dissolved in ethanol (2.5 L) and to this solution was added 3-bromo-2,2-bis(bromomethyl)propan-1-ol(500 g, 1539 mmol) and 4-methylbenzenesulfonamide (316 g, 1847 mmol). The reaction mixture was heated to 85° C. for 2 days, then cooled to room temperature and to this was added 8% sodium hydroxide solution (2.5 L). The mixture was stirred for 2 hours and a white solid was filtered off. The collected solid was stirred in water (1 L) and filtered. This process was repeated 3 times. The solid was then stirred with methanol (1 L), filtered and dried through air to afford 6-tosyl-2-oxa-6-azaspiro[3.3]heptane (250 g, 984 mmol, 64% yield) as an off-white solid. LCMS retention time 1.16 min [DDS2]. MS m/z: 254.2 (M+H)

Intermediate 438C:
(3-(bromomethyl)-1-tosylazetidin-3-yl)methanol

(438C)

To a suspension of 6-tosyl-2-oxa-6-azaspiro[3.3]heptane (240 g, 947 mmol) in diethyl ether (2.5 L) at 0° C. was added a solution of hydrobromic acid in acetic acid (171 mL, 1042 mmol) in diethyl ether (1.5 L) drop-wise. The resulting solution was stirred at 0° C. for 30 minutes, warmed to room temperature and stirred for an additional 2 hours. To this was added a 10% sodium bicarbonate solution until pH=8 was reached. MTBE was added and the phases were separated. The aqueous phase was extracted with ethyl acetate, and the combined organics were washed with water and then brine, then dried over anhydrous sodium sulfate, filtered and concentrated in vaccuo to afford the (3-(bromomethyl)-1-tosylazetidin-3-yl)methanol (302 g, 904 mmol, 95% yield) as a white solid. LCMS retention time 1.34 min [DDS2]. MS m/z: 334.1/336.1 (M+H). $^1$H NMR (300 MHz, CHLOROFORM-d) δ 7.83-7.64 (m, 2H), 7.47-7.32 (m, 2H), 3.69 (d, J=5.0 Hz, 2H), 3.65-3.59 (m, 2H), 3.58-3.52 (m, 2H), 3.46 (s, 2H), 2.48 (s, 3H), 1.71 (t, J=5.0 Hz, 1H).

Intermediate 438D:
3,3-bis(bromomethyl)-1-tosylazetidine

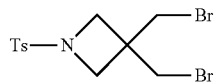

(438D)

In a 1 L round bottom flask, (3-(bromomethyl)-1-tosylazetidin-3-yl)methanol (54 g, 162 mmol) was dissolved in DCM (540 mL) and carbon tetrabromide (86 g, 259 mmol) was added. The solution was cooled in an ice bath and triphenylphosphine (67.8 g, 259 mmol) was added portionwise. The resulting mixture was warmed to 25° C. and stirred for 18 hours. The reaction mixture was concentrated and ethyl acetate was added and the mixture was stirred for 10 minutes, then a white solid was filtered off. The filtrate was concentrated under reduced pressure and purified by silica gel chromatography to afford 3,3-bis(bromomethyl)-1-tosylazetidine (50 g, 126 mmol, 78% yield) as a white solid. LCMS retention time 1.87 min [DDS2]. MS m/z: 398.1 (M+H). $^1$H NMR (400 MHz, CHLOROFORM-d) δ 7.81-7.70 (m, 2H), 7.42 (d, J=8.0 Hz, 2H), 3.61 (s, 4H), 3.55 (s, 4H), 2.50 (s, 3H).

Intermediate 438E:
6-tosyl-2-thia-6-azaspiro[3.3]heptane

(438E)

To a solution of 3,3-bis(bromomethyl)-1-tosylazetidine (35 g, 88 mmol) in a mixture of acetonitrile (350 mL) and water (35 mL) was added sodium sulfide nonahydrate (106 g, 441 mmol) and the reaction mixture was stirred at 50° C. for 3 hours. The reaction mixture was concentrated under reduced pressure and diluted with EtOAc and water. The phases were separated and the aqueous phase was extracted with EtOAc. The combined organics were washed with brine, dried over anhydrous sodium sulfate, filtered, and concentrated to give 6-tosyl-2-thia-6-azaspiro[3.3]heptane (21 g, 78 mmol, 88% yield) as a white solid LCMS retention time 1.56 min [DDS2]. MS m/z: 270.1 (M+H). $^1$H NMR (300 MHz, CHLOROFORM-d) δ 7.76-7.68 (m, 2H), 7.37 (d, J=7.9 Hz, 2H), 3.78 (s, 4H), 3.14 (s, 4H), 2.46 (s, 3H).

Intermediate 438F:
6-tosyl-2-thia-6-azaspiro[3.3]heptane 2,2-dioxide

(438F)

To a 4 L flask was added 6-tosyl-2-thia-6-azaspiro[3.3]heptane (175 g, 650 mmol) and DCM (2.75 L). The mixture was cooled to 0° C. and mCPBA (320 g, 1299 mmol) was added over 30 minutes, then the reaction mixture was warmed to 25° C. and stirred for 3 hours. The mixture was diluted with DCM and washed with a 5% NaOH solution (3×1 L). The combined organics were washed with water and brine, then dried over anhydrous sodium sulfate, filtered and concentrated. The crude material was purified by silica gel chromatography to afford 6-tosyl-2-thia-6-azaspiro[3.3] heptane 2,2-dioxide (135 g, 449 mmol, 69% yield) as a white solid. LCMS retention time 1.16 min [DDS2]. MS m/z: 302.1 (M+H). $^1$H NMR (300 MHz, CHLOROFORM-d) δ 7.79-7.66 (m, 2H), 7.40 (d, J=7.9 Hz, 2H), 4.12 (s, 4H), 3.97 (s, 4H), 2.47 (s, 3H).

Intermediate 438A: 2-thia-6-azaspiro[3.3]heptane 2,2-dioxide hydrochloride

(438A)

6-tosyl-2-thia-6-azaspiro[3.3]heptane 2,2-dioxide (40 g, 133 mmol) and magnesium (32.3 g, 1327 mmol) were taken in dry methanol (1600 mL) and heated to 50° C. for 18 hours. The mixture was cooled to room temperature and stirred for an additional 18 hours. To this was added sodium sulfate decahydrate (428 g, 1327 mmol) and DCM (2 L) and the mixture was stirred for 1 hour and filtered. The solid was suspended in DCM (2 L), stirred and the suspension was filtered. The combined filtrate was concentrated to near dryness. Residual water was evaporated and the resulting solid was taken in DCM (200 mL). The suspension was filtered through sodium sulfate and the filtrate collected. To this was added 4M HCl in dioxane (25 mL) and the resulting solid was filtered and washed with DCM to afford 2-thia-6-azaspiro[3.3]heptane 2,2-dioxide HCl (15.2 g, 65% yield) as a white solid. $^1$H NMR (499 MHz, DMSO-$d_6$) δ 9.47-9.16 (m, 2H), 4.50 (s, 4H), 4.30-4.09 (m, 4H).

Example 491

6-(3-isopropyl-5-(2-azaspiro[3.5]nonan-7-yl)-1H-pyrrolo[3,2-b]pyridin-2-yl)-7,8-dimethyl-[1,2,4]triazolo[1,5-a]pyridine

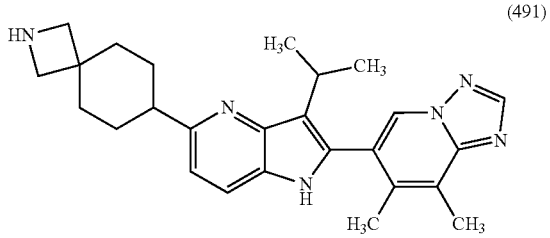 [SMILES: Cc1c(-c2[nH]c3ccc(C4CCC5(CC4)CNC5)nc3c2C(C)C)cn2ncnc2c1C]
(491)

Intermediate 491A: 5-chloro-3-isopropyl-2-(4,4,5,5-tetramethyl-1,3,2-dioxaborolan-2-yl)-1H-pyrrolo[3,2-b]pyridine

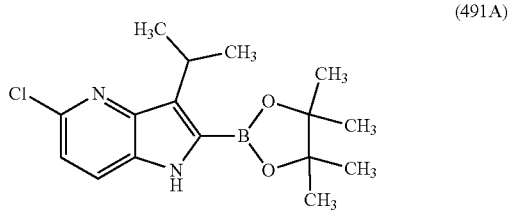 [SMILES: CC(C)c1c(B2OC(C)(C)C(C)(C)O2)[nH]c2ccc(Cl)nc12]
(491A)

tert-Butyl 5-chloro-3-isopropyl-1H-pyrrolo[3,2-b]pyridine-1-carboxylate was prepared according to the general method described above for Intermediate 1C. A solution containing tert-butyl 5-chloro-3-isopropyl-1H-pyrrolo[3,2-b]pyridine-1-carboxylate (3.00 g, 10.18 mmol) and 2-isopropoxy-4,4,5,5-tetramethyl-1,3,2-dioxaborolane (3.11 mL, 15.27 mmol) in dry THF (25 mL), under a nitrogen atmosphere, was cooled in a dry ice/acetone bath at −78° C. and treated with LDA (2M in TIF) (6.36 mL, 12.72 mmol). The mixture was stirred at −78° C. for 30 minutes and allowed to warm to −30° C. over 1 hour and stirred at −30° C. for 30 minutes. The reaction mixture was treated with 1.5 M aqueous $KH_2PO_4$ solution, water and DCM. The organic layer was collected, dried over anhydrous sodium sulfate, filtered and concentrated. The crude product was purified by silica gel chromatography to afford tert-butyl 5-chloro-3-isopropyl-2-(4,4,5,5-tetramethyl-1,3,2-dioxaborolan-2-yl)-1H-pyrrolo[3,2-b]pyridine-1-carboxylate. LCMS retention time 1.31 min [Method A]. MS m/z: 420.8/422.3 (M+H). This material was transferred to a 40 mL vial and flushed with nitrogen gas. The mixture was sealed and was heated at 160° C. for 1.5 hours to afford 5-chloro-3-isopropyl-2-(4,4,5,5-tetramethyl-1,3,2-dioxaborolan-2-yl)-1H-pyrrolo[3,2-b] pyridine (2.4 g, 7.49 mmol, 74% yield) as a tan solid. LCMS retention time 1.16 min [Method A]. MS m/z: 321.1/323.1 (M+H).

Intermediate 491B: tert-butyl 5-chloro-2-(7,8-dimethyl-[1,2,4]triazolo[1,5-a]pyridin-6-yl)-3-isopropyl-1H-pyrrolo[3,2-b]pyridine-1-carboxylate

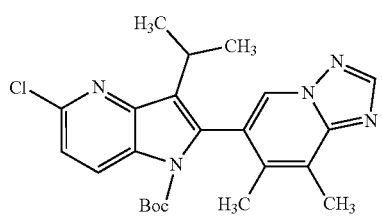
(491B)

In a 40 mL reaction vial was added 5-chloro-3-isopropyl-2-(4,4,5,5-tetramethyl-1,3,2-dioxaborolan-2-yl)-1H-pyrrolo [3,2-b]pyridine (1.000 g, 3.12 mmol), 1,1'-bis(di-tert-butylphosphino)ferrocene palladium dichloride (0.041 g, 0.062 mmol)$_6$-bromo-7,8-dimethyl-[1,2,4]triazolo[1,5-a] pyridine (0.705 g, 3.12 mmol) and THF (40 mL). The reaction was sealed and pump/purged three times with nitrogen gas. To this was added aqueous potassium phosphate, tribasic (2M, 4.68 mL, 9.36 mmol) and the reaction was heated to 65° C. for 1 hour. The mixture was diluted with ethyl acetate and washed with water, then brine and dried over anhydrous sodium sulfate. The solids were filtered off and the filtrate was concentrated. The crude material was purified by silica gel chromatography to give 6-(5-chloro-3-isopropyl-1H-pyrrolo[3,2-b]pyridin-2-yl)-7,8-dimethyl-[1,2,4]triazolo[1,5-a]pyridine as a tan/brown solid. To this was added THF (100 mL) and BOC-anhydride (0.724 mL, 3.12 mmol). A crystal of DMAP was added and the reaction was capped and stirred for 18 hours at 25° C., then concentrated under reduced pressure. To this residue was added DCM and water and the mixture was transferred to a separatory funnel. The layers were separated and the combined organics were washed with brine, dried over anhydrous sodium sulfate, filtered and concentrated to afford 5a: tert-butyl 5-chloro-2-(7,8-dimethyl-[1,2,4]triazolo[1,5-a]pyridin-6-yl)-3-isopropyl-1H-pyrrolo[3,2-b]pyridine-1-carboxylate (0.9 g, 2.046 mmol, 65% yield). LCMS retention time 1.17 min [Method A]. MS m/z: 440.1 (M+H)

Example 491

To a solution of tert-butyl 5-chloro-2-(7,8-dimethyl-[1,2,4]triazolo[1,5-a]pyridin-6-yl)-3-isopropyl-1H-pyrrolo[3,2-b]pyridine-1-carboxylate (0.20 g, 0.455 mmol), tert-butyl 7-(4,4,5,5-tetramethyl-1,3,2-dioxaborolan-2-yl)-2-azaspiro[3.5]non-6-ene-2-carboxylate (0.119 g, 0.341 mmol), and potassium phosphate, tribasic (0.682 mL, 1.364 mmol) in THF (300 mL) was added PdCl$_2$(dppf)-CH$_2$Cl$_2$ adduct (9.28 mg, 0.011 mmol) and the biphasic mixture was degassed with nitrogen for 10 minutes. The reaction vessel was sealed. The reaction mixture was stirred at 90° C. for 2 hours, then was diluted with ethyl acetate and washed with saturated sodium chloride solution. The organic layer was dried with magnesium sulfate, filtered and concentrated. The crude material was purified by silica gel chromatography to give tert-butyl 5-(2-(tert-butoxycarbonyl)-2-azaspiro[3.5]nonan-7-yl)-2-(7,8-dimethyl-[1,2,4]triazolo[1,5-a]pyridin-6-yl)-3-isopropyl-1H-pyrrolo[3,2-b]pyridine-1-carboxylate. LCMS retention time 1.114 min [Method A]. MS m/z: 629.5 (M+H). To 0.2 g of this intermediate, in a Parr bottle was added ethyl acetate (15 mL) and 10% Pd/C (0.015 g, 0.014 mmol) under a nitrogen atmosphere. The vessel was placed on the Parr apparatus and pump/purged three times with nitrogen gas. The vessel was then pressurized to 50 psi with hydrogen gas and shaken for 1 hour. The vessel was diluted with 100 mL of methanol and the contents was filtered through tightly packed Celite. Upon concentration 0.020 g of the crude residue was purified by preparative LC-MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 24 minutes, then a 5-minute hold at 100% B; Flow: 20 mL/min. Fractions containing the product were combined and dried via centrifugal evaporation to afford 6-(3-isopropyl-5-(2-azaspiro[3.5]nonan-7-yl)-1H-pyrrolo[3,2-b]pyridin-2-yl)-7,8-dimethyl-[1,2,4]triazolo[1,5-a]pyridine (6.0 mg, 0.0140 mmol); m/z (429.4, M+H). Retention time, 1.262 min using LCMS Column: Waters Acquity UPLC BEH C18, 2.1×50 mm, 1.7 m particles; Mobile Phase A: 5:95 acetonitrile:water with 10 mM ammonium acetate; Mobile Phase B: 95:5 acetonitrile:water with 10 mM. $^1$H NMR (500 MHz, DMSO-d$_6$) δ 11.12-11.08 (m, 1H), 8.77 (s, 1H), 8.48 (s, 1H), 7.61 (d, J=8.2 Hz, 1H), 7.01 (d, J=8.2 Hz, 1H), 3.61-3.39 (m, 1H), 2.89 (br t, J=6.9 Hz, 1H), 2.70 (br s, 1H), 2.59 (s, 3H), 2.55 (s, 5H), 2.17 (s, 3H), 2.14-2.03 (m, 2H), 1.91-1.75 (m, 6H), 1.68-1.50 (m, 4H), 1.39 (br d, J=6.7 Hz, 6H).

Example 590

6-(3-isopropyl-5-((1-methylpiperidin-4-yl)methoxy)-1H-pyrrolo[3,2-b]pyridin-2-yl)-8-methoxy-[1,2,4]triazolo[1,5-a]pyridine

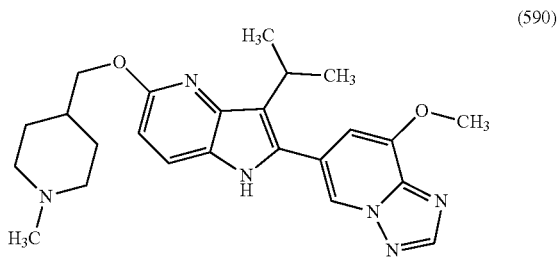 [SMILES: COc1cc(-c2[nH]c3ccc(OCC4CCN(C)CC4)nc3c2C(C)C)cn2ncnc12]

(590)

To a 1 dram vial with pressure relief septum was added 6-(3-isopropyl-5-(piperidin-4-ylmethoxy)-1H-pyrrolo[3,2-b]pyridin-2-yl)-8-methoxy-[1,2,4]triazolo[1,5-a]pyridine, 2 TFA (15 mg, 0.023 mmol), DMF (1 mL), and DIEA (4.04 µL, 0.023 mmol). Formaldehyde (37% in water) (8.61 µL, 0.116 mmol) was added. The reaction mixture was stirred at room temperature for 10 minutes. To the reaction mixture was added acetic acid (1.324 µL, 0.023 mmol) and sodium triacetoxyborohydride (4.90 mg, 0.023 mmol). The reaction mixture was stirred at room temperature overnight. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-100% B over 19 minutes, then a 5-minute hold at 100% B; Flow: 20 mL/min. Fractions containing the product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 14-39% B over 25 minutes, then a 2-minute hold at 39% B; Flow: 20 mL/min. Fractions containing the product were combined and dried via centrifugal evaporation. LC/MS was used to analyze the final compound. Injection 1 conditions: Column: Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 435.39 (M+H); Retention Time: 1.17 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 435.43 (M+H); Retention Time: 0.94 min. Isolated 6-(3-isopropyl-5-((1-methylpiperidin-4-yl)methoxy)-1H-pyrrolo[3,2-b]pyridin-2-yl)-8- methoxy-[1,2,4]triazolo[1,5-a]pyridine (5.9 mg, 0.013 mmol, 56.9% yield). $^1$H NMR (500 MHz, DMSO-$d_6$) δ 11.30-11.25 (m, 1H), 8.51 (s, 1H), 8.46 (s, 1H), 7.69 (d, J=8.9 Hz, 1H), 7.12 (s, 1H), 6.58 (d, J=8.9 Hz, 1H), 4.20-4.14 (m, 2H), 4.04 (s, 1H), 3.63-3.51 (m, 1H), 3.30-3.20 (m, 2H), 3.03 (br d, J=11.6 Hz, 2H), 2.37-2.28 (m, 4H), 1.81 (br d, J=11.0 Hz, 4H), 1.52-1.46 (m, 6H), 1.45-1.35 (m, 2H).

Example 591

6-(3-isopropyl-5-((1-(tetrahydro-2H-pyran-4-yl)piperidin-4-yl)methoxy)-1H-pyrrolo[3,2-b]pyridin-2-yl)-8-methoxy-[1,2,4]triazolo[1,5-a]pyridine

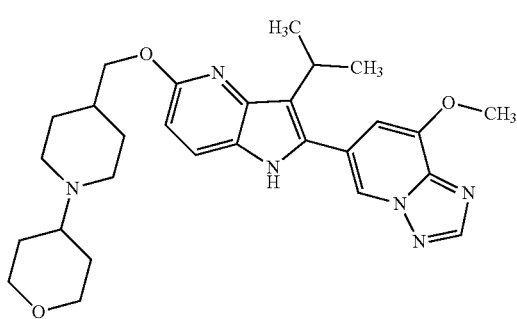

(591)

To a 1 dram vial containing 6-(3-isopropyl-5-(piperidin-4-ylmethoxy)-1H-pyrrolo[3,2-b]pyridin-2-yl)-8-methoxy-[1,2,4]triazolo[1,5-a]pyridine, 2 TFA (15 mg, 0.023 mmol) was added DMF (0.5 mL), DIEA (0.012 mL, 0.069 mmol), and dihydro-2H-pyran-4(3H)-one (2.316 mg, 0.023 mmol). The reaction mixture was stirred for 5 minutes. Sodium triacetoxyborohydride (14.71 mg, 0.069 mmol) and acetic acid (1.324 μL, 0.023 mmol) were added, and the reaction mixture was stirred for 6 hours. The crude material was purified via preparative LC/MS with the following conditions: Column: Xbridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 19 minutes, then a 5-minute hold at 100% B; Flow: 20 mL/min. Fractions containing the product were combined and dried via centrifugal evaporation. LC/MS was used to analyze the final compound. Injection 1 conditions: Column: Waters Xbridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 505.53 (M+H); Retention Time: 1.23 min. Injection 2 conditions: Column: Waters Xbridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 505.52 (M+H); Retention Time: 1 min. Isolated 6-(3-isopropyl-5-((1-(tetrahydro-2H-pyran-4-yl)piperidin-4-yl)methoxy)-1H-pyrrolo[3,2-b]pyridin-2-yl)-8-methoxy-[1,2,4]triazolo[1,5-a]pyridine (10.8 mg, 0.021 mmol, 89% yield). $^1$H NMR (500 MHz, DMSO-$d_6$) δ 11.29 (s, 1H), 8.59 (s, 1H), 8.50 (s, 1H), 7.67 (d, J=8.9 Hz, 1H), 7.17 (s, 1H), 6.57 (d, J=8.5 Hz, 1H), 4.17 (br d, J=6.4 Hz, 2H), 4.07 (s, 3H), 3.89-3.82 (m, 2H), 3.29-3.22 (m, 2H), 2.91 (br d, J=10.4 Hz, 2H), 2.09 (br t, J=11.1 Hz, 2H), 1.90 (s, 2H), 1.82-1.71 (m, 3H), 1.66 (br d, J=12.5 Hz, 2H), 1.54-1.50 (m, 6H), 1.41 (qd, J=12.0, 4.7 Hz, 2H), 1.33-1.21 (m, 2H).

Example 592

6-(3-isopropyl-5-((1-isopropylazetidin-3-yl)methoxy)-1H-pyrrolo[3,2-b]pyridin-2-yl)-8-methoxy-[1,2,4]triazolo[1,5-a]pyridine

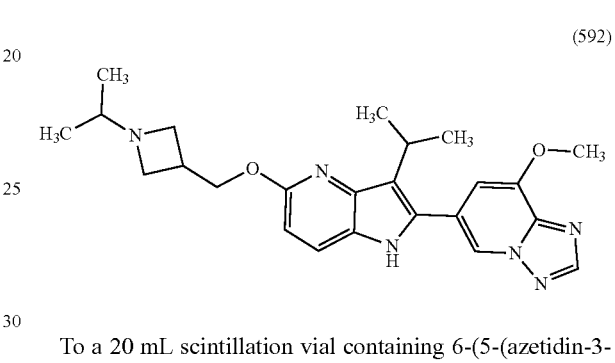

(592)

To a 20 mL scintillation vial containing 6-(5-(azetidin-3-ylmethoxy)-3-isopropyl-1H-pyrrolo[3,2-b]pyridin-2-yl)-8-methoxy-[1,2,4]triazolo[1,5-a]pyridine (15 mg, 0.038 mmol) was added DMF (1 mL) and propan-2-one (2.220 mg, 0.038 mmol). The reaction mixture was stirred at room temperature for 10 minutes. Acetic acid (2.188 μL, 0.038 mmol) and sodium triacetoxyborohydride (24.30 mg, 0.115 mmol) were added and the reaction mixture was stirred at room temperature overnight. A drop of water was added, and the crude material was purified via preparative LC/MS with the following conditions: Column: Xbridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 22 minutes, then a 4-minute hold at 100% B; Flow: 20 mL/min. Fractions containing the product were combined and dried via centrifugal evaporation. LC/MS was used to analyze the final compound. Injection 1 conditions: Column: Waters Xbridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 435.24 (M+H); Retention Time: 1.27 min. Injection 2 conditions: Column: Waters Xbridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 435.21 (M+H); Retention Time: 1.08 min. Isolated 6-(3-isopropyl-5-((1-isopropylazetidin-3-yl)methoxy)-1H-pyrrolo[3,2-b]pyridin-2-yl)-8-methoxy-[1,2,4]triazolo[1,5-a]pyridine (5.4 mg, 0.012 mmol, 31.5% yield). $^1$H NMR (500 MHz, DMSO-$d_6$)

δ 11.32 (s, 1H), 8.57 (s, 1H), 8.50 (s, 1H), 7.68 (d, J=8.9 Hz, 1H), 7.17 (s, 1H), 6.57 (d, J=8.5 Hz, 1H), 4.41 (br d, J=6.7 Hz, 2H), 4.06 (s, 3H), 3.33-3.19 (m, 3H), 2.98 (br t, J=6.7 Hz, 2H), 2.81-2.70 (m, 1H), 2.36-2.25 (m, 1H), 1.56-1.48 (m, 6H), 0.86-0.81 (m, 6H).

Example 593

6-(3-isopropyl-5-((1-propylpiperidin-4-yl)oxy)-1H-pyrrolo[3,2-b]pyridin-2-yl)-8-methoxy-[1,2,4]triazolo[1,5-a]pyridine

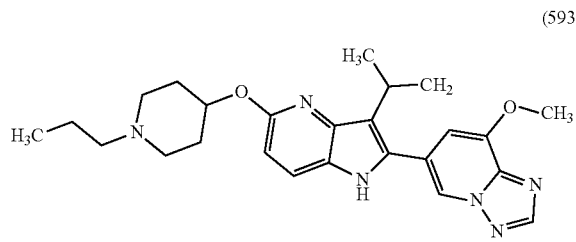

(593)

To a 1 dram vial containing 6-(3-isopropyl-5-(piperidin-4-yloxy)-1H-pyrrolo[3,2-b]pyridin-2-yl)-8-methoxy-[1,2,4]triazolo[1,5-a]pyridine, 2 TFA (15 mg, 0.024 mmol) was added DMF (500 µL), DIEA (12.39 µL, 0.071 mmol), and propionaldehyde (4.12 mg, 0.071 mmol). The reaction mixture was stirred at room temperature for 5 minutes. Acetic acid (1.353 µL, 0.024 mmol) and sodium triacetoxyborohydride (15.03 mg, 0.071 mmol) were added to the reaction mixture. The reaction mixture was stirred for 1 hour. The crude material was purified via preparative LC/MS with the following conditions: Column: Xbridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 19 minutes, then a 5-minute hold at 100% B; Flow: 20 mL/min. Fractions containing the product were combined and dried via centrifugal evaporation. LC/MS was used to analyze the final compound. Injection 1 conditions: Column: Waters Xbridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 448.94 (M+H); Retention Time: 1.3 min. Injection 2 conditions: Column: Waters Xbridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 449.05 (M+H); Retention Time: 1.05 min. Isolated 6-(3-isopropyl-5-((1-propylpiperidin-4-yl)oxy)-1H-pyrrolo[3,2-b]pyridin-2-yl)-8-methoxy-[1,2,4]triazolo[1,5-a]pyridine (8.6 mg, 0.019 mmol, 79% yield). $^1$H NMR (500 MHz, DMSO-d$_6$) δ 11.29 (s, 1H), 8.58 (s, 1H), 8.51 (s, 1H), 7.67 (d, J=8.5 Hz, 1H), 7.18 (s, 1H), 6.55 (d, J=8.9 Hz, 1H), 5.05-4.93 (m, 1H), 4.08 (s, 3H), 3.31-3.19 (m, 1H), 2.77 (br s, 2H), 2.27 (br t, J=7.3 Hz, 2H), 2.19 (br t, J=9.8 Hz, 2H), 2.12-2.03 (m, 2H), 1.75-1.64 (m, 2H), 1.51 (s, 6H), 1.48-1.41 (m, 2H), 0.86 (t, J=7.2 Hz, 3H).

Example 594

6-(3-isopropyl-5-((1-methylpiperidin-4-yl)oxy)-1H-pyrrolo[3,2-b]pyridin-2-yl)-8-methyl-[1,2,4]triazolo[1,5-a]pyridine

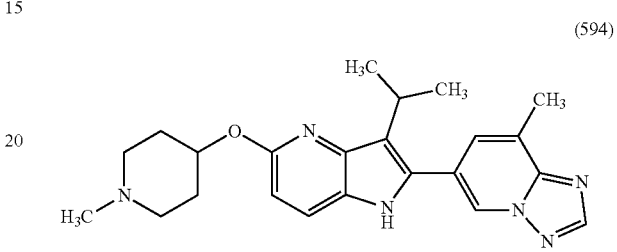

(594)

To a 1 dram vial containing 6-(3-isopropyl-5-(piperidin-4-yloxy)-1H-pyrrolo[3,2-b] pyridin-2-yl)-8-methyl-[1,2,4]triazolo[1,5-a]pyridine, 2 TFA (27 mg, 0.044 mmol) was added DMF (0.5 mL), DIEA (0.023 mL, 0.131 mmol), and formaldehyde (0.016 mL, 0.218 mmol). The reaction mixture was stirred for 5 minutes. Acetic acid (2.499 µl, 0.044 mmol) and sodium triacetoxyborohydride (27.8 mg, 0.131 mmol) were added. The reaction mixture was stirred for 10 minutes. The material was dissolved in DMF (2 mL) and purified via preparative LC/MS with the following conditions: Column: Xbridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 4-minute hold at 100% B; Flow: 20 mL/min. Fractions containing the product were combined and dried via centrifugal evaporation. LC/MS was used to analyze the final compound. Injection 1 conditions: Column: Waters Xbridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 405.36 (M+H); Retention Time: 1.01 min. Injection 2 conditions: Column: Waters Xbridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 405.37 (M+H); Retention Time: 1.25 min. Isolated 6-(3-isopropyl-5-((1-methylpiperidin-4-yl)oxy)-1H-pyrrolo[3,2-b]pyridin-2-yl)-8-methyl-[1,2,4]triazolo[1,5-a]pyridine (0.8 mg, 1.879 µmol, 4.3% yield). $^1$H NMR (500 MHz, DMSO-d$_6$) δ 11.33 (br s, 1H), 8.85 (s, 1H), 8.54 (s, 1H), 7.67-7.61 (m, 2H), 6.53 (d, J=8.7 Hz, 1H), 4.99 (br s, 1H), 3.33-3.12 (m, 2H), 2.26-2.11 (m, 5H), 2.06 (br d, J=10.9 Hz, 2H), 1.76 (s, 4H), 1.74-1.65 (m, 2H), 1.54-1.44 (m, 6H).

Example 595

6-(3-isopropyl-5-((1-(tetrahydro-2H-pyran-4-yl)azetidin-3-yl)oxy)-1H-pyrrolo[3,2-b]pyridin-2-yl)-8-methoxy-[1,2,4]triazolo[1,5-a]pyridine

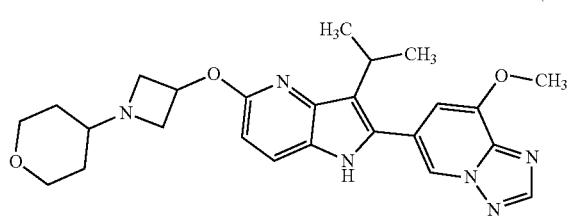

(595)

To a 1 dram vial containing 6-(5-(azetidin-3-yloxy)-3-isopropyl-H-pyrrolo[3,2-b]pyridin-2-yl)-8-methoxy-[1,2,4]triazolo[1,5-a]pyridine (10 mg, 0.026 mmol) was added DMF (1 mL), DIEA (0.014 mL, 0.079 mmol), and tetrahydro-4H-pyran-4-one (2.65 mg, 0.026 mmol). The reaction mixture was stirred for 5 minutes. Acetic acid (1.513 µL, 0.026 mmol) and sodium triacetoxyborohydride (28.0 mg, 0.132 mmol) were added and the reaction mixture was stirred for 1 hour. The crude material was purified via preparative LC/MS with the following conditions: Column: Xbridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 22 minutes, then a 5-minute hold at 100% B; Flow: 20 mL/min. Fractions containing the product were combined and dried via centrifugal evaporation. The material was further purified via preparative LC/MS with the following conditions: Column: Xbridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 20 minutes, then a 4-minute hold at 100% B; Flow: 20 mL/min. Fractions containing the product were combined and dried via centrifugal evaporation. LC/MS was used to analyze the final compound. Injection 1 conditions: Column: Waters Xbridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 463.0 (M+H); Retention Time: 1.45 min. Injection 2 conditions: Column: Waters Xbridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 463.4 (M+H); Retention Time: 1.09 min. Isolated 6-(3-isopropyl-5-((1-(tetrahydro-2H-pyran-4-yl)azetidin-3-yl)oxy)-1H-pyrrolo[3,2-b]pyridin-2-yl)-8-methoxy-[1,2,4]triazolo[1,5-a]pyridine, 2 TFA (2.8 mg, 3.95 µmol, 15% yield). $^1$H NMR (500 MHz, DMSO-$d_6$) δ 8.82 (s, 1H), 8.57 (s, 1H), 8.47 (d, J=8.9 Hz, 1H), 7.21 (d, J=8.9 Hz, 1H), 7.16 (s, 1H), 5.71 (br s, 1H), 5.41 (br t, J=10.3 Hz, 1H), 5.10-5.02 (m, 1H), 4.13-4.04 (m, 3H), 3.96-3.88 (m, 2H), 3.63-3.52 (m, 1H), 3.65-3.52 (m, 2H), 2.00-1.88 (m, 2H), 1.60-1.47 (m, 2H), 1.32 (dd, J=17.1, 7.1 Hz, 6H).

Example 596

6-(3-isopropyl-5-((1-methylazetidin-3-yl)oxy)-1H-pyrrolo[3,2-b]pyridin-2-yl)-8-methoxy-[1,2,4]triazolo[1,5-a]pyridine

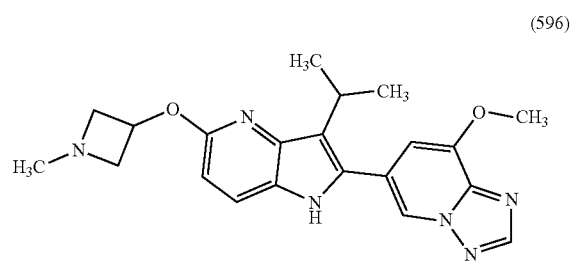

(596)

To a 1 dram vial containing 6-(5-(azetidin-3-yloxy)-3-isopropyl-1H-pyrrolo[3,2-b] pyridin-2-yl)-8-methoxy-[1,2,4]triazolo[1,5-a]pyridine (10 mg, 0.026 mmol) was added DMF (1 mL), formaldehyde (9.84 µL, 0.132 mmol) and DIEA (0.014 mL, 0.079 mmol). The reaction mixture was stirred at room temperature for 30 minutes and acetic acid (1.513 µL, 0.026 mmol) and sodium triacetoxyborohydride (28.0 mg, 0.132 mmol) were added to the reaction mixture. After 10 min, a drop of water was added and the crude material was purified via preparative LC/MS with the following conditions: Column: Xbridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 4-minute hold at 100% B; Flow: 20 mL/min. Fractions containing the product were combined and dried via centrifugal evaporation. LC/MS was used to analyze the final compound. Injection 1 conditions: Column: Waters Xbridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 393.08 (M+H); Retention Time: 1.01 min. Injection 2 conditions: Column: Waters Xbridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 393.22 (M+H); Retention Time: 1 min. Isolated 6-(3-isopropyl-5-((1-methylazetidin-3-yl)oxy)-1H-pyrrolo[3,2-b]pyridin-2-yl)-8-methoxy-[1,2,4]triazolo[1,5-a] pyridine (1.6 mg, 3.95 µmol, 15% yield). $^1$H NMR (500 MHz, DMSO-$d_6$) δ 11.38 (br s, 1H), 8.60 (s, 1H), 8.55-8.49 (m, 1H), 7.74-7.67 (m, 1H), 7.19 (s, 1H), 6.60 (br d, J=8.5 Hz, 1H), 5.16-5.07 (m, 1H), 4.09 (s, 3H), 3.82 (br t, J=6.1 Hz, 1H), 3.32-3.19 (m, 1H), 3.19-3.11 (m, 1H), 3.05-2.93 (m, 2H), 2.32 (s, 3H), 1.55-1.48 (m, 6H).

Example 597

1-(4-(((3-isopropyl-2-(8-methoxy-[1,2,4]triazolo[1,5-a]pyridin-6-yl)-1H-pyrrolo[3,2-b]pyridin-5-yl)oxy)methyl)piperidin-1-yl)-2-methylpropan-2-ol

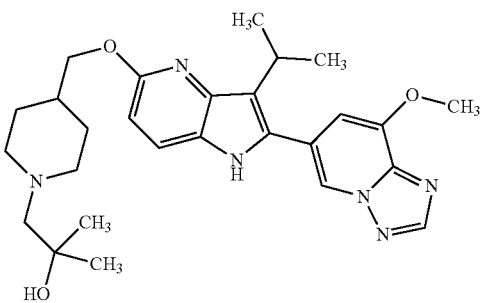

(597)

To a 1 dram vial containing 6-(3-isopropyl-5-(piperidin-4-ylmethoxy)-1H-pyrrolo[3,2-b]pyridin-2-yl)-8-methoxy-[1,2,4]triazolo[1,5-a]pyridine, 2 TFA (25 mg, 0.039 mmol) was added MeOH (500 μL), potassium carbonate (10.65 mg, 0.077 mmol), and 2,2-dimethyloxirane (8.34 mg, 0.116 mmol). The vial was sealed and the reaction mixture was stirred at room temperature overnight. The reaction mixture was filtered and concentrated under vacuum. The solid material was dissolved in DMF and the crude material was purified via preparative LC/MS with the following conditions: Column: Xbridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 19 minutes, then a 5-minute hold at 100% B; Flow: 20 mL/min. Fractions containing the product were combined and dried via centrifugal evaporation. LC/MS was used to analyze the final compound. Conditions: Column: Waters Xbridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 493.58 (M+H); Retention Time: 1.28 min. Isolated 1-(4-(((3-isopropyl-2-(8-methoxy-[1,2,4]triazolo[1,5-a]pyridin-6-yl)-1H-pyrrolo[3,2-b]pyridin-5-yl)oxy)methyl)piperidin-1-yl)-2-methylpropan-2-ol (11 mg, 0.022 mmol, 57.9% yield). $^1$H NMR (500 MHz, DMSO-$d_6$) δ 11.33-11.26 (m, 1H), 8.55 (s, 1H), 8.48 (s, 1H), 7.68 (d, J=8.5 Hz, 1H), 7.15 (s, 1H), 6.57 (d, J=8.5 Hz, 1H), 4.17 (br d, J=6.1 Hz, 2H), 4.08-4.03 (m, 3H), 3.29-3.18 (m, 1H), 2.99 (br d, J=11.0 Hz, 2H), 2.72 (s, 2H), 2.26 (s, 2H), 2.17 (br t, J=11.3 Hz, 2H), 1.69 (br d, J=12.2 Hz, 2H), 1.54-1.47 (m, 6H), 1.43-1.29 (m, 2H), 1.10-1.04 (m, 6H).

Example 598

6-(3-isopropyl-5-((1-isopropylpiperidin-4-yl)methoxy)-1H-pyrrolo[3,2-b]pyridin-2-yl)-8-methoxy-[1,2,4]triazolo[1,5-a]pyridine

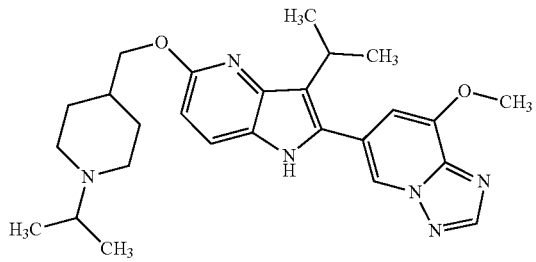

(598)

To a 1 dram vial with pressure relief septum was added 6-(3-isopropyl-5-(piperidin-4-ylmethoxy)-1H-pyrrolo[3,2-b]pyridin-2-yl)-8-methoxy-[1,2,4]triazolo[1,5-a]pyridine, 2 TFA (15 mg, 0.023 mmol), DMF (1 mL), and DIEA (4.04 μL, 0.023 mmol). Acetone (8.49 μL, 0.116 mmol) was added. The reaction mixture was stirred at room temperature for 10 minutes. Acetic acid (1.324 μL, 0.023 mmol) and sodium triacetoxyborohydride (4.90 mg, 0.023 mmol) were added. The reaction mixture was stirred at room temperature overnight. The crude material was purified via preparative LC/MS with the following conditions: Column: Xbridge C18, 19×200 mm, 5-m particles; Mobile Phase A: 5:95 acetonitrile:water with 0.1% trifluoroacetic acid; Mobile Phase B: 95:5 acetonitrile:water with 0.1% trifluoroacetic acid; Gradient: 5-50% B over 20 minutes, then a 5-minute hold at 100% B; Flow: 20 mL/min. Fractions containing the product were combined and dried via centrifugal evaporation. LC/MS was used to analyze the final compound. Injection 1 conditions: Column: Waters Xbridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 463.26 (M+H); Retention Time: 1.46 min. Injection 2 conditions: Column: Waters Xbridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 462.98 (M+H); Retention Time: 1.22 min. Isolated 6-(3-isopropyl-5-((1-isopropylpiperidin-4-yl)methoxy)-1H-pyrrolo[3,2-b]pyridin-2-yl)-8-methoxy-[1,2,4]triazolo[1,5-a]pyridine, 2 TFA (11.1 mg, 0.016 mmol, 67.4% yield). $^1$H NMR (500 MHz, DMSO-$d_6$) δ 11.35 (s, 1H), 8.56 (s, 1H), 8.53-8.47 (m, 1H), 7.70 (d, J=8.5 Hz, 1H), 7.30 (s, 1H), 6.59 (d, J=8.5 Hz, 1H), 4.22 (d, J=5.8 Hz, 2H), 4.06 (s, 3H), 3.45-3.36 (m, 2H), 3.28-3.19 (m, 1H), 3.02-2.84 (m, 3H), 2.14-2.05 (m, 1H), 2.02 (br d, J=15.3 Hz, 2H), 1.66-1.54 (m, 2H), 1.51 (d, J=7.0 Hz, 6H), 1.24 (d, J=6.4 Hz, 6H).

Example 600

6-(3-isopropyl-5-((1-methylpiperidin-4-yl)oxy)-1H-pyrrolo[3,2-b]pyridin-2-yl)-8-methoxy-[1,2,4]triazolo[1,5-a]pyridine

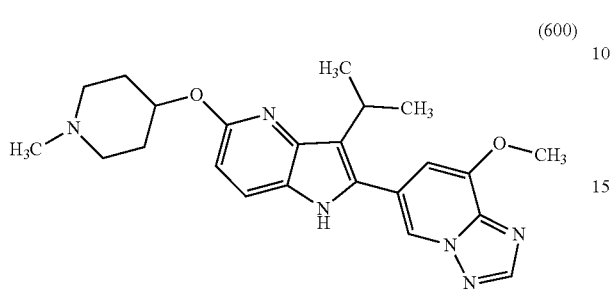

(600)

To a 20 mL vial containing tert-butyl 5-((1-(tert-butoxycarbonyl)piperidin-4-yl)oxy)-3-isopropyl-2-(8-methoxy-[1,2,4]triazolo[1,5-a]pyridin-6-yl)-1H-pyrrolo[3,2-b]pyridine-1-carboxylate (60 mg, 0.099 mmol) was added DCM (500 µl) and TFA (500 µl). The reaction mixture was stirred at rt for 3 hours. The reaction mixture was concentrated under a stream of nitrogen and dried under vacuum. To the reaction mixture was added DMF (1 mL), DIEA (17.27 µl, 0.099 mmol), formaldehyde (37% in water) (36.8 µL, 0.494 mmol), and acetic acid (5.66 µl, 0.099 mmol). The reaction mixture was stirred for 5 minutes. Sodium triacetoxyborohydride (62.9 mg, 0.297 mmol) was added and the reaction mixture was stirred at rt for 1 hour. A drop of water was added and the crude material was purified via preparative LC/MS with the following conditions: Column: Xbridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 4-minute hold at 100% B; Flow: 20 mL/min. Fractions containing the product were combined and dried via centrifugal evaporation. LC/MS was used to analyze the final compound. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. Isolated 6-(3-isopropyl-5-((1-methylpiperidin-4-yl)oxy)-1H-pyrrolo[3,2-b]pyridin-2-yl)-8-methoxy-[1,2,4]triazolo[1,5-a]pyridine (25.9 mg, 0.060 mmol, 61.0% yield). LC MS rt=0.971 (m+1=421) [QC-ACN-TFA-XB]. 1H NMR (500 MHz, DMSO-$d_6$) δ 11.30 (s, 1H), 8.58 (s, 1H), 8.51 (s, 1H), 7.67 (d, J=8.9 Hz, 1H), 7.18 (s, 1H), 6.55 (d, J=8.5 Hz, 1H), 5.00 (br s, 1H), 4.08 (s, 3H), 3.32-3.11 (m, 1H), 2.70 (br s, 1H), 2.57-2.54 (m, 1H), 2.20 (s, 3H), 2.07 (br s, 2H), 1.91 (br s, 2H), 1.72 (br d, J=9.8 Hz, 2H), 1.52 (br d, J=6.7 Hz, 6H).

Example 601

6-(3-isopropyl-5-methoxy-1H-pyrrolo[3,2-b]pyridin-2-yl)-8-methoxy-[1,2,4]triazolo[1,5-a] pyridine (601)

Intermediate 601A: tert-butyl 5-chloro-3-isopropyl-1H-pyrrolo[3,2-b]pyridine-1-carboxylate (601A)

To a 100 mL round-bottom flask cooled to 0° C. was added 5-chloro-3-isopropyl-1H-pyrrolo[3,2-b]pyridine (1.33 g) [material synthesized similarly as above for Intermediate 1B] THF (10 mL), TEA (1.428 mL, 10.25 mmol), and DMAP (0.083 g, 0.683 mmol). BOC-anhydride (1.745 mL, 7.52 mmol) was added slowly over 10 minutes and the reaction stirred for 30 minutes. The reaction was concentrated under vacuum to give an oil. The oil was purified by column chromatography on a Teledyne Isco instrument (24 g Silica, 100% Hexanes-80% EtOAc/Hexanes). Like fractions were combined and concentrated under vacuum to give a slight yellow oil, tert-butyl 5-chloro-3-isopropyl-1H-pyrrolo[3,2-b]pyridine-1-carboxylate (2.06 g). LC MS rt=1.20 min. (m+1=295) [B1]. $^1$H NMR (400 MHz, DMSO-$d_6$) δ 8.28 (d, J=8.7 Hz, 1H), 7.71 (s, 1H), 7.38 (d, J=8.7 Hz, 1H), 3.22-3.08 (m, 1H), 1.62 (s, 9H), 1.31 (d, J=6.8 Hz, 6H).

Intermediate 601B: tert-butyl 5-((1-(tert-butoxycarbonyl)piperidin-4-yl)oxy)-3-isopropyl-1H-pyrrolo[3,2-b]pyridine-1-carboxylate (601B)

A 1 dram vial containing tert-butyl 4-hydroxypiperidine-1-carboxylate (137 mg, 0.678 mmol), cesium carbonate (166 mg, 0.509 mmol), toluene (1 mL), and methanesulfonato (2-(di-t-butylphosphino)-3-methoxy-6-methyl-2',4',6'-tri-1-propyl-1,1'-biphenyl)(2'-amino-1,1'-biphenyl-2-yl)palladium(II) (8.53 mg, 10.18 μmol) under a nitrogen atmosphere was heated to 90° C. for 3 minutes. tert-butyl 5-chloro-3-isopropyl-1H-pyrrolo[3,2-b]pyridine-1-carboxylate (100 mg, 0.339 mmol) is added to the reaction and heated overnight at 90° C. The temperature was increased to 110° C. for 4 hours. The reaction was filtered through a pad of Celite and concentrated under vacuum. The resulting oil was purified by column chromatography on a Teledyne Isco instrument (24 g Silica, 100% Hexanes-100% EtOAc). Like fractions were combined and concentrated under vacuum to afford tert-butyl 5-((1-(tert-butoxycarbonyl)piperidin-4-yl)oxy)-3-isopropyl-1H-pyrrolo[3,2-b]pyridine-1-carboxylate (37 mg, 0.081 mmol, 24% yield). LC MS rt=1.33 min. (m+1=460) [B1].

Intermediate 601C: tert-butyl 5-((1-(tert-butoxycarbonyl)azetidin-3-yl)methoxy)-3-isopropyl-1H-pyrrolo[3,2-b]pyridine-1-carboxylate

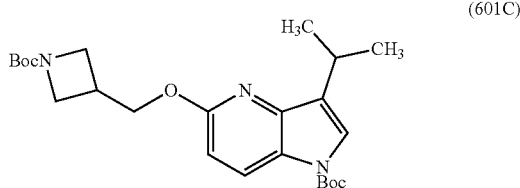 [SMILES: CC(C)c1cn(C(=O)OC(C)(C)C)c2ccc(OCC3CN(C(=O)OC(C)(C)C)C3)nc12]

A 1 dram vial containing tert-butyl 3-(hydroxymethyl)azetidine-1-carboxylate (60.7 mg, 0.324 mmol), cesium carbonate (158 mg, 0.486 mmol), toluene (2 mL), and methanesulfonato(2-(di-t-butylphosphino)-3-methoxy-6-methyl-2',4',6'-tri-1-propyl-1,1'-biphenyl)(2'-amino-1,1'-biphenyl-2-yl)palladium(II) (8.16 mg, 9.73 μmol) under a nitrogen atmosphere was heated to 105° C. for 5 minutes. tert-butyl 5-bromo-3-isopropyl-1H-pyrrolo[3,2-b]pyridine-1-carboxylate (110 mg, 0.324 mmol) in toluene (1 mL) was added to the reaction and heated overnight at 105° C. The reaction was diluted with water (10 mL) and extracted with EtOAc (3×10 mL). The organic layers were combined and passed over a pad of Celite and concentrated under vacuum to give clear oil. Purified by column chromatography on a Teledyne Isco instrument (24 g Silica, 100% Hexanes-50% EtOAc/hexanes). Like fractions were combined and concentrated under vacuum to give tert-butyl 5-((1-(tert-butoxycarbonyl)azetidin-3-yl)methoxy)-3-isopropyl-1H-pyrrolo[3,2-b]pyridine-1-carboxylate (107 mg, 0.228 mmol, 70.4% yield). LC MS rt=1.26 min. (m+1=446) [B1]. $^1$H NMR (400 MHz, CHLOROFORM-d) δ 8.27-8.09 (m, 1H), 7.44 (br. s., 1H), 6.64 (d, J=8.9 Hz, 1H), 4.51 (d, J=6.7 Hz, 2H), 4.08 (t, J=8.6 Hz, 2H), 3.85 (dd, J=8.7, 5.4 Hz, 2H), 3.21 (dt, J=13.2, 6.7 Hz, 1H), 3.02 (dquin, J=13.6, 6.8 Hz, 1H), 1.67 (s, 9H), 1.46 (s, 9H), 1.38 (d, J=7.0 Hz, 6H).

Intermediate 601D: tert-butyl 5-((1-(tert-butoxycarbonyl)piperidin-4-yl)methoxy)-3-isopropyl-1H-pyrrolo[3,2-b]pyridine-1-carboxylate

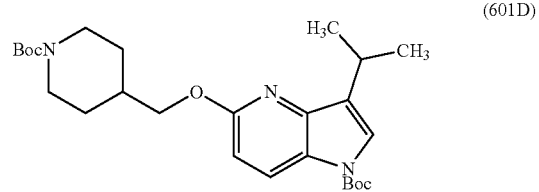 [SMILES: CC(C)c1cn(C(=O)OC(C)(C)C)c2ccc(OCC3CCN(C(=O)OC(C)(C)C)CC3)nc12]

A 1 dram vial containing tert-butyl 4-(hydroxymethyl)piperidine-1-carboxylate (337 mg, 1.565 mmol), cesium carbonate (765 mg, 2.348 mmol), toluene (5 mL), and methanesulfonato(2-(di-t-butylphosphino)-3-methoxy-6-methyl-2',4',6'-tri-1-propyl-1,1'-biphenyl)(2'-amino-1,1'-biphenyl-2-yl)palladium(II) (39.4 mg, 0.047 mmol) under a nitrogen atmosphere was heated to 105° C. for 5 minutes. tert-Butyl 5-bromo-3-isopropyl-1H-pyrrolo[3,2-b]pyridine-1-carboxylate (531 mg, 1.565 mmol) in toluene (1 mL) was added to the reaction and heated for 3 hours at 105° C. The reaction was diluted with water (10 mL) and extracted with EtOAc (3×10 mL). The organic layers were combined and passed over a pad of Celite and concentrated under vacuum to give a clear oil. Purified by column chromatography on a Teledyne Isco instrument (24 g Silica, 100% Hexanes-50% EtOAc/hexanes). Like fractions were combined and concentrated under vacuum to give tert-butyl 5-((1-(tert-butoxycarbonyl)piperidin-4-yl)methoxy)-3-isopropyl-1H-pyrrolo[3,2-b]pyridine-1-carboxylate (408 mg, 0.861 mmol, 55.0% yield). LC MS rt=1.33 min (m+1=474) [B1]. $^1$H NMR (400 MHz, CHLOROFORM-d) δ 8.26-8.00 (m, 1H), 7.50-7.33 (m, 1H), 6.67-6.57 (m, 1H), 4.24 (d, J=6.5 Hz, 2H), 4.21-4.02 (m, 2H), 3.26-3.14 (m, 1H), 2.64 (br d, J=7.5 Hz, 2H), 2.10-1.92 (m, 1H), 1.87-1.79 (m, 2H), 1.74-1.61 (m, 9H), 1.49-1.44 (m, 9H), 1.38 (d, J=6.8 Hz, 6H), 1.33-1.22 (m, 2H).

Intermediate 601E: tert-butyl 3-isopropyl-5-methoxy-1H-pyrrolo[3,2-b]pyridine-1-carboxylate

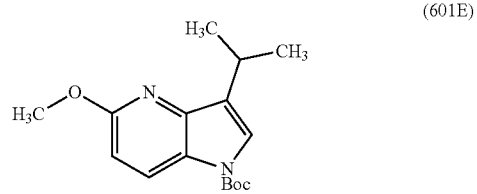 [SMILES: COc1ccc2c(n1)c(C(C)C)cn2C(=O)OC(C)(C)C]

A 1 dram vial containing methanol (0.918 mL, 22.70 mmol), cesium carbonate (1109 mg, 3.40 mmol), toluene (5 mL), and methanesulfonato(2-(di-t-butylphosphino)-3-methoxy-6-methyl-2',4',6'-tri-1-propyl-1,1'-biphenyl)(2'-amino-1,1'-biphenyl-2-yl)palladium(II) (38.1 mg, 0.045 mmol) under a nitrogen atmosphere was heated to 105° C. for 5 minutes. tert-Butyl 5-bromo-3-isopropyl-H-pyrrolo[3,2-b]pyridine-1-carboxylate (770 mg, 2.270 mmol) in toluene was added to the reaction and heated at 105° C. After 30 minutes, the reaction was diluted with water (10 mL) and extracted with EtOAc (3×10 mL). The organic layers were combined and passed over a pad of Celite and concentrated under vacuum to give a clear oil. Purified by column chromatography on a Teledyne Isco instrument (24 g Silica, 100% Hexanes-50% EtOAc/hexanes). Like fractions were combined and concentrated under vacuum to give tert-butyl 3-isopropyl-5-methoxy-1H-pyrrolo[3,2-b]pyridine-1-carboxylate (48 mg, 0.165 mmol, 7.3% yield). LC MS rt=1.22 min. (m+1=291) [B1].

Intermediate 601F: tert-butyl 3-isopropyl-5-methoxy-2-(4,4,5,5-tetramethyl-1,3,2-dioxaborolan-2-yl)-1H-pyrrolo[3,2-b]pyridine-1-carboxylate

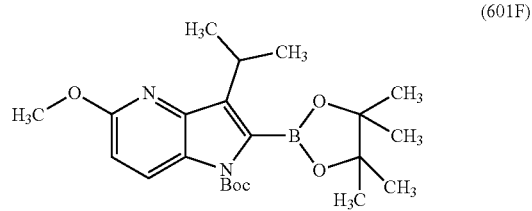

(601F)

To a nitrogen flushed 20 mL vial with a pressure relief septum was added tert-butyl 3-isopropyl-5-methoxy-1H-pyrrolo[3,2-b]pyridine-1-carboxylate (70 mg, 0.241 mmol), THF (2 mL), and 2-isopropoxy-4,4,5,5-tetramethyl-1,3,2-dioxaborolane (0.054 mL, 0.265 mmol). The vial was cooled to −40° C. in a dry ice/NMP bath. LDA (0.301 mL, 0.603 mmol) was added dropwise over 15 minutes. The reaction was warmed to 0° C. The reaction was cooled to −40° C. and quenched with saturated KHSO4. The reaction was warmed to room temperature, diluted with water (10 mL) and extracted with EtOAc (3×10 mL). Organic layers were combined, dried over sodium sulfate, filtered, and concentrated under vacuum to give a clear oil. The clear oil was purified by column chromatography on a Teledyne Isco instrument (12 g Silica, 100% Hexanes-50% EtOAc/Hexanes). Like fractions were combined and concentrated under vacuum to give tert-butyl 3-isopropyl-5-methoxy-2-(4,4,5,5-tetramethyl-1,3,2-dioxaborolan-2-yl)-1H-pyrrolo[3,2-b]pyridine-1-carboxylate (50 mg, 0.120 mmol, 49.8% yield). LC MS rt=1.34 min. (m+1=417) [B1].

Example 601

To a 2 dram vial with pressure relief septum was added tert-butyl 3-isopropyl-5-methoxy-2-(4,4,5,5-tetramethyl-1,3,2-dioxaborolan-2-yl)-1H-pyrrolo[3,2-b]pyridine-1-carboxylate (50 mg, 0.120 mmol), 6-bromo-8-methoxy-[1,2,4]triazolo[1,5-a]pyridine (27.4 mg, 0.120 mmol), 2nd generation Xphos precatalyst (4.72 mg, 6.00 μmol), and THF (1 mL). The reaction was evacuated and flushed with nitrogen several times. Aqueous tripotassium phosphate (3 M, 0.040 mL, 0.120 mmol) was added and the vial was evacuated and flushed with nitrogen several times. The reaction was heated at 65° C. for 1 hour. The reaction mixture was diluted with brine (1 mL) and extracted with EtOAc (3×2 mL). The organic layers were combined, dried over sodium sulfate, filtered, and dried under vacuum. The resulting oil was purified by column chromatography on a Teledyne Isco instrument (12 g Silica, 100% hexanes-100% EtOAc). Like fractions were combined and concentrated under vacuum. The resulting oil was treated with 1:1 TFA:DCM for 30 minutes, then concentrated under a stream of nitrogen. The resulting oil was neutralized with sodium bicarbonate and extracted with EtOAc. The organic layer was dried over sodium sulfate, filtered and concentrated to give a solid, 6-(3-isopropyl-5-methoxy-1H-pyrrolo[3,2-b]pyridin-2-yl)-8-methoxy-[1,2,4]triazolo[1,5-a]pyridine (11.4 mg, 0.032 mmol, 26.7% yield). LC MS rt=0.77 min. (m+1=338) [B1]. $^{1}$H NMR (400 MHz, DMSO-$d_6$) δ 11.31 (s, 1H), 8.60 (d, J=1.2 Hz, 1H), 8.52 (s, 1H), 7.68 (d, J=8.7 Hz, 1H), 7.19 (d, J=1.1 Hz, 1H), 6.59 (d, J=8.7 Hz, 1H), 4.08 (s, 3H), 4.06-3.98 (m, 1H), 3.89 (s, 3H), 1.57-1.52 (m, 6H).

Example 602

2-(4-(((3-isopropyl-2-(8-methoxy-[1,2,4]triazolo[1,5-a]pyridin-6-yl)-1H-pyrrolo[3,2-b]pyridin-5-yl)oxy)methyl)piperidin-1-yl)-N,N-dimethylacetamide

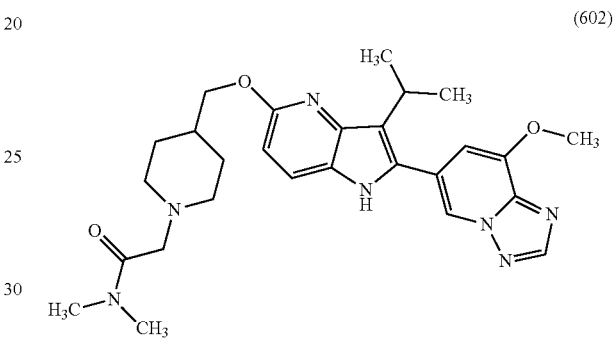

(602)

To a 1 dram vial containing 6-(3-isopropyl-5-(piperidin-4-ylmethoxy)-1H-pyrrolo[3,2-b]pyridin-2-yl)-8-methoxy-[1,2,4]triazolo[1,5-a]pyridine, 2 TFA (15 mg, 0.023 mmol) was added DMF (1 mL), DIEA (0.012 mL, 0.069 mmol), and 2-chloro-N,N-dimethylacetamide (4.22 mg, 0.035 mmol). The reaction mixture was stirred at room temperature overnight. The crude material was purified via preparative LC/MS with the following conditions: Column: Xbridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the product were combined and dried via centrifugal evaporation. LC/MS was used to analyze the final compound. Injection 1 conditions: Column: Waters Xbridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 506.1 (M+H); Retention Time: 1.28 min. Injection 2 conditions: Column: Waters Xbridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 506.25 (M+H); Retention Time: 1.01 min. Isolated 2-(4-(((3-isopropyl-2-(8-methoxy-[1,2,4]triazolo[1,5-a]pyridin-6-yl)-1H-pyrrolo[3,2-b]pyridin-5-yl)oxy)methyl)piperidin-1-yl)-N,N-dimethylacetamide (4.2 mg, 8.06 µmol, 34.8% yield). $^1$H NMR (500 MHz, DMSO-d$_6$) δ 11.30 (s, 1H), 8.59 (s, 1H), 8.50 (s, 1H), 7.67 (d, J=8.9 Hz, 1H), 7.18 (s, 1H), 6.57 (d, J=8.5 Hz, 1H), 4.18 (d, J=6.1 Hz, 2H), 4.07 (s, 3H), 3.29-3.20 (m, 1H), 3.09 (s, 2H), 3.02 (s, 3H), 2.88-2.82 (m, 2H), 2.80 (s, 3H), 2.00 (br t, J=10.7 Hz, 2H), 1.86-1.76 (m, 1H), 1.73 (br d, J=12.2 Hz, 2H), 1.53 (br d, J=1.0 Hz, 6H), 1.37-1.25 (m, 2H).

Example 603

6-(3-isopropyl-5-((1-isopropylpiperidin-4-yl)oxy)-1H-pyrrolo[3,2-b]pyridin-2-yl)-8-methoxy-[1,2,4]triazolo[1,5-a]pyridine

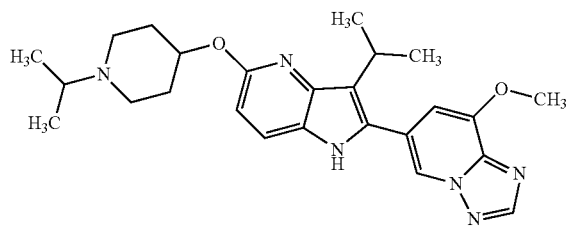

(603)

To a 2 dram vial containing tert-butyl 5-((1-(tert-butoxycarbonyl)piperidin-4-yl)oxy)-3-isopropyl-2-(8-methoxy-[1,2,4]triazolo[1,5-a]pyridin-6-yl)-1H-pyrrolo[3,2-b]pyridine-1-carboxylate (31 mg, 0.051 mmol) was added DCM (1 mL) and TFA (1 mL). The reaction mixture was stirred at room temperature for 30 minutes. The reaction mixture was concentrated under a stream of nitrogen and dried under vacuum. To the resulting oil was added DMF (1 mL), DIEA (0.027 mL, 0.153 mmol), and acetone (0.019 mL, 0.255 mmol). The reaction mixture was stirred at room temperature for 30 minutes. Sodium triacetoxyborohydride (54.1 mg, 0.255 mmol) and acetic acid (2.93 µL, 0.051 mmol) were added, and the reaction mixture was stirred at room temperature overnight. The crude material was purified via preparative LC/MS with the following conditions: Column: Xbridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 27 minutes, then a 3-minute hold at 100% B; Flow: 20 mL/min. Fractions containing the product were combined and dried via centrifugal evaporation. The yield of the product was 4.5 mg. LC/MS was used to analyze the final compound. Injection 1 conditions: Column: Waters Xbridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 449 (M+H); Retention Time: 1.22 min. Injection 2 conditions: Column: Waters Xbridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 449.29 (M+H); Retention Time: 1.07 min.

Example 604

6-(3-isopropyl-5-((1-(2-(methylsulfonyl)ethyl)piperidin-4-yl)methoxy)-1H-pyrrolo[3,2-b]pyridin-2-yl)-8-methoxy-[1,2,4]triazolo[1,5-a]pyridine

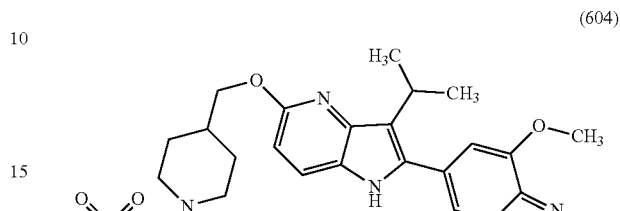

(604)

To a 1 dram vial containing 6-(3-isopropyl-5-(piperidin-4-ylmethoxy)-1H-pyrrolo[3,2-b]pyridin-2-yl)-8-methoxy-[1,2,4]triazolo[1,5-a]pyridine, 2 TFA (15 mg, 0.023 mmol) was added DMF (0.75 mL), DIEA (4.04 µL, 0.023 mmol), and 1-bromo-2-(methylsulfonyl)ethane (4.33 mg, 0.023 mmol). The reaction mixture was stirred at room temperature overnight. The reaction mixture was heated to 70° C. for 3 hours. The crude material was purified via preparative LC/MS with the following conditions: Column: Xbridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 19 minutes, then a 5-minute hold at 100% B; Flow: 20 mL/min. Fractions containing the product were combined and dried via centrifugal evaporation. LC/MS was used to analyze the final compound. Injection 1 conditions: Column: Waters Xbridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 527.45 (M+H); Retention Time: 1.5 min. Injection 2 conditions: Column: Waters Xbridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 527.47 (M+H); Retention Time: 0.98 min. Isolated 6-(3-isopropyl-5-((1-(2-(methylsulfonyl)ethyl)piperidin-4-yl)methoxy)-1H-pyrrolo[3,2-b]pyridin-2-yl)-8-methoxy-[1,2,4]triazolo[1,5-a]pyridine (3.8 mg, 7.00 µmol, 30.3% yield). $^1$H NMR (500 MHz, DMSO-d$_6$) δ 11.29 (s, 1H), 8.58 (s, 1H), 8.50 (s, 1H), 7.67 (d, J=8.9 Hz, 1H), 7.17 (s, 1H), 6.57 (d, J=8.9 Hz, 1H), 4.18 (br d, J=6.4 Hz, 2H), 4.07 (s, 3H), 3.89 (s, 1H), 3.29-3.20 (m, 2H), 3.02 (s, 3H), 2.92 (br d, J=11.0 Hz, 2H), 2.68 (t, J=6.7 Hz, 2H), 1.95 (br t, J=10.8 Hz, 2H), 1.87-1.79 (m, 1H), 1.78-1.72 (m, 2H), 1.55-1.49 (m, 6H), 1.37-1.24 (m, 2H).

Examples 605 and 611

4-((3-isopropyl-2-(8-methoxy-[1,2,4]triazolo[1,5-a]pyridin-6-yl)-1H-pyrrolo[3,2-b]pyridin-5-yl)oxy)-N,N-dipropylcyclohexan-1-amine

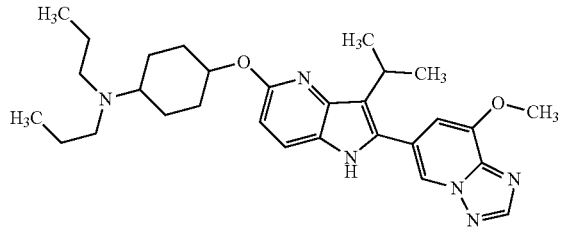

(605 and 611)

To a 1 dram vial containing 4-((3-isopropyl-2-(8-methoxy-[1,2,4]triazolo[1,5-a]pyridin-6-yl)-1H-pyrrolo[3,2-b]pyridin-5-yl)oxy)cyclohexan-1-amine, 2 TFA (15 mg, 0.023 mmol) was added DCM (1 mL), DMF (0.5 mL), DIEA (8.08 μL, 0.046 mmol), and propionaldehyde (3.32 μL, 0.046 mmol). The reaction mixture was stirred at room temperature for 30 minutes. Acetic acid (1.324 μL, 0.023 mmol) and sodium triacetoxyborohydride (14.71 mg, 0.069 mmol) were added to the reaction mixture. The reaction mixture was stirred for 3 hours. A drop of water and DMF (1 mL) were added, and then the crude material was purified via preparative LC/MS with the following conditions: Column: Xbridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 22-62% B over 20 minutes, then a 4-minute hold at 100% B; Flow: 20 mL/min. Fractions containing the product were combined and dried via centrifugal evaporation to afford two compounds: Isolate 1 and Isolate 2. These compounds were cis and trans isomers, but the identities of isomers in the isolates were not assigned.

Example 605: Isolate 1: 4-((3-isopropyl-2-(8-methoxy-[1,2,4]triazolo[1,5-a]pyridin-6-yl)-1H-pyrrolo[3,2-b]pyridin-5-yl)oxy)-N,N-dipropylcyclohexan-1-amine (9.9 mg, 0.020 mmol, 85% yield). LC/MS was used to analyze the final compound. Injection 1 conditions: Column: Waters Xbridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 505.48 (M+H); Retention Time: 1.51 min. Injection 2 conditions: Column: Waters Xbridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 505.46 (M+H); Retention Time: 1.24 min. $^1$H NMR (500 MHz, DMSO-$d_6$) δ 11.28 (s, 1H), 8.58 (s, 1H), 8.50 (s, 1H), 7.68-7.60 (m, 1H), 7.18 (s, 1H), 6.50 (d, J=8.9 Hz, 1H), 4.86 (br s, 1H), 4.27 (q, J=7.0 Hz, 1H), 4.07 (s, 2H), 3.25 (br dd, J=10.2, 6.0 Hz, 1H), 3.19-3.10 (m, 1H), 2.89 (s, 1H), 2.70-2.67 (m, 1H), 2.73 (s, 1H), 2.47-2.33 (m, 3H), 2.26 (br s, 1H), 1.79 (br s, 1H), 1.53 (br d, J=6.7 Hz, 6H), 1.44-1.33 (m, 6H), 1.32-1.20 (m, 1H), 0.99 (d, J=6.4 Hz, 3H), 0.84 (t, J=7.3 Hz, 4H).

Example 611: Isolate 2: 4-((3-isopropyl-2-(8-methoxy-[1,2,4]triazolo[1,5-a]pyridin-6-yl)-1H-pyrrolo[3,2-b]pyridin-5-yl)oxy)-N,N-dipropylcyclohexan-1-amine (4.2 mg, 7.91 μmol, 34.2% yield). LC/MS was used to analyze the final compound. Injection 1 conditions: Column: Waters Xbridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 505.46 (M+H); Retention Time: 1.57 min. Injection 2 conditions: Column: Waters Xbridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 505.46 (M+H); Retention Time: 1.3 min. $^1$H NMR (500 MHz, DMSO-$d_6$) δ 11.28 (s, 1H), 8.58 (s, 1H), 8.50 (s, 1H), 7.94 (s, 1H), 7.66 (d, J=8.5 Hz, 1H), 7.17 (s, 1H), 6.58 (d, J=8.5 Hz, 1H), 5.20 (br s, 1H), 4.07 (s, 3H), 3.29-3.22 (m, 1H), 3.19-3.11 (m, 1H), 2.89 (s, 1H), 2.73 (s, 1H), 2.46-2.34 (m, 2H), 2.13 (br s, 1H), 1.76 (br s, 1H), 1.60 (br d, J=8.9 Hz, 3H), 1.51 (br d, J=6.7 Hz, 5H), 1.42-1.35 (m, 4H), 0.99 (d, J=6.1 Hz, 3H), 0.84 (t, J=7.2 Hz, 6H).

Example 606

6-(3-isopropyl-5-((1-propylpiperidin-4-yl)methoxy)-1H-pyrrolo[3,2-b]pyridin-2-yl)-8-methoxy-[1,2,4]triazolo[1,5-a]pyridine

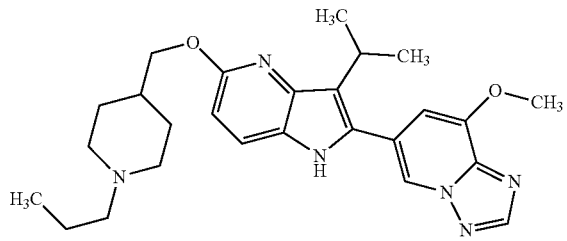

(606)

To a 1 dram vial containing 6-(3-isopropyl-5-(piperidin-4-ylmethoxy)-1H-pyrrolo[3,2-b]pyridin-2-yl)-8-methoxy-[1,2,4]triazolo[1,5-a]pyridine, 2 TFA (15 mg, 0.023 mmol) was added DMF (0.5 mL), DIEA (0.012 mL, 0.069 mmol), propionaldehyde (6.72 mg, 0.116 mmol). The reaction mixture was stirred for 5 minutes. Sodium triacetoxyborohydride (14.71 mg, 0.069 mmol) and acetic acid (1.324 μL, 0.023 mmol) were added and the reaction was stirred at room temperature for 6 hours. One drop of water was added, and the crude material was purified via preparative LC/MS with the following conditions: Column: Xbridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 25 minutes, then a 5-minute hold at 100% B; Flow: 20 mL/min. Fractions containing the product were combined and dried via centrifugal evaporation. LC/MS was used to analyze the final compound. Injection 1 conditions: Column: Waters Xbridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 462.94 (M+H); Retention Time: 1.51 min. Injection 2 conditions: Column: Waters Xbridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 463.3 (M+H); Retention Time: 1.25 min. Isolated 6-(3-isopropyl-5-((1-propylpiperidin-4-yl)methoxy)-1H-pyrrolo[3,2-b]pyridin-2-yl)-8-methoxy-[1,2,4]triazolo[1,5-a]pyridine (8.6 mg, 0.019 mmol, 80% yield). $^1$H NMR (500 MHz, DMSO-$d_6$) δ 11.33-11.26 (m, 1H), 8.62-8.55 (m, 1H), 8.53-8.47 (m, 1H), 7.71-7.63 (m, 1H), 7.18 (s, 1H), 6.58 (d, J=8.5 Hz, 1H), 4.21-4.16 (m, 2H), 4.08 (s, 3H), 3.30-3.19 (m, 1H), 2.89 (br d, J=10.7 Hz, 2H), 2.23 (br t, J=7.3 Hz, 2H), 1.93-1.80 (m, 3H), 1.75 (br d, J=12.2 Hz, 2H), 1.52 (br d, J=7.0 Hz, 6H), 1.44 (dq, J=14.5, 7.4 Hz, 2H), 1.38-1.26 (m, 2H), 0.84 (t, J=7.5 Hz, 3H).

Example 607

6-(3-isopropyl-5-((1-(tetrahydro-2H-pyran-4-yl)piperidin-4-yl)oxy)-1H-pyrrolo[3,2-b]pyridin-2-yl)-8-methoxy-[1,2,4]triazolo[1,5-a]pyridine

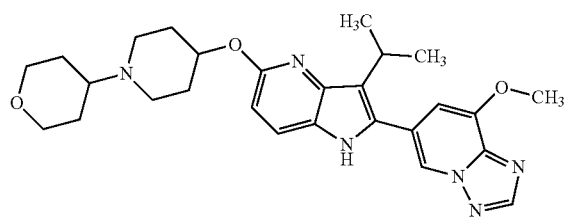

(607)

To a 1 dram vial containing 6-(3-isopropyl-5-(piperidin-4-yloxy)-1H-pyrrolo[3,2-b]pyridin-2-yl)-8-methoxy-[1,2,4]triazolo[1,5-a]pyridine, 2 TFA (15 mg, 0.024 mmol) is added DMF (500 μL), DIEA (12.39 μL, 0.071 mmol), and dihydro-2H-pyran-4(3H)-one (2.367 mg, 0.024 mmol). The reaction mixture was stirred at room temperature for 5 minutes. Acetic acid (1.353 μL, 0.024 mmol) and sodium triacetoxyborohydride (15.03 mg, 0.071 mmol) were added to the reaction. The reaction mixture was stirred overnight. The crude material was purified via preparative LC/MS with the following conditions: Column: Xbridge C18, 19×200 mm, 5-μm particles; Mobile Phase A: 5:95 acetonitrile: water with 10-mM ammonium acetate; Mobile Phase B: 95:5 acetonitrile:water with 10-mM ammonium acetate; Gradient: 10-50% B over 20 minutes, then a 4-minute hold at 100% B; Flow: 20 mL/min. Fractions containing the product were combined and dried via centrifugal evaporation. The material was further purified via preparative LC/MS with the following conditions: Column: Xbridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 3-minute hold at 100% B; Flow: 20 mL/min. Fractions containing the product were combined and dried via centrifugal evaporation. LC/MS was used to analyze the final compound. Injection 1 conditions: Column: Waters Xbridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 491.21 (M+H); Retention Time: 1.33 min. Injection 2 conditions: Column: Waters Xbridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 491.16 (M+H); Retention Time: 1.07 min. Isolated 6-(3-isopropyl-5-((1-(tetrahydro-2H-pyran-4-yl)piperidin-4-yl)oxy)-1H-pyrrolo[3,2-b]pyridin-2-yl)-8-methoxy-[1,2,4]triazolo[1,5-a]pyridine (6.7 mg, 0.013 mmol, 56% yield). $^1$H NMR (500 MHz, DMSO-$d_6$) δ 11.28 (s, 1H), 8.57 (s, 1H), 8.50 (s, 1H), 7.66 (d, J=8.5 Hz, 1H), 7.16 (s, 1H), 6.54 (d, J=8.5 Hz, 1H), 5.03-4.93 (m, 1H), 4.11-4.03 (m, 3H), 3.88 (br d, J=7.6 Hz, 2H), 3.32-3.21 (m, 3H), 2.86 (br d, J=10.4 Hz, 2H), 2.41-2.32 (m, 2H), 2.13-2.03 (m, 2H), 1.94-1.86 (m, 1H), 1.73-1.61 (m, 4H), 1.51 (br d, J=7.0 Hz, 6H), 1.48-1.36 (m, 2H).

Example 608

6-(3-isopropyl-5-((1-methylazetidin-3-yl)methoxy)-1H-pyrrolo[3,2-b]pyridin-2-yl)-8-methoxy-[1,2,4]triazolo[1,5-a]pyridine

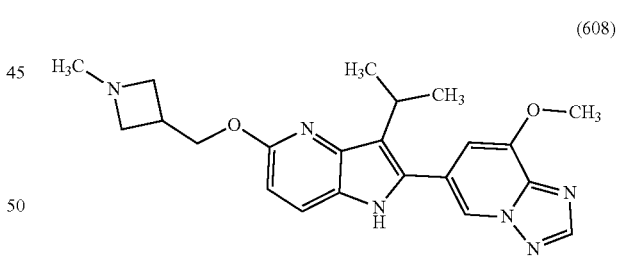

(608)

To a 20 mL scintillation vial containing tert-butyl 5-((1-(tert-butoxycarbonyl) azetidin-3-yl)methoxy)-3-isopropyl-2-(8-methoxy-[1,2,4]triazolo[1,5-a]pyridin-6-yl)-1H-pyrrolo[3,2-b]pyridine-1-carboxylate (40 mg, 0.067 mmol) was added DCM (500 mL) and TFA (500 mL). The reaction mixture was stirred at room temperature for 3 hours, concentrated under a stream of nitrogen and dried under vacuum. The resulting oil was dissolved in DMF (1 mL) and DIEA (0.035 mL, 0.202 mmol) and formaldehyde (37% in water) (0.025 mL, 0.337 mmol) were added. The reaction mixture was stirred at room temperature for 10 minutes. Acetic acid (3.86 μL, 0.067 mmol) and sodium triacetoxyborohydride (42.9 mg, 0.202 mmol) were added and the reaction mixture was stirred at room temperature overnight.

The crude material was purified via preparative LC/MS with the following conditions: Column: Xbridge C18, 19×200 mm, 5-m particles; Mobile Phase A: 5:95 acetonitrile:water with 10-mM ammonium acetate; Mobile Phase B: 95:5 acetonitrile:water with 10-mM ammonium acetate; Gradient: 10-50% B over 19 minutes, then a 5-minute hold at 100% B; Flow: 20 mL/min. Fractions containing the product were combined and dried via centrifugal evaporation. The material was further purified via preparative LC/MS with the following conditions: Column: Xbridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 8-33% B over 25 minutes, then a 2-minute hold at 33% B; Flow: 20 mL/min. Fractions containing the product were combined and dried via centrifugal evaporation. LC/MS was used to analyze the final compound. Injection 1 conditions: Column: Waters Xbridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 407.34 (M+H); Retention Time: 0.96 min. Injection 2 conditions: Column: Waters Xbridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 406.93 (M+H); Retention Time: 1.11 min. Isolated 6-(3-isopropyl-5-((1-methylazetidin-3-yl)methoxy)-1H-pyrrolo[3,2-b]pyridin-2-yl)-8-methoxy-[1,2,4]triazolo[1,5-a]pyridine, 2 TFA (1.7 mg, 2.63 μmol, 3.9% yield). $^1$H NMR (500 MHz, DMSO-d$_6$) δ 11.47-11.38 (m, 1H), 8.61 (s, 1H), 8.53 (s, 1H), 7.74 (d, J=8.7 Hz, 1H), 7.19 (s, 1H), 6.68 (dd, J=8.5, 5.9 Hz, 1H), 4.54-4.40 (m, 2H), 4.08 (s, 3H), 3.99-3.90 (m, 1H), 3.60-3.50 (m, 1H), 3.49-3.42 (m, 1H), 3.29-3.23 (m, 2H), 2.90-2.81 (m, 3H), 2.73 (s, 1H), 1.54 (br d, J=5.6 Hz, 6H).

Example 609

2-(4-((3-isopropyl-2-(8-methoxy-[1,2,4]triazolo[1,5-a]pyridin-6-yl)-1H-pyrrolo[3,2-b]pyridin-5-yl)oxy)piperidin-1-yl)-N,N-dimethylacetamide (609)

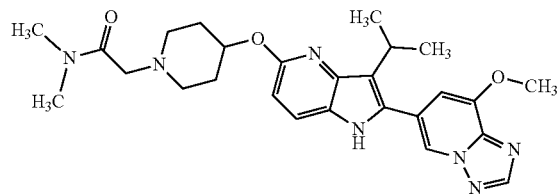

To a 1 dram vial containing 6-(3-isopropyl-5-(piperidin-4-yloxy)-1H-pyrrolo[3,2-b] pyridin-2-yl)-8-methoxy-[1,2,4]triazolo[1,5-a]pyridine, 2 TFA (20 mg, 0.032 mmol) was added DMF (1 mL), DIEA (0.017 mL, 0.095 mmol), and 2-chloro-N,N-dimethylacetamide (11.50 mg, 0.095 mmol). The reaction mixture was stirred at room temperature overnight. The crude material was purified via preparative LC/MS with the following conditions: Column: Xbridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 4-minute hold at 100% B; Flow: 20 mL/min. Fractions containing the product were combined and dried via centrifugal evaporation. LC/MS was used to analyze the final compound. Injection 1 conditions: Column: Waters Xbridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 492.13 (M+H); Retention Time: 1.25 min. Injection 2 conditions: Column: Waters Xbridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 492.01 (M+H); Retention Time: 1.28 min. Isolated 2-(4-((3-isopropyl-2-(8-methoxy-[1,2,4]triazolo[1,5-a]pyridin-6-yl)-1H-pyrrolo[3,2-b]pyridin-5-yl)oxy)piperidin-1-yl)-N,N-dimethylacetamide (11.2 mg, 0.023 mmol, 71.6% yield). $^1$H NMR (500 MHz, DMSO-d$_6$) δ 11.30 (s, 1H), 8.60 (s, 1H), 8.52 (s, 1H), 7.67 (d, J=8.9 Hz, 1H), 7.19 (s, 1H), 6.55 (d, J=8.5 Hz, 1H), 5.04-4.96 (m, 1H), 4.08 (s, 3H), 3.32-3.22 (m, 1H), 3.18 (s, 2H), 3.04 (s, 2H), 2.89-2.73 (m, 4H), 2.36 (br t, J=9.3 Hz, 2H), 2.12-2.05 (m, 2H), 1.90 (br s, 1H), 1.74-1.64 (m, 2H), 1.56-1.48 (m, 6H), 1.24 (s, 1H).

Examples 610 and 614

4-((3-isopropyl-2-(8-methoxy-[1,2,4]triazolo[1,5-a]pyridin-6-yl)-1H-pyrrolo[3,2-b]pyridin-5-yl)oxy)-N,N-dimethylcyclohexan-1-amine (610 and 614)

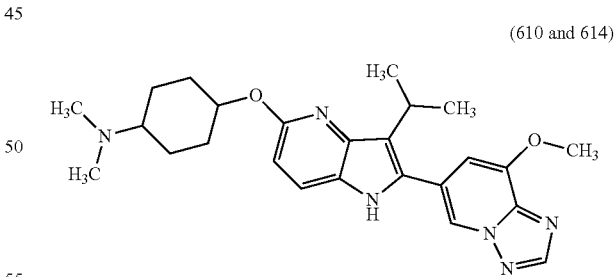

To a 1 dram vial containing 4-((3-isopropyl-2-(8-methoxy-[1,2,4]triazolo[1,5-a]pyridin-6-yl)-1H-pyrrolo[3,2-b]pyridin-5-yl)oxy)cyclohexan-1-amine, 2 TFA (15 mg, 0.023 mmol) was added DMF (0.5 mL), DCM (1 mL), DIEA (8.08 μL, 0.046 mmol), and formaldehyde (1.911 μL, 0.069 mmol). The reaction mixture was stirred at room temperature for 30 minutes. Acetic acid (1.324 μL, 0.023 mmol) and sodium triacetoxyborohydride (14.71 mg, 0.069 mmol) were added and the reaction mixture was stirred at room temperature for 1 hour. The crude material was purified via preparative LC/MS with the following conditions:

Column: Xbridge C18, 19×200 mm, 5-m particles; Mobile Phase A: 5:95 acetonitrile:water with 0.1% trifluoroacetic acid; Mobile Phase B: 95:5 acetonitrile:water with 0.1% trifluoroacetic acid; Gradient: 5-50% B over 20 minutes, then a 6-minute hold at 100% B; Flow: 20 mL/min. Fractions containing the product were combined and dried via centrifugal evaporation to afford two compounds: Isolate 1 and Isolate 2. These compounds are cis and trans isomers, but the identities of the isomers in the isolates were not assigned.

Example 610: Isolate 1: 4-((3-isopropyl-2-(8-methoxy-[1,2,4]triazolo[1,5-a]pyridin-6-yl)-1H-pyrrolo[3,2-b]pyridin-5-yl)oxy)-N,N-dimethylcyclohexan-1-amine, 2 TFA (8.5 mg, 0.012 mmol, 53.2% yield). LC/MS was used to analyze the final compound. Injection 1 conditions: Column: Waters Xbridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 449.37 (M+H); Retention Time: 1.11 min. Injection 2 conditions: Column: Waters Xbridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 449.36 (M+H); Retention Time: 0.91 min. 1H NMR (500 MHz, DMSO-$d_6$) δ 11.36 (s, 1H), 8.59 (s, 1H), 8.52 (s, 1H), 7.69 (d, J=8.9 Hz, 1H), 7.17 (s, 1H), 6.54 (d, J=8.5 Hz, 1H), 4.96-4.86 (m, 1H), 4.12-4.04 (m, 3H), 3.31-3.20 (m, 2H), 2.38 (br d, J=11.6 Hz, 2H), 2.18-2.07 (m, 2H), 1.73-1.58 (m, 3H), 1.55-1.38 (m, 11H).

Example 614: Isolate 2: 4-((3-isopropyl-2-(8-methoxy-[1,2,4]triazolo[1,5-a]pyridin-6-yl)-1H-pyrrolo[3,2-b]pyridin-5-yl)oxy)-N,N-dimethylcyclohexan-1-amine, 2 TFA (3.1 mg, 4.44 μmol, 19% yield). LC/MS was used to analyze the final compound. Injection 1 conditions: Column: Waters Xbridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 449.38 (M+H); Retention Time: 1.26 min. Injection 2 conditions: Column: Waters Xbridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 449.38 (M+H); Retention Time: 0.99 min. $^1$H NMR (500 MHz, DMSO-$d_6$) δ 11.39-11.32 (m, 1H), 8.61-8.56 (m, 1H), 8.52 (s, 1H), 7.71 (d, J=8.9 Hz, 1H), 7.17 (s, 1H), 6.60 (d, J=8.9 Hz, 1H), 5.25 (br s, 1H), 4.08 (s, 3H), 3.31-3.23 (m, 2H), 2.25 (br d, J=10.7 Hz, 2H), 1.95-1.84 (m, 2H), 1.81-1.66 (m, 4H), 1.55-1.47 (m, 6H).

Example 612

6-(3-isopropyl-5-((1-isopropylazetidin-3-yl)oxy)-1H-pyrrolo[3,2-b]pyridin-2-yl)-8-methoxy-[1,2,4]triazolo[1,5-a]pyridine

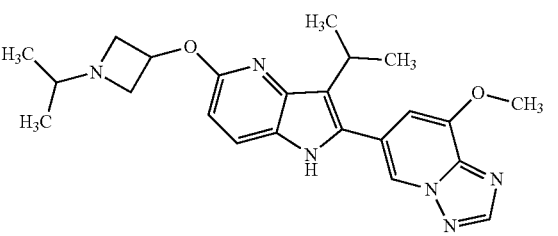

(612)

To a 1 dram vial containing 6-(5-(azetidin-3-yloxy)-3-isopropyl-1H-pyrrolo[3,2-b] pyridin-2-yl)-8-methoxy-[1,2,4]triazolo[1,5-a]pyridine (10 mg, 0.026 mmol) was added DMF (1 mL), DIEA (0.014 mL, 0.079 mmol), and propan-2-one (1.535 mg, 0.026 mmol). The reaction mixture was stirred at room temperature for 30 minutes. Acetic acid (1.513 μL, 0.026 mmol) and sodium triacetoxyborohydride (28.0 mg, 0.132 mmol) were added and the reaction mixture was stirred at room temperature overnight. The crude material was purified via preparative LC/MS with the following conditions: Column: Xbridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 4-minute hold at 100% B; Flow: 20 mL/min. Fractions containing the product were combined and dried via centrifugal evaporation. LC/MS was used to analyze the final compound. Injection 1 conditions: Column: Waters Xbridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Observed Mass: 421.04 (M+H); Retention Time: 1.4 min. Injection 2 conditions: Column: Waters Xbridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Observed Mass: 420.96 (M+H); Retention Time: 1.17 min. Isolated 6-(3-isopropyl-5-((1-isopropylazetidin-3-yl)oxy)-1H-pyrrolo[3,2-b]pyridin-2-yl)-8-methoxy-[1,2,4]triazolo[1,5-a]pyridine (5.2 mg, 0.012 mmol, 44.9% yield).

Example 613

1-(4-((3-isopropyl-2-(8-methoxy-[1,2,4]triazolo[1,5-a]pyridin-6-yl)-1H-pyrrolo[3,2-b]pyridin-5-yl)oxy)piperidin-1-yl)-2-methylpropan-2-ol

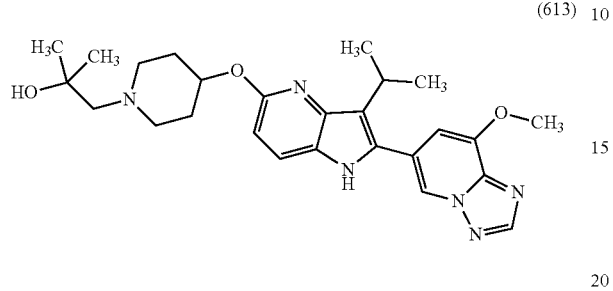

(613)

To a 1 dram vial containing 6-(3-isopropyl-5-(piperidin-4-yloxy)-1H-pyrrolo[3,2-b]pyridin-2-yl)-8-methoxy-[1,2,4]triazolo[1,5-a]pyridine, 2 TFA (15 mg, 0.024 mmol) was added MeOH (500 µL), potassium carbonate (9.80 mg, 0.071 mmol), and 2,2-dimethyloxirane (1.705 mg, 0.024 mmol). The reaction mixture was stirred at rt overnight then filtered and concentrated under vacuum. The crude material was dissolved in DMF and purified via preparative LC/MS with the following conditions: Column: Xbridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 4-minute hold at 100% B; Flow: 20 mL/min. Fractions containing the product were combined and dried via centrifugal evaporation. LC/MS was used to analyze the final compound. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. Isolated 1-(4-((3-isopropyl-2-(8-methoxy-[1,2,4]triazolo[1,5-a]pyridin-6-yl)-1H-pyrrolo[3,2-b]pyridin-5-yl)oxy)piperidin-1-yl)-2-methylpropan-2-ol (9.8 mg, 0.019 mmol, 81% yield). LCMS retention time 1.20 min, m/z=479.2 (M+H) [QC-ACN-AA-XB]. 1H NMR (500 MHz, DMSO-$d_6$) δ 11.30 (s, 1H), 8.59 (s, 1H), 8.51 (s, 1H), 7.67 (d, J=8.5 Hz, 1H), 7.18 (s, 1H), 6.55 (d, J=8.9 Hz, 1H), 4.98 (br s, 1H), 4.08 (s, 3H), 3.25 (dt, J=13.6, 6.6 Hz, 1H), 2.91 (br d, J=11.0 Hz, 2H), 2.38 (br t, J=9.2 Hz, 2H), 2.06 (br d, J=10.7 Hz, 2H), 1.79-1.62 (m, 2H), 1.57-1.46 (m, 6H), 1.23 (s, 3H), 1.10 (s, 6H).

Example 649

6-(5-(azetidin-3-yl)-3-isopropyl-1H-pyrrolo[3,2-b]pyridin-2-yl)-7,8-dimethyl-[1,2,4]triazolo[1,5-a]pyridine

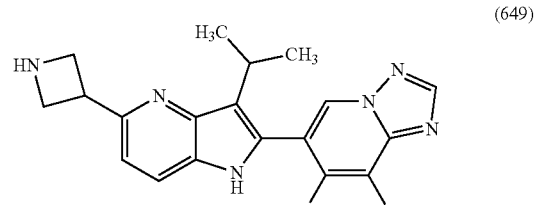

(649)

Intermediate 649A: tert-butyl 5-(1-(tert-butoxycarbonyl)azetidin-3-yl)-3-isopropyl-1H-pyrrolo[3,2-b]pyridine-1-carboxylate

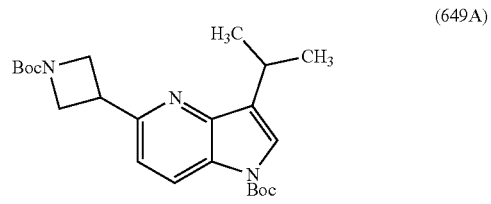 [SMILES: CC(C)c1cn(C(=O)OC(C)(C)C)c2ccc(C3CN(C(=O)OC(C)(C)C)C3)nc12]

(649A)

A suspension of tert-butyl 5-bromo-3-isopropyl-1H-pyrrolo[3,2-b]pyridine-1-carboxylate (150 mg, 0.442 mmol), tert-butyl 3-bromoazetidine-1-carboxylate (209 mg, 0.884 mmol), tris(trimethylsilyl)silane (165 mg, 0.663 mmol), [Ir(dF(CF$_3$)ppy)$_2$(dtbbpy)]PF$_6$ (1.24 mg, 1.11 µmol), and Na$_2$CO$_3$ (187 mg, 1.77 mmol) in 1,4-dioxane (3.5 mL) in a vial with a pressure-relief septum-lined cap and a stir bar was degassed with nitrogen gas for 5 minutes. To a separate vial was added nickel(II) chloride ethylene glycol dimethyl ether complex (7.29 mg, 0.033 mmol) and 4,4'-di-tert-butyl-2,2'-bipyridine (10.7 mg, 0.040 mmol), which was evacuated and backfilled with nitrogen gas followed by 1,4-dioxane (0.88 mL). This mixture was degassed with nitrogen gas for 10 minutes and stirred. The resulting solution containing the nickel complex was added to the suspension containing all other reagents, and then the resulting mixture was further degassed with nitrogen gas for another 10 minutes. The vessel was then sealed and placed in a rack with stirring and irradiation with 34 W Kessil KSH 150B blue grow lamps and a cooling fan for 17 hours. Upon completion, the reaction mixture was diluted with DCM, filtered, and concentrated. The crude material was taken up in hexanes with a trace of DCM for solubility and purified by silica gel column chromatography on a Teledyne Isco instrument eluting with Hex/DCM 0-100%, then Hex/EtOAc 0-50% to afford tert-butyl 5-(1-(tert-butoxycarbonyl)azetidin-3-yl)-3-isopropyl-1H-pyrrolo[3,2-b]pyridine-1-carboxylate (100 mg, 0.241 mmol, 54.4% yield). LCMS retention time 1.04 [TS]. MS (E$^+$) m/z: 416.3 (M+H). This reaction was repeated several times to obtain larger quantities of material.

Intermediate 649B: tert-butyl 5-(1-(tert-butoxycarbonyl)azetidin-3-yl)-3-isopropyl-2-(4,4,5,5-tetramethyl-1,3,2-dioxaborolan-2-yl)-1H-pyrrolo[3,2-b]pyridine-1-carboxylate

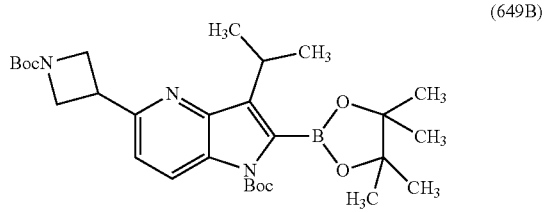 [SMILES: CC(C)c1c(B2OC(C)(C)C(C)(C)O2)n(C(=O)OC(C)(C)C)c2ccc(C3CN(C(=O)OC(C)(C)C)C3)nc12]

(649B)

A solution containing tert-butyl 5-(1-(tert-butoxycarbonyl)azetidin-3-yl)-3-isopropyl-1H-pyrrolo[3,2-b]pyridine-1-carboxylate (456 mg, 1.10 mmol) and 2-isopropoxy-4,4,5,5-tetramethyl-1,3,2-dioxaborolane (448 µL, 2.195 mmol) in dry THF (5.5 mL) under a nitrogen atmosphere was cooled in a dry ice/acetone bath to −78° C. and treated with LDA (2M in THF, 2.75 mL, 5.50 mmol). The mixture was allowed to warm to −30° C. over 30 min and stirred at −30° C. for 30 min. The reaction was then quenched with saturated aqueous NH₄Cl solution, water, and DCM. The organic layer was separated, dried over sodium sulfate, filtered and concentrated. The crude material was combined with the crude material from a similar experiment following the same procedure using 100 mg (0.241 mmol) of starting material tert-butyl 5-(1-(tert-butoxycarbonyl)azetidin-3-yl)-3-isopropyl-1H-pyrrolo[3,2-b]pyridine-1-carboxylate. The combined crude materials were purified by silica gel column chromatography on a Teledyne Isco instrument loading in hexanes and eluting with Hex/EtOAc 0-50% to afford tert-butyl 5-(1-(tert-butoxycarbonyl)azetidin-3-yl)-3-isopropyl-2-(4,4,5,5-tetramethyl-1,3,2-dioxaborolan-2-yl)-1H-pyrrolo[3,2-b]pyridine-1-carboxylate (340 mg) combined from both experiments. LCMS retention time 1.18 [TS]. MS (E⁺) m/z: 542.3 (M+H). ¹H NMR (499 MHz, CHLOROFORM-d) δ 7.96 (d, J=8.4 Hz, 1H), 7.03 (d, J=8.5 Hz, 1H), 4.34-4.27 (m, 2H), 4.27-4.22 (m, 2H), 3.99-3.89 (m, 1H), 3.37-3.26 (m, 1H), 1.66 (s, 9H), 1.47 (s, 9H), 1.48 (br d, J=7.0 Hz, 6H), 1.44 (s, 12H).

Intermediate 649C: tert-butyl 3-(3-isopropyl-2-(4,4,5,5-tetramethyl-1,3,2-dioxaborolan-2-yl)-1H-pyrrolo[3,2-b]pyridin-5-yl)azetidine-1-carboxylate

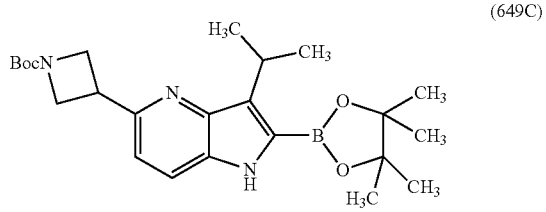 [SMILES: CC(C)c1c(B2OC(C)(C)C(C)(C)O2)[nH]c2ccc(C3CN(C(=O)OC(C)(C)C)C3)nc12]

(649C)

In a reaction vial with a pressure-relief septum-lined cap and stir bar, neat tert-butyl 5-(1-(tert-butoxycarbonyl)azetidin-3-yl)-3-isopropyl-2-(4,4,5,5-tetramethyl-1,3,2-dioxaborolan-2-yl)-1H-pyrrolo[3,2-b]pyridine-1-carboxylate (340 mg, 0.628 mmol) under a nitrogen atmosphere was heated to 160° C. with slow stirring for 45 minutes. Upon completion, the material was dissolved in DCM and concentrated to afford tert-butyl 3-(3-isopropyl-2-(4,4,5,5-tetramethyl-1,3,2-dioxaborolan-2-yl)-1H-pyrrolo[3,2-b]pyridin-5-yl)azetidine-1-carboxylate as an off-white foam considered to be quantitative yield. Carried forward as is. Note: material converted to the free boronic acid on LCMS and was observed as such, although NMR indicated that the product was purely the compound. LCMS retention time (boronic acid) 0.67 [TS]. MS (E⁺) m/z: 360.2 (M+H, boronic acid). ¹H NMR (499 MHz, CHLOROFORM-d) δ 8.23 (br s, 1H), 7.53 (d, J=8.4 Hz, 1H), 7.01 (d, J=8.5 Hz, 1H), 4.36-4.24 (m, 4H), 4.01-3.92 (m, 1H), 3.73 (spt, J=7.0 Hz, 1H), 1.53 (d, J=7.0 Hz, 6H), 1.48 (s, 9H), 1.36 (s, 12H).

Intermediate 649D: tert-butyl 3-(2-(7,8-dimethyl-[1,2,4]triazolo[1,5-a]pyridin-6-yl)-3-isopropyl-1H-pyrrolo[3,2-b]pyridin-5-yl)azetidine-1-carboxylate

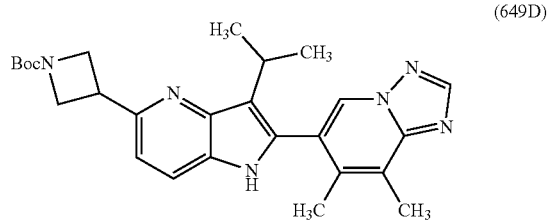 [SMILES: Cc1c(-c2[nH]c3ccc(C4CN(C(=O)OC(C)(C)C)C4)nc3c2C(C)C)cn2ncnc2c1C]

(649D)

To a mixture of tert-butyl 3-(3-isopropyl-2-(4,4,5,5-tetramethyl-1,3,2-dioxaborolan-2-yl)-1H-pyrrolo[3,2-b]pyridin-5-yl)azetidine-1-carboxylate (138 mg, 0.313 mmol), 6-bromo-7,8-dimethyl-[1,2,4]triazolo[1,5-a]pyridine (78 mg, 0.344 mmol), and 2$^{nd}$ generation Xphos precatalyst (12.3 mg, 0.016 mmol) in 1,4-dioxane (2.1 mL) was added aqueous K₃PO₄ (3M, 0.31 mL, 0.93 mmol) and the biphasic mixture was degassed with nitrogen gas for 10 min. The reaction vial was sealed and stirred at 65° C. for 1.5 hours. Upon completion, the reaction mixture was cooled to room temperature and concentrated. The crude material was suspended in DCM and purified by silica gel column chromatography on a Teledyne Isco instrument eluting with Hex/EtOAc 0-100% to afford tert-butyl 3-(2-(7,8-dimethyl-[1,2,4]triazolo[1,5-a]pyridin-6-yl)-3-isopropyl-1H-pyrrolo[3,2-b]pyridin-5-yl)azetidine-1-carboxylate (111 mg, 0.241 mmol, 77% yield). LCMS retention time 0.72 [TS]. MS (E⁺) m/z: 461.3 (M+H).

Example 649

To a solution of tert-butyl 3-(2-(7,8-dimethyl-[1,2,4]triazolo[1,5-a]pyridin-6-yl)-3-isopropyl-1H-pyrrolo[3,2-b]pyridin-5-yl)azetidine-1-carboxylate (111 mg, 0.241 mmol) in DCM (4.8 mL) at room temperature was added 4M HCl in 1,4-dioxane (1.2 mL, 4.80 mmol). The reaction mixture was stirred at room temperature for 5 minutes. Upon completion, the reaction mixture was concentrated to afford 6-(5-(azetidin-3-yl)-3-isopropyl-1H-pyrrolo[3,2-b]pyridin-2-yl)-7,8-dimethyl-[1,2,4]triazolo[1,5-a]pyridine, HCl (0.241 mmol) in recovery considered to be quantitative. The majority of this material was carried forward as is. An aliquot of this material (approximated to be 0.012 mmol) was purified via preparative LC/MS with the following conditions: Column: Xbridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-90% B over 20 minutes, then a 4-minute hold at 100% B; Flow: 20 mL/min. The fractions containing the product were combined and dried via centrifugal evaporation to afford 6-(5-(azetidin-3-yl)-3-isopropyl-1H-pyrrolo[3,2-b]pyridin-2-yl)-7,8-dimethyl-[1,2,4]triazolo[1,5-a]pyridine (2.5 mg, 6.80 µmol). LCMS retention time 0.69 [QC-ACN-TFA-XB]. MS (E$^+$) m/z: 361.3 (M+H). $^1$H NMR (500 MHz, DMSO-d$_6$) δ 8.80 (s, 1H), 8.47 (s, 1H), 7.65 (d, J=8.2 Hz, 1H), 7.08 (d, J=8.5 Hz, 1H), 4.18-4.09 (m, 1H), 4.09-3.96 (m, 2H), 3.91-3.80 (m, 2H), 2.96-2.87 (m, 1H), 2.59 (s, 3H), 2.16 (s, 3H), 1.42 (br d, J=6.7 Hz, 6H).

Example 653

6-(3-isopropyl-5-(1-(2-(methylsulfonyl)ethyl)azetidin-3-yl)-1H-pyrrolo[3,2-b]pyridin-2-yl)-7,8-dimethyl-[1,2,4]triazolo[1,5-a]pyridine

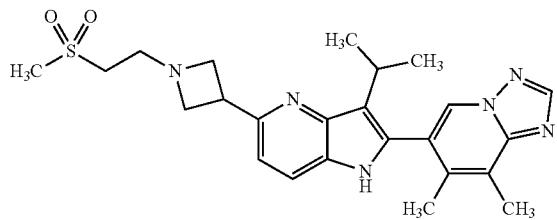

(653)

To a solution of 6-(5-(azetidin-3-yl)-3-isopropyl-1H-pyrrolo[3,2-b]pyridin-2-yl)-7,8-dimethyl-[1,2,4]triazolo[1,5-a]pyridine, HCl (18.26 mg, 0.046 mmol) in DMF (1 mL) was added Et$_3$N (0.032 mL, 0.230 mmol) and 1-bromo-2-(methylsulfonyl)ethane (12.9 mg, 0.069 mmol). The resulting solution was stirred for 90 minutes at room temperature, and then another aliquot of 1-bromo-2-(methylsulfonyl)ethane (12.9 mg, 0.069 mmol) was added. The reaction mixture was stirred for 60 minutes more and then diluted with a few drops of water, DMF, and purified via preparative LC/MS with the following conditions: Column: Xbridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-100% B over 20 minutes, then a 4-minute hold at 100% B; Flow: 20 mL/min. The fractions containing the product were combined and dried via centrifugal evaporation to afford 6-(3-isopropyl-5-(1-(2-(methylsulfonyl)ethyl)azetidin-3-yl)-1H-pyrrolo[3,2-b]pyridin-2-yl)-7,8-dimethyl-[1,2,4]triazolo[1,5-a]pyridine (15.7 mg, 0.033 mmol, 71.7% yield). LCMS retention time 0.8 min [QC-ACN-TFA-XB]. MS (E$^+$) m/z: 467.4 (M+H). $^1$H NMR (500 MHz, DMSO-d$_6$) δ 11.17 (s, 1H), 8.76 (s, 1H), 8.46 (s, 1H), 7.63 (d, J=8.2 Hz, 1H), 7.08 (d, J=8.2 Hz, 1H), 3.83 (quin, J=7.6 Hz, 1H), 3.75-3.69 (m, 2H), 3.38 (t, J=7.2 Hz, 2H), 3.20-3.12 (m, 2H), 3.05 (s, 3H), 2.93-2.83 (m, 3H), 2.58 (s, 3H), 2.15 (s, 3H), 1.40 (br d, J=7.0 Hz, 6H).

Example 660

4-isopropyl-2-(3-isopropyl-2-(8-methoxy-[1,2,4]triazolo[1,5-a]pyridin-6-yl)-1H-pyrrolo[3,2-b]pyridin-5-yl)morpholine

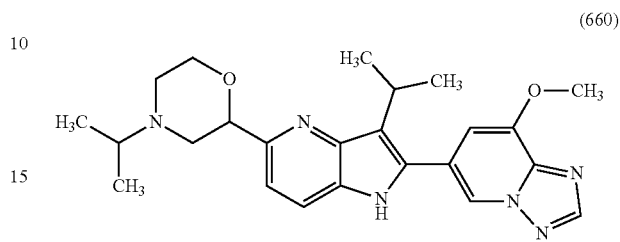

(660)

2-(3-isopropyl-2-(8-methoxy-[1,2,4]triazolo[1,5-a]pyridin-6-yl)-1H-pyrrolo[3,2-b]pyridin-5-yl)morpholine, TFA (22.99 mg, 0.0454 mmol) and Et$_3$N (0.05 mL, 0.359 mmol) were mixed in DMF (0.454 mL). Acetone (0.018 mL, 0.245 mmol) was added to the reaction vial followed by sodium triacetoxyborohydride (28.9 mg, 0.136 mmol) and the reaction mixture was stirred for 17 hours at room temperature. At this time, another aliquot of acetone (0.018 mL, 0.245 mmol) and sodium triacetoxyborohydride (28.9 mg, 0.136 mmol) were each added. The reaction mixture was stirred for 7 hours more at room temperature. The reaction was quenched by the addition of water, 1.5 M aqueous K$_2$HPO$_4$ solution, and DCM. The organic layer was separated, concentrated, and diluted with DMSO. The material was purified via preparative LC/MS with the following conditions: Column: Xbridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 11% B, 11-51% B over 20 minutes, then a 4-minute hold at 100% B; Flow Rate: 20 mL/min; Column Temperature: 25° C. Fraction collection was triggered by MS and UV signals. Fractions containing the product were combined and dried via centrifugal evaporation. The material was further purified via preparative LC/MS with the following conditions: Column: Xbridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 12% B, 1$^{2-35}$% B over 25 minutes, then a 2-minute hold at 100% B; Flow Rate: 20 mL/min; Column Temperature: 25° C. Fraction collection was triggered by UV signals. Fractions containing the product were combined and dried via centrifugal evaporation. The material was further purified via preparative LC/MS with the following conditions: Column: Xbridge C18, 200 mm×30 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 10% B, 10-50% B over 20 minutes, then a 2-minute hold at 100% B; Flow Rate: 45 mL/min; Column Temperature: 25° C. Fraction collection was triggered by MS and UV signals. Fractions containing the product were combined and dried via centrifugal evaporation. The material was further purified via preparative LC/MS with the following conditions: Column: Xbridge C18,200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 11% B, 11-35% B over 25 minutes, then a 2-minute hold at 100% B; Flow Rate: 20 mL/min; Column Temperature: 25° C. Fraction collection was triggered by UV signals. The fractions containing the product were combined and dried via centrifugal evaporation to afford 4-isopropyl-2-(3-isopropyl-2-(8-methoxy-[1,2,4]triazolo[1,5-a]pyridin-6-yl)-1H-pyrrolo[3,2-b]pyridin-5-yl)morpholine, TFA (10.5 mg, 0.019 mmol, 41.2% yield). LCMS retention time 1.02 [QC-ACN-TFA-XB]. MS (E+) m/z: 435.1 (M+H). $^1$H NMR (500 MHz, DMSO-d$_6$) δ 11.49 (br s, 1H), 8.61 (s, 1H), 8.48 (s, 1H), 7.82 (br d, J=8.3 Hz, 1H), 7.32 (br d, J=8.4 Hz, 1H), 7.17 (s, 1H), 5.06-4.89 (m, 1H), 4.36-4.17 (m, 1H), 4.08 (s, 3H), 4.01 (br t, J=12.1 Hz, 1H), 3.77-3.15 (m, 6H), 1.58-1.47 (m, 6H), 1.40-1.26 (m, 6H).

Example 671

2-(3-isopropyl-2-(8-methoxy-[1,2,4]triazolo[1,5-a]pyridin-6-yl)-1H-pyrrolo[3,2-b]pyridin-5-yl)morpholine

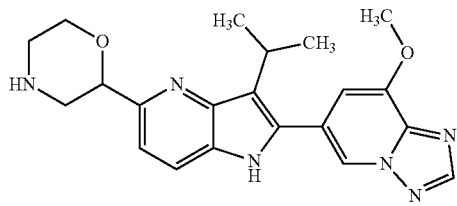

(671)

Intermediate 671A: tert-butyl 2-(1-(tert-butoxycarbonyl)-3-isopropyl-1H-pyrrolo[3,2-b]pyridin-5-yl)morpholine-4-carboxylate

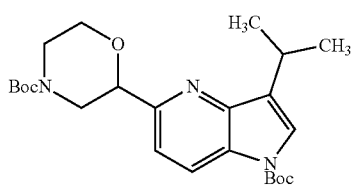

(671A)

A solution of tert-butyl 5-bromo-3-isopropyl-1H-pyrrolo[3,2-b]pyridine-1-carboxylate (0.925 g, 2.73 mmol), 4-(tert-butoxycarbonyl)morpholine-2-carboxylic acid (0.946 g, 4.09 mmol), [Ir(dF(Me)ppy)$_2$(dtbbpy)]PF$_6$ (0.028 g, 0.027 mmol), 2-tert-butyl-1,1,3,3-tetramethylguanidine (0.701 g, 4.09 mmol), nickel(II) chloride ethylene glycol dimethyl ether complex (0.030 g, 0.136 mmol), 4,4'-di-tert-butyl-2,2'-bipyridine (0.037 g, 0.136 mmol) in DMSO (27.3 mL) in a vial with a pressure-relief septum-lined cap and stir bar was degassed with nitrogen for 15 minutes. The resulting solution was sealed and placed in a rack with stirring and irradiation with 34 W Kessil KSH 150B blue grow lamps and a cooling fan for 68 hours. This reaction was set up in duplicate vials side by side. Upon completion, the duplicate reaction vials were combined and diluted with water and DCM. The organic layer was washed with water three times, dried over sodium sulfate, filtered, and concentrated to afford a crude brown oil. This material was purified by silica gel column chromatography on a Teledyne Isco instrument eluting with Hex/EtOAc 0-50% to afford tert-butyl 2-(1-(tert-butoxycarbonyl)-3-isopropyl-1H-pyrrolo[3,2-b]pyridin-5-yl)morpholine-4-carboxylate (1.7 g). LCMS retention time 1.23 [TS]. MS (E+) m/z: 446.3 (M+H). $^1$H NMR (400 MHz, CHLOROFORM-d) δ 8.29 (br s, 1H), 7.51 (br s, 1H), 7.39 (d, J=8.5 Hz, 1H), 4.64 (dd, J=10.5, 2.7 Hz, 1H), 4.55-4.25 (m, 1H), 4.16-3.88 (m, 2H), 3.76 (td, J=11.7, 2.4 Hz, 1H), 3.38-3.25 (m, 1H), 3.18-3.01 (m, 1H), 3.00-2.91 (m, 1H), 1.67 (s, 9H), 1.49 (s, 9H), 1.38 (d, J=6.6 Hz, 6H).

Intermediate 671B: tert-butyl 2-(1-(tert-butoxycarbonyl)-3-isopropyl-2-(4,4,5,5-tetramethyl-1,3,2-dioxaborolan-2-yl)-1H-pyrrolo[3,2-b]pyridin-5-yl)morpholine-4-carboxylate

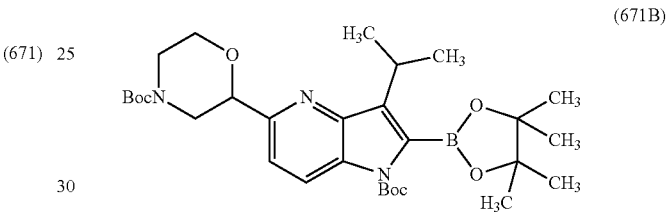

(671B)

A solution containing tert-butyl 2-(1-(tert-butoxycarbonyl)-3-isopropyl-1H-pyrrolo[3,2-b]pyridin-5-yl)morpholine-4-carboxylate (1.67 g, 3.75 mmol) and 2-isopropoxy-4,4,5,5-tetramethyl-1,3,2-dioxaborolane (0.918 mL, 4.50 mmol) in dry THF (19 mL) under a nitrogen atmosphere was cooled in a dry ice/acetone bath to −78° C. and treated with LDA (2M in THF, 2.81 mL, 5.62 mmol). The mixture was allowed to warm to −20° C. slowly over 2 hours. The reaction mixture was then re-cooled to −60° C. and additional 2-isopropoxy-4,4,5,5-tetramethyl-1,3,2-dioxaborolane (0.31 mL, 1.52 mmol) and LDA (2M in THF, 0.93 mL, 1.86 mmol) were added sequentially. The reaction mixture darkened, the bath was quickly changed to a −40° C. bath, and the reaction was quickly finished. Upon completion, the reaction mixture was treated with saturated aqueous NH$_4$Cl solution, water, and DCM. The organic layer was separated, dried over sodium sulfate, filtered and concentrated. The crude isolate was purified via silica gel column chromatography on a Teledyne Isco instrument eluting with Hex/EtOAc 0-50%. Concentration of the fractions containing product provided tert-butyl 2-(1-(tert-butoxycarbonyl)-3-isopropyl-2-(4,4,5,5-tetramethyl-1,3,2-dioxaborolan-2-yl)-1H-pyrrolo[3,2-b]pyridin-5-yl)morpholine-4-carboxylate (1.65 g, 2.89 mmol, 77% yield). LCMS retention time 1.32 [TS]. MS (E+) m/z: 572.5 (M+H). $^1$H NMR (499 MHz, CHLOROFORM-d) δ 8.01 (d, J=8.7 Hz, 1H), 7.32 (d, J=8.6 Hz, 1H), 4.67-4.55 (m, 1H), 4.54-4.34 (m, 1H), 4.16-3.84 (m, 2H), 3.81-3.70 (m, 1H), 3.36-3.26 (m, 1H), 3.16-2.90 (m, 2H), 1.66 (s, 9H), 1.50 (s, 9H), 1.46-1.42 (m, 18H).

Intermediate 671C: tert-butyl 2-(3-isopropyl-2-(4,4,5,5-tetramethyl-1,3,2-dioxaborolan-2-yl)-1H-pyrrolo[3,2-b]pyridin-5-yl)morpholine-4-carboxylate

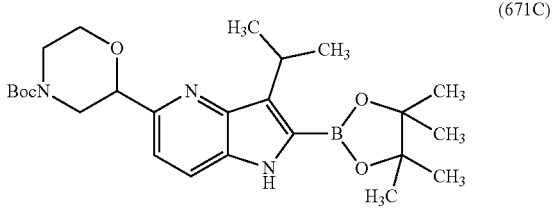 [SMILES: CC(C)c1c(B2OC(C)(C)C(C)(C)O2)[nH]c2ccc(C3CN(C(=O)OC(C)(C)C)CCO3)nc12]
(671C)

A vial with a pressure-relief septum-lined cap containing tert-butyl 2-(1-(tert-butoxycarbonyl)-3-isopropyl-2-(4,4,5,5-tetramethyl-1,3,2-dioxaborolan-2-yl)-1H-pyrrolo[3,2-b]pyridin-5-yl)morpholine-4-carboxylate (1.65 g, 2.89 mmol) was heated with slow stirring at 165° C. under nitrogen atmosphere with an inlet of nitrogen gas from a manifold line and then remained at room temperature overnight. Heating was then resumed for 90 minutes until the material had formed a brown melt that solidified into a brown glass upon cooling to room temperature. The material was dissolved in DCM, transferred to a round bottom flask, and concentrated to obtain an off-white foam, tert-butyl 2-(3-isopropyl-2-(4,4,5,5-tetramethyl-1,3,2-dioxaborolan-2-yl)-1H-pyrrolo[3,2-b]pyridin-5-yl)morpholine-4-carboxylate, treated as quantitative recovery (2.88 mmol) and carried forward as is. Note: observed conversion to boronic acid when analyzed on LCMS, although NMR indicated that the product was purely the compound. LCMS retention time 0.73 (boronic acid) [TS]. MS (ES$^+$) m/z: 390.2 (boronic acid). $^1$H NMR (499 MHz, CHLOROFORM-d) δ 8.27 (br s, 1H), 7.58 (d, J=8.5 Hz, 1H), 7.30 (d, J=8.5 Hz, 1H), 4.65-4.61 (m, 1H), 4.59-4.32 (m, 1H), 4.13-3.86 (m, 2H), 3.82-3.67 (m, 2H), 3.04 (br dd, J=13.4, 10.7 Hz, 2H), 1.52-1.48 (m, 15H), 1.36 (s, 12H).

Intermediate 671D: tert-butyl 2-(3-isopropyl-2-(8-methoxy-[1,2,4]triazolo[1,5-a]pyridin-6-yl)-1H-pyrrolo[3,2-b]pyridin-5-yl)morpholine-4-carboxylate

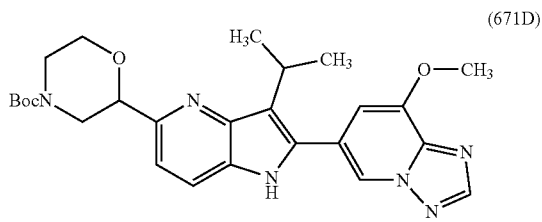 [SMILES: COc1cc(-c2[nH]c3ccc(C4CN(C(=O)OC(C)(C)C)CCO4)nc3c2C(C)C)cn2ncnc12]
(671D)

To a solution of tert-butyl 2-(3-isopropyl-2-(4,4,5,5-tetramethyl-1,3,2-dioxaborolan-2-yl)-1H-pyrrolo[3,2-b]pyridin-5-yl)morpholine-4-carboxylate (197 mg, 0.418 mmol), 6-bromo-8-methoxy-[1,2,4]triazolo[1,5-a]pyridine (105 mg, 0.460 mmol), and 2$^{nd}$ generation Xphos precatalyst (16.4 mg, 0.021 mmol) in 1,4-dioxane (2.8 mL) was added aqueous K$_3$PO$_4$ (2M, 627 µl, 1.254 mmol), and the biphasic mixture was degassed with nitrogen for 5 min. The reaction vessel was sealed and stirred at 70° C. for 2 hours. Upon completion, the reaction mixture was cooled to room temperature and concentrated. The crude material was suspended in DCM and purified by silica gel column chromatography on a Teledyne Isco instrument eluting with Hex/EtOAc 0-100% to give tert-butyl 2-(3-isopropyl-2-(8-methoxy-[1,2,4]triazolo[1,5-a]pyridin-6-yl)-1H-pyrrolo[3,2-b]pyridin-5-yl)morpholine-4-carboxylate (177 mg, 0.359 mmol, 86% yield). LCMS retention time 0.82 [TS]. MS (ES$^+$) m/z: 493.6 (M+H).

Example 671

To a solution of tert-butyl 2-(3-isopropyl-2-(8-methoxy-[1,2,4]triazolo[1,5-a]pyridin-6-yl)-1H-pyrrolo[3,2-b]pyridin-5-yl)morpholine-4-carboxylate (8.9 mg, 0.018 mmol) in DCM (0.5 mL) at room temperature was added TFA (0.5 mL). The reaction mixture was concentrated after 30 minutes to give crude material which was taken up in DMF with a few drops of Et$_3$N and purified via preparative LC/MS with the following conditions: Column: Xbridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 3-40% B over 20 minutes, then a 4-minute hold at 100% B; Flow: 20 mL/min. The fractions containing the product were combined and dried via centrifugal evaporation to afford 2-(3-isopropyl-2-(8-methoxy-[1,2,4]triazolo[1,5-a]pyridin-6-yl)-1H-pyrrolo[3,2-b]pyridin-5-yl)morpholine (5.3 mg, 0.013 mmol, 72.4% yield). LCMS retention time 0.97 [QC-ACN-AA-XB]. MS (E$^+$) m/z: 393.1. $^1$H NMR (500 MHz, DMSO-d$_6$) δ 11.43 (s, 1H), 8.62 (s, 1H), 8.51 (s, 1H), 7.73 (br d, J=8.5 Hz, 1H), 7.22 (br d, J=8.2 Hz, 1H), 7.18 (s, 1H), 4.57 (br d, J=8.5 Hz, 1H), 4.07 (s, 3H), 3.93 (br d, J=10.4 Hz, 1H), 3.74-3.62 (m, 1H), 3.56-3.44 (m, 1H), 3.36-3.23 (m, 1H), 3.23-3.16 (m, 1H), 2.81 (br s, 2H), 2.71 (br t, J=11.3 Hz, 1H), 1.52 (br d, J=6.7 Hz, 6H). For the derivatization of this material, this procedure was repeated on larger scale as described here: To a solution of tert-butyl 2-(3-isopropyl-2-(8-methoxy-[1,2,4]triazolo[1,5-a]pyridin-6-yl)-1H-pyrrolo[3,2-b]pyridin-5-yl)morpholine-4-carboxylate (112 mg, 0.227 mmol) in DCM (6 mL) at room temperature was added TFA (3 mL). The reaction mixture was concentrated after 30 minutes to give material considered quantitative recovery of 2-(3-isopropyl-2-(8-methoxy-[1,2,4]triazolo[1,5-a]pyridin-6-yl)-1H-pyrrolo[3,2-b]pyridin-5-yl)morpholine, TFA (0.227 mmol). Carried forward as is.

Example 680

6-(3-isopropyl-5-(piperazin-2-yl)-1H-pyrrolo[3,2-b]pyridin-2-yl)-7,8-dimethyl-[1,2,4]triazolo[1,5-a]pyridine

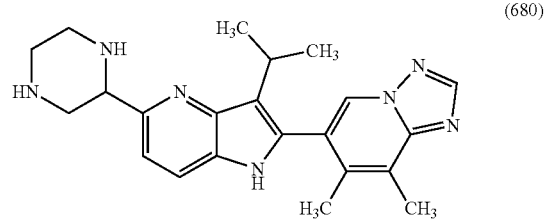 [SMILES: Cc1c(-c2[nH]c3ccc(C4CNCCN4)nc3c2C(C)C)cn2ncnc2c1C]
(680)

A mixture of tert-butyl 5-bromo-2-(7,8-dimethyl-[1,2,4]triazolo[1,5-a]pyridin-6-yl)-3-isopropyl-1H-pyrrolo[3,2-b]pyridine-1-carboxylate (72.3 mg, 0.100 mmol), 1,4-bis(tert-butoxycarbonyl)piperazine-2-carboxylic acid (49.6 mg, 0.150 mmol), [Ir(dF(Me)ppy)$_2$(dtbbpy)]PF$_6$ (1.0 mg, 1.000 µmol), 2-tert-butyl-1,1,3,3-tetramethylguanidine (25.7 mg, 0.150 mmol), nickel(II) chloride ethylene glycol dimethyl ether complex (1.1 mg, 5.00 µmol), and 4,4'-di-tert-butyl-2,2'-bipyridine (1.3 mg, 5.00 µmol) in DMSO (3 mL) in a vial with a pressure-relief septum-lined cap and stir bar was degassed with nitrogen for 15 minutes. The resulting mixture was sealed and placed in a rack with stirring and irradiation with 34 W Kessil KSH 150B blue grow lamps and a cooling fan for 48 hours. Upon completion, the reaction mixture was diluted with water and DCM. The organic layer was washed with water three times, dried over sodium sulfate, filtered, and concentrated to afford a crude brown oil. The crude material was partially purified by silica gel column chromatography on a Teledyne Isco instrument eluting with Hex/EtOAc 0-50% to give material that still contained a significant amount of impurities. This material was carried forward and suspended in DCM (1 mL) and TFA (1 mL) and stirred for 30 minutes at room temperature. Upon completion, the material was concentrated and suspended in TFA (2 mL) with stirring for 3 hours at room temperature. Upon completion, the reaction mixture was concentrated, dissolved in methanol with a few drops of Et$_3$N, and purified via the following conditions: Column: Xbridge C18, 200 mm×30 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 2-minute hold at 100% B; Flow Rate: 45 mL/min; Column Temperature: 25° C. Fraction collection was triggered by MS and UV signals. Fractions containing the product were combined and dried via centrifugal evaporation to afford 6-(3-isopropyl-5-(piperazin-2-yl)-1H-pyrrolo[3,2-b]pyridin-2-yl)-7,8-dimethyl-[1,2,4]triazolo[1,5-a]pyridine, TFA (9.5 mg, 0.019 mmol, 19 yield). LCMS retention time 0.91[QC-ACN-TFA-XB]. MS (E+) m/z: 390.0 (M+H). Select NMR peaks: $^1$H NM/R(500 MHz, DMSO-d$_6$) δ11.60 (s, 1H), 8.82 (s, 1H), 8.48 (s, 1H), 7.86 (d, J=8.5 Hz, 1H), 7.30 (br d, J=8.5 Hz, 1H), 4.83 (br d, J=10.4 Hz, 1H), 3.92 (br d, J=13.4 Hz, 1H), 2.97 (dt, J=13.5, 6.5 Hz, 1H), 2.59 (s, 3H), 2.13 (s, 3H), 1.40 (br d, J=4.9 Hz, 6H)

The following examples were prepared according to the general procedures described in the above examples.

TABLE 1

| Ex. No. | Structure | Mol. Wt. | LCMS M⁺ | Ret Time (min) | HPLC Method |
|---|---|---|---|---|---|
| 12 | 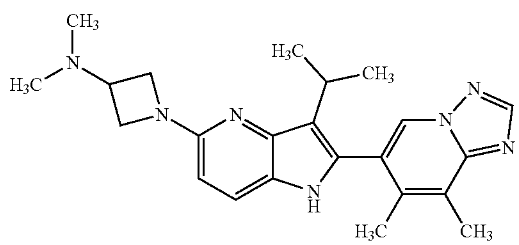 | 403.53 | 404.3 | 1.2 | QC-ACN-AA-XB |
| 13 | 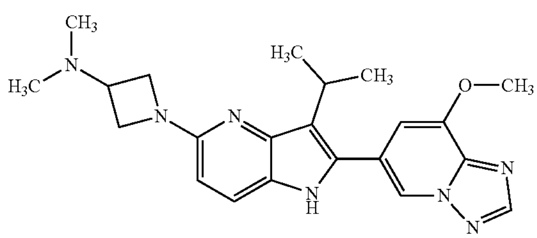 | 405.51 | 406.3 | 0.71 | QC-ACN-TFA-XB |
| 314 | 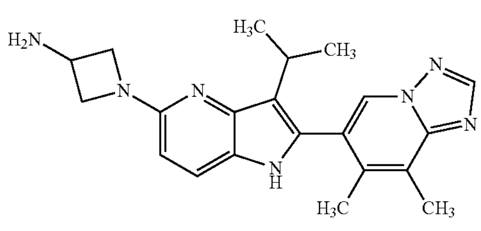 [SMILES: Cc1c(-c2[nH]c3ccc(N4CC(N)C4)nc3c2C(C)C)cn2ncnc2c1C] | 375.48 | 376.3 | 0.96 | QC-ACN-AA-XB |
| 15 | 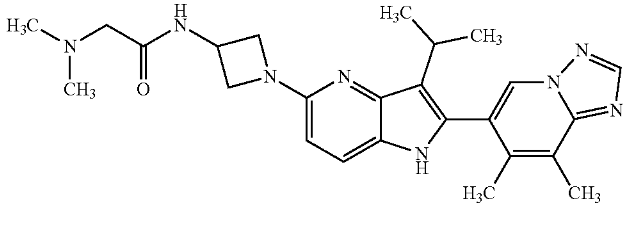 [SMILES: Cc1c(-c2[nH]c3ccc(N4CC(NC(=O)CN(C)C)C4)nc3c2C(C)C)cn2ncnc2c1C] | 460.59 | 461.5 | 0.76 | QC-ACN-TFA-XB |

TABLE 1-continued

| Ex. No. | Structure | Mol. Wt. | LCMS M+ | Ret Time (min) | HPLC Method |
|---|---|---|---|---|---|
| 16 | 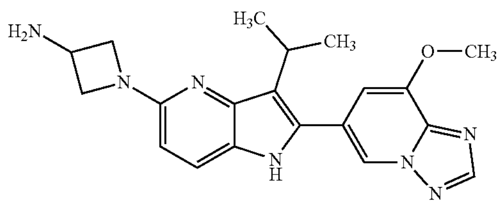 | 377.45 | 378.2 | 0.67 | QC-ACN-TFA-XB |
| 17 | 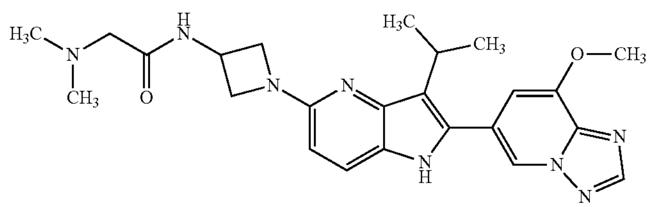 [SMILES: COc1cc(-c2[nH]c3ccc(N4CC(NC(=O)CN(C)C)C4)nc3c2C(C)C)cn2ncnc12] | 462.56 | 463.4 | 1.06 | QC-ACN-AA-XB |
| 18 | 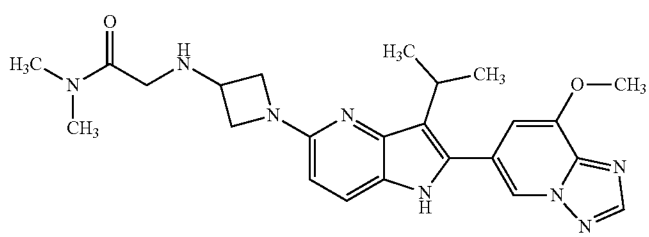 [SMILES: COc1cc(-c2[nH]c3ccc(N4CC(NCC(=O)N(C)C)C4)nc3c2C(C)C)cn2ncnc12] | 462.56 | 463.2 | 0.7 | QC-ACN-TFA-XB |
| 19 | 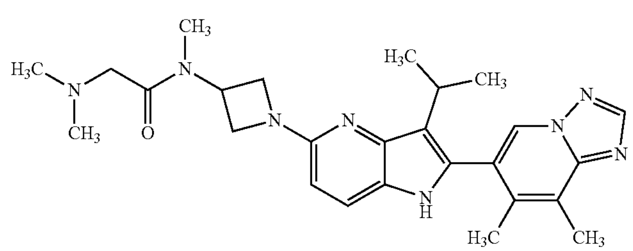 [SMILES: Cc1c(-c2[nH]c3ccc(N4CC(N(C)C(=O)CN(C)C)C4)nc3c2C(C)C)cn2ncnc2c1C] | 474.61 | 475.1 | 1 | QC-ACN-TFA-XB |
| 20 | 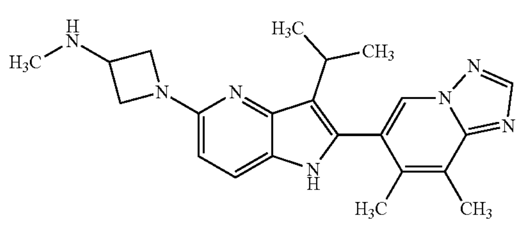 [SMILES: CNC1CN(c2ccc3[nH]c(-c4cn5ncnc5c(C)c4C)c(C(C)C)c3n2)C1] | 389.51 | 390.2 | 1.14 | QC-ACN-AA-XB |
| 21 | 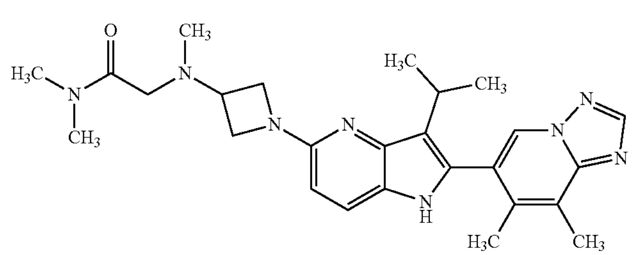 [SMILES: Cc1c(-c2[nH]c3ccc(N4CC(N(C)CC(=O)N(C)C)C4)nc3c2C(C)C)cn2ncnc2c1C] | 474.61 | 475.2 | 0.76 | QC-ACN-TFA-XB |

TABLE 1-continued

| Ex. No. | Structure | Mol. Wt. | LCMS M+ | Ret Time (min) | HPLC Method |
|---|---|---|---|---|---|
| 22 | 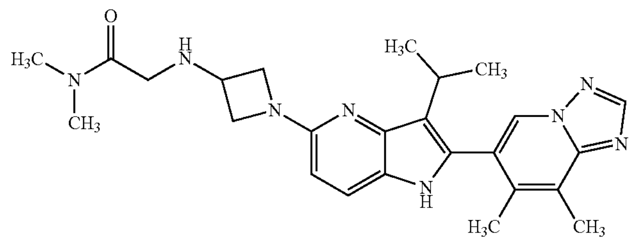 [SMILES: Cc1c(-c2[nH]c3ccc(N4CC(NCC(=O)N(C)C)C4)nc3c2C(C)C)cn2ncnc2c1C] | 460.59 | 460.9 | 0.97 | QC-ACN-TFA-XB |
| 23 | 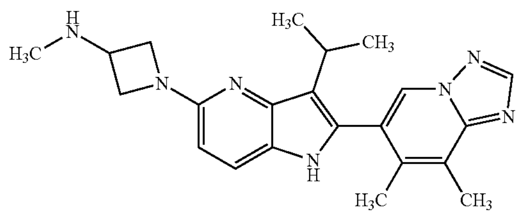 [SMILES: CNC1CN(c2ccc3[nH]c(-c4cn5ncnc5c(C)c4C)c(C(C)C)c3n2)C1] | 389.51 | 390.1 | 1.05 | QC-ACN-TFA-XB |
| 24 | 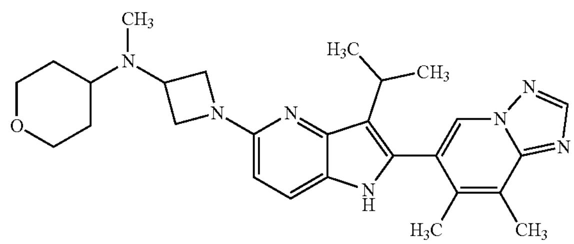 [SMILES: Cc1c(-c2[nH]c3ccc(N4CC(N(C)C5CCOCC5)C4)nc3c2C(C)C)cn2ncnc2c1C] | 473.63 | 474.2 | 1.52 | QC-ACN-AA-XB |
| 25 | 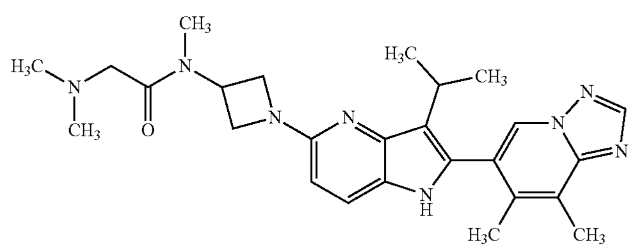 | 474.61 | 475.1 | 1.18 | QC-ACN-TFA-XB |
| 26 | 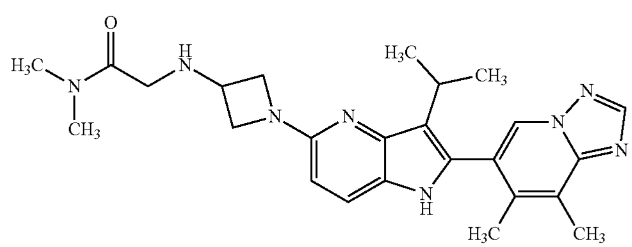 [SMILES: Cc1c(-c2[nH]c3ccc(N4CC(NCC(=O)N(C)C)C4)nc3c2C(C)C)cn2ncnc2c1C] | 460.59 | 460.9 | 0.68 | QC-ACN-TFA-XB |
| 27 | 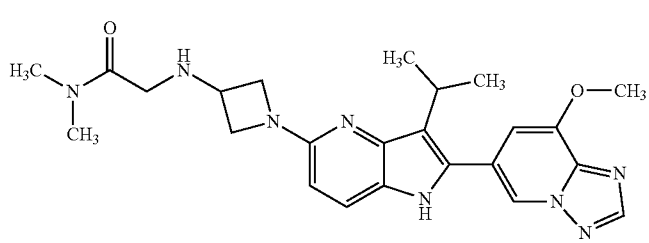 [SMILES: COc1cc(-c2[nH]c3ccc(N4CC(NCC(=O)N(C)C)C4)nc3c2C(C)C)cn2ncnc12] | 462.56 | 463.4 | 0.81 | QC-ACN-AA-XB |

TABLE 1-continued
| Ex. No. | Structure | Mol. Wt. | LCMS M+ | Ret Time (min) | HPLC Method |
|---|---|---|---|---|---|
| 28 | 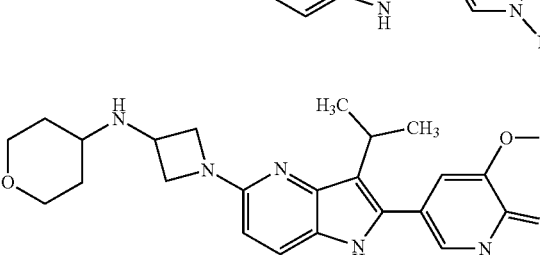 | 476.59 | 477.4 | 1.04 | QC-ACN-AA-XB |
| 29 | 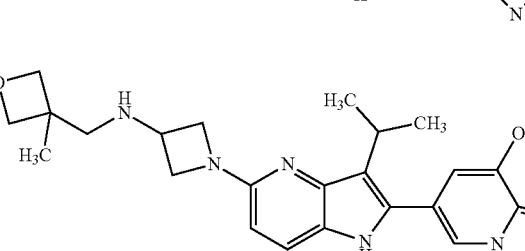 | 461.57 | 462.1 | 0.73 | QC-ACN-TFA-XB |
| 30 | 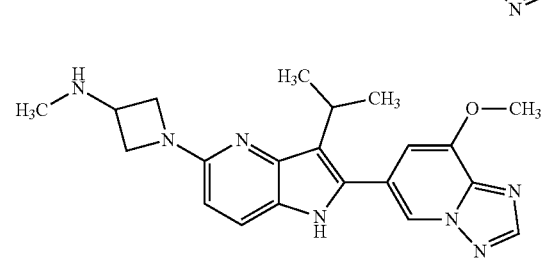 | 461.57 | 462.3 | 1.41 | QC-ACN-AA-XB |
| 31 | 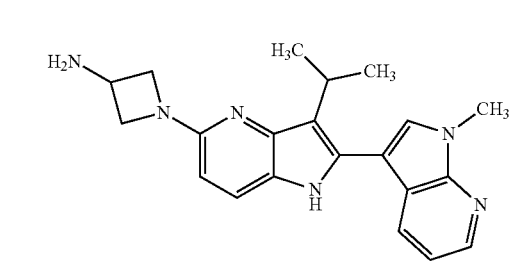 [SMILES: CC(C)c1c(-c2cn(C)c3ncccc23)[nH]c2ccc(N3CC(N)C3)nc12] | 391.48 | 392.2 | 0.67 | QC-ACN-TFA-XB |
| 32 | 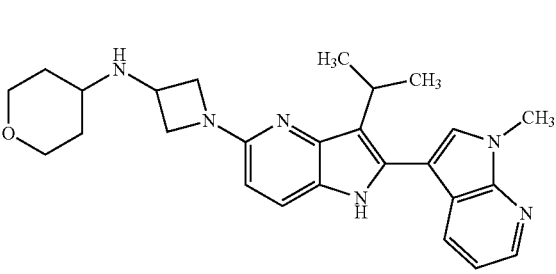 | 360.47 | 361.2 | 1.19 | QC-ACN-AA-XB |
| 33 | 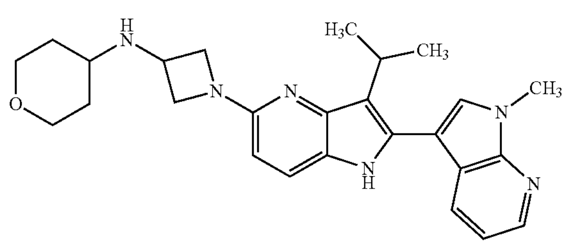 [SMILES: CC(C)c1c(-c2cn(C)c3ncccc23)[nH]c2ccc(N3CC(NC4CCOCC4)C3)nc12] | 444.58 | 445.1 | 1.37 | QC-ACN-AA-XB |

TABLE 1-continued

| Ex. No. | Structure | Mol. Wt. | LCMS M+ | Ret Time (min) | HPLC Method |
|---|---|---|---|---|---|
| 34 | 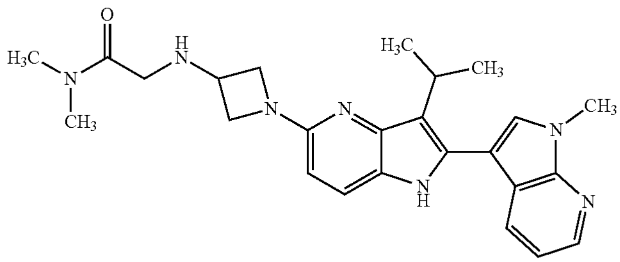 | 445.57 | 446.1 | 0.82 | QC-ACN-TFA-XB |
| 35 | 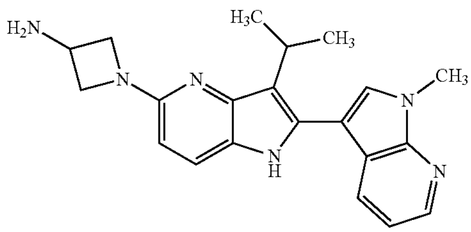 [SMILES: CC(C)c1c(-c2cn(C)c3ncccc23)[nH]c2ccc(N3CC(N)C3)nc12] | 360.47 | 361.1 | 0.82 | QC-ACN-AA-XB |
| 36 | 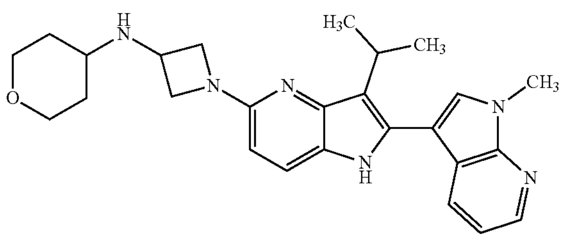 [SMILES: CC(C)c1c(-c2cn(C)c3ncccc23)[nH]c2ccc(N3CC(NC4CCOCC4)C3)nc12] | 444.58 | 445.2 | 1.12 | QC-ACN-AA-XB |
| 37 | 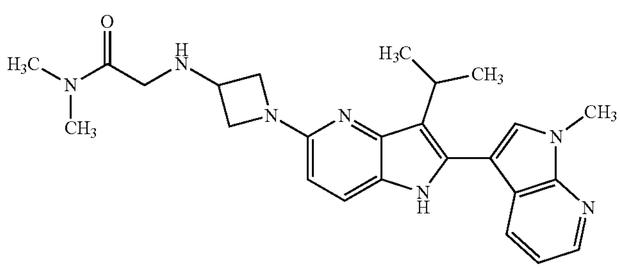 | 445.57 | 446.1 | 0.72 | QC-ACN-TFA-XB |
| 38 | 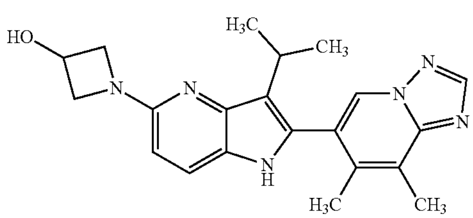 [SMILES: Cc1c(-c2[nH]c3ccc(N4CC(O)C4)nc3c2C(C)C)cn2ncnc2c1C] | 376.46 | 377.2 | 0.88 | QC-ACN-TFA-XB |
| 39 | 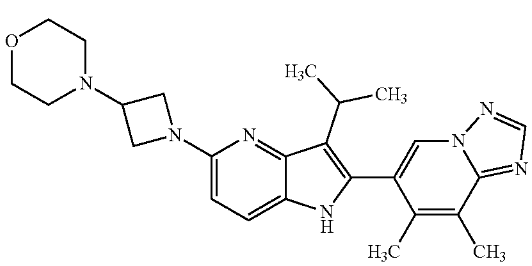 [SMILES: Cc1c(-c2[nH]c3ccc(N4CC(N5CCOCC5)C4)nc3c2C(C)C)cn2ncnc2c1C] | 445.57 | 446.1 | 0.77 | QC-ACN-TFA-XB |

TABLE 1-continued

| Ex. No. | Structure | Mol. Wt. | LCMS M+ | Ret Time (min) | HPLC Method |
|---|---|---|---|---|---|
| 40 | 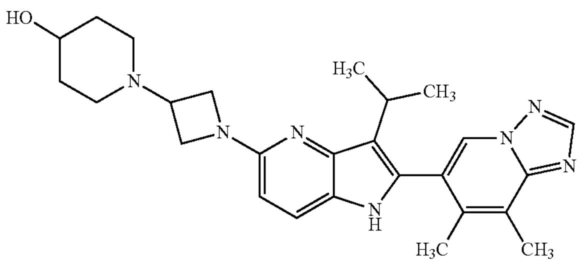 [SMILES: Cc1c(-c2[nH]c3ccc(N4CC(N5CCC(O)CC5)C4)nc3c2C(C)C)cn2ncnc2c1C] | 459.60 | 460.1 | 1.25 | QC-ACN-AA-XB |
| 41 | 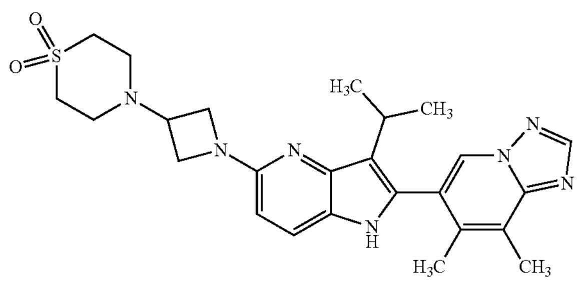 [SMILES: Cc1c(-c2[nH]c3ccc(N4CC(N5CCS(=O)(=O)CC5)C4)nc3c2C(C)C)cn2ncnc2c1C] | 493.63 | 494 | 1.46 | QC-ACN-AA-XB |
| 42 | 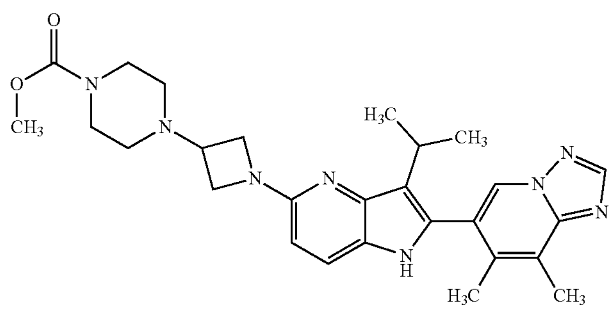 [SMILES: COC(=O)N1CCN(C2CN(c3ccc4[nH]c(-c5cn6ncnc6c(C)c5C)c(C(C)C)c4n3)C2)CC1] | 502.62 | 503.1 | 1.66 | QC-ACN-AA-XB |
| 43 | 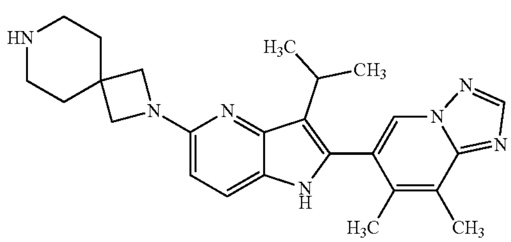 [SMILES: Cc1c(-c2[nH]c3ccc(N4CC5(CCNCC5)C4)nc3c2C(C)C)cn2ncnc2c1C] | 429.57 | 430.4 | 1.1 | QC-ACN-AA-XB |
| 44 | 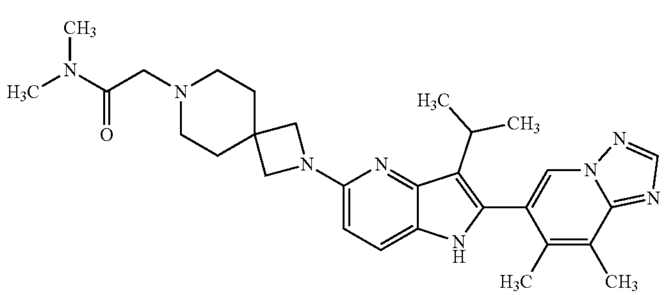 [SMILES: Cc1c(-c2[nH]c3ccc(N4CC5(CCN(CC(=O)N(C)C)CC5)C4)nc3c2C(C)C)cn2ncnc2c1C] | 514.68 | 515.4 | 1.29 | QC-ACN-AA-XB |

TABLE 1-continued

| Ex. No. | Structure | Mol. Wt. | LCMS M+ | Ret Time (min) | HPLC Method |
|---|---|---|---|---|---|
| 45 | 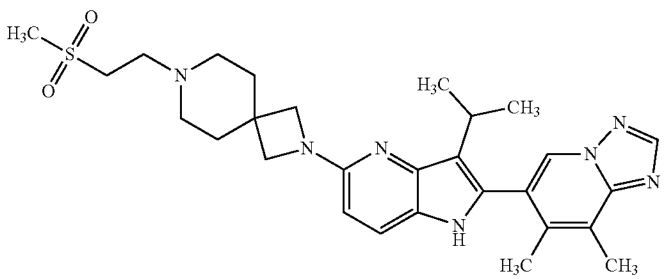 [SMILES: Cc1c(-c2[nH]c3ccc(N4CC5(CCN(CCS(C)(=O)=O)CC5)C4)nc3c2C(C)C)cn2ncnc2c1C] | 535.71 | 536.4 | 0.84 | QC-ACN-TFA-XB |
| 46 | 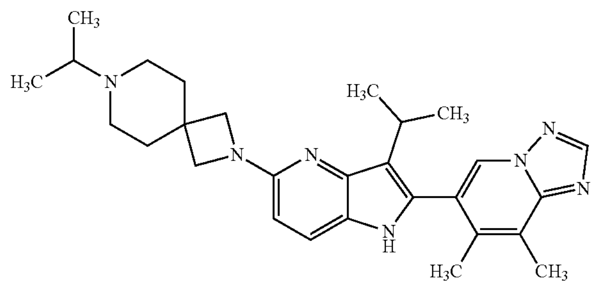 [SMILES: Cc1c(-c2[nH]c3ccc(N4CC5(CCN(C(C)C)CC5)C4)nc3c2C(C)C)cn2ncnc2c1C] | 471.65 | 472.1 | 1.42 | QC-ACN-AA-XB |
| 47 | 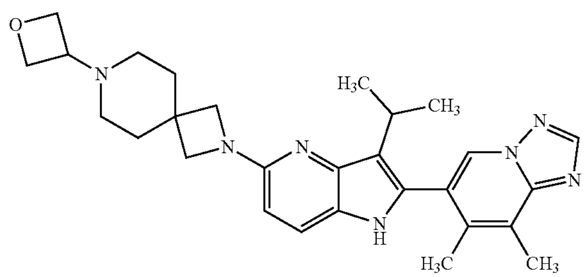 [SMILES: Cc1c(-c2[nH]c3ccc(N4CC5(CCN(C6COC6)CC5)C4)nc3c2C(C)C)cn2ncnc2c1C] | 485.64 | 486.4 | 0.8 | QC-ACN-TFA-XB |
| 48 | 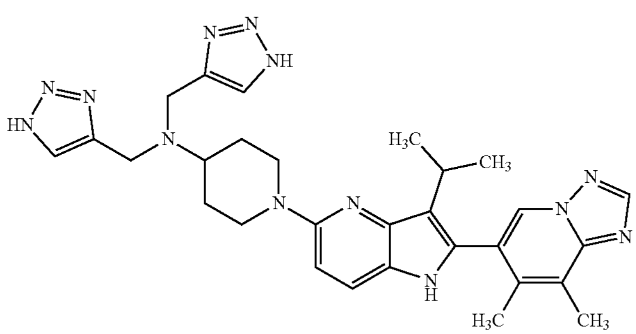 [SMILES: Cc1c(-c2[nH]c3ccc(N4CCC(N(Cc5c[nH]nn5)Cc5c[nH]nn5)CC4)nc3c2C(C)C)cn2ncnc2c1C] | 565.69 | 566.6 | 0.81 | QC-ACN-TFA-XB |
| 49 | 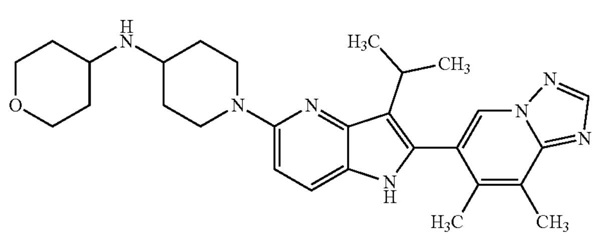 | 487.65 | 488.3 | 1.46 | QC-ACN-AA-XB |

TABLE 1-continued

| Ex. No. | Structure | Mol. Wt. | LCMS M+ | Ret Time (min) | HPLC Method |
|---|---|---|---|---|---|
| 50 | 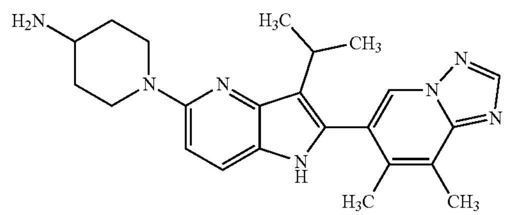 [SMILES: Cc1c(-c2[nH]c3ccc(N4CCC(N)CC4)nc3c2C(C)C)cn2ncnc2c1C] | 403.53 | 404.3 | 0.74 | QC-ACN-TFA-XB |
| 51 | 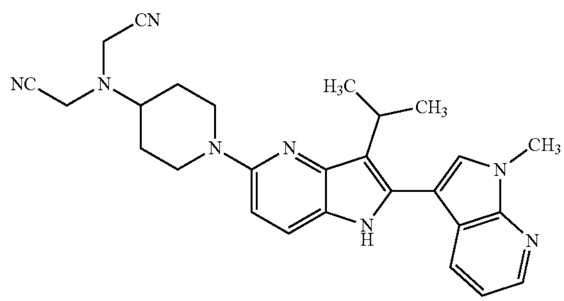 [SMILES: CC(C)c1c(-c2cn(C)c3ncccc23)[nH]c2ccc(N3CCC(N(CC#N)CC#N)CC3)nc12] | 466.59 | 467.2 | 1.27 | QC-ACN-AA-XB |
| 52 | 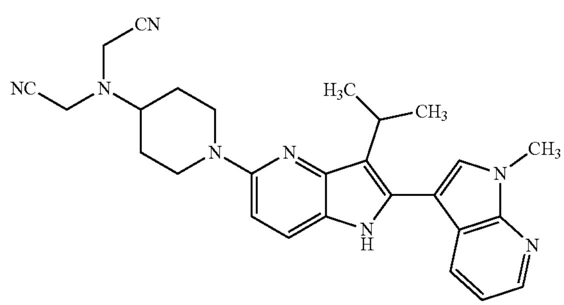 [SMILES: CC(C)c1c(-c2cn(C)c3ncccc23)[nH]c2ccc(N3CCC(N(CC#N)CC#N)CC3)nc12] | 466.59 | 467.2 | 1.36 | QC-ACN-AA-XB |
| 53 | 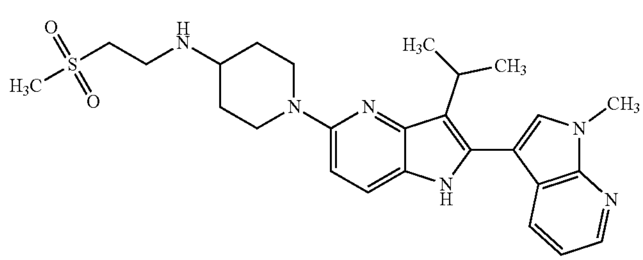 | 494.66 | 495.2 | 1.56 | QC-ACN-AA-XB |
| 54 | 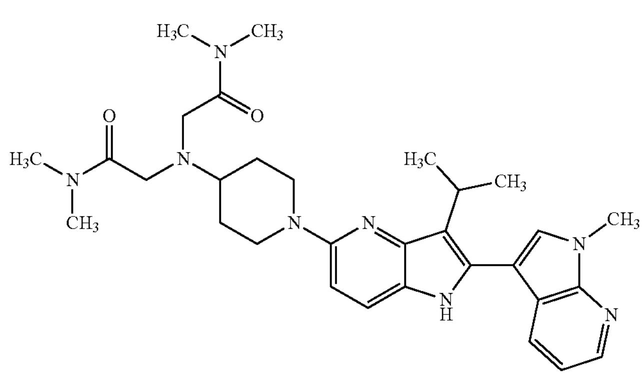 | 558.73 | 559.2 | 1.64 | QC-ACN-AA-XB |

TABLE 1-continued

| Ex. No. | Structure | Mol. Wt. | LCMS M+ | Ret Time (min) | HPLC Method |
|---|---|---|---|---|---|
| 55 | 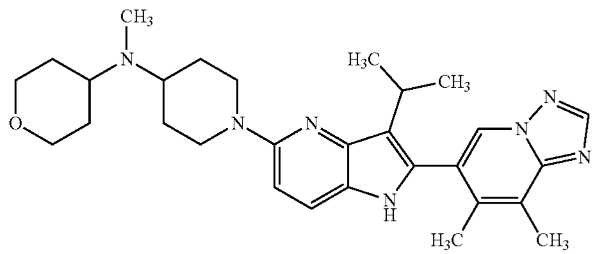 [SMILES: Cc1c(-c2[nH]c3ccc(N4CCC(N(C)C5CCOCC5)CC4)nc3c2C(C)C)cn2ncnc2c1C] | 501.68 | 502.2 | 0.8 | QC-ACN-TFA-XB |
| 56 | 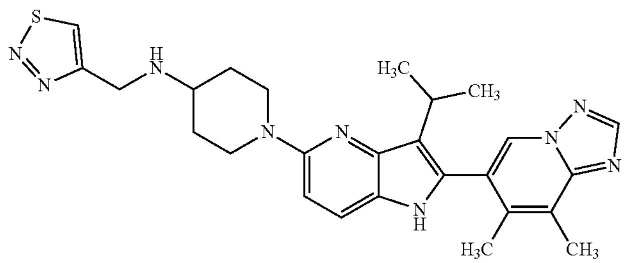 [SMILES: Cc1c(-c2[nH]c3ccc(N4CCC(NCc5csnn5)CC4)nc3c2C(C)C)cn2ncnc2c1C] | 501.66 | 502.2 | 1.62 | QC-ACN-AA-XB |
| 57 | 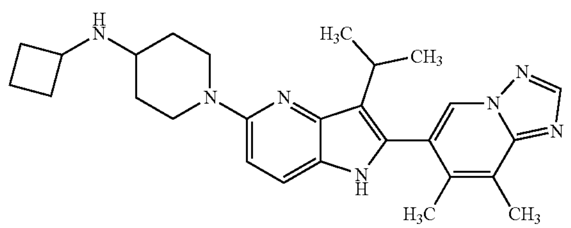 [SMILES: Cc1c(-c2[nH]c3ccc(N4CCC(NC5CCC5)CC4)nc3c2C(C)C)cn2ncnc2c1C] | 457.63 | 458.2 | 0.85 | QC-ACN-TFA-XB |
| 58 | 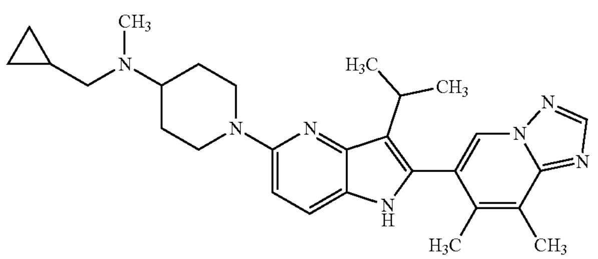 [SMILES: Cc1c(-c2[nH]c3ccc(N4CCC(N(C)CC5CC5)CC4)nc3c2C(C)C)cn2ncnc2c1C] | 471.65 | 472.3 | 0.89 | QC-ACN-TFA-XB |
| 59 | 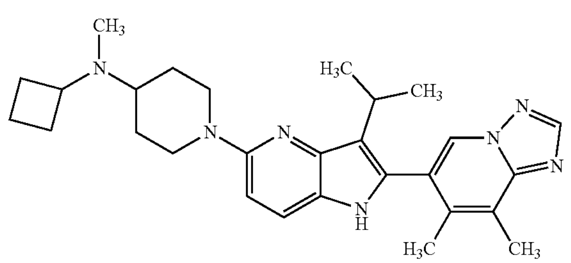 [SMILES: Cc1c(-c2[nH]c3ccc(N4CCC(N(C)C5CCC5)CC4)nc3c2C(C)C)cn2ncnc2c1C] | 471.65 | 471.9 | 1.58 | QC-ACN-AA-XB |
| 60 | 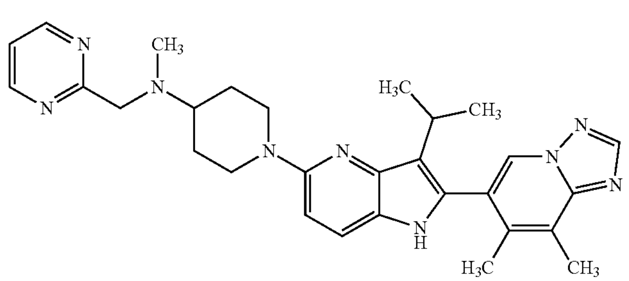 [SMILES: Cc1c(-c2[nH]c3ccc(N4CCC(N(C)Cc5ncccn5)CC4)nc3c2C(C)C)cn2ncnc2c1C] | 509.66 | 510.2 | 1.49 | QC-ACN-AA-XB |

TABLE 1-continued

| Ex. No. | Structure | Mol. Wt. | LCMS M+ | Ret Time (min) | HPLC Method |
|---|---|---|---|---|---|
| 61 | 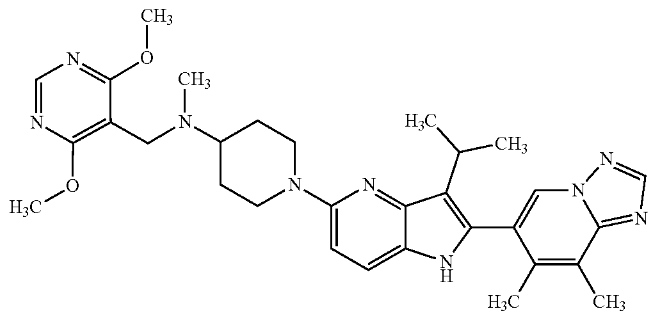 [SMILES: COc1ncnc(OC)c1CN(C)C1CCN(c2ccc3[nH]c(-c4cn5ncnc5c(C)c4C)c(C(C)C)c3n2)CC1] | 569.71 | 570.2 | 1.64 | QC-ACN-AA-XB |
| 62 | 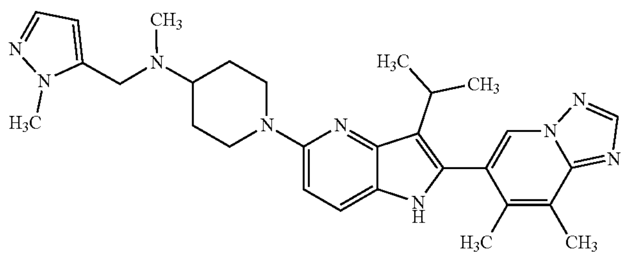 | 511.68 | 512.2 | 0.85 | QC-ACN-TFA-XB |
| 63 | 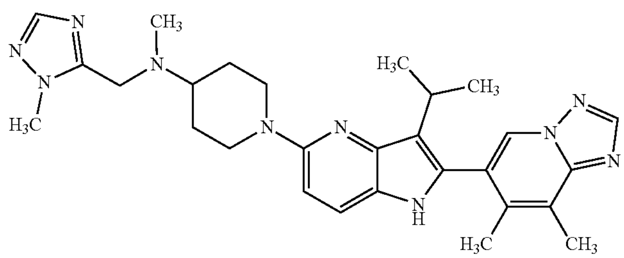 [SMILES: Cc1c(-c2[nH]c3ccc(N4CCC(N(C)Cc5ccnn5C)CC4)nc3c2C(C)C)cn2ncnc2c1C] | 512.67 | 513 | 0.82 | QC-ACN-TFA-XB |
| 64 | 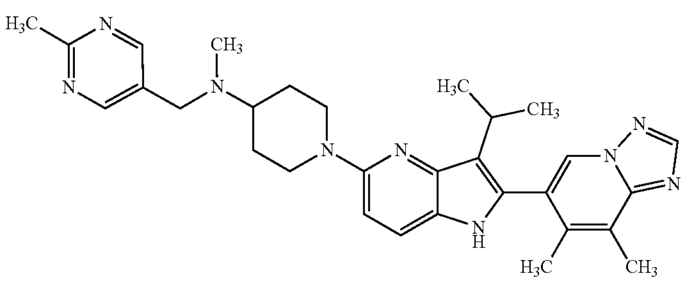 [SMILES: Cc1ncc(CN(C)C2CCN(c3ccc4[nH]c(-c5cn6ncnc6c(C)c5C)c(C(C)C)c4n3)CC2)cn1] | 523.69 | 524.2 | 1.72 | QC-ACN-AA-XB |
| 65 | 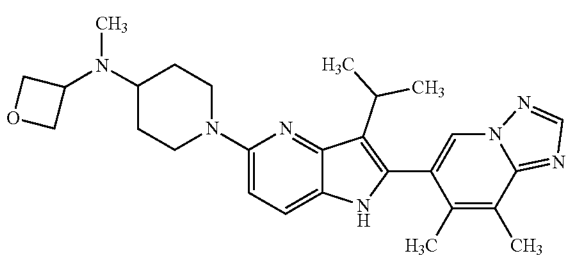 [SMILES: Cc1c(-c2[nH]c3ccc(N4CCC(N(C)C5COC5)CC4)nc3c2C(C)C)cn2ncnc2c1C] | 473.63 | 474.2 | 0.79 | QC-ACN-TFA-XB |

TABLE 1-continued

| Ex. No. | Structure | Mol. Wt. | LCMS M+ | Ret Time (min) | HPLC Method |
|---|---|---|---|---|---|
| 66 | 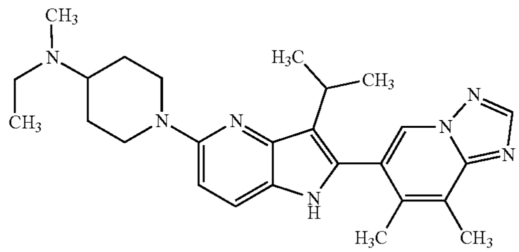 [SMILES: CCN(C)C1CCN(c2ccc3[nH]c(-c4cn5ncnc5c(C)c4C)c(C(C)C)c3n2)CC1] | 445.62 | 446.1 | 1.22 | QC-ACN-AA-XB |
| 67 | 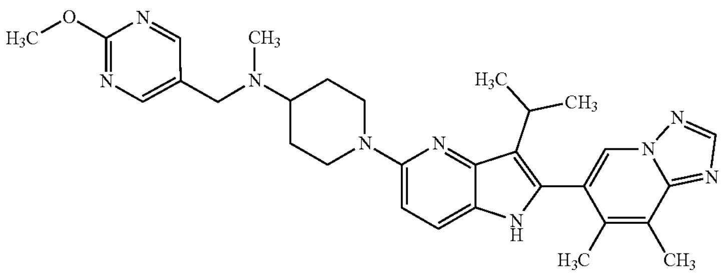 [SMILES: COc1ncc(CN(C)C2CCN(c3ccc4[nH]c(-c5cn6ncnc6c(C)c5C)c(C(C)C)c4n3)CC2)cn1] | 539.69 | 540.3 | 0.84 | QC-ACN-TFA-XB |
| 68 | 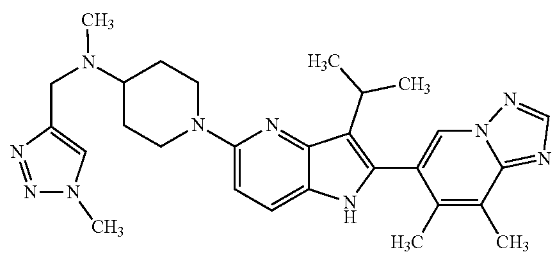 [SMILES: Cc1c(-c2[nH]c3ccc(N4CCC(N(C)Cc5cn(C)nn5)CC4)nc3c2C(C)C)cn2ncnc2c1C] | 512.67 | 513.2 | 1.28 | QC-ACN-AA-XB |
| 69 | 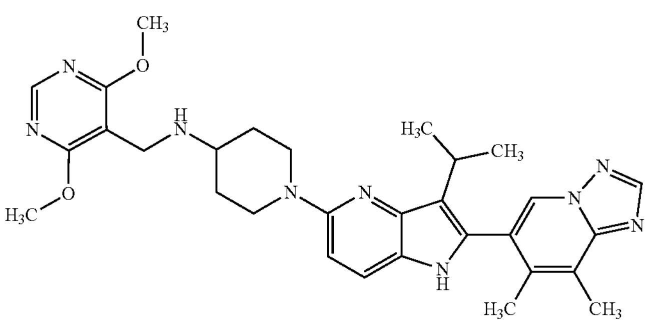 [SMILES: COc1ncnc(OC)c1CNC1CCN(c2ccc3[nH]c(-c4cn5ncnc5c(C)c4C)c(C(C)C)c3n2)CC1] | 555.69 | 556.1 | 1.14 | QC-ACN-TFA-XB |
| 70 | 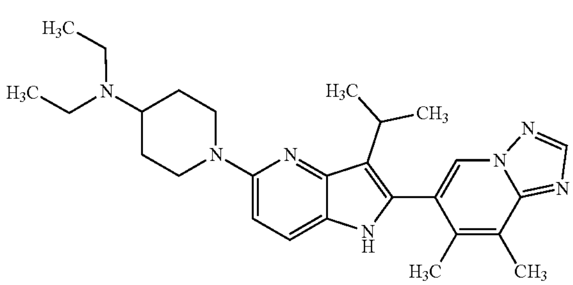 | 459.64 | 460.3 | 1.39 | QC-ACN-AA-XB |

TABLE 1-continued

| Ex. No. | Structure | Mol. Wt. | LCMS M+ | Ret Time (min) | HPLC Method |
|---|---|---|---|---|---|
| 71 | 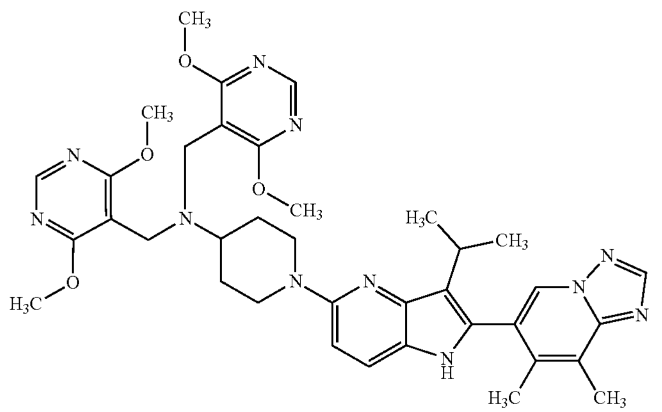 [SMILES: COc1ncnc(OC)c1CN(Cc1c(OC)ncnc1OC)C1CCN(c2ccc3[nH]c(-c4cn5ncnc5c(C)c4C)c(C(C)C)c3n2)CC1] | 707.84 | 708.5 | 1.13 | QC-ACN-TFA-XB |
| 72 | 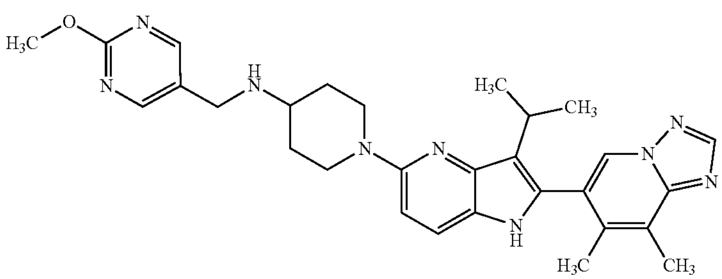 [SMILES: COc1ncc(CNC2CCN(c3ccc4[nH]c(-c5cn6ncnc6c(C)c5C)c(C(C)C)c4n3)CC2)cn1] | 525.66 | 526.3 | 1.64 | QC-ACN-AA-XB |
| 73 | 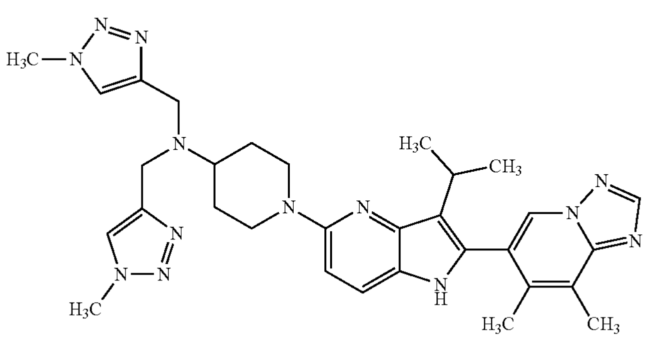 [SMILES: Cc1c(-c2[nH]c3ccc(N4CCC(N(Cc5cn(C)nn5)Cc5cn(C)nn5)CC4)nc3c2C(C)C)cn2ncnc2c1C] | 593.74 | 594.1 | 1.56 | QC-ACN-AA-XB |
| 74 | 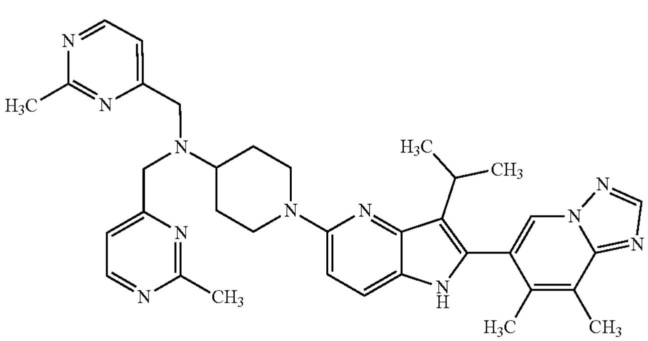 [SMILES: Cc1nccc(CN(Cc2ccnc(C)n2)C2CCN(c3ccc4[nH]c(-c5cn6ncnc6c(C)c5C)c(C(C)C)c4n3)CC2)n1] | 615.79 | 616.2 | 1.18 | QC-ACN-TFA-XB |

TABLE 1-continued
| Ex. No. | Structure | Mol. Wt. | LCMS M+ | Ret Time (min) | HPLC Method |
|---|---|---|---|---|---|
| 75 | 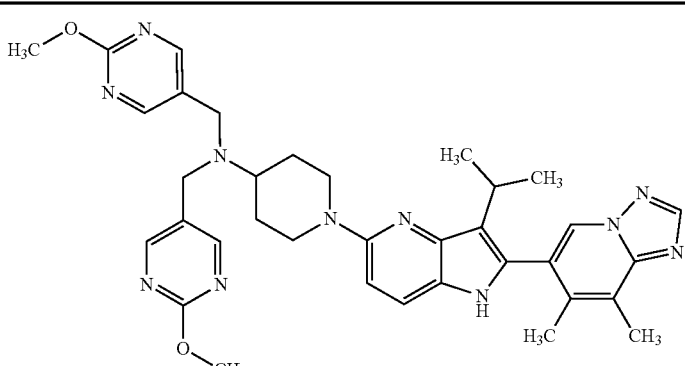 | 647.79 | 648.5 | 1.07 | QC-ACN-TFA-XB |
| 76 | 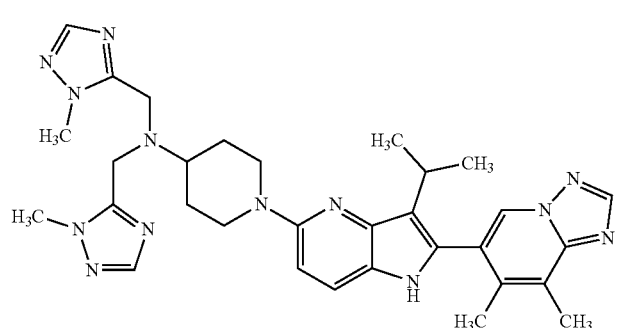 | 593.74 | 594.2 | 1.54 | QC-ACN-AA-XB |
| 77 | 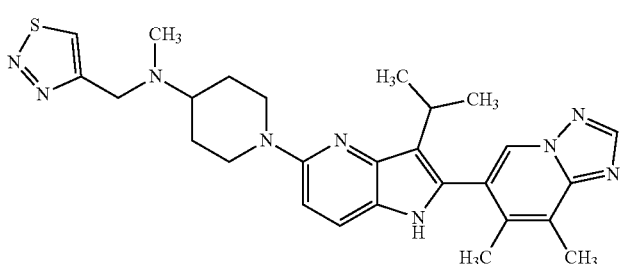 | 515.68 | 516.8 | 1.67 | QC-ACN-AA-XB |
| 78 | 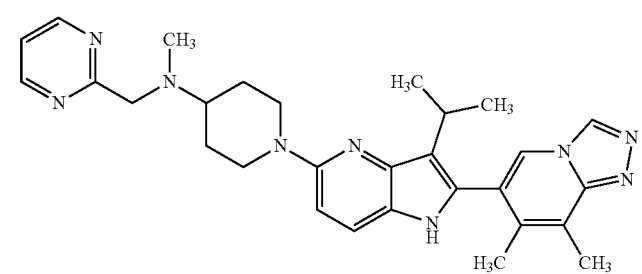 [SMILES: Cc1c(-c2[nH]c3ccc(N4CCC(N(C)Cc5ncccn5)CC4)nc3c2C(C)C)cn2cnnc2c1C] | 509.66 | 510.3 | 1.15 | QC-ACN-AA-XB |
| 79 | 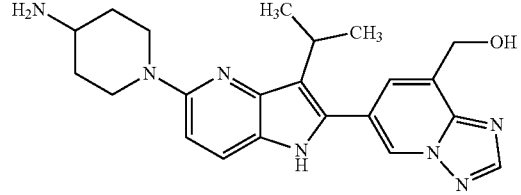 [SMILES: CC(C)c1c(-c2cc(CO)c3ncnn3c2)[nH]c2ccc(N3CCC(N)CC3)nc12] | 405.51 | 406.1 | 0.65 | QC-ACN-TFA-XB |

TABLE 1-continued

| Ex. No. | Structure | Mol. Wt. | LCMS M+ | Ret Time (min) | HPLC Method |
|---|---|---|---|---|---|
| 80 | 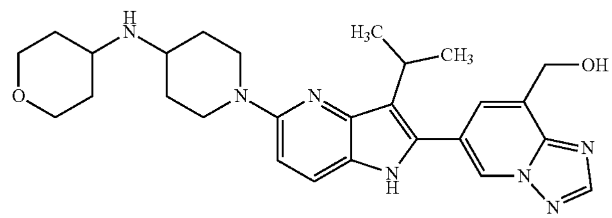 [SMILES: CC(C)c1c(-c2cc(CO)c3ncnn3c2)[nH]c2ccc(N3CCC(NC4CCOCC4)CC3)nc12] | 489.62 | 490.4 | 0.73 | QC-ACN-TFA-XB |
| 81 | 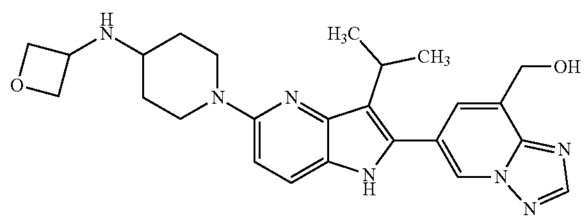 | 461.57 | 462.3 | 0.62 | QC-ACN-TFA-XB |
| 82 | 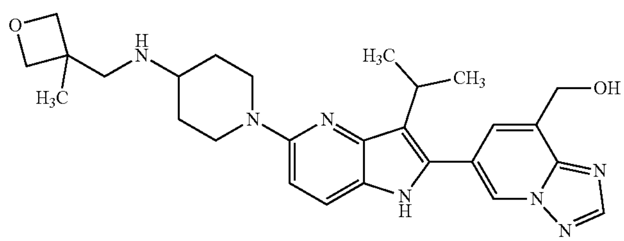 [SMILES: CC(C)c1c(-c2cc(CO)c3ncnn3c2)[nH]c2ccc(N3CCC(NCC4(C)COC4)CC3)nc12] | 489.62 | 489.9 | 1.32 | QC-ACN-AA-XB |
| 83 | 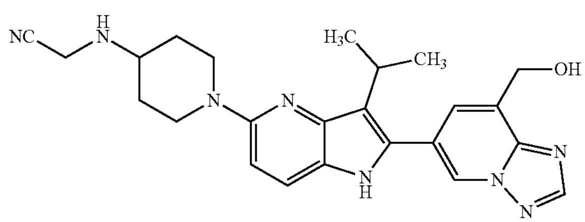 [SMILES: CC(C)c1c(-c2cc(CO)c3ncnn3c2)[nH]c2ccc(N3CCC(NCC#N)CC3)nc12] | 444.54 | 445.4 | 1.33 | QC-ACN-AA-XB |
| 84 | 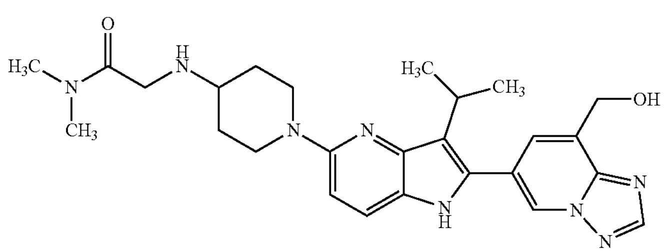 [SMILES: CC(C)c1c(-c2cc(CO)c3ncnn3c2)[nH]c2ccc(N3CCC(NCC(=O)N(C)C)CC3)nc12] | 490.61 | 491 | 1.24 | QC-ACN-TFA-XB |
| 85 | 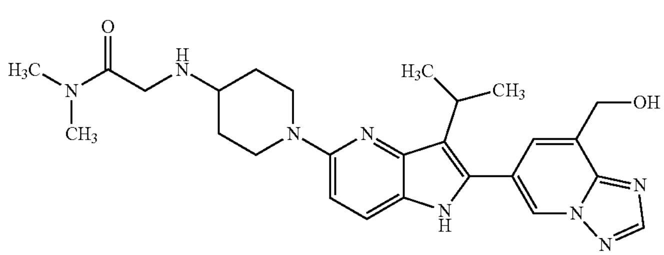 [SMILES: CC(C)c1c(-c2cc(CO)c3ncnn3c2)[nH]c2ccc(N3CCC(NCC(=O)N(C)C)CC3)nc12] | 490.61 | 490.9 | 0.9 | QC-ACN-TFA-XB |

TABLE 1-continued

| Ex. No. | Structure | Mol. Wt. | LCMS M+ | Ret Time (min) | HPLC Method |
|---|---|---|---|---|---|
| 86 | 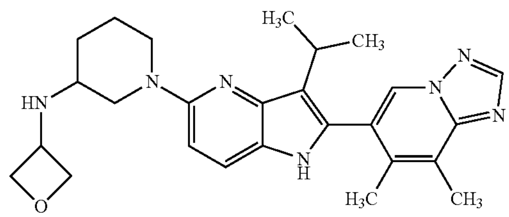 [SMILES: Cc1c(-c2[nH]c3ccc(N4CCCC(NC5COC5)C4)nc3c2C(C)C)cn2ncnc2c1C] | 459.60 | 460 | 0.83 | QC-ACN-TFA-XB |
| 87 | 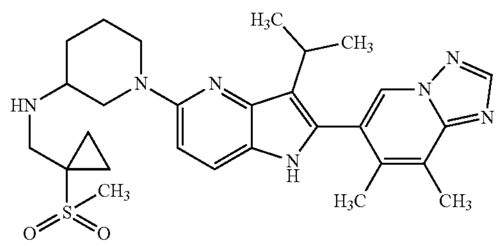 [SMILES: Cc1c(-c2[nH]c3ccc(N4CCCC(NCC5(S(C)(=O)=O)CC5)C4)nc3c2C(C)C)cn2ncnc2c1C] | 535.71 | 536.2 | 0.89 | QC-ACN-TFA-XB |
| 88 | 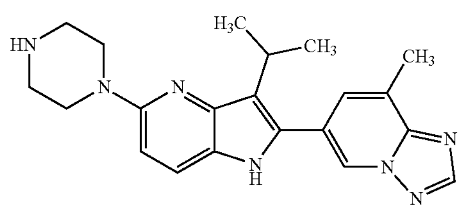 [SMILES: Cc1cc(-c2[nH]c3ccc(N4CCNCC4)nc3c2C(C)C)cn2ncnc12] | 375.48 | 376.3 | 1.09 | QC-ACN-AA-XB |
| 89 | 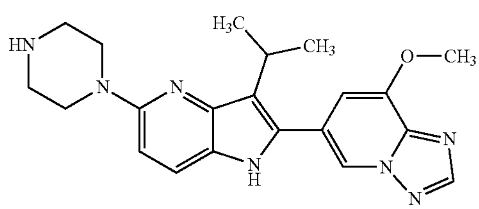 | 391.48 | 392.3 | 0.98 | QC-ACN-AA-XB |
| 90 | 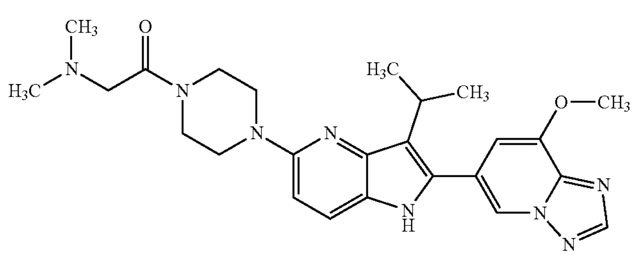 [SMILES: COc1cc(-c2[nH]c3ccc(N4CCN(C(=O)CN(C)C)CC4)nc3c2C(C)C)cn2ncnc12] | 476.59 | 477.22 | 1.44 | QC-ACN-AA-XB |
| 91 | 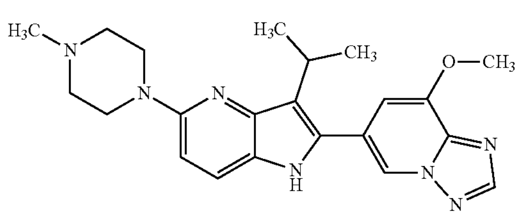 [SMILES: COc1cc(-c2[nH]c3ccc(N4CCN(C)CC4)nc3c2C(C)C)cn2ncnc12] | 405.51 | 406.2 | 1.48 | QC-ACN-AA-XB |

TABLE 1-continued

| Ex. No. | Structure | Mol. Wt. | LCMS M+ | Ret Time (min) | HPLC Method |
|---|---|---|---|---|---|
| 92 | 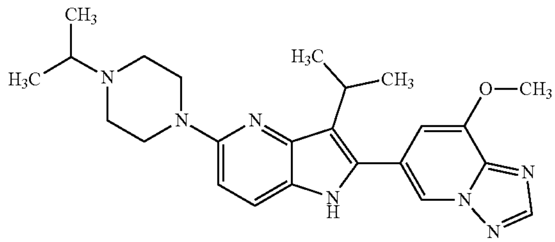 [SMILES: COc1cc(-c2[nH]c3ccc(N4CCN(C(C)C)CC4)nc3c2C(C)C)cn2ncnc12] | 433.56 | 434.4 | 1.01 | QC-ACN-TFA-XB |
| 93 | 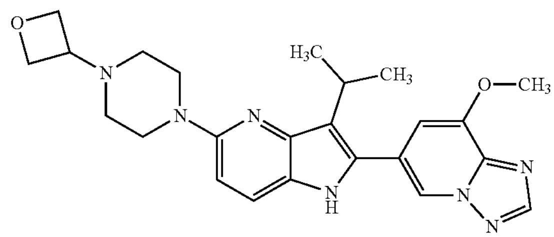 [SMILES: COc1cc(-c2[nH]c3ccc(N4CCN(C5COC5)CC4)nc3c2C(C)C)cn2ncnc12] | 447.54 | 448.4 | 0.93 | QC-ACN-TFA-XB |
| 94 | 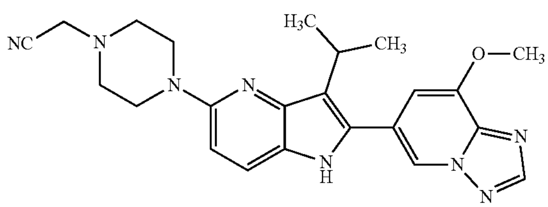 [SMILES: COc1cc(-c2[nH]c3ccc(N4CCN(CC#N)CC4)nc3c2C(C)C)cn2ncnc12] | 430.52 | 431.3 | 1.58 | QC-ACN-AA-XB |
| 95 | 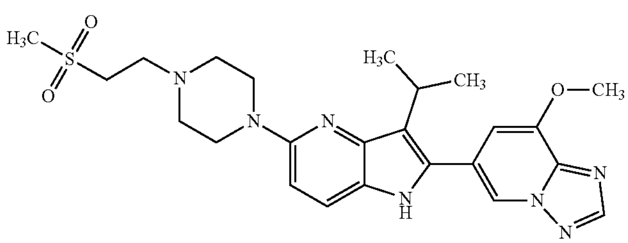 [SMILES: COc1cc(-c2[nH]c3ccc(N4CCN(CCS(C)(=O)=O)CC4)nc3c2C(C)C)cn2ncnc12] | 497.62 | 498.2 | 1.6 | QC-ACN-AA-XB |
| 96 | 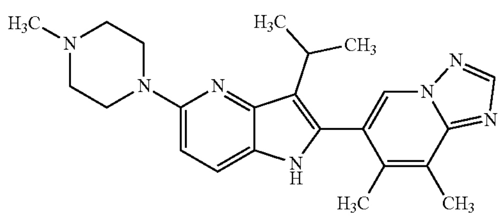 | 403.53 | 404.3 | 1.31 | QC-ACN-AA-XB |
| 97 | 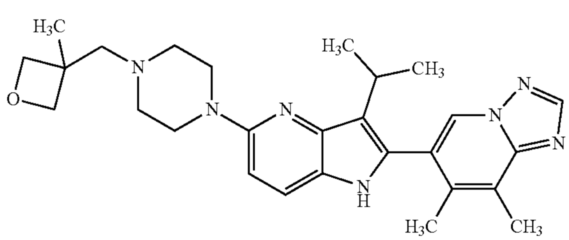 [SMILES: Cc1c(-c2[nH]c3ccc(N4CCN(CC5(C)COC5)CC4)nc3c2C(C)C)cn2ncnc2c1C] | 473.63 | 474.4 | 1.84 | QC-ACN-AA-XB |

TABLE 1-continued

| Ex. No. | Structure | Mol. Wt. | LCMS M+ | Ret Time (min) | HPLC Method |
|---|---|---|---|---|---|
| 98 | 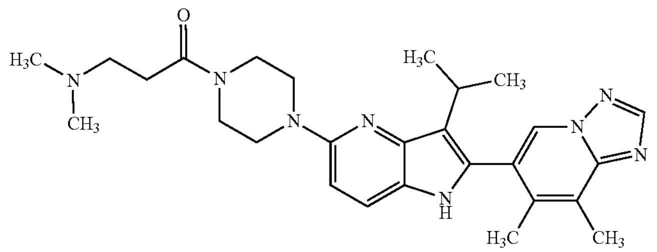 [SMILES: Cc1c(-c2[nH]c3ccc(N4CCN(C(=O)CCN(C)C)CC4)nc3c2C(C)C)cn2ncnc2c1C] | 488.64 | 489.4 | 1.23 | QC-ACN-AA-XB |
| 99 | 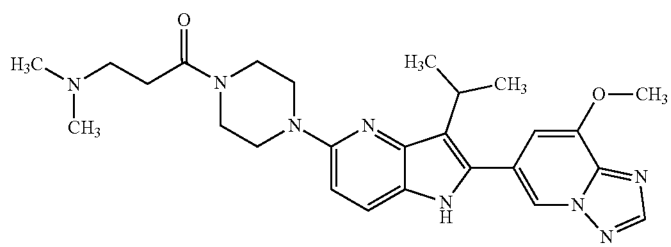 [SMILES: COc1cc(-c2[nH]c3ccc(N4CCN(C(=O)CCN(C)C)CC4)nc3c2C(C)C)cn2ncnc12] | 490.61 | 491.2 | 1.12 | QC-ACN-AA-XB |
| 100 | 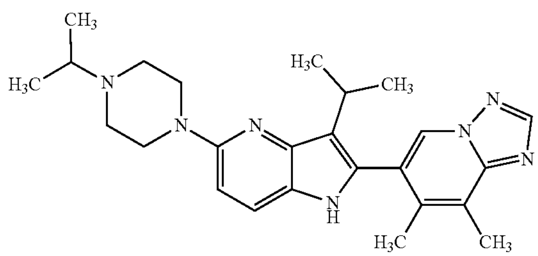 [SMILES: Cc1c(-c2[nH]c3ccc(N4CCN(C(C)C)CC4)nc3c2C(C)C)cn2ncnc2c1C] | 431.59 | 432.11 | 1.62 | QC-ACN-AA-XB |
| 101 | 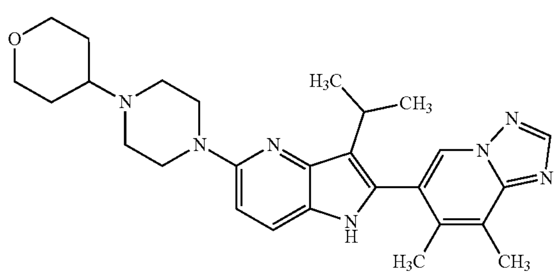 | 473.63 | 474.4 | 1.5 | QC-ACN-AA-XB |
| 102 | 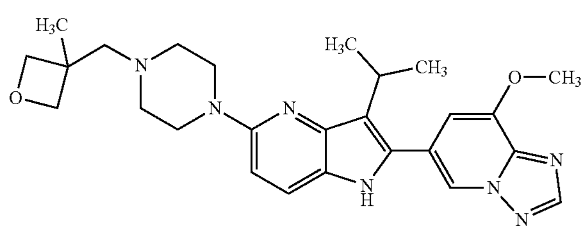 [SMILES: COc1cc(-c2[nH]c3ccc(N4CCN(CC5(C)COC5)CC4)nc3c2C(C)C)cn2ncnc12] | 475.60 | 476.4 | 0.84 | QC-ACN-TFA-XB |
| 103 | 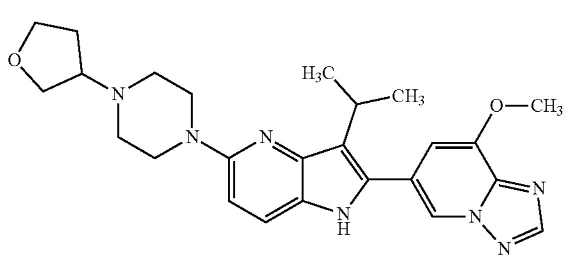 [SMILES: COc1cc(-c2[nH]c3ccc(N4CCN(C5CCOC5)CC4)nc3c2C(C)C)cn2ncnc12] | 461.57 | 462.2 | 1.47 | QC-ACN-AA-XB |

TABLE 1-continued

| Ex. No. | Structure | Mol. Wt. | LCMS M+ | Ret Time (min) | HPLC Method |
|---|---|---|---|---|---|
| 104 | 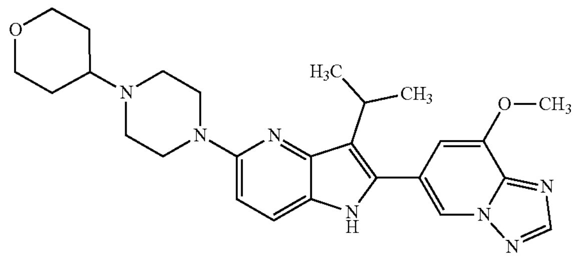 [SMILES: COc1cc(-c2[nH]c3ccc(N4CCN(C5CCOCC5)CC4)nc3c2C(C)C)cn2ncnc12] | 475.60 | 476.4 | 0.84 | QC-ACN-TFA-XB |
| 105 | 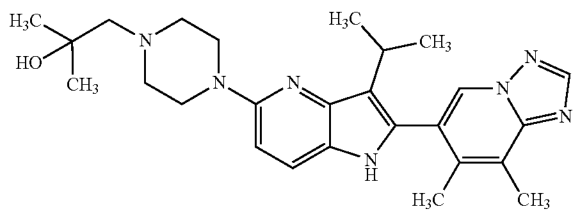 [SMILES: Cc1c(-c2[nH]c3ccc(N4CCN(CC(C)(C)O)CC4)nc3c2C(C)C)cn2ncnc2c1C] | 461.61 | 461.9 | 1.92 | QC-ACN-AA-XB |
| 106 | 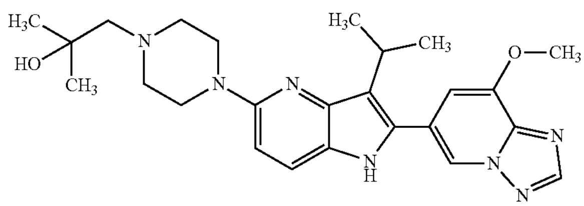 [SMILES: COc1cc(-c2[nH]c3ccc(N4CCN(CC(C)(C)O)CC4)nc3c2C(C)C)cn2ncnc12] | 463.59 | 464 | 1.5 | QC-ACN-AA-XB |
| 107 | 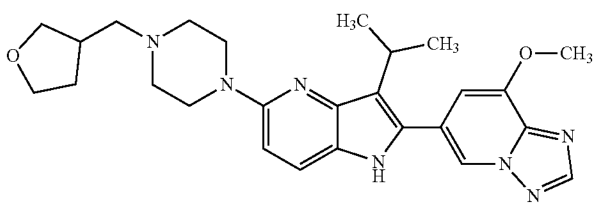 [SMILES: COc1cc(-c2[nH]c3ccc(N4CCN(CC5CCOC5)CC4)nc3c2C(C)C)cn2ncnc12] | 475.60 | 476.2 | 1.72 | QC-ACN-AA-XB |
| 108 | 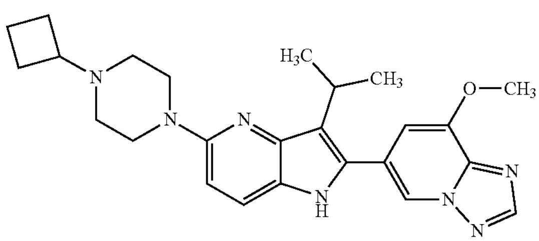 [SMILES: COc1cc(-c2[nH]c3ccc(N4CCN(C5CCC5)CC4)nc3c2C(C)C)cn2ncnc12] | 445.57 | 446.2 | 1.13 | QC-ACN-TFA-XB |
| 109 | 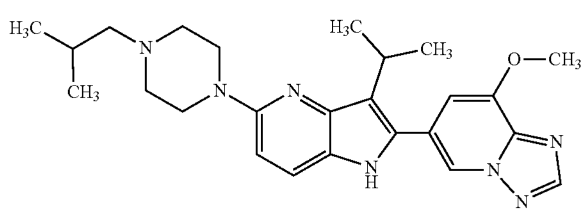 [SMILES: COc1cc(-c2[nH]c3ccc(N4CCN(CC(C)C)CC4)nc3c2C(C)C)cn2ncnc12] | 447.59 | 447.9 | 2.18 | QC-ACN-AA-XB |
| 110 | 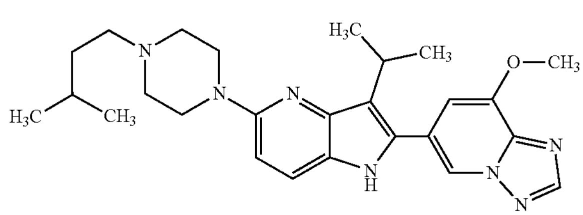 [SMILES: COc1cc(-c2[nH]c3ccc(N4CCN(CCC(C)C)CC4)nc3c2C(C)C)cn2ncnc12] | 461.61 | 462.2 | 2.07 | QC-ACN-AA-XB |

TABLE 1-continued

| Ex. No. | Structure | Mol. Wt. | LCMS M+ | Ret Time (min) | HPLC Method |
|---|---|---|---|---|---|
| 111 | 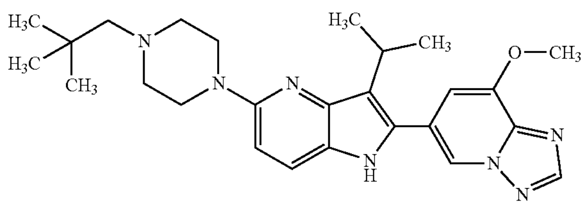 [SMILES: COc1cc(-c2[nH]c3ccc(N4CCN(CC(C)(C)C)CC4)nc3c2C(C)C)cn2ncnc12] | 461.61 | 462.2 | 1.3 | QC-ACN-TFA-XB |
| 112 | 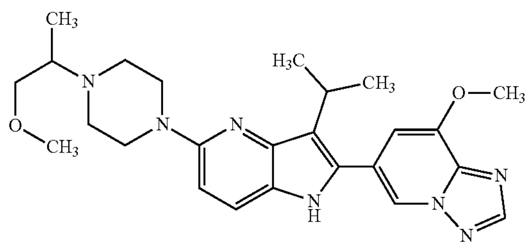 [SMILES: COCC(C)N1CCN(c2ccc3[nH]c(-c4cc(OC)c5ncnn5c4)c(C(C)C)c3n2)CC1] | 463.59 | 464.2 | 1.7 | QC-ACN-AA-XB |
| 113 | 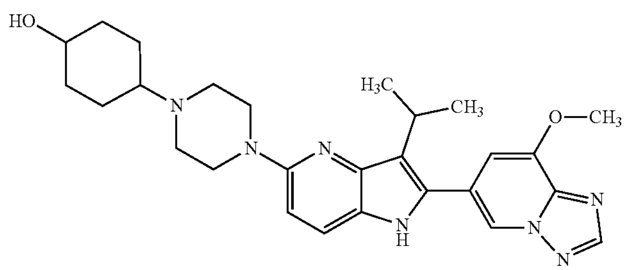 [SMILES: COc1cc(-c2[nH]c3ccc(N4CCN(C5CCC(O)CC5)CC4)nc3c2C(C)C)cn2ncnc12] | 489.62 | 490.2 | 1.04 | QC-ACN-TFA-XB |
| 114 | 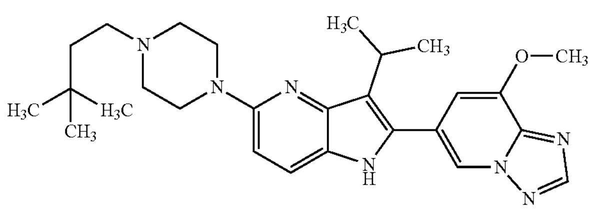 [SMILES: COc1cc(-c2[nH]c3ccc(N4CCN(CCC(C)(C)C)CC4)nc3c2C(C)C)cn2ncnc12] | 475.64 | 475.9 | 1.42 | QC-ACN-TFA-XB |
| 115 | 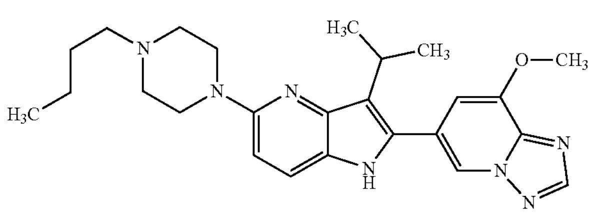 [SMILES: CCCCN1CCN(c2ccc3[nH]c(-c4cc(OC)c5ncnn5c4)c(C(C)C)c3n2)CC1] | 447.59 | 448.3 | 1.89 | QC-ACN-AA-XB |
| 116 | 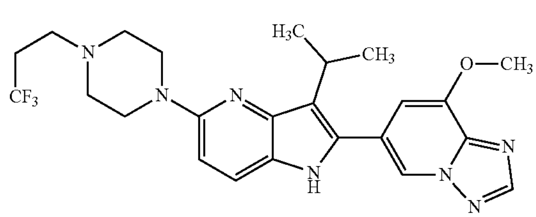 [SMILES: COc1cc(-c2[nH]c3ccc(N4CCN(CCC(F)(F)F)CC4)nc3c2C(C)C)cn2ncnc12] | 487.53 | 488.3 | 2.06 | QC-ACN-AA-XB |

TABLE 1-continued

| Ex. No. | Structure | Mol. Wt. | LCMS M+ | Ret Time (min) | HPLC Method |
|---|---|---|---|---|---|
| 117 | 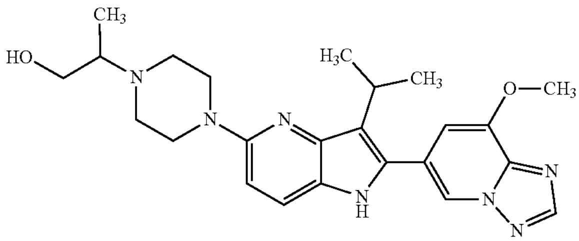 [SMILES: COc1cc(-c2[nH]c3ccc(N4CCN(C(C)CO)CC4)nc3c2C(C)C)cn2ncnc12] | 449.56 | 450.3 | 1.47 | QC-ACN-AA-XB |
| 118 | 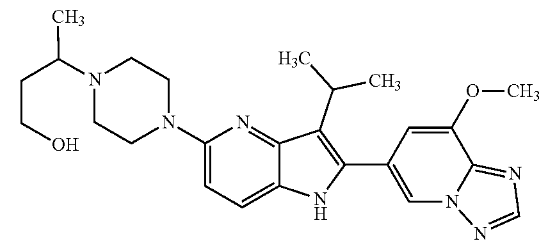 [SMILES: COc1cc(-c2[nH]c3ccc(N4CCN(C(C)CCO)CC4)nc3c2C(C)C)cn2ncnc12] | 463.59 | 463.9 | 1.42 | QC-ACN-AA-XB |
| 119 | 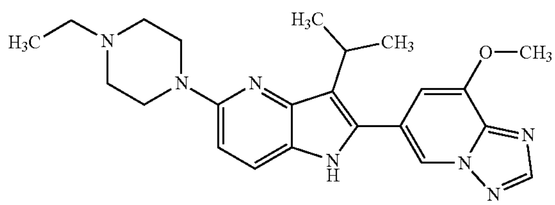 [SMILES: CCN1CCN(c2ccc3[nH]c(-c4cc(OC)c5ncnn5c4)c(C(C)C)c3n2)CC1] | 419.53 | 420.13 | 1.04 | QC-ACN-TFA-XB |
| 120 | 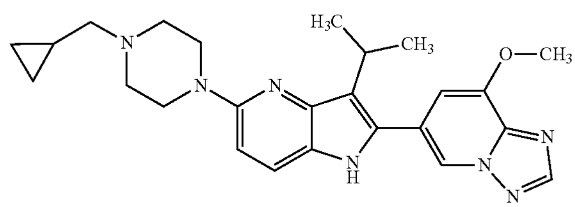 [SMILES: COc1cc(-c2[nH]c3ccc(N4CCN(CC5CC5)CC4)nc3c2C(C)C)cn2ncnc12] | 445.57 | 446.2 | 0.97 | QC-ACN-TFA-XB |
| 121 | 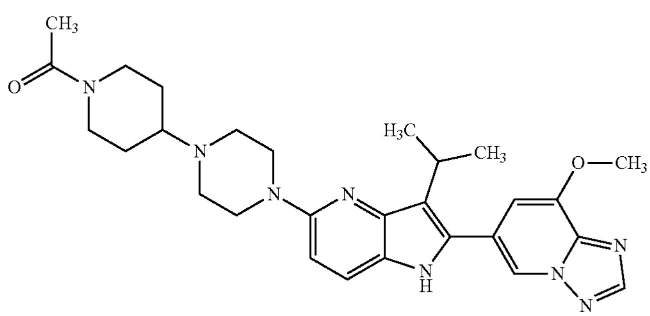 [SMILES: COc1cc(-c2[nH]c3ccc(N4CCN(C5CCN(C(C)=O)CC5)CC4)nc3c2C(C)C)cn2ncnc12] | 516.65 | 517.1 | 1.54 | QC-ACN-AA-XB |
| 122 | 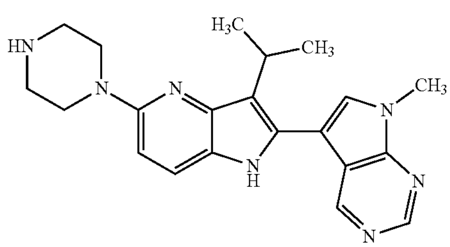 [SMILES: CC(C)c1c(-c2cn(C)c3ncncc23)[nH]c2ccc(N3CCNCC3)nc12] | 375.48 | 376.11 | 1.17 | QC-ACN-AA-XB |

TABLE 1-continued

| Ex. No. | Structure | Mol. Wt. | LCMS M+ | Ret Time (min) | HPLC Method |
|---|---|---|---|---|---|
| 123 | 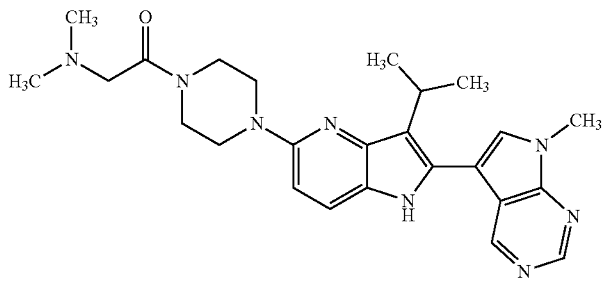 | 460.59 | 461.2 | 0.88 | QC-ACN-TFA-XB |
| 124 | 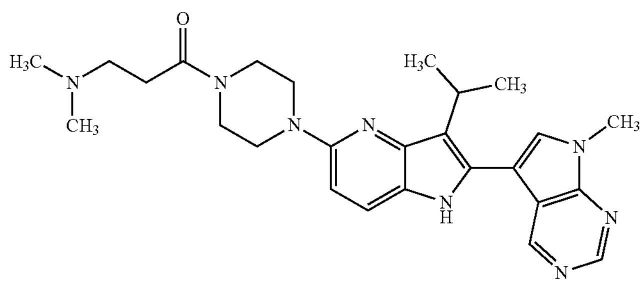 | 474.61 | 475.4 | 0.67 | QC-ACN-TFA-XB |
| 125 | 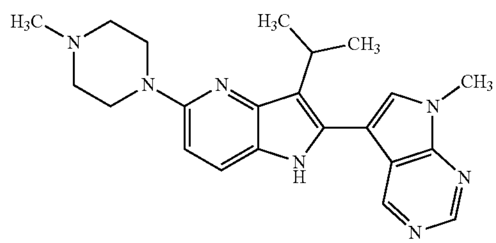 | 389.51 | 390.3 | 1.25 | QC-ACN-AA-XB |
| 126 | 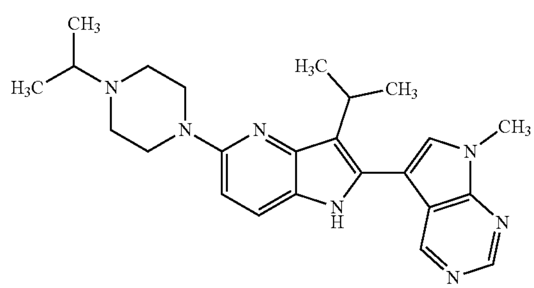 [SMILES: CC(C)c1c(-c2cn(C)c3ncncc23)[nH]c2ccc(N3CCN(C(C)C)CC3)nc12] | 417.56 | 418.3 | 0.75 | QC-ACN-TFA-XB |
| 127 | 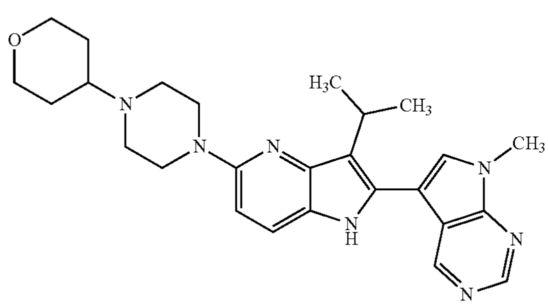 [SMILES: CC(C)c1c(-c2cn(C)c3ncncc23)[nH]c2ccc(N3CCN(C4CCOCC4)CC3)nc12] | 459.60 | 460.4 | 1.43 | QC-ACN-AA-XB |

TABLE 1-continued

| Ex. No. | Structure | Mol. Wt. | LCMS M+ | Ret Time (min) | HPLC Method |
|---|---|---|---|---|---|
| 128 | 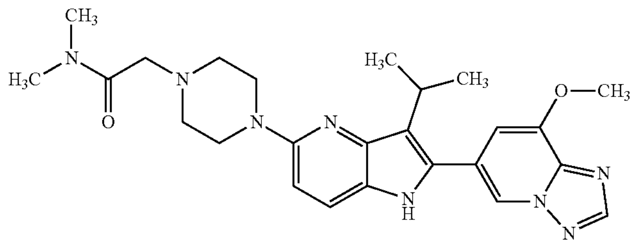 [SMILES: COc1cc(-c2[nH]c3ccc(N4CCN(CC(=O)N(C)C)CC4)nc3c2C(C)C)cn2ncnc12] | 476.59 | 477.4 | 1.41 | QC-ACN-AA-XB |
| 129 | 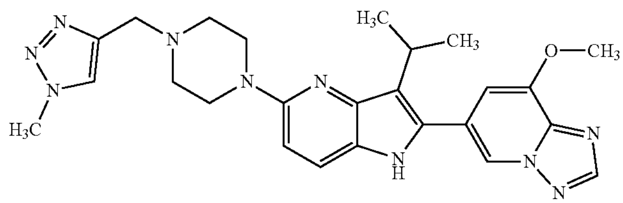 [SMILES: COc1cc(-c2[nH]c3ccc(N4CCN(Cc5cn(C)nn5)CC4)nc3c2C(C)C)cn2ncnc12] | 486.58 | 487.4 | 0.87 | QC-ACN-TFA-XB |
| 130 | 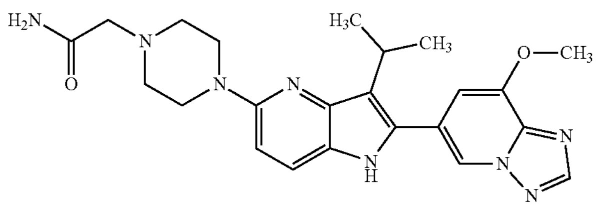 [SMILES: COc1cc(-c2[nH]c3ccc(N4CCN(CC(N)=O)CC4)nc3c2C(C)C)cn2ncnc12] | 448.53 | 449.4 | 1.29 | QC-ACN-AA-XB |
| 131 | 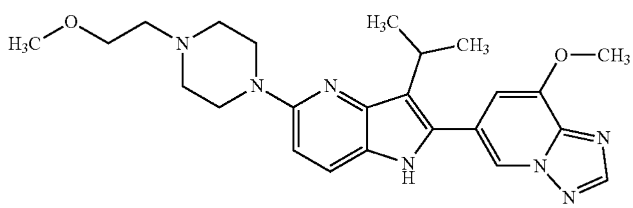 [SMILES: COCCN1CCN(c2ccc3[nH]c(-c4cc(OC)c5ncnn5c4)c(C(C)C)c3n2)CC1] | 449.56 | 450.37 | 0.93 | QC-ACN-TFA-XB |
| 132 | 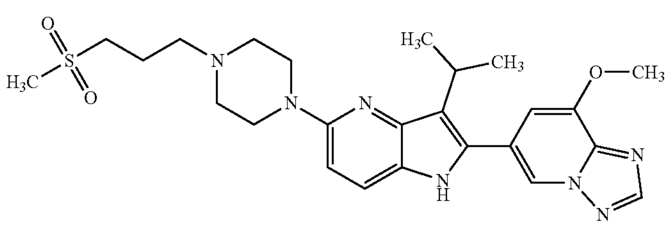 [SMILES: COc1cc(-c2[nH]c3ccc(N4CCN(CCCS(C)(=O)=O)CC4)nc3c2C(C)C)cn2ncnc12] | 511.65 | 512.2 | 1.51 | QC-ACN-AA-XB |
| 133 | 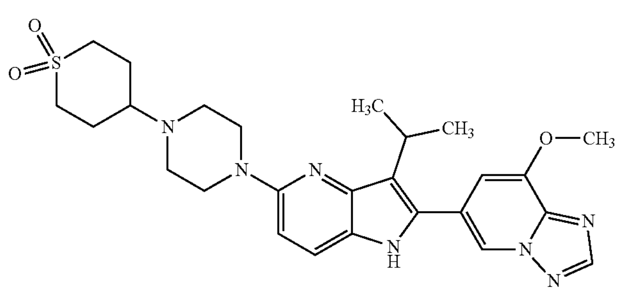 [SMILES: COc1cc(-c2[nH]c3ccc(N4CCN(C5CCS(=O)(=O)CC5)CC4)nc3c2C(C)C)cn2ncnc12] | 523.66 | 524.3 | 1.65 | QC-ACN-AA-XB |

TABLE 1-continued
| Ex. No. | Structure | Mol. Wt. | LCMS M+ | Ret Time (min) | HPLC Method |
|---|---|---|---|---|---|
| 134 | 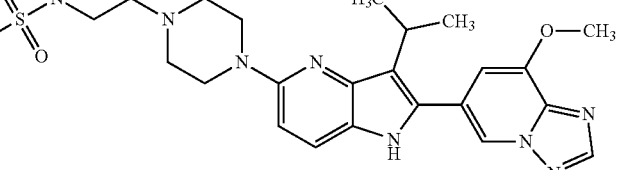 | 512.63 | 513.3 | 1.47 | QC-ACN-AA-XB |
| 135 | 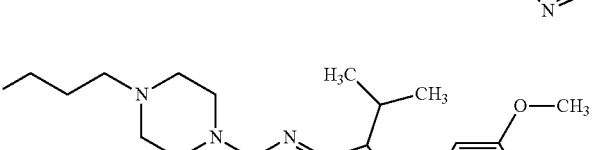 | 501.56 | 502.4 | 1.14 | QC-ACN-TFA-XB |
| 136 | 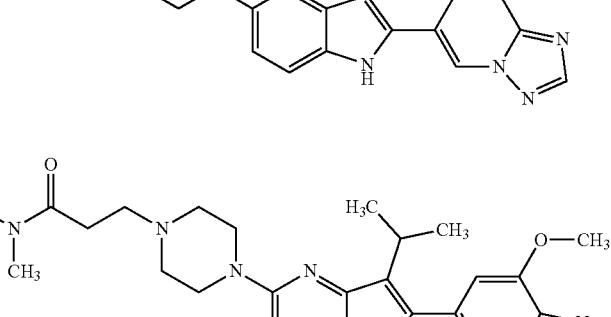 | 490.61 | 491.2 | 1.08 | QC-ACN-TFA-XB |
| 137 | 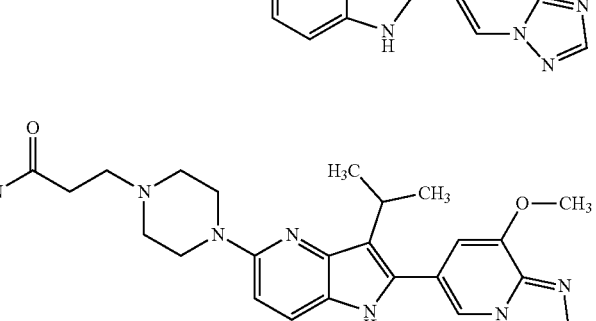 | 462.56 | 463 | 1.28 | QC-ACN-AA-XB |
| 138 | 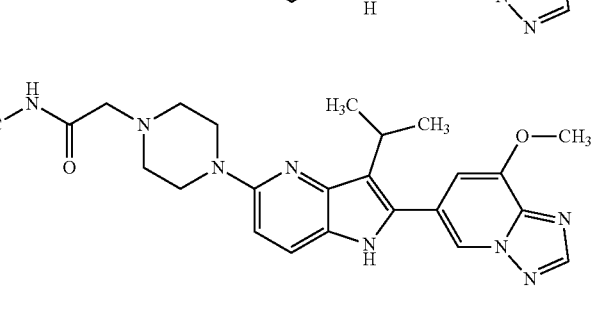 | 462.56 | 463.4 | 1.4 | QC-ACN-AA-XB |
| 139 | 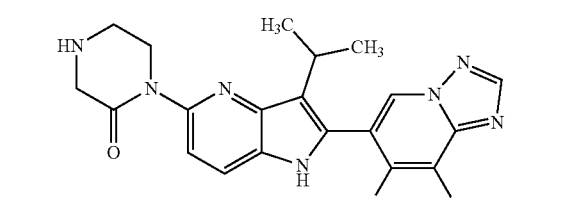 | 403.49 | 404.2 | 0.87 | QC-ACN-TFA-XB |

TABLE 1-continued

| Ex. No. | Structure | Mol. Wt. | LCMS M+ | Ret Time (min) | HPLC Method |
|---|---|---|---|---|---|
| 140 | 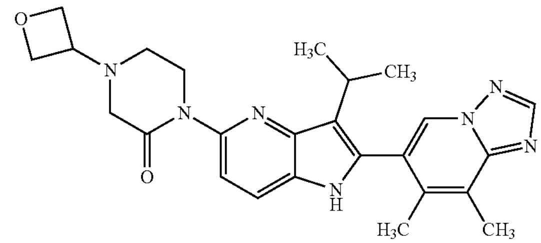 [SMILES: Cc1c(-c2[nH]c3ccc(N4CCN(C5COC5)CC4=O)nc3c2C(C)C)cn2ncnc2c1C] | 459.55 | 460.3 | 1.05 | QC-ACN-TFA-XB |
| 141 | 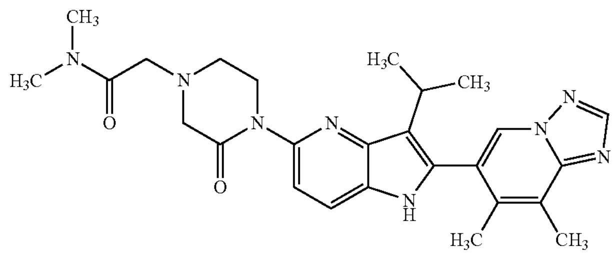 [SMILES: Cc1c(-c2[nH]c3ccc(N4CCN(CC(=O)N(C)C)CC4=O)nc3c2C(C)C)cn2ncnc2c1C] | 488.60 | 489.4 | 1.28 | QC-ACN-AA-XB |
| 142 | 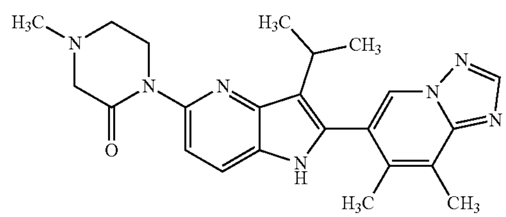 [SMILES: Cc1c(-c2[nH]c3ccc(N4CCN(C)CC4=O)nc3c2C(C)C)cn2ncnc2c1C] | 417.52 | 418.3 | 1.34 | QC-ACN-AA-XB |
| 143 | 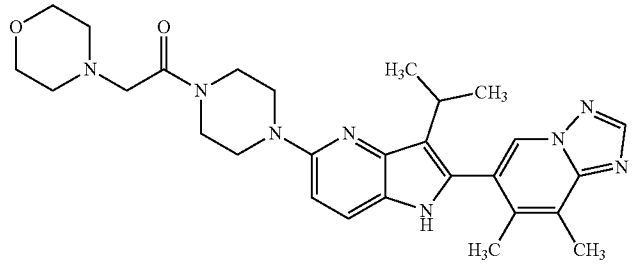 [SMILES: Cc1c(-c2[nH]c3ccc(N4CCN(C(=O)CN5CCOCC5)CC4)nc3c2C(C)C)cn2ncnc2c1C] | 516.65 | 517.4 | 1.49 | QC-ACN-AA-XB |
| 144 | 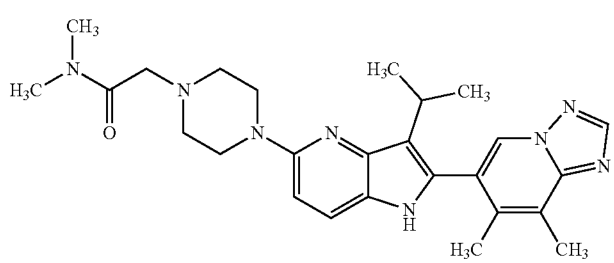 [SMILES: Cc1c(-c2[nH]c3ccc(N4CCN(CC(=O)N(C)C)CC4)nc3c2C(C)C)cn2ncnc2c1C] | 474.61 | 475.1 | 1.11 | QC-ACN-TFA-XB |
| 145 | 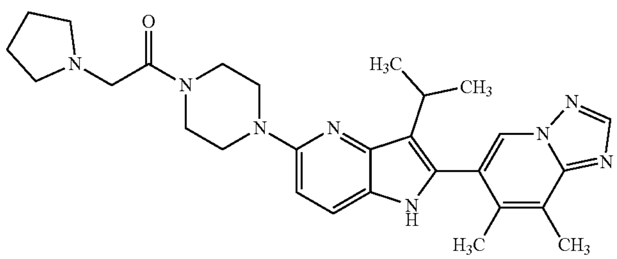 [SMILES: Cc1c(-c2[nH]c3ccc(N4CCN(C(=O)CN5CCCC5)CC4)nc3c2C(C)C)cn2ncnc2c1C] | 500.65 | 501.2 | 1.47 | QC-ACN-TFA-XB |

TABLE 1-continued

| Ex. No. | Structure | Mol. Wt. | LCMS M+ | Ret Time (min) | HPLC Method |
|---|---|---|---|---|---|
| 146 | 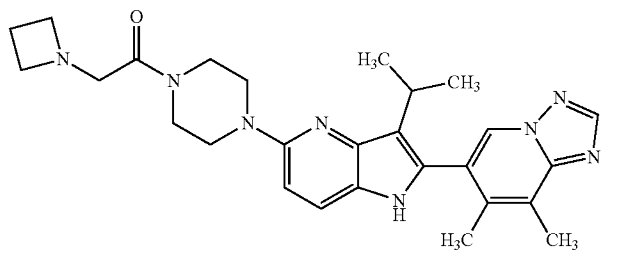 [SMILES: Cc1c(-c2[nH]c3ccc(N4CCN(C(=O)CN5CCC5)CC4)nc3c2C(C)C)cn2ncnc2c1C] | 486.62 | 487.4 | 0.8 | QC-ACN-TFA-XB |
| 147 | 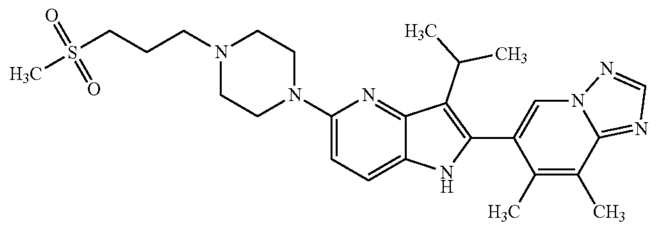 [SMILES: Cc1c(-c2[nH]c3ccc(N4CCN(CCCS(C)(=O)=O)CC4)nc3c2C(C)C)cn2ncnc2c1C] | 509.67 | 510.4 | 1.41 | QC-ACN-AA-XB |
| 148 | 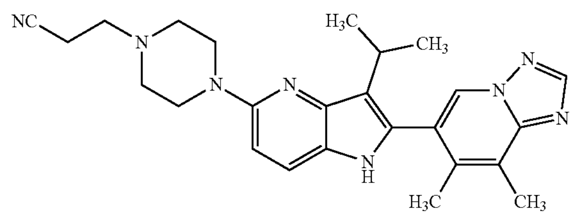 [SMILES: Cc1c(-c2[nH]c3ccc(N4CCN(CCC#N)CC4)nc3c2C(C)C)cn2ncnc2c1C] | 442.57 | 443.2 | 1.82 | QC-ACN-AA-XB |
| 149 | 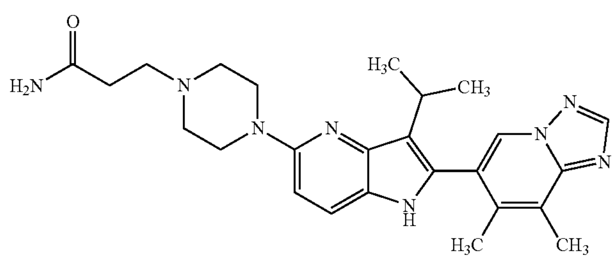 [SMILES: Cc1c(-c2[nH]c3ccc(N4CCN(CCC(N)=O)CC4)nc3c2C(C)C)cn2ncnc2c1C] | 460.59 | 460.9 | 1.41 | QC-ACN-AA-XB |
| 150 | 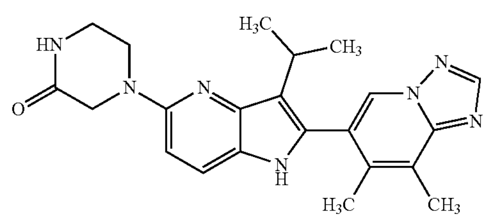 [SMILES: Cc1c(-c2[nH]c3ccc(N4CCNC(=O)C4)nc3c2C(C)C)cn2ncnc2c1C] | 403.49 | 404.4 | 1.36 | QC-ACN-AA-XB |
| 151 | 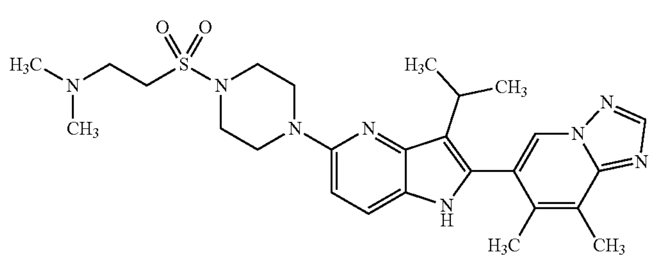 [SMILES: Cc1c(-c2[nH]c3ccc(N4CCN(S(=O)(=O)CCN(C)C)CC4)nc3c2C(C)C)cn2ncnc2c1C] | 524.69 | 525.1 | 1.74 | QC-ACN-AA-XB |

TABLE 1-continued

| Ex. No. | Structure | Mol. Wt. | LCMS M+ | Ret Time (min) | HPLC Method |
|---|---|---|---|---|---|
| 152 | 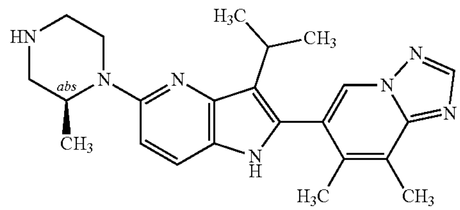 [SMILES: Cc1c(-c2[nH]c3ccc(N4CCNC[C@@H]4C)nc3c2C(C)C)cn2ncnc2c1C] | 403.53 | 404.1 | 1.95 | QC-ACN-AA-XB |
| 153 | 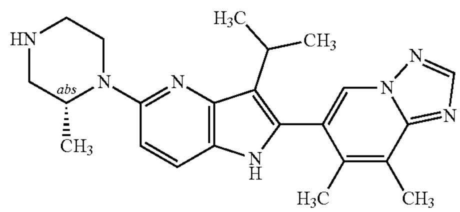 [SMILES: Cc1c(-c2[nH]c3ccc(N4CCNC[C@H]4C)nc3c2C(C)C)cn2ncnc2c1C] | 403.53 | 404.1 | 1.31 | QC-ACN-AA-XB |
| 154 | 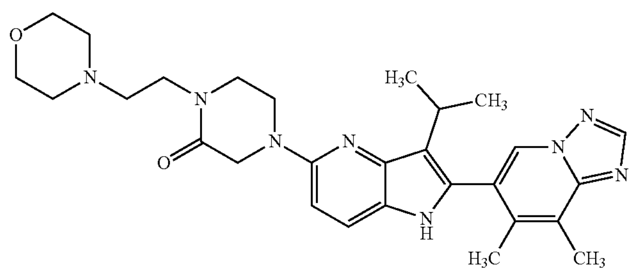 [SMILES: Cc1c(-c2[nH]c3ccc(N4CCN(CCN5CCOCC5)C(=O)C4)nc3c2C(C)C)cn2ncnc2c1C] | 516.65 | 517.2 | 1.14 | QC-ACN-TFA-XB |
| 155 | 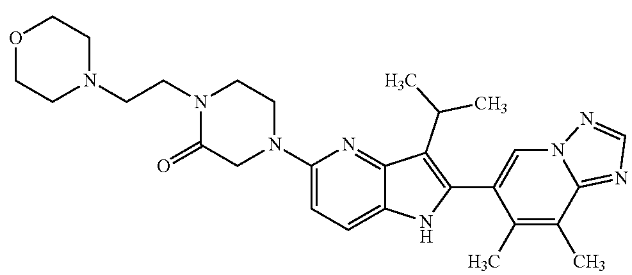 [SMILES: Cc1c(-c2[nH]c3ccc(N4CCN(CCN5CCOCC5)C(=O)C4)nc3c2C(C)C)cn2ncnc2c1C] | 516.65 | 517.2 | 1.49 | QC-ACN-AA-XB |
| 156 | 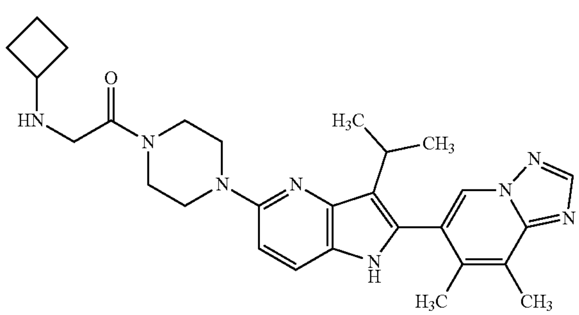 [SMILES: Cc1c(-c2[nH]c3ccc(N4CCN(C(=O)CNC5CCC5)CC4)nc3c2C(C)C)cn2ncnc2c1C] | 500.65 | 501.2 | 1.4 | QC-ACN-AA-XB |
| 157 | 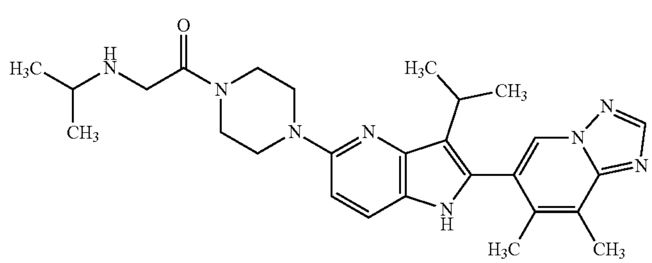 [SMILES: Cc1c(-c2[nH]c3ccc(N4CCN(C(=O)CNC(C)C)CC4)nc3c2C(C)C)cn2ncnc2c1C] | 488.64 | 488.9 | 1.38 | QC-ACN-AA-XB |

TABLE 1-continued

| Ex. No. | Structure | Mol. Wt. | LCMS M+ | Ret Time (min) | HPLC Method |
|---|---|---|---|---|---|
| 158 | 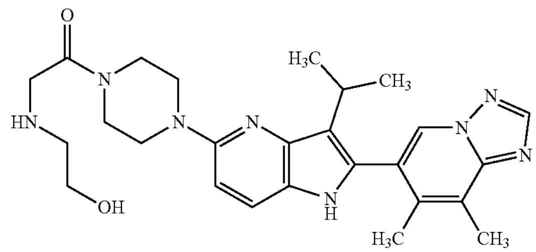 [SMILES: Cc1c(-c2[nH]c3ccc(N4CCN(C(=O)CNCCO)CC4)nc3c2C(C)C)cn2ncnc2c1C] | 490.61 | 491.1 | 1.05 | QC-ACN-TFA-XB |
| 159 | 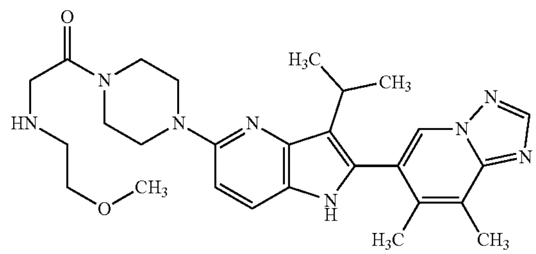 [SMILES: COCCNCC(=O)N1CCN(c2ccc3[nH]c(-c4cn5ncnc5c(C)c4C)c(C(C)C)c3n2)CC1] | 504.64 | 1009.4 (2M + H) | 1.4 | QC-ACN-AA-XB |
| 160 | 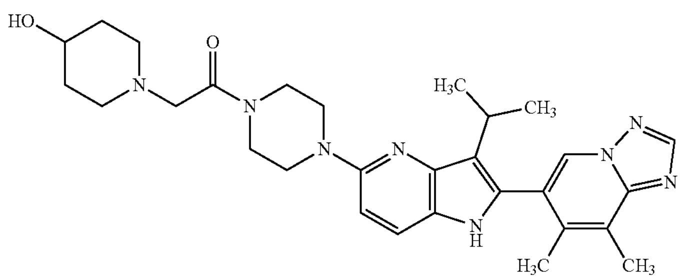 [SMILES: Cc1c(-c2[nH]c3ccc(N4CCN(C(=O)CN5CCC(O)CC5)CC4)nc3c2C(C)C)cn2ncnc2c1C] | 530.68 | 531.2 | 1.35 | QC-ACN-AA-XB |
| 161 | 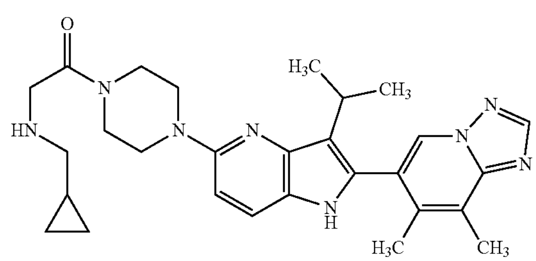 [SMILES: Cc1c(-c2[nH]c3ccc(N4CCN(C(=O)CNCC5CC5)CC4)nc3c2C(C)C)cn2ncnc2c1C] | 500.65 | 501.20 | 1.43 | QC-ACN-TFA-XB |
| 162 | 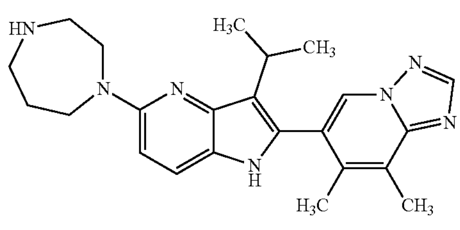 [SMILES: Cc1c(-c2[nH]c3ccc(N4CCCNCC4)nc3c2C(C)C)cn2ncnc2c1C] | 403.53 | 404.3 | 0.8 | QC-ACN-TFA-XB |
| 163 | 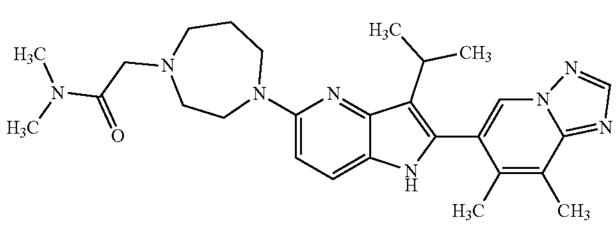 [SMILES: Cc1c(-c2[nH]c3ccc(N4CCCN(CC(=O)N(C)C)CC4)nc3c2C(C)C)cn2ncnc2c1C] | 488.64 | 489.3 | 1.38 | QC-ACN-AA-XB |

TABLE 1-continued

| Ex. No. | Structure | Mol. Wt. | LCMS M+ | Ret Time (min) | HPLC Method |
|---|---|---|---|---|---|
| 164 | 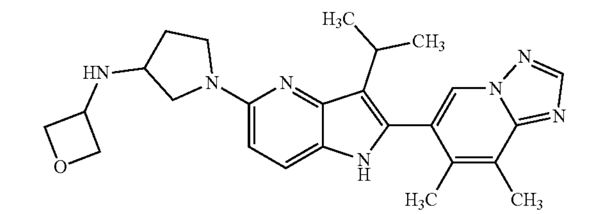 [SMILES: Cc1c(-c2[nH]c3ccc(N4CCC(NC5COC5)C4)nc3c2C(C)C)cn2ncnc2c1C] | 445.57 | 446.4 | 1.43 | QC-ACN-AA-XB |
| 165 | 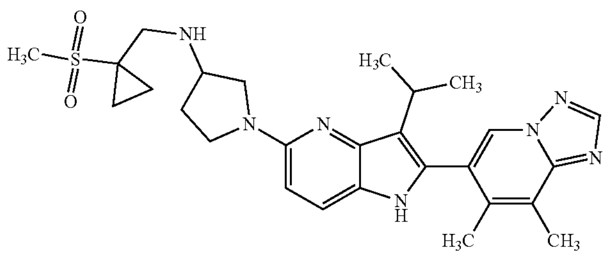 [SMILES: Cc1c(-c2[nH]c3ccc(N4CCC(NCC5(S(C)(=O)=O)CC5)C4)nc3c2C(C)C)cn2ncnc2c1C] | 521.68 | 522.4 | 0.83 | QC-ACN-TFA-XB |
| 166 | 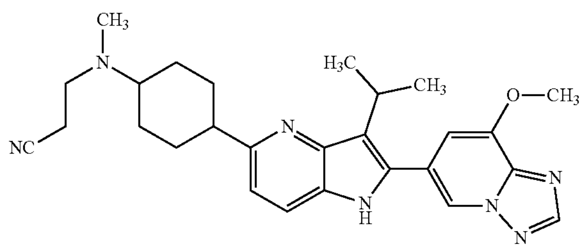 | 471.61 | 471.9 | 1.06 | QC-ACN-TFA-XB |
| 167 | 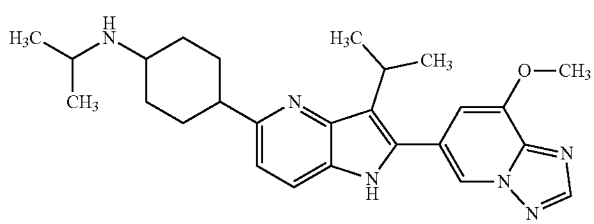 [SMILES: COc1cc(-c2[nH]c3ccc(C4CCC(NC(C)C)CC4)nc3c2C(C)C)cn2ncnc12] | 446.60 | 447.2 | 1.06 | QC-ACN-TFA-XB |
| 168 | 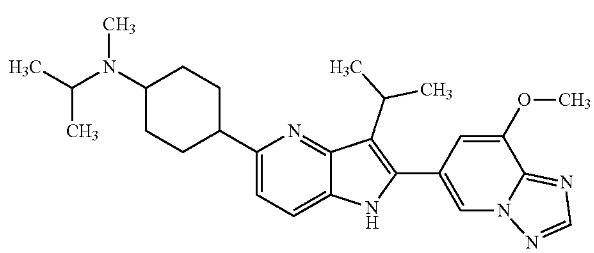 [SMILES: COc1cc(-c2[nH]c3ccc(C4CCC(N(C)C(C)C)CC4)nc3c2C(C)C)cn2ncnc12] | 460.63 | 461.2 | 1.35 | QC-ACN-AA-XB |
| 169 | 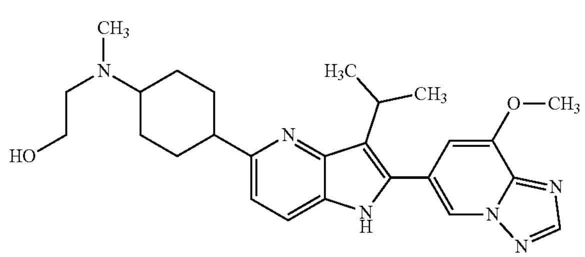 | 462.60 | 463 | 1.21 | QC-ACN-AA-XB |

TABLE 1-continued

| Ex. No. | Structure | Mol. Wt. | LCMS M+ | Ret Time (min) | HPLC Method |
|---|---|---|---|---|---|
| 170 | 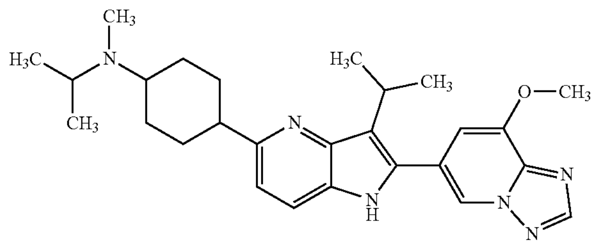 [SMILES: COc1cc(-c2[nH]c3ccc(C4CCC(N(C)C(C)C)CC4)nc3c2C(C)C)cn2ncnc12] | 460.63 | 461 | 1.56 | QC-ACN-AA-XB |
| 171 | 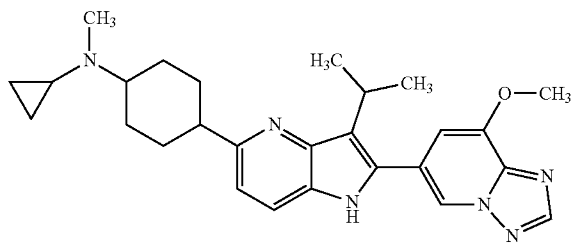 [SMILES: COc1cc(-c2[nH]c3ccc(C4CCC(N(C)C5CC5)CC4)nc3c2C(C)C)cn2ncnc12] | 458.61 | 459.4 | 0.77 | QC-ACN-TFA-XB |
| 172 | 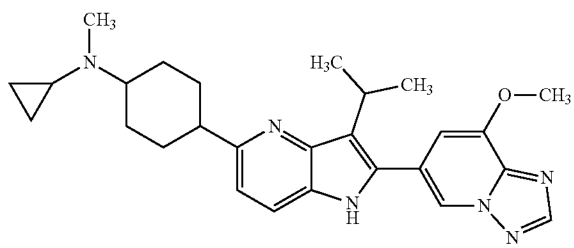 [SMILES: COc1cc(-c2[nH]c3ccc(C4CCC(N(C)C5CC5)CC4)nc3c2C(C)C)cn2ncnc12] | 458.61 | 459.3 | 1.49 | QC-ACN-AA-XB |
| 173 | 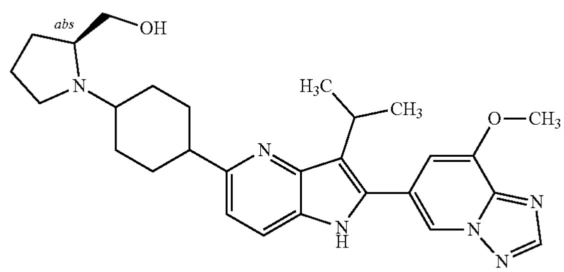 [SMILES: COc1cc(-c2[nH]c3ccc(C4CCC(N5CCC[C@H]5CO)CC4)nc3c2C(C)C)cn2ncnc12] | 488.64 | 489 | 1.28 | QC-ACN-AA-XB |
| 174 | 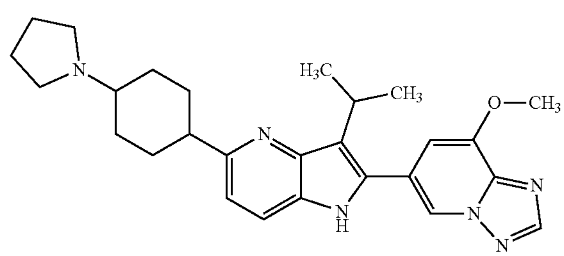 [SMILES: COc1cc(-c2[nH]c3ccc(C4CCC(N5CCCC5)CC4)nc3c2C(C)C)cn2ncnc12] | 458.61 | 459.2 | 1.02 | QC-ACN-TFA-XB |
| 175 | 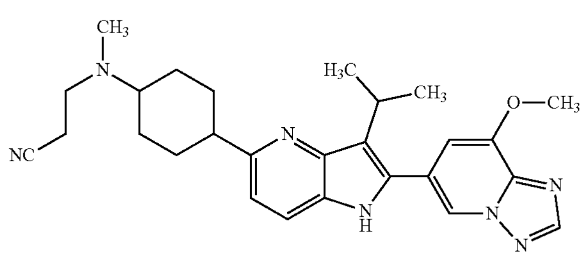 [SMILES: COc1cc(-c2[nH]c3ccc(C4CCC(N(C)CCC#N)CC4)nc3c2C(C)C)cn2ncnc12] | 471.61 | 472.2 | 0.75 | QC-ACN-TFA-XB |

TABLE 1-continued
| Ex. No. | Structure | Mol. Wt. | LCMS M+ | Ret Time (min) | HPLC Method |
|---|---|---|---|---|---|
| 176 | 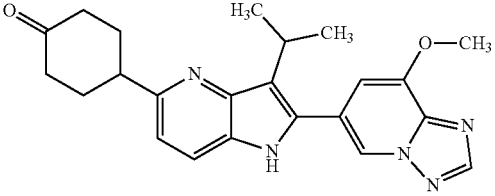 [SMILES: COc1cc(-c2[nH]c3ccc(C4CCC(=O)CC4)nc3c2C(C)C)cn2ncnc12] | 403.49 | 404.2 | 1.68 | QC-ACN-AA-XB |
| 177 | 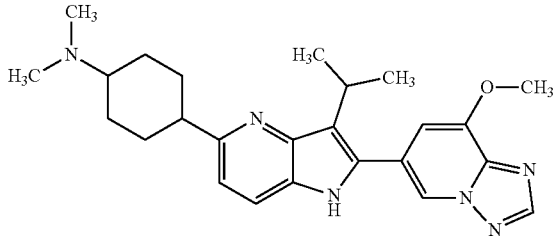 [SMILES: COc1cc(-c2[nH]c3ccc(C4CCC(N(C)C)CC4)nc3c2C(C)C)cn2ncnc12] | 432.57 | 433.1 | 1.29 | QC-ACN-AA-XB |
| 178 | 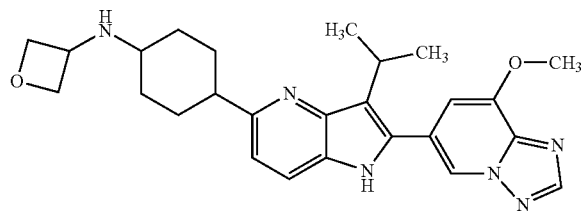 [SMILES: COc1cc(-c2[nH]c3ccc(C4CCC(NC5COC5)CC4)nc3c2C(C)C)cn2ncnc12] | 460.58 | 461.4 | 0.73 | QC-ACN-TFA-XB |
| 179 | 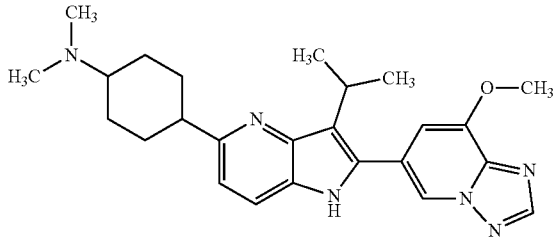 [SMILES: COc1cc(-c2[nH]c3ccc(C4CCC(N(C)C)CC4)nc3c2C(C)C)cn2ncnc12] | 432.57 | 433.1 | 1 | QC-ACN-TFA-XB |
| 180 | 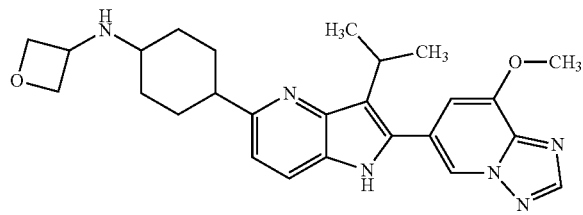 [SMILES: COc1cc(-c2[nH]c3ccc(C4CCC(NC5COC5)CC4)nc3c2C(C)C)cn2ncnc12] | 460.58 | 461.1 | 1.6 | QC-ACN-AA-XB |
| 181 | 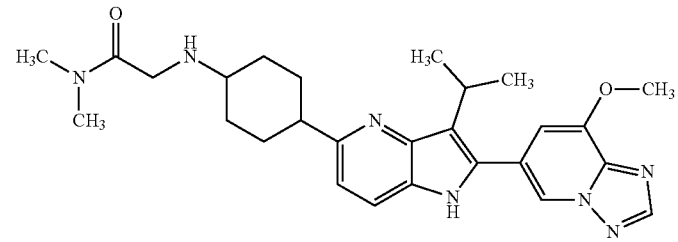 [SMILES: COc1cc(-c2[nH]c3ccc(C4CCC(NCC(=O)N(C)C)CC4)nc3c2C(C)C)cn2ncnc12] | 489.62 | 490.3 | 1.14 | QC-ACN-AA-XB |

TABLE 1-continued

| Ex. No. | Structure | Mol. Wt. | LCMS M+ | Ret Time (min) | HPLC Method |
|---|---|---|---|---|---|
| 182 | 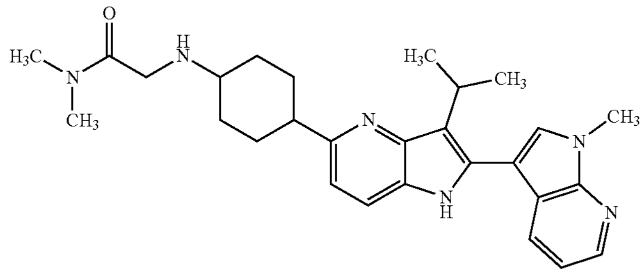 | 472.64 | 473.4 | 0.92 | QC-ACN-TFA-XB |
| 183 | 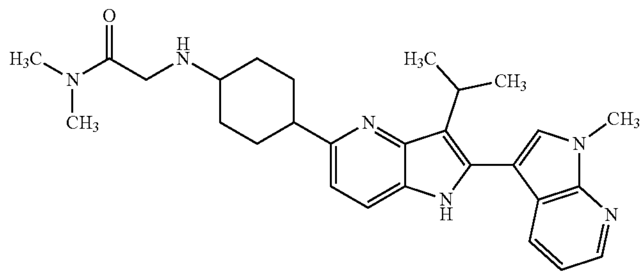 | 472.64 | 473.3 | 1.42 | QC-ACN-AA-XB |
| 184 | 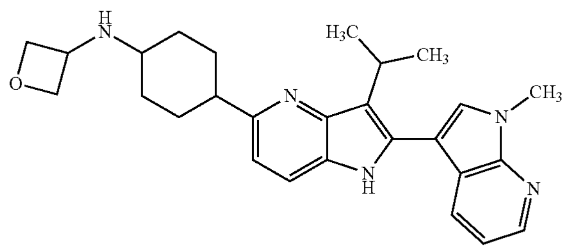 [SMILES: CC(C)c1c(-c2cn(C)c3ncccc23)[nH]c2ccc(C3CCC(NC4COC4)CC3)nc12] | 443.60 | 444.2 | 1.51 | QC-ACN-AA-XB |
| 185 | 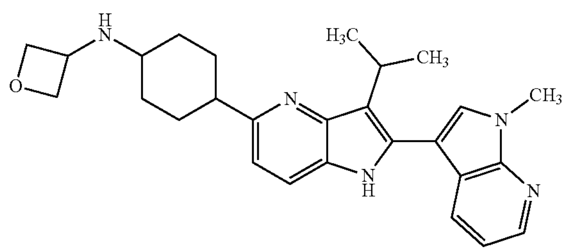 [SMILES: CC(C)c1c(-c2cn(C)c3ncccc23)[nH]c2ccc(C3CCC(NC4COC4)CC3)nc12] | 443.60 | 444.3 | 0.88 | QC-ACN-TFA-XB |
| 186 | 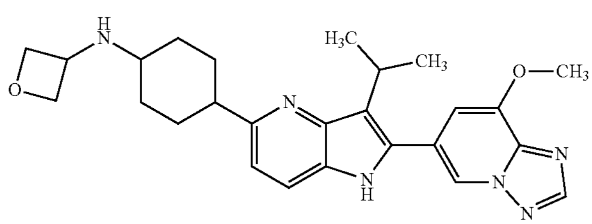 [SMILES: COc1cc(-c2[nH]c3ccc(C4CCC(NC5COC5)CC4)nc3c2C(C)C)cn2ncnc12] | 460.58 | 461.5 | 0.75 | QC-ACN-TFA-XB |
| 187 | 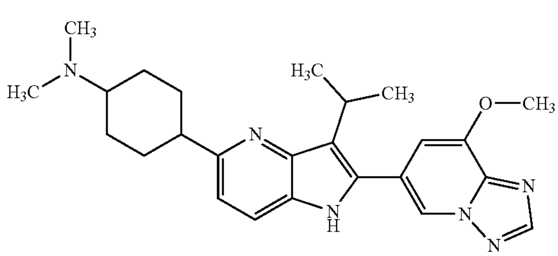 [SMILES: COc1cc(-c2[nH]c3ccc(C4CCC(N(C)C)CC4)nc3c2C(C)C)cn2ncnc12] | 432.57 | 433.3 | 1.26 | QC-ACN-AA-XB |

TABLE 1-continued

| Ex. No. | Structure | Mol. Wt. | LCMS M+ | Ret Time (min) | HPLC Method |
|---|---|---|---|---|---|
| 188 | 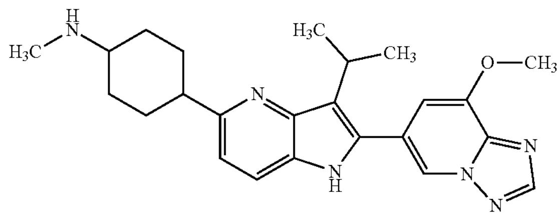 [SMILES: CNC1CCC(c2ccc3[nH]c(-c4cc(OC)c5ncnn5c4)c(C(C)C)c3n2)CC1] | 418.55 | 419.2 | 0.67 | QC-ACN-TFA-XB |
| 189 | 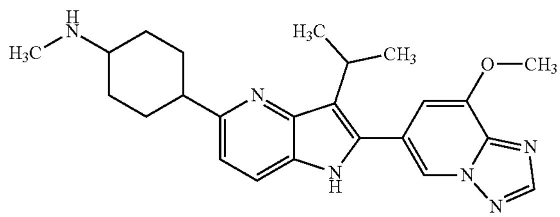 [SMILES: CNC1CCC(c2ccc3[nH]c(-c4cc(OC)c5ncnn5c4)c(C(C)C)c3n2)CC1] | 418.55 | 419.1 | 1.28 | QC-ACN-AA-XB |
| 190 | 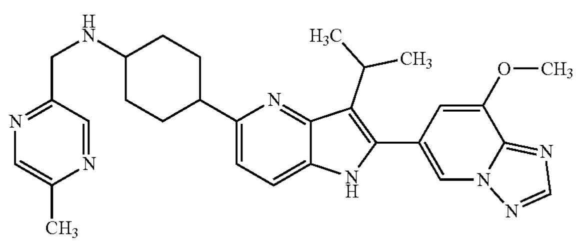 [SMILES: COc1cc(-c2[nH]c3ccc(C4CCC(NCc5cnc(C)cn5)CC4)nc3c2C(C)C)cn2ncnc12] | 510.65 | 511.2 | 1.23 | QC-ACN-AA-XB |
| 191 | 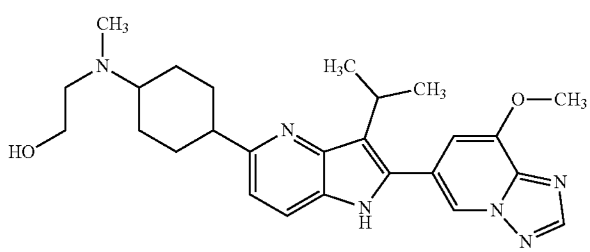 [SMILES: COc1cc(-c2[nH]c3ccc(C4CCC(N(C)CCO)CC4)nc3c2C(C)C)cn2ncnc12] | 462.60 | 463 | 1.07 | QC-ACN-AA-XB |
| 192 | 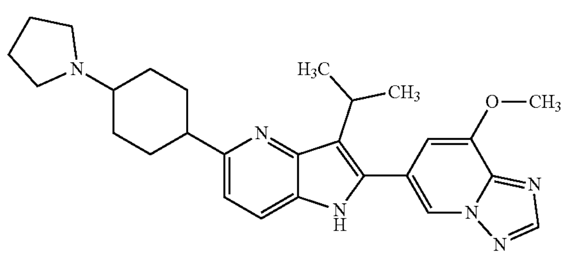 [SMILES: COc1cc(-c2[nH]c3ccc(C4CCC(N5CCCC5)CC4)nc3c2C(C)C)cn2ncnc12] | 458.61 | 459.1 | 1.31 | QC-ACN-AA-XB |
| 193 | 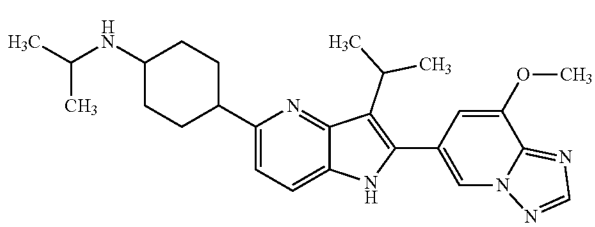 [SMILES: COc1cc(-c2[nH]c3ccc(C4CCC(NC(C)C)CC4)nc3c2C(C)C)cn2ncnc12] | 446.60 | 447.1 | 1.48 | QC-ACN-AA-XB |

TABLE 1-continued

| Ex. No. | Structure | Mol. Wt. | LCMS M+ | Ret Time (min) | HPLC Method |
|---|---|---|---|---|---|
| 194 | 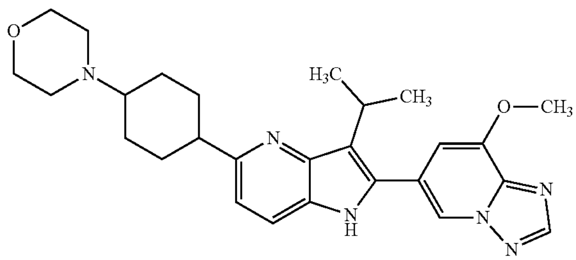 [SMILES: COc1cc(-c2[nH]c3ccc(C4CCC(N5CCOCC5)CC4)nc3c2C(C)C)cn2ncnc12] | 474.61 | 475.2 | 0.98 | QC-ACN-TFA-XB |
| 195 | 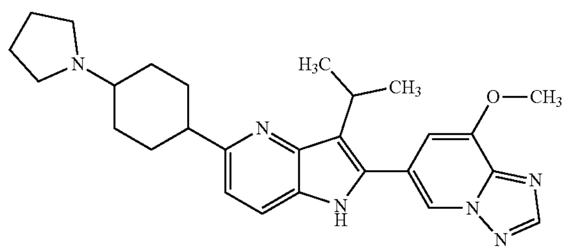 [SMILES: COc1cc(-c2[nH]c3ccc(C4CCC(N5CCCC5)CC4)nc3c2C(C)C)cn2ncnc12] | 458.61 | 459.3 | 0.76 | QC-ACN-TFA-XB |
| 196 | 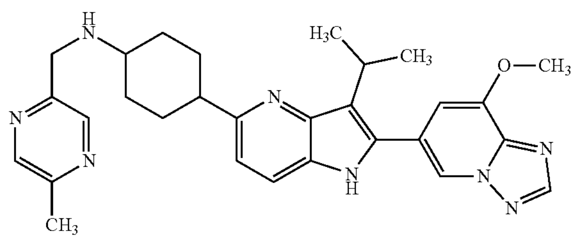 [SMILES: COc1cc(-c2[nH]c3ccc(C4CCC(NCc5cnc(C)cn5)CC4)nc3c2C(C)C)cn2ncnc12] | 510.65 | 511.5 | 1.43 | QC-ACN-AA-XB |
| 197 | 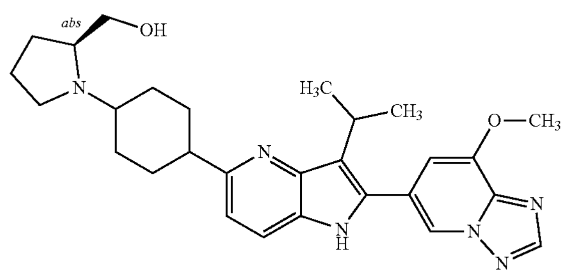 [SMILES: COc1cc(-c2[nH]c3ccc(C4CCC(N5CCC[C@H]5CO)CC4)nc3c2C(C)C)cn2ncnc12] | 488.64 | 489 | 1.16 | QC-ACN-AA-XB |
| 198 | 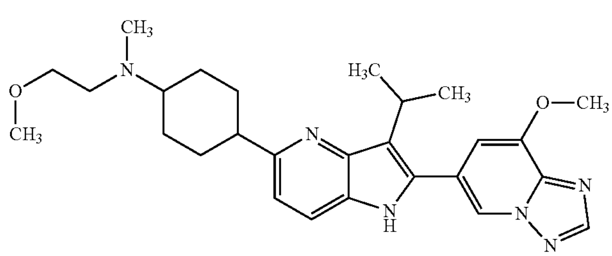 [SMILES: COCCN(C)C1CCC(c2ccc3[nH]c(-c4cc(OC)c5ncnn5c4)c(C(C)C)c3n2)CC1] | 476.63 | 477.3 | 1.19 | QC-ACN-AA-XB |
| 199 | 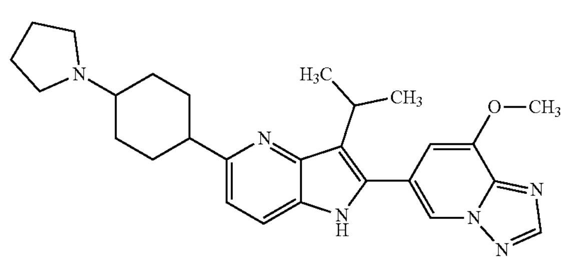 [SMILES: COc1cc(-c2[nH]c3ccc(C4CCC(N5CCCC5)CC4)nc3c2C(C)C)cn2ncnc12] | 458.61 | 459.2 | 0.79 | QC-ACN-TFA-XB |

| Ex. No. | Structure | Mol. Wt. | LCMS M+ | Ret Time (min) | HPLC Method |
|---|---|---|---|---|---|
| 200 | 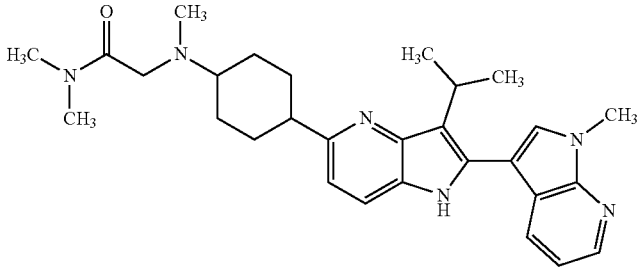 | 486.66 | 487.4 | 1.58 | QC-ACN-AA-XB |
| 201 | 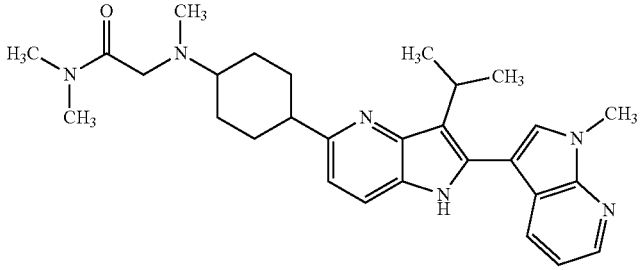 | 486.66 | 487.1 | 1.53 | QC-ACN-AA-XB |
| 202 | 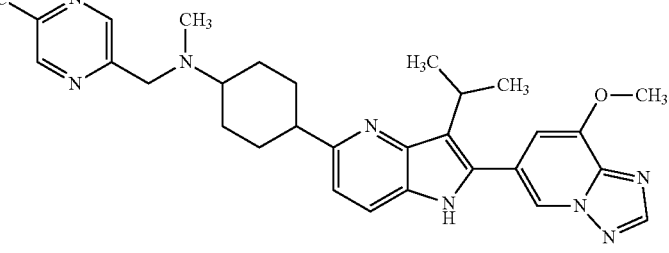 | 524.67 | 525.2 | 0.81 | QC-ACN-TFA-XB |
| 203 | 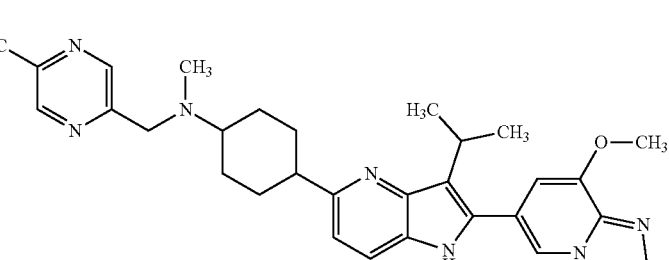 | 524.67 | 525.4 | 0.81 | QC-ACN-TFA-XB |
| 204 | 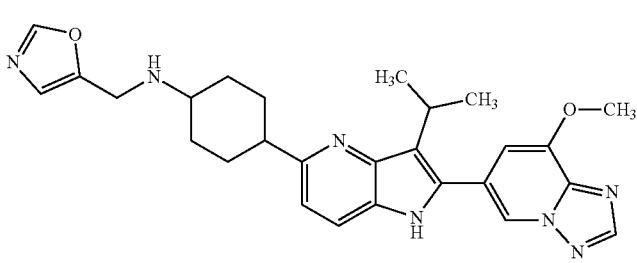 [SMILES: COc1cc(-c2[nH]c3ccc(C4CCC(NCc5cnco5)CC4)nc3c2C(C)C)cn2ncnc12] | 485.59 | 486.3 | 1.26 | QC-ACN-AA-XB |

TABLE 1-continued

| Ex. No. | Structure | Mol. Wt. | LCMS M+ | Ret Time (min) | HPLC Method |
|---|---|---|---|---|---|
| 205 | 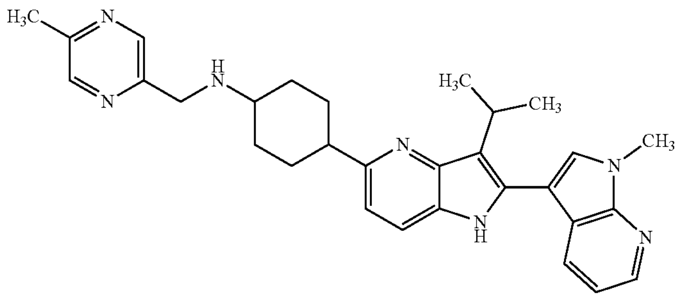 | 493.66 | 494.2 | 1.17 | QC-ACN-TFA-XB |
| 206 | 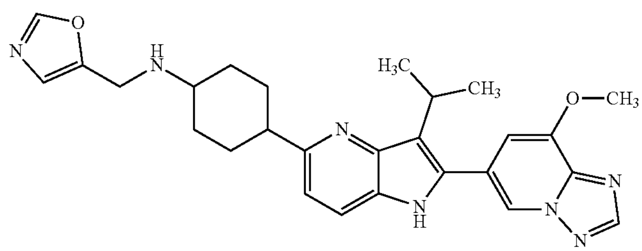 [SMILES: COc1cc(-c2[nH]c3ccc(C4CCC(NCc5cnco5)CC4)nc3c2C(C)C)cn2ncnc12] | 485.59 | 486.2 | 1.7 | QC-ACN-AA-XB |
| 207 | 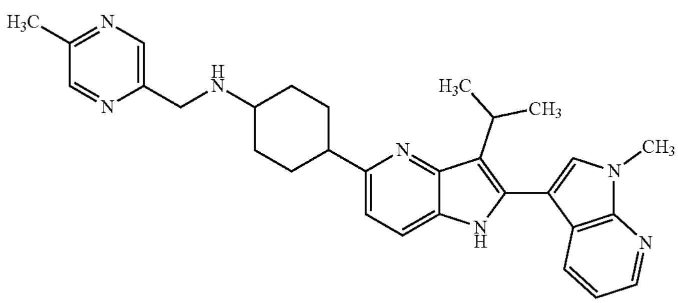 | 493.66 | 494.2 | 0.94 | QC-ACN-TFA-XB |
| 208 | 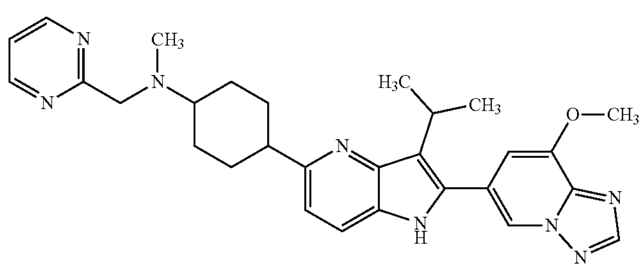 [SMILES: COc1cc(-c2[nH]c3ccc(C4CCC(N(C)Cc5ncccn5)CC4)nc3c2C(C)C)cn2ncnc12] | 510.65 | 511.4 | 0.87 | QC-ACN-TFA-XB |
| 209 | 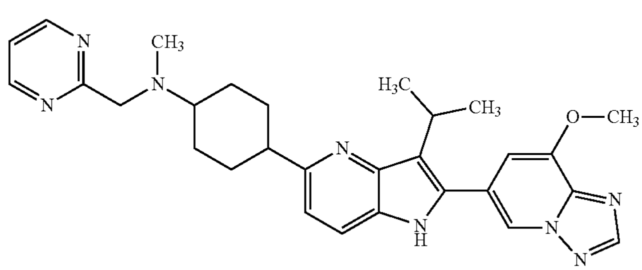 [SMILES: COc1cc(-c2[nH]c3ccc(C4CCC(N(C)Cc5ncccn5)CC4)nc3c2C(C)C)cn2ncnc12] | 510.65 | 511.32 | 1.19 | QC-ACN-AA-XB |

TABLE 1-continued
| Ex. No. | Structure | Mol. Wt. | LCMS M+ | Ret Time (min) | HPLC Method |
|---|---|---|---|---|---|
| 210 | 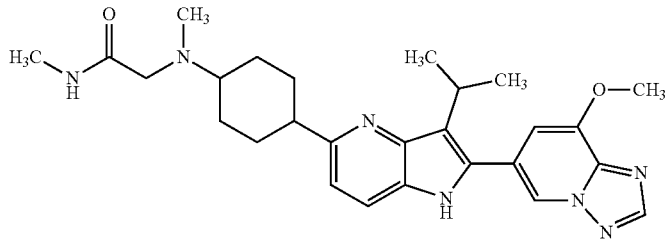 [SMILES: CNC(=O)CN(C)C1CCC(c2ccc3[nH]c(-c4cc(OC)c5ncnn5c4)c(C(C)C)c3n2)CC1] | 489.62 | 490.4 | 1.06 | QC-ACN-TFA-XB |
| 211 | 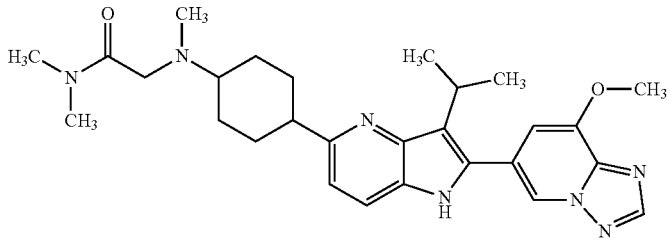 [SMILES: COc1cc(-c2[nH]c3ccc(C4CCC(N(C)CC(=O)N(C)C)CC4)nc3c2C(C)C)cn2ncnc12] | 503.65 | 504.4 | 1.11 | QC-ACN-AA-XB |
| 212 | 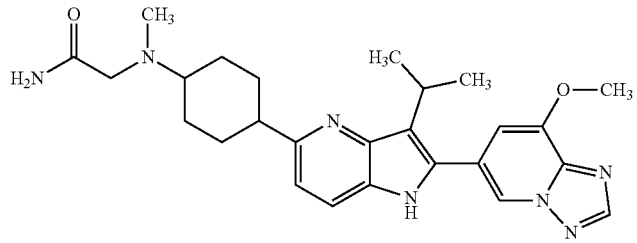 [SMILES: COc1cc(-c2[nH]c3ccc(C4CCC(N(C)CC(N)=O)CC4)nc3c2C(C)C)cn2ncnc12] | 475.60 | 476.1 | 1.17 | QC-ACN-AA-XB |
| 213 | 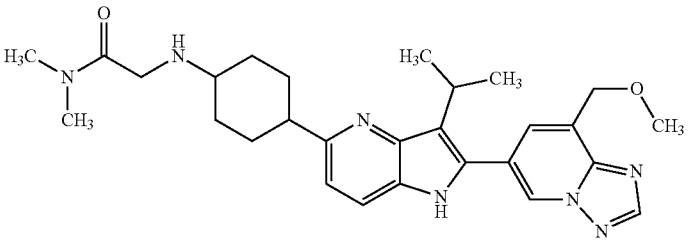 | 503.65 | 504.3 | 1.16 | QC-ACN-AA-XB |
| 214 | 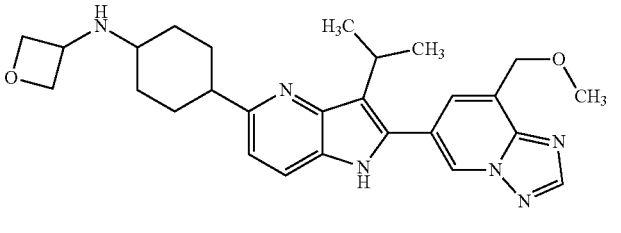 [SMILES: COCc1cc(-c2[nH]c3ccc(C4CCC(NC5COC5)CC4)nc3c2C(C)C)cn2ncnc12] | 474.61 | 475.3 | 0.85 | QC-ACN-TFA-XB |
| 215 | 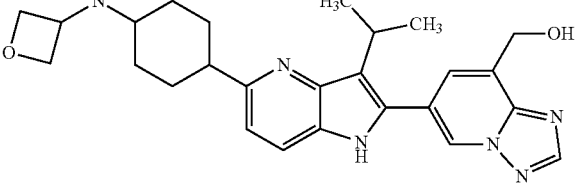 | 460.58 | 461.1 | 1.21 | QC-ACN-AA-XB |

TABLE 1-continued

| Ex. No. | Structure | Mol. Wt. | LCMS M+ | Ret Time (min) | HPLC Method |
|---|---|---|---|---|---|
| 216 | 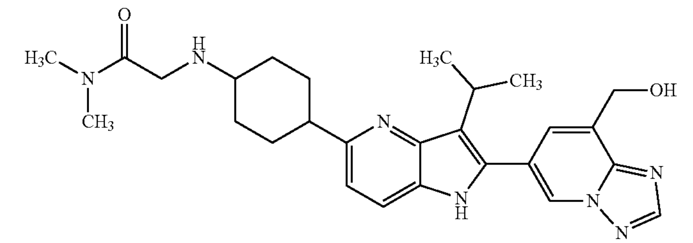 [SMILES: CC(C)c1c(-c2cc(CO)c3ncnn3c2)[nH]c2ccc(C3CCC(NCC(=O)N(C)C)CC3)nc12] | 489.62 | 490.3 | 0.78 | QC-ACN-TFA-XB |
| 217 | 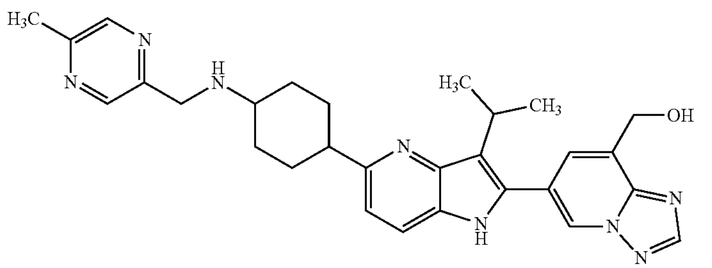 [SMILES: Cc1cnc(CNC2CCC(c3ccc4[nH]c(-c5cc(CO)c6ncnn6c5)c(C(C)C)c4n3)CC2)cn1] | 510.65 | 511.4 | 0.83 | QC-ACN-TFA-XB |
| 218 | 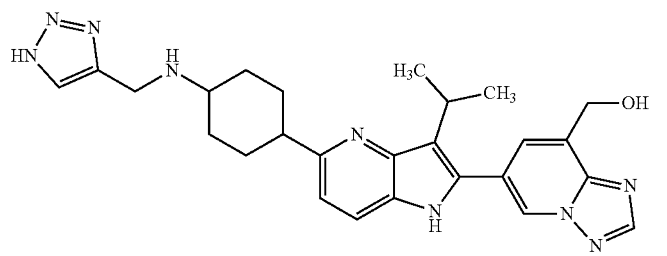 [SMILES: CC(C)c1c(-c2cc(CO)c3ncnn3c2)[nH]c2ccc(C3CCC(NCc4c[nH]nn4)CC3)nc12] | 485.60 | 486.1 | 1.06 | QC-ACN-AA-XB |
| 219 | 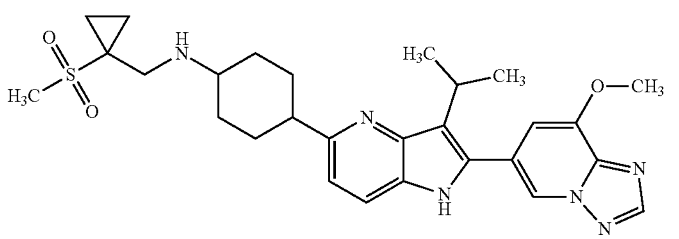 [SMILES: COc1cc(-c2[nH]c3ccc(C4CCC(NCC5(S(C)(=O)=O)CC5)CC4)nc3c2C(C)C)cn2ncnc12] | 536.70 | 537.3 | 1.62 | QC-ACN-AA-XB |
| 220 | 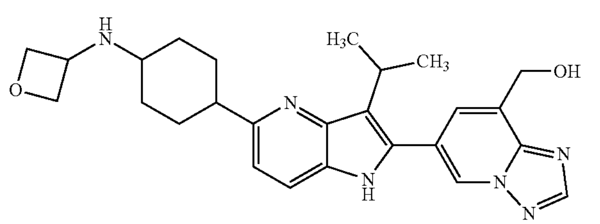 [SMILES: CC(C)c1c(-c2cc(CO)c3ncnn3c2)[nH]c2ccc(C3CCC(NC4COC4)CC3)nc12] | 460.58 | 461.3 | 0.76 | QC-ACN-TFA-XB |
| 221 | 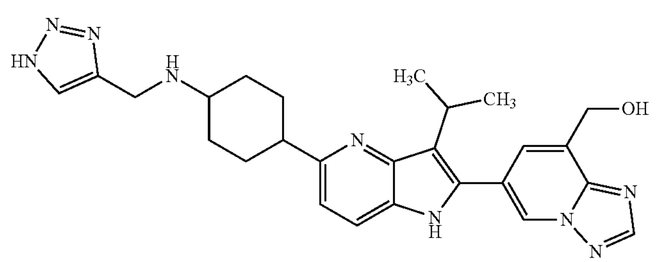 [SMILES: CC(C)c1c(-c2cc(CO)c3ncnn3c2)[nH]c2ccc(C3CCC(NCc4c[nH]nn4)CC3)nc12] | 485.60 | 486.1 | 0.63 | QC-ACN-TFA-XB |

TABLE 1-continued

| Ex. No. | Structure | Mol. Wt. | LCMS M+ | Ret Time (min) | HPLC Method |
|---|---|---|---|---|---|
| 222 | 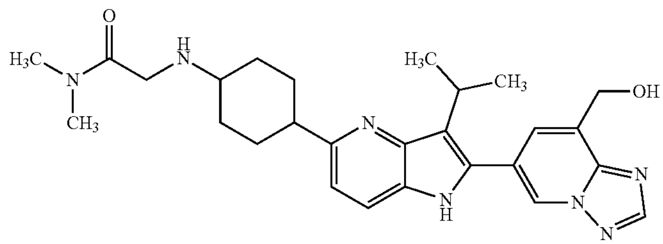 [SMILES: CC(C)c1c(-c2cc(CO)c3ncnn3c2)[nH]c2ccc(C3CCC(NCC(=O)N(C)C)CC3)nc12] | 489.62 | 490.3 | 1.07 | QC-ACN-AA-XB |
| 223 | 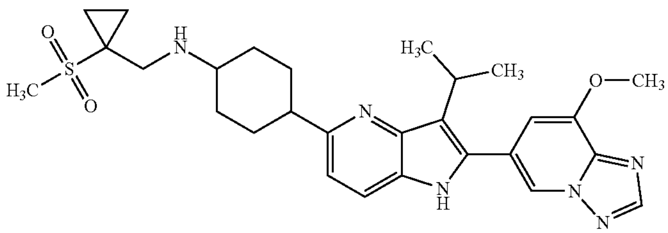 [SMILES: COc1cc(-c2[nH]c3ccc(C4CCC(NCC5(S(C)(=O)=O)CC5)CC4)nc3c2C(C)C)cn2ncnc12] | 536.70 | 537.3 | 0.85 | QC-ACN-TFA-XB |
| 224 | 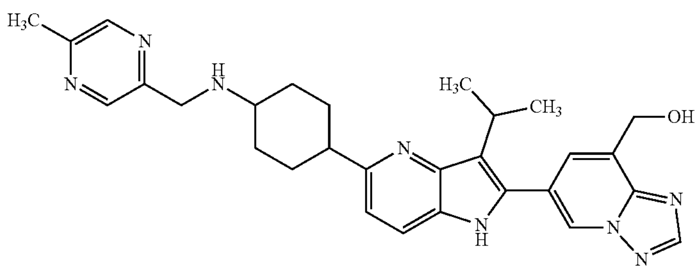 [SMILES: Cc1cnc(CNC2CCC(c3ccc4[nH]c(-c5cc(CO)c6ncnn6c5)c(C(C)C)c4n3)CC2)cn1] | 510.65 | 511.3 | 1.03 | QC-ACN-AA-XB |
| 225 | 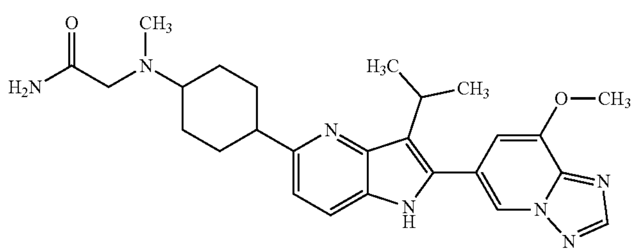 [SMILES: COc1cc(-c2[nH]c3ccc(C4CCC(N(C)CC(N)=O)CC4)nc3c2C(C)C)cn2ncnc12] | 475.60 | 476.4 | 1.37 | QC-ACN-AA-XB |
| 226 | 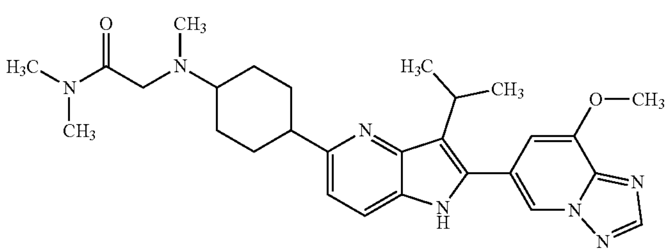 [SMILES: COc1cc(-c2[nH]c3ccc(C4CCC(N(C)CC(=O)N(C)C)CC4)nc3c2C(C)C)cn2ncnc12] | 503.65 | 504.4 | 1.32 | QC-ACN-AA-XB |
| 227 | 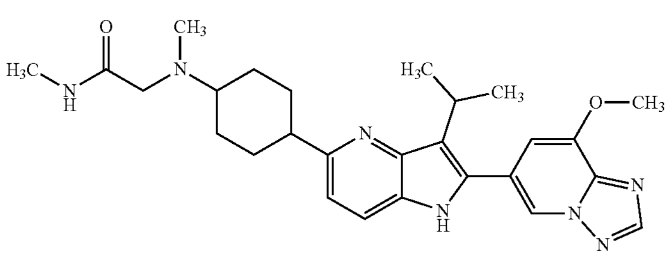 [SMILES: CNC(=O)CN(C)C1CCC(c2ccc3[nH]c(-c4cc(OC)c5ncnn5c4)c(C(C)C)c3n2)CC1] | 489.62 | 490.1 | 0.73 | QC-ACN-TFA-XB |

TABLE 1-continued

| Ex. No. | Structure | Mol. Wt. | LCMS M+ | Ret Time (min) | HPLC Method |
|---|---|---|---|---|---|
| 228 | 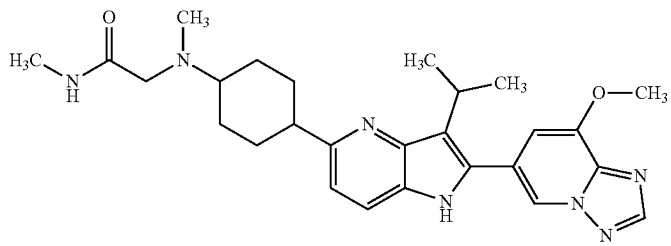 [SMILES: CNC(=O)CN(C)C1CCC(c2ccc3[nH]c(-c4cc(OC)c5ncnn5c4)c(C(C)C)c3n2)CC1] | 489.62 | 490.3 | 1.53 | QC-ACN-AA-XB |
| 229 | 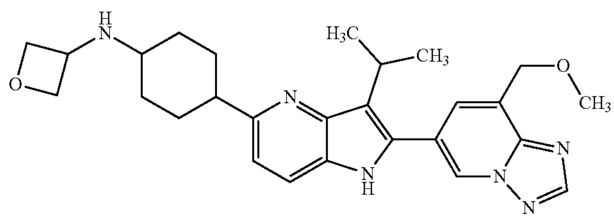 [SMILES: COCc1cc(-c2[nH]c3ccc(C4CCC(NC5COC5)CC4)nc3c2C(C)C)cn2ncnc12] | 474.61 | 475.1 | 0.76 | QC-ACN-TFA-XB |
| 230 | 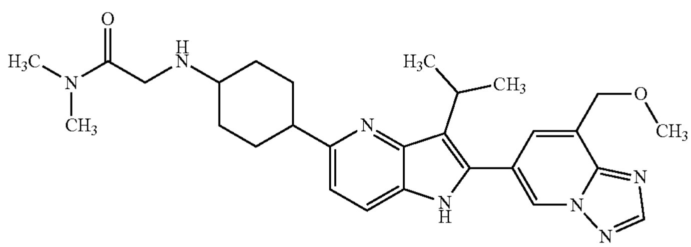 | 503.65 | 504.3 | 1.24 | QC-ACN-AA-XB |
| 231 | 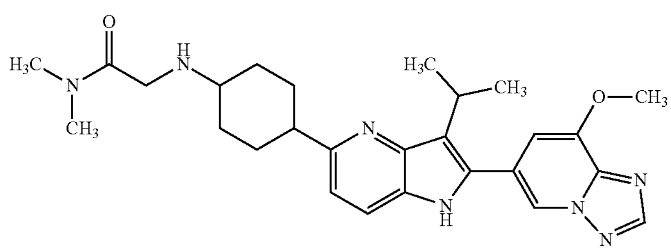 [SMILES: COc1cc(-c2[nH]c3ccc(C4CCC(NCC(=O)N(C)C)CC4)nc3c2C(C)C)cn2ncnc12] | 489.62 | 490.3 | 1.1 | QC-ACN-AA-XB |
| 232 | 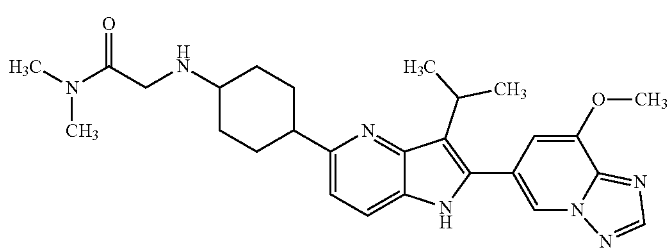 [SMILES: COc1cc(-c2[nH]c3ccc(C4CCC(NCC(=O)N(C)C)CC4)nc3c2C(C)C)cn2ncnc12] | 489.62 | 490.3 | 1.26 | QC-ACN-AA-XB |
| 233 | 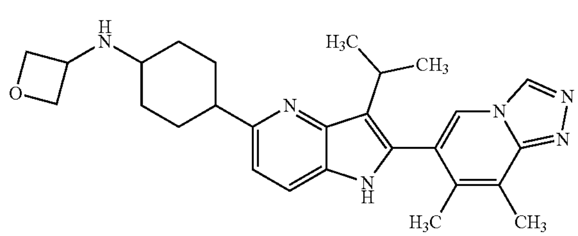 [SMILES: Cc1c(-c2[nH]c3ccc(C4CCC(NC5COC5)CC4)nc3c2C(C)C)cn2cnnc2c1C] | 458.61 | 459.4 | 1.27 | QC-ACN-AA-XB |

TABLE 1-continued

| Ex. No. | Structure | Mol. Wt. | LCMS M+ | Ret Time (min) | HPLC Method |
|---|---|---|---|---|---|
| 234 | 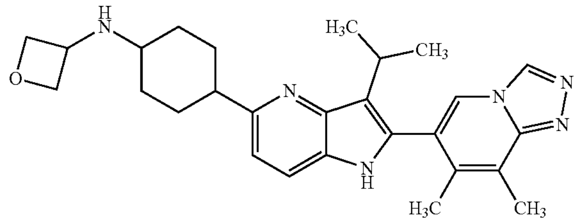 [SMILES: Cc1c(-c2[nH]c3ccc(C4CCC(NC5COC5)CC4)nc3c2C(C)C)cn2cnnc2c1C] | 458.61 | 459.3 | 1.09 | QC-ACN-AA-XB |
| 235 | 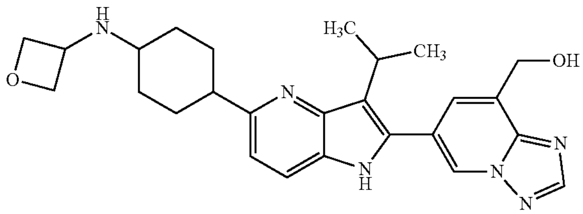 [SMILES: CC(C)c1c(-c2cc(CO)c3ncnn3c2)[nH]c2ccc(C3CCC(NC4COC4)CC3)nc12] | 460.58 | 461.3 | 0.62 | QC-ACN-TFA-XB |
| 236 | 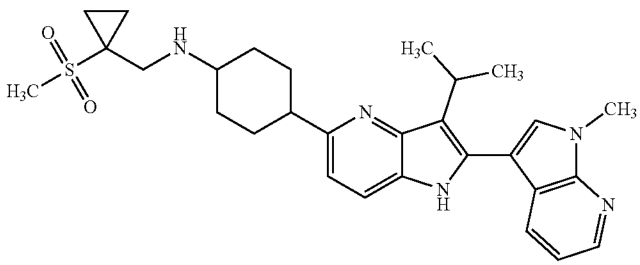 | 519.71 | 520 | 1.8 | QC-ACN-AA-XB |
| 237 | 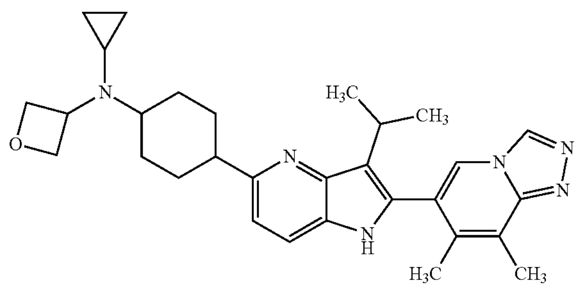 [SMILES: Cc1c(-c2[nH]c3ccc(C4CCC(N(C5CC5)C5COC5)CC4)nc3c2C(C)C)cn2cnnc2c1C] | 498.68 | 499.2 | 1.79 | QC-ACN-AA-XB |
| 238 | 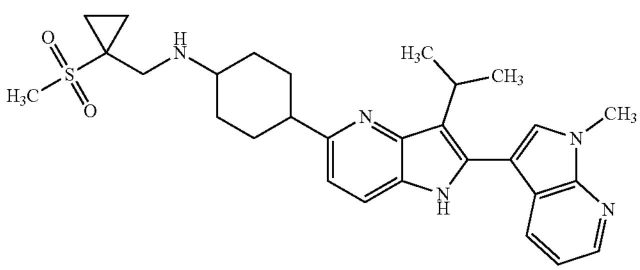 | 519.71 | 520.3 | 0.93 | QC-ACN-TFA-XB |
| 239 | 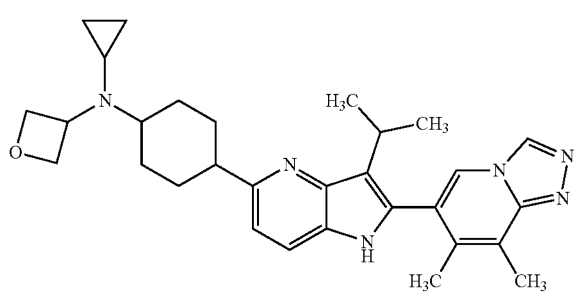 [SMILES: Cc1c(-c2[nH]c3ccc(C4CCC(N(C5CC5)C5COC5)CC4)nc3c2C(C)C)cn2cnnc2c1C] | 498.68 | 499.3 | 1.9 | QC-ACN-AA-XB |

TABLE 1-continued

| Ex. No. | Structure | Mol. Wt. | LCMS M+ | Ret Time (min) | HPLC Method |
|---|---|---|---|---|---|
| 240 | 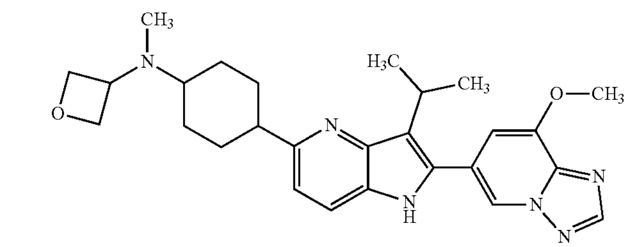 [SMILES: COc1cc(-c2[nH]c3ccc(C4CCC(N(C)C5COC5)CC4)nc3c2C(C)C)cn2ncnc12] | 474.61 | 475.2 | 1.53 | QC-ACN-AA-XB |
| 241 | 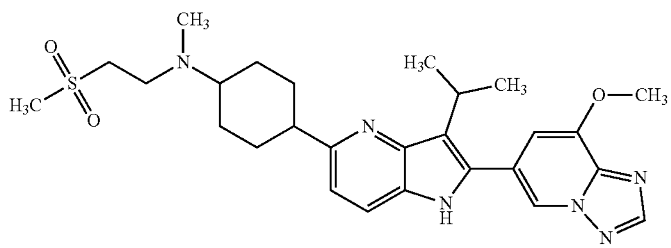 [SMILES: COc1cc(-c2[nH]c3ccc(C4CCC(N(C)CCS(C)(=O)=O)CC4)nc3c2C(C)C)cn2ncnc12] | 524.68 | 525.2 | 0.76 | QC-ACN-TFA-XB |
| 242 | 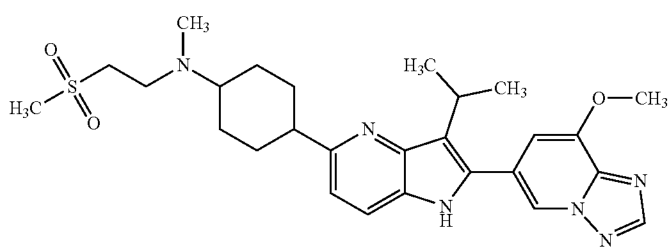 [SMILES: COc1cc(-c2[nH]c3ccc(C4CCC(N(C)CCS(C)(=O)=O)CC4)nc3c2C(C)C)cn2ncnc12] | 524.68 | 525.3 | 1.58 | QC-ACN-AA-XB |
| 243 | 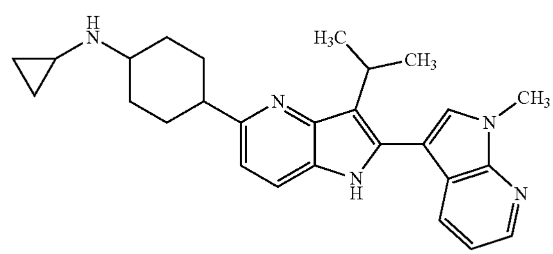 [SMILES: CC(C)c1c(-c2cn(C)c3ncccc23)[nH]c2ccc(C3CCC(NC4CC4)CC3)nc12] | 427.60 | 428.1 | 1.52 | QC-ACN-AA-XB |
| 244 | 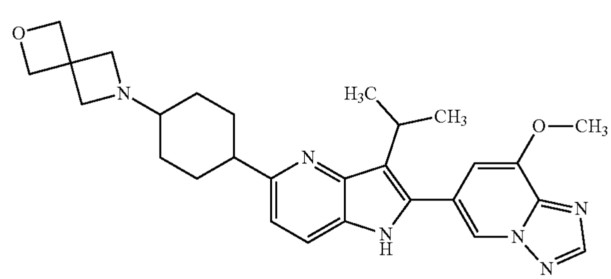 [SMILES: COc1cc(-c2[nH]c3ccc(C4CCC(N5CC6(COC6)C5)CC4)nc3c2C(C)C)cn2ncnc12] | 486.62 | 487.3 | 1.1 | QC-ACN-AA-XB |

TABLE 1-continued
| Ex. No. | Structure | Mol. Wt. | LCMS M+ | Ret Time (min) | HPLC Method |
|---|---|---|---|---|---|
| 245 | 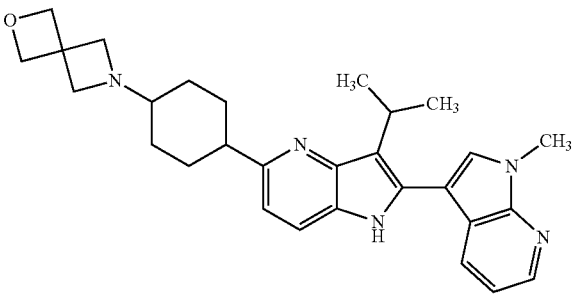 [SMILES: CC(C)c1c(-c2cn(C)c3ncccc23)[nH]c2ccc(C3CCC(N4CC5(COC5)C4)CC3)nc12] | 469.63 | 470.3 | 1.35 | QC-ACN-AA-XB |
| 246 | 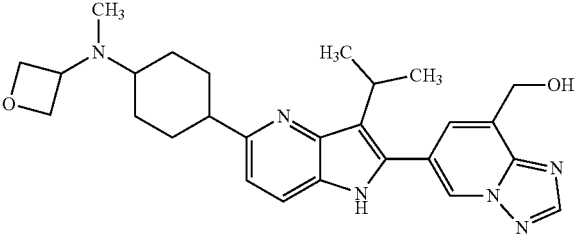 [SMILES: CC(C)c1c(-c2cc(CO)c3ncnn3c2)[nH]c2ccc(C3CCC(N(C)C4COC4)CC3)nc12] | 474.61 | 475.3 | 0.63 | QC-ACN-TFA-XB |
| 247 | 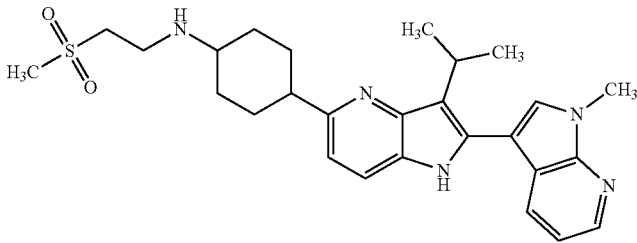 | 493.67 | 494.3 | 0.92 | QC-ACN-TFA-XB |
| 248 | 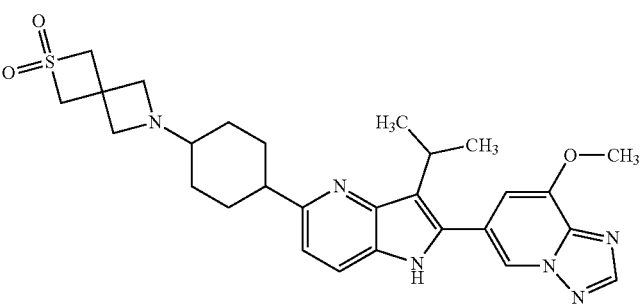 [SMILES: COc1cc(-c2[nH]c3ccc(C4CCC(N5CC6(C5)CS(=O)(=O)C6)CC4)nc3c2C(C)C)cn2ncnc12] | 534.68 | 535.2 | 1.52 | QC-ACN-AA-XB |
| 249 | 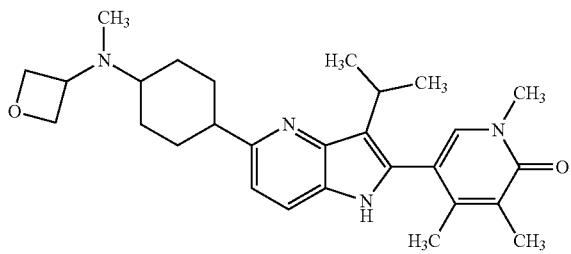 | 462.64 | 463.1 | 0.75 | QC-ACN-TFA-XB |

TABLE 1-continued
| Ex. No. | Structure | Mol. Wt. | LCMS M+ | Ret Time (min) | HPLC Method |
|---|---|---|---|---|---|
| 250 | 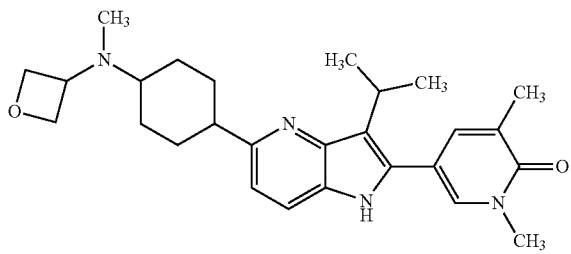 [SMILES: Cc1cc(-c2[nH]c3ccc(C4CCC(N(C)C5COC5)CC4)nc3c2C(C)C)cn(C)c1=O] | 448.61 | 449 | 1.55 | QC-ACN-AA-XB |
| 251 | 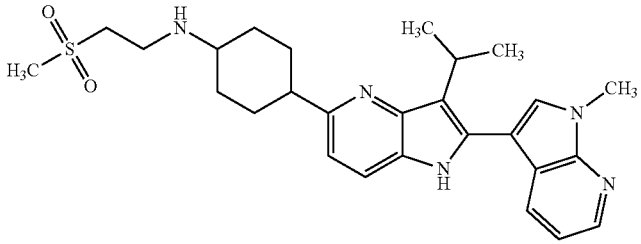 | 493.67 | 494.3 | 1.47 | QC-ACN-AA-XB |
| 252 | 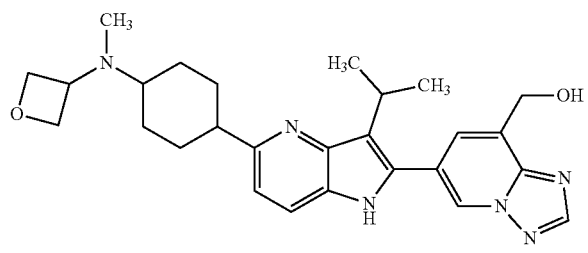 [SMILES: CC(C)c1c(-c2cc(CO)c3ncnn3c2)[nH]c2ccc(C3CCC(N(C)C4COC4)CC3)nc12] | 474.61 | 475.3 | 1.34 | QC-ACN-AA-XB |
| 253 | 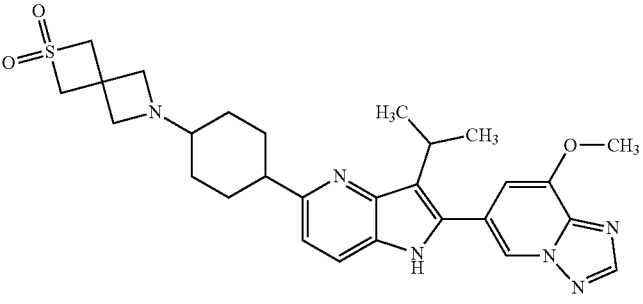 [SMILES: COc1cc(-c2[nH]c3ccc(C4CCC(N5CC6(C5)CS(=O)(=O)C6)CC4)nc3c2C(C)C)cn2ncnc12] | 534.68 | 535.2 | 1.32 | QC-ACN-AA-XB |
| 254 | 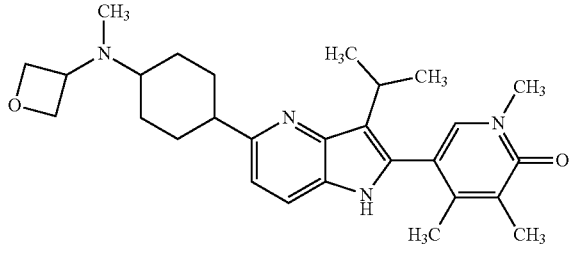 | 462.64 | 463.3 | 1.55 | QC-ACN-AA-XB |

TABLE 1-continued

| Ex. No. | Structure | Mol. Wt. | LCMS M+ | Ret Time (min) | HPLC Method |
|---|---|---|---|---|---|
| 255 | 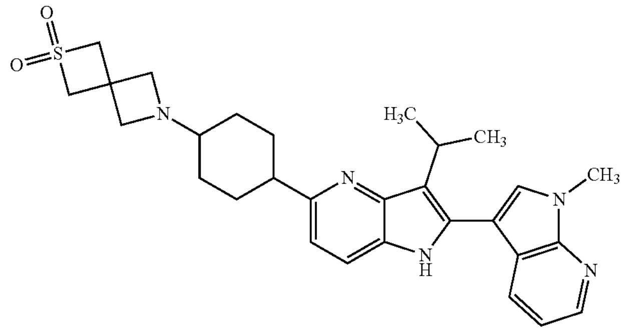 [SMILES: CC(C)c1c(-c2cn(C)c3ncccc23)[nH]c2ccc(C3CCC(N4CC5(C4)CS(=O)(=O)C5)CC3)nc12] | 517.69 | 518.1 | 1.45 | QC-ACN-AA-XB |
| 256 | 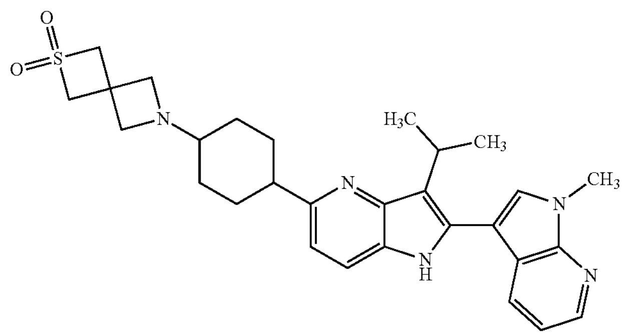 [SMILES: CC(C)c1c(-c2cn(C)c3ncccc23)[nH]c2ccc(C3CCC(N4CC5(C4)CS(=O)(=O)C5)CC3)nc12] | 517.69 | 518.2 | 1 | QC-ACN-TFA-XB |
| 257 | 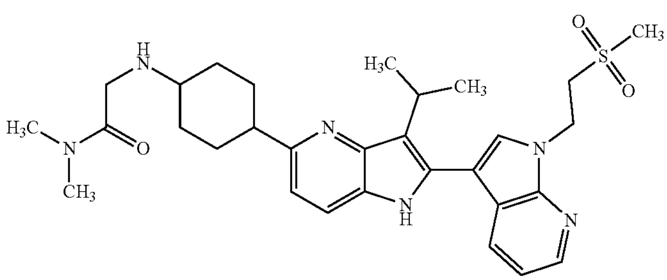 | 564.75 | 565.3 | 1.3 | QC-ACN-AA-XB |
| 258 | 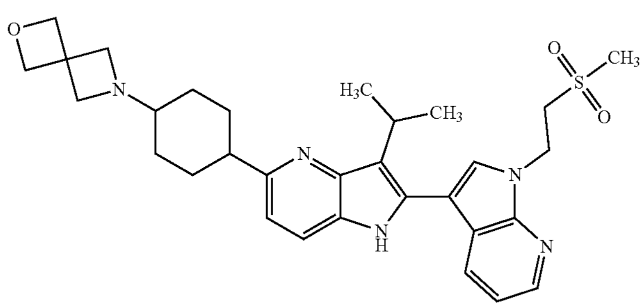 [SMILES: CC(C)c1c(-c2cn(CCS(C)(=O)=O)c3ncccc23)[nH]c2ccc(C3CCC(N4CC5(COC5)C4)CC3)nc12] | 561.75 | 562.4 | 1.23 | QC-ACN-AA-XB |
| 259 | 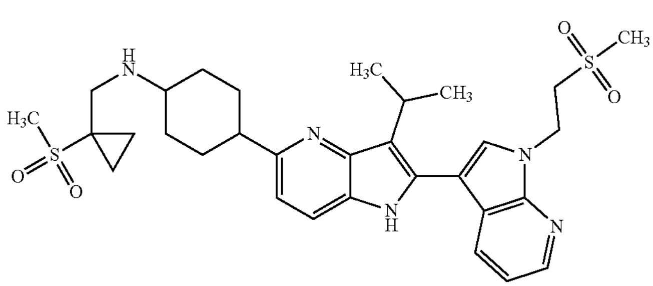 [SMILES: CC(C)c1c(-c2cn(CCS(C)(=O)=O)c3ncccc23)[nH]c2ccc(C3CCC(NCC4(S(C)(=O)=O)CC4)CC3)nc12] | 611.82 | 612.2 | 1.52 | QC-ACN-AA-XB |

TABLE 1-continued

| Ex. No. | Structure | Mol. Wt. | LCMS M+ | Ret Time (min) | HPLC Method |
|---|---|---|---|---|---|
| 260 | 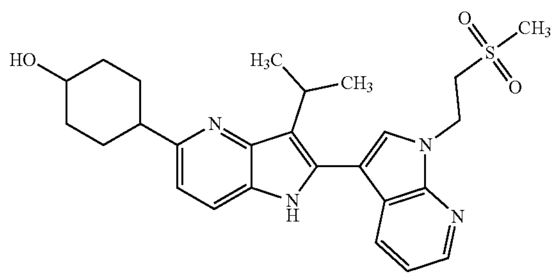 [SMILES: CC(C)c1c(-c2cn(CCS(C)(=O)=O)c3ncccc23)[nH]c2ccc(C3CCC(O)CC3)nc12] | 480.63 | 481.3 | 1.49 | QC-ACN-AA-XB |
| 261 | 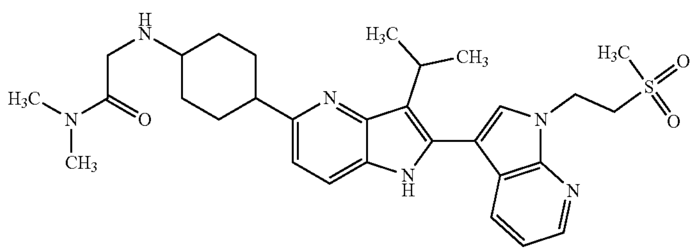 [SMILES: CC(C)c1c(-c2cn(CCS(C)(=O)=O)c3ncccc23)[nH]c2ccc(C3CCC(NCC(=O)N(C)C)CC3)nc12] | 564.75 | 565.5 | 0.9 | QC-ACN-AA-XB |
| 262 | 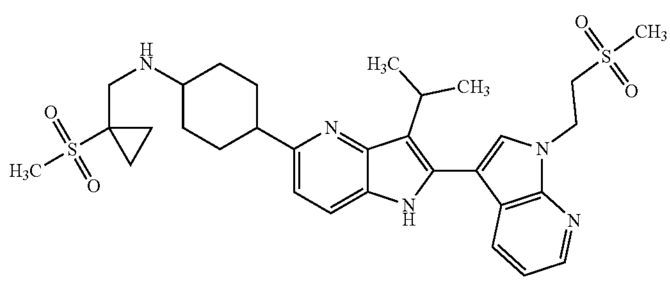 | 611.82 | 612.4 | 1.74 | QC-ACN-AA-XB |
| 263 | 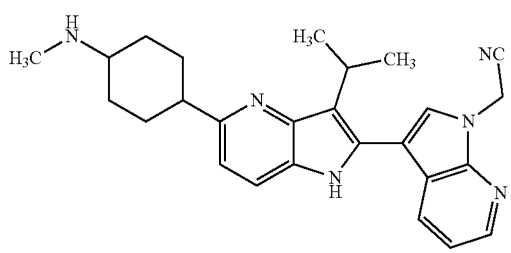 [SMILES: CNC1CCC(c2ccc3[nH]c(-c4cn(CC#N)c5ncccc45)c(C(C)C)c3n2)CC1] | 426.57 | 427.3 | 1.28 | QC-ACN-AA-XB |
| 264 | 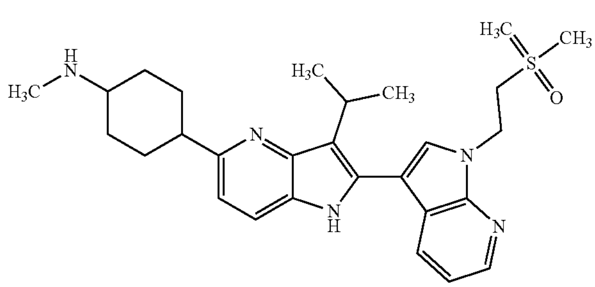 | 493.67 | 494.1 | 0.88 | QC-ACN-TFA-XB |

TABLE 1-continued

| Ex. No. | Structure | Mol. Wt. | LCMS M+ | Ret Time (min) | HPLC Method |
|---|---|---|---|---|---|
| 265 | 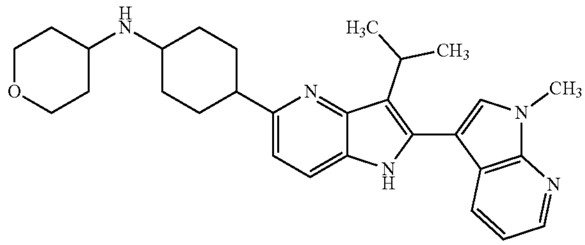 [SMILES: CC(C)c1c(-c2cn(C)c3ncccc23)[nH]c2ccc(C3CCC(NC4CCOCC4)CC3)nc12] | 471.65 | 472.4 | 1.37 | QC-ACN-AA-XB |
| 266 | 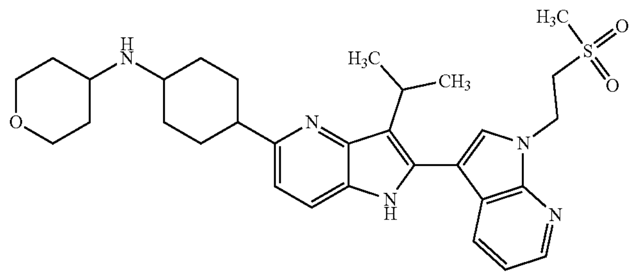 [SMILES: CC(C)c1c(-c2cn(CCS(C)(=O)=O)c3ncccc23)[nH]c2ccc(C3CCC(NC4CCOCC4)CC3)nc12] | 563.76 | 564.2 | 0.92 | QC-ACN-TFA-XB |
| 267 | 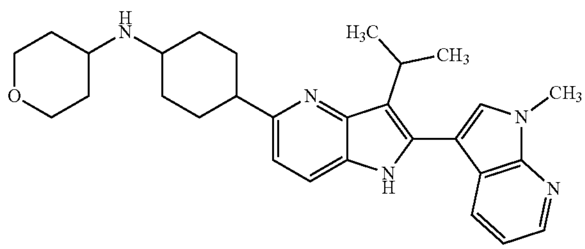 [SMILES: CC(C)c1c(-c2cn(C)c3ncccc23)[nH]c2ccc(C3CCC(NC4CCOCC4)CC3)nc12] | 471.65 | 472.4 | 1.48 | QC-ACN-AA-XB |
| 268 | 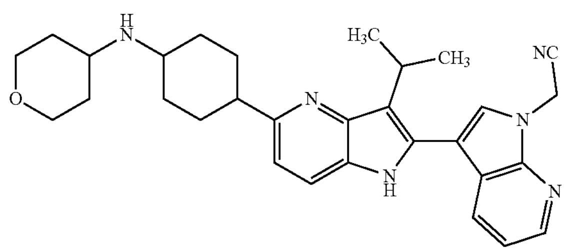 [SMILES: CC(C)c1c(-c2cn(CC#N)c3ncccc23)[nH]c2ccc(C3CCC(NC4CCOCC4)CC3)nc12] | 496.66 | 497.4 | 1.47 | QC-ACN-AA-XB |
| 269 | 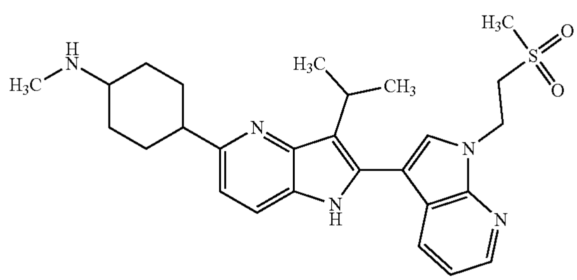 [SMILES: CNC1CCC(c2ccc3[nH]c(-c4cn(CCS(C)(=O)=O)c5ncccc45)c(C(C)C)c3n2)CC1] | 493.67 | 494.4 | 1.27 | QC-ACN-AA-XB |
| 270 | 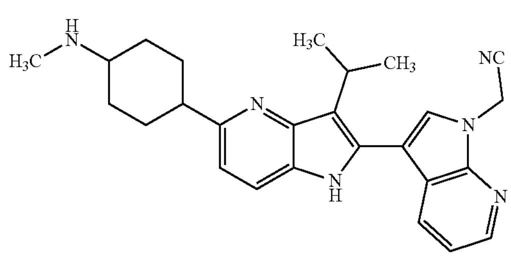 [SMILES: CNC1CCC(c2ccc3[nH]c(-c4cn(CC#N)c5ncccc45)c(C(C)C)c3n2)CC1] | 426.57 | 427.3 | 1.38 | QC-ACN-AA-XB |

TABLE 1-continued

| Ex. No. | Structure | Mol. Wt. | LCMS M+ | Ret Time (min) | HPLC Method |
|---|---|---|---|---|---|
| 271 | 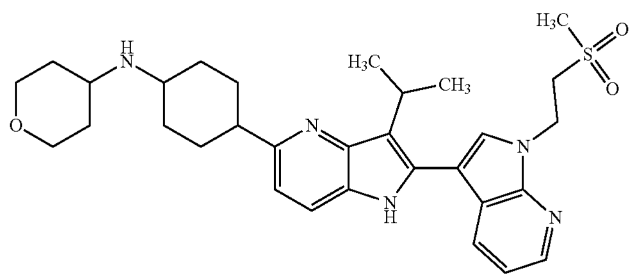 [SMILES: CC(C)c1c(-c2cn(CCS(C)(=O)=O)c3ncccc23)[nH]c2ccc(C3CCC(NC4CCOCC4)CC3)nc12] | 563.76 | 564.1 | 1.44 | QC-ACN-AA-XB |
| 272 | 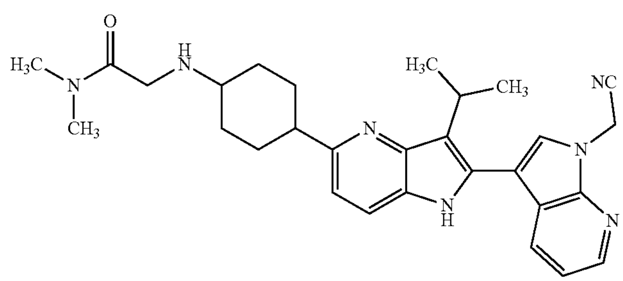 | 497.65 | 498.4 | 0.98 | QC-ACN-TFA-XB |
| 273 | 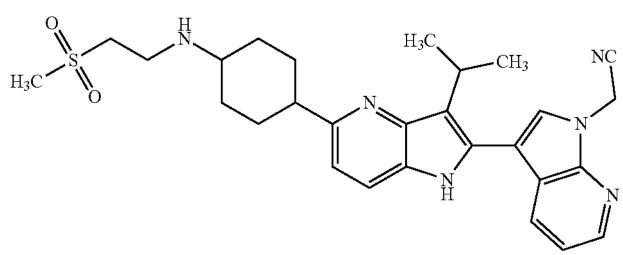 [SMILES: CC(C)c1c(-c2cn(CC#N)c3ncccc23)[nH]c2ccc(C3CCC(NCCS(C)(=O)=O)CC3)nc12] | 518.68 | 519.1 | 1.57 | QC-ACN-AA-XB |
| 274 | 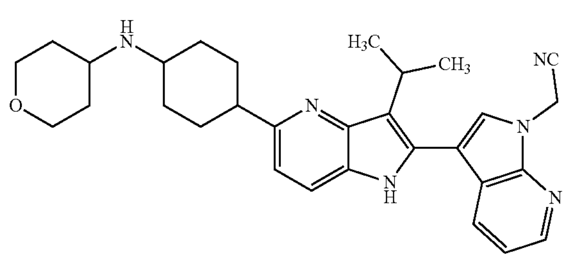 [SMILES: CC(C)c1c(-c2cn(CC#N)c3ncccc23)[nH]c2ccc(C3CCC(NC4CCOCC4)CC3)nc12] | 496.66 | 497.2 | 1.44 | QC-ACN-AA-XB |
| 275 | 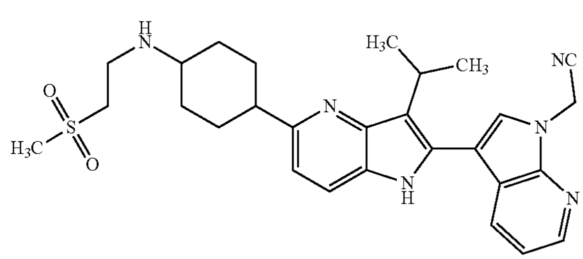 [SMILES: CC(C)c1c(-c2cn(CC#N)c3ncccc23)[nH]c2ccc(C3CCC(NCCS(C)(=O)=O)CC3)nc12] | 518.68 | 519.3 | 1.47 | QC-ACN-AA-XB |

TABLE 1-continued

| Ex. No. | Structure | Mol. Wt. | LCMS M+ | Ret Time (min) | HPLC Method |
|---|---|---|---|---|---|
| 276 | 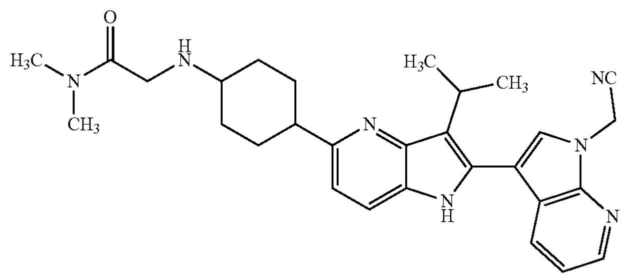 [SMILES: CC(C)c1c(-c2cn(CC#N)c3ncccc23)[nH]c2ccc(C3CCC(NCC(=O)N(C)C)CC3)nc12] | 497.65 | 498.4 | 1.41 | QC-ACN-AA-XB |
| 277 | 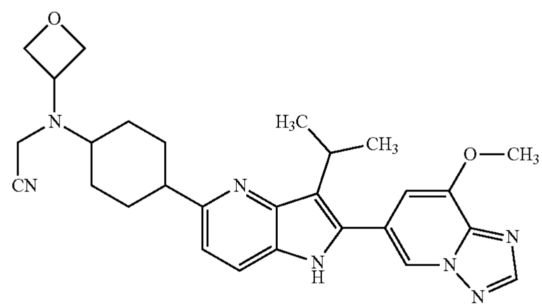 [SMILES: COc1cc(-c2[nH]c3ccc(C4CCC(N(CC#N)C5COC5)CC4)nc3c2C(C)C)cn2ncnc12] | 499.62 | 500 | 1.27 | QC-ACN-TFA-XB |
| 278 | 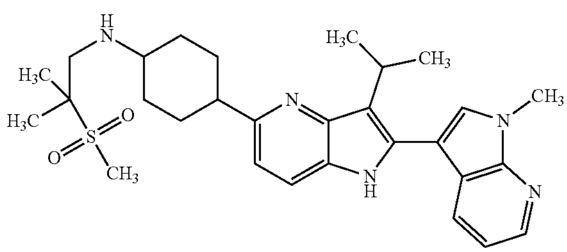 [SMILES: CC(C)c1c(-c2cn(C)c3ncccc23)[nH]c2ccc(C3CCC(NCC(C)(C)S(C)(=O)=O)CC3)nc12] | 521.72 | 522.3 | 0.99 | QC-ACN-TFA-XB |
| 279 | 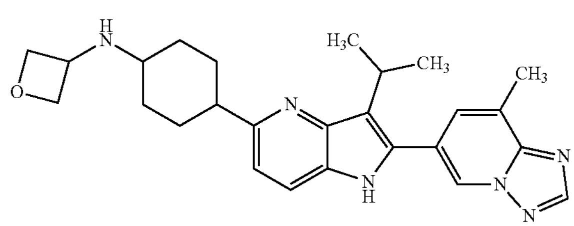 [SMILES: Cc1cc(-c2[nH]c3ccc(C4CCC(NC5COC5)CC4)nc3c2C(C)C)cn2ncnc12] | 444.58 | 445.3 | 1.31 | QC-ACN-AA-XB |
| 280 | 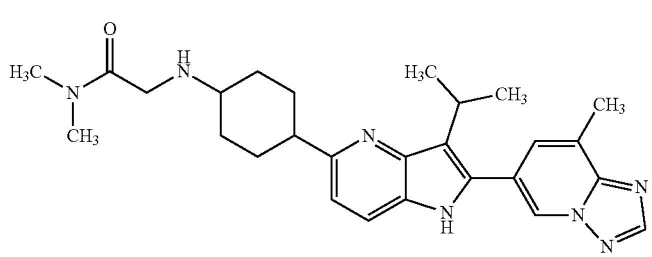 [SMILES: Cc1cc(-c2[nH]c3ccc(C4CCC(NCC(=O)N(C)C)CC4)nc3c2C(C)C)cn2ncnc12] | 473.63 | 474.4 | 0.81 | QC-ACN-TFA-XB |

TABLE 1-continued

| Ex. No. | Structure | Mol. Wt. | LCMS M+ | Ret Time (min) | HPLC Method |
|---|---|---|---|---|---|
| 281 | 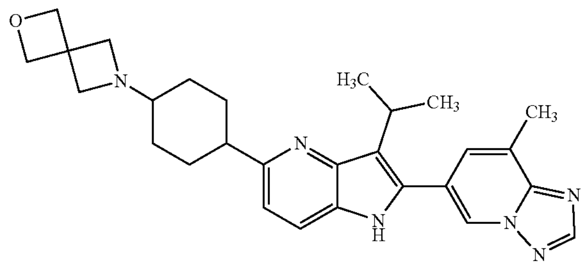 [SMILES: Cc1cc(-c2[nH]c3ccc(C4CCC(N5CC6(COC6)C5)CC4)nc3c2C(C)C)cn2ncnc12] | 470.62 | 471.2 | 0.77 | QC-ACN-TFA-XB |
| 282 | 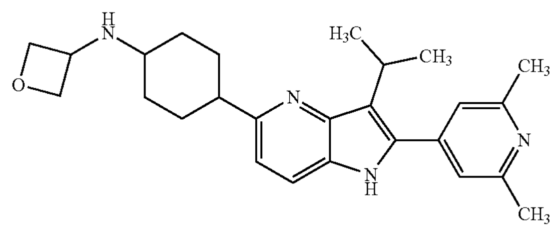 [SMILES: Cc1cc(-c2[nH]c3ccc(C4CCC(NC5COC5)CC4)nc3c2C(C)C)cc(C)n1] | 418.59 | 419 | 1.55 | QC-ACN-AA-XB |
| 283 | 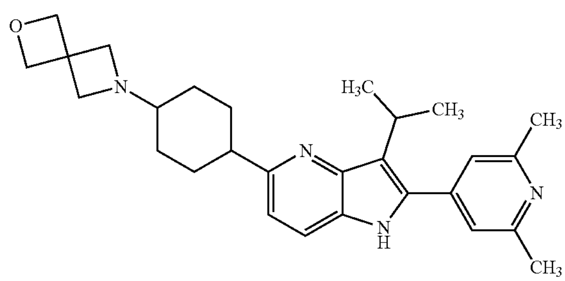 [SMILES: Cc1cc(-c2[nH]c3ccc(C4CCC(N5CC6(COC6)C5)CC4)nc3c2C(C)C)cc(C)n1] | 444.62 | 445 | 1.45 | QC-ACN-AA-XB |
| 284 | 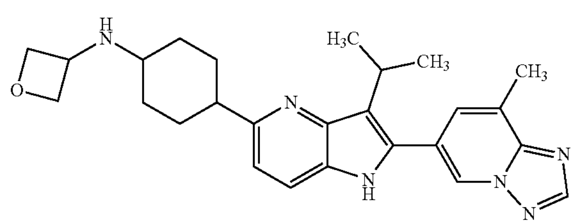 [SMILES: Cc1cc(-c2[nH]c3ccc(C4CCC(NC5COC5)CC4)nc3c2C(C)C)cn2ncnc12] | 444.58 | 445.3 | 0.79 | QC-ACN-TFA-XB |
| 285 | 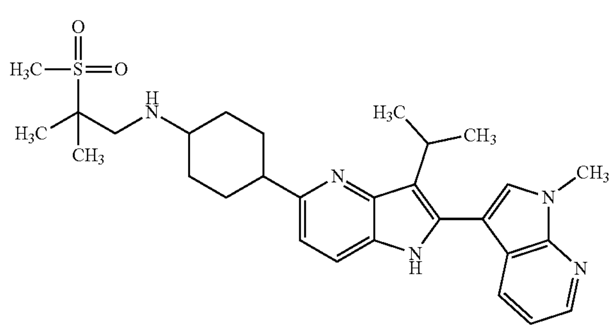 | 521.72 | 522.4 | 1.96 | QC-ACN-AA-XB |

US 11,053,244 B1
TABLE 1-continued
| Ex. No. | Structure | Mol. Wt. | LCMS M+ | Ret Time (min) | HPLC Method |
|---|---|---|---|---|---|
| 286 | 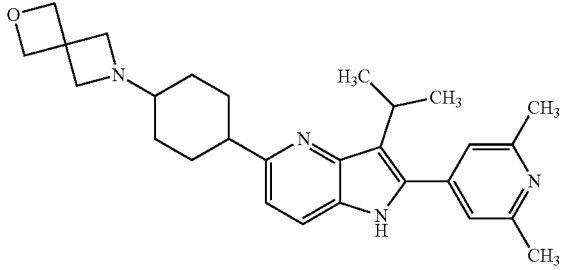 [SMILES: Cc1cc(-c2[nH]c3ccc(C4CCC(N5CC6(COC6)C5)CC4)nc3c2C(C)C)cc(C)n1] | 444.62 | 445.19 | 1.57 | QC-ACN-TFA-XB |
| 287 | 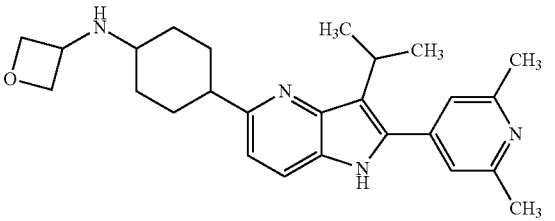 [SMILES: Cc1cc(-c2[nH]c3ccc(C4CCC(NC5COC5)CC4)nc3c2C(C)C)cc(C)n1] | 418.59 | 419.3 | 0.62 | QC-ACN-TFA-XB |
| 288 | 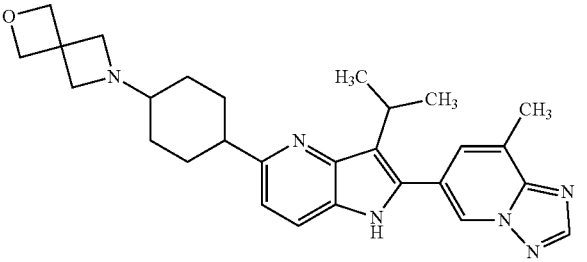 [SMILES: Cc1cc(-c2[nH]c3ccc(C4CCC(N5CC6(COC6)C5)CC4)nc3c2C(C)C)cn2ncnc12] | 470.62 | 471.2 | 0.79 | QC-ACN-TFA-XB |
| 289 | 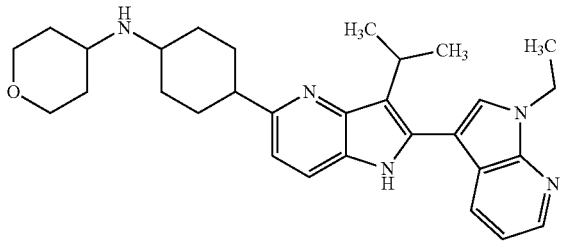 | 485.68 | 486.3 | 1.07 | QC-ACN-TFA-XB |
| 290 | 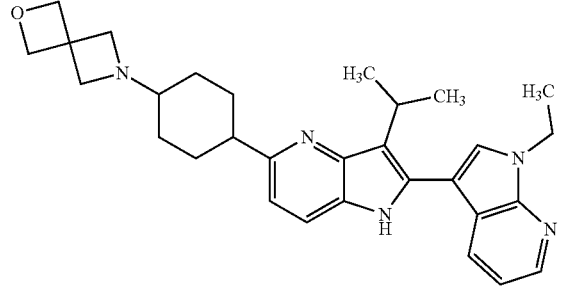 [SMILES: CCn1cc(-c2[nH]c3ccc(C4CCC(N5CC6(COC6)C5)CC4)nc3c2C(C)C)c2cccnc21] | 483.66 | 484.4 | 1.05 | QC-ACN-TFA-XB |

TABLE 1-continued
| Ex. No. | Structure | Mol. Wt. | LCMS M+ | Ret Time (min) | HPLC Method |
|---|---|---|---|---|---|
| 291 | 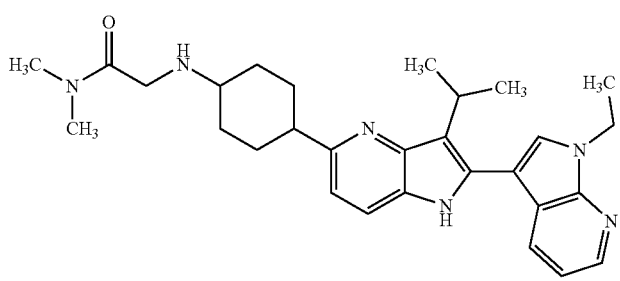 | 486.66 | 487.4 | 1.06 | QC-ACN-TFA-XB |
| 292 | 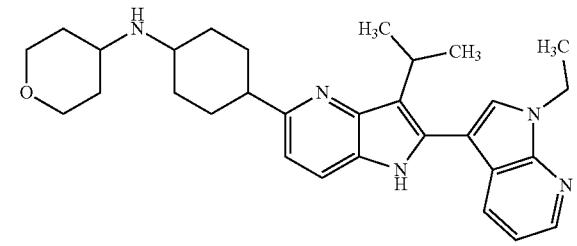 [SMILES: CCn1cc(-c2[nH]c3ccc(C4CCC(NC5CCOCC5)CC4)nc3c2C(C)C)c2cccnc21] | 485.68 | 486.4 | 1.58 | QC-ACN-AA-XB |
| 293 | 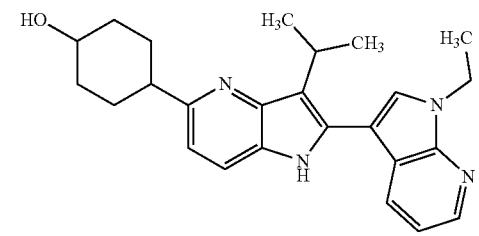 [SMILES: CCn1cc(-c2[nH]c3ccc(C4CCC(O)CC4)nc3c2C(C)C)c2cccnc21] | 402.54 | 403.2 | 1.62 | QC-ACN-AA-XB |
| 294 | 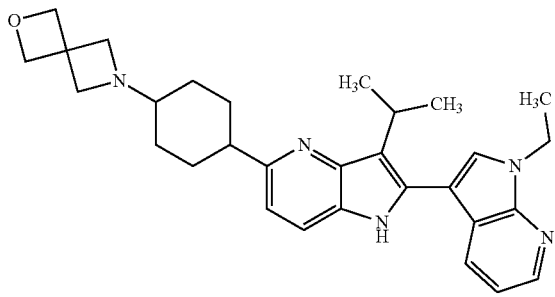 [SMILES: CCn1cc(-c2[nH]c3ccc(C4CCC(N5CC6(COC6)C5)CC4)nc3c2C(C)C)c2cccnc21] | 483.66 | 484.3 | 1.52 | QC-ACN-AA-XB |
| 295 | 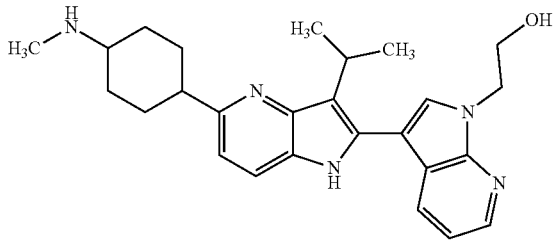 [SMILES: CNC1CCC(c2ccc3[nH]c(-c4cn(CCO)c5ncccc45)c(C(C)C)c3n2)CC1] | 431.58 | 432.2 | 1.12 | QC-ACN-TFA-XB |

TABLE 1-continued

| Ex. No. | Structure | Mol. Wt. | LCMS M+ | Ret Time (min) | HPLC Method |
|---|---|---|---|---|---|
| 296 | 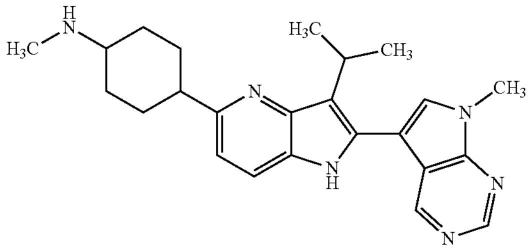 | 402.55 | 403.3 | 1.06 | QC-ACN-AA-XB |
| 297 | 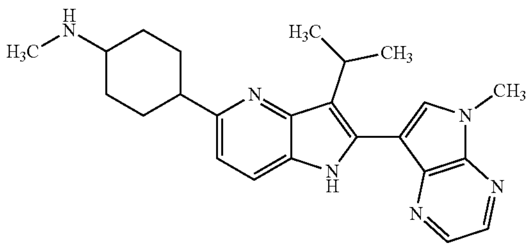 | 402.55 | 403.32 | | QC-ACN-AA-XB |
| 299 | 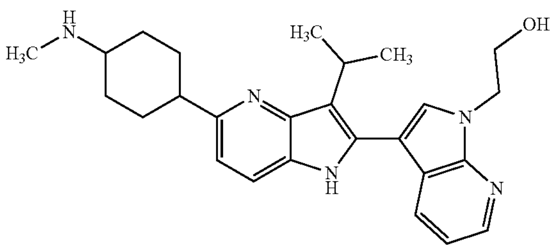 [SMILES: CNC1CCC(c2ccc3[nH]c(-c4cn(CCO)c5ncccc45)c(C(C)C)c3n2)CC1] | 431.58 | 432.4 | 0.78 | QC-ACN-TFA-XB |
| 300 | 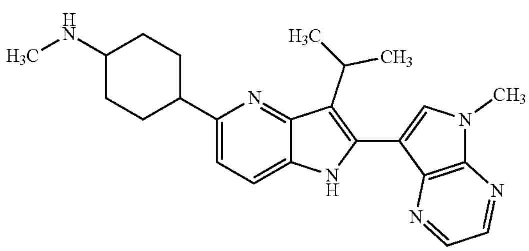 | 402.55 | 403.1 | 1.49 | QC-ACN-TFA-XB |
| 301 | 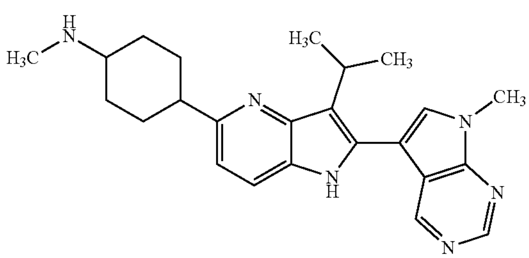 | 402.55 | 403.3 | 1.14 | QC-ACN-AA-XB |
| 302 | 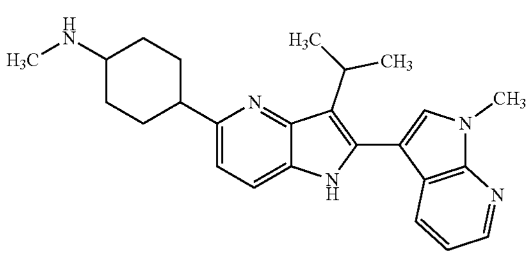 | 401.56 | 402.1 | 0.8 | QC-ACN-TFA-XB |

TABLE 1-continued

| Ex. No. | Structure | Mol. Wt. | LCMS M+ | Ret Time (min) | HPLC Method |
|---|---|---|---|---|---|
| 303 | 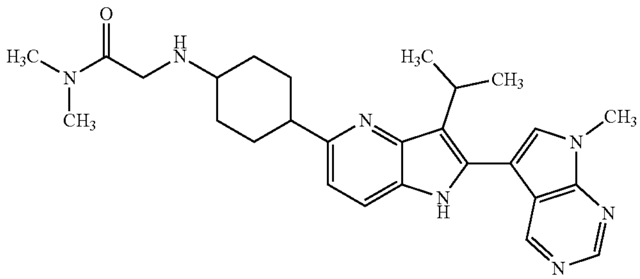 | 473.63 | 474.2 | 1.14 | QC-ACN-AA-XB |
| 304 | 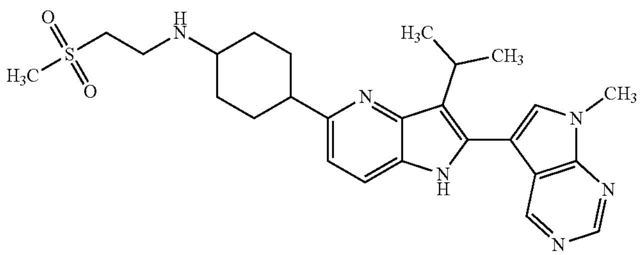 | 494.66 | 495.2 | 0.64 | QC-ACN-TFA-XB |
| 305 | 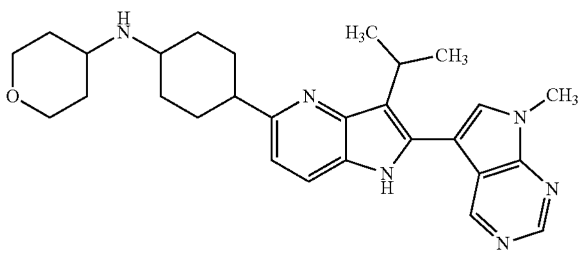 [SMILES: CC(C)c1c(-c2cn(C)c3ncncc23)[nH]c2ccc(C3CCC(NC4CCOCC4)CC3)nc12] | 472.64 | 473.3 | 1.22 | QC-ACN-AA-XB |
| 306 | 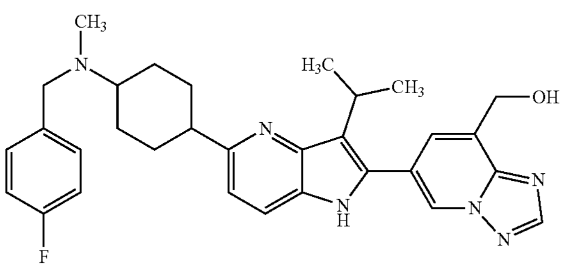 [SMILES: CC(C)c1c(-c2cc(CO)c3ncnn3c2)[nH]c2ccc(C3CCC(N(C)Cc4ccc(F)cc4)CC3)nc12] | 526.66 | 527.1 | 1.68 | QC-ACN-AA-XB |
| 307 | 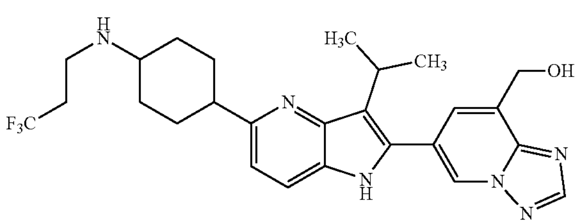 [SMILES: CC(C)c1c(-c2cc(CO)c3ncnn3c2)[nH]c2ccc(C3CCC(NCCC(F)(F)F)CC3)nc12] | 500.57 | 501.4 | 1.53 | QC-ACN-AA-XB |
| 308 | 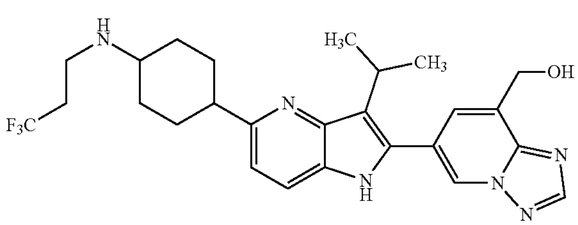 [SMILES: CC(C)c1c(-c2cc(CO)c3ncnn3c2)[nH]c2ccc(C3CCC(NCCC(F)(F)F)CC3)nc12] | 500.57 | 501.1 | 1.01 | QC-ACN-TFA-XB |

TABLE 1-continued

| Ex. No. | Structure | Mol. Wt. | LCMS M+ | Ret Time (min) | HPLC Method |
|---|---|---|---|---|---|
| 309 | 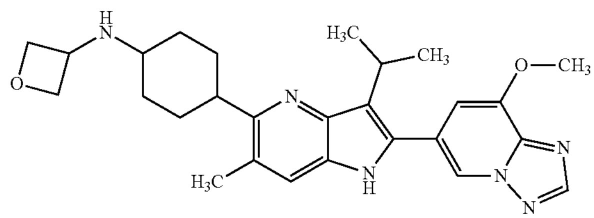 | 474.61 | 475.3 | 1.6 | E |
| 310 | 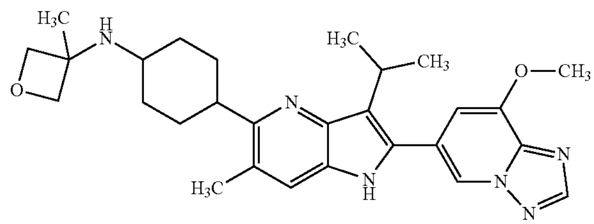 [SMILES: COc1cc(-c2[nH]c3cc(C)c(C4CCC(NC5(C)COC5)CC4)nc3c2C(C)C)cn2ncnc12] | 488.64 | 489 | 1.66 | E |
| 311 | 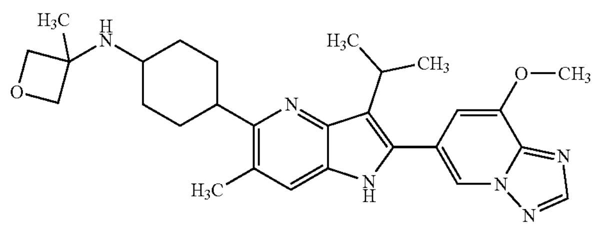 [SMILES: COc1cc(-c2[nH]c3cc(C)c(C4CCC(NC5(C)COC5)CC4)nc3c2C(C)C)cn2ncnc12] | 488.64 | 489.4 | 1.81 | E |
| 312 | 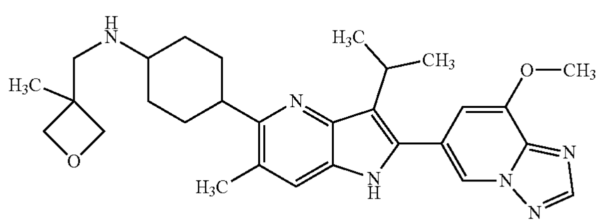 [SMILES: COc1cc(-c2[nH]c3cc(C)c(C4CCC(NCC5(C)COC5)CC4)nc3c2C(C)C)cn2ncnc12] | 502.66 | 503.3 | 1.5 | E |
| 313 | 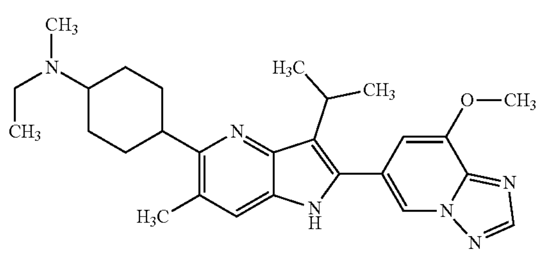 [SMILES: CCN(C)C1CCC(c2nc3c(C(C)C)c(-c4cc(OC)c5ncnn5c4)[nH]c3cc2C)CC1] | 460.63 | 461.3 | 1.44 | E |
| 314 | 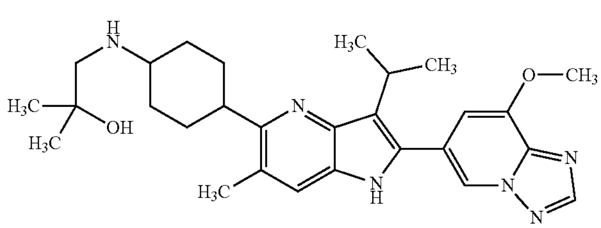 [SMILES: COc1cc(-c2[nH]c3cc(C)c(C4CCC(NCC(C)(C)O)CC4)nc3c2C(C)C)cn2ncnc12] | 490.65 | 491.4 | 1.46 | E |

TABLE 1-continued

| Ex. No. | Structure | Mol. Wt. | LCMS M+ | Ret Time (min) | HPLC Method |
|---|---|---|---|---|---|
| 315 | 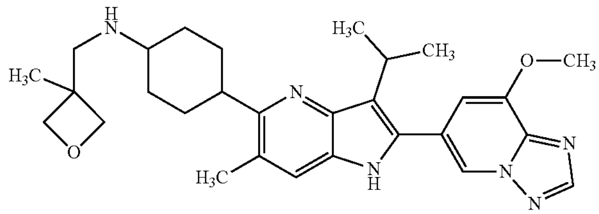 [SMILES: COc1cc(-c2[nH]c3cc(C)c(C4CCC(NCC5(C)COC5)CC4)nc3c2C(C)C)cn2ncnc12] | 502.66 | 503 | 1.67 | E |
| 316 | 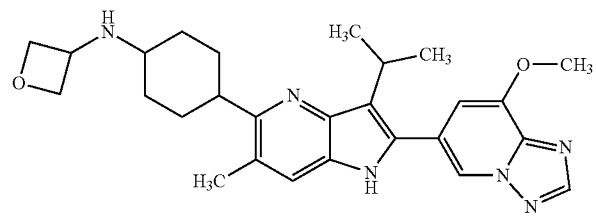 [SMILES: COc1cc(-c2[nH]c3cc(C)c(C4CCC(NC5COC5)CC4)nc3c2C(C)C)cn2ncnc12] | 474.61 | 475.4 | 1.69 | E |
| 317 | 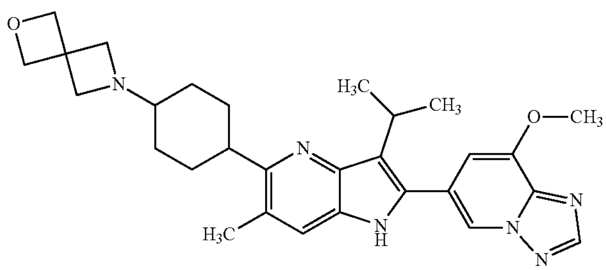 [SMILES: COc1cc(-c2[nH]c3cc(C)c(C4CCC(N5CC6(COC6)C5)CC4)nc3c2C(C)C)cn2ncnc12] | 500.65 | 501.3 | 1.51 | E |
| 318 | 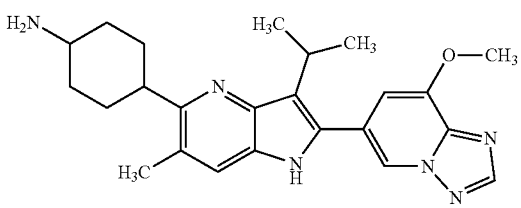 [SMILES: COc1cc(-c2[nH]c3cc(C)c(C4CCC(N)CC4)nc3c2C(C)C)cn2ncnc12] | 418.55 | 419.3 | 1.24 | E |
| 319 | 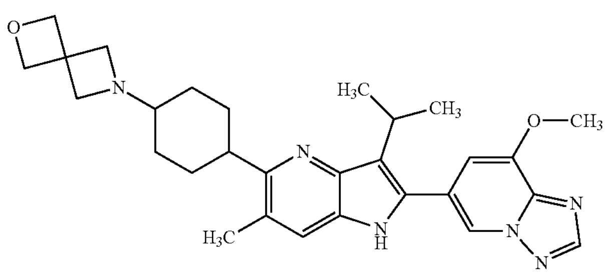 [SMILES: COc1cc(-c2[nH]c3cc(C)c(C4CCC(N5CC6(COC6)C5)CC4)nc3c2C(C)C)cn2ncnc12] | 500.65 | 501.3 | 1.5 | E |
| 320 | 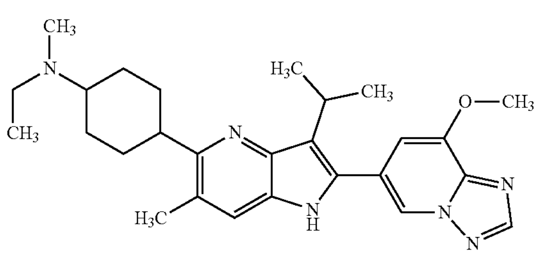 [SMILES: CCN(C)C1CCC(c2nc3c(C(C)C)c(-c4cc(OC)c5ncnn5c4)[nH]c3cc2C)CC1] | 460.63 | 461.4 | 1.44 | E |

TABLE 1-continued
| Ex. No. | Structure | Mol. Wt. | LCMS M+ | Ret Time (min) | HPLC Method |
|---|---|---|---|---|---|
| 321 | 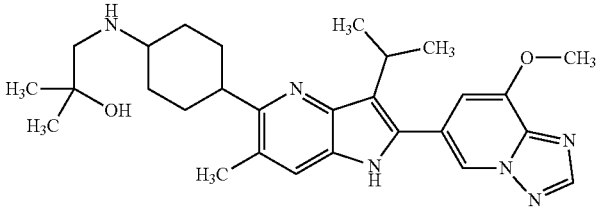 [SMILES: COc1cc(-c2[nH]c3cc(C)c(C4CCC(NCC(C)(C)O)CC4)nc3c2C(C)C)cn2ncnc12] | 490.65 | 491.4 | 1.4 | E |
| 322 | 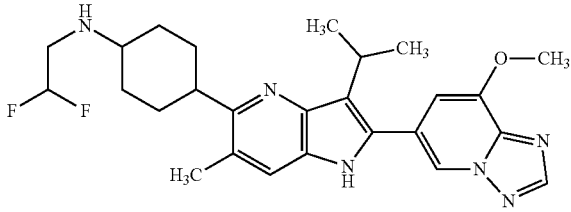 [SMILES: COc1cc(-c2[nH]c3cc(C)c(C4CCC(NCC(F)F)CC4)nc3c2C(C)C)cn2ncnc12] | 482.58 | 483.3 | 2.01 | E |
| 323 | 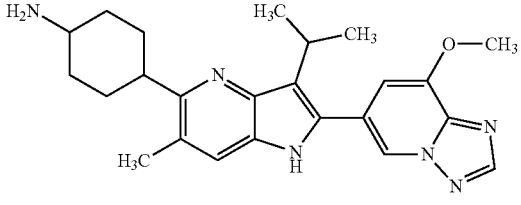 | 418.55 | 419.3 | 1.26 | E |
| 324 | 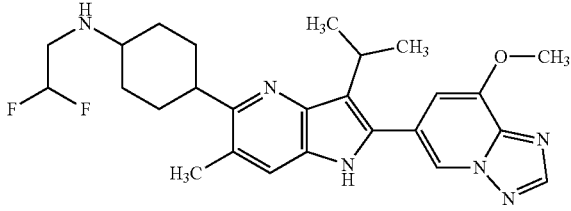 | 482.58 | 483 | 2.16 | E |
| 325 | 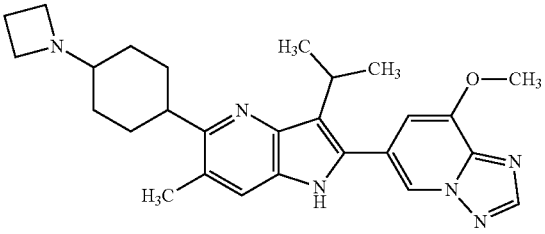 [SMILES: COc1cc(-c2[nH]c3cc(C)c(C4CCC(N5CCC5)CC4)nc3c2C(C)C)cn2ncnc12] | 458.61 | 459 | 1.39 | E |
| 326 | 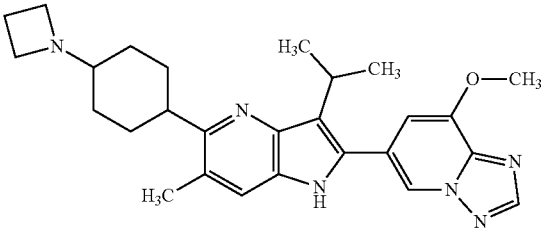 [SMILES: COc1cc(-c2[nH]c3cc(C)c(C4CCC(N5CCC5)CC4)nc3c2C(C)C)cn2ncnc12] | 458.61 | 459 | 1.15 | E |

TABLE 1-continued

| Ex. No. | Structure | Mol. Wt. | LCMS M+ | Ret Time (min) | HPLC Method |
|---|---|---|---|---|---|
| 327 | 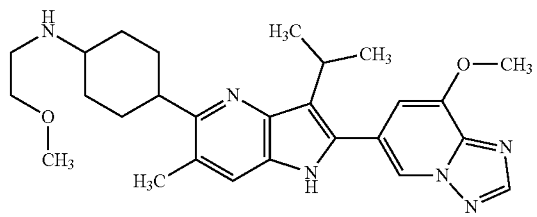 [SMILES: COCCNC1CCC(c2nc3c(C(C)C)c(-c4cc(OC)c5ncnn5c4)[nH]c3cc2C)CC1] | 476.63 | 477.4 | 1.46 | E |
| 328 | 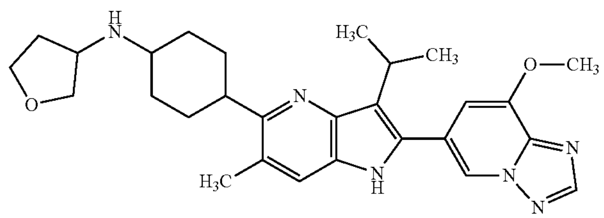 | 488.64 | 489 | 1.45 | E |
| 329 | 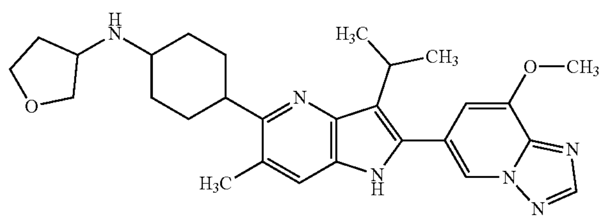 | 488.64 | 489 | 1.52 | E |
| 330 | 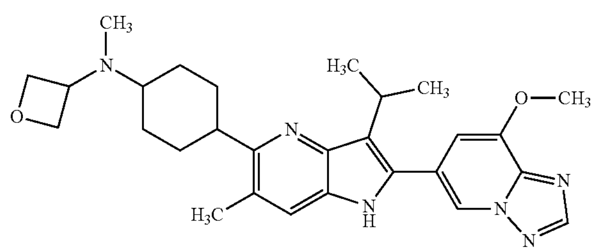 [SMILES: COc1cc(-c2[nH]c3cc(C)c(C4CCC(N(C)C5COC5)CC4)nc3c2C(C)C)cn2ncnc12] | 488.64 | 489 | 1.8 | E |
| 331 | 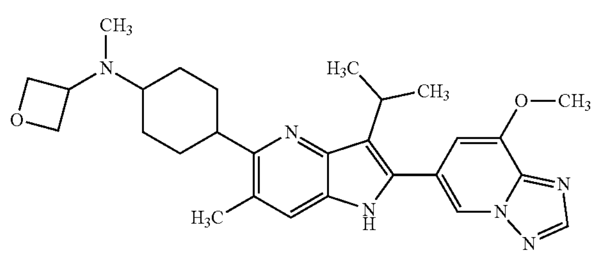 [SMILES: COc1cc(-c2[nH]c3cc(C)c(C4CCC(N(C)C5COC5)CC4)nc3c2C(C)C)cn2ncnc12] | 488.64 | 489.3 | 1.83 | E |
| 332 | 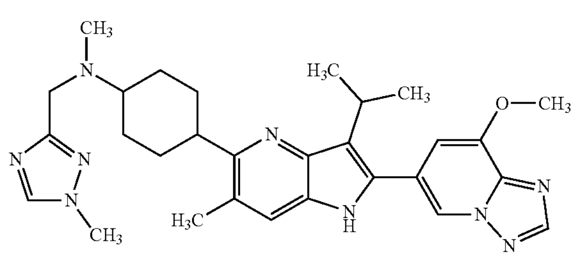 [SMILES: COc1cc(-c2[nH]c3cc(C)c(C4CCC(N(C)Cc5ncn(C)n5)CC4)nc3c2C(C)C)cn2ncnc12] | 527.68 | 528.4 | 1.51 | E |

TABLE 1-continued

| Ex. No. | Structure | Mol. Wt. | LCMS M+ | Ret Time (min) | HPLC Method |
|---|---|---|---|---|---|
| 333 | 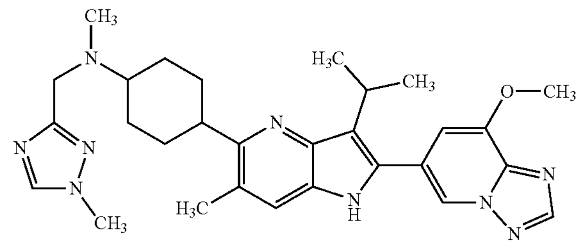 [SMILES: COc1cc(-c2[nH]c3cc(C)c(C4CCC(N(C)Cc5ncn(C)n5)CC4)nc3c2C(C)C)cn2ncnc12] | 527.68 | 528.4 | 1.49 | E |
| 334 | 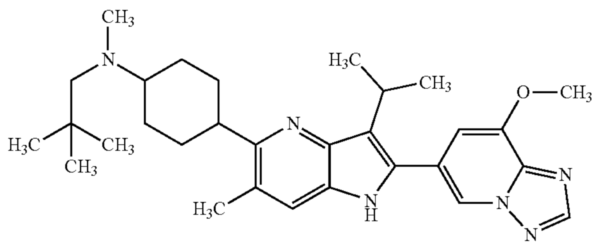 [SMILES: COc1cc(-c2[nH]c3cc(C)c(C4CCC(N(C)CC(C)(C)C)CC4)nc3c2C(C)C)cn2ncnc12] | 502.71 | 503 | 1.8 | E |
| 335 | 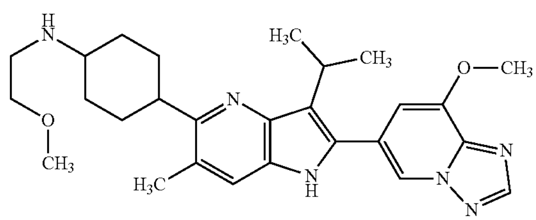 [SMILES: COCCNC1CCC(c2nc3c(C(C)C)c(-c4cc(OC)c5ncnn5c4)[nH]c3cc2C)CC1] | 476.63 | 477 | 1.43 | E |
| 336 | 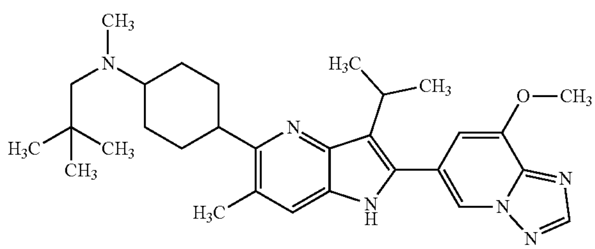 [SMILES: COc1cc(-c2[nH]c3cc(C)c(C4CCC(N(C)CC(C)(C)C)CC4)nc3c2C(C)C)cn2ncnc12] | 502.71 | 503 | 1.89 | E |
| 337 | 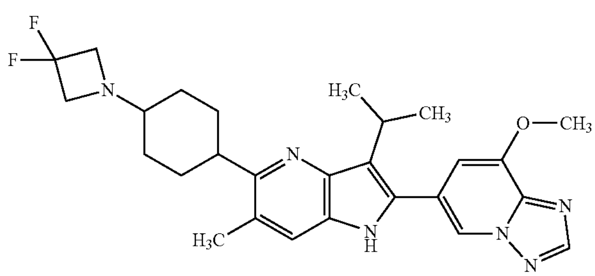 [SMILES: COc1cc(-c2[nH]c3cc(C)c(C4CCC(N5CC(F)(F)C5)CC4)nc3c2C(C)C)cn2ncnc12] | 494.59 | 495.3 | 2.1 | E |
| 338 | 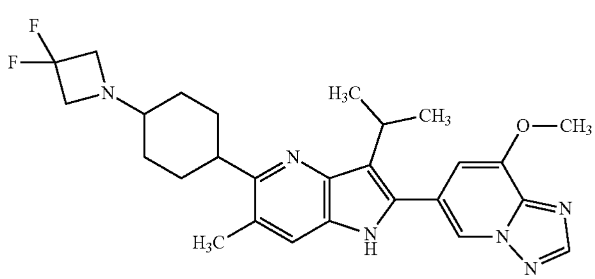 [SMILES: COc1cc(-c2[nH]c3cc(C)c(C4CCC(N5CC(F)(F)C5)CC4)nc3c2C(C)C)cn2ncnc12] | 494.59 | 495.3 | 2.35 | E |

TABLE 1-continued
| Ex. No. | Structure | Mol. Wt. | LCMS M+ | Ret Time (min) | HPLC Method |
|---|---|---|---|---|---|
| 339 | 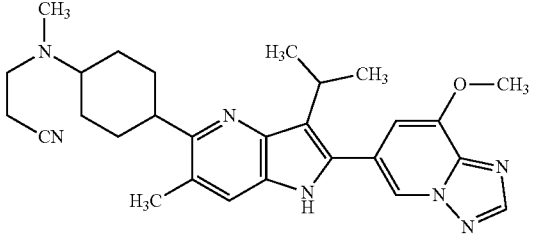 [SMILES: COc1cc(-c2[nH]c3cc(C)c(C4CCC(N(C)CCC#N)CC4)nc3c2C(C)C)cn2ncnc12] | 485.64 | 486.3 | 1.95 | E |
| 340 | 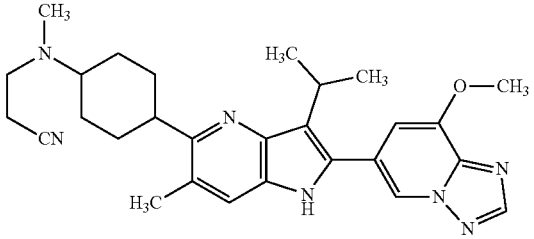 [SMILES: COc1cc(-c2[nH]c3cc(C)c(C4CCC(N(C)CCC#N)CC4)nc3c2C(C)C)cn2ncnc12] | 485.64 | 486.4 | 2 | E |
| 341 | 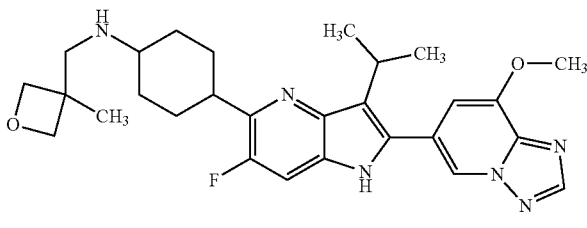 [SMILES: COc1cc(-c2[nH]c3cc(F)c(C4CCC(NCC5(C)COC5)CC4)nc3c2C(C)C)cn2ncnc12] | 506.63 | 507 | 1.57 | E |
| 342 | 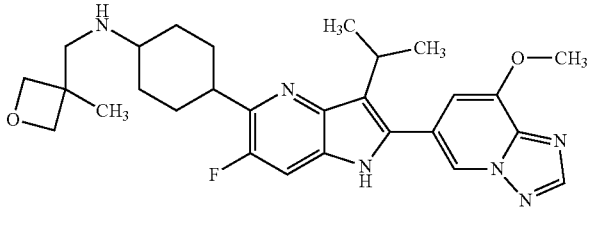 [SMILES: COc1cc(-c2[nH]c3cc(F)c(C4CCC(NCC5(C)COC5)CC4)nc3c2C(C)C)cn2ncnc12] | 506.63 | 507 | 1.76 | E |
| 343 | 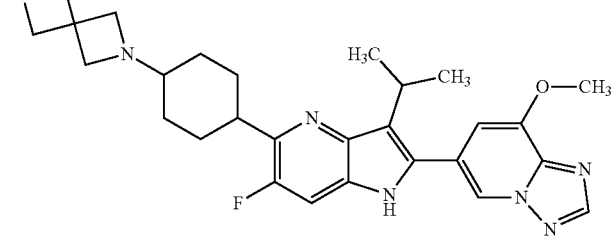 | 504.61 | 505.3 | 1.65 | E |
| 344 | 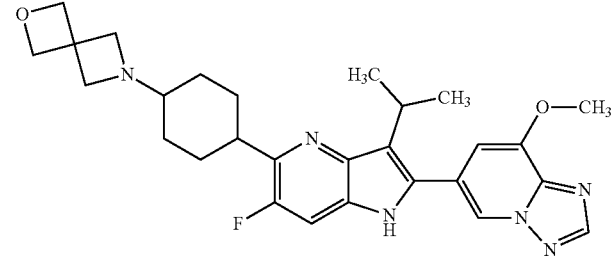 [SMILES: COc1cc(-c2[nH]c3cc(F)c(C4CCC(N5CC6(COC6)C5)CC4)nc3c2C(C)C)cn2ncnc12] | 504.61 | 505.3 | 1.71 | E |

TABLE 1-continued

| Ex. No. | Structure | Mol. Wt. | LCMS M+ | Ret Time (min) | HPLC Method |
|---|---|---|---|---|---|
| 345 | 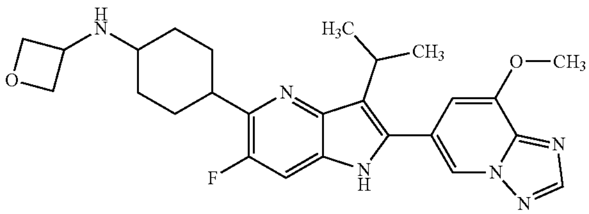 [SMILES: COc1cc(-c2[nH]c3cc(F)c(C4CCC(NC5COC5)CC4)nc3c2C(C)C)cn2ncnc12] | 478.57 | 479.3 | 1.65 | E |
| 346 | 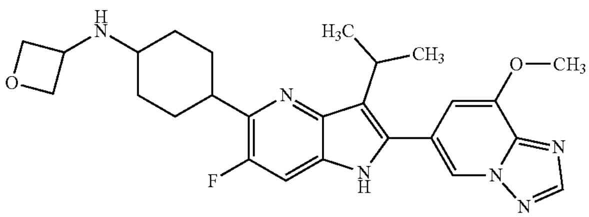 [SMILES: COc1cc(-c2[nH]c3cc(F)c(C4CCC(NC5COC5)CC4)nc3c2C(C)C)cn2ncnc12] | 478.57 | 479.3 | 1.77 | E |
| 347 | 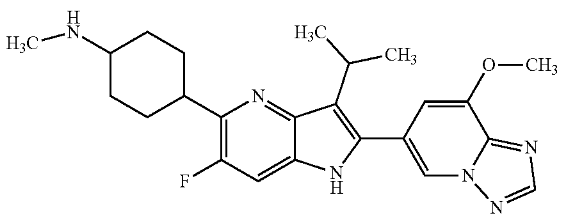 [SMILES: CNC1CCC(c2nc3c(C(C)C)c(-c4cc(OC)c5ncnn5c4)[nH]c3cc2F)CC1] | 436.54 | 437 | 1.33 | E |
| 348 | 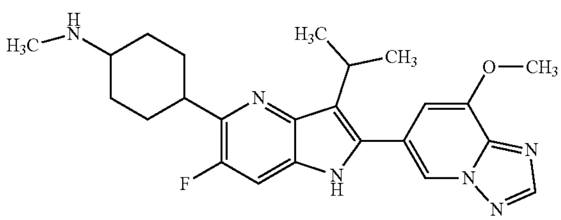 [SMILES: CNC1CCC(c2nc3c(C(C)C)c(-c4cc(OC)c5ncnn5c4)[nH]c3cc2F)CC1] | 436.54 | 437 | 1.41 | E |
| 349 | 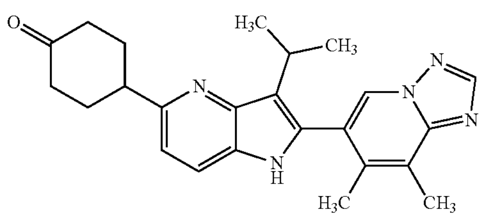 [SMILES: Cc1c(-c2[nH]c3ccc(C4CCC(=O)CC4)nc3c2C(C)C)cn2ncnc2c1C] | 401.51 | 402.3 | 1.69 | QC-ACN-AA-XB |
| 350 | 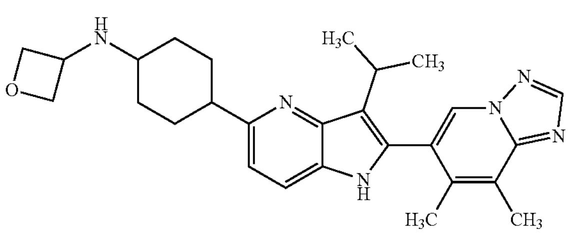 [SMILES: Cc1c(-c2[nH]c3ccc(C4CCC(NC5COC5)CC4)nc3c2C(C)C)cn2ncnc2c1C] | 458.61 | 459.5 | 1.32 | QC-ACN-AA-XB |
| 351 | 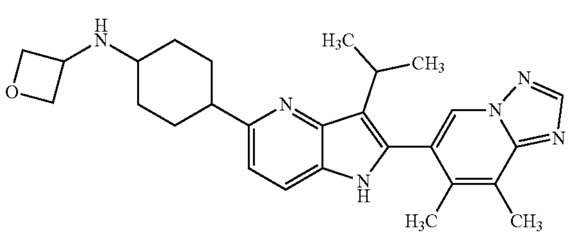 [SMILES: Cc1c(-c2[nH]c3ccc(C4CCC(NC5COC5)CC4)nc3c2C(C)C)cn2ncnc2c1C] | 458.61 | 459 | 1.67 | QC-ACN-AA-XB |

TABLE 1-continued

| Ex. No. | Structure | Mol. Wt. | LCMS M+ | Ret Time (min) | HPLC Method |
|---|---|---|---|---|---|
| 352 | 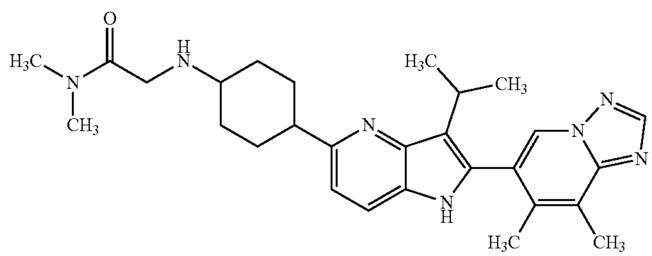 | 487.65 | 488.5 | 0.8 | QC-ACN-TFA-XB |
| 353 | 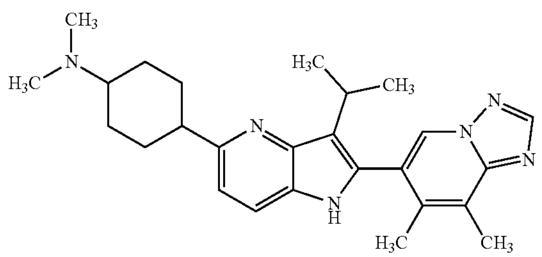 [SMILES: Cc1c(-c2[nH]c3ccc(C4CCC(N(C)C)CC4)nc3c2C(C)C)cn2ncnc2c1C] | 430.60 | 431.5 | 1.19 | QC-ACN-AA-XB |
| 354 | 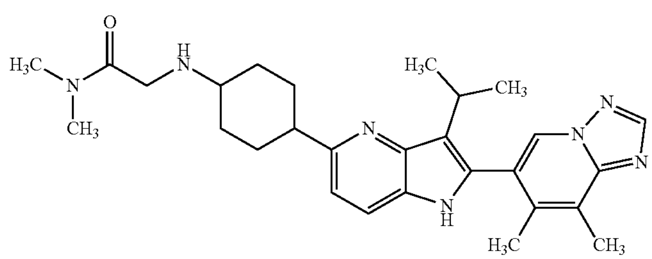 [SMILES: Cc1c(-c2[nH]c3ccc(C4CCC(NCC(=O)N(C)C)CC4)nc3c2C(C)C)cn2ncnc2c1C] | 487.65 | 488.4 | 0.8 | QC-ACN-TFA-XB |
| 355 | 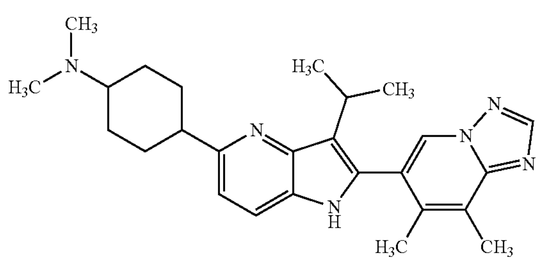 [SMILES: Cc1c(-c2[nH]c3ccc(C4CCC(N(C)C)CC4)nc3c2C(C)C)cn2ncnc2c1C] | 430.60 | 431.3 | 0.8 | QC-ACN-TFA-XB |
| 356 | 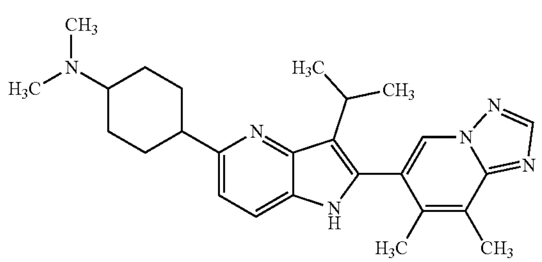 [SMILES: Cc1c(-c2[nH]c3ccc(C4CCC(N(C)C)CC4)nc3c2C(C)C)cn2ncnc2c1C] | 430.60 | 431.1 | 1.31 | QC-ACN-AA-XB |
| 357 | 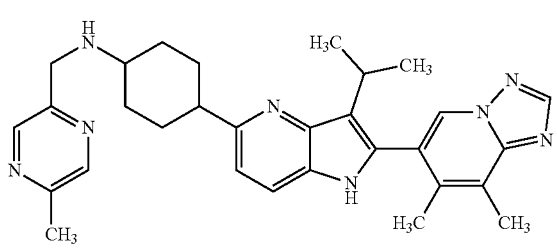 [SMILES: Cc1cnc(CNC2CCC(c3ccc4[nH]c(-c5cn6ncnc6c(C)c5C)c(C(C)C)c4n3)CC2)cn1] | 508.67 | 509 | 1.26 | QC-ACN-AA-XB |

TABLE 1-continued

| Ex. No. | Structure | Mol. Wt. | LCMS M+ | Ret Time (min) | HPLC Method |
|---|---|---|---|---|---|
| 358 | 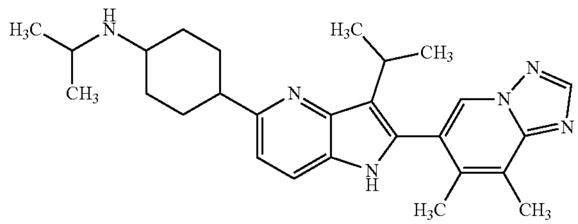 [SMILES: Cc1c(-c2[nH]c3ccc(C4CCC(NC(C)C)CC4)nc3c2C(C)C)cn2ncnc2c1C] | 444.63 | 445.4 | 0.81 | QC-ACN-TFA-XB |
| 359 | 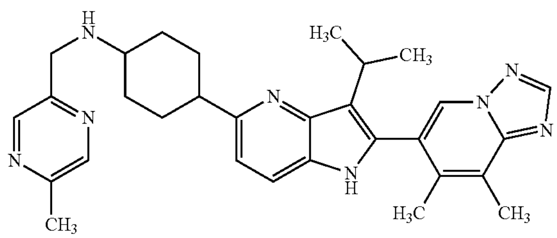 [SMILES: Cc1cnc(CNC2CCC(c3ccc4[nH]c(-c5cn6ncnc6c(C)c5C)c(C(C)C)c4n3)CC2)cn1] | 508.67 | 509 | 1.42 | QC-ACN-AA-XB |
| 360 | 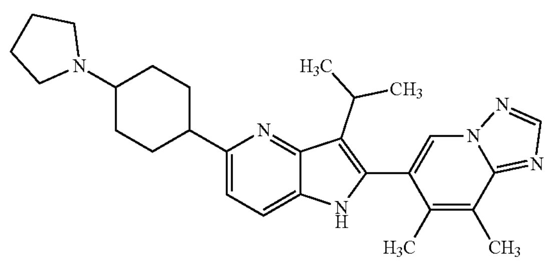 [SMILES: Cc1c(-c2[nH]c3ccc(C4CCC(N5CCCC5)CC4)nc3c2C(C)C)cn2ncnc2c1C] | 456.64 | 457.1 | 0.85 | QC-ACN-TFA-XB |
| 361 | 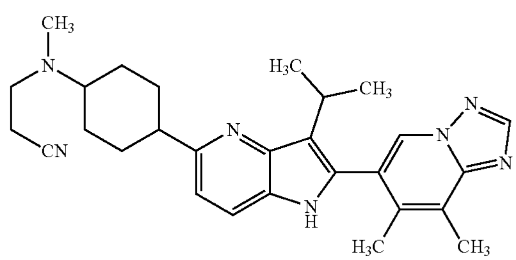 [SMILES: Cc1c(-c2[nH]c3ccc(C4CCC(N(C)CCC#N)CC4)nc3c2C(C)C)cn2ncnc2c1C] | 469.64 | 470.2 | 0.74 | QC-ACN-TFA-XB |
| 362 | 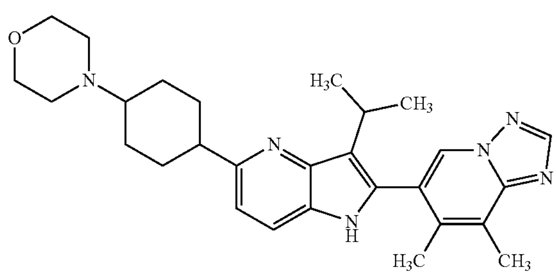 [SMILES: Cc1c(-c2[nH]c3ccc(C4CCC(N5CCOCC5)CC4)nc3c2C(C)C)cn2ncnc2c1C] | 472.64 | 473.2 | 1.28 | QC-ACN-AA-XB |
| 363 | 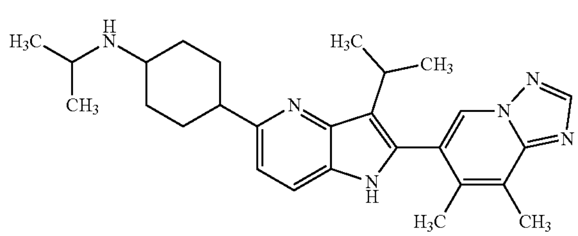 | 444.63 | 445.4 | 1.37 | QC-ACN-AA-XB |

TABLE 1-continued

| Ex. No. | Structure | Mol. Wt. | LCMS M+ | Ret Time (min) | HPLC Method |
|---|---|---|---|---|---|
| 364 | 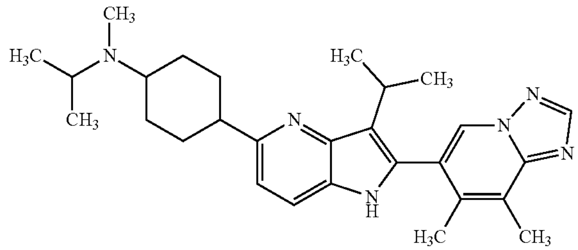 [SMILES: Cc1c(-c2[nH]c3ccc(C4CCC(N(C)C(C)C)CC4)nc3c2C(C)C)cn2ncnc2c1C] | 458.65 | 459.1 | 1.43 | QC-ACN-AA-XB |
| 365 | 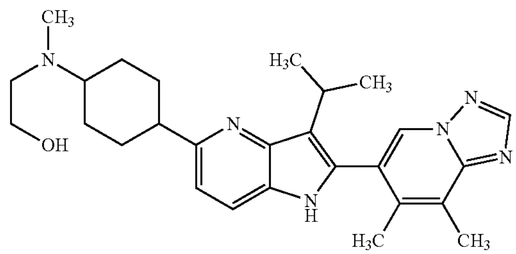 | 460.63 | 461.2 | 1.25 | QC-ACN-AA-XB |
| 366 | 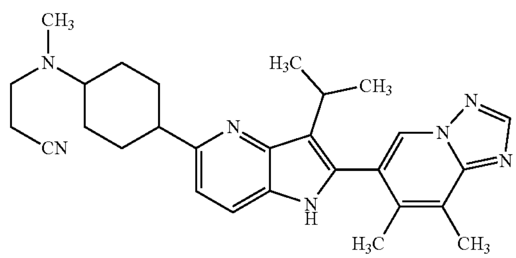 [SMILES: Cc1c(-c2[nH]c3ccc(C4CCC(N(C)CCC#N)CC4)nc3c2C(C)C)cn2ncnc2c1C] | 469.64 | 470 | 1.69 | QC-ACN-AA-XB |
| 367 | 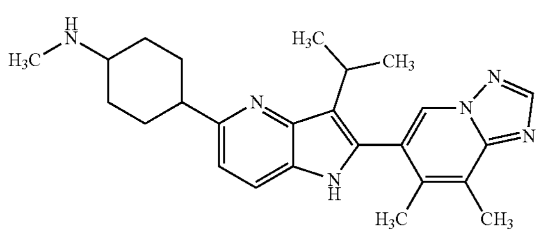 [SMILES: CNC1CCC(c2ccc3[nH]c(-c4cn5ncnc5c(C)c4C)c(C(C)C)c3n2)CC1] | 416.57 | 418.3 | 1.2 | QC-ACN-AA-XB |
| 368 | 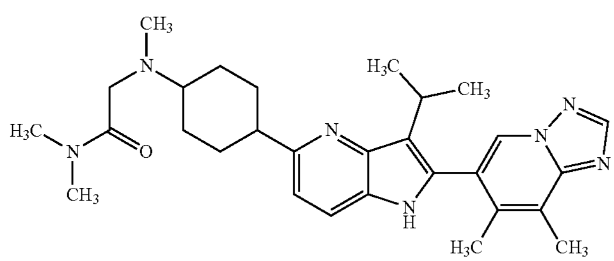 | 501.68 | 502.3 | 1.23 | QC-ACN-AA-XB |
| 369 | 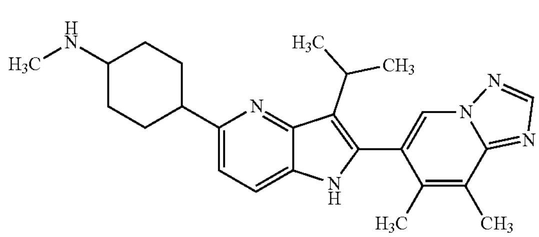 [SMILES: CNC1CCC(c2ccc3[nH]c(-c4cn5ncnc5c(C)c4C)c(C(C)C)c3n2)CC1] | 416.57 | 417.1 | 1.32 | QC-ACN-AA-XB |

TABLE 1-continued
| Ex. No. | Structure | Mol. Wt. | LCMS M+ | Ret Time (min) | HPLC Method |
|---|---|---|---|---|---|
| 370 | 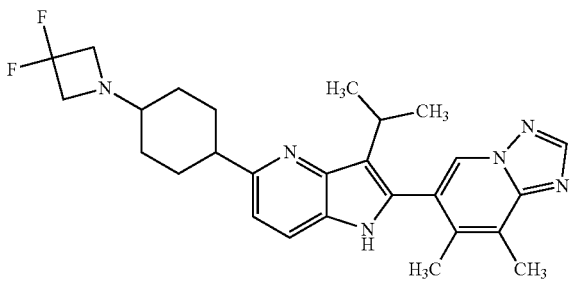 [SMILES: Cc1c(-c2[nH]c3ccc(C4CCC(N5CC(F)(F)C5)CC4)nc3c2C(C)C)cn2ncnc2c1C] | 478.59 | 478.9 | 2.06 | QC-ACN-AA-XB |
| 371 | 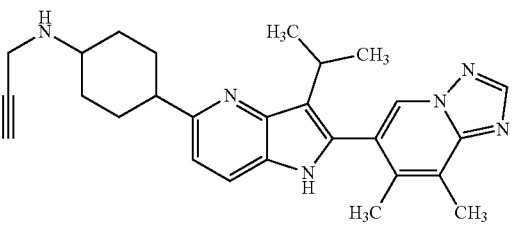 [SMILES: C#CCNC1CCC(c2ccc3[nH]c(-c4cn5ncnc5c(C)c4C)c(C(C)C)c3n2)CC1] | 440.60 | 440.9 | 1.7 | QC-ACN-AA-XB |
| 372 | 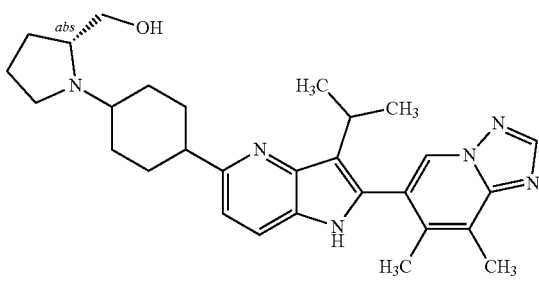 [SMILES: Cc1c(-c2[nH]c3ccc(C4CCC(N5CCC[C@@H]5CO)CC4)nc3c2C(C)C)cn2ncnc2c1C] | 486.66 | 486.9 | 1.08 | QC-ACN-TFA-XB |
| 373 | 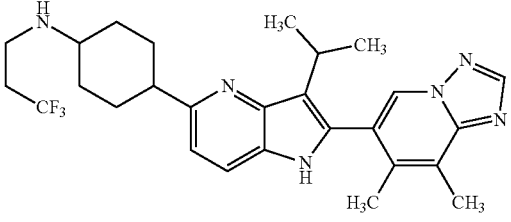 | 498.60 | 498.9 | 1.87 | QC-ACN-AA-XB |
| 374 | 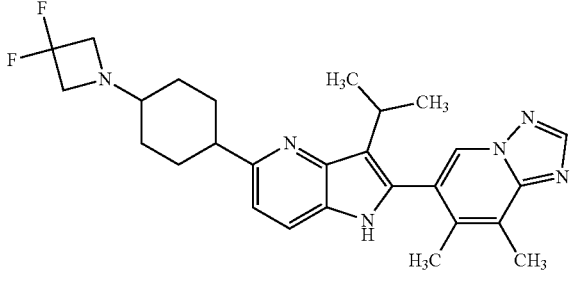 [SMILES: Cc1c(-c2[nH]c3ccc(C4CCC(N5CC(F)(F)C5)CC4)nc3c2C(C)C)cn2ncnc2c1C] | 478.59 | 479.2 | 1.12 | QC-ACN-TFA-XB |
| 375 | 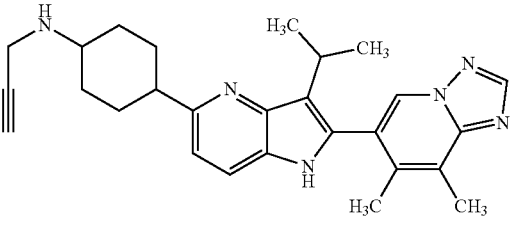 [SMILES: C#CCNC1CCC(c2ccc3[nH]c(-c4cn5ncnc5c(C)c4C)c(C(C)C)c3n2)CC1] | 440.60 | 441.2 | 1.06 | QC-ACN-TFA-XB |

TABLE 1-continued

| Ex. No. | Structure | Mol. Wt. | LCMS M+ | Ret Time (min) | HPLC Method |
|---|---|---|---|---|---|
| 376 | 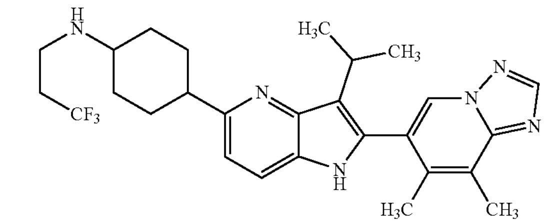 | 498.60 | 499.2 | 1.68 | QC-ACN-AA-XB |
| 377 | 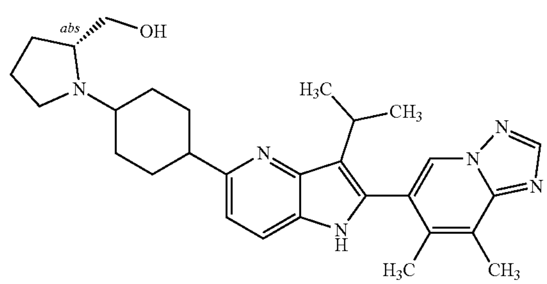 [SMILES: Cc1c(-c2[nH]c3ccc(C4CCC(N5CCC[C@@H]5CO)CC4)nc3c2C(C)C)cn2ncnc2c1C] | 486.66 | 486.9 | 1.32 | QC-ACN-AA-XB |
| 378 | 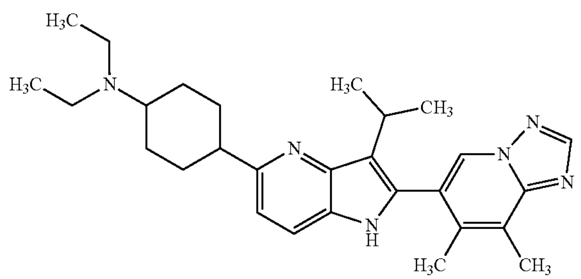 [SMILES: CCN(CC)C1CCC(c2ccc3[nH]c(-c4cn5ncnc5c(C)c4C)c(C(C)C)c3n2)CC1] | 458.65 | 458.97 | 1.1 | QC-ACN-TFA-XB |
| 379 | 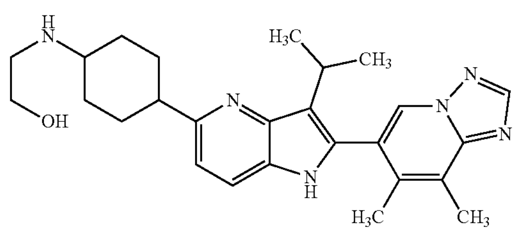 [SMILES: Cc1c(-c2[nH]c3ccc(C4CCC(NCCO)CC4)nc3c2C(C)C)cn2ncnc2c1C] | 446.60 | 446.9 | 0.95 | QC-ACN-TFA-XB |
| 380 | 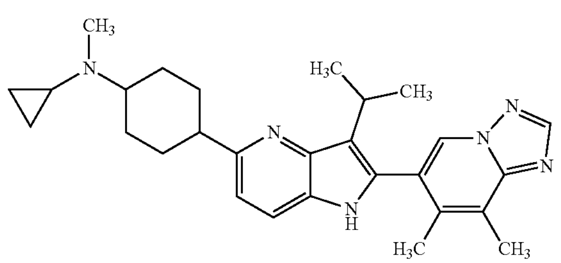 [SMILES: Cc1c(-c2[nH]c3ccc(C4CCC(N(C)C5CC5)CC4)nc3c2C(C)C)cn2ncnc2c1C] | 456.64 | 457.1 | 1.41 | QC-ACN-AA-XB |
| 381 | 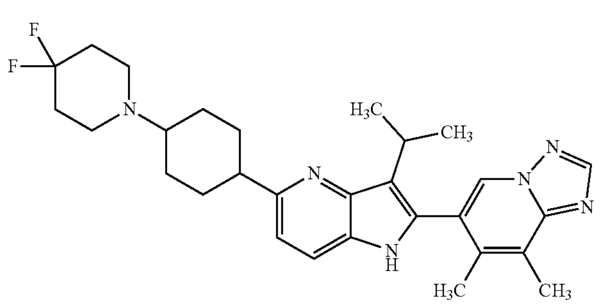 [SMILES: Cc1c(-c2[nH]c3ccc(C4CCC(N5CCC(F)(F)CC5)CC4)nc3c2C(C)C)cn2ncnc2c1C] | 506.65 | 506.9 | 1.14 | QC-ACN-TFA-XB |

TABLE 1-continued

| Ex. No. | Structure | Mol. Wt. | LCMS M+ | Ret Time (min) | HPLC Method |
|---|---|---|---|---|---|
| 382 | 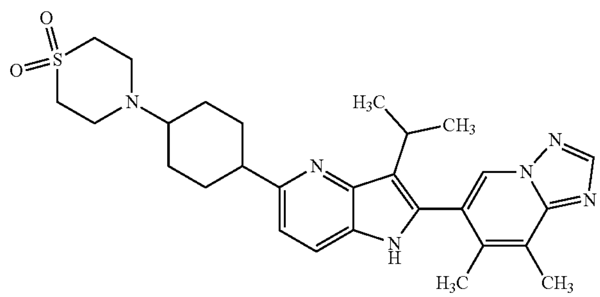 [SMILES: Cc1c(-c2[nH]c3ccc(C4CCC(N5CCS(=O)(=O)CC5)CC4)nc3c2C(C)C)cn2ncnc2c1C] | 520.70 | 521.2 | 1.08 | QC-ACN-TFA-XB |
| 383 | 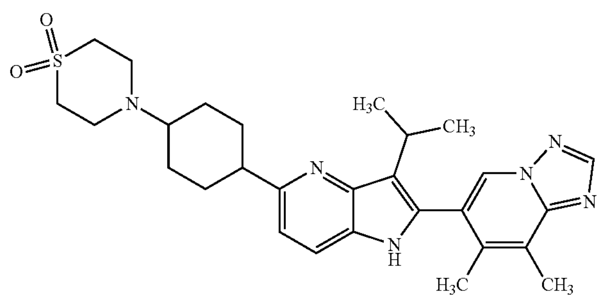 [SMILES: Cc1c(-c2[nH]c3ccc(C4CCC(N5CCS(=O)(=O)CC5)CC4)nc3c2C(C)C)cn2ncnc2c1C] | 520.70 | 521.1 | 1.82 | QC-ACN-AA-XB |
| 384 | 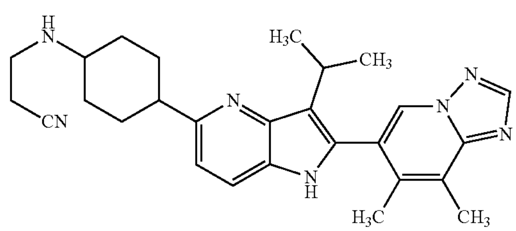 [SMILES: Cc1c(-c2[nH]c3ccc(C4CCC(NCCC#N)CC4)nc3c2C(C)C)cn2ncnc2c1C] | 455.61 | 456.2 | 1.45 | QC-ACN-AA-XB |
| 385 | 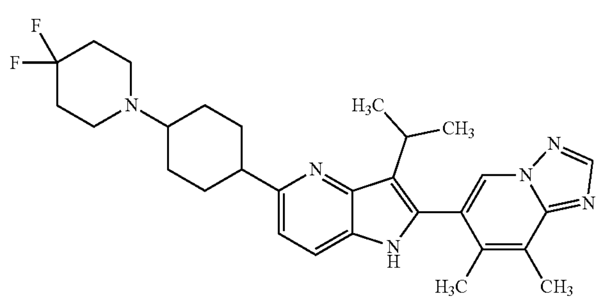 [SMILES: Cc1c(-c2[nH]c3ccc(C4CCC(N5CCC(F)(F)CC5)CC4)nc3c2C(C)C)cn2ncnc2c1C] | 506.65 | 506.9 | 1.13 | QC-ACN-TFA-XB |
| 386 | 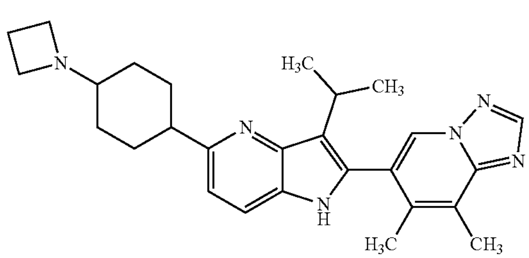 [SMILES: Cc1c(-c2[nH]c3ccc(C4CCC(N5CCC5)CC4)nc3c2C(C)C)cn2ncnc2c1C] | 442.61 | 443.19 | 1.01 | QC-ACN-AA-XB |

TABLE 1-continued

| Ex. No. | Structure | Mol. Wt. | LCMS M+ | Ret Time (min) | HPLC Method |
|---|---|---|---|---|---|
| 387 | 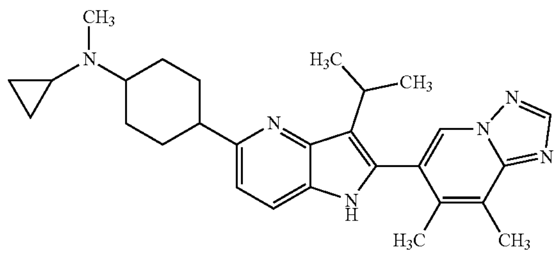 [SMILES: Cc1c(-c2[nH]c3ccc(C4CCC(N(C)C5CC5)CC4)nc3c2C(C)C)cn2ncnc2c1C] | 456.64 | 457.2 | 0.78 | QC-ACN-TFA-XB |
| 388 | 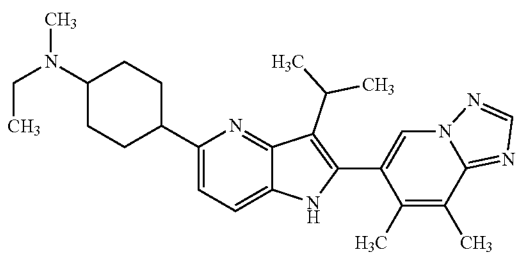 [SMILES: CCN(C)C1CCC(c2ccc3[nH]c(-c4cn5ncnc5c(C)c4C)c(C(C)C)c3n2)CC1] | 444.63 | 445.3 | 0.78 | QC-ACN-TFA-XB |
| 389 | 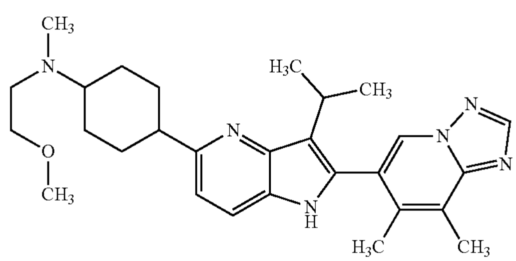 [SMILES: COCCN(C)C1CCC(c2ccc3[nH]c(-c4cn5ncnc5c(C)c4C)c(C(C)C)c3n2)CC1] | 474.65 | 475.1 | 1.27 | QC-ACN-AA-XB |
| 390 | 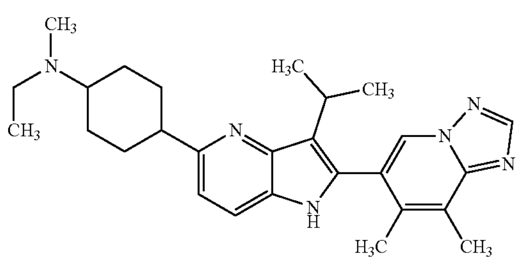 [SMILES: CCN(C)C1CCC(c2ccc3[nH]c(-c4cn5ncnc5c(C)c4C)c(C(C)C)c3n2)CC1] | 444.63 | 445.3 | 1.3 | QC-ACN-AA-XB |
| 391 | 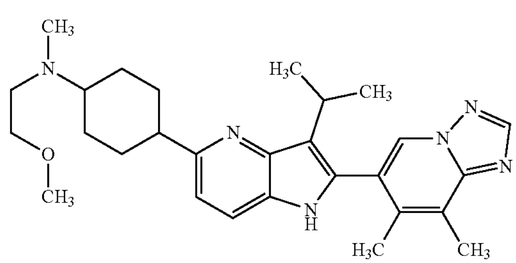 [SMILES: COCCN(C)C1CCC(c2ccc3[nH]c(-c4cn5ncnc5c(C)c4C)c(C(C)C)c3n2)CC1] | 474.65 | 475.3 | 1.36 | QC-ACN-AA-XB |

TABLE 1-continued

| Ex. No. | Structure | Mol. Wt. | LCMS M+ | Ret Time (min) | HPLC Method |
|---|---|---|---|---|---|
| 392 | 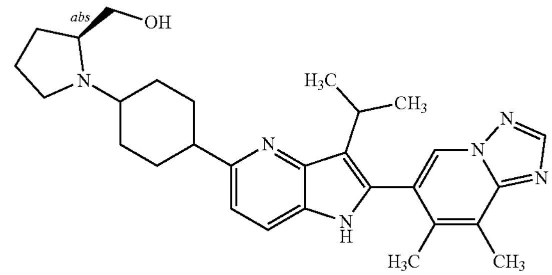 [SMILES: Cc1c(-c2[nH]c3ccc(C4CCC(N5CCC[C@H]5CO)CC4)nc3c2C(C)C)cn2ncnc2c1C] | 486.66 | 487.4 | 0.79 | QC-ACN-TFA-XB |
| 393 | 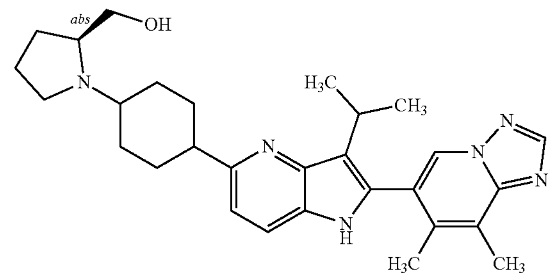 [SMILES: Cc1c(-c2[nH]c3ccc(C4CCC(N5CCC[C@H]5CO)CC4)nc3c2C(C)C)cn2ncnc2c1C] | 486.66 | 487 | 1.17 | QC-ACN-AA-XB |
| 394 | 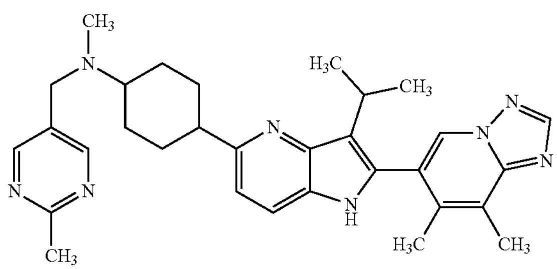 [SMILES: Cc1ncc(CN(C)C2CCC(c3ccc4[nH]c(-c5cn6ncnc6c(C)c5C)c(C(C)C)c4n3)CC2)cn1] | 522.70 | 523.1 | 1.56 | QC-ACN-AA-XB |
| 395 | 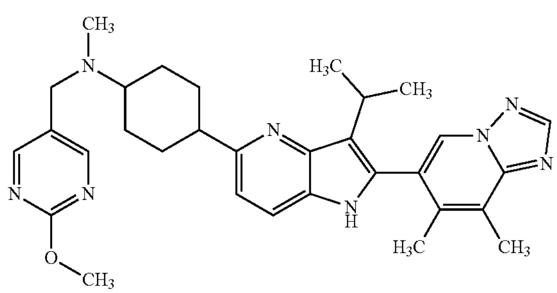 [SMILES: COc1ncc(CN(C)C2CCC(c3ccc4[nH]c(-c5cn6ncnc6c(C)c5C)c(C(C)C)c4n3)CC2)cn1] | 538.70 | 539.3 | 1.85 | QC-ACN-AA-XB |
| 396 | 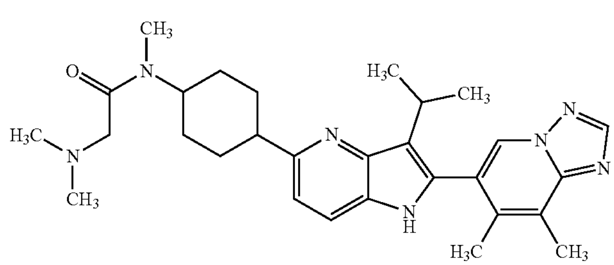 | 501.68 | 502.3 | 1.27 | QC-ACN-AA-XB |

TABLE 1-continued

| Ex. No. | Structure | Mol. Wt. | LCMS M+ | Ret Time (min) | HPLC Method |
|---|---|---|---|---|---|
| 397 | 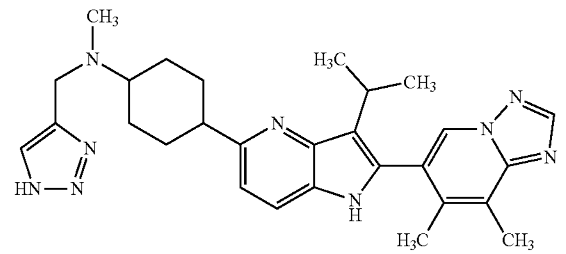 [SMILES: Cc1c(-c2[nH]c3ccc(C4CCC(N(C)Cc5c[nH]nn5)CC4)nc3c2C(C)C)cn2ncnc2c1C] | 497.65 | 498.2 | 1.3 | QC-ACN-AA-XB |
| 398 | 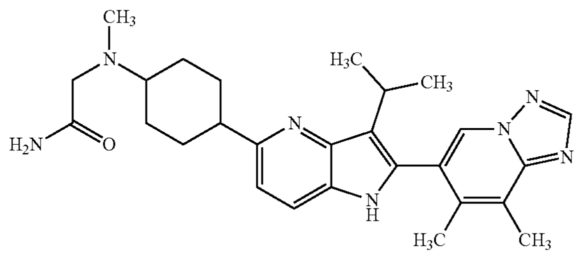 [SMILES: Cc1c(-c2[nH]c3ccc(C4CCC(N(C)CC(N)=O)CC4)nc3c2C(C)C)cn2ncnc2c1C] | 473.63 | 474.3 | 1.56 | QC-ACN-AA-XB |
| 399 | 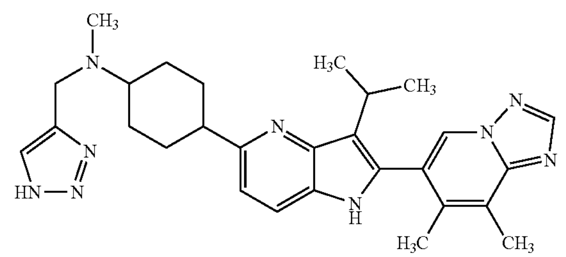 [SMILES: Cc1c(-c2[nH]c3ccc(C4CCC(N(C)Cc5c[nH]nn5)CC4)nc3c2C(C)C)cn2ncnc2c1C] | 497.65 | 520.1 | 1.4 | QC-ACN-AA-XB |
| 400 | 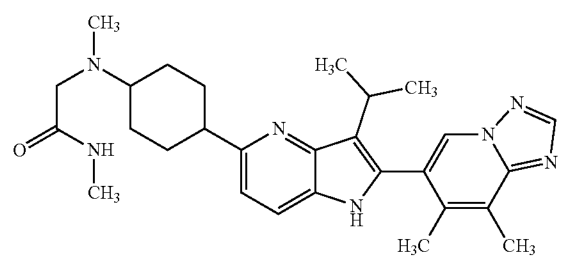 [SMILES: CNC(=O)CN(C)C1CCC(c2ccc3[nH]c(-c4cn5ncnc5c(C)c4C)c(C(C)C)c3n2)CC1] | 487.65 | 488.2 | 0.79 | QC-ACN-TFA-XB |
| 401 | 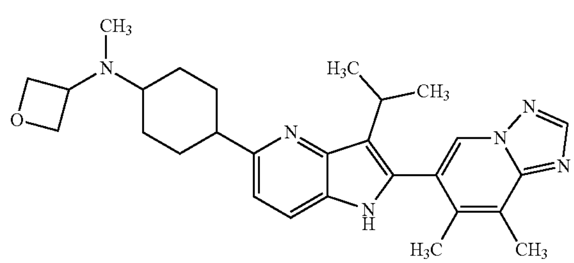 | 472.64 | 473.2 | 1.54 | QC-ACN-AA-XB |
| 402 | 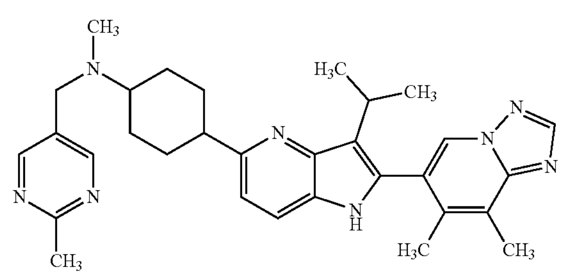 [SMILES: Cc1ncc(CN(C)C2CCC(c3ccc4[nH]c(-c5cn6ncnc6c(C)c5C)c(C(C)C)c4n3)CC2)cn1] | 522.70 | 523.2 | 1.8 | QC-ACN-AA-XB |

TABLE 1-continued
| Ex. No. | Structure | Mol. Wt. | LCMS M+ | Ret Time (min) | HPLC Method |
|---|---|---|---|---|---|
| 403 | 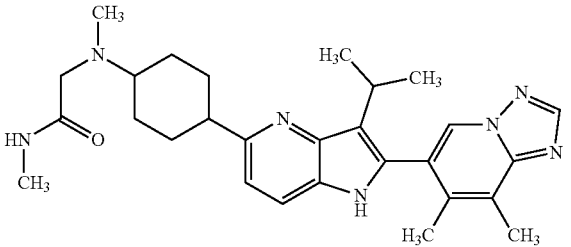 [SMILES: CNC(=O)CN(C)C1CCC(c2ccc3[nH]c(-c4cn5ncnc5c(C)c4C)c(C(C)C)c3n2)CC1] | 487.65 | 488.1 | 1.66 | QC-ACN-AA-XB |
| 404 | 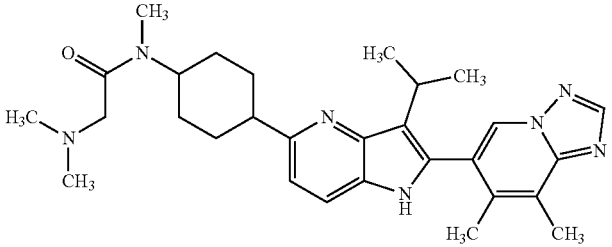 [SMILES: Cc1c(-c2[nH]c3ccc(C4CCC(N(C)C(=O)CN(C)C)CC4)nc3c2C(C)C)cn2ncnc2c1C] | 501.68 | 502.2 | 1.49 | QC-ACN-AA-XB |
| 405 | 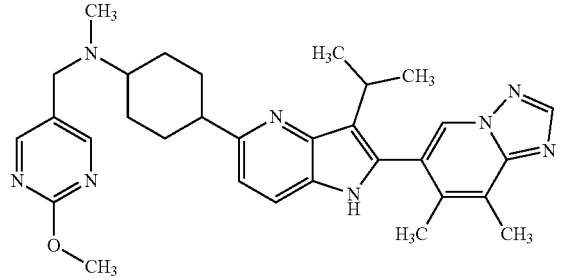 [SMILES: COc1ncc(CN(C)C2CCC(c3ccc4[nH]c(-c5cn6ncnc6c(C)c5C)c(C(C)C)c4n3)CC2)cn1] | 538.70 | 539.2 | 0.86 | QC-ACN-TFA-XB |
| 406 | 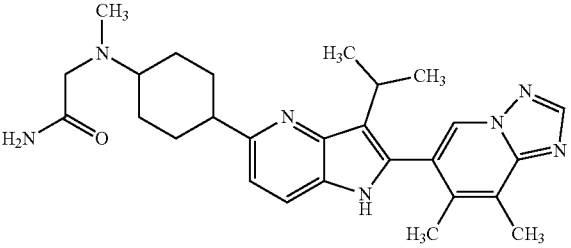 | 473.63 | 474.1 | 1.53 | QC-ACN-AA-XB |
| 407 | 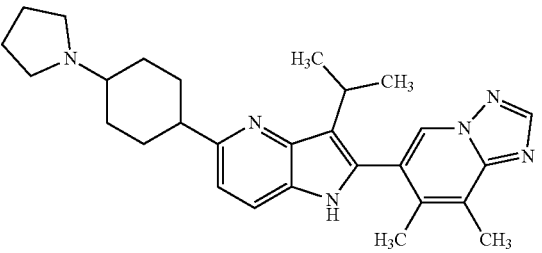 [SMILES: Cc1c(-c2[nH]c3ccc(C4CCC(N5CCCC5)CC4)nc3c2C(C)C)cn2ncnc2c1C] | 456.64 | 457.2 | 1.43 | QC-ACN-AA-XB |

TABLE 1-continued
| Ex. No. | Structure | Mol. Wt. | LCMS M+ | Ret Time (min) | HPLC Method |
|---|---|---|---|---|---|
| 408 | 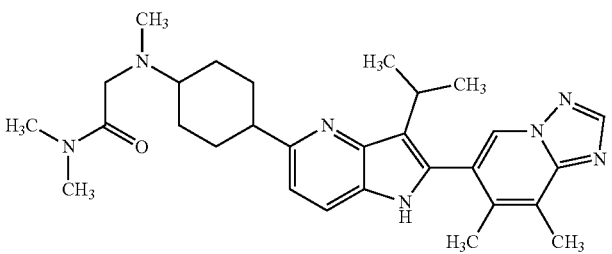 [SMILES: Cc1c(-c2[nH]c3ccc(C4CCC(N(C)CC(=O)N(C)C)CC4)nc3c2C(C)C)cn2ncnc2c1C] | 501.68 | 502.2 | 1.44 | QC-ACN-AA-XB |
| 409 | 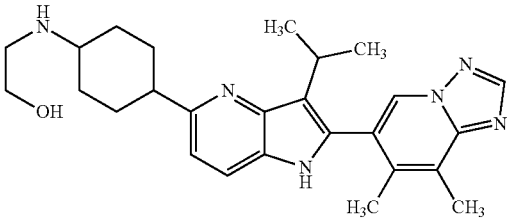 | 446.60 | 447 | 0.99 | QC-ACN-TFA-XB |
| 410 | 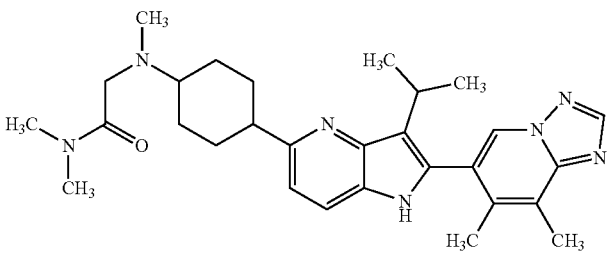 [SMILES: Cc1c(-c2[nH]c3ccc(C4CCC(N(C)CC(=O)N(C)C)CC4)nc3c2C(C)C)cn2ncnc2c1C] | 501.68 | 502.2 | 0.84 | QC-ACN-TFA-XB |
| 411 | 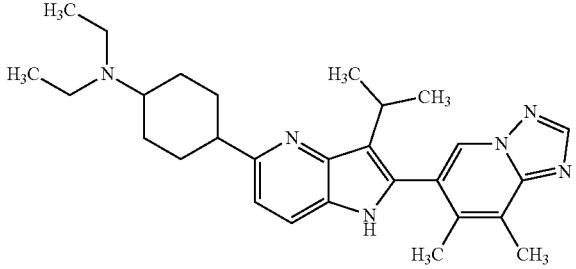 [SMILES: CCN(CC)C1CCC(c2ccc3[nH]c(-c4cn5ncnc5c(C)c4C)c(C(C)C)c3n2)CC1] | 458.65 | 459.4 | 1.39 | QC-ACN-AA-XB |
| 412 | 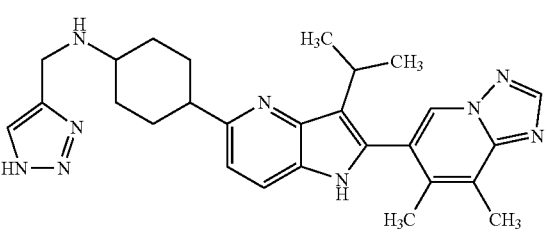 [SMILES: Cc1c(-c2[nH]c3ccc(C4CCC(NCc5c[nH]nn5)CC4)nc3c2C(C)C)cn2ncnc2c1C] | 483.62 | 484.1 | 1.19 | QC-ACN-AA-XB |
| 413 | 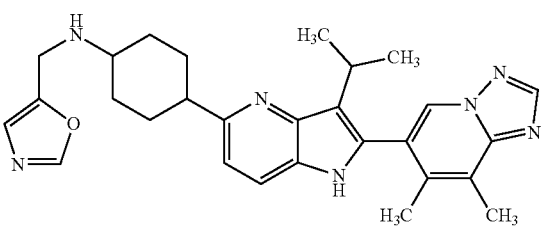 [SMILES: Cc1c(-c2[nH]c3ccc(C4CCC(NCc5cnco5)CC4)nc3c2C(C)C)cn2ncnc2c1C] | 483.62 | 484.4 | 1.48 | QC-ACN-AA-XB |

TABLE 1-continued

| Ex. No. | Structure | Mol. Wt. | LCMS M+ | Ret Time (min) | HPLC Method |
|---|---|---|---|---|---|
| 414 | 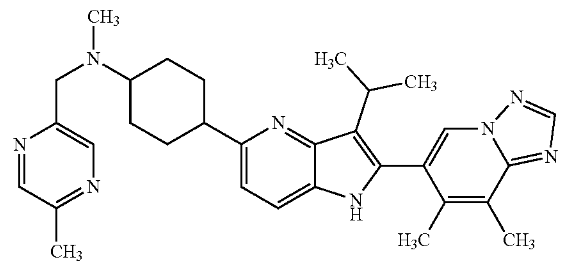 [SMILES: Cc1cnc(CN(C)C2CCC(c3ccc4[nH]c(-c5cn6ncnc6c(C)c5C)c(C(C)C)c4n3)CC2)cn1] | 522.70 | 523.2 | 0.83 | QC-ACN-TFA-XB |
| 415 | 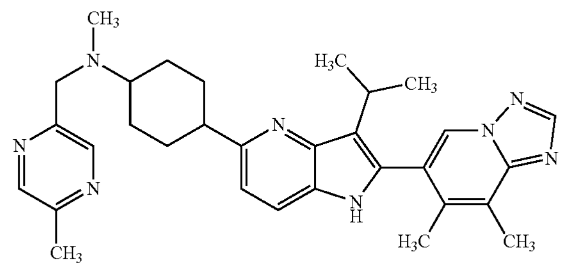 [SMILES: Cc1cnc(CN(C)C2CCC(c3ccc4[nH]c(-c5cn6ncnc6c(C)c5C)c(C(C)C)c4n3)CC2)cn1] | 522.70 | 523.4 | 1.37 | QC-ACN-AA-XB |
| 416 | 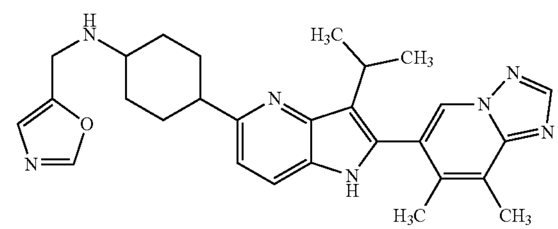 [SMILES: Cc1c(-c2[nH]c3ccc(C4CCC(NCc5cnco5)CC4)nc3c2C(C)C)cn2ncnc2c1C] | 483.62 | 484.1 | 1.57 | QC-ACN-AA-XB |
| 417 | 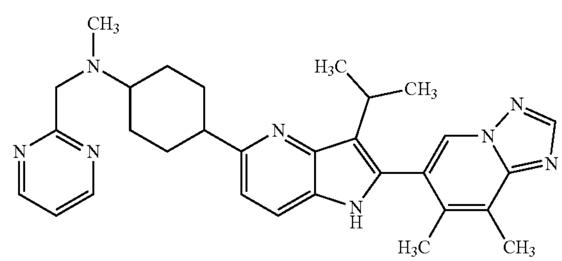 [SMILES: Cc1c(-c2[nH]c3ccc(C4CCC(N(C)Cc5ncccn5)CC4)nc3c2C(C)C)cn2ncnc2c1C] | 508.67 | 509.2 | 1.41 | QC-ACN-AA-XB |
| 418 | 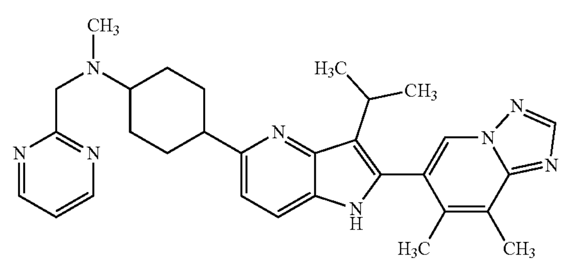 [SMILES: Cc1c(-c2[nH]c3ccc(C4CCC(N(C)Cc5ncccn5)CC4)nc3c2C(C)C)cn2ncnc2c1C] | 508.67 | 509.3 | 1.55 | QC-ACN-AA-XB |
| 419 | 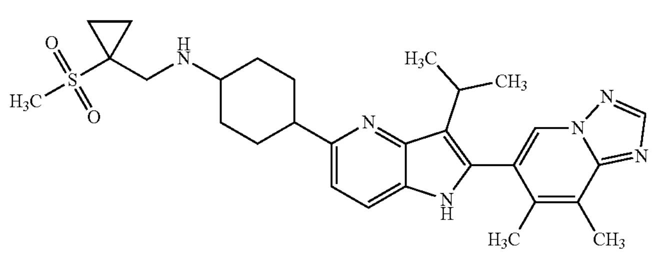 [SMILES: Cc1c(-c2[nH]c3ccc(C4CCC(NCC5(S(C)(=O)=O)CC5)CC4)nc3c2C(C)C)cn2ncnc2c1C] | 534.72 | 535.3 | 1.66 | QC-ACN-AA-XB |

TABLE 1-continued

| Ex. No. | Structure | Mol. Wt. | LCMS M+ | Ret Time (min) | HPLC Method |
|---|---|---|---|---|---|
| 420 | 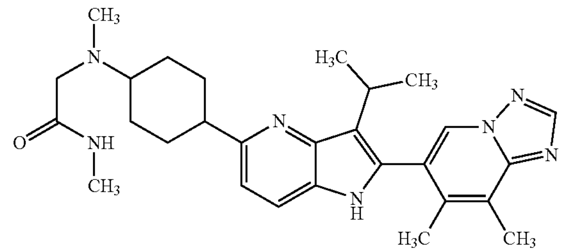 [SMILES: CNC(=O)CN(C)C1CCC(c2ccc3[nH]c(-c4cn5ncnc5c(C)c4C)c(C(C)C)c3n2)CC1] | 487.65 | 488.3 | 1.37 | QC-ACN-AA-XB |
| 421 | 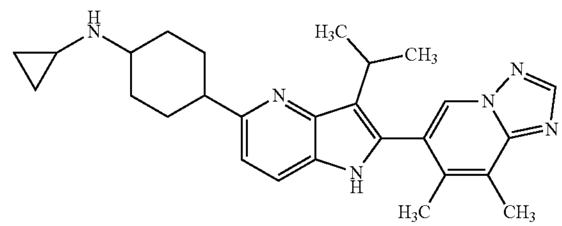 [SMILES: Cc1c(-c2[nH]c3ccc(C4CCC(NC5CC5)CC4)nc3c2C(C)C)cn2ncnc2c1C] | 442.61 | 443.1 | 1.29 | QC-ACN-AA-XB |
| 422 | 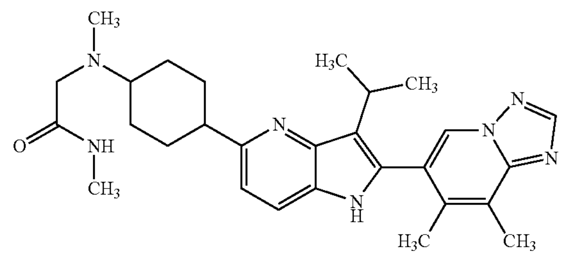 [SMILES: CNC(=O)CN(C)C1CCC(c2ccc3[nH]c(-c4cn5ncnc5c(C)c4C)c(C(C)C)c3n2)CC1] | 487.65 | 488.29 | 1.48 | QC-ACN-AA-XB |
| 423 | 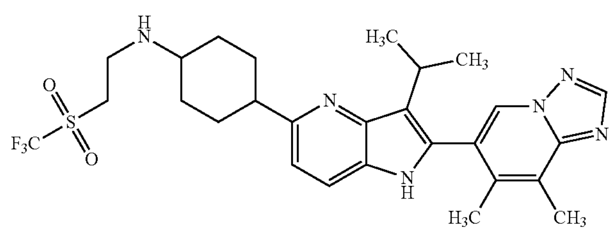 [SMILES: Cc1c(-c2[nH]c3ccc(C4CCC(NCCS(=O)(=O)C(F)(F)F)CC4)nc3c2C(C)C)cn2ncnc2c1C] | 562.66 | 563.4 | 1.39 | QC-ACN-TFA-XB |
| 424 | 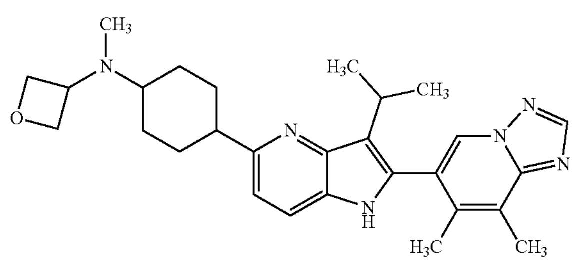 [SMILES: Cc1c(-c2[nH]c3ccc(C4CCC(N(C)C5COC5)CC4)nc3c2C(C)C)cn2ncnc2c1C] | 472.64 | 473.3 | 1.38 | QC-ACN-AA-XB |
| 425 | 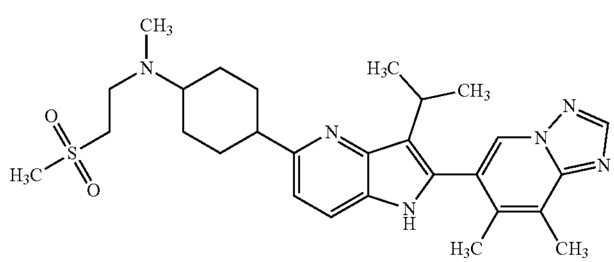 | 522.71 | 523.2 | 1.44 | QC-ACN-AA-XB |

TABLE 1-continued

| Ex. No. | Structure | Mol. Wt. | LCMS M+ | Ret Time (min) | HPLC Method |
|---|---|---|---|---|---|
| 426 | 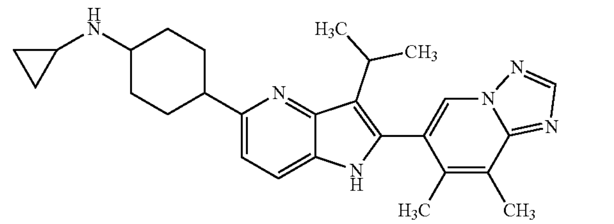 [SMILES: Cc1c(-c2[nH]c3ccc(C4CCC(NC5CC5)CC4)nc3c2C(C)C)cn2ncnc2c1C] | 442.61 | 443.3 | 1.31 | QC-ACN-AA-XB |
| 427 | 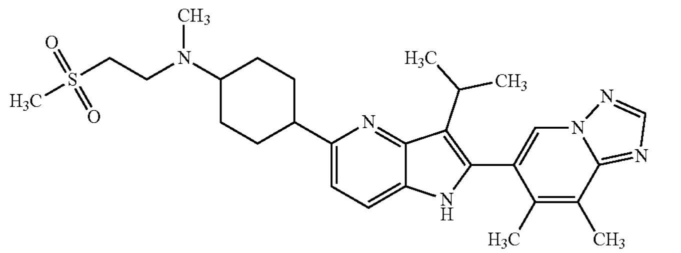 [SMILES: Cc1c(-c2[nH]c3ccc(C4CCC(N(C)CCS(C)(=O)=O)CC4)nc3c2C(C)C)cn2ncnc2c1C] | 522.71 | 523.2 | 1.62 | QC-ACN-AA-XB |
| 428 | 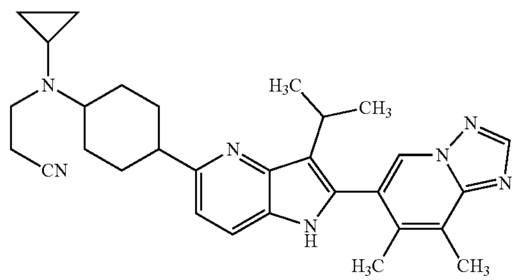 [SMILES: Cc1c(-c2[nH]c3ccc(C4CCC(N(CCC#N)C5CC5)CC4)nc3c2C(C)C)cn2ncnc2c1C] | 495.68 | 496.2 | 2.22 | QC-ACN-AA-XB |
| 429 | 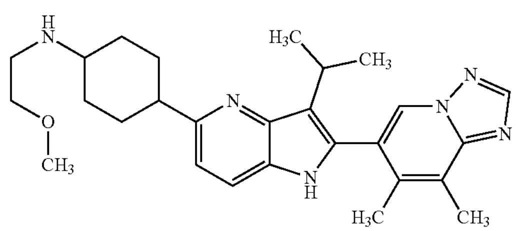 [SMILES: COCCNC1CCC(c2ccc3[nH]c(-c4cn5ncnc5c(C)c4C)c(C(C)C)c3n2)CC1] | 460.63 | 461 | 1.21 | QC-ACN-AA-XB |
| 430 | 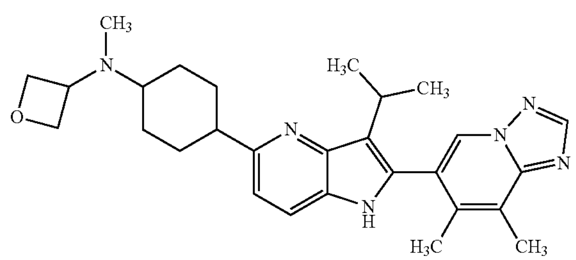 [SMILES: Cc1c(-c2[nH]c3ccc(C4CCC(N(C)C5COC5)CC4)nc3c2C(C)C)cn2ncnc2c1C] | 472.64 | 473.4 | 0.77 | QC-ACN-TFA-XB |
| 431 | 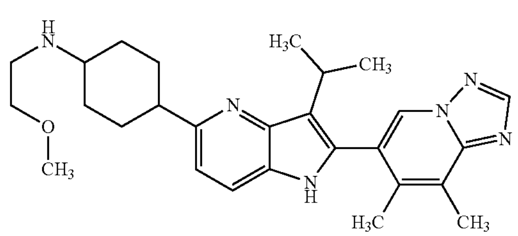 [SMILES: COCCNC1CCC(c2ccc3[nH]c(-c4cn5ncnc5c(C)c4C)c(C(C)C)c3n2)CC1] | 460.63 | 461 | 0.83 | QC-ACN-TFA-XB |

TABLE 1-continued

| Ex. No. | Structure | Mol. Wt. | LCMS M+ | Ret Time (min) | HPLC Method |
|---|---|---|---|---|---|
| 432 | 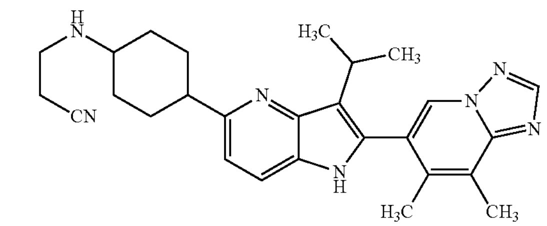 | 455.61 | 456.2 | 1.23 | QC-ACN-TFA-XB |
| 433 | 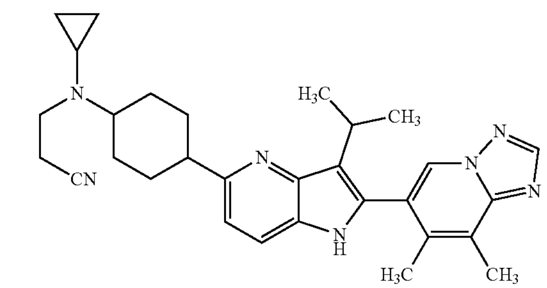 [SMILES: Cc1c(-c2[nH]c3ccc(C4CCC(N(CCC#N)C5CC5)CC4)nc3c2C(C)C)cn2ncnc2c1C] | 495.68 | 496.1 | 2.34 | QC-ACN-AA-XB |
| 434 | 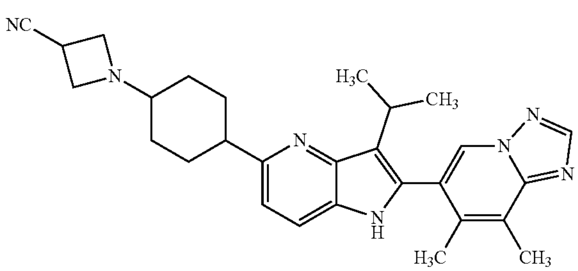 [SMILES: Cc1c(-c2[nH]c3ccc(C4CCC(N5CC(C#N)C5)CC4)nc3c2C(C)C)cn2ncnc2c1C] | 467.62 | 467.9 | 0.79 | QC-ACN-TFA-XB |
| 435 | 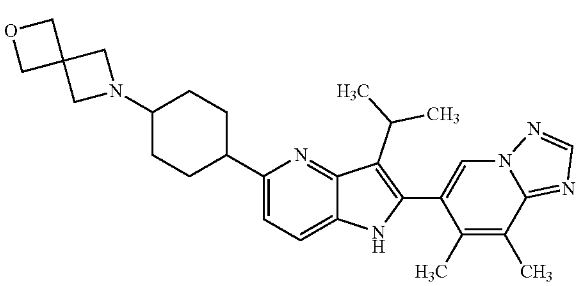 [SMILES: Cc1c(-c2[nH]c3ccc(C4CCC(N5CC6(COC6)C5)CC4)nc3c2C(C)C)cn2ncnc2c1C] | 484.65 | 485.2 | 0.81 | QC-ACN-TFA-XB |
| 436 | 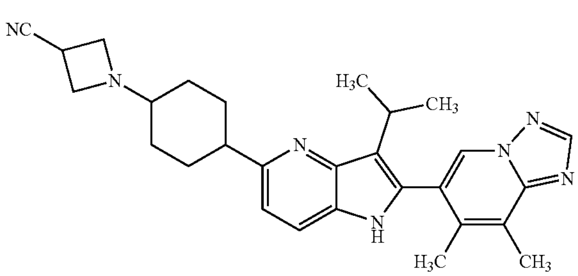 [SMILES: Cc1c(-c2[nH]c3ccc(C4CCC(N5CC(C#N)C5)CC4)nc3c2C(C)C)cn2ncnc2c1C] | 467.62 | 468.3 | 1.96 | QC-ACN-AA-XB |

TABLE 1-continued

| Ex. No. | Structure | Mol. Wt. | LCMS M+ | Ret Time (min) | HPLC Method |
|---|---|---|---|---|---|
| 437 | 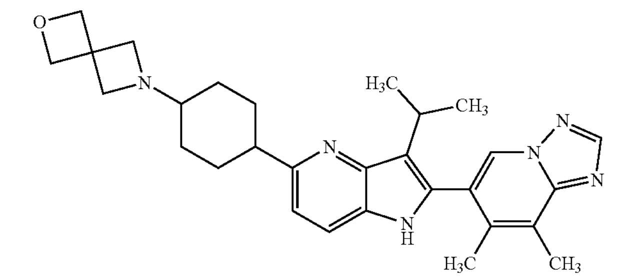 [SMILES: Cc1c(-c2[nH]c3ccc(C4CCC(N5CC6(COC6)C5)CC4)nc3c2C(C)C)cn2ncnc2c1C] | 484.65 | 485.3 | 1.14 | QC-ACN-AA-XB |
| 438 | 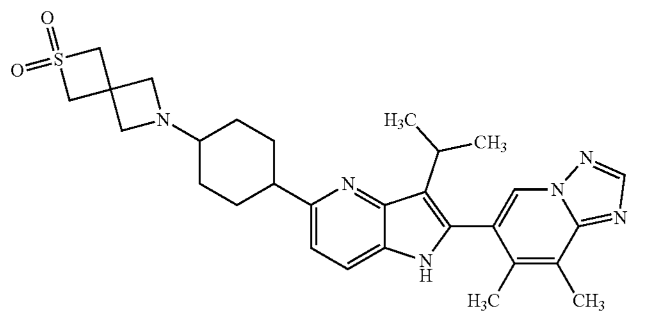 [SMILES: Cc1c(-c2[nH]c3ccc(C4CCC(N5CC6(C5)CS(=O)(=O)C6)CC4)nc3c2C(C)C)cn2ncnc2c1C] | 532.71 | 533.4 | 1.41 | QC-ACN-AA-XB |
| 439 | 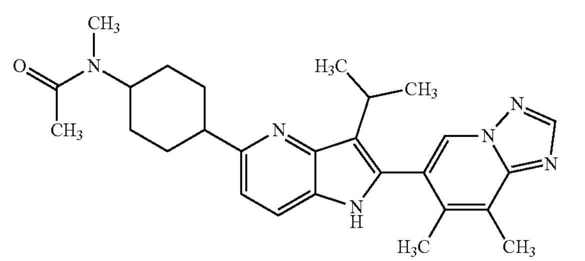 [SMILES: CC(=O)N(C)C1CCC(c2ccc3[nH]c(-c4cn5ncnc5c(C)c4C)c(C(C)C)c3n2)CC1] | 458.61 | 459.4 | 1.01 | QC-ACN-TFA-XB |
| 440 | 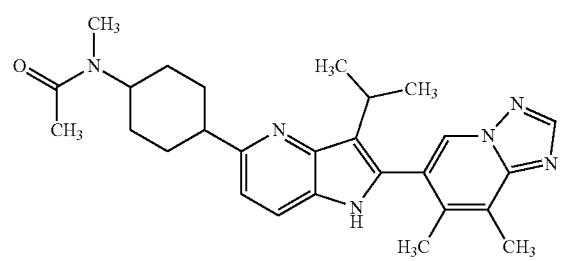 [SMILES: CC(=O)N(C)C1CCC(c2ccc3[nH]c(-c4cn5ncnc5c(C)c4C)c(C(C)C)c3n2)CC1] | 458.61 | 459.3 | 0.97 | QC-ACN-TFA-XB |
| 441 | 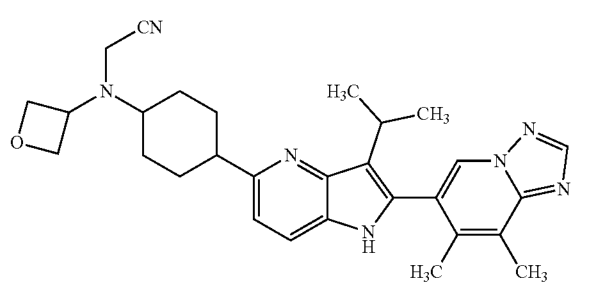 [SMILES: Cc1c(-c2[nH]c3ccc(C4CCC(N(CC#N)C5COC5)CC4)nc3c2C(C)C)cn2ncnc2c1C] | 497.65 | 497.9 | 1.77 | QC-ACN-AA-XB |

TABLE 1-continued

| Ex. No. | Structure | Mol. Wt. | LCMS M+ | Ret Time (min) | HPLC Method |
|---|---|---|---|---|---|
| 442 | 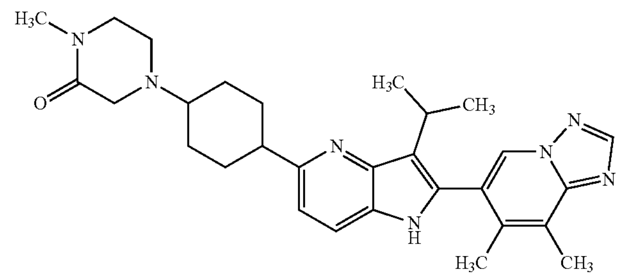 [SMILES: Cc1c(-c2[nH]c3ccc(C4CCC(N5CCN(C)C(=O)C5)CC4)nc3c2C(C)C)cn2ncnc2c1C] | 499.66 | 500.2 | 1.51 | QC-ACN-AA-XB |
| 443 | 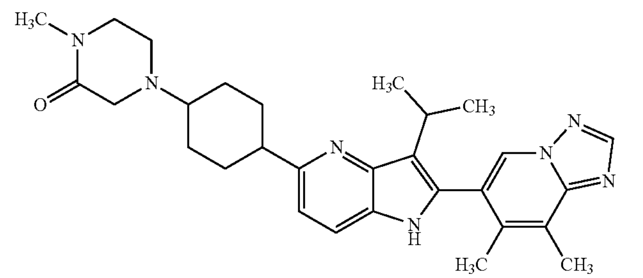 [SMILES: Cc1c(-c2[nH]c3ccc(C4CCC(N5CCN(C)C(=O)C5)CC4)nc3c2C(C)C)cn2ncnc2c1C] | 499.66 | 500.2 | 1.58 | QC-ACN-AA-XB |
| 444 | 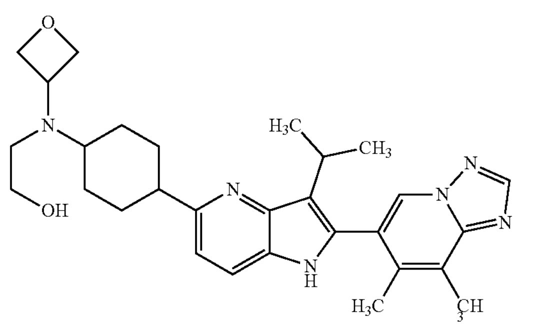 [SMILES: Cc1c(-c2[nH]c3ccc(C4CCC(N(CCO)C5COC5)CC4)nc3c2C(C)C)cn2ncnc2c1C] | 502.66 | 503.1 | 1.45 | QC-ACN-AA-XB |
| 445 | 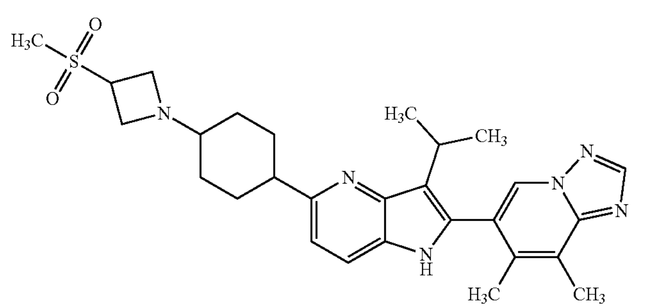 [SMILES: Cc1c(-c2[nH]c3ccc(C4CCC(N5CC(S(C)(=O)=O)C5)CC4)nc3c2C(C)C)cn2ncnc2c1C] | 520.70 | 521.4 | 0.81 | QC-ACN-TFA-XB |
| 446 | 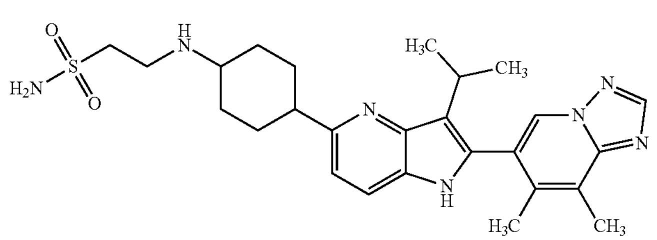 [SMILES: Cc1c(-c2[nH]c3ccc(C4CCC(NCCS(C)(=O)=O)CC4)nc3c2C(C)C)cn2ncnc2c1C] | 509.67 | 510.3 | 0.78 | QC-ACN-TFA-XB |

TABLE 1-continued
| Ex. No. | Structure | Mol. Wt. | LCMS M+ | Ret Time (min) | HPLC Method |
|---|---|---|---|---|---|
| 447 | 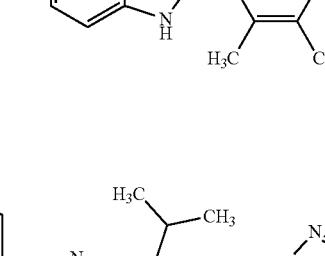 | 509.67 | 510.4 | 0.8 | QC-ACN-TFA-XB |
| 448 | 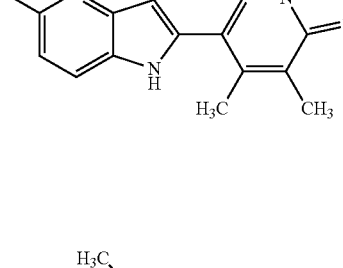 | 520.70 | 521.4 | 0.83 | QC-ACN-TFA-XB |
| 449 | 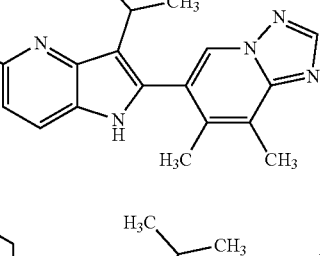 | 529.69 | 530.3 | 1.4 | QC-ACN-AA-XB |
| 450 | 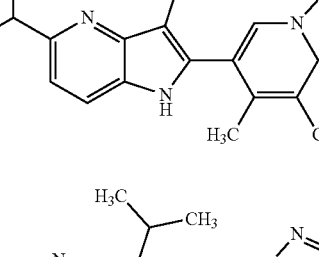 | 508.69 | 509.4 | 1.25 | QC-ACN-AA-XB |
| 451 | 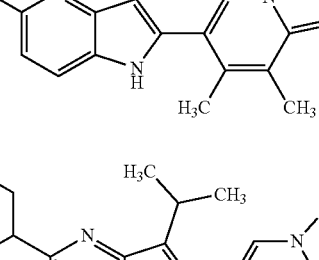 | 486.66 | 487.3 | 0.9 | QC-ACN-TFA-XB |
| 452 | 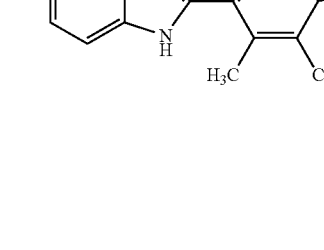 | 508.69 | 509.4 | 0.84 | QC-ACN-TFA-XB |

TABLE 1-continued

| Ex. No. | Structure | Mol. Wt. | LCMS M+ | Ret Time (min) | HPLC Method |
|---|---|---|---|---|---|
| 453 | 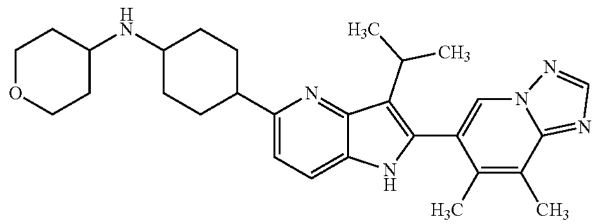 [SMILES: Cc1c(-c2[nH]c3ccc(C4CCC(NC5CCOCC5)CC4)nc3c2C(C)C)cn2ncnc2c1C] | 486.66 | 487.4 | 1.41 | QC-ACN-AA-XB |
| 454 | 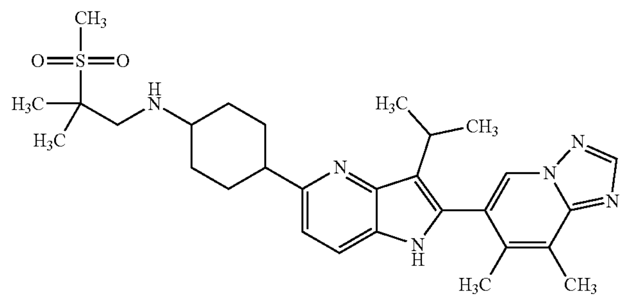 [SMILES: Cc1c(-c2[nH]c3ccc(C4CCC(NCC(C)(C)S(C)(=O)=O)CC4)nc3c2C(C)C)cn2ncnc2c1C] | 536.74 | 537.2 | 0.84 | QC-ACN-TFA-XB |
| 455 | 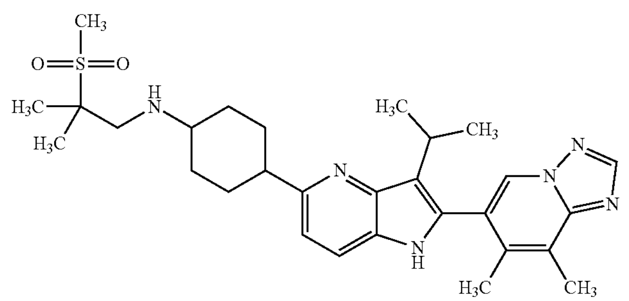 [SMILES: Cc1c(-c2[nH]c3ccc(C4CCC(NCC(C)(C)S(C)(=O)=O)CC4)nc3c2C(C)C)cn2ncnc2c1C] | 536.74 | 537.4 | 1.86 | QC-ACN-AA-XB |
| 456 | 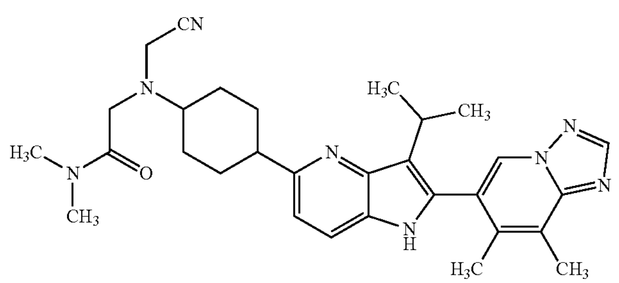 | 526.69 | 527.4 | 1.09 | QC-ACN-TFA-XB |
| 457 | 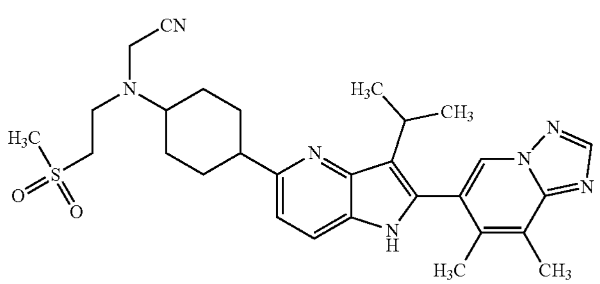 [SMILES: Cc1c(-c2[nH]c3ccc(C4CCC(N(CC#N)CCS(C)(=O)=O)CC4)nc3c2C(C)C)cn2ncnc2c1C] | 547.72 | 548.4 | 1.86 | QC-ACN-AA-XB |

TABLE 1-continued

| Ex. No. | Structure | Mol. Wt. | LCMS M+ | Ret Time (min) | HPLC Method |
|---|---|---|---|---|---|
| 458 | 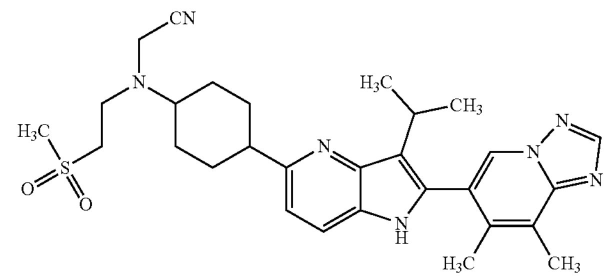 [SMILES: Cc1c(-c2[nH]c3ccc(C4CCC(N(CC#N)CCS(C)(=O)=O)CC4)nc3c2C(C)C)cn2ncnc2c1C] | 547.72 | 548.1 | 1.78 | QC-ACN-AA-XB |
| 459 | 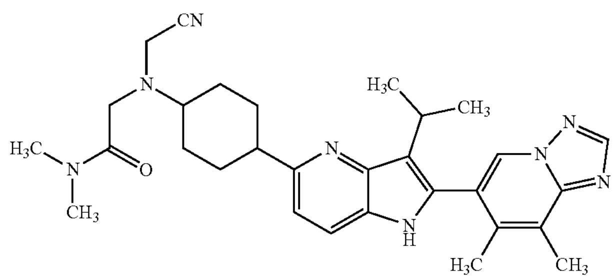 | 526.69 | 527.4 | 1.8 | QC-ACN-AA-XB |
| 460 | 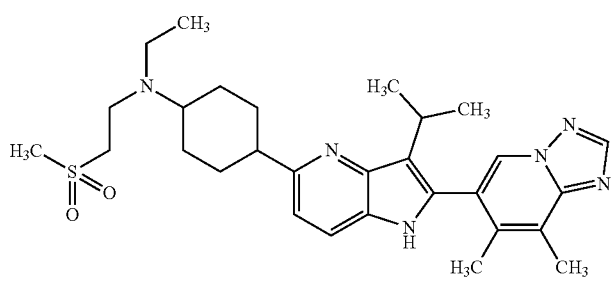 [SMILES: CCN(CCS(C)(=O)=O)C1CCC(c2ccc3[nH]c(-c4cn5ncnc5c(C)c4C)c(C(C)C)c3n2)CC1] | 536.74 | 537.2 | 0.77 | QC-ACN-TFA-XB |
| 461 | 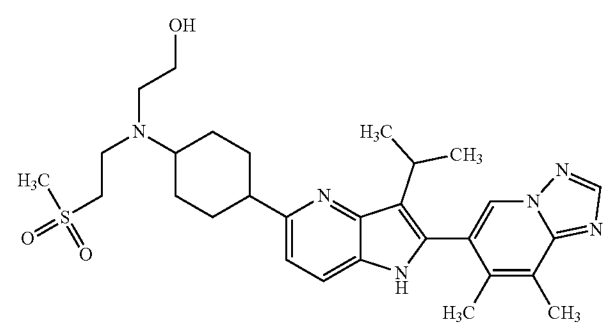 [SMILES: Cc1c(-c2[nH]c3ccc(C4CCC(N(CCO)CCS(C)(=O)=O)CC4)nc3c2C(C)C)cn2ncnc2c1C] | 552.74 | 553.4 | 0.86 | QC-ACN-TFA-XB |
| 462 | 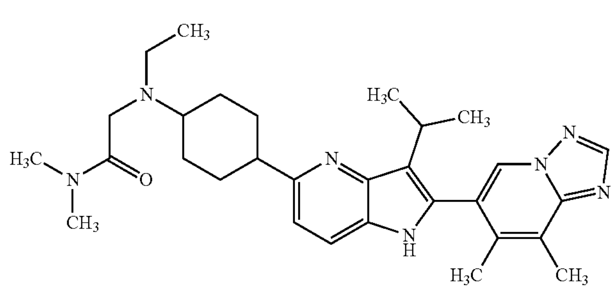 [SMILES: CCN(CC(=O)N(C)C)C1CCC(c2ccc3[nH]c(-c4cn5ncnc5c(C)c4C)c(C(C)C)c3n2)CC1] | 515.71 | 516.1 | 0.94 | QC-ACN-TFA-XB |

TABLE 1-continued

| Ex. No. | Structure | Mol. Wt. | LCMS M+ | Ret Time (min) | HPLC Method |
|---|---|---|---|---|---|
| 463 | 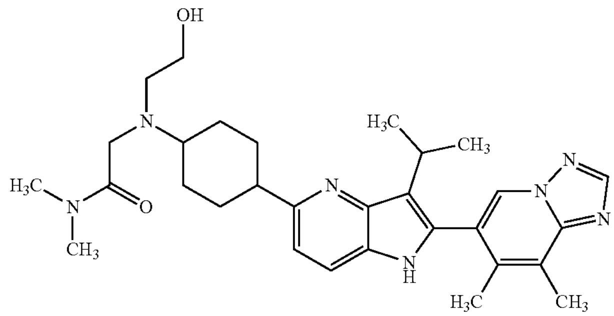 [SMILES: Cc1c(-c2[nH]c3ccc(C4CCC(N(CCO)CC(=O)N(C)C)CC4)nc3c2C(C)C)cn2ncnc2c1C] | 531.71 | 532.4 | 0.95 | QC-ACN-TFA-XB |
| 464 | 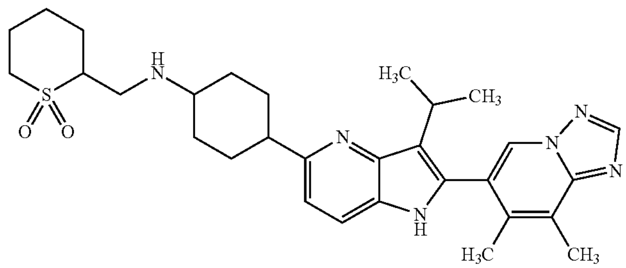 [SMILES: Cc1c(-c2[nH]c3ccc(C4CCC(NCC5CCCCS5(=O)=O)CC4)nc3c2C(C)C)cn2ncnc2c1C] | 548.75 | 549.1 | 0.85 | QC-ACN-TFA-XB |
| 465 | 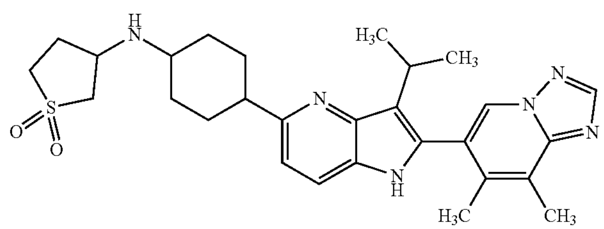 [SMILES: Cc1c(-c2[nH]c3ccc(C4CCC(NC5CCS(=O)(=O)C5)CC4)nc3c2C(C)C)cn2ncnc2c1C] | 520.70 | 521.4 | 1.46 | QC-ACN-AA-XB |
| 466 | 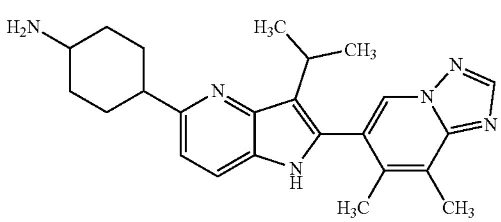 | 402.55 | 403.3 | 0.85 | QC-ACN-TFA-XB |
| 467 | 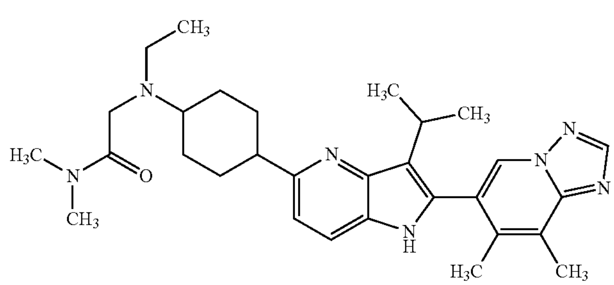 | 515.71 | 516.4 | 0.78 | QC-ACN-TFA-XB |

TABLE 1-continued

| Ex. No. | Structure | Mol. Wt. | LCMS M+ | Ret Time (min) | HPLC Method |
|---|---|---|---|---|---|
| 468 | 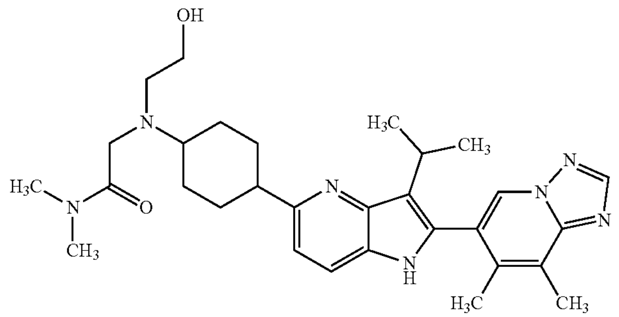 [SMILES: Cc1c(-c2[nH]c3ccc(C4CCC(N(CCO)CC(=O)N(C)C)CC4)nc3c2C(C)C)cn2ncnc2c1C] | 531.71 | 532.4 | 1.52 | QC-ACN-AA-XB |
| 469 | 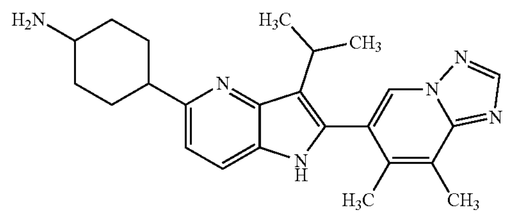 [SMILES: Cc1c(-c2[nH]c3ccc(C4CCC(N)CC4)nc3c2C(C)C)cn2ncnc2c1C] | 402.55 | 403.3 | 0.87 | QC-ACN-TFA-XB |
| 470 | 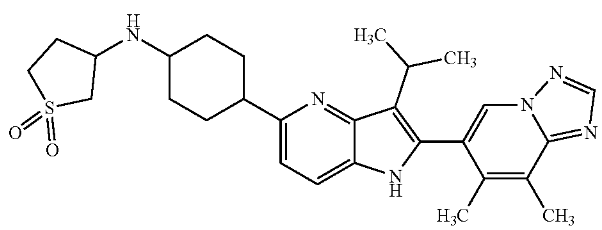 [SMILES: Cc1c(-c2[nH]c3ccc(C4CCC(NC5CCS(=O)(=O)C5)CC4)nc3c2C(C)C)cn2ncnc2c1C] | 520.70 | 521.4 | 1.84 | QC-ACN-AA-XB |
| 471 | 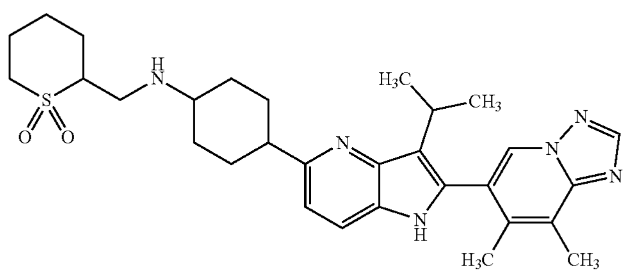 | 548.75 | 549.4 | 0.96 | QC-ACN-TFA-XB |
| 472 | 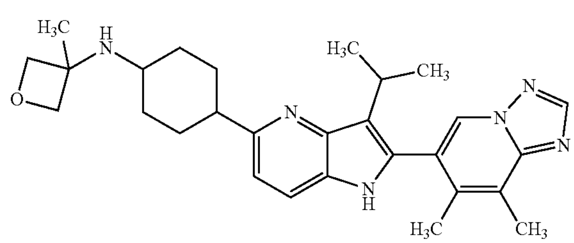 [SMILES: Cc1c(-c2[nH]c3ccc(C4CCC(NC5(C)COC5)CC4)nc3c2C(C)C)cn2ncnc2c1C] | 472.64 | 473.4 | 0.8 | QC-ACN-TFA-XB |
| 473 | 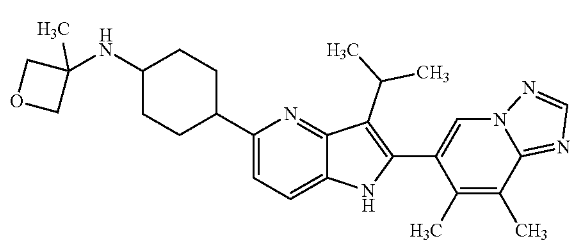 | 472.64 | 473.4 | 0.82 | QC-ACN-TFA-XB |

TABLE 1-continued

| Ex. No. | Structure | Mol. Wt. | LCMS M+ | Ret Time (min) | HPLC Method |
|---|---|---|---|---|---|
| 474 | 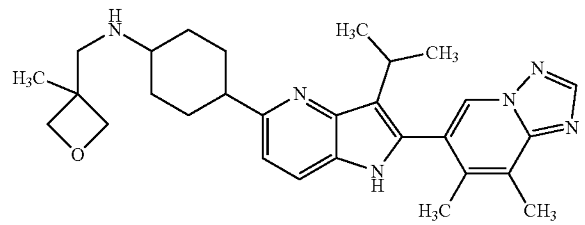 [SMILES: Cc1c(-c2[nH]c3ccc(C4CCC(NCC5(C)COC5)CC4)nc3c2C(C)C)cn2ncnc2c1C] | 486.66 | 487.1 | 1.18 | QC-ACN-AA-XB |
| 475 | 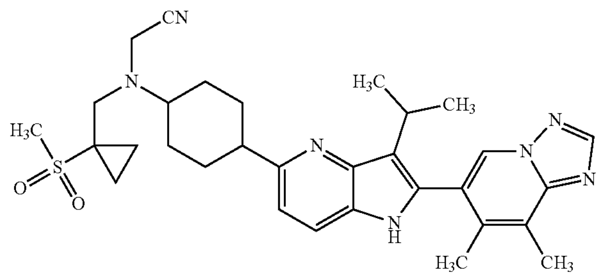 [SMILES: Cc1c(-c2[nH]c3ccc(C4CCC(N(CC#N)CC5(S(C)(=O)=O)CC5)CC4)nc3c2C(C)C)cn2ncnc2c1C] | 573.76 | 574.5 | 1.86 | QC-ACN-AA-XB |
| 476 | 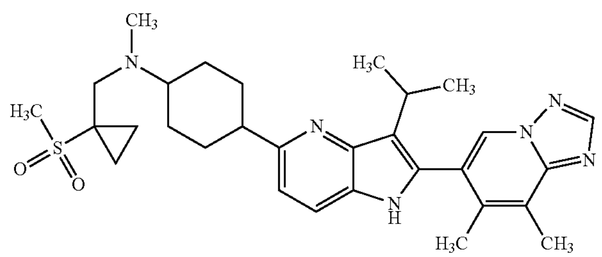 [SMILES: Cc1c(-c2[nH]c3ccc(C4CCC(N(C)CC5(S(C)(=O)=O)CC5)CC4)nc3c2C(C)C)cn2ncnc2c1C] | 548.75 | 549.4 | 2.17 | QC-ACN-AA-XB |
| 477 | 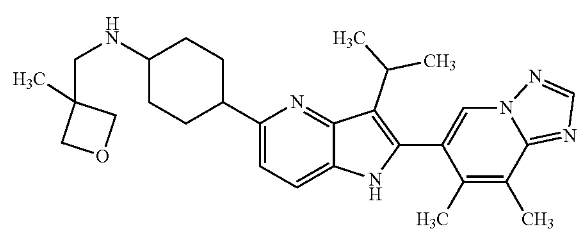 [SMILES: Cc1c(-c2[nH]c3ccc(C4CCC(NCC5(C)COC5)CC4)nc3c2C(C)C)cn2ncnc2c1C] | 486.66 | 487.5 | 1.34 | QC-ACN-AA-XB |
| 478 | 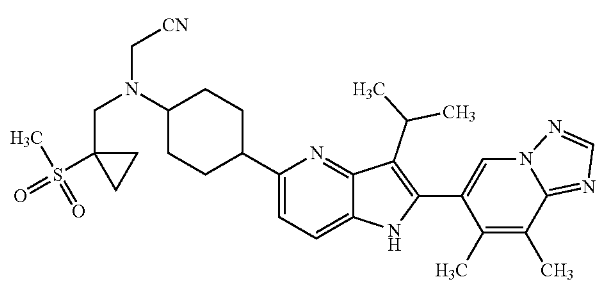 [SMILES: Cc1c(-c2[nH]c3ccc(C4CCC(N(CC#N)CC5(S(C)(=O)=O)CC5)CC4)nc3c2C(C)C)cn2ncnc2c1C] | 573.76 | 574.2 | 1.62 | QC-ACN-TFA-XB |
| 479 | 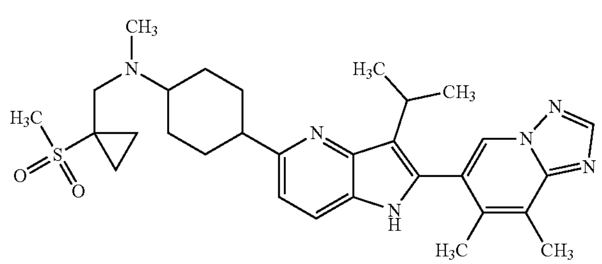 [SMILES: Cc1c(-c2[nH]c3ccc(C4CCC(N(C)CC5(S(C)(=O)=O)CC5)CC4)nc3c2C(C)C)cn2ncnc2c1C] | 548.75 | 549.5 | 1.95 | QC-ACN-AA-XB |

TABLE 1-continued

| Ex. No. | Structure | Mol. Wt. | LCMS M+ | Ret Time (min) | HPLC Method |
|---|---|---|---|---|---|
| 480 | 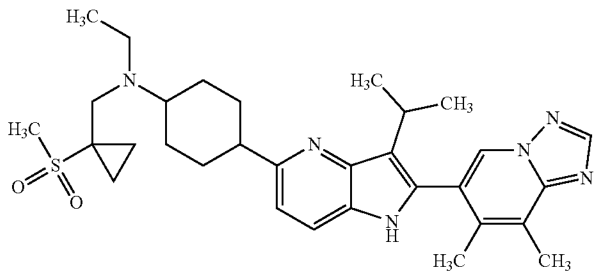 [SMILES: CCN(CC1(S(C)(=O)=O)CC1)C1CCC(c2ccc3[nH]c(-c4cn5ncnc5c(C)c4C)c(C(C)C)c3n2)CC1] | 562.78 | 563.5 | 0.93 | QC-ACN-TFA-XB |
| 481 | 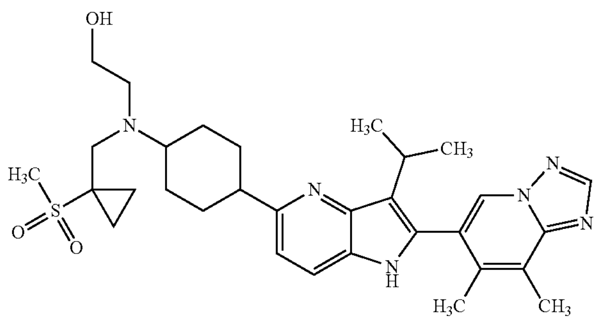 [SMILES: Cc1c(-c2[nH]c3ccc(C4CCC(N(CCO)CC5(S(C)(=O)=O)CC5)CC4)nc3c2C(C)C)cn2ncnc2c1C] | 578.78 | 579.3 | 1.85 | QC-ACN-AA-XB |
| 482 | 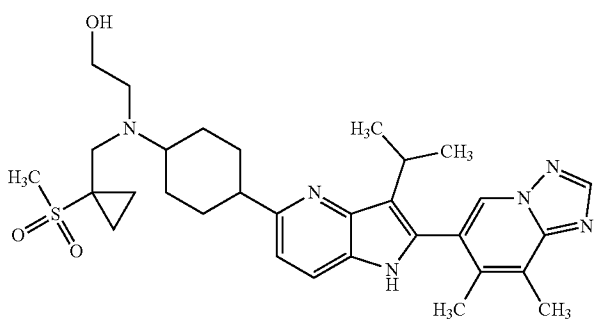 [SMILES: Cc1c(-c2[nH]c3ccc(C4CCC(N(CCO)CC5(S(C)(=O)=O)CC5)CC4)nc3c2C(C)C)cn2ncnc2c1C] | 578.78 | 579.5 | 1.85 | QC-ACN-AA-XB |
| 483 | 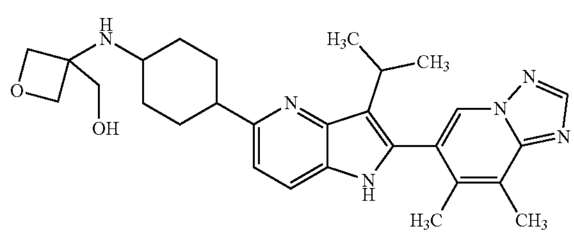 [SMILES: Cc1c(-c2[nH]c3ccc(C4CCC(NC5(CO)COC5)CC4)nc3c2C(C)C)cn2ncnc2c1C] | 488.64 | 489.4 | 0.76 | QC-ACN-TFA-XB |
| 484 | 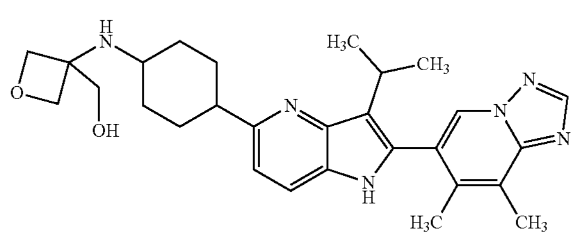 [SMILES: Cc1c(-c2[nH]c3ccc(C4CCC(NC5(CO)COC5)CC4)nc3c2C(C)C)cn2ncnc2c1C] | 488.64 | 489.2 | 1.04 | QC-ACN-TFA-XB |

TABLE 1-continued
| Ex. No. | Structure | Mol. Wt. | LCMS M+ | Ret Time (min) | HPLC Method |
|---|---|---|---|---|---|
| 485 | 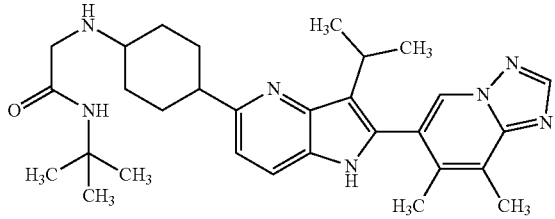 [SMILES: Cc1c(-c2[nH]c3ccc(C4CCC(NCC(=O)NC(C)(C)C)CC4)nc3c2C(C)C)cn2ncnc2c1C] | 515.71 | 516.5 | 1.59 | QC-ACN-AA-XB |
| 486 | 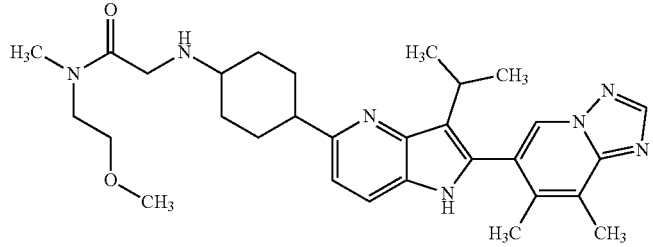 [SMILES: COCCN(C)C(=O)CNC1CCC(c2ccc3[nH]c(-c4cn5ncnc5c(C)c4C)c(C(C)C)c3n2)CC1] | 531.71 | 267 | 1.13 | QC-ACN-TFA-XB |
| 487 | 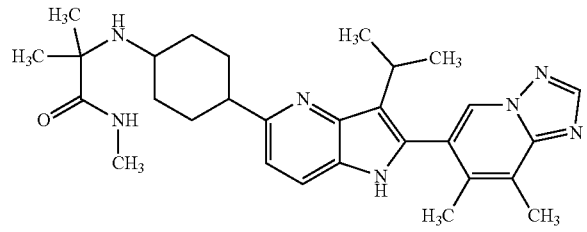 [SMILES: CNC(=O)C(C)(C)NC1CCC(c2ccc3[nH]c(-c4cn5ncnc5c(C)c4C)c(C(C)C)c3n2)CC1] | 501.68 | 502.4 | 0.81 | QC-ACN-TFA-XB |
| 488 | 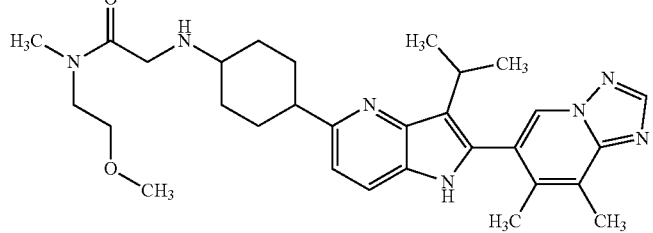 | 531.71 | 532.6 | 1.52 | QC-ACN-AA-XB |
| 489 | 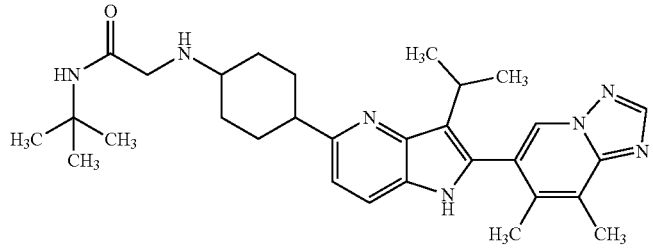 [SMILES: Cc1c(-c2[nH]c3ccc(C4CCC(NCC(=O)NC(C)(C)C)CC4)nc3c2C(C)C)cn2ncnc2c1C] | 515.71 | 516.5 | 1.9 | QC-ACN-AA-XB |
| 490 | 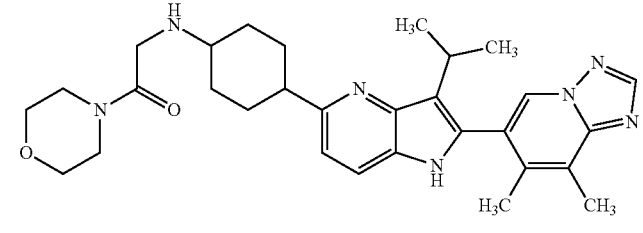 [SMILES: Cc1c(-c2[nH]c3ccc(C4CCC(NCC(=O)N5CCOCC5)CC4)nc3c2C(C)C)cn2ncnc2c1C] | 529.69 | 552.2 | 1.38 | QC-ACN-AA-XB |

TABLE 1-continued

| Ex. No. | Structure | Mol. Wt. | LCMS M+ | Ret Time (min) | HPLC Method |
|---|---|---|---|---|---|
| 491 | 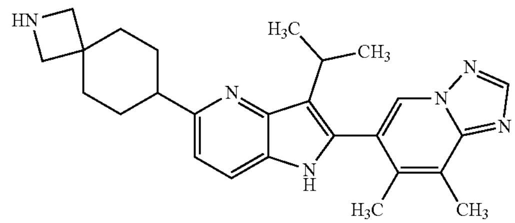 [SMILES: Cc1c(-c2[nH]c3ccc(C4CCC5(CC4)CNC5)nc3c2C(C)C)cn2ncnc2c1C] | 428.58 | 429.4 | 1.26 | QC-ACN-AA-XB |
| 492 | 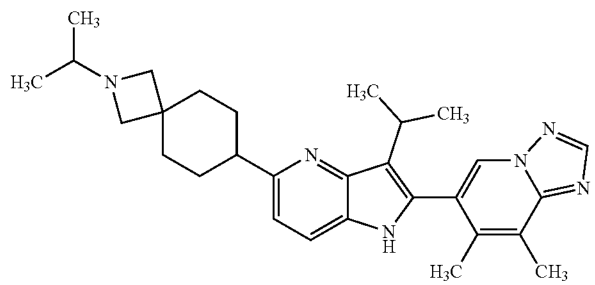 [SMILES: Cc1c(-c2[nH]c3ccc(C4CCC5(CC4)CN(C(C)C)C5)nc3c2C(C)C)cn2ncnc2c1C] | 470.67 | 236.1 | 1.51 | QC-ACN-AA-XB |
| 493 | 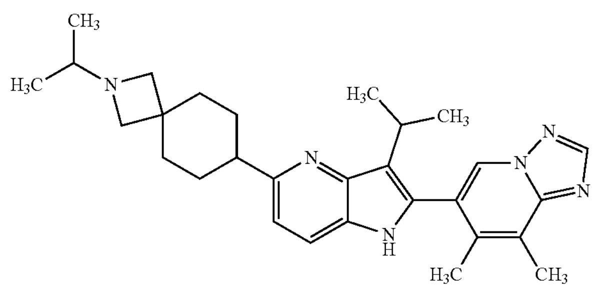 [SMILES: Cc1c(-c2[nH]c3ccc(C4CCC5(CC4)CN(C(C)C)C5)nc3c2C(C)C)cn2ncnc2c1C] | 470.67 | 471.4 | 2.55 | QC-ACN-TFA-XB |
| 494 | 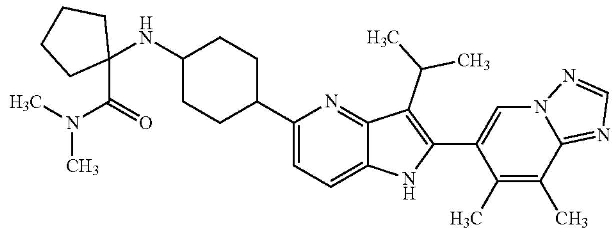 [SMILES: Cc1c(-c2[nH]c3ccc(C4CCC(NC5(C(=O)N(C)C)CCCC5)CC4)nc3c2C(C)C)cn2ncnc2c1C] | 541.74 | 542.3 | 2.34 | QC-ACN-AA-XB |
| 495 | 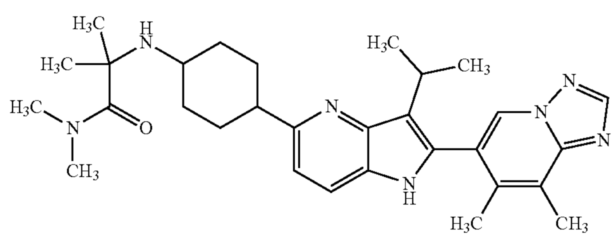 [SMILES: Cc1c(-c2[nH]c3ccc(C4CCC(NC(C)(C)C(=O)N(C)C)CC4)nc3c2C(C)C)cn2ncnc2c1C] | 515.71 | 516.5 | 0.88 | QC-ACN-TFA-XB |
| 496 | 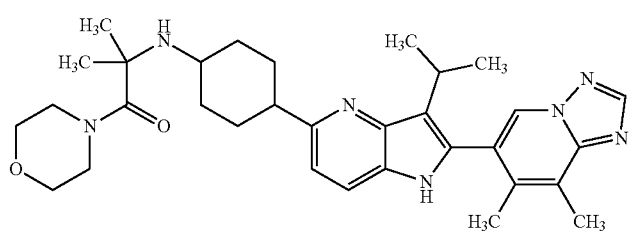 [SMILES: Cc1c(-c2[nH]c3ccc(C4CCC(NC(C)(C)C(=O)N5CCOCC5)CC4)nc3c2C(C)C)cn2ncnc2c1C] | 557.74 | 558.3 | 1.03 | QC-ACN-TFA-XB |

TABLE 1-continued

| Ex. No. | Structure | Mol. Wt. | LCMS M+ | Ret Time (min) | HPLC Method |
|---|---|---|---|---|---|
| 497 | 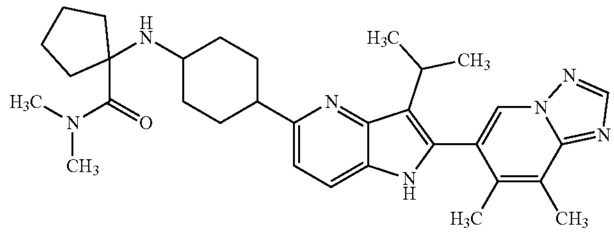 [SMILES: Cc1c(-c2[nH]c3ccc(C4CCC(NC5(C(=O)N(C)C)CCCC5)CC4)nc3c2C(C)C)cn2ncnc2c1C] | 541.74 | 564.2 | 2.33 | QC-ACN-AA-XB |
| 498 | 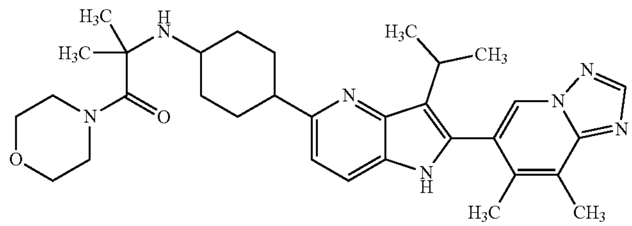 [SMILES: Cc1c(-c2[nH]c3ccc(C4CCC(NC(C)(C)C(=O)N5CCOCC5)CC4)nc3c2C(C)C)cn2ncnc2c1C] | 557.74 | 558.4 | 0.92 | QC-ACN-TFA-XB |
| 499 | 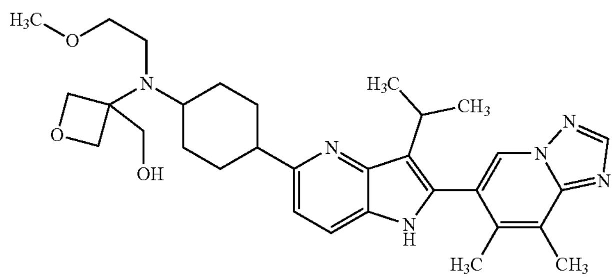 [SMILES: COCCN(C1CCC(c2ccc3[nH]c(-c4cn5ncnc5c(C)c4C)c(C(C)C)c3n2)CC1)C1(CO)COC1] | 546.72 | 547.4 | 1.56 | QC-ACN-AA-XB |
| 500 | 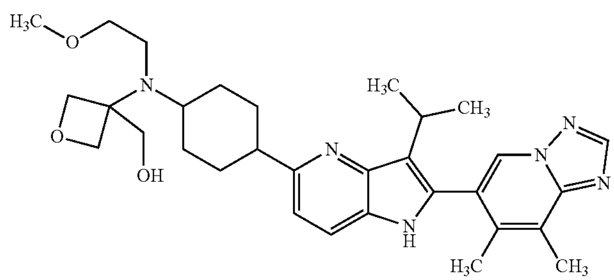 [SMILES: COCCN(C1CCC(c2ccc3[nH]c(-c4cn5ncnc5c(C)c4C)c(C(C)C)c3n2)CC1)C1(CO)COC1] | 546.72 | 547 | 1.09 | QC-ACN-TFA-XB |
| 501 | 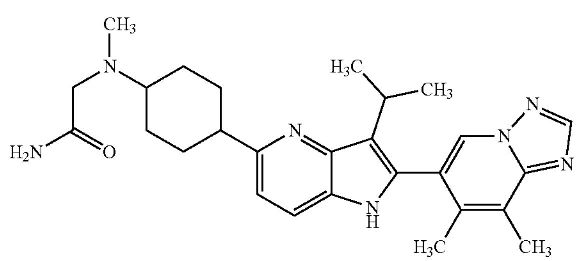 [SMILES: Cc1c(-c2[nH]c3ccc(C4CCC(N(C)CC(N)=O)CC4)nc3c2C(C)C)cn2ncnc2c1C] | 473.63 | 474.5 | 0.87 | QC-ACN-TFA-XB |
| 502 | 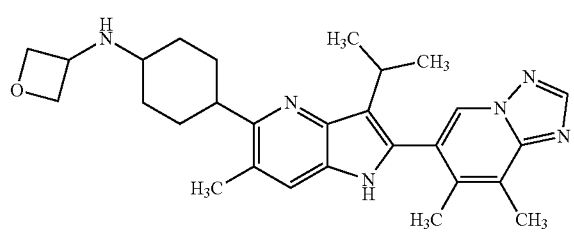 [SMILES: Cc1cc2[nH]c(-c3cn4ncnc4c(C)c3C)c(C(C)C)c2nc1C1CCC(NC2COC2)CC1] | 472.64 | 473.4 | 1.69 | E |

TABLE 1-continued

| Ex. No. | Structure | Mol. Wt. | LCMS M+ | Ret Time (min) | HPLC Method |
|---|---|---|---|---|---|
| 503 | 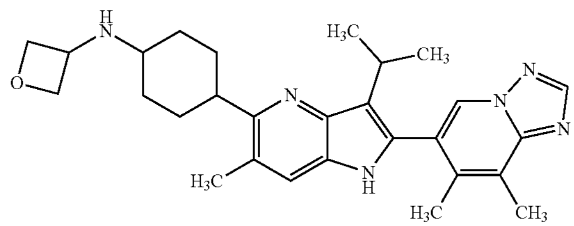 [SMILES: Cc1cc2[nH]c(-c3cn4ncnc4c(C)c3C)c(C(C)C)c2nc1C1CCC(NC2COC2)CC1] | 472.64 | 473.3 | 1.74 | E |
| 504 | 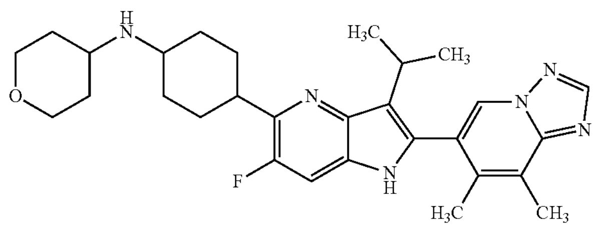 [SMILES: Cc1c(-c2[nH]c3cc(F)c(C4CCC(NC5CCOCC5)CC4)nc3c2C(C)C)cn2ncnc2c1C] | 504.65 | 505.3 | 1.48 | E |
| 505 | 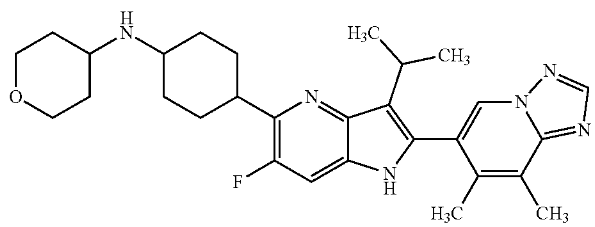 | 504.65 | 505.4 | 1.54 | E |
| 506 | 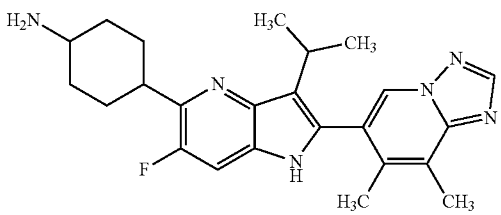 [SMILES: Cc1c(-c2[nH]c3cc(F)c(C4CCC(N)CC4)nc3c2C(C)C)cn2ncnc2c1C] | 420.54 | 421.3 | 1.31 | E |
| 507 | 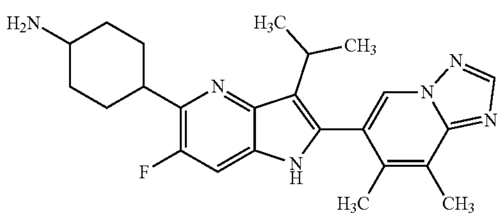 | 420.54 | 421.3 | 1.36 | E |
| 508 | 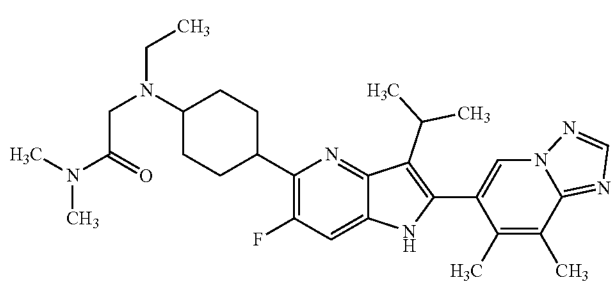 [SMILES: CCN(CC(=O)N(C)C)C1CCC(c2nc3c(C(C)C)c(-c4cn5ncnc5c(C)c4C)[nH]c3cc2F)CC1] | 533.70 | 534 | 1.59 | E |

TABLE 1-continued

| Ex. No. | Structure | Mol. Wt. | LCMS M+ | Ret Time (min) | HPLC Method |
|---|---|---|---|---|---|
| 509 | 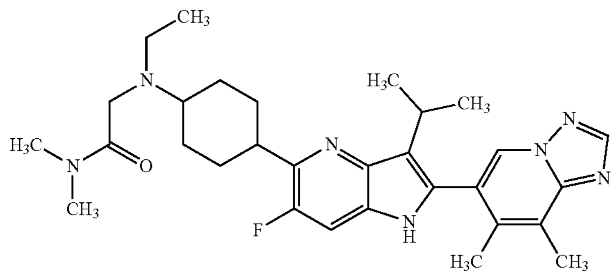 [SMILES: CCN(CC(=O)N(C)C)C1CCC(c2nc3c(C(C)C)c(-c4cn5ncnc5c(C)c4C)[nH]c3cc2F)CC1] | 533.70 | 534.3 | 1.66 | E |
| 510 | 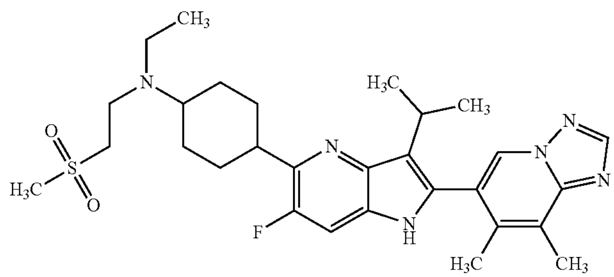 [SMILES: CCN(CCS(C)(=O)=O)C1CCC(c2nc3c(C(C)C)c(-c4cn5ncnc5c(C)c4C)[nH]c3cc2F)CC1] | 554.73 | 555.4 | 2.09 | E |
| 511 | 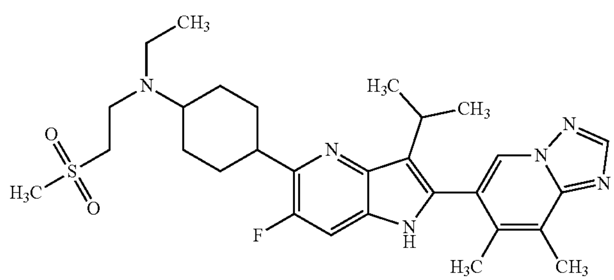 [SMILES: CCN(CCS(C)(=O)=O)C1CCC(c2nc3c(C(C)C)c(-c4cn5ncnc5c(C)c4C)[nH]c3cc2F)CC1] | 554.73 | 555.3 | 2.03 | E |
| 512 | 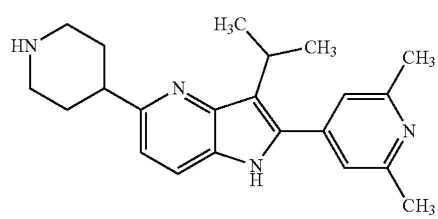 [SMILES: Cc1cc(-c2[nH]c3ccc(C4CCNCC4)nc3c2C(C)C)cc(C)n1] | 348.49 | 349.3 | 1.63 | QC-ACN-AA-XB |
| 513 | 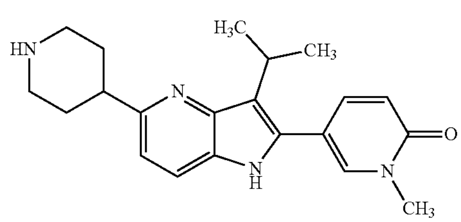 | 350.47 | 351.3 | 0.58 | QC-ACN-TFA-XB |
| 514 | 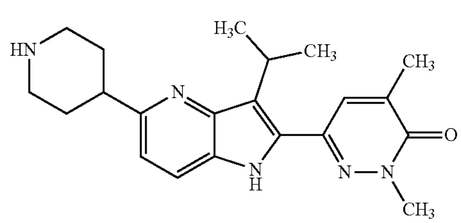 | 365.48 | 366 | 0.67 | QC-ACN-TFA-XB |

TABLE 1-continued

| Ex. No. | Structure | Mol. Wt. | LCMS M+ | Ret Time (min) | HPLC Method |
|---|---|---|---|---|---|
| 515 | 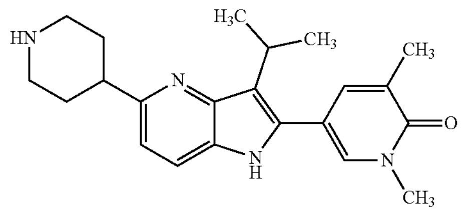 [SMILES: Cc1cc(-c2[nH]c3ccc(C4CCNCC4)nc3c2C(C)C)cn(C)c1=O] | 364.49 | 365.3 | 0.99 | QC-ACN-AA-XB |
| 516 | 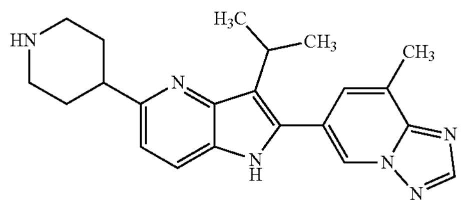 | 374.49 | 375.1 | 1.15 | QC-ACN-AA-XB |
| 517 | 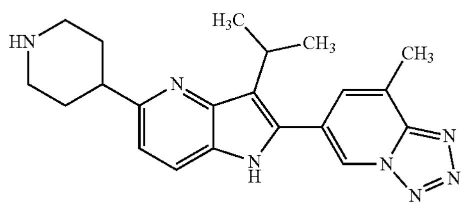 [SMILES: Cc1cc(-c2[nH]c3ccc(C4CCNCC4)nc3c2C(C)C)cn2nnnc12] | 375.48 | 376 | 0.99 | QC-ACN-TFA-XB |
| 518 | 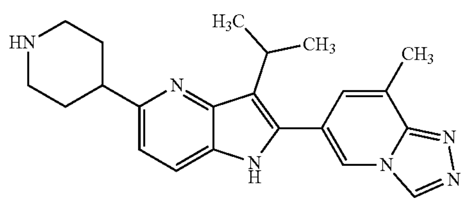 [SMILES: Cc1cc(-c2[nH]c3ccc(C4CCNCC4)nc3c2C(C)C)cn2cnnc12] | 374.49 | 374.9 | 0.95 | QC-ACN-AA-XB |
| 519 | 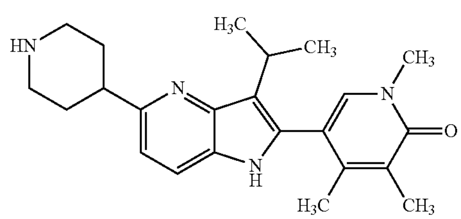 [SMILES: Cc1c(-c2[nH]c3ccc(C4CCNCC4)nc3c2C(C)C)cn(C)c(=O)c1C] | 378.52 | 379 | 1.47 | QC-ACN-AA-XB |
| 520 | 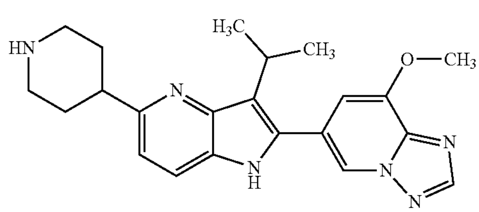 [SMILES: COc1cc(-c2[nH]c3ccc(C4CCNCC4)nc3c2C(C)C)cn2ncnc12] | 390.49 | 391.4 | 0.52 | B1 |
| 521 | 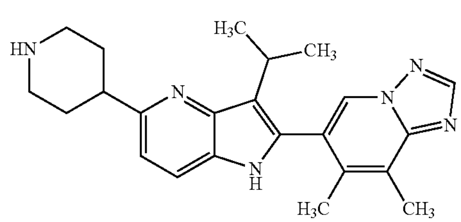 [SMILES: Cc1c(-c2[nH]c3ccc(C4CCNCC4)nc3c2C(C)C)cn2ncnc2c1C] | 388.52 | 389.3 | 0.58 | B1 |

TABLE 1-continued

| Ex. No. | Structure | Mol. Wt. | LCMS M+ | Ret Time (min) | HPLC Method |
|---|---|---|---|---|---|
| 522 | 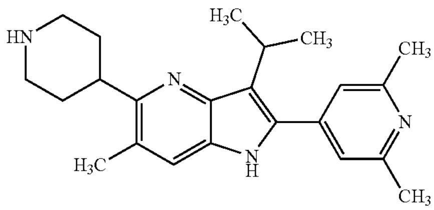 [SMILES: Cc1cc(-c2[nH]c3cc(C)c(C4CCNCC4)nc3c2C(C)C)cc(C)n1] | 362.52 | 363.3 | 1.46 | E |
| 523 | 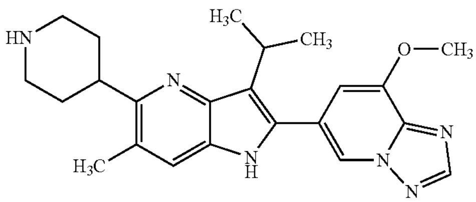 | 404.52 | 405.1 | 1.25 | E |
| 524 | 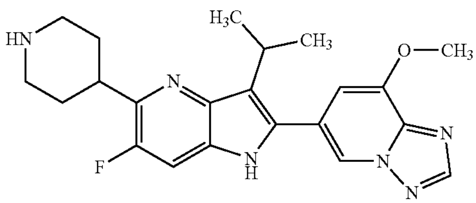 [SMILES: COc1cc(-c2[nH]c3cc(F)c(C4CCNCC4)nc3c2C(C)C)cn2ncnc12] | 408.48 | 409.1 | 1.23 | E |
| 525 | 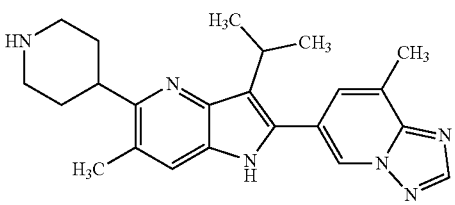 [SMILES: Cc1cc2[nH]c(-c3cc(C)c4ncnn4c3)c(C(C)C)c2nc1C1CCNCC1] | 388.52 | 389.2 | 2.46 | R |
| 526 | 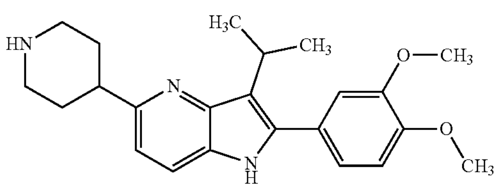 [SMILES: COc1ccc(-c2[nH]c3ccc(C4CCNCC4)nc3c2C(C)C)cc1OC] | 379.50 | 380.7 | 2.524 | D |
| 527 | 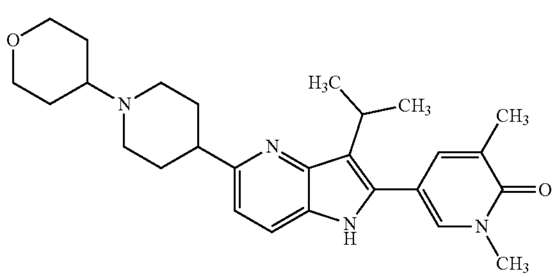 [SMILES: Cc1cc(-c2[nH]c3ccc(C4CCN(C5CCOCC5)CC4)nc3c2C(C)C)cn(C)c1=O] | 448.61 | 449.3 | 0.52 | B1 |
| 528 | 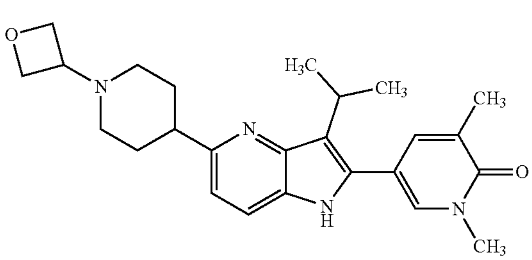 [SMILES: Cc1cc(-c2[nH]c3ccc(C4CCN(C5COC5)CC4)nc3c2C(C)C)cn(C)c1=O] | 420.56 | 421.3 | 0.51 | B1 |

TABLE 1-continued

| Ex. No. | Structure | Mol. Wt. | LCMS M+ | Ret Time (min) | HPLC Method |
|---|---|---|---|---|---|
| 529 | 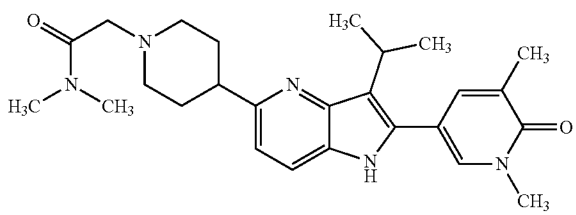 [SMILES: Cc1cc(-c2[nH]c3ccc(C4CCN(CC(=O)N(C)C)CC4)nc3c2C(C)C)cn(C)c1=O] | 449.60 | 450.3 | 0.52 | B1 |
| 530 | 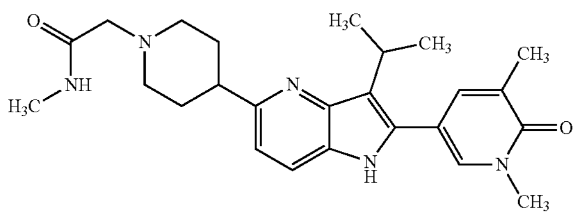 [SMILES: CNC(=O)CN1CCC(c2ccc3[nH]c(-c4cc(C)c(=O)n(C)c4)c(C(C)C)c3n2)CC1] | 435.57 | 436.3 | 0.51 | B1 |
| 531 | 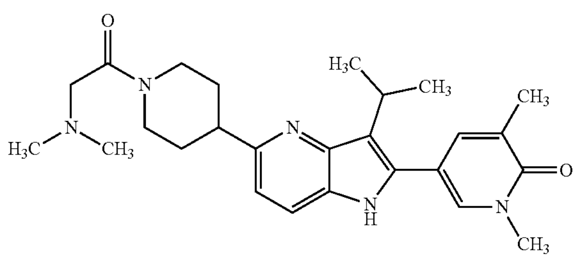 [SMILES: Cc1cc(-c2[nH]c3ccc(C4CCN(C(=O)CN(C)C)CC4)nc3c2C(C)C)cn(C)c1=O] | 449.60 | 450.3 | 0.51 | B1 |
| 532 | 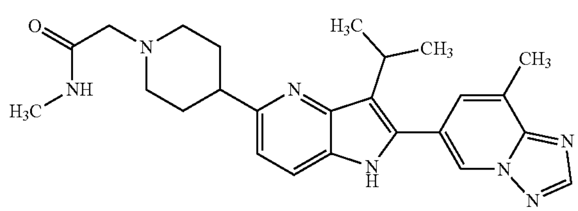 [SMILES: CNC(=O)CN1CCC(c2ccc3[nH]c(-c4cc(C)c5ncnn5c4)c(C(C)C)c3n2)CC1] | 445.57 | 446.3 | 0.54 | B1 |
| 533 | 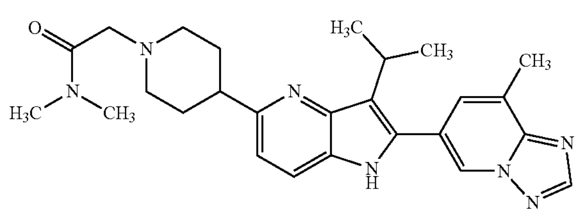 [SMILES: Cc1cc(-c2[nH]c3ccc(C4CCN(CC(=O)N(C)C)CC4)nc3c2C(C)C)cn2ncnc12] | 459.60 | 460.3 | 0.55 | B1 |
| 534 | 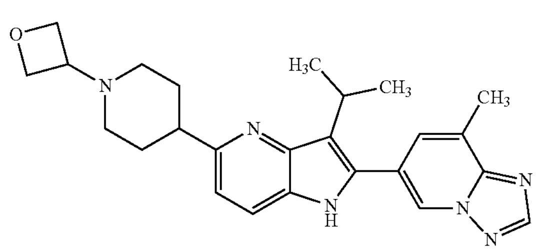 [SMILES: Cc1cc(-c2[nH]c3ccc(C4CCN(C5COC5)CC4)nc3c2C(C)C)cn2ncnc12] | 430.56 | 431.3 | 0.55 | B1 |

TABLE 1-continued
| Ex. No. | Structure | Mol. Wt. | LCMS M+ | Ret Time (min) | HPLC Method |
|---|---|---|---|---|---|
| 535 | 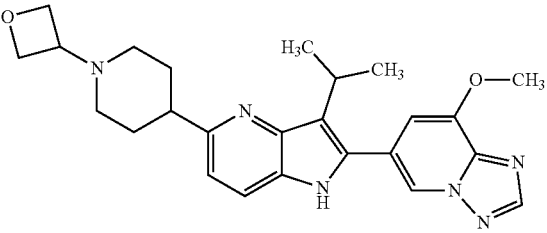 [SMILES: COc1cc(-c2[nH]c3ccc(C4CCN(C5COC5)CC4)nc3c2C(C)C)cn2ncnc12] | 446.56 | 447 | 0.53 | B1 |
| 536 | 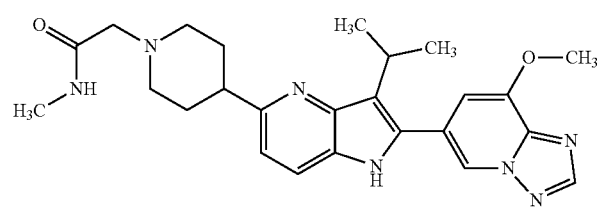 [SMILES: CNC(=O)CN1CCC(c2ccc3[nH]c(-c4cc(OC)c5ncnn5c4)c(C(C)C)c3n2)CC1] | 461.57 | 462 | 1.4 | QC-ACN-AA-XB |
| 537 | 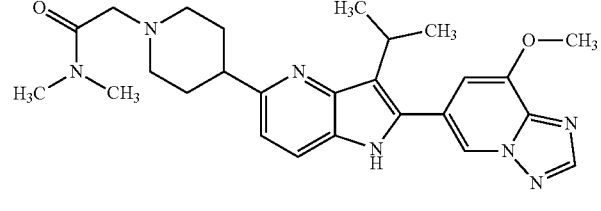 [SMILES: COc1cc(-c2[nH]c3ccc(C4CCN(CC(=O)N(C)C)CC4)nc3c2C(C)C)cn2ncnc12] | 475.60 | 476.1 | 0.72 | QC-ACN-TFA-XB |
| 538 | 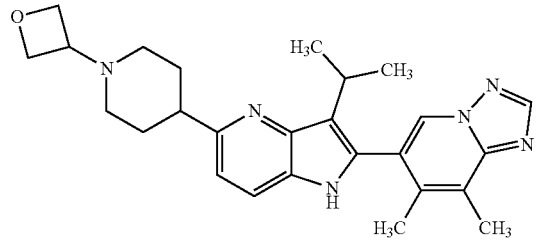 [SMILES: Cc1c(-c2[nH]c3ccc(C4CCN(C5COC5)CC4)nc3c2C(C)C)cn2ncnc2c1C] | 444.58 | 445.3 | 0.55 | B1 |
| 539 | 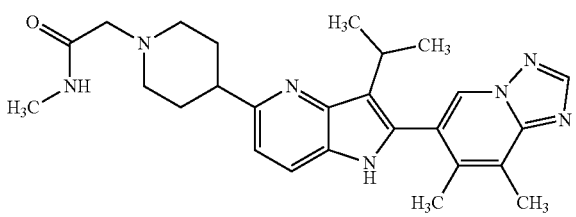 [SMILES: CNC(=O)CN1CCC(c2ccc3[nH]c(-c4cn5ncnc5c(C)c4C)c(C(C)C)c3n2)CC1] | 459.60 | 460.3 | 0.55 | B1 |
| 540 | 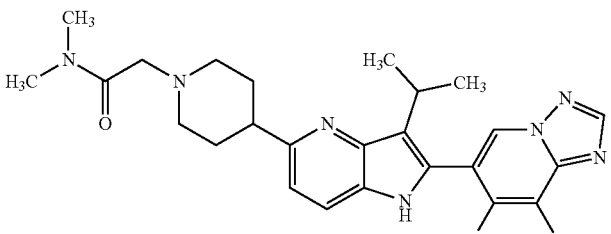 | 473.63 | 474.4 | 0.56 | B1 |

TABLE 1-continued

| Ex. No. | Structure | Mol. Wt. | LCMS M+ | Ret Time (min) | HPLC Method |
|---|---|---|---|---|---|
| 541 | 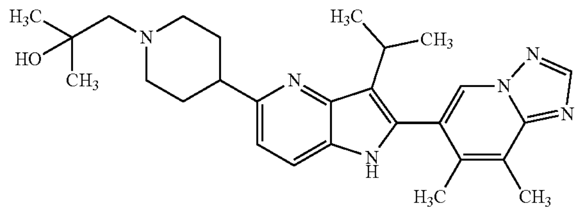 [SMILES: Cc1c(-c2[nH]c3ccc(C4CCN(CC(C)(C)O)CC4)nc3c2C(C)C)cn2ncnc2c1C] | 460.63 | 461.4 | 0.58 | B1 |
| 542 | 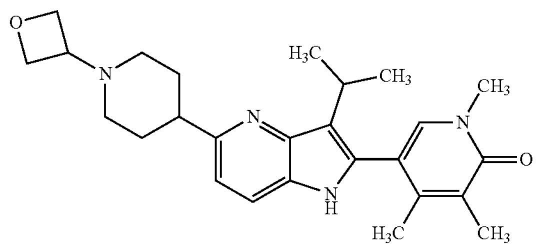 [SMILES: Cc1c(-c2[nH]c3ccc(C4CCN(C5COC5)CC4)nc3c2C(C)C)cn(C)c(=O)c1C] | 434.58 | 435.4 | 0.53 | B1 |
| 543 | 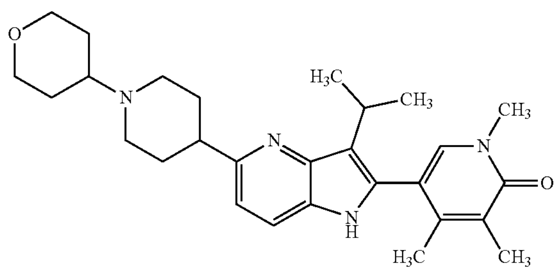 | 462.64 | 463.4 | 0.55 | B1 |
| 544 | 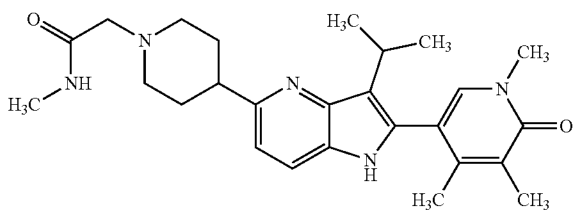 [SMILES: CNC(=O)CN1CCC(c2ccc3[nH]c(-c4cn(C)c(=O)c(C)c4C)c(C(C)C)c3n2)CC1] | 449.60 | 450.4 | 0.52 | B1 |
| 545 | 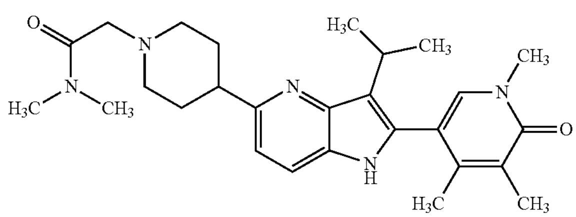 [SMILES: Cc1c(-c2[nH]c3ccc(C4CCN(CC(=O)N(C)C)CC4)nc3c2C(C)C)cn(C)c(=O)c1C] | 463.63 | 464.4 | 0.54 | B1 |
| 546 | 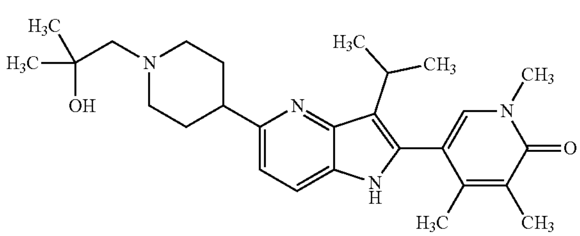 [SMILES: Cc1c(-c2[nH]c3ccc(C4CCN(CC(C)(C)O)CC4)nc3c2C(C)C)cn(C)c(=O)c1C] | 450.63 | 451.4 | 0.55 | B1 |

TABLE 1-continued
| Ex. No. | Structure | Mol. Wt. | LCMS M+ | Ret Time (min) | HPLC Method |
|---|---|---|---|---|---|
| 547 | 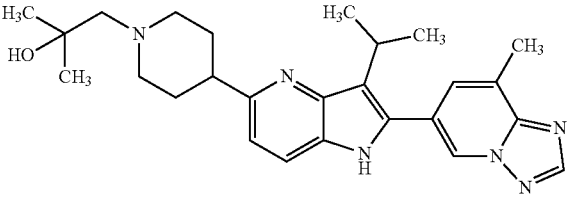 [SMILES: Cc1cc(-c2[nH]c3ccc(C4CCN(CC(C)(C)O)CC4)nc3c2C(C)C)cn2ncnc12] | 446.60 | 447.3 | 0.55 | B1 |
| 548 | 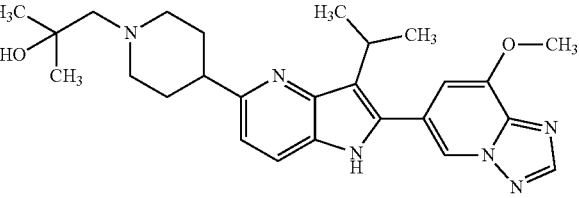 | 462.60 | 463.9 | 0.52 | B1 |
| 549 | 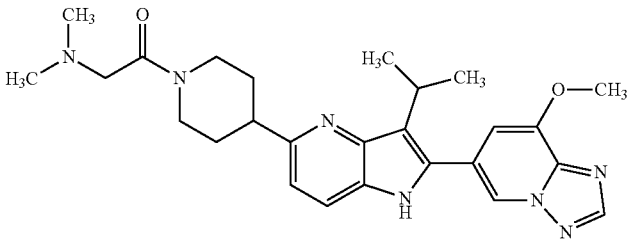 [SMILES: COc1cc(-c2[nH]c3ccc(C4CCN(C(=O)CN(C)C)CC4)nc3c2C(C)C)cn2ncnc12] | 475.60 | 476.4 | 1.15 | QC-ACN-AA-XB |
| 550 | 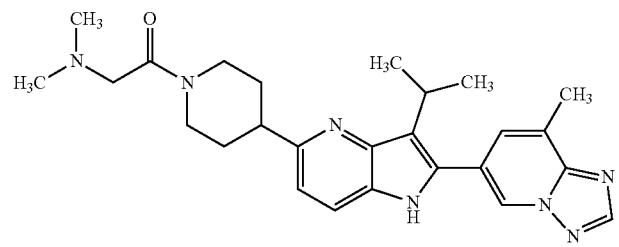 [SMILES: Cc1cc(-c2[nH]c3ccc(C4CCN(C(=O)CN(C)C)CC4)nc3c2C(C)C)cn2ncnc12] | 459.60 | 460 | 1.4 | QC-ACN-AA-XB |
| 551 | 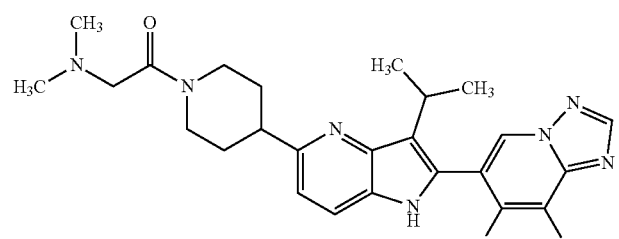 | 473.63 | 474 | 0.53 | B1 |
| 552 | 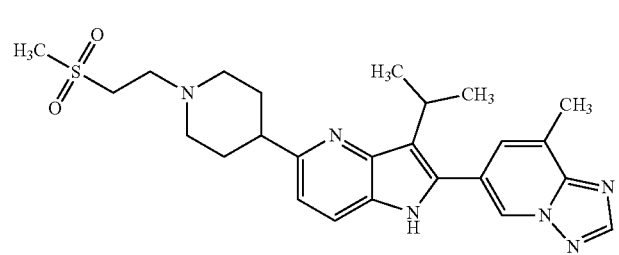 [SMILES: Cc1cc(-c2[nH]c3ccc(C4CCN(CCS(C)(=O)=O)CC4)nc3c2C(C)C)cn2ncnc12] | 480.63 | 481.3 | 0.53 | B1 |

TABLE 1-continued

| Ex. No. | Structure | Mol. Wt. | LCMS M+ | Ret Time (min) | HPLC Method |
|---|---|---|---|---|---|
| 553 | 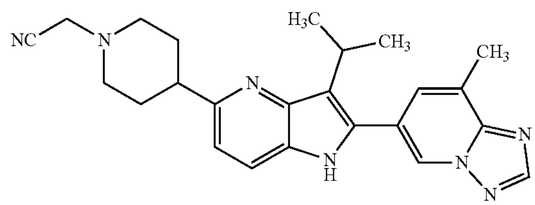 [SMILES: Cc1cc(-c2[nH]c3ccc(C4CCN(CC#N)CC4)nc3c2C(C)C)cn2ncnc12] | 413.53 | 414.3 | 0.63 | B1 |
| 554 | 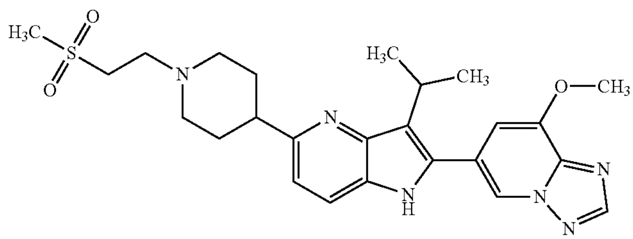 [SMILES: COc1cc(-c2[nH]c3ccc(C4CCN(CCS(C)(=O)=O)CC4)nc3c2C(C)C)cn2ncnc12] | 496.63 | 497.3 | 0.56 | B1 |
| 555 | 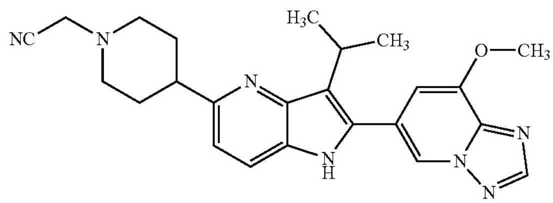 [SMILES: COc1cc(-c2[nH]c3ccc(C4CCN(CC#N)CC4)nc3c2C(C)C)cn2ncnc12] | 429.53 | 430.9 | 0.58 | B1 |
| 556 | 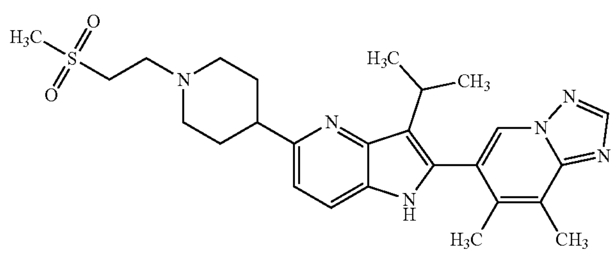 [SMILES: Cc1c(-c2[nH]c3ccc(C4CCN(CCS(C)(=O)=O)CC4)nc3c2C(C)C)cn2ncnc2c1C] | 494.66 | 495.3 | 0.6 | B1 |
| 557 | 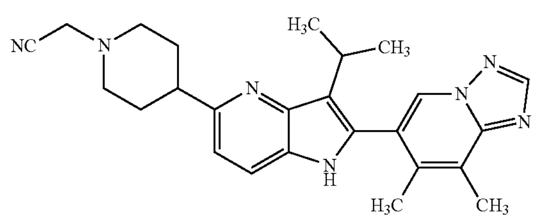 [SMILES: Cc1c(-c2[nH]c3ccc(C4CCN(CC#N)CC4)nc3c2C(C)C)cn2ncnc2c1C] | 427.56 | 428.3 | 0.66 | B1 |
| 558 | 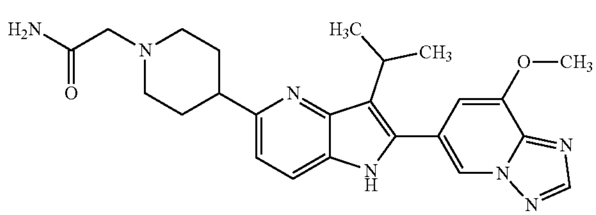 [SMILES: COc1cc(-c2[nH]c3ccc(C4CCN(CC(N)=O)CC4)nc3c2C(C)C)cn2ncnc12] | 447.54 | 448 | 1.12 | QC-ACN-AA-XB |
| 559 | 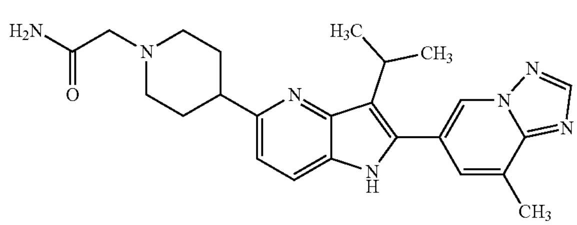 [SMILES: Cc1cc(-c2[nH]c3ccc(C4CCN(CC(N)=O)CC4)nc3c2C(C)C)cn2ncnc12] | 431.54 | 432.4 | 0.67 | QC-ACN-AA-XB |

TABLE 1-continued

| Ex. No. | Structure | Mol. Wt. | LCMS M+ | Ret Time (min) | HPLC Method |
|---|---|---|---|---|---|
| 560 | 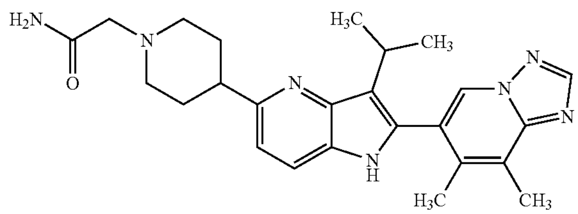 [SMILES: Cc1c(-c2[nH]c3ccc(C4CCN(CC(N)=O)CC4)nc3c2C(C)C)cn2ncnc2c1C] | 445.57 | 446 | 1.16 | QC-ACN-AA-XB |
| 561 | 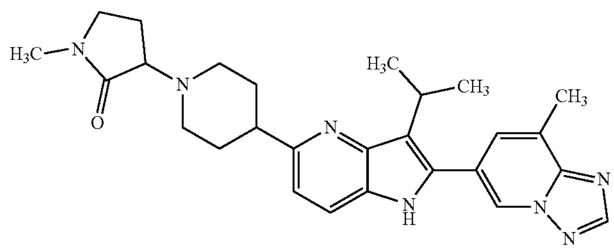 [SMILES: Cc1cc(-c2[nH]c3ccc(C4CCN(C5CCN(C)C5=O)CC4)nc3c2C(C)C)cn2ncnc12] | 471.61 | 471.9 | 0.53 | B1 |
| 562 | 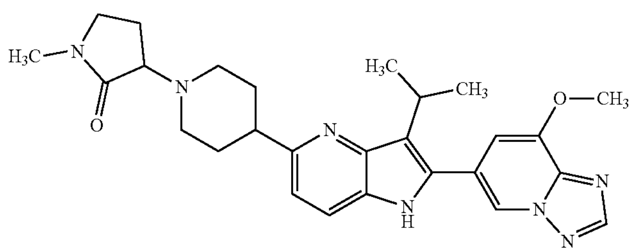 [SMILES: COc1cc(-c2[nH]c3ccc(C4CCN(C5CCN(C)C5=O)CC4)nc3c2C(C)C)cn2ncnc12] | 487.61 | 487.9 | 0.51 | B1 |
| 563 | 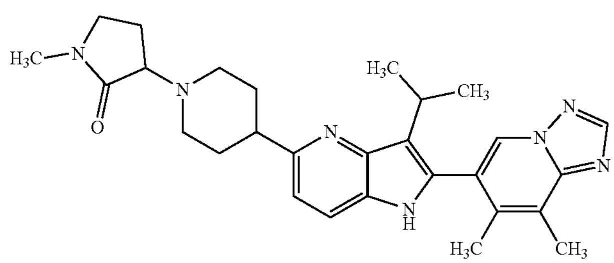 [SMILES: Cc1c(-c2[nH]c3ccc(C4CCN(C5CCN(C)C5=O)CC4)nc3c2C(C)C)cn2ncnc2c1C] | 485.64 | 485.9 | 0.52 | B1 |
| 564 | 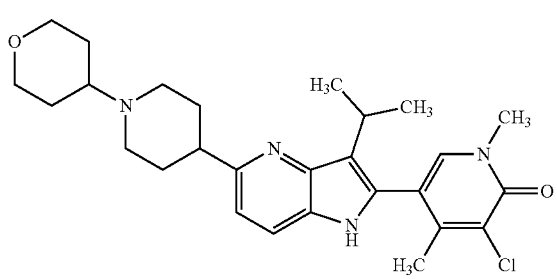 [SMILES: Cc1c(-c2[nH]c3ccc(C4CCN(C5CCOCC5)CC4)nc3c2C(C)C)cn(C)c(=O)c1Cl] | 483.05 | 471.9 | 0.53 | B1 |
| 565 | 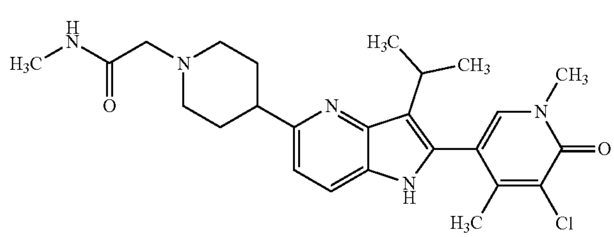 [SMILES: CNC(=O)CN1CCC(c2ccc3[nH]c(-c4cn(C)c(=O)c(Cl)c4C)c(C(C)C)c3n2)CC1] | 470.01 | 470.3 | 1.46 | QC-ACN-AA-XB |

TABLE 1-continued

| Ex. No. | Structure | Mol. Wt. | LCMS M+ | Ret Time (min) | HPLC Method |
|---|---|---|---|---|---|
| 566 | 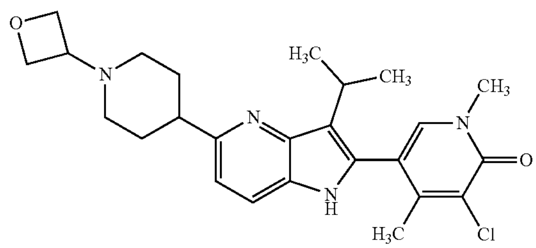 | 455.00 | 455.4 | 0.71 | QC-ACN-TFA-XB |
| 567 | 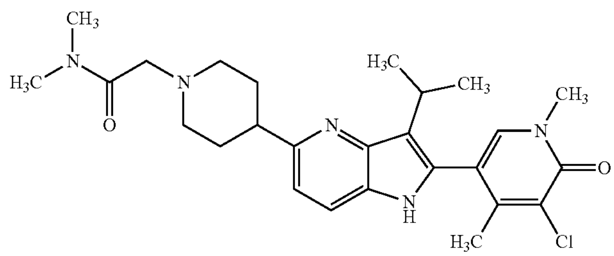 [SMILES: Cc1c(-c2[nH]c3ccc(C4CCN(CC(=O)N(C)C)CC4)nc3c2C(C)C)cn(C)c(=O)c1Cl] | 484.04 | 484.5 | 0.74 | QC-ACN-TFA-XB |
| 568 | 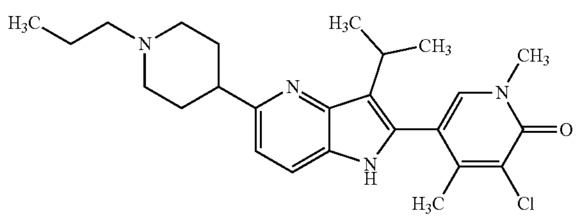 [SMILES: CCCN1CCC(c2ccc3[nH]c(-c4cn(C)c(=O)c(Cl)c4C)c(C(C)C)c3n2)CC1] | 441.02 | 441.1 | 1.39 | QC-ACN-AA-XB |
| 569 | 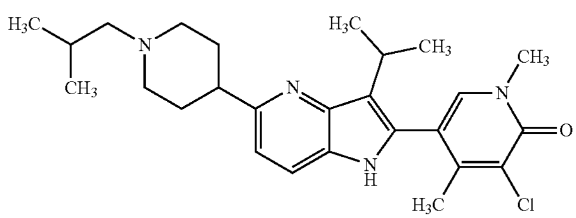 [SMILES: Cc1c(-c2[nH]c3ccc(C4CCN(CC(C)C)CC4)nc3c2C(C)C)cn(C)c(=O)c1Cl] | 455.04 | 455.15 | 0.84 | QC-ACN-TFA-XB |
| 570 | 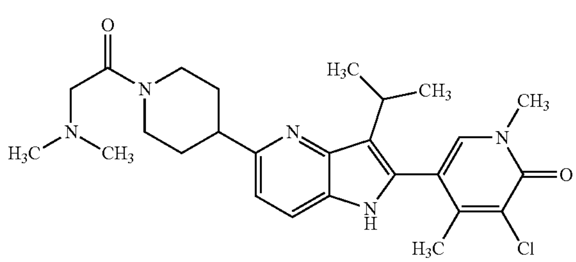 [SMILES: Cc1c(-c2[nH]c3ccc(C4CCN(C(=O)CN(C)C)CC4)nc3c2C(C)C)cn(C)c(=O)c1Cl] | 484.04 | 483.9 | 0.53 | B1 |
| 571 | 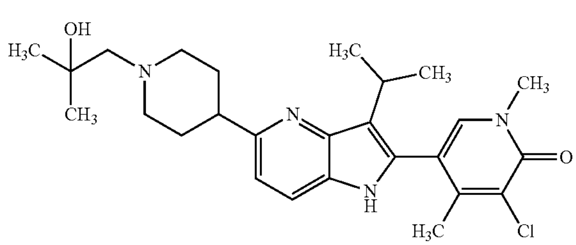 [SMILES: Cc1c(-c2[nH]c3ccc(C4CCN(CC(C)(C)O)CC4)nc3c2C(C)C)cn(C)c(=O)c1Cl] | 471.04 | 471.9 | 0.54 | B1 |

TABLE 1-continued

| Ex. No. | Structure | Mol. Wt. | LCMS M+ | Ret Time (min) | HPLC Method |
|---|---|---|---|---|---|
| 572 | 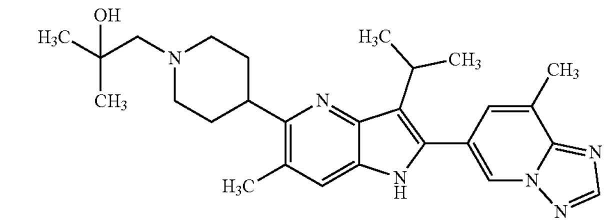 [SMILES: Cc1cc2[nH]c(-c3cc(C)c4ncnn4c3)c(C(C)C)c2nc1C1CCN(CC(C)(C)O)CC1] | 460.63 | 461.2 | 1.6 | E |
| 573 | 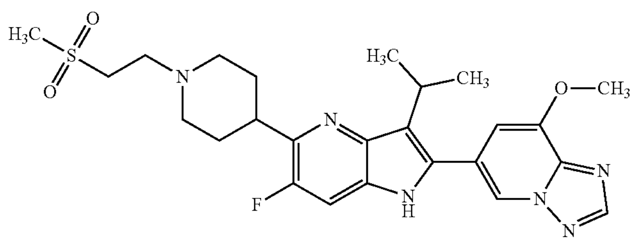 | 514.62 | 515.2 | 2.14 | E |
| 574 | 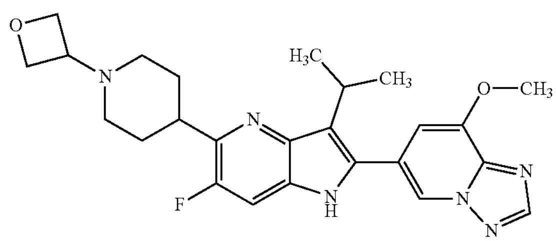 | 464.55 | 465.2 | 1.66 | E |
| 575 | 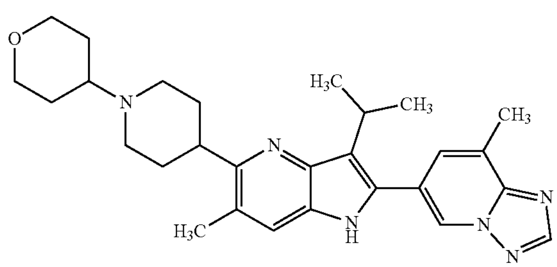 | 472.64 | 473.2 | 1.5 | E |
| 576 | 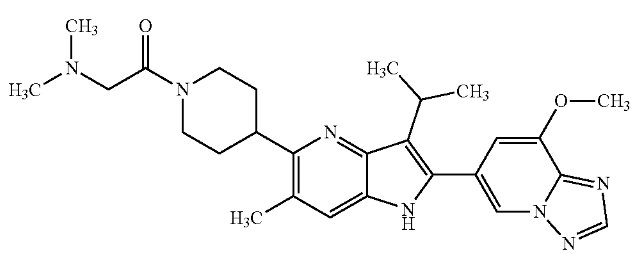 [SMILES: COc1cc(-c2[nH]c3cc(C)c(C4CCN(C(=O)CN(C)C)CC4)nc3c2C(C)C)cn2ncnc12] | 489.62 | 490.2 | 1.52 | E |
| 577 | 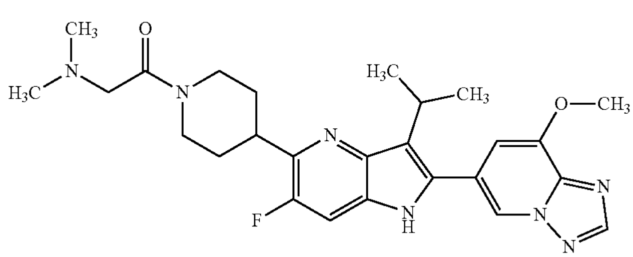 [SMILES: COc1cc(-c2[nH]c3cc(F)c(C4CCN(C(=O)CN(C)C)CC4)nc3c2C(C)C)cn2ncnc12] | 493.59 | 494.1 | 1.85 | E |

TABLE 1-continued

| Ex. No. | Structure | Mol. Wt. | LCMS M+ | Ret Time (min) | HPLC Method |
|---|---|---|---|---|---|
| 578 | 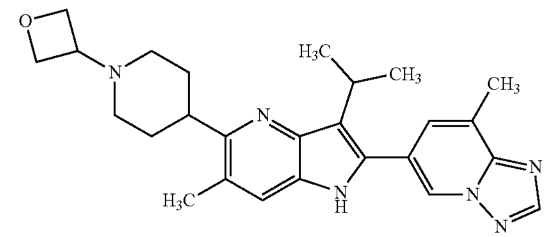 | 444.58 | 445.2 | 1.94 | E |
| 579 | 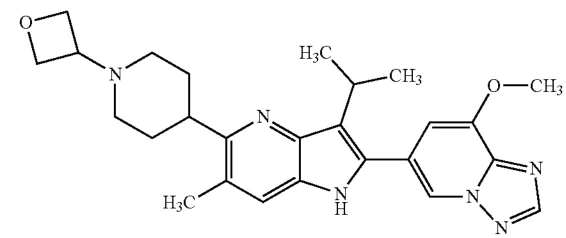 | 460.58 | 461.2 | 1.88 | E |
| 580 | 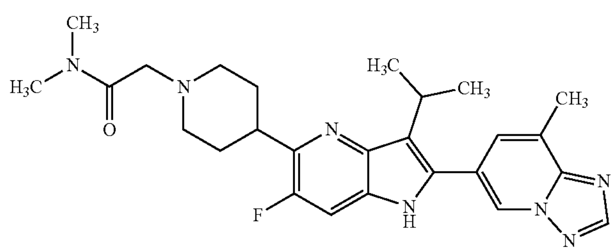 [SMILES: Cc1cc(-c2[nH]c3cc(F)c(C4CCN(CC(=O)N(C)C)CC4)nc3c2C(C)C)cn2ncnc12] | 477.59 | 478.3 | 1.4 | E |
| 581 | 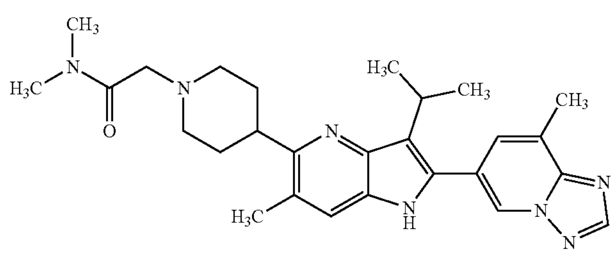 [SMILES: Cc1cc2[nH]c(-c3cc(C)c4ncnn4c3)c(C(C)C)c2nc1C1CCN(CC(=O)N(C)C)CC1] | 473.63 | 474.2 | 1.54 | E |
| 582 | 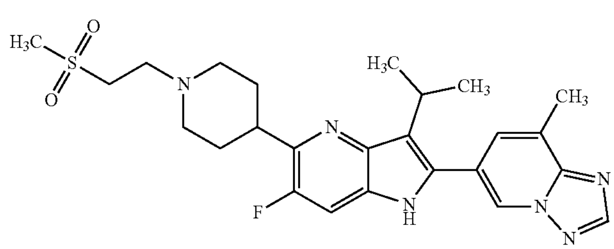 | 498.62 | 499.3 | 1.63 | E |
| 583 | 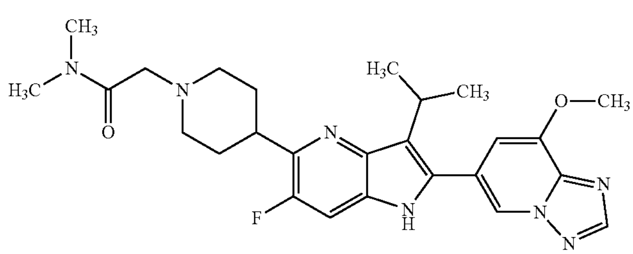 [SMILES: COc1cc(-c2[nH]c3cc(F)c(C4CCN(CC(=O)N(C)C)CC4)nc3c2C(C)C)cn2ncnc12] | 493.59 | 494.3 | 1.36 | E |

TABLE 1-continued

| Ex. No. | Structure | Mol. Wt. | LCMS M+ | Ret Time (min) | HPLC Method |
|---|---|---|---|---|---|
| 584 | 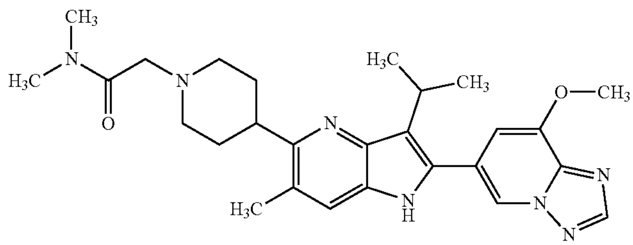 [SMILES: COc1cc(-c2[nH]c3cc(C)c(C4CCN(CC(=O)N(C)C)CC4)nc3c2C(C)C)cn2ncnc12] | 489.62 | 490.2 | 1.5 | E |
| 585 | 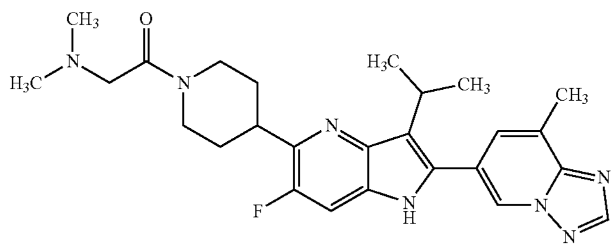 [SMILES: Cc1cc(-c2[nH]c3cc(F)c(C4CCN(C(=O)CN(C)C)CC4)nc3c2C(C)C)cn2ncnc12] | 477.59 | 478.2 | 1.89 | E |
| 586 | 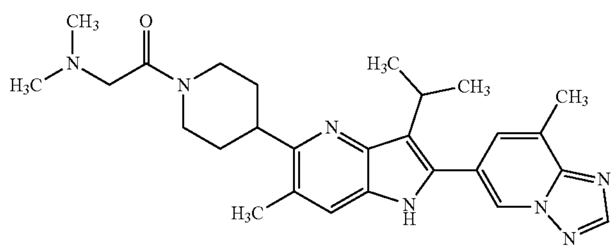 [SMILES: Cc1cc2[nH]c(-c3cc(C)c4ncnn4c3)c(C(C)C)c2nc1C1CCN(C(=O)CN(C)C)CC1] | 473.63 | 474.2 | 1.55 | E |
| 587 | 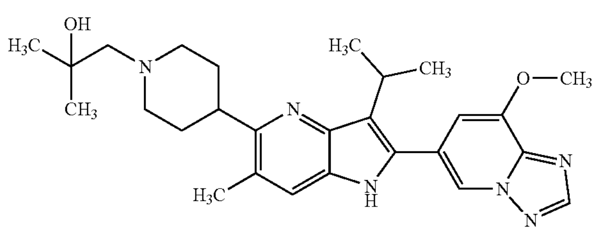 [SMILES: COc1cc(-c2[nH]c3cc(C)c(C4CCN(CC(C)(C)O)CC4)nc3c2C(C)C)cn2ncnc12] | 476.63 | 477.2 | 1.56 | E |
| 588 | 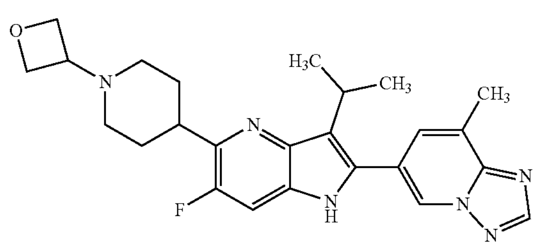 [SMILES: Cc1cc(-c2[nH]c3cc(F)c(C4CCN(C5COC5)CC4)nc3c2C(C)C)cn2ncnc12] | 448.55 | 449.3 | 1.71 | E |
| 589 | 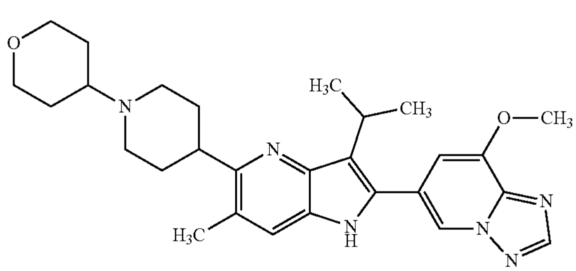 [SMILES: COc1cc(-c2[nH]c3cc(C)c(C4CCN(C5CCOCC5)CC4)nc3c2C(C)C)cn2ncnc12] | 488.64 | 489.2 | 1.46 | E |

TABLE 1-continued

| Ex. No. | Structure | Mol. Wt. | LCMS M+ | Ret Time (min) | HPLC Method |
|---|---|---|---|---|---|
| 590 | 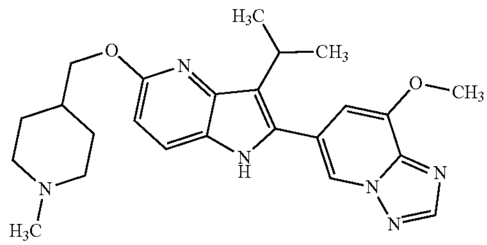 [SMILES: COc1cc(-c2[nH]c3ccc(OCC4CCN(C)CC4)nc3c2C(C)C)cn2ncnc12] | 434.54 | 435.4 | 0.94 | QC-ACN-TFA-XB |
| 591 | 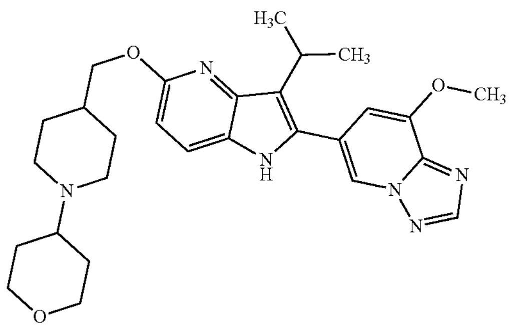 [SMILES: COc1cc(-c2[nH]c3ccc(OCC4CCN(C5CCOCC5)CC4)nc3c2C(C)C)cn2ncnc12] | 504.64 | 505.5 | 1.23 | QC-ACN-AA-XB |
| 592 | 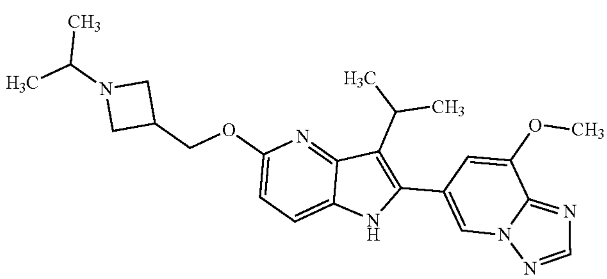 [SMILES: COc1cc(-c2[nH]c3ccc(OCC4CN(C(C)C)C4)nc3c2C(C)C)cn2ncnc12] | 434.54 | 435.2 | 1.08 | QC-ACN-TFA-XB |
| 593 | 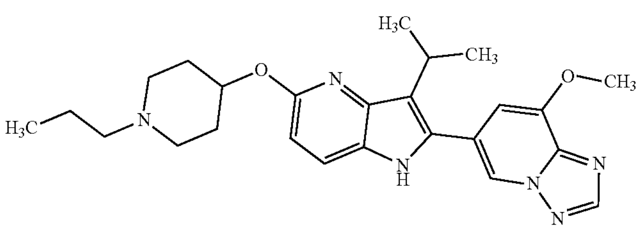 | 448.57 | 448.9 | 1.3 | QC-ACN-AA-XB |
| 594 | 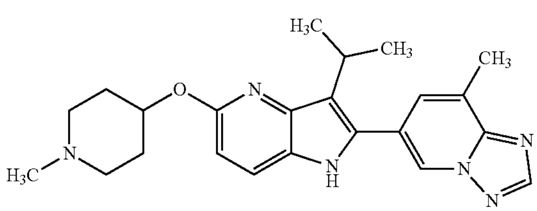 [SMILES: Cc1cc(-c2[nH]c3ccc(OC4CCN(C)CC4)nc3c2C(C)C)cn2ncnc12] | 404.52 | 405.4 | 1.01 | QC-ACN-TFA-XB |
| 595 | 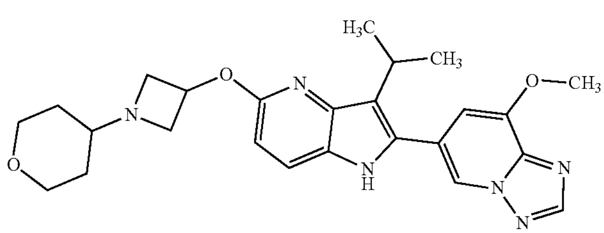 [SMILES: COc1cc(-c2[nH]c3ccc(OC4CN(C5CCOCC5)C4)nc3c2C(C)C)cn2ncnc12] | 462.55 | 463.3 | 1.31 | QC-ACN-AA-XB |

TABLE 1-continued

| Ex. No. | Structure | Mol. Wt. | LCMS M+ | Ret Time (min) | HPLC Method |
|---|---|---|---|---|---|
| 596 | 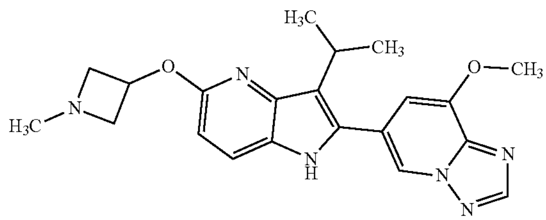 | 392.46 | 393.2 | 1 | QC-ACN-TFA-XB |
| 597 | 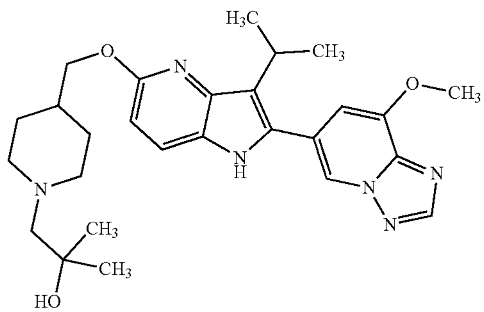 | 492.62 | 493.6 | 1.28 | QC-ACN-AA-XB |
| 598 | 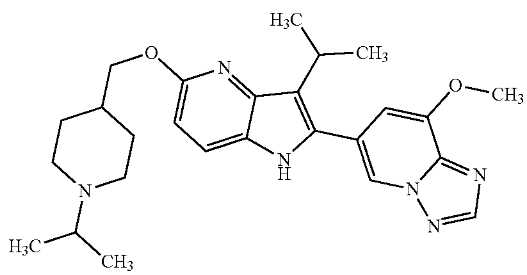 | 462.60 | 463 | 1.22 | QC-ACN-TFA-XB |
| 599 | 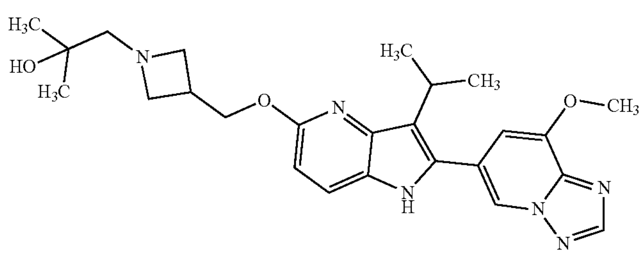 | 464.57 | 465.2 | 1.11 | QC-ACN-TFA-XB |
| 600 | 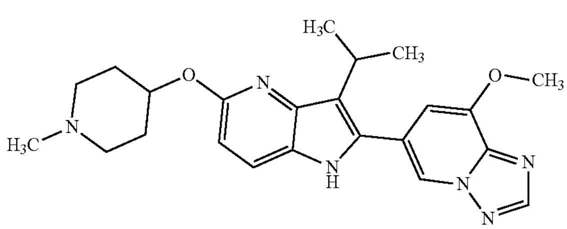 | 420.52 | 421.2 | 1.17 | QC-ACN-AA-XB |
| 601 | 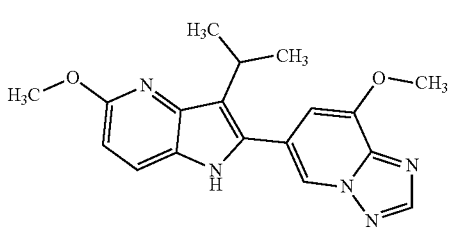 | 337.38 | 338 | 0.77 | B1 |

TABLE 1-continued

| Ex. No. | Structure | Mol. Wt. | LCMS M+ | Ret Time (min) | HPLC Method |
|---|---|---|---|---|---|
| 602 | 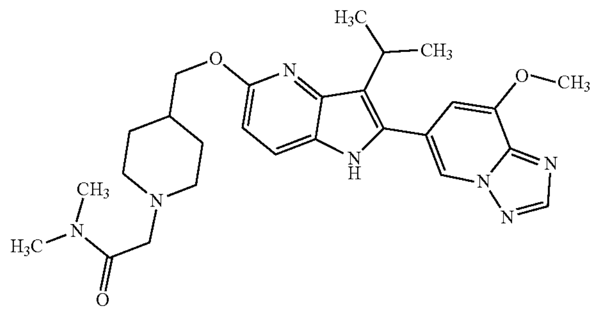 | 505.62 | 506.2 | 1.01 | QC-ACN-TFA-XB |
| 603 | 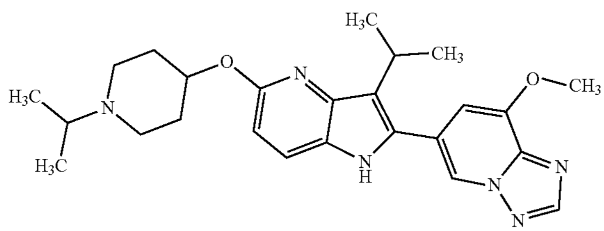 [SMILES: COc1cc(-c2[nH]c3ccc(OC4CCN(C(C)C)CC4)nc3c2C(C)C)cn2ncnc12] | 448.57 | 449 | 1.22 | QC-ACN-AA-XB |
| 604 | 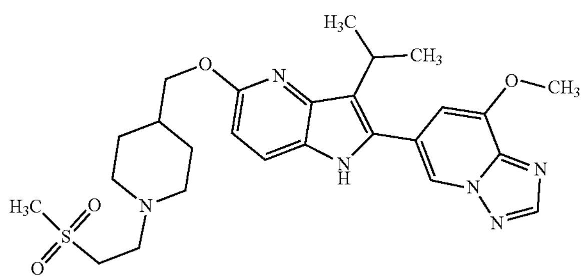 | 526.66 | 527.5 | 0.98 | QC-ACN-TFA-XB |
| 605 | 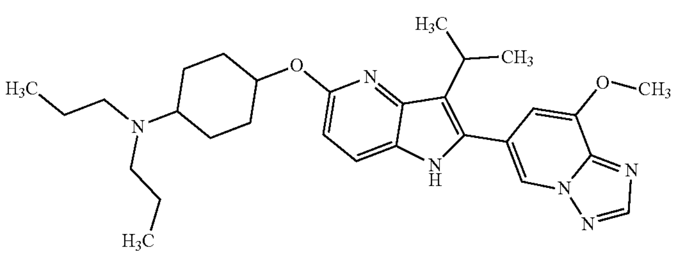 [SMILES: CCCN(CCC)C1CCC(Oc2ccc3[nH]c(-c4cc(OC)c5ncnn5c4)c(C(C)C)c3n2)CC1] | 504.68 | 505.5 | 1.51 | QC-ACN-AA-XB |
| 606 | 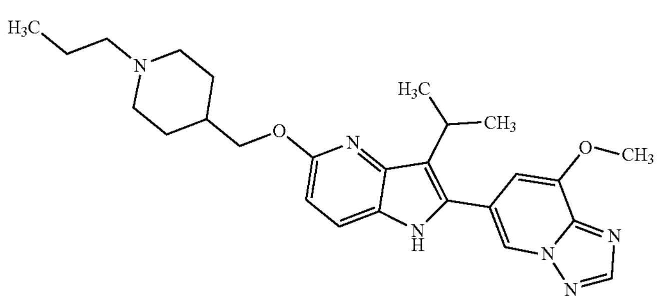 [SMILES: CCCN1CCC(COc2ccc3[nH]c(-c4cc(OC)c5ncnn5c4)c(C(C)C)c3n2)CC1] | 462.60 | 462.9 | 1.51 | QC-ACN-AA-XB |

TABLE 1-continued

| Ex. No. | Structure | Mol. Wt. | LCMS M+ | Ret Time (min) | HPLC Method |
|---|---|---|---|---|---|
| 607 | 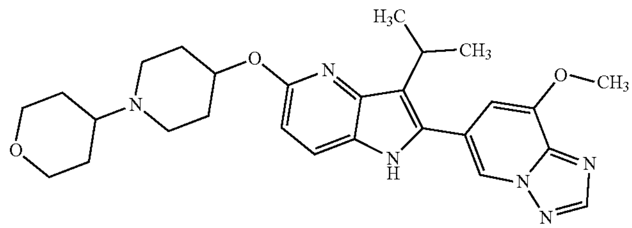 [SMILES: COc1cc(-c2[nH]c3ccc(OC4CCN(C5CCOCC5)CC4)nc3c2C(C)C)cn2ncnc12] | 490.61 | 491.2 | 1.33 | QC-ACN-AA-XB |
| 608 | 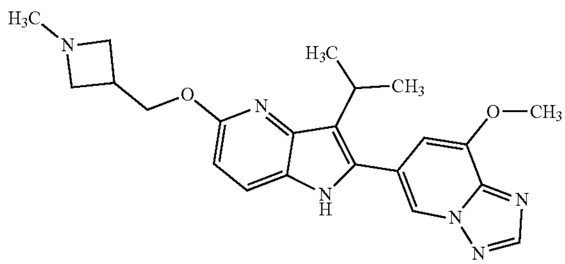 | 406.49 | 407.3 | 0.96 | QC-ACN-TFA-XB |
| 609 | 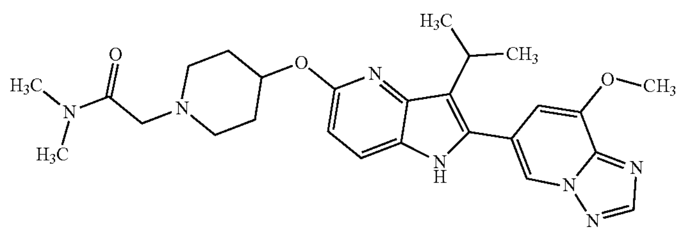 | 491.60 | 492 | 1.28 | QC-ACN-AA-XB |
| 610 | 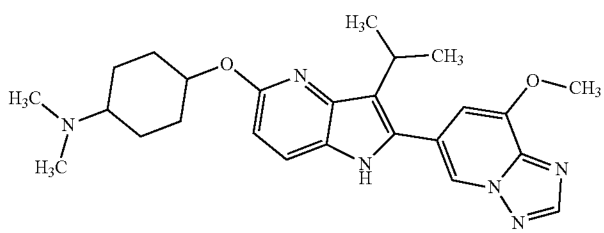 | 448.57 | 449.4 | 1.11 | QC-ACN-AA-XB |
| 611 | 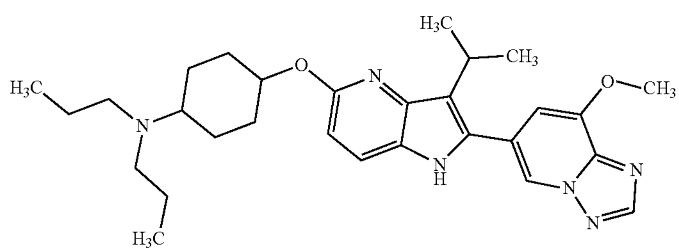 [SMILES: CCCN(CCC)C1CCC(Oc2ccc3[nH]c(-c4cc(OC)c5ncnn5c4)c(C(C)C)c3n2)CC1] | 504.68 | 505.5 | 1.3 | QC-ACN-TFA-XB |
| 612 | 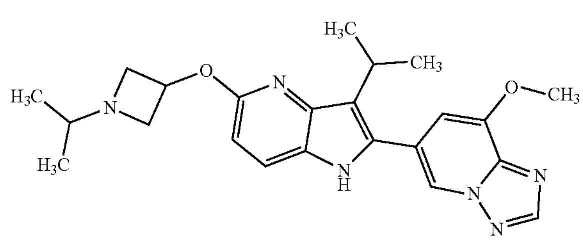 [SMILES: COc1cc(-c2[nH]c3ccc(OC4CN(C(C)C)C4)nc3c2C(C)C)cn2ncnc12] | 420.52 | 421 | 1.4 | QC-ACN-AA-XB |

TABLE 1-continued
| Ex. No. | Structure | Mol. Wt. | LCMS M+ | Ret Time (min) | HPLC Method |
|---|---|---|---|---|---|
| 613 | 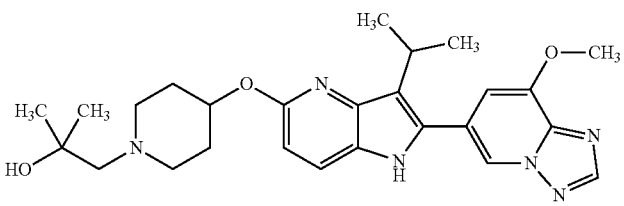 [SMILES: COc1cc(-c2[nH]c3ccc(OC4CCN(CC(C)(C)O)CC4)nc3c2C(C)C)cn2ncnc12] | 478.60 | 479.2 | 1.2 | QC-ACN-AA-XB |
| 614 | 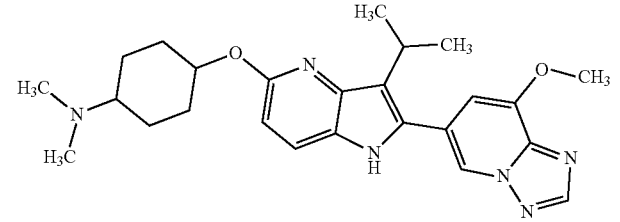 | 448.57 | 449.4 | 0.99 | QC-ACN-TFA-XB |
| 615 | 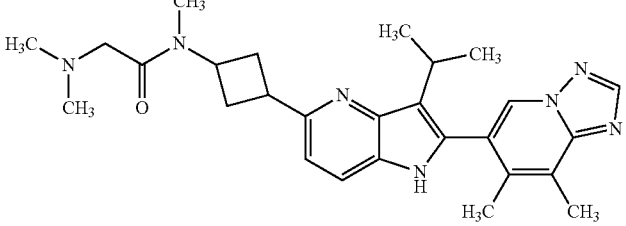 | 473.63 | 474.25 | 1.31 | QC-ACN-AA-XB |
| 616 | 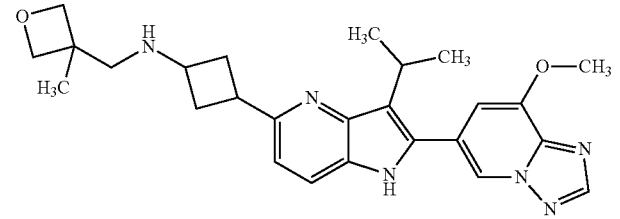 [SMILES: COc1cc(-c2[nH]c3ccc(C4CC(NCC5(C)COC5)C4)nc3c2C(C)C)cn2ncnc12] | 460.58 | 461.3 | 1.38 | QC-ACN-AA-XB |
| 617 | 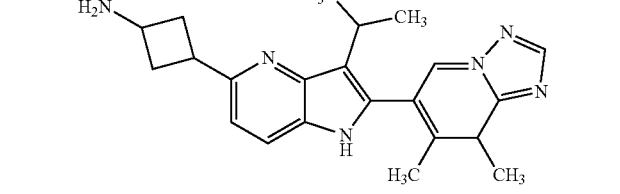 | 374.49 | 375 | 0.7 | QC-ACN-TFA-XB |
| 618 | 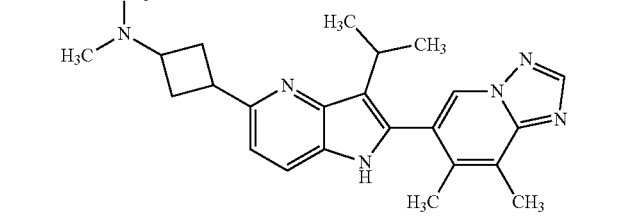 | 402.55 | 403.2 | 0.99 | QC-ACN-TFA-XB |

TABLE 1-continued
| Ex. No. | Structure | Mol. Wt. | LCMS M+ | Ret Time (min) | HPLC Method |
|---|---|---|---|---|---|
| 619 | 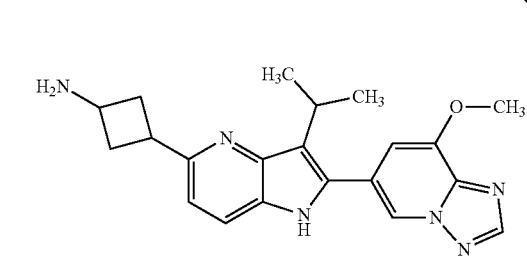 | 461.57 | 462.2 | 1.24 | QC-ACN-AA-XB |
| 620 | 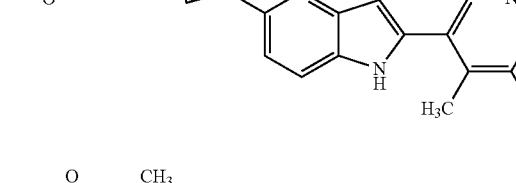 | 376.46 | 377.4 | 0.96 | QC-ACN-AA-XB |
| 621 | 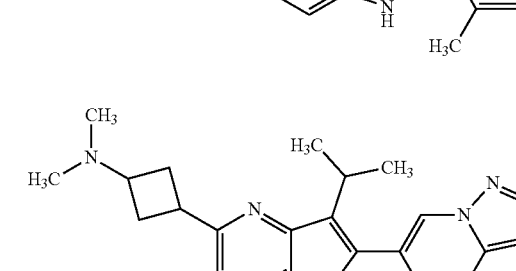 | 494.66 | 495.2 | 0.77 | QC-ACN-TFA-XB |
| 622 | 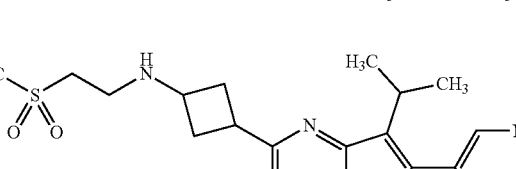 | 473.63 | 474.1 | 0.98 | QC-ACN-TFA-XB |
| 623 | 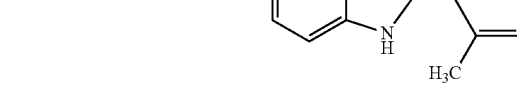 | 402.55 | 402.9 | 0.72 | QC-ACN-TFA-XB |
| 624 | 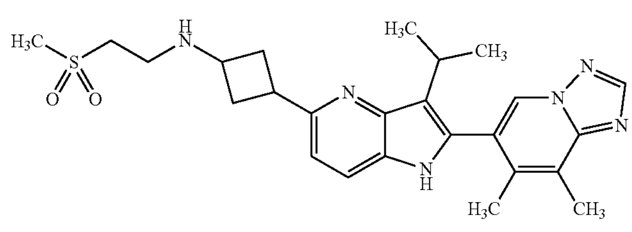 [SMILES: Cc1c(-c2[nH]c3ccc(C4CC(NCCS(C)(=O)=O)C4)nc3c2C(C)C)cn2ncnc2c1C] | 480.63 | 481.4 | 1.19 | QC-ACN-AA-XB |

TABLE 1-continued

| Ex. No. | Structure | Mol. Wt. | LCMS M+ | Ret Time (min) | HPLC Method |
|---|---|---|---|---|---|
| 625 | 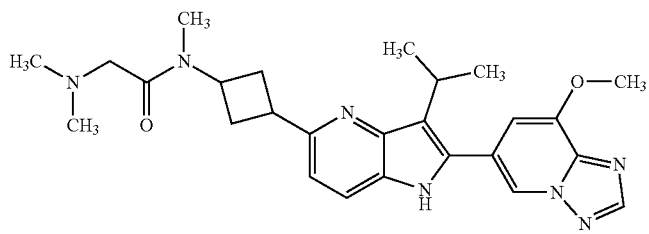 | 475.60 | 476.3 | 1.22 | QC-ACN-AA-XB |
| 626 | 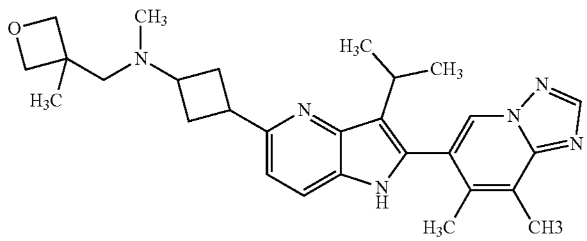 [SMILES: Cc1c(-c2[nH]c3ccc(C4CC(N(C)CC5(C)COC5)C4)nc3c2C(C)C)cn2ncnc2c1C] | 472.64 | 473.2 | 0.78 | QC-ACN-TFA-XB |
| 627 | 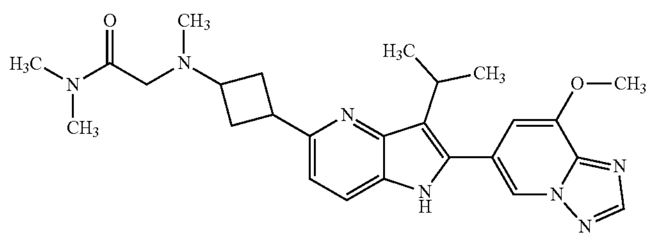 [SMILES: COc1cc(-c2[nH]c3ccc(C4CC(N(C)CC(=O)N(C)C)C4)nc3c2C(C)C)cn2ncnc12] | 475.60 | 476.2 | 0.73 | QC-ACN-TFA-XB |
| 628 | 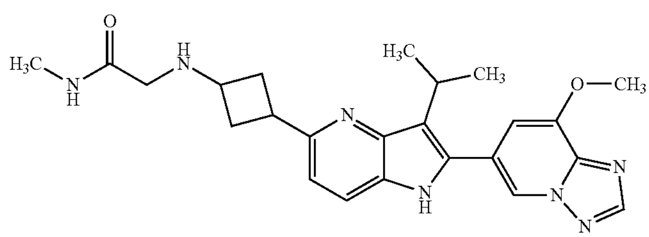 [SMILES: CNC(=O)CNC1CC(c2ccc3[nH]c(-c4cc(OC)c5ncnn5c4)c(C(C)C)c3n2)C1] | 447.54 | 448.2 | 0.67 | QC-ACN-TFA-XB |
| 629 | 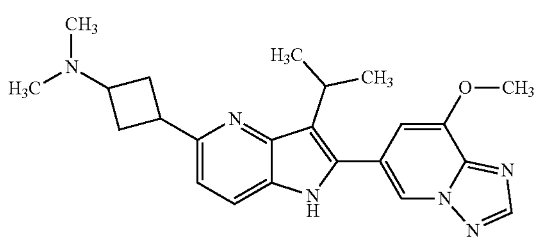 | 404.52 | 405 | 1.1 | QC-ACN-AA-XB |
| 630 | 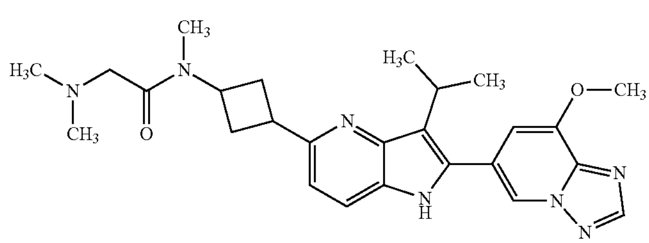 | 475.60 | 476.4 | 0.74 | QC-ACN-TFA-XB |

| Ex. No. | Structure | Mol. Wt. | LCMS M+ | Ret Time (min) | HPLC Method |
|---|---|---|---|---|---|
| 631 | 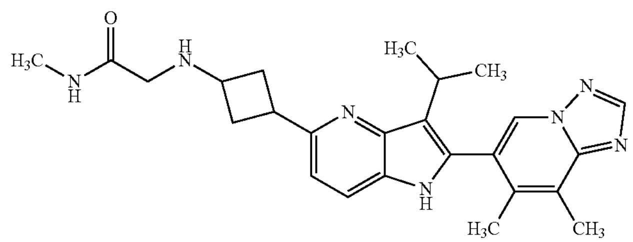 [SMILES: CNC(=O)CNC1CC(c2ccc3[nH]c(-c4cn5ncnc5c(C)c4C)c(C(C)C)c3n2)C1] | 445.57 | 446.2 | 1.19 | QC-ACN-AA-XB |
| 632 | 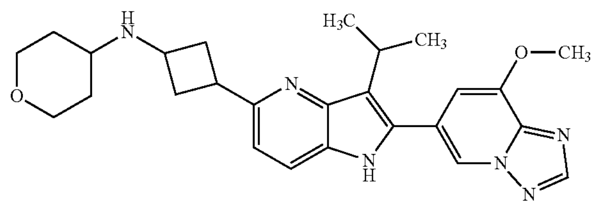 [SMILES: COc1cc(-c2[nH]c3ccc(C4CC(NC5CCOCC5)C4)nc3c2C(C)C)cn2ncnc12] | 460.58 | 461.2 | 1.19 | QC-ACN-AA-XB |
| 633 | 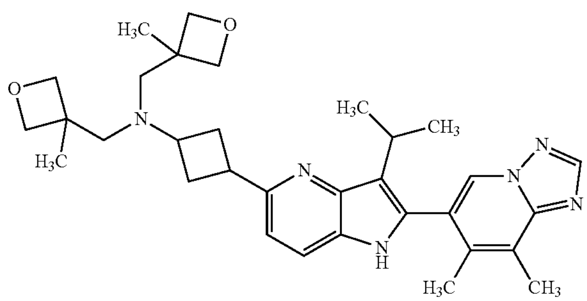 [SMILES: Cc1c(-c2[nH]c3ccc(C4CC(N(CC5(C)COC5)CC5(C)COC5)C4)nc3c2C(C)C)cn2ncnc2c1C] | 542.73 | 543.3 | 1.04 | QC-ACN-TFA-XB |
| 634 | 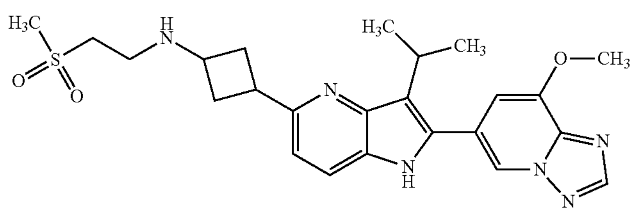 [SMILES: COc1cc(-c2[nH]c3ccc(C4CC(NCCS(C)(=O)=O)C4)nc3c2C(C)C)cn2ncnc12] | 482.60 | 483 | 1.22 | QC-ACN-AA-XB |
| 635 | 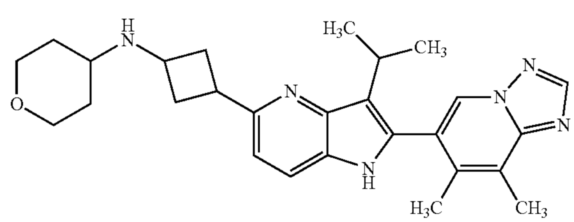 [SMILES: Cc1c(-c2[nH]c3ccc(C4CC(NC5CCOCC5)C4)nc3c2C(C)C)cn2ncnc2c1C] | 458.61 | 459.22 | 1.23 | QC-ACN-AA-XB |
| 636 | 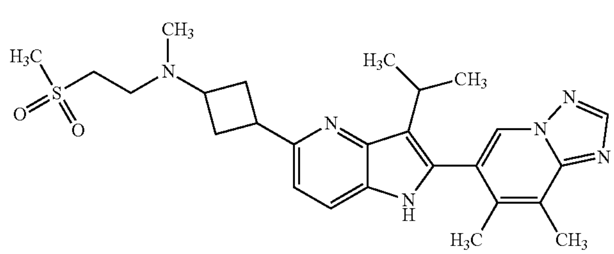 [SMILES: Cc1c(-c2[nH]c3ccc(C4CC(N(C)CCS(C)(=O)=O)C4)nc3c2C(C)C)cn2ncnc2c1C] | 494.66 | 495.2 | 1.54 | QC-ACN-AA-XB |

TABLE 1-continued

| Ex. No. | Structure | Mol. Wt. | LCMS M+ | Ret Time (min) | HPLC Method |
|---|---|---|---|---|---|
| 637 | 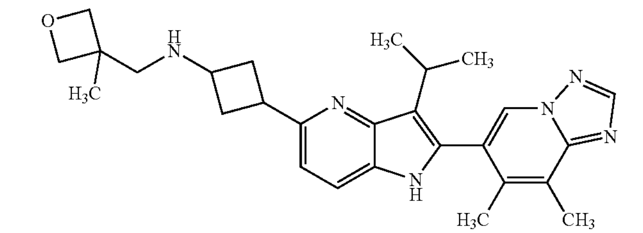 [SMILES: Cc1c(-c2[nH]c3ccc(C4CC(NCC5(C)COC5)C4)nc3c2C(C)C)cn2ncnc2c1C] | 458.61 | 459.1 | 1.43 | QC-ACN-AA-XB |
| 638 | 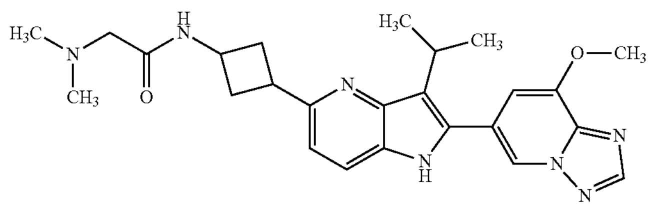 [SMILES: COc1cc(-c2[nH]c3ccc(C4CC(NC(=O)CN(C)C)C4)nc3c2C(C)C)cn2ncnc12] | 461.57 | 462.4 | 0.74 | QC-ACN-TFA-XB |
| 639 | 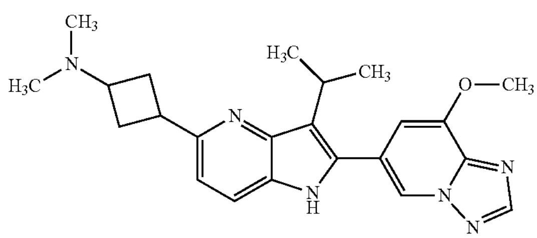 [SMILES: COc1cc(-c2[nH]c3ccc(C4CC(N(C)C)C4)nc3c2C(C)C)cn2ncnc12] | 404.52 | 405 | 1.12 | QC-ACN-AA-XB |
| 640 | 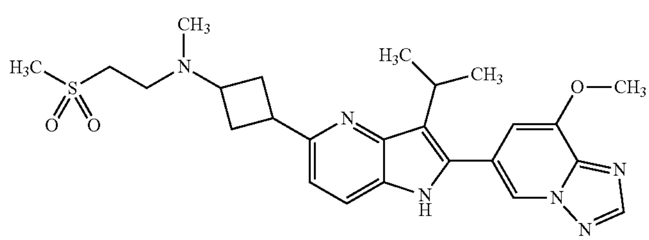 [SMILES: COc1cc(-c2[nH]c3ccc(C4CC(N(C)CCS(C)(=O)=O)C4)nc3c2C(C)C)cn2ncnc12] | 496.63 | 497.1 | 1.42 | QC-ACN-AA-XB |
| 641 | 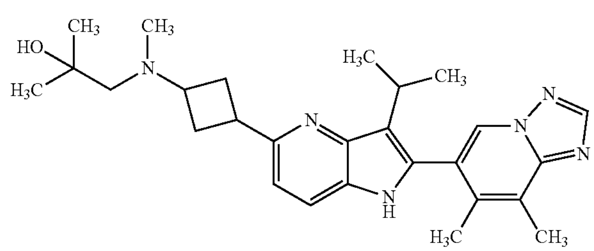 [SMILES: Cc1c(-c2[nH]c3ccc(C4CC(N(C)CC(C)(C)O)C4)nc3c2C(C)C)cn2ncnc2c1C] | 460.63 | 461.1 | 0.78 | QC-ACN-AA-XB |
| 642 | 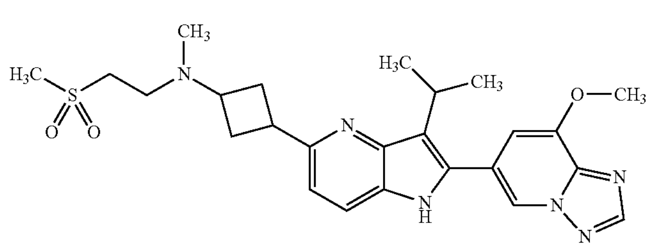 [SMILES: COc1cc(-c2[nH]c3ccc(C4CC(N(C)CCS(C)(=O)=O)C4)nc3c2C(C)C)cn2ncnc12] | 496.63 | 497.1 | 1.47 | QC-ACN-AA-XB |

TABLE 1-continued

| Ex. No. | Structure | Mol. Wt. | LCMS M+ | Ret Time (min) | HPLC Method |
|---|---|---|---|---|---|
| 643 | 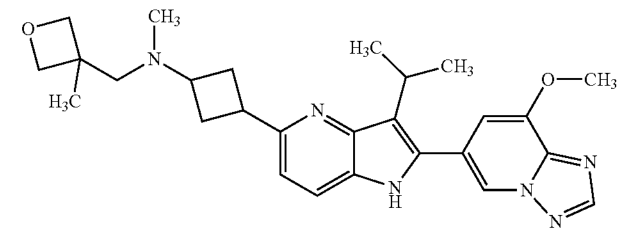 [SMILES: COc1cc(-c2[nH]c3ccc(C4CC(N(C)CC5(C)COC5)C4)nc3c2C(C)C)cn2ncnc12] | 474.61 | 475.3 | 0.71 | QC-ACN-TFA-XB |
| 644 | 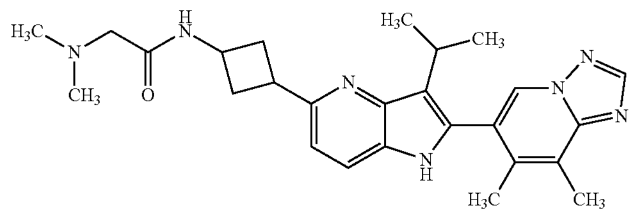 [SMILES: Cc1c(-c2[nH]c3ccc(C4CC(NC(=O)CN(C)C)C4)nc3c2C(C)C)cn2ncnc2c1C] | 459.60 | 460.5 | 1.2 | QC-ACN-AA-XB |
| 645 | 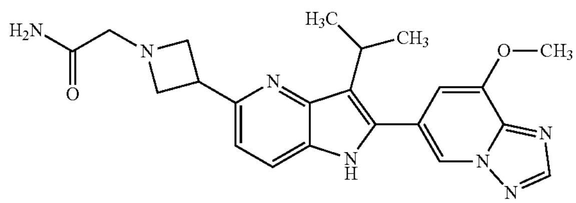 [SMILES: COc1cc(-c2[nH]c3ccc(C4CN(CC(N)=O)C4)nc3c2C(C)C)cn2ncnc12] | 419.49 | 420.3 | 0.93 | QC-ACN-AA-XB |
| 646 | 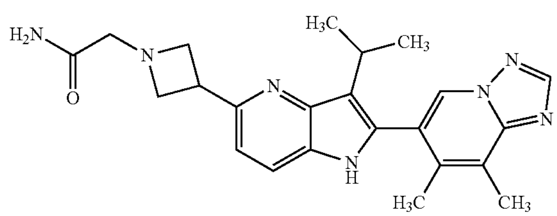 [SMILES: Cc1c(-c2[nH]c3ccc(C4CN(CC(N)=O)C4)nc3c2C(C)C)cn2ncnc2c1C] | 417.52 | 418.4 | 0.96 | QC-ACN-AA-XB |
| 647 | 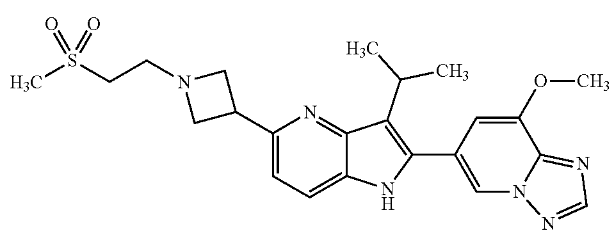 [SMILES: COc1cc(-c2[nH]c3ccc(C4CN(CCS(C)(=O)=O)C4)nc3c2C(C)C)cn2ncnc12] | 468.58 | 469.4 | 0.78 | QC-ACN-TFA-XB |
| 648 | 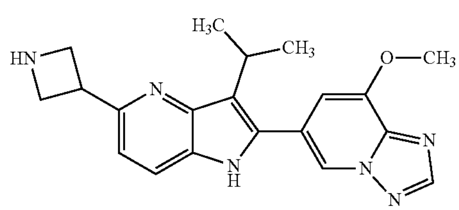 [SMILES: COc1cc(-c2[nH]c3ccc(C4CNC4)nc3c2C(C)C)cn2ncnc12] | 362.44 | 363.3 | 0.65 | QC-ACN-TFA-XB |
| 649 | 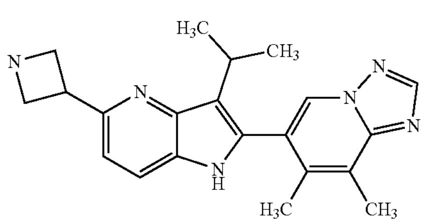 [SMILES: Cc1c(-c2[nH]c3ccc(C4CNC4)nc3c2C(C)C)cn2ncnc2c1C] | 360.47 | 361.3 | 0.69 | QC-ACN-TFA-XB |

TABLE 1-continued
| Ex. No. | Structure | Mol. Wt. | LCMS M+ | Ret Time (min) | HPLC Method |
|---|---|---|---|---|---|
| 650 | 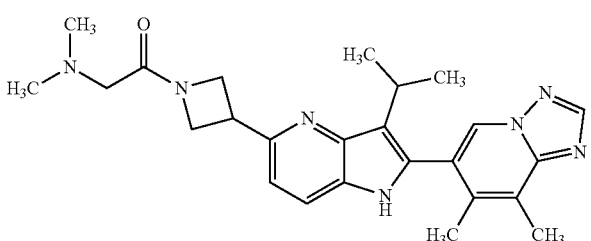 | 445.57 | 446 | 0.98 | QC-ACN-TFA-XB |
| 651 | 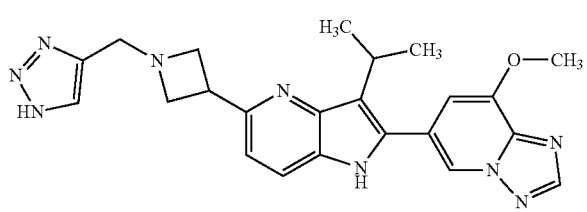 [SMILES: COc1cc(-c2[nH]c3ccc(C4CN(Cc5c[nH]nn5)C4)nc3c2C(C)C)cn2ncnc12] | 443.52 | 444.4 | 0.74 | QC-ACN-TFA-XB |
| 652 | 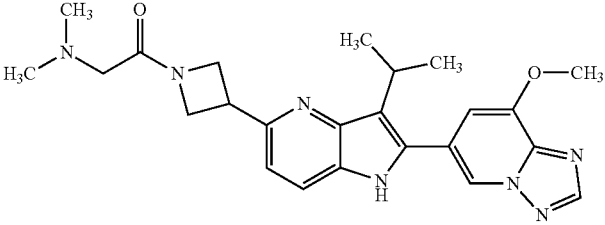 [SMILES: COc1cc(-c2[nH]c3ccc(C4CN(C(=O)CN(C)C)C4)nc3c2C(C)C)cn2ncnc12] | 447.54 | 448.4 | 0.68 | QC-ACN-TFA-XB |
| 653 | 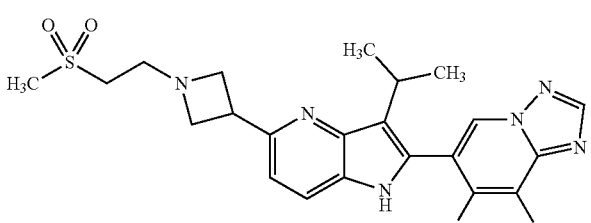 | 466.60 | 467.4 | 0.8 | QC-ACN-TFA-XB |
| 654 | 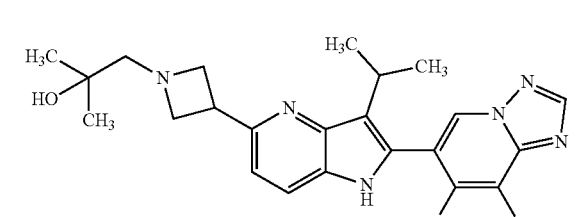 | 432.57 | 433.4 | 0.84 | QC-ACN-TFA-XB |
| 655 | 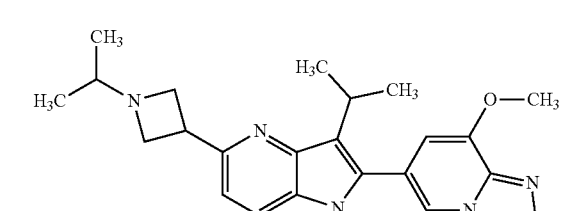 | 404.52 | 405.2 | 1.2 | QC-ACN-AA-XB |

TABLE 1-continued

| Ex. No. | Structure | Mol. Wt. | LCMS M+ | Ret Time (min) | HPLC Method |
|---|---|---|---|---|---|
| 656 | 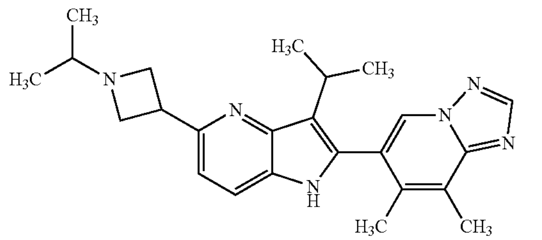 | 402.55 | 403.3 | 0.89 | QC-ACN-TFA-XB |
| 657 | 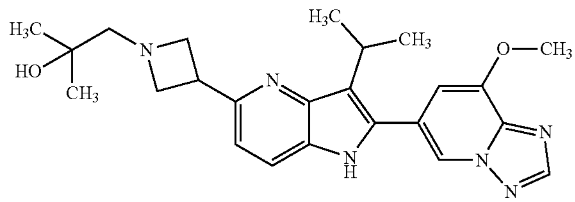 [SMILES: COc1cc(-c2[nH]c3ccc(C4CN(CC(C)(C)O)C4)nc3c2C(C)C)cn2ncnc12] | 434.54 | 435.41 | 0.83 | QC-ACN-TFA-XB |
| 658 | 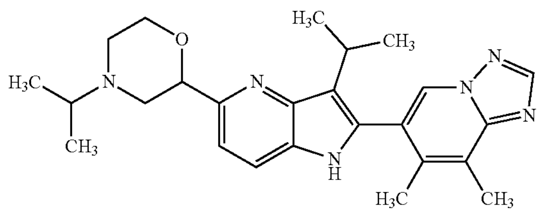 [SMILES: Cc1c(-c2[nH]c3ccc(C4CN(C(C)C)CCO4)nc3c2C(C)C)cn2ncnc2c1C] | 432.57 | 433.2 | 1.48 | QC-ACN-AA-XB |
| 659 | 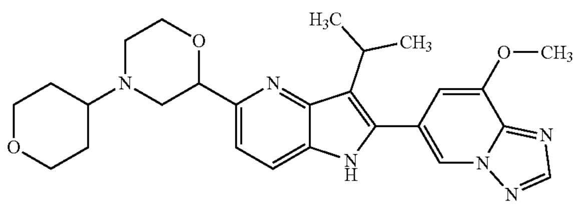 [SMILES: COc1cc(-c2[nH]c3ccc(C4CN(C5CCOCC5)CCO4)nc3c2C(C)C)cn2ncnc12] | 476.58 | 477.4 | 1.42 | QC-ACN-AA-XB |
| 660 | 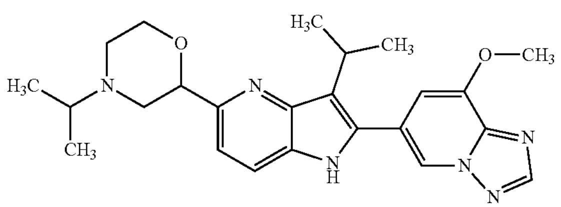 [SMILES: COc1cc(-c2[nH]c3ccc(C4CN(C(C)C)CCO4)nc3c2C(C)C)cn2ncnc12] | 434.54 | 435.1 | 1.02 | QC-ACN-TFA-XB |
| 661 | 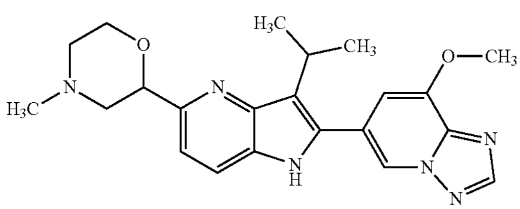 [SMILES: COc1cc(-c2[nH]c3ccc(C4CN(C)CCO4)nc3c2C(C)C)cn2ncnc12] | 406.49 | 407.3 | 1.26 | QC-ACN-AA-XB |
| 662 | 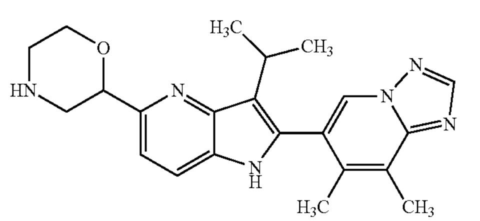 [SMILES: Cc1c(-c2[nH]c3ccc(C4CNCCO4)nc3c2C(C)C)cn2ncnc2c1C] | 390.49 | 391.2 | 0.99 | QC-ACN-AA-XB |

TABLE 1-continued

| Ex. No. | Structure | Mol. Wt. | LCMS M+ | Ret Time (min) | HPLC Method |
|---|---|---|---|---|---|
| 663 | 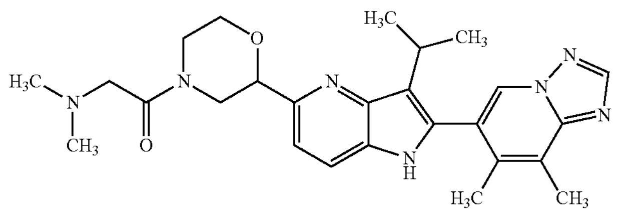 [SMILES: Cc1c(-c2[nH]c3ccc(C4CN(C(=O)CN(C)C)CCO4)nc3c2C(C)C)cn2ncnc2c1C] | 475.60 | 476.2 | 0.79 | QC-ACN-TFA-XB |
| 664 | 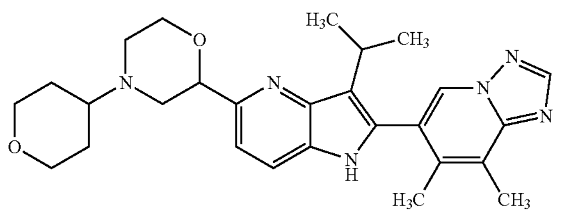 [SMILES: Cc1c(-c2[nH]c3ccc(C4CN(C5CCOCC5)CCO4)nc3c2C(C)C)cn2ncnc2c1C] | 474.61 | 475.3 | 1.41 | QC-ACN-AA-XB |
| 665 | 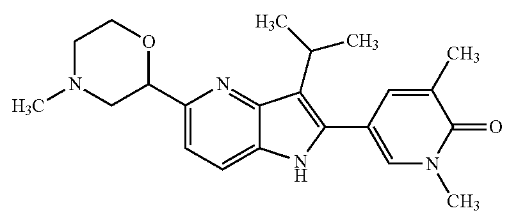 [SMILES: Cc1cc(-c2[nH]c3ccc(C4CN(C)CCO4)nc3c2C(C)C)cn(C)c1=O] | 380.49 | 381.1 | 1.34 | QC-ACN-AA-XB |
| 666 | 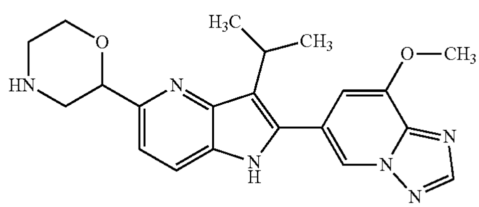 [SMILES: COc1cc(-c2[nH]c3ccc(C4CNCCO4)nc3c2C(C)C)cn2ncnc12] | 392.46 | 393.2 | 0.75 | QC-ACN-TFA-XB |
| 667 | 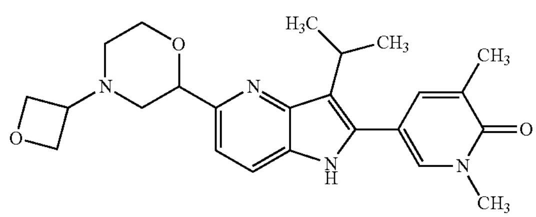 [SMILES: Cc1cc(-c2[nH]c3ccc(C4CN(C5COC5)CCO4)nc3c2C(C)C)cn(C)c1=O] | 422.53 | 423.2 | 0.75 | QC-ACN-TFA-XB |
| 668 | 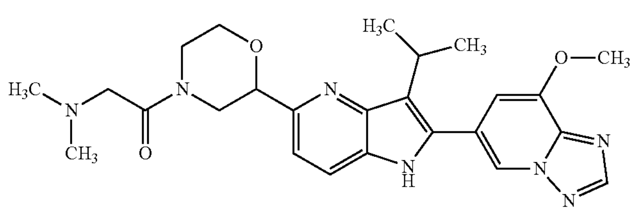 [SMILES: COc1cc(-c2[nH]c3ccc(C4CN(C(=O)CN(C)C)CCO4)nc3c2C(C)C)cn2ncnc12] | 477.57 | 478.3 | 1.06 | QC-ACN-AA-XB |
| 669 | 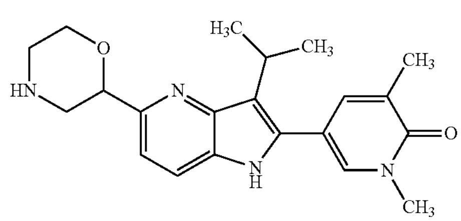 [SMILES: Cc1cc(-c2[nH]c3ccc(C4CNCCO4)nc3c2C(C)C)cn(C)c1=O] | 366.47 | 367.1 | 0.86 | QC-ACN-AA-XB |

… TABLE 1-continued

| Ex. No. | Structure | Mol. Wt. | LCMS M+ | Ret Time (min) | HPLC Method |
|---|---|---|---|---|---|
| 670 | 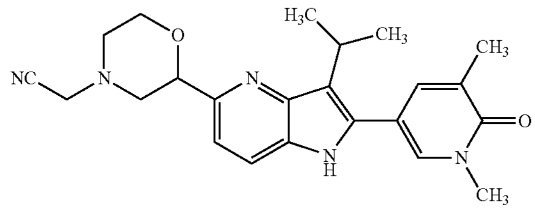 [SMILES: Cc1cc(-c2[nH]c3ccc(C4CN(CC#N)CCO4)nc3c2C(C)C)cn(C)c1=O] | 405.50 | 406.3 | 1.38 | QC-ACN-AA-XB |
| 671 | 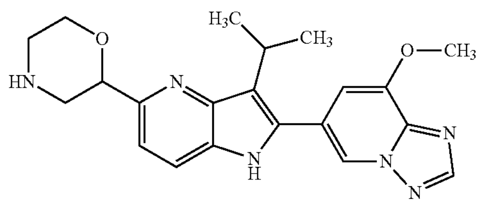 [SMILES: COc1cc(-c2[nH]c3ccc(C4CNCCO4)nc3c2C(C)C)cn2ncnc12] | 392.46 | 393.1 | 0.97 | QC-ACN-AA-XB |
| 672 | 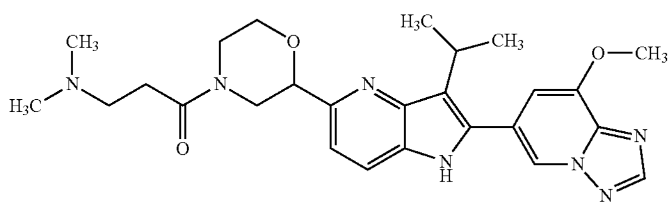 [SMILES: COc1cc(-c2[nH]c3ccc(C4CN(C(=O)CCN(C)C)CCO4)nc3c2C(C)C)cn2ncnc12] | 491.60 | 492.3 | 1.06 | QC-ACN-AA-XB |
| 673 | 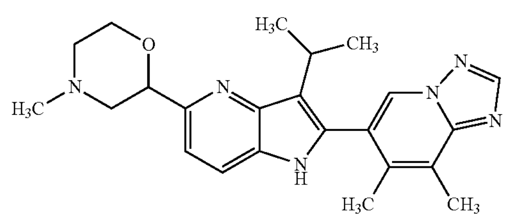 [SMILES: Cc1c(-c2[nH]c3ccc(C4CN(C)CCO4)nc3c2C(C)C)cn2ncnc2c1C] | 404.52 | 405.2 | 1.2 | QC-ACN-AA-XB |
| 674 | 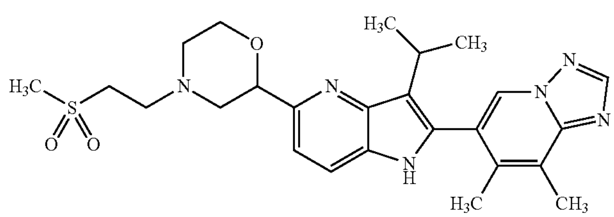 [SMILES: Cc1c(-c2[nH]c3ccc(C4CN(CCS(C)(=O)=O)CCO4)nc3c2C(C)C)cn2ncnc2c1C] | 496.63 | 497.3 | 1.35 | QC-ACN-AA-XB |
| 675 | 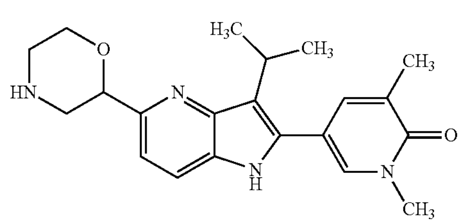 | 366.47 | 367 | 0.77 | QC-ACN-TFA-XB |
| 676 | 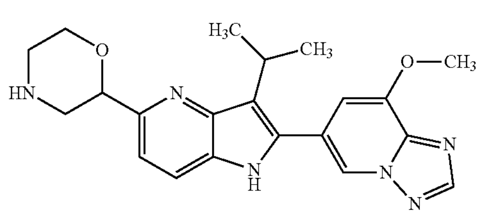 [SMILES: COc1cc(-c2[nH]c3ccc(C4CNCCO4)nc3c2C(C)C)cn2ncnc12] | 392.46 | 393.3 | 0.76 | QC-ACN-TFA-XB |

TABLE 1-continued

| Ex. No. | Structure | Mol. Wt. | LCMS M+ | Ret Time (min) | HPLC Method |
|---|---|---|---|---|---|
| 677 | 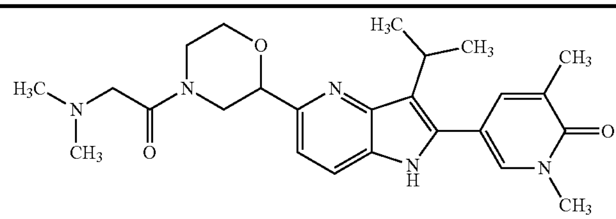 | 451.57 | 452.2 | 0.95 | QC-ACN-AA-XB |
| 678 | 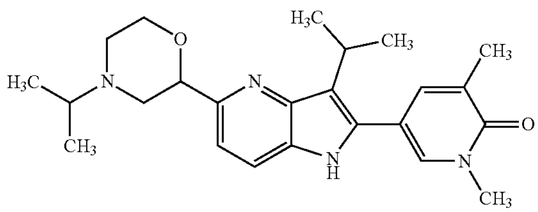 [SMILES: Cc1cc(-c2[nH]c3ccc(C4CN(C(C)C)CCO4)nc3c2C(C)C)cn(C)c1=O] | 408.55 | 409.3 | 0.82 | QC-ACN-TFA-XB |
| 679 | 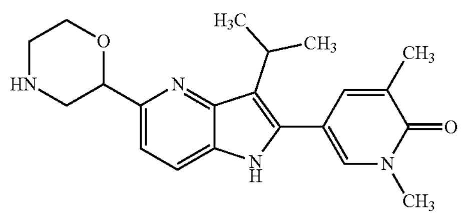 [SMILES: Cc1cc(-c2[nH]c3ccc(C4CNCCO4)nc3c2C(C)C)cn(C)c1=O] | 366.47 | 367.2 | 0.97 | QC-ACN-AA-XB |
| 680 | 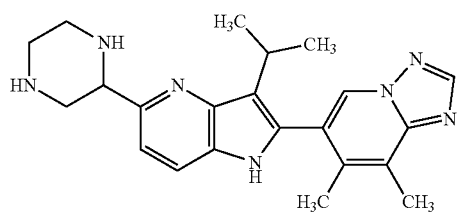 [SMILES: Cc1c(-c2[nH]c3ccc(C4CNCCN4)nc3c2C(C)C)cn2ncnc2c1C] | 389.51 | 390.1 | 1.13 | QC-ACN-AA-XB |
| 681 | 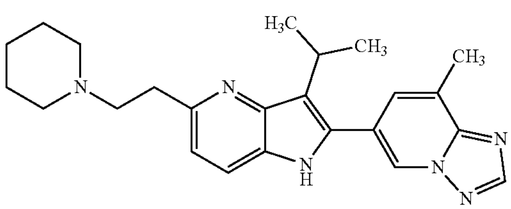 [SMILES: Cc1cc(-c2[nH]c3ccc(CCN4CCCCC4)nc3c2C(C)C)cn2ncnc12] | 402.55 | 403.1 | 1.24 | QC-ACN-AA-XB |
| 682 | 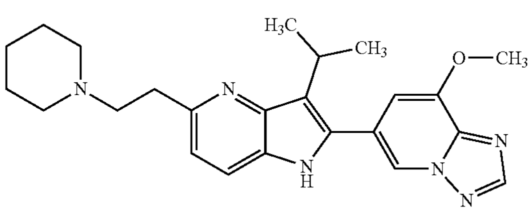 [SMILES: COc1cc(-c2[nH]c3ccc(CCN4CCCCC4)nc3c2C(C)C)cn2ncnc12] | 418.55 | 419.4 | 0.77 | QC-ACN-TFA-XB |
| 683 | 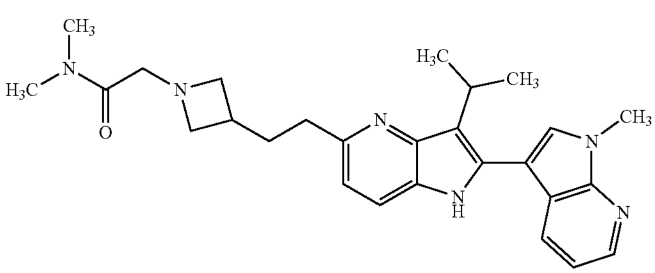 | 458.61 | 458.9 | 1.31 | QC-ACN-AA-XB |

TABLE 1-continued

| Ex. No. | Structure | Mol. Wt. | LCMS M+ | Ret Time (min) | HPLC Method |
|---|---|---|---|---|---|
| 684 | 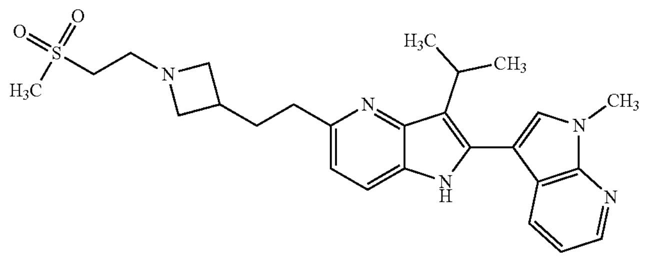 [SMILES: CC(C)c1c(-c2cn(C)c3ncccc23)[nH]c2ccc(CCC3CN(CCS(C)(=O)=O)C3)nc12] | 479.64 | 480.1 | 1.47 | QC-ACN-AA-XB |
| 685 | 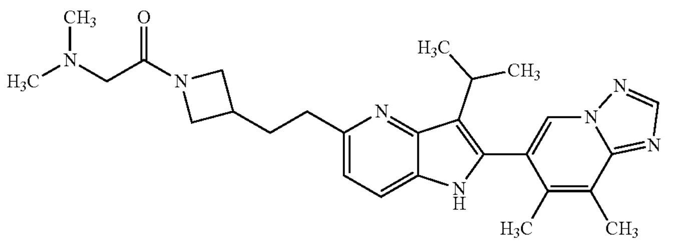 [SMILES: Cc1c(-c2[nH]c3ccc(CCC4CN(C(=O)CN(C)C)C4)nc3c2C(C)C)cn2ncnc2c1C] | 473.63 | 474.3 | 1.49 | QC-ACN-AA-XB |
| 686 | 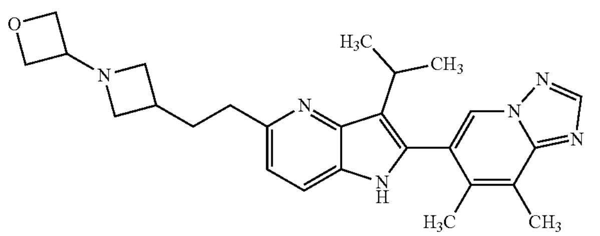 [SMILES: Cc1c(-c2[nH]c3ccc(CCC4CN(C5COC5)C4)nc3c2C(C)C)cn2ncnc2c1C] | 444.58 | 445.2 | 0.92 | QC-ACN-AA-XB |
| 687 | 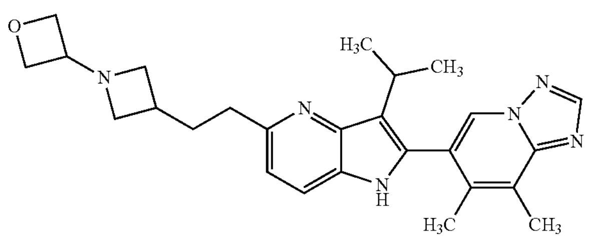 [SMILES: Cc1c(-c2[nH]c3ccc(CCC4CN(C5COC5)C4)nc3c2C(C)C)cn2ncnc2c1C] | 444.58 | 445.1 | 0.73 | QC-ACN-TFA-XB |
| 688 | 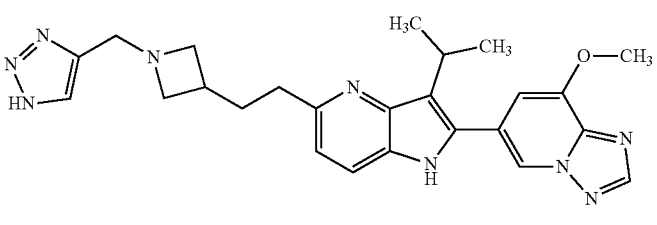 [SMILES: COc1cc(-c2[nH]c3ccc(CCC4CN(Cc5c[nH]nn5)C4)nc3c2C(C)C)cn2ncnc12] | 471.57 | 472.2 | 1 | QC-ACN-AA-XB |
| 689 | 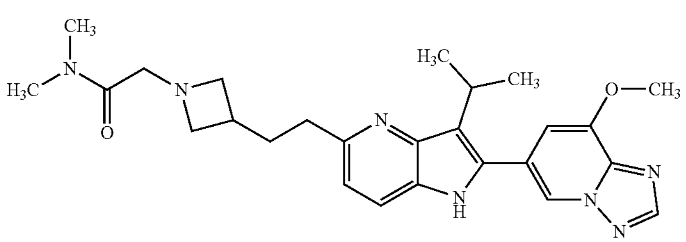 [SMILES: COc1cc(-c2[nH]c3ccc(CCC4CN(CC(=O)N(C)C)C4)nc3c2C(C)C)cn2ncnc12] | 475.60 | 475.9 | 1.28 | QC-ACN-AA-XB |

TABLE 1-continued

| Ex. No. | Structure | Mol. Wt. | LCMS M+ | Ret Time (min) | HPLC Method |
|---|---|---|---|---|---|
| 690 | 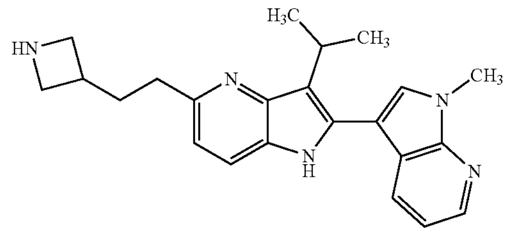 [SMILES: CC(C)c1c(-c2cn(C)c3ncccc23)[nH]c2ccc(CCC3CNC3)nc12] | 373.50 | 374.1 | 0.84 | QC-ACN-TFA-XB |
| 691 | 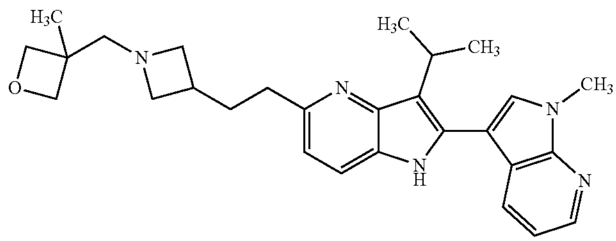 [SMILES: CC(C)c1c(-c2cn(C)c3ncccc23)[nH]c2ccc(CCC3CN(CC4(C)COC4)C3)nc12] | 457.62 | 457.9 | 1.64 | QC-ACN-AA-XB |
| 692 | 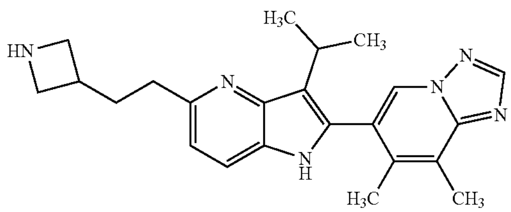 [SMILES: Cc1c(-c2[nH]c3ccc(CCC4CNC4)nc3c2C(C)C)cn2ncnc2c1C] | 388.52 | 389.1 | 0.72 | QC-ACN-TFA-XB |
| 693 | 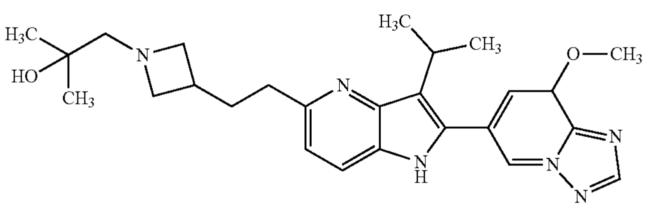 | 462.60 | 463 | 1.29 | QC-ACN-AA-XB |
| 694 | 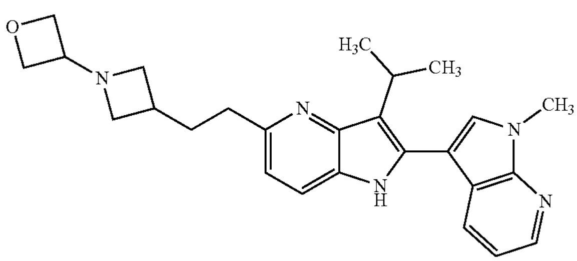 [SMILES: CC(C)c1c(-c2cn(C)c3ncccc23)[nH]c2ccc(CCC3CN(C4COC4)C3)nc12] | 429.57 | 430.2 | 0.71 | QC-ACN-TFA-XB |
| 695 | 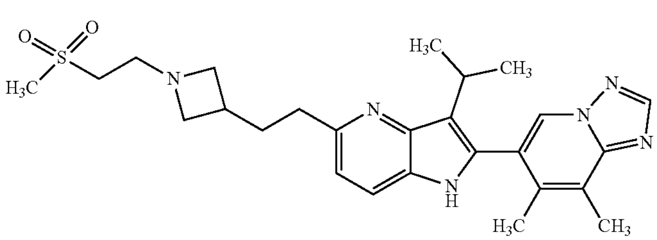 [SMILES: Cc1c(-c2[nH]c3ccc(CCC4CN(CCS(C)(=O)=O)C4)nc3c2C(C)C)cn2ncnc2c1C] | 494.66 | 495.4 | 1.14 | QC-ACN-AA-XB |

TABLE 1-continued

| Ex. No. | Structure | Mol. Wt. | LCMS M+ | Ret Time (min) | HPLC Method |
|---|---|---|---|---|---|
| 696 | 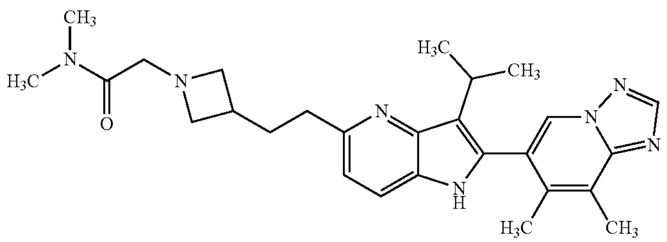 [SMILES: Cc1c(-c2[nH]c3ccc(CCC4CN(CC(=O)N(C)C)C4)nc3c2C(C)C)cn2ncnc2c1C] | 473.63 | 474.37 | 1.07 | QC-ACN-AA-XB |
| 697 | 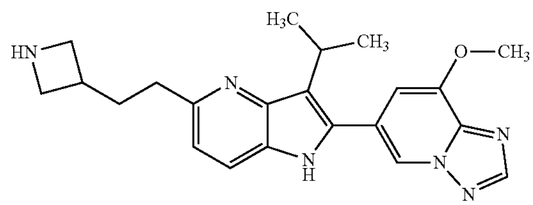 [SMILES: COc1cc(-c2[nH]c3ccc(CCC4CNC4)nc3c2C(C)C)cn2ncnc12] | 390.49 | 391.3 | 0.95 | QC-ACN-AA-XB |
| 698 | 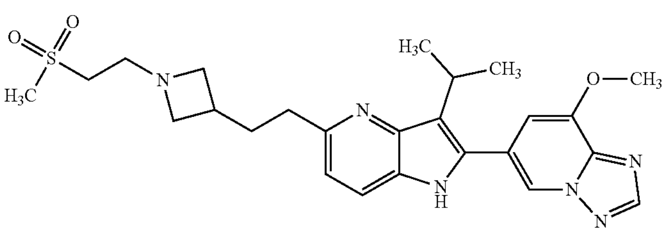 [SMILES: COc1cc(-c2[nH]c3ccc(CCC4CN(CCS(C)(=O)=O)C4)nc3c2C(C)C)cn2ncnc12] | 496.63 | 497.3 | 1.09 | QC-ACN-AA-XB |
| 699 | 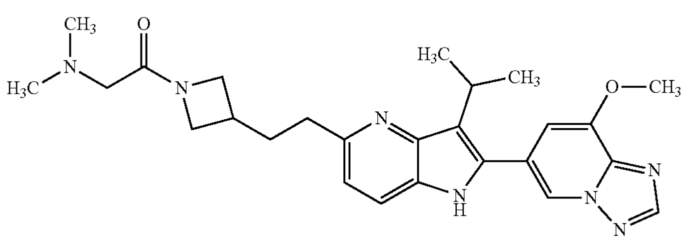 [SMILES: COc1cc(-c2[nH]c3ccc(CCC4CN(C(=O)CN(C)C)C4)nc3c2C(C)C)cn2ncnc12] | 475.60 | 476.4 | 0.76 | QC-ACN-TFA-XB |
| 700 | 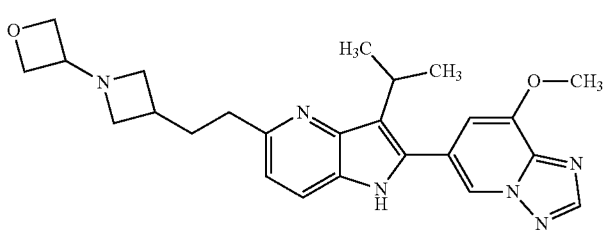 [SMILES: COc1cc(-c2[nH]c3ccc(CCC4CN(C5COC5)C4)nc3c2C(C)C)cn2ncnc12] | 446.56 | 447.3 | 1.08 | QC-ACN-AA-XB |
| 701 | 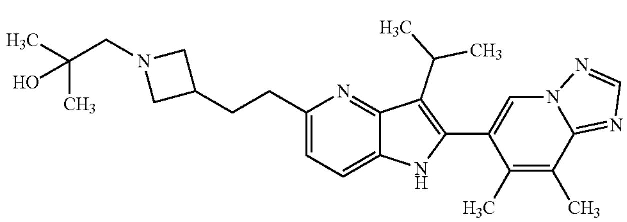 [SMILES: Cc1c(-c2[nH]c3ccc(CCC4CN(CC(C)(C)O)C4)nc3c2C(C)C)cn2ncnc2c1C] | 460.63 | 461.4 | 1.1 | QC-ACN-AA-XB |

TABLE 1-continued

| Ex. No. | Structure | Mol. Wt. | LCMS M+ | Ret Time (min) | HPLC Method |
|---|---|---|---|---|---|
| 702 | 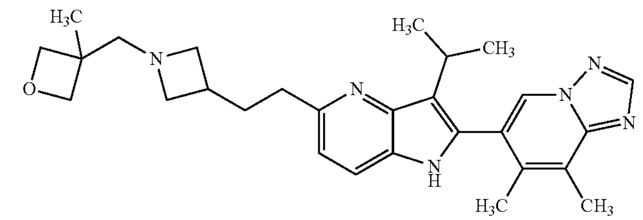 [SMILES: Cc1c(-c2[nH]c3ccc(CCC4CN(CC5(C)COC5)C4)nc3c2C(C)C)cn2ncnc2c1C] | 472.64 | 473.4 | 1.12 | QC-ACN-AA-XB |
| 703 | 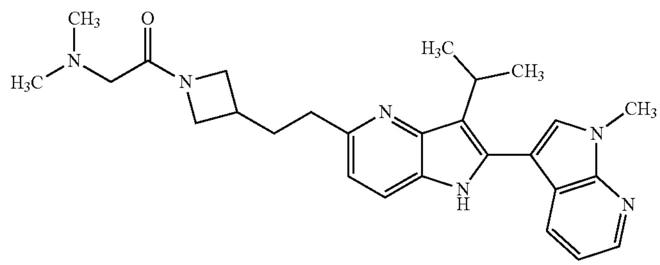 | 458.61 | 459.4 | 1.2 | QC-ACN-AA-XB |
| 704 | 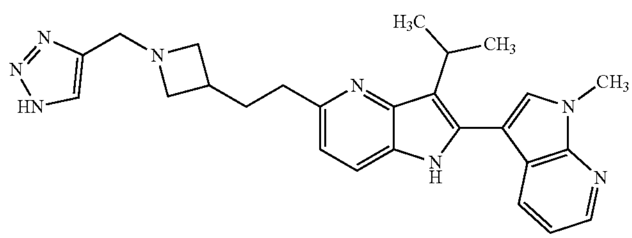 [SMILES: CC(C)c1c(-c2cn(C)c3ncccc23)[nH]c2ccc(CCC3CN(Cc4c[nH]nn4)C3)nc12] | 454.58 | 454.9 | 1.35 | QC-ACN-AA-XB |
| 705 | 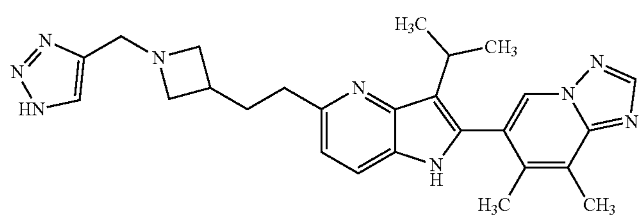 [SMILES: Cc1c(-c2[nH]c3ccc(CCC4CN(Cc5c[nH]nn5)C4)nc3c2C(C)C)cn2ncnc2c1C] | 469.60 | 470.47 | 0.74 | QC-ACN-TFA-XB |
| 706 | 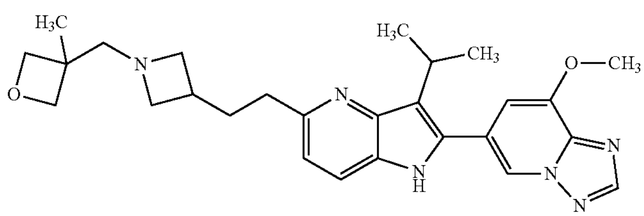 [SMILES: COc1cc(-c2[nH]c3ccc(CCC4CN(CC5(C)COC5)C4)nc3c2C(C)C)cn2ncnc12] | 474.61 | 475.4 | 1.1 | QC-ACN-AA-XB |
| 707 | 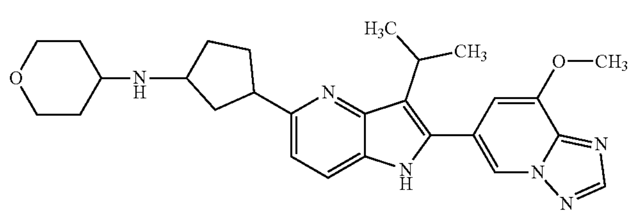 | 474.61 | 475.4 | 1.27 | E |

TABLE 1-continued

| Ex. No. | Structure | Mol. Wt. | LCMS M+ | Ret Time (min) | HPLC Method |
|---|---|---|---|---|---|
| 708 | 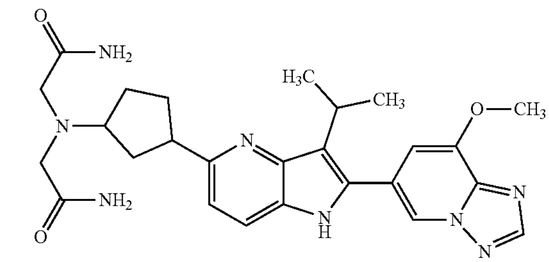 [SMILES: COc1cc(-c2[nH]c3ccc(C4CCC(N(CC(N)=O)CC(N)=O)C4)nc3c2C(C)C)cn2ncnc12] | 504.60 | 505 | 1.26 | E |
| 709 | 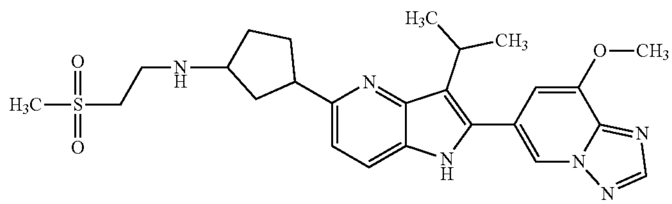 | 496.63 | 497 | 1.05 | E |
| 710 | 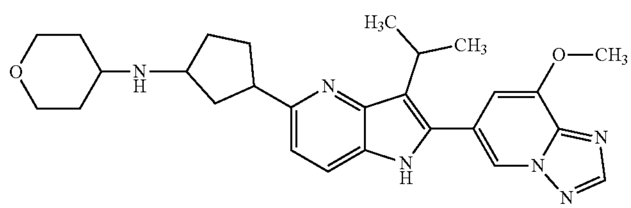 | 474.61 | 475.3 | 1.27 | E |
| 711 | 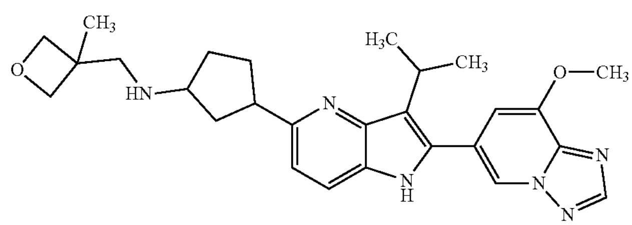 [SMILES: COc1cc(-c2[nH]c3ccc(C4CCC(NCC5(C)COC5)C4)nc3c2C(C)C)cn2ncnc12] | 474.61 | 475.3 | 1.33 | E |
| 712 | 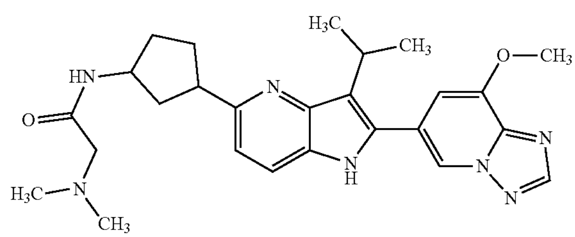 [SMILES: COc1cc(-c2[nH]c3ccc(C4CCC(NC(=O)CN(C)C)C4)nc3c2C(C)C)cn2ncnc12] | 475.60 | 476.3 | 1.55 | E |
| 713 | 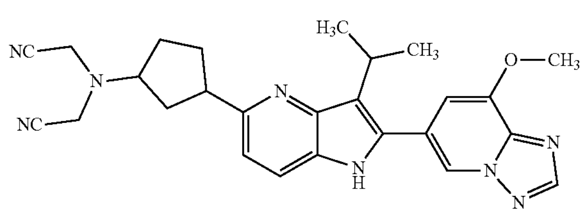 [SMILES: COc1cc(-c2[nH]c3ccc(C4CCC(N(CC#N)CC#N)C4)nc3c2C(C)C)cn2ncnc12] | 468.57 | 469 | 1.8 | E |
| 714 | 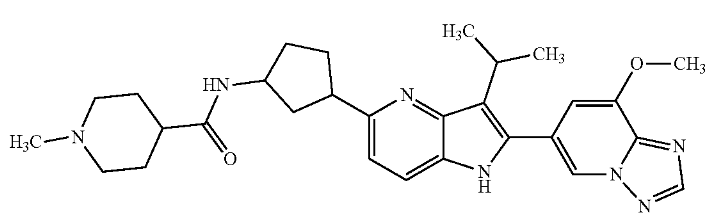 [SMILES: COc1cc(-c2[nH]c3ccc(C4CCC(NC(=O)C5CCN(C)CC5)C4)nc3c2C(C)C)cn2ncnc12] | 515.66 | 516.4 | 1.35 | E |

TABLE 1-continued
| Ex. No. | Structure | Mol. Wt. | LCMS M+ | Ret Time (min) | HPLC Method |
|---|---|---|---|---|---|
| 715 | 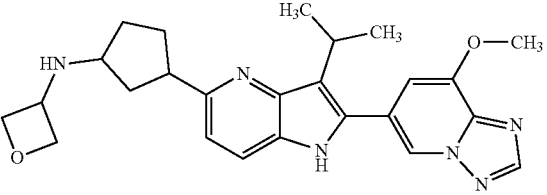 [SMILES: COc1cc(-c2[nH]c3ccc(C4CCC(NC5COC5)C4)nc3c2C(C)C)cn2ncnc12] | 446.56 | 447.3 | 1.43 | E |
| 716 | 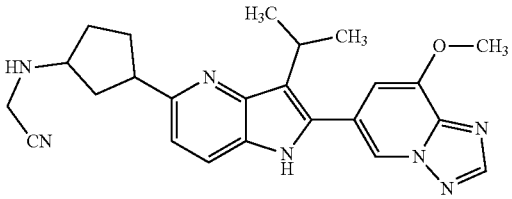 [SMILES: COc1cc(-c2[nH]c3ccc(C4CCC(NCC#N)C4)nc3c2C(C)C)cn2ncnc12] | 429.53 | 430.3 | 1.94 | E |
| 717 | 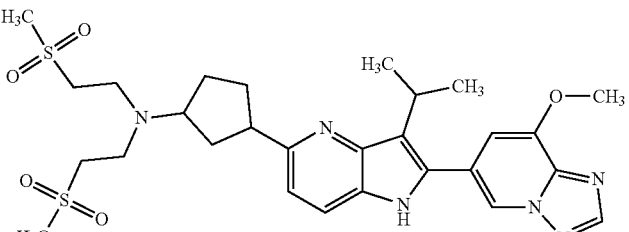 | 602.77 | 603.3 | 1.34 | E |
| 718 | 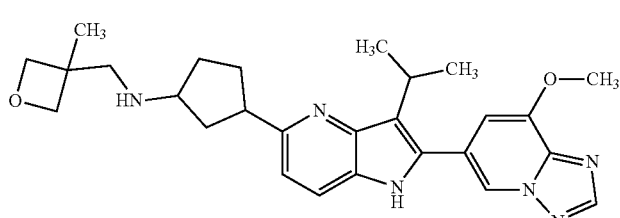 | 474.61 | 475.4 | 1.34 | E |
| 719 | 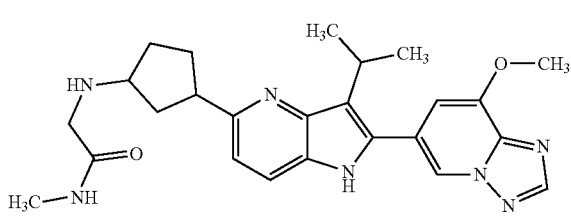 [SMILES: CNC(=O)CNC1CCC(c2ccc3[nH]c(-c4cc(OC)c5ncnn5c4)c(C(C)C)c3n2)C1] | 461.57 | 462.3 | 1.29 | E |
| 720 | 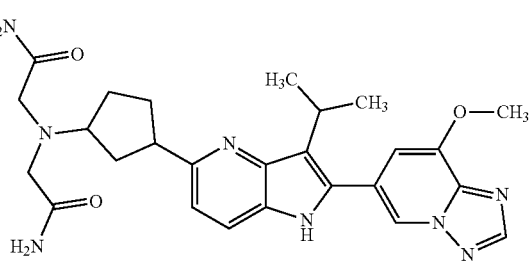 | 504.60 | 505.3 | 1.26 | E |

TABLE 1-continued

| Ex. No. | Structure | Mol. Wt. | LCMS M+ | Ret Time (min) | HPLC Method |
|---|---|---|---|---|---|
| 721 | 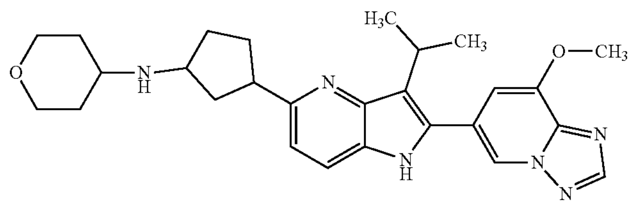 [SMILES: COc1cc(-c2[nH]c3ccc(C4CCC(NC5CCOCC5)C4)nc3c2C(C)C)cn2ncnc12] | 474.61 | 475 | 1.27 | E |
| 722 | 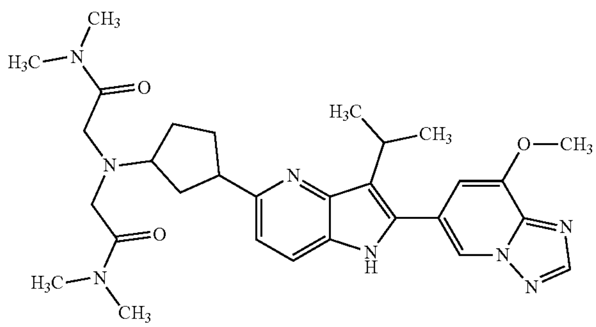 [SMILES: COc1cc(-c2[nH]c3ccc(C4CCC(N(CC(=O)N(C)C)CC(=O)N(C)C)C4)nc3c2C(C)C)cn2ncnc12] | 560.70 | 561 | 1.5 | E |
| 723 | 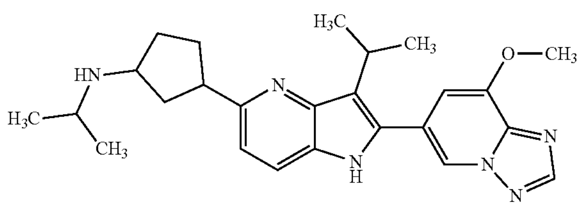 [SMILES: COc1cc(-c2[nH]c3ccc(C4CCC(NC(C)C)C4)nc3c2C(C)C)cn2ncnc12] | 432.57 | 433.3 | 1.32 | E |
| 724 | 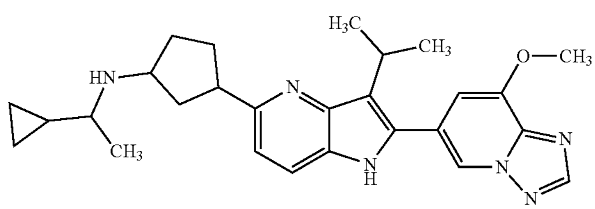 [SMILES: COc1cc(-c2[nH]c3ccc(C4CCC(NC(C)C5CC5)C4)nc3c2C(C)C)cn2ncnc12] | 458.61 | 459.3 | 1.46 | E |
| 725 | 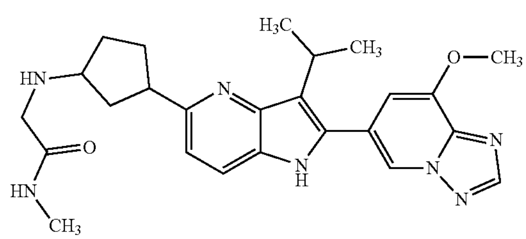 [SMILES: CNC(=O)CNC1CCC(c2ccc3[nH]c(-c4cc(OC)c5ncnn5c4)c(C(C)C)c3n2)C1] | 461.57 | 462.3 | 1.3 | E |
| 726 | 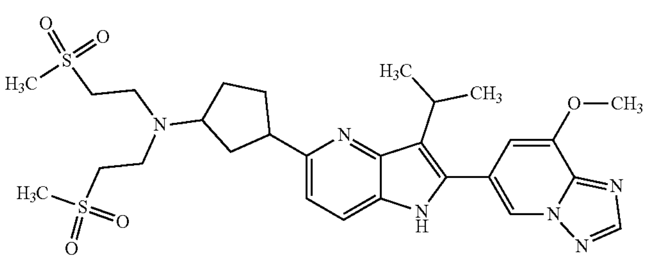 [SMILES: COc1cc(-c2[nH]c3ccc(C4CCC(N(CCS(C)(=O)=O)CCS(C)(=O)=O)C4)nc3c2C(C)C)cn2ncnc12] | 602.77 | 603 | 1.34 | E |

TABLE 1-continued

| Ex. No. | Structure | Mol. Wt. | LCMS M+ | Ret Time (min) | HPLC Method |
|---|---|---|---|---|---|
| 727 | 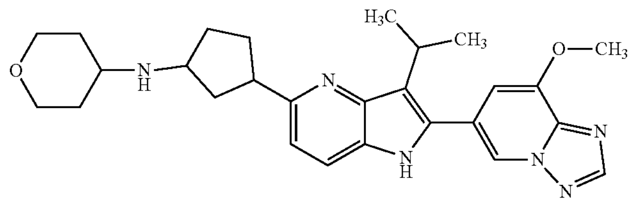 [SMILES: COc1cc(-c2[nH]c3ccc(C4CCC(NC5CCOCC5)C4)nc3c2C(C)C)cn2ncnc12] | 474.61 | 475.4 | 1.38 | E |
| 728 | 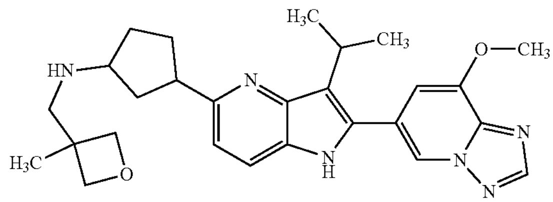 [SMILES: COc1cc(-c2[nH]c3ccc(C4CCC(NCC5(C)COC5)C4)nc3c2C(C)C)cn2ncnc12] | 474.61 | 475.3 | 1.35 | E |
| 729 | 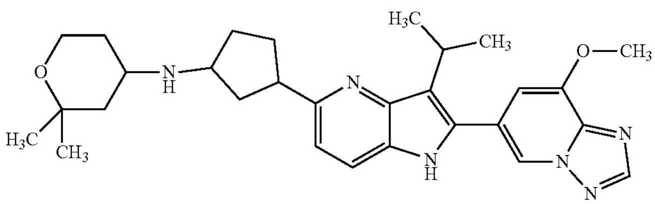 [SMILES: COc1cc(-c2[nH]c3ccc(C4CCC(NC5CCOC(C)(C)C5)C4)nc3c2C(C)C)cn2ncnc12] | 502.66 | 503.3 | 1.41 | E |
| 730 | 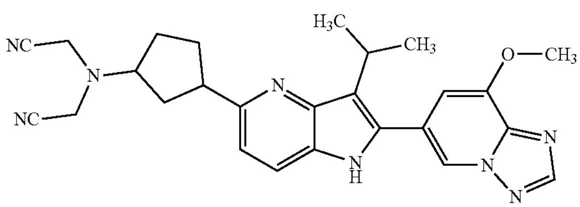 [SMILES: COc1cc(-c2[nH]c3ccc(C4CCC(N(CC#N)CC#N)C4)nc3c2C(C)C)cn2ncnc12] | 468.57 | 469 | 1.8 | E |
| 731 | 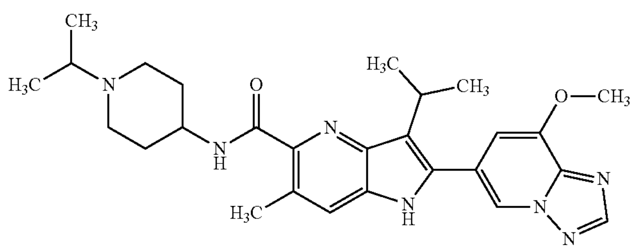 [SMILES: COc1cc(-c2[nH]c3cc(C)c(C(=O)NC4CCN(C(C)C)CC4)nc3c2C(C)C)cn2ncnc12] | 489.62 | 490.1 | 1.34 | E |
| 732 | 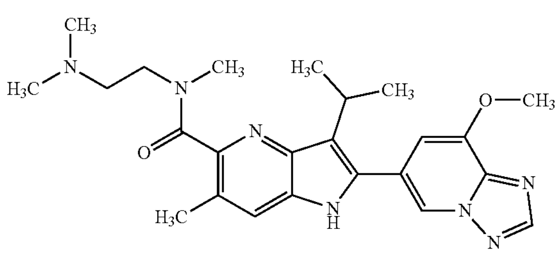 [SMILES: COc1cc(-c2[nH]c3cc(C)c(C(=O)N(C)CCN(C)C)nc3c2C(C)C)cn2ncnc12] | 449.56 | 450.1 | 1.19 | E |
| 733 | 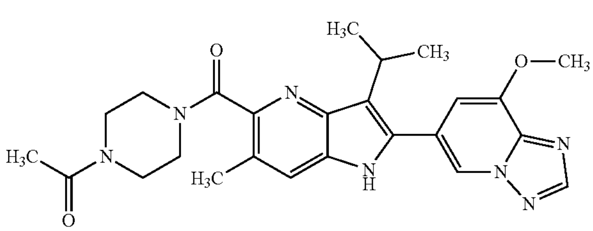 [SMILES: COc1cc(-c2[nH]c3cc(C)c(C(=O)N4CCN(C(C)=O)CC4)nc3c2C(C)C)cn2ncnc12] | 475.55 | 476.1 | 1.29 | E |

TABLE 1-continued

| Ex. No. | Structure | Mol. Wt. | LCMS M+ | Ret Time (min) | HPLC Method |
|---|---|---|---|---|---|
| 734 | 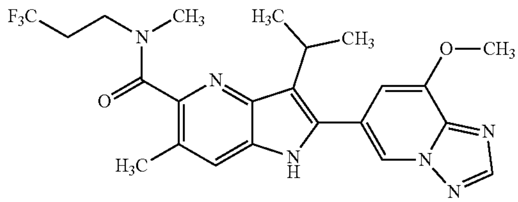 [SMILES: COc1cc(-c2[nH]c3cc(C)c(C(=O)N(C)CCC(F)(F)F)nc3c2C(C)C)cn2ncnc12] | 474.49 | 475.1 | 1.86 | E |
| 735 | 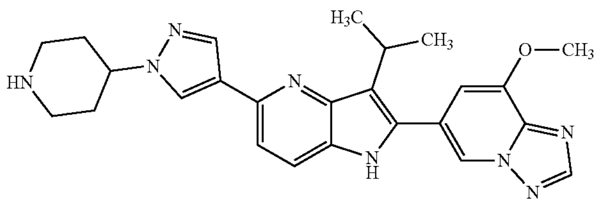 [SMILES: COc1cc(-c2[nH]c3ccc(-c4cnn(C5CCNCC5)c4)nc3c2C(C)C)cn2ncnc12] | 440.56 | 441.2 | 1.32 | QC-ACN-AA-XB |
| 736 | 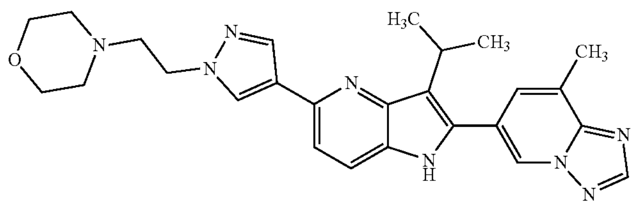 [SMILES: Cc1cc(-c2[nH]c3ccc(-c4cnn(CCN5CCOCC5)c4)nc3c2C(C)C)cn2ncnc12] | 470.58 | 470.9 | 1.57 | QC-ACN-AA-XB |

Example 737

6-(5-((2S,5R)-2,5-dimethylpiperazin-1-yl)-3-isopropyl-1H-pyrrolo[3,2-b]pyridin-2-yl)-7,8-dimethyl-[1,2,4]triazolo[1,5-a]pyridine

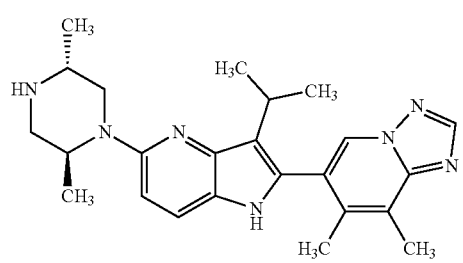

(737)

Intermediate 737A: tert-butyl 5-((2S,5R)₀₋₄-(tert-butoxycarbonyl)-2,5-dimethylpiperazin-1-yl)-2-(7,8-dimethyl-[1,2,4]triazolo[1,5-a]pyridin-6-yl)-3-isopropyl-1H-pyrrolo[3,2-b]pyridine-1-carboxylate

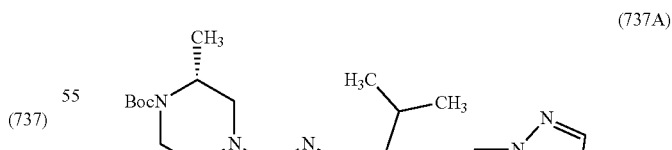

(737A)

A suspension of tert-butyl 5-bromo-2-(7,8-dimethyl-[1,2,4]triazolo[1,5-a]pyridin-6-yl)-3-isopropyl-1H-pyrrolo[3,2-b]pyridine-1-carboxylate (600 mg, 1.24 mmol), tert-butyl (2R,5S)-2,5-dimethylpiperazine-1-carboxylate, HCl (466 mg, 1.86 mmol), Pd$_2$(dba)$_3$ (113 mg, 0.124 mmol), dicyclohexyl(2',6'-di-isopropoxy-[1,1'-biphenyl]-2-yl)phosphine (69.4 mg, 0.149 mmol), and Cs$_2$CO$_3$ (1.82 g, 5.57 mmol) in 1,4-dioxane (12.5 mL) in a reaction vial with a pressure-relief septum-lined cap and a stir bar was degassed with nitrogen gas for 5 minutes. The reaction vial was sealed and placed in a heating block with stirring at 105° C. for 6.5 hours, then cooled to room temperature, and remained at room temperature overnight. The reaction was then restarted by the addition of tert-butyl (2R,5S)-2,5-dimethylpiperazine-1-carboxylate, HCl (233 mg, 0.93 mmol), Pd$_2$(dba)$_3$ (57 mg, 0.062 mmol), dicyclohexyl(2',6'-di-isopropoxy-[1,1'-biphenyl]-2-yl)phosphine (35 mg, 0.075 mmol), and Cs$_2$CO$_3$ (908 mg, 2.79 mmol), degassed with nitrogen gas, and heated to 105° C. with stirring for 4 hours more. Upon completion, the reaction mixture was cooled to room temperature and remained at room temperature overnight. The reaction mixture was then filtered, concentrated, and taken up in DCM. The crude material was purified by silica gel column chromatography on a Teledyne Isco instrument eluting in Hex/EtOAc 0-100% to afford tert-butyl 5-((2S,5R)$_{0-4}$-(tert-butoxycarbonyl)-2,5-dimethylpiperazin-1-yl)-2-(7,8-dimethyl-[1,2,4]triazolo[1,5-a]pyridin-6-yl)-3-isopropyl-1H-pyrrolo[3,2-b]pyridine-1-carboxylate (698 mg, 1.130 mmol, 91% yield). LCMS retention time 1.26 [TS]. MS (E$^+$) m/z: 618.7 (M+H).

Example 737 tert-Butyl 5-((2S,5R)$_{0-4}$-(tert-butoxycarbonyl)-2,5-dimethylpiperazin-1-yl)-2-(7,8-dimethyl-[1,2,4]triazolo[1,5-a]pyridin-6-yl)-3-isopropyl-1H-pyrrolo[3,2-b]pyridine-1-carboxylate (698 mg, 1.13 mmol) was suspended in TFA (6 mL) at room temperature and stirred for 3 hours. The reaction mixture was then concentrated, redissolved in CHCl$_3$/iPrOH 3/1 and neutralized with 1.5M aqueous K$_2$HPO$_4$ solution in a separatory funnel. The organic layer was separated, dried over sodium sulfate, filtered, and concentrated to afford material considered to be quantitative of 6-(5-((2S,5R)-2,5-dimethylpiperazin-1-yl)-3-isopropyl-1H-pyrrolo[3,2-b]pyridin-2-yl)-7,8-dimethyl-[1,2,4]triazolo[1,5-a]pyridine (1.13 mmol).

For characterization purposes, a portion of the crude product from a separate preparation of 6-(5-((2S,5R)-2,5-dimethylpiperazin-1-yl)-3-isopropyl-1H-pyrrolo[3,2-b]pyridin-2-yl)-7,8-dimethyl-[1,2,4]triazolo[1,5-a]pyridine run on smaller scale was purified by preparative LC/MS using the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25 C. Fraction collection was triggered by MS and UV signals. The fractions containing the product were combined and dried via centrifugal evaporation to afford 6-(5-((2S,5R)-2,5-dimethylpiperazin-1-yl)-3-isopropyl-1H-pyrrolo[3,2-b]pyridin-2-yl)-7,8-dimethyl-[1,2,4]triazolo[1,5-a]pyridine, TFA (15.5 mg). LCMS retention time 0.93 [QC-ACN-TFA-XB]. MS (E$^+$) m/z: 418.5 (M+H). Select NMR peaks: $^1$H NMR (500 MHz, DMSO-d$_6$) δ 11.09 (s, 1H), 9.03 (br s, 1H), 8.78 (s, 2H), 8.47 (s, 1H), 7.64 (br d, J=8.9 Hz, 1H), 6.82 (br d, J=8.5 Hz, 1H), 4.18-4.04 (m, 1H), 3.67-3.53 (m, 1H), 3.45-3.33 (m, 1H), 3.11-2.97 (m, 1H), 2.86-2.75 (m, 1H), 2.59 (s, 3H), 2.17 (s, 3H), 1.42-1.35 (m, 6H), 1.29 (br d, J=6.4 Hz, 3H), 1.16 (br d, J=6.4 Hz, 3H).

Example 738

1-((2R,5S)$_{0-4}$-(2-(7,8-dimethyl-[1,2,4]triazolo[1,5-a]pyridin-6-yl)-3-isopropyl-1H-pyrrolo[3,2-b]pyridin-5-yl)-2,5-dimethylpiperazin-1-yl)-2-(pyrrolidin-1-yl)ethan-1-one

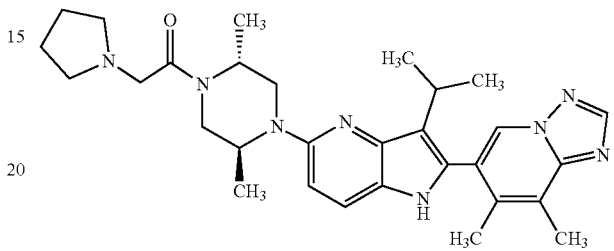

(738)

Intermediate 738A: 2-chloro-1-((2R,5S)$_{0-4}$-(2-(7,8-dimethyl-[1,2,4]triazolo[1,5-a]pyridin-6-yl)-3-isopropyl-1H-pyrrolo[3,2-b]pyridin-5-yl)-2,5-dimethylpiperazin-1-yl)ethan-1-one

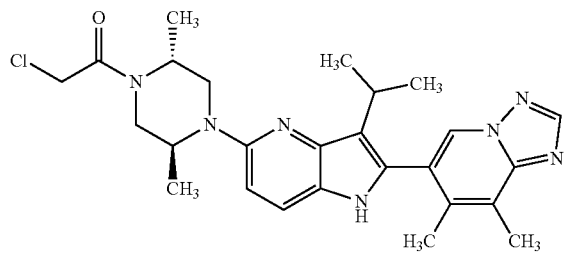

(738A)

6-(5-((2S,5R)-2,5-dimethylpiperazin-1-yl)-3-isopropyl-1H-pyrrolo[3,2-b]pyridin-2-yl)-7,8-dimethyl-[1,2,4]triazolo[1,5-a]pyridine (0.496 mmol) was suspended in DCM (4 mL). Et$_3$N (0.346 mL, 2.48 mmol) and 2-chloroacetyl chloride (0.079 mL, 0.992 mmol) were added sequentially. The reaction mixture was stirred at room temperature for 30 minutes. Another aliquot of 2-chloroacetyl chloride (0.025 mL, 0.314 mmol) was added. The reaction mixture was stirred for an additional 2 minutes. The reaction was quenched by addition of water, DCM, and 1.5 M aqueous K$_2$HPO$_4$ solution. The layers were separated, and the aqueous layer was extracted with DCM. The combined organic layer was dried over sodium sulfate, filtered, and concentrated to afford crude material which was considered quantitative recovery of 2-chloro-1-((2R,5S)$_{0-4}$-(2-(7,8-dimethyl-[1,2,4]triazolo[1,5-a]pyridin-6-yl)-3-isopropyl-1H-pyrrolo[3,2-b]pyridin-5-yl)-2,5-dimethylpiperazin-1-yl)ethan-1-one (0.496 mmol). LCMS retention time 0.70 [TS]. MS (E+) m/z: 494.4 (M+H).

Example 738

2-Chloro-1-((2R,5S)$_{0-4}$-(2-(7,8-dimethyl-[1,2,4]triazolo[1,5-a]pyridin-6-yl)-3-isopropyl-1H-pyrrolo[3,2-b]pyridin-5-yl)-2,5-dimethylpiperazin-1-yl)ethan-1-one (0.0496 mmol) was suspended in DMF (1 mL). Pyrrolidine (0.050 mL, 0.609 mmol) was added, and the reaction mixture was stirred for 19 hours at room temperature. Upon completion, the reaction mixture was diluted with a few drops of water, DMF, filtered, and purified by preparative LC/MS via the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 16% B, 16-56% B over 20 minutes, then a 4-minute hold at 100% B; Flow Rate: 20 mL/min; Column Temperature: 25° C. Fraction collection was triggered by MS signals. The fractions containing the product were combined and dried via centrifugal evaporation to afford 1-((2R,5S)$_{0-4}$-(2-(7,8-dimethyl-[1,2,4]triazolo[1,5-a]pyridin-6-yl)-3-isopropyl-1H-pyrrolo[3,2-b]pyridin-5-yl)-2,5-dimethylpiperazin-1-yl)-2-(pyrrolidin-1-yl)ethan-1-one (14.2 mg, 0.027 mmol, 54.1% yield). LCMS retention time 1.46 [QC-ACN-AA-XB]. MS (E$^+$) m/z: 529.5 (M+H). Select NMR peaks (rotamers present): $^1$H NMR (500 MHz, DMSO-d$_6$) δ 10.82 (s, 1H), 8.70 (br s, 1H), 8.45 (s, 1H), 7.54 (d, J=8.9 Hz, 1H), 6.71 (br dd, J=8.8, 6.0 Hz, 1H), 2.80-2.72 (m, 1H), 2.56 (s, 3H), 2.15 (s, 3H), 1.76-1.61 (m, 4H), 1.36 (br d, J=5.8 Hz, 6H), 1.29-0.93 (m, 6H).

Example 739

1-((2R,5S)$_{0-4}$-(2-(7,8-dimethyl-[1,2,4]triazolo[1,5-a]pyridin-6-yl)-3-isopropyl-1H-pyrrolo[3,2-b]pyridin-5-yl)-2,5-dimethylpiperazin-1-yl)-3-(pyrrolidin-1-yl)propan-1-one

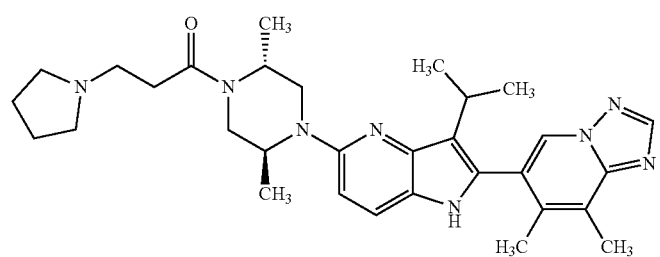

(739)

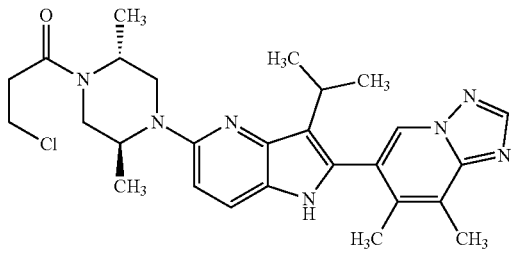

(739A)

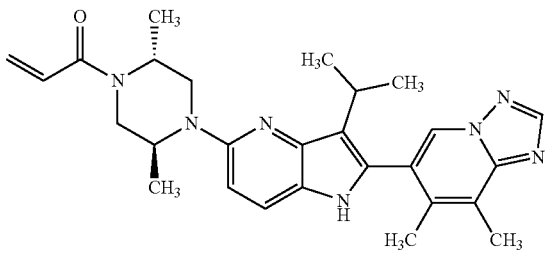

(739B)

6-(5-((2S,5R)-2,5-dimethylpiperazin-1-yl)-3-isopropyl-1H-pyrrolo[3,2-b]pyridin-2-yl)-7,8-dimethyl-[1,2,4]triazolo[1,5-a]pyridine (0.496 mmol) was suspended in DCM (4 mL). Et$_3$N (0.35 mL, 2.48 mmol) and 3-chloropropanoyl chloride (0.095 mL, 0.992 mmol) were added sequentially and the reaction mixture was stirred for 15 minutes at room temperature. Upon completion, the reaction was quenched. The reaction mixture was worked up by dilution with water, DCM, and 1.5M aqueous K$_2$HPO$_4$ solution. The organic layer was separated and the aqueous layer was extracted with DCM. The combined organic layer was dried over sodium sulfate, filtered, and concentrated to afford crude material which was carried into the next steps as is and considered quantitative recovery of both materials (0.496 mmol total) as a mixture of an unidentified ratio of 3-chloro-1-((2R,5S)$_{0-4}$-(2-(7,8-dimethyl-[1,2,4]triazolo[1,5-a]pyridin-6-yl)-3-isopropyl-1H-pyrrolo[3,2-b]pyridin-5-yl)-2,5-dimethylpiperazin-1-yl)propan-1-one (LCMS retention time 0.72 [TS]. MS (E+) m/z: 508.5 (M+H)) and 1-((2R,5S)$_{0-4}$-(2-(7,8-dimethyl-[1,2,4]triazolo[1,5-a]pyridin-6-yl)-3-isopropyl-1H-pyrrolo[3,2-b]pyridin-5-yl)-2,5-dimethylpiperazin-1-yl)prop-2-en-1-one (LCMS retention time 0.68 [TS]. MS (E$^+$) m/z: 472.5 (M+H).

Intermediates 739A and 739B: 3-chloro-1-((2R,5S)$_{0-4}$-(2-(7,8-dimethyl-[1,2,4]triazolo[1,5-a]pyridin-6-yl)-3-isopropyl-1H-pyrrolo[3,2-b]pyridin-5-yl)-2,5-dimethylpiperazin-1-yl)propan-1-one and 1-((2R,5S)$_{0-4}$-(2-(7,8-dimethyl-[1,2,4]triazolo[1,5-a]pyridin-6-yl)-3-isopropyl-1H-pyrrolo[3,2-b]pyridin-5-yl)-2,5-dimethylpiperazin-1-yl)prop-2-en-1-one

Example 739

A mixture of 3-chloro-1-((2R,5S)$_{0-4}$-(2-(7,8-dimethyl-[1,2,4]triazolo[1,5-a]pyridin-6-yl)-3-isopropyl-1H-pyrrolo[3,2-b]pyridin-5-yl)-2,5-dimethylpiperazin-1-yl)propan-1-one and 1-((2R,5S)$_{0-4}$-(2-(7,8-dimethyl-[1,2,4]triazolo[1,5-a]pyridin-6-yl)-3-isopropyl-1H-pyrrolo[3,2-b]pyridin-5-yl)-2,5-dimethylpiperazin-1-yl)prop-2-en-1-one (0.0413 mmol) was suspended in DMF (1 mL). Pyrrolidine (0.05 mL, 0.609 mmol) was added and the reaction mixture was stirred at room temperature for 20 hours. Upon completion, the reaction mixture was diluted with a few drops of water, DMF, filtered, and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 15% B, 15-55% B over 20 minutes, then a 4-minute hold at 100% B; Flow Rate: 20 mL/min; Column Temperature: 25 C. Fraction collection was triggered by MS signals. The fractions containing the product were combined and dried via centrifugal evaporation to afford 1-((2R,5S)$_{0-4}$-(2-(7,8-dimethyl-[1,2,4]triazolo[1,5-a]pyridin-6-yl)-3-isopropyl-1H-pyrrolo[3,2-b]pyridin-5-yl)-2,5-dimethylpiperazin-1-yl)-3-(pyrrolidin-1-yl)propan-1-one (18.0 mg, 0.032 mmol, 78% yield). LCMS retention time 1.07 [QC-ACN-TFA-XB]. MS (E+) m/z: 543.4 (M+H). Select NMR peaks (rotamers present): $^1$H NMR (500 MHz, DMSO-d$_6$) δ 10.83 (s, 1H), 8.73 (br s, 1H), 8.47-8.44 (m, 1H), 7.54 (d, J=9.0 Hz, 1H), 6.76-6.67 (m, 1H), 2.81-2.62 (m, 3H), 2.57 (s, 3H), 2.16 (s, 3H), 1.68 (br d, J=2.8 Hz, 4H), 1.37 (br d, J=6.6 Hz, 6H), 1.30-0.94 (m, 6H).

Example 740

6-(3-isopropyl-5-(2,6-diazaspiro[3.3]heptan-2-yl)-1H-pyrrolo[3,2-b]pyridin-2-yl)-7,8-dimethyl-[1,2,4]triazolo[1,5-a]pyridine

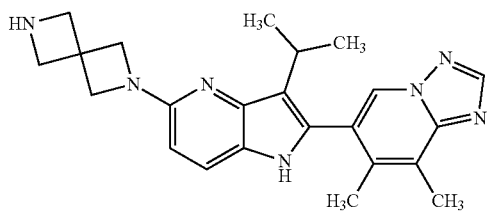

(740)

Intermediate 740A: tert-butyl 5-(6-(tert-butoxycarbonyl)-2,6-diazaspiro[3.3]heptan-2-yl)-2-(7,8-dimethyl-[1,2,4]triazolo[1,5-a]pyridin-6-yl)-3-isopropyl-1H-pyrrolo[3,2-b]pyridine-1-carboxylate

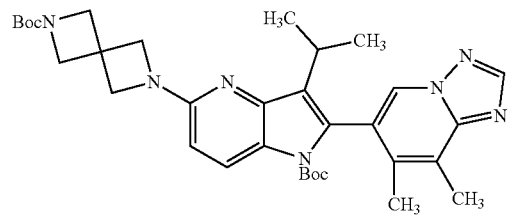

(740A)

A suspension of tert-butyl 5-bromo-2-(7,8-dimethyl-[1,2,4]triazolo[1,5-a]pyridin-6-yl)-3-isopropyl-1H-pyrrolo[3,2-b]pyridine-1-carboxylate (150 mg, 0.310 mmol), tert-butyl 2,6-diazaspiro[3.3]heptane-2-carboxylate, 0.5 oxalic acid salt (113 mg, 0.464 mmol), $2^{nd}$ generation RuPhos precatalyst (11 mg, 0.014 mmol), and Cs$_2$CO$_3$ (353 mg, 1.084 mmol) in 1,4-dioxane (3.1 mL) was degassed with nitrogen for 5 minutes in a reaction vial with a pressure-relief septum-lined cap. The reaction vial was sealed and placed in a heating block at 100° C. with stirring. After 2 hours, more RuPhos $2^{nd}$ generation precatalyst (27 mg, 0.035 mmol) was added, the suspension was further degassed, and the reaction mixture was taken back up to 100° C. with stirring for 2 hours. Upon completion, the reaction mixture was filtered, concentrated, and purified by silica gel column chromatography eluting with Hex/EtOAc 0-100% to afford tert-butyl 5-(6-(tert-butoxycarbonyl)-2,6-diazaspiro[3.3]heptan-2-yl)-2-(7,8-dimethyl-[1,2,4]triazolo[1,5-a]pyridin-6-yl)-3-isopropyl-1H-pyrrolo[3,2-b]pyridine-1-carboxylate (124 mg, 66.5% yield) containing some co-eluting impurities. LCMS retention time 0.99 [TS]. MS (E$^+$) m/z: 602.3 (M+H).

Example 740

A solution of tert-butyl 5-(6-(tert-butoxycarbonyl)-2,6-diazaspiro[3.3]heptan-2-yl)-2-(7,8-dimethyl-[1,2,4]triazolo[1,5-a]pyridin-6-yl)-3-isopropyl-1H-pyrrolo[3,2-b]pyridine-1-carboxylate (124 mg, 0.206 mmol) in TFA (3 mL) was stirred at room temperature for 2 hours. Upon completion, the reaction mixture was concentrated and considered quantitative recovery of 6-(3-isopropyl-5-(2,6-diazaspiro[3.3]heptan-2-yl)-1H-pyrrolo[3,2-b]pyridin-2-yl)-7,8-dimethyl-[1,2,4]triazolo[1,5-a]pyridine, TFA (0.206 mmol). 90% of this material was carried on as is. 10% of this material was purified by preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by MS and UV signals. Fractions containing the product were combined and dried via centrifugal evaporation. The material was further purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-40% B over 20 minutes, then a 4-minute hold at 100% B; Flow Rate: 20 mL/min; Column Temperature: 25 C. Fraction collection was triggered by MS signals. The fractions containing the product were combined and dried via centrifugal evaporation to afford 6-(3-isopropyl-5-(2,6-diazaspiro[3.3]heptan-2-yl)-1H-pyrrolo[3,2-b]pyridin-2-yl)-7,8-dimethyl-[1,2,4]triazolo[1,5-a]pyridine (3.1 mg, 0.0075 mmol). LCMS retention time 1.21 [QC-ACN-AA-XB]. MS (E$^+$) m/z: 402.0 (M+H). Select NMR peaks: $^1$H NMR (500 MHz, DMSO-d$_6$) δ 10.85 (s, 1H), 8.75 (s, 1H), 8.46 (s, 1H), 7.52 (br d, J=8.5 Hz, 1H), 6.28 (br d, J=8.9 Hz, 1H), 4.00 (s, 4H), 2.84-2.77 (m, 1H), 2.16 (s, 3H), 1.36 (br d, J=6.7 Hz, 6H).

Example 741

6-(3-isopropyl-5-(6-methyl-2,6-diazaspiro[3.3]heptan-2-yl)-1H-pyrrolo[3,2-b]pyridin-2-yl)-7,8-dimethyl-[1,2,4]triazolo[1,5-a]pyridine (741)

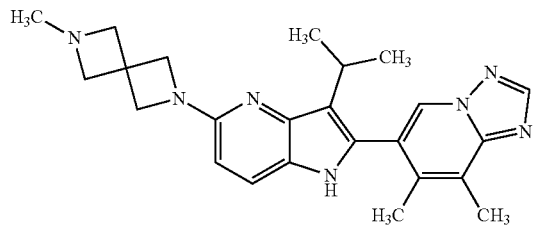

6-(3-isopropyl-5-(2,6-diazaspiro[3.3]heptan-2-yl)-1H-pyrrolo[3,2-b]pyridin-2-yl)-7,8-dimethyl-[1,2,4]triazolo[1,5-a]pyridine, TFA (15.93 mg, 0.0309 mmol) and Et$_3$N (0.05 mL, 0.359 mmol) were mixed in DMF (1 mL). Formaldehyde (37% wt in water, 25 µL, 0.336 mmol) was added to the reaction vial followed by sodium triacetoxyborohydride (54 mg, 0.255 mmol). The reaction mixture was stirred at room temperature for 90 minutes. Upon completion, the reaction was quenched by the addition of water, 1.5 M aqueous K$_2$HPO$_4$ solution, and DCM. The organic layer was separated and concentrated. The crude material was dissolved in DMF for purification via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by MS and UV signals. Fractions containing the product were combined and dried via centrifugal evaporation. The material was further purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 1% B, 1-41% B over 20 minutes, then a 4-minute hold at 100% B; Flow Rate: 20 mL/min; Column Temperature: 25° C. Fraction collection was triggered by MS signals. The fractions containing the product were combined and dried via centrifugal evaporation to afford 6-(3-isopropyl-5-(6-methyl-2,6-diazaspiro[3.3]heptan-2-yl)-1H-pyrrolo[3,2-b]pyridin-2-yl)-7,8-dimethyl-[1,2,4]triazolo[1,5-a]pyridine (3.2 mg, 7.70 µmol, 25% yield). LCMS retention time 1.29 [QC-ACN-AA-XB]. MS (E$^+$) m/z: 415.9 (M+H). Select NMR peaks: $^1$H NMR (500 MHz, DMSO-d$_6$) δ 10.82 (s, 1H), 8.73 (s, 1H), 8.45 (s, 1H), 7.51 (d, J=8.5 Hz, 1H), 6.26 (d, J=8.5 Hz, 1H), 3.96 (s, 4H), 2.84-2.75 (m, 1H), 2.57 (s, 3H), 2.22 (s, 3H), 2.14 (s, 3H), 1.34 (br d, J=6.7 Hz, 6H).

Example 742

2-(6-(2-(7,8-dimethyl-[1,2,4]triazolo[1,5-a]pyridin-6-yl)-3-isopropyl-1H-pyrrolo[3,2-b]pyridin-5-yl)-2,6-diazaspiro[3.3]heptan-2-yl)-N,N-dimethylacetamide (742)

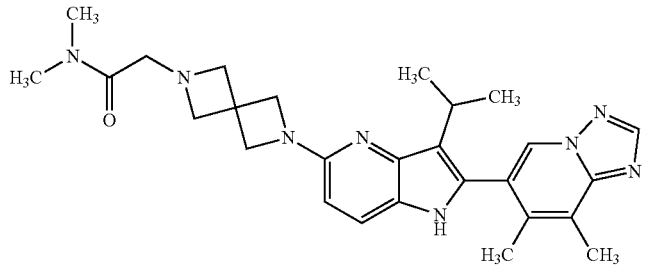

6-(3-isopropyl-5-(2,6-diazaspiro[3.3]heptan-2-yl)-1H-pyrrolo[3,2-b]pyridin-2-yl)-7,8-dimethyl-[1,2,4]triazolo[1,5-a]pyridine, TFA (15.93 mg, 0.0309 mmol) and DBU (0.05 mL, 0.332 mmol) were mixed in DMF (1 mL). Excess 2-chloro-N,N-dimethylacetamide (approximately 18 µL) was added to the reaction vial and the mixture was stirred for 1.5 hours. Upon completion, the reaction mixture was diluted with a few drops of water, DMF, and the crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 10% B, 10-50% B over 20 minutes, then a 4-minute hold at 100% B; Flow Rate: 20 mL/min; Column Temperature: 25 C. Fraction collection was triggered by MS signals. The fractions containing the product were combined and dried via centrifugal evaporation to afford 2-(6-(2-(7,8- dimethyl-[1,2,4]triazolo[1,5-a]pyridin-6-yl)-3-isopropyl-1H-pyrrolo[3,2-b]pyridin-5-yl)-2,6-diazaspiro[3.3]heptan-2-yl)-N,N-dimethylacetamide (6.6 mg, 0.013 mmol, 43.6% yield). LCMS retention time 1.33 [QC-ACN-AA-XB]. MS (E+) m/z: 486.9 (M+H). Select NMR peaks: $^1$H NMR (500 MHz, DMSO-$d_6$) δ 10.81 (s, 1H), 8.74 (s, 1H), 8.46 (s, 1H), 7.51 (d, J=8.5 Hz, 1H), 6.27 (d, J=8.5 Hz, 1H), 2.58 (s, 3H), 2.15 (s, 3H), 1.35 (br d, J=6.4 Hz, 6H).

Example 743

1-(6-(2-(7,8-dimethyl-[1,2,4]triazolo[1,5-a]pyridin-6-yl)-3-isopropyl-1H-pyrrolo[3,2-b]pyridin-5-yl)-2,6-diazaspiro[3.3]heptan-2-yl)-2-(dimethylamino)ethan-1-one

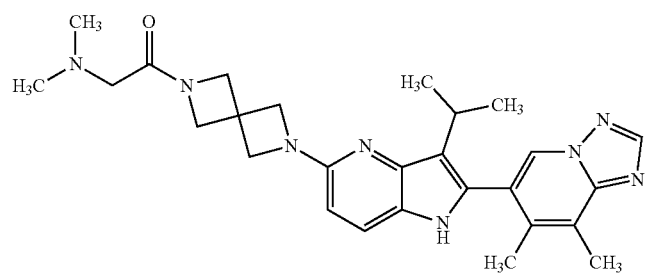

(743)

A solution of 6-(3-isopropyl-5-(2,6-diazaspiro[3.3]heptan-2-yl)-1H-pyrrolo[3,2-b]pyridin-2-yl)-7,8-dimethyl-[1,2,4]triazolo[1,5-a]pyridine, TFA (15.93 mg, 0.0309 mmol) in methanol was converted to the HCl salt form by adding 1 mL of 4 N HCl in dioxane and concentrating to dryness. The material was taken up in methanol a second time, 1 mL of 4N HCl in dioxane was again added, and the material was concentrated to dryness. The material was then suspended in DMF (1 mL) and N,N-dimethylglycine (20 mg, 0.194 mmol), Et$_3$N (0.1 mL, 0.717 mmol), and T3P (50% in DMF, 0.090 mL, 0.155 mmol) were added sequentially at room temperature with stirring. After 1.5 hours, another aliquot of N,N-dimethylglycine (9 mg, 0.087 mmol), Et$_3$N (0.1 mL, 0.717 mmol), and T3P (50% in DMF, 0.090 mL, 0.155 mmol) were added and the reaction mixture was stirred for 26 hours at room temperature. Upon completion, the reaction was quenched by the addition of water, 1.5 M aqueous K$_2$HPO$_4$ solution, and DCM. The organic layer was separated, concentrated, and the crude isolate was diluted with DMF. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 16% B, 16-56% B over 20 minutes, then a 4-minute hold at 100% B; Flow Rate: 20 mL/min; Column Temperature: 25° C. Fraction collection was triggered by MS signals. Fractions containing the product were combined and dried via centrifugal evaporation. The material was further purified via preparative LC/MS with the following conditions: Column: XBridge Phenyl, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 12% B, 12-52% B over 25 minutes, then a 6-minute hold at 100% B; Flow Rate: 20 mL/min; Column Temperature: 25° C. Fraction collection was triggered by MS signals. The fractions containing the product were combined and dried via centrifugal evaporation to afford 1-(6-(2-(7,8-dimethyl-[1,2,4]triazolo[1,5-a]pyridin-6-yl)-3-isopropyl-1H-pyrrolo[3,2-b]pyridin-5-yl)-2,6-diazaspiro[3.3]heptan-2-yl)-2-(dimethylamino)ethan-1-one (2.5 mg, 5.03 μmol, 16% yield). LCMS retention time 1.17 [QC-ACN-AA-XB]. MS (E+) m/z: 487.1 (M+H). $^1$H NMR (500 MHz, DMSO-$d_6$) δ 10.85 (s, 1H), 8.72 (s, 1H), 8.45 (s, 1H), 7.53 (br d, J=8.9 Hz, 1H), 6.29 (br d, J=8.5 Hz, 1H), 4.35 (s, 2H), 4.07 (br s, 2H), 4.04 (s, 4H), 2.90 (s, 2H), 2.84-2.74 (m, 1H), 2.57 (s, 3H), 2.17 (s, 6H), 2.14 (s, 3H), 1.34 (br d, J=6.4 Hz, 6H).

Example 744

6-(5-(6-ethyl-2,6-diazaspiro[3.3]heptan-2-yl)-3-isopropyl-1H-pyrrolo[3,2-b]pyridin-2-yl)-7,8-dimethyl-[1,2,4]triazolo[1,5-a]pyridine

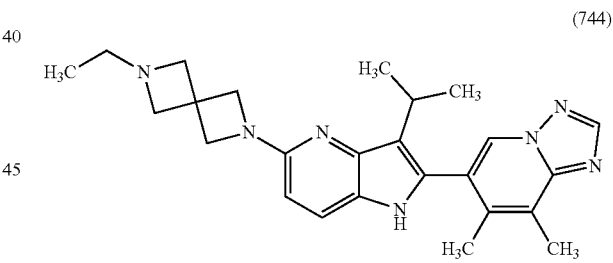

(744)

Alternate synthesis of Intermediate 740A: tert-butyl 5-(6-(tert-butoxycarbonyl)-2,6-diazaspiro[3.3]heptan-2-yl)-2-(7,8-dimethyl-[1,2,4]triazolo[1,5-a]pyridin-6-yl)-3-isopropyl-1H-pyrrolo[3,2-b]pyridine-1-carboxylate

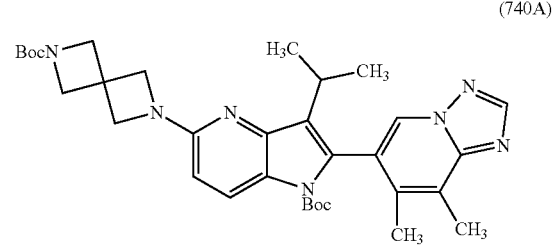 [SMILES: Cc1c(-c2c(C(C)C)c3nc(C4CC5(C4)CN(C(=O)OC(C)(C)C)C5)ccc3n2C(=O)OC(C)(C)C)cn2ncnc2c1C]

(740A)

A suspension of tert-butyl 5-bromo-2-(7,8-dimethyl-[1,2,4]triazolo[1,5-a]pyridin-6-yl)-3-isopropyl-1H-pyrrolo[3,2-b]pyridine-1-carboxylate (332 mg, 0.685 mmol), Pd$_2$(dba)$_3$ (62.8 mg, 0.069 mmol), dicyclohexyl(2',6'-di-isopropoxy-[1,1'-biphenyl]-2-yl)phosphine (38.4 mg, 0.082 mmol), and Cs$_2$CO$_3$ (902 mg, 2.77 mmol) in 1,4-dioxane (6.9 mL) in a vial with a pressure-relief septum-lined cap and stir bar was degassed with nitrogen for 5 minutes. The mixture was sealed and placed in a heating block at 105° C. with stirring for 7 hrs and then remained at room temperature overnight. The reaction mixture was filtered, concentrated, and purified by silica gel column chromatography eluting with Hex/EtOAc 0-100% to afford tert-butyl 5-(6-(tert-butoxycarbonyl)-2,6-diazaspiro[3.3]heptan-2-yl)-2-(7,8-dimethyl-[1,2,4]triazolo[1,5-a]pyridin-6-yl)-3-isopropyl-1H-pyrrolo[3,2-b]pyridine-1-carboxylate (0.685 mmol) considered to be quantitative recovery.

Alternate Synthesis of Example 740: 6-(3-isopropyl-5-(2,6-diazaspiro[3.3]heptan-2-yl)-1H-pyrrolo[3,2-b]pyridin-2-yl)-7,8-dimethyl-[1,2,4]triazolo[1,5-a]pyridine

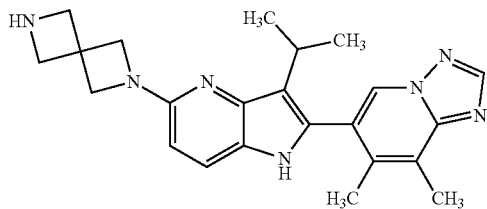

(740)

A solution of tert-butyl 5-(6-(tert-butoxycarbonyl)-2,6-diazaspiro[3.3]heptan-2-yl)-2-(7,8-dimethyl-[1,2,4]triazolo[1,5-a]pyridin-6-yl)-3-isopropyl-1H-pyrrolo[3,2-b]pyridine-1-carboxylate (0.685 mmol) in TFA (3.5 mL) at room temperature was stirred for 2 hours. Upon completion, the material was concentrated, taken up in 3/1 CHCl$_3$/iPrOH and neutralized by mixing with 1.5 M aqueous K$_2$HPO$_4$ solution and water in a separatory funnel. The aqueous layer was extracted with 3/1 CHC3/iPrOH. The combined organic layer was dried over sodium sulfate, filtered, and concentrated to afford crude material, considered quantitative recovery of 6-(3-isopropyl-5-(2,6-diazaspiro[3.3]heptan-2-yl)-1H-pyrrolo[3,2-b]pyridin-2-yl)-7,8-dimethyl-[1,2,4]triazolo[1,5-a]pyridine (0.685 mmol). LCMS retention time 0.53 [TS]. MS (E$^+$) m/z: 402.3 (M+H).

Intermediate 744A: 1-(6-(2-(7,8-dimethyl-[1,2,4]triazolo[1,5-a]pyridin-6-yl)-3-isopropyl-1H-pyrrolo[3,2-b]pyridin-5-yl)-2,6-diazaspiro[3.3]heptan-2-yl)ethan-1-one

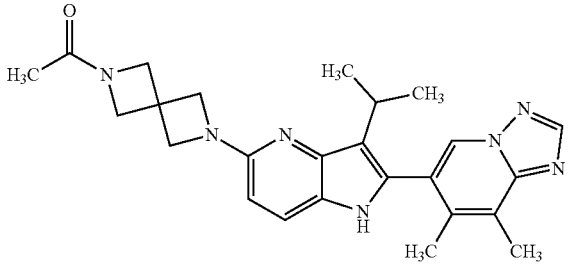

(744A)

To a stirred suspension of 6-(3-isopropyl-5-(2,6-diazaspiro[3.3]heptan-2-yl)-1H-pyrrolo[3,2-b]pyridin-2-yl)-7,8-dimethyl-[1,2,4]triazolo[1,5-a]pyridine (0.173 mmol) in DCM (3 mL) were sequentially added Et$_3$N (0.121 mL, 0.865 mmol) and acetic anhydride (0.025 mL, 0.260 mmol). After 10 minutes, the reaction mixture was concentrated to afford crude material. This material was purified by silica gel column chromatography on a Teledyne Isco instrument eluting with Hex/EtOAc 0-100% then DCM/MeOH 0-10% to afford 1-(6-(2-(7,8-dimethyl-[1,2,4]triazolo[1,5-a]pyridin-6-yl)-3-isopropyl-1H-pyrrolo[3,2-b]pyridin-5-yl)-2,6-diazaspiro[3.3]heptan-2-yl)ethan-1-one (66 mg, 0.149 mmol, 86% yield). LCMS retention time 0.60 [TS]. MS (E$^+$) m/z: 444.5 (M+H).

Example 744

To a stirred solution of 1-(6-(2-(7,8-dimethyl-[1,2,4]triazolo[1,5-a]pyridin-6-yl)-3-isopropyl-1H-pyrrolo[3,2-b]pyridin-5-yl)-2,6-diazaspiro[3.3]heptan-2-yl)ethan-1-one (66 mg, 0.149 mmol) in THF (3 mL) was added LiAlH4 (17 mg, 0.446 mmol), and the vial was sealed at room temperature. After 90 minutes, the reaction was quenched by the addition of DCM and 1.5 M aqueous K$_2$HPO$_4$ solution. The organic layer was separated and the aqueous layer was extracted with DCM. The combined organic layer was dried over sodium sulfate, filtered, and concentrated. The obtained crude material was taken up in DMF and purified by preparative LC/MS with the following conditions: Column: XBridge C18, 200 mm×30 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 9% B, 9-49% B over 20 minutes, then a 2-minute hold at 100% B; Flow Rate: 45 mL/min; Column Temperature: 25° C. Fraction collection was triggered by MS and UV signals. Fractions containing the product were combined and dried via centrifugal evaporation. The material was further purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 8% B, 8-48% B over 20 minutes, then a 4-minute hold at 100% B; Flow Rate: 20 mL/min; Column Temperature: 25 C. Fraction collection was triggered by MS and UV signals. The fractions containing the product were combined and dried via centrifugal evaporation to afford 6-(5-(6-ethyl-2,6-diazaspiro[3.3]heptan-2-yl)-3-isopropyl-1H pyrrolo[3,2-b]pyridin-2-yl)-7,8-dimethyl-[1,2,4]triazolo[1,5-a]pyridine (43.4 mg, 0.100 mmol, 67.5% yield). LCMS retention time 1.31 [QC-ACN-AA-XB]. MS (E⁺) m/z: 430.1 (M+H). $^1$H NMR (500 MHz, DMSO-d$_6$) δ 10.83 (s, 1H), 8.67 (s, 1H), 8.44 (s, 1H), 7.53 (d, J=8.9 Hz, 1H), 6.28 (d, J=8.5 Hz, 1H), 3.99 (s, 4H), 2.83-2.75 (m, 1H), 2.68-2.59 (m, 2H), 2.55 (s, 3H), 2.12 (s, 3H), 1.32 (br d, J=6.4 Hz, 6H), 0.93 (br t, J=7.0 Hz, 3H).

Example 745

6-(3-isopropyl-5-(2-azaspiro[3.3]heptan-6-yl)-1H-pyrrolo[3,2-b]pyridin-2-yl)-7,8-dimethyl-[1,2,4]triazolo[1,5-a]pyridine

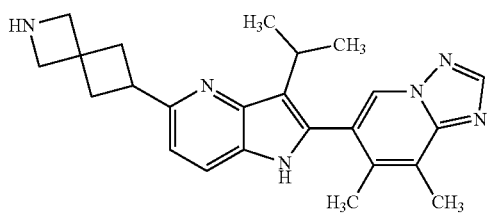

(745)

Intermediate 745A: tert-butyl 6-((methylsulfonyl)oxy)-2-azaspiro[3.3]heptane-2-carboxylate

(745A)

To a solution of tert-butyl 6-hydroxy-2-azaspiro[3.3]heptane-2-carboxylate (2.0 g, 9.38 mmol) in DCM (45 mL) at room temperature was added Et$_3$N (3.27 mL, 23.4 mmol) and MsCl (1.1 mL, 14.1 mmol) sequentially. After 3.25 hours, the reaction was quenched by the addition of water and DCM. The layers were separated and the aqueous layer was extracted with DCM. The combined organic layer was dried over sodium sulfate, filtered, and concentrated to afford crude material considered to be quantitative of tert-butyl 6-((methylsulfonyl)oxy)-2-azaspiro[3.3]heptane-2-carboxylate (9.38 mmol, 100% yield).

Intermediate 745B: tert-butyl 6-iodo-2-azaspiro[3.3]heptane-2-carboxylate

(745B)

tert-Butyl 6-((methylsulfonyl)oxy)-2-azaspiro[3.3]heptane-2-carboxylate (4.69 mmol) was suspended in ethyl methyl ketone (19 mL) and sodium iodide (3.52 g, 23.5 mmol) was added. The mixture was degassed with nitrogen gas for 10 minutes, then the reaction vial sealed with a pressure-relief septum-lined cap and heated to 100° C. with stirring for 19.75 hours. An identical reaction was set up in duplicate and run in parallel. Upon completion, the reaction mixtures were cooled to room temperature and quenched by the addition of water and DCM. The parallel reaction mixtures were combined for workup. The layers were separated, and the aqueous layer was extracted with DCM. The combined organic layer was dried over sodium sulfate, filtered, and concentrated to afford a crude oil. This material was dissolved in DCM and purified on silica gel column chromatography on a Teledyne Isco instrument eluting with Hex/EtOAc 0-60%. The fractions containing the material were concentrated and repurified as above eluting with Hex/EtOAc 0-40% to give tert-butyl 6-iodo-2-azaspiro[3.3]heptane-2-carboxylate (2.1 g) total combined from both parallel runs as a white solid. $^1$H NMR (499 MHz, CHLOROFORM-d) δ 4.29 (quin, J=7.8 Hz, 1H), 3.95 (s, 2H), 3.92 (s, 2H), 2.97-2.87 (m, 2H), 2.75-2.66 (m, 2H), 1.42 (s, 9H).

Intermediate 745C: tert-butyl 5-(2-(tert-butoxycarbonyl)-2-azaspiro[3.3]heptan-6-yl)-2-(7,8-dimethyl-[1,2,4]triazolo[1,5-a]pyridin-6-yl)-3-isopropyl-1H-pyrrolo[3,2-b]pyridine-1-carboxylate

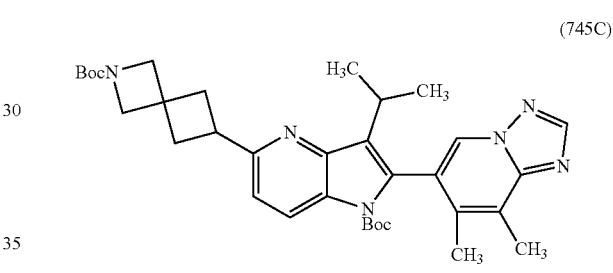

(745C)

In a 100-mL round-bottom flask with a stir bar, a suspension of tert-butyl 5-bromo-2-(7,8-dimethyl-[1,2,4]triazolo[1,5-a]pyridin-6-yl)-3-isopropyl-1H-pyrrolo[3,2-b]pyridine-1-carboxylate (1.57 g, 3.25 mmol), tert-butyl 6-iodo-2-azaspiro[3.3]heptane-2-carboxylate (2.1 g, 6.50 mmol), tris(trimethylsilyl)silane (1.21 g, 4.87 mmol), [Ir(dF(CF$_3$)ppy)$_2$(dtbbpy)]PF$_6$ (0.036 g, 0.032 mmol), and Na$_2$CO$_3$ (1.38 g, 13.0 mmol) in 1,4-dioxane (30 mL) was degassed through a rubber septum with a line of nitrogen gas for 15 minutes. To a vial with a stir bar was added nickel(II) chloride ethylene glycol dimethyl ether complex (0.018 g, 0.081 mmol) and 4,4'-di-tert-butyl-2,2'-bipyridine (0.026 g, 0.097 mmol), which was purged with nitrogen gas. 1,4-Dioxane (6 mL) was added and the resulting mixture was degassed with nitrogen gas for 10 minutes and stirred. The resulting solution was then added to the reaction flask. The resulting mixture was further degassed with nitrogen gas for another 15 minutes, and then the nitrogen gas line was removed and a nitrogen balloon was affixed to the flask via a needle through the septum. The reaction vessel was secured over a stir plate with stirring, a cooling fan, and irradiation from 34 W Kessil KSH 150B blue grow lamps (12 cm apart, flask in between) for 66 hours. Upon completion, the reaction mixture was filtered, concentrated, and redissolved in DCM. The material was purified by silica gel column chromatography on a Teledyne Isco instrument eluting with Hex/EtOAc 0-60% to afford tert-butyl 5-(2-(tert-butoxycarbonyl)-2-azaspiro[3.3]heptan-6-yl)-2-(7,8-dimethyl-[1,2,4]triazolo[1,5-a]pyridin-6-yl)-3-isopropyl-1H-pyrrolo[3,2-b]pyridine-1-carboxylate (1.27 g, 2.11 mmol, 65.1% yield) containing a small amount of co-eluting impurities. LCMS retention time 1.13 [TS]. MS (E⁺) m/z: 601.7 (M+H). ¹H NMR (499 MHz, CHLOROFORM-d) δ 8.35 (s, 1H), 8.34 (d, J=8.6 Hz, 1H), 8.33 (s, 1H), 7.05 (d, J=8.6 Hz, 1H), 4.05 (s, 2H), 3.96 (s, 2H), 3.60 (quin, J=8.1 Hz, 1H), 2.86-2.77 (m, 1H), 2.66 (s, 3H), 2.65-2.56 (m, 4H), 2.13 (s, 3H), 1.46-1.41 (m, 15H), 1.22 (s, 9H).

Example 745

A solution of tert-butyl 5-(2-(tert-butoxycarbonyl)-2-azaspiro[3.3]heptan-6-yl)-2-(7,8-dimethyl-[1,2,4]triazolo[1,5-a]pyridin-6-yl)-3-isopropyl-1H-pyrrolo[3,2-b]pyridine-1-carboxylate (584 mg, 0.972 mmol) in TFA (6 mL) was stirred for 2 hours at room temperature. Upon completion, the reaction mixture was concentrated and dissolved in 3/1 CHCl₃/iPrOH. This organic layer was neutralized by mixing in a separatory funnel with 1.5 M aqueous K₂HPO₄ solution. The aqueous layer was extracted with 3/1 CHCl₃/iPrOH, and the combined organic layer was dried over sodium sulfate, filtered, and concentrated to afford material considered to be quantitative recovery of 6-(3-isopropyl-5-(2-azaspiro[3.3]heptan-6-yl)-1H-pyrrolo[3,2-b]pyridin-2-yl)-7,8-dimethyl-[1,2,4]triazolo[1,5-a]pyridine (0.972 mmol). The majority of this material was carried forward as is. A portion (5%) of this material was purified by preparative LCMS using the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 5% B, 5-45% B over 20 minutes, then a 4-minute hold at 100% B; Flow Rate: 20 mL/min; Column Temperature: 25° C. Fraction collection was triggered by MS and UV signals. Fractions containing the product were combined and dried via centrifugal evaporation. The material was further purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 5% B, 5-55% B over 20 minutes, then a 4-minute hold at 100% B; Flow Rate: 20 mL/min; Column Temperature: 25° C. Fraction collection was triggered by MS signals. The fractions containing the product were combined and dried via centrifugal evaporation to afford 6-(3-isopropyl-5-(2-azaspiro[3.3]heptan-6-yl)-1H-pyrrolo[3,2-b]pyridin-2-yl)-7,8-dimethyl-[1,2,4]triazolo[1,5-a]pyridine (4.5 mg, 0.0106 mmol). LCMS retention time 1.05 [QC-ACN-TFA-XB]. MS (E⁺) m/z: 401.3 (M+H). Select NMR peaks: ¹H NMR (500 MHz, DMSO-d₆) δ 8.76 (s, 1H), 8.46 (s, 1H), 7.59 (d, J=8.5 Hz, 1H), 6.96 (d, J=8.2 Hz, 1H), 2.93-2.83 (m, 1H), 2.58 (s, 3H), 2.15 (s, 3H), 1.39 (br d, J=6.7 Hz, 6H).

Example 746

1-(6-(2-(7,8-dimethyl-[1,2,4]triazolo[1,5-a]pyridin-6-yl)-3-isopropyl-1H-pyrrolo[3,2-b]pyridin-5-yl)-2-azaspiro[3.3]heptan-2-yl)-3-(dimethylamino)propan-1-one

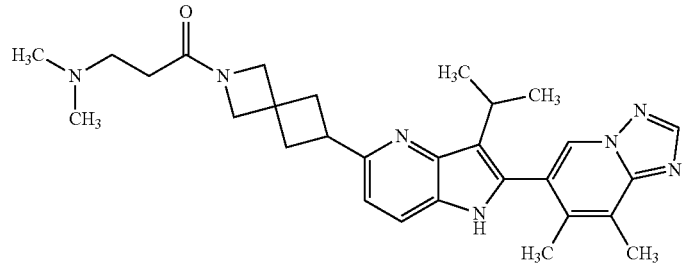

(746)

To a solution of 6-(3-isopropyl-5-(2-azaspiro[3.3]heptan-6-yl)-1H-pyrrolo[3,2-b]pyridin-2-yl)-7,8-dimethyl-[1,2,4]triazolo[1,5-a]pyridine (19.5 mg, 0.0486 mmol), 3-(dimethylamino)propanoic acid (18 mg, 0.154 mmol), and Et₃N (0.05 mL, 0.359 mmol) in DMF (1 mL) was added T3P (0.057 mL, 0.097 mmol). The mixture was stirred at room temperature for 1.5 hours. Upon completion, the reaction was quenched. The reaction mixture was worked up by the addition of water, 1.5 M aqueous K₂HPO₄ solution, and DCM. The organic layer was separated, concentrated, and diluted with DMF. The material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 10% B, 10-50% B over 25 minutes, then a 4-minute hold at 100% B; Flow Rate: 20 mL/min; Column Temperature: 25° C. Fraction collection was triggered by MS signals. Fractions containing the product were combined and dried via centrifugal evaporation to afford 1-(6-(2-(7,8-dimethyl-[1,2,4]triazolo[1,5-a] pyridin-6-yl)-3-isopropyl-1H-pyrrolo[3,2-b]pyridin-5-yl)-2-azaspiro[3.3]heptan-2-yl)-3-(dimethylamino)propan-1-one (6.2 mg, 0.012 mmol, 24% yield). LCMS retention time 1.31 [QC-ACN-AA-XB]. MS (E⁺) m/z: 500.3 (M+H). Select NMR peaks, rotamers present: ¹H NMR (500 MHz, DMSO-d₆) δ 11.13 (br s, 1H), 8.80 (s, 1H), 8.47 (s, 1H), 7.60 (d, J=8.5 Hz, 1H), 6.97 (br d, J=8.5 Hz, 1H), 4.25 (s, 1H), 4.17 (s, 1H), 3.96 (s, 1H), 3.84 (s, 1H), 3.62-3.52 (m, 1H), 2.94-2.86 (m, 1H), 2.59 (s, 3H), 2.16 (s, 6H), 2.14 (s, 3H), 1.47-1.37 (m, 6H).

The following examples were prepared according to the general procedures described in the above examples.

TABLE 2

| Ex. No. | Structure | Obs. MS Ion | RT | QC Method |
|---|---|---|---|---|
| 737 | 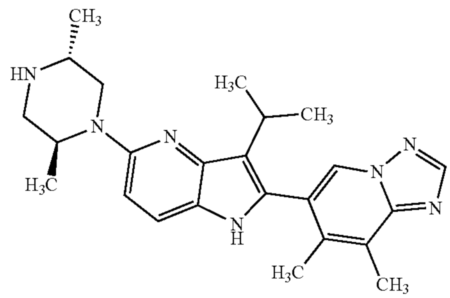 [SMILES: Cc1c(-c2[nH]c3ccc(N4C[C@@H](C)NC[C@@H]4C)nc3c2C(C)C)cn2ncnc2c1C] | 418.40 | 1.26 | QC-ACN-AA-XB |
| 738 | 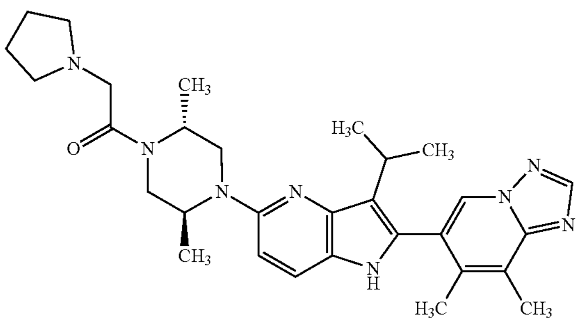 [SMILES: Cc1c(-c2[nH]c3ccc(N4C[C@@H](C)N(C(=O)CN5CCCC5)C[C@@H]4C)nc3c2C(C)C)cn2ncnc2c1C] | 529.30 | 0.89 | QC-ACN-TFA-XB |
| 739 | 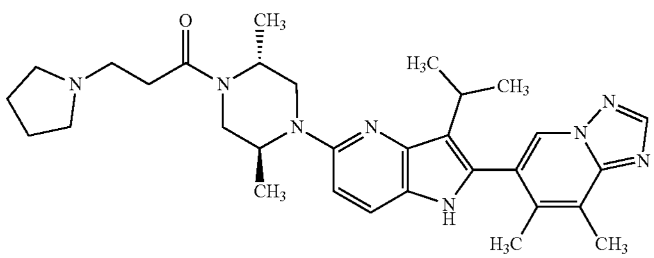 [SMILES: Cc1c(-c2[nH]c3ccc(N4C[C@@H](C)N(C(=O)CCN5CCCC5)C[C@@H]4C)nc3c2C(C)C)cn2ncnc2c1C] | 543.40 | 1.07 | QC-ACN-TFA-XB |
| 740 | 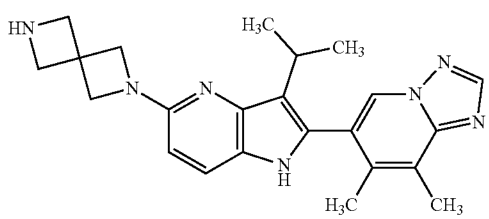 [SMILES: Cc1c(-c2[nH]c3ccc(N4CC5(CNC5)C4)nc3c2C(C)C)cn2ncnc2c1C] | 402.30 | 0.97 | QC-ACN-TFA-XB |
| 741 | 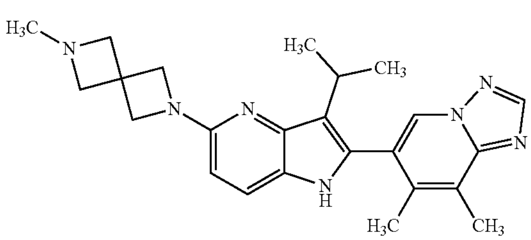 [SMILES: Cc1c(-c2[nH]c3ccc(N4CC5(CN(C)C5)C4)nc3c2C(C)C)cn2ncnc2c1C] | 415.90 | 1.29 | QC-ACN-AA-XB |

TABLE 2-continued

| Ex. No. | Structure | Obs. MS Ion | RT | QC Method |
|---|---|---|---|---|
| 742 | 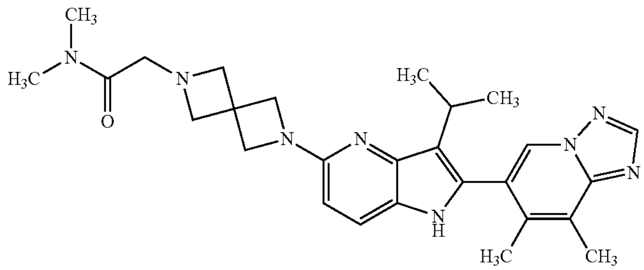 [SMILES: Cc1c(-c2[nH]c3ccc(N4CC5(CN(CC(=O)N(C)C)C5)C4)nc3c2C(C)C)cn2ncnc2c1C] | 487.20 | 0.96 | QC-ACN-TFA-XB |
| 743 | 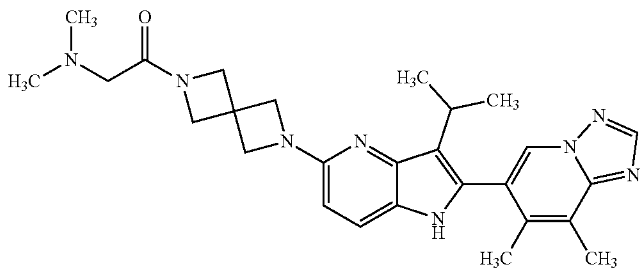 [SMILES: Cc1c(-c2[nH]c3ccc(N4CC5(CN(C(=O)CN(C)C)C5)C4)nc3c2C(C)C)cn2ncnc2c1C] | 486.90 | 0.99 | QC-ACN-TFA-XB |
| 744 | 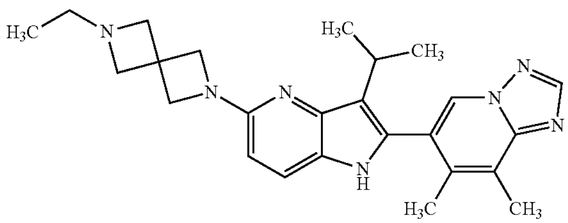 [SMILES: CCN1CC2(C1)CN(c1ccc3[nH]c(-c4cn5ncnc5c(C)c4C)c(C(C)C)c3n1)C2] | 430.10 | 1.21 | QC-ACN-AA-XB |
| 745 | 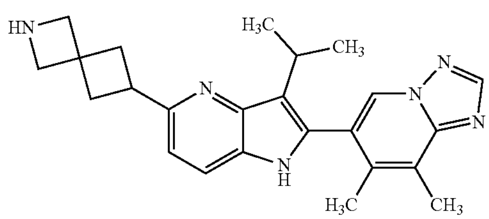 [SMILES: Cc1c(-c2[nH]c3ccc(C4CC5(CNC5)C4)nc3c2C(C)C)cn2ncnc2c1C] | 401.30 | 1.04 | QC-ACN-TFA-XB |
| 746 | 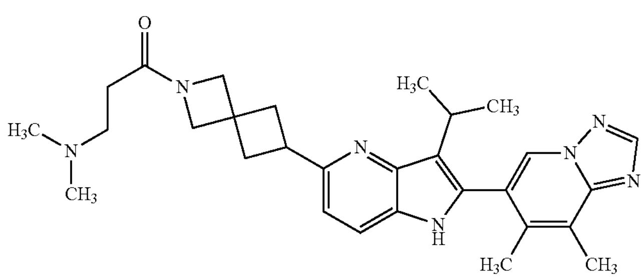 [SMILES: Cc1c(-c2[nH]c3ccc(C4CC5(C4)CN(C(=O)CCN(C)C)C5)nc3c2C(C)C)cn2ncnc2c1C] | 500.30 | 1.31 | QC-ACN-AA-XB |
| 747 | 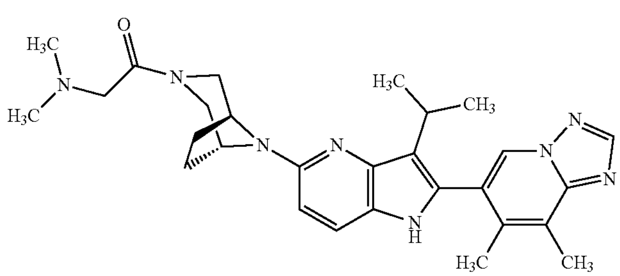 [SMILES: Cc1c(-c2[nH]c3ccc(N4[C@@H]5CC[C@H]4CN(C(=O)CN(C)C)C5)nc3c2C(C)C)cn2ncnc2c1C] | 501.50 | 1.45 | QC-ACN-AA-XB |

TABLE 2-continued

| Ex. No. | Structure | Obs. MS Ion | RT | QC Method |
|---|---|---|---|---|
| 748 | 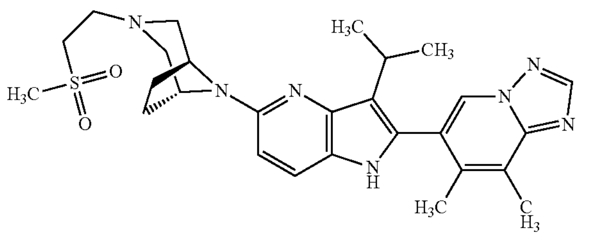 [SMILES: Cc1c(-c2[nH]c3ccc(N4[C@@H]5CC[C@H]4CN(CCS(C)(=O)=O)C5)nc3c2C(C)C)cn2ncnc2c1C] | 522.30 | 1.17 | QC-ACN-TFA-XB |
| 749 | 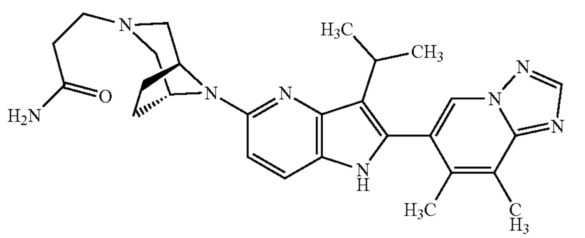 [SMILES: Cc1c(-c2[nH]c3ccc(N4[C@@H]5CC[C@H]4CN(CCC(N)=O)C5)nc3c2C(C)C)cn2ncnc2c1C] | 487.20 | 1.55 | QC-ACN-AA-XB |
| 750 | 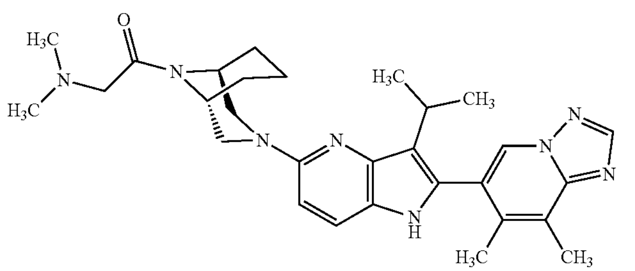 [SMILES: Cc1c(-c2[nH]c3ccc(N4C[C@H]5CCC[C@@H](C4)N5C(=O)CN(C)C)nc3c2C(C)C)cn2ncnc2c1C] | 515.40 | 1.02 | QC-ACN-TFA-XB |
| 751 | 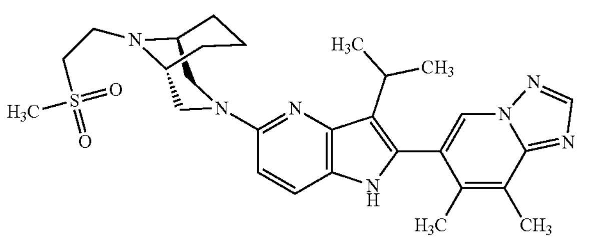 [SMILES: Cc1c(-c2[nH]c3ccc(N4C[C@H]5CCC[C@@H](C4)N5CCS(C)(=O)=O)nc3c2C(C)C)cn2ncnc2c1C] | 536.20 | 2.02 | QC-ACN-AA-XB |
| 752 | 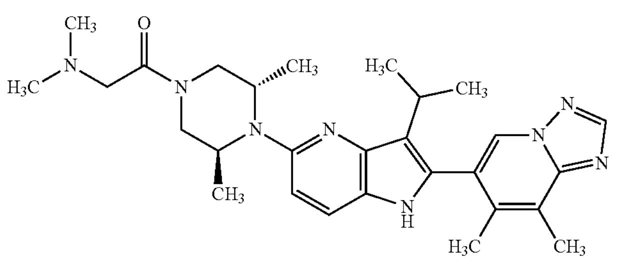 [SMILES: Cc1c(-c2[nH]c3ccc(N4[C@@H](C)CN(C(=O)CN(C)C)C[C@@H]4C)nc3c2C(C)C)cn2ncnc2c1C] | 503.40 | 1.42 | QC-ACN-AA-XB |
| 753 | 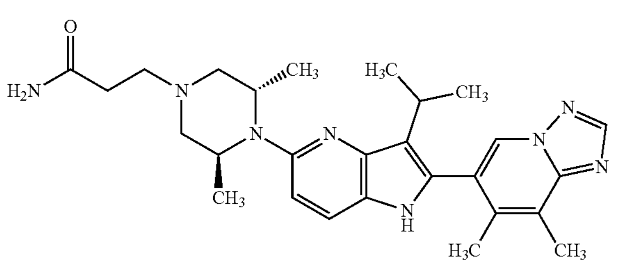 [SMILES: Cc1c(-c2[nH]c3ccc(N4[C@@H](C)CN(CCC(N)=O)C[C@@H]4C)nc3c2C(C)C)cn2ncnc2c1C] | 489.40 | 0.87 | QC-ACN-TFA-XB |

TABLE 2-continued

| Ex. No. | Structure | Obs. MS Ion | RT | QC Method |
|---|---|---|---|---|
| 754 | 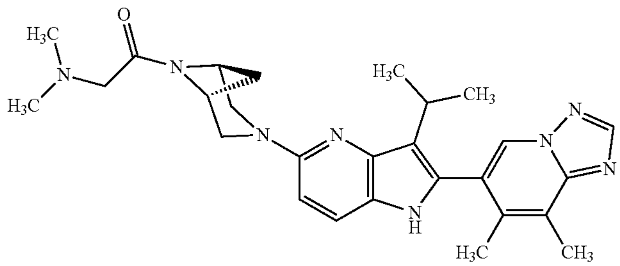 [SMILES: Cc1c(-c2[nH]c3ccc(N4C[C@H]5C[C@@H](C4)N5C(=O)CN(C)C)nc3c2C(C)C)cn2ncnc2c1C] | 487.10 | 1.53 | QC-ACN-AA-XB |
| 755 | 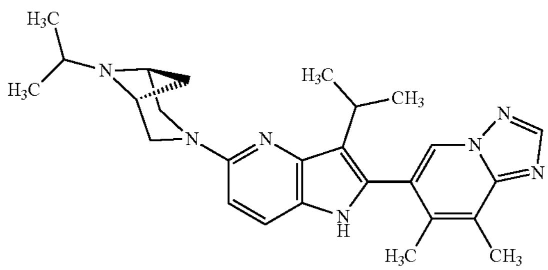 [SMILES: Cc1c(-c2[nH]c3ccc(N4C[C@H]5C[C@@H](C4)N5C(C)C)nc3c2C(C)C)cn2ncnc2c1C] | 444.20 | 1.33 | QC-ACN-AA-XB |
| 756 | 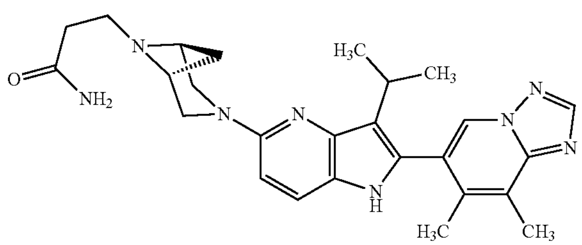 [SMILES: Cc1c(-c2[nH]c3ccc(N4C[C@H]5C[C@@H](C4)N5CCC(N)=O)nc3c2C(C)C)cn2ncnc2c1C] | 473.40 | 1.16 | QC-ACN-AA-XB |
| 757 | 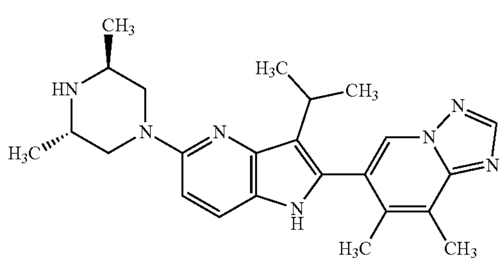 [SMILES: Cc1c(-c2[nH]c3ccc(N4C[C@H](C)N[C@@H](C)C4)nc3c2C(C)C)cn2ncnc2c1C] | 418.20 | 1.22 | QC-ACN-AA-XB |
| 758 | 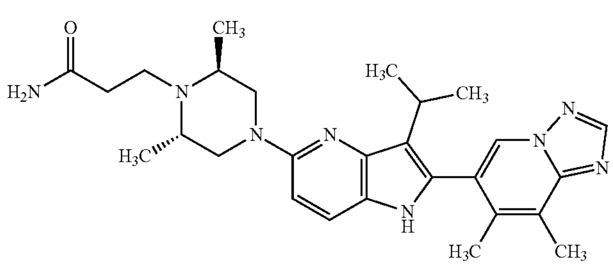 [SMILES: Cc1c(-c2[nH]c3ccc(N4C[C@H](C)N(CCC(N)=O)[C@@H](C)C4)nc3c2C(C)C)cn2ncnc2c1C] | 489.00 | 1.38 | QC-ACN-AA-XB |

TABLE 2-continued

| Ex. No. | Structure | Obs. MS Ion | RT | QC Method |
|---|---|---|---|---|
| 759 | 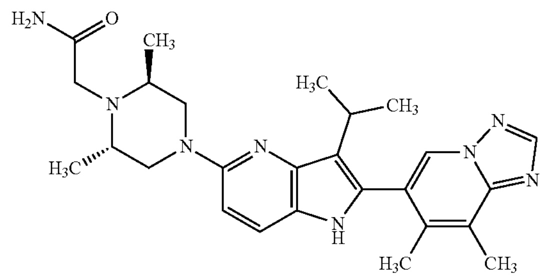 [SMILES: Cc1c(-c2[nH]c3ccc(N4C[C@H](C)N(CC(N)=O)[C@@H](C)C4)nc3c2C(C)C)cn2ncnc2c1C] | 475.20 | 1.73 | QC-ACN-AA-XB |
| 760 | 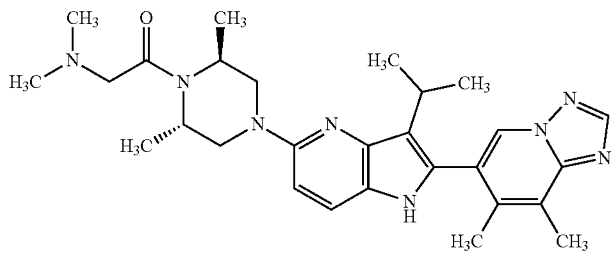 [SMILES: Cc1c(-c2[nH]c3ccc(N4C[C@H](C)N(C(=O)CN(C)C)[C@@H](C)C4)nc3c2C(C)C)cn2ncnc2c1C] | 503.30 | 0.84 | QC-ACN-TFA-XB |
| 761 | 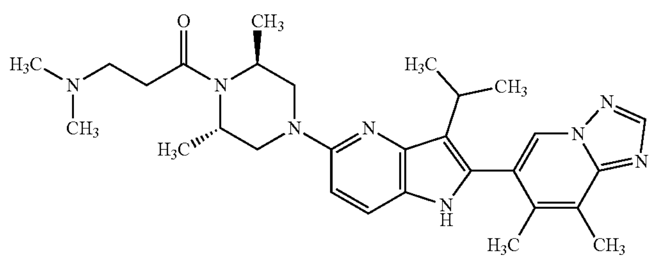 [SMILES: Cc1c(-c2[nH]c3ccc(N4C[C@H](C)N(C(=O)CCN(C)C)[C@@H](C)C4)nc3c2C(C)C)cn2ncnc2c1C] | 517.30 | 0.87 | QC-ACN-TFA-XB |
| 762 | 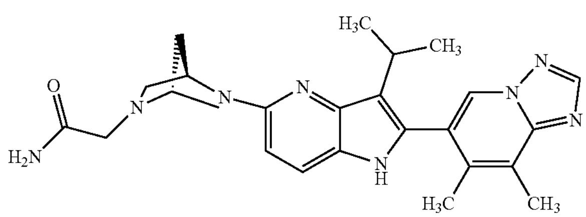 | 459.40 | 0.76 | QC-ACN-TFA-XB |
| 763 | 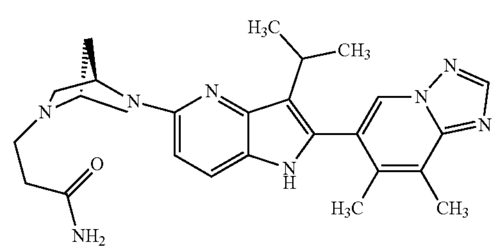 | 472.90 | 1.33 | QC-ACN-AA-XB |
| 764 | 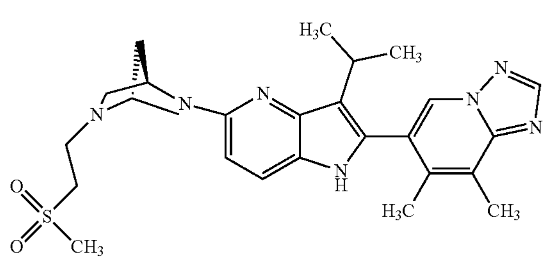 | 508.10 | 0.98 | QC-ACN-TFA-XB |

TABLE 2-continued

| Ex. No. | Structure | Obs. MS Ion | RT | QC Method |
|---|---|---|---|---|
| 765 | 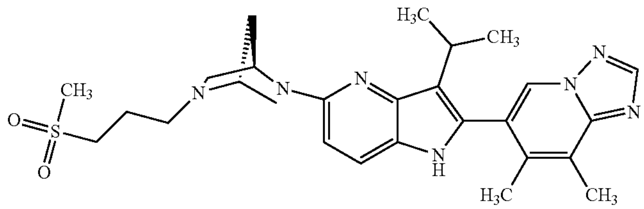 | 522.50 | 0.81 | QC-ACN-TFA-XB |
| 766 | 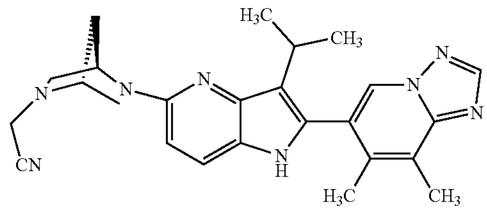 | 440.90 | 1.76 | QC-ACN-AA-XB |
| 767 | 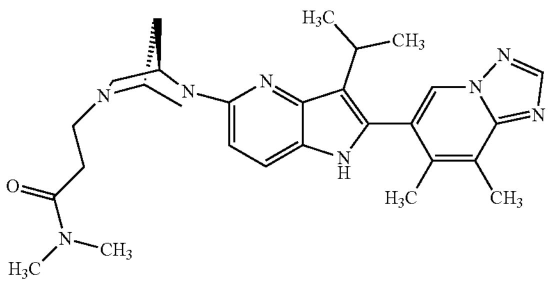 | 501.20 | 1.49 | QC-ACN-AA-XB |
| 768 | 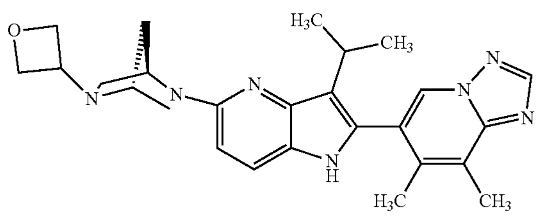 | 458.10 | 0.96 | QC-ACN-TFA-XB |
| 769 | 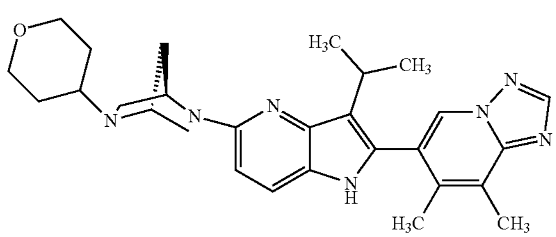 | 243.60 | 1.44 | QC-ACN-AA-XB |
| 770 | 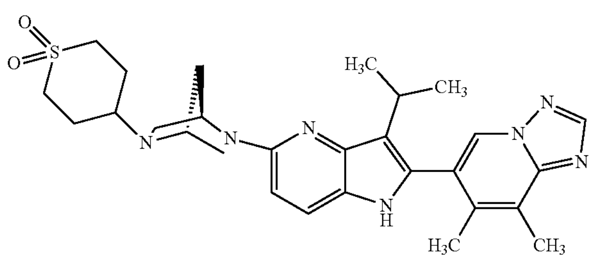 | 534.10 | 1.64 | QC-ACN-AA-XB |

TABLE 2-continued

| Ex. No. | Structure | Obs. MS Ion | RT | QC Method |
|---|---|---|---|---|
| 771 | 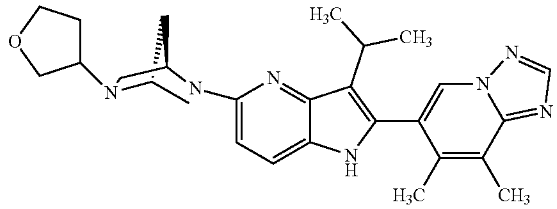 | 470.10 | 1.66 | QC-ACN-AA-XB |
| 772 | 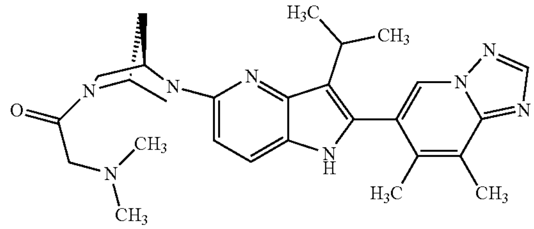 | 244.00 | 1.50 | QC-ACN-AA-XB |
| 773 | 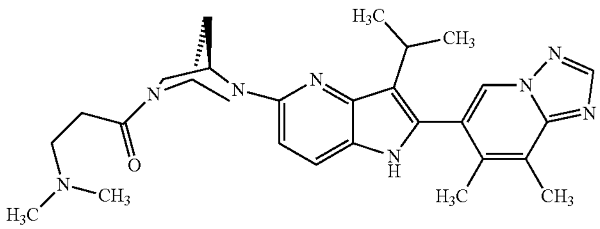 | 501.20 | 1.48 | QC-ACN-AA-XB |
| 774 | 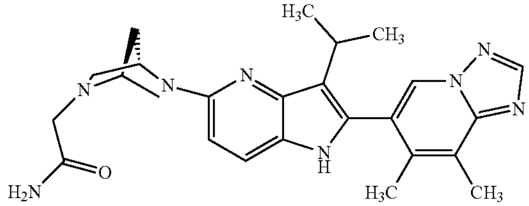 | 459.10 | 1.58 | QC-ACN-AA-XB |
| 775 | 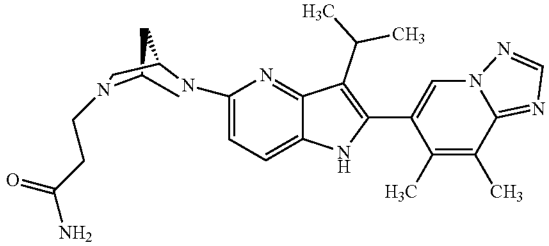 | 473.40 | 1.20 | QC-ACN-AA-XB |
| 776 | 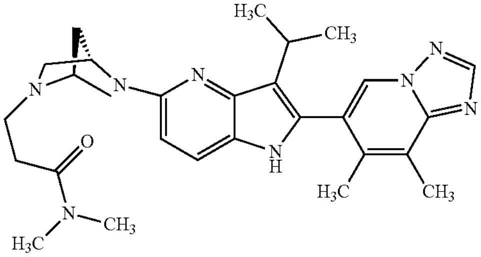 | 501.00 | 1.42 | QC-ACN-AA-XB |

TABLE 2-continued

| Ex. No. | Structure | Obs. MS Ion | RT | QC Method |
|---|---|---|---|---|
| 777 | 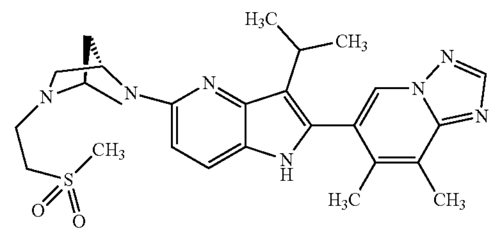 | 508.40 | 0.99 | QC-ACN-TFA-XB |
| 778 | 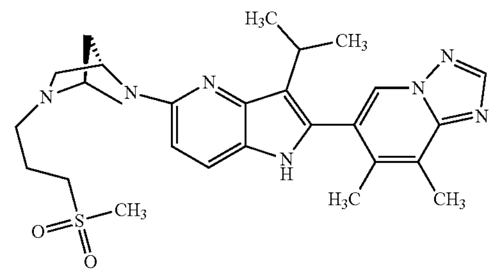 | 522.20 | 1.40 | QC-ACN-AA-XB |
| 779 | 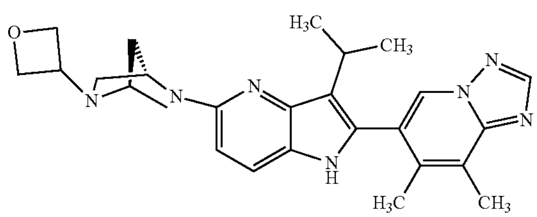 | 458.10 | 0.98 | QC-ACN-TFA-XB |
| 780 | 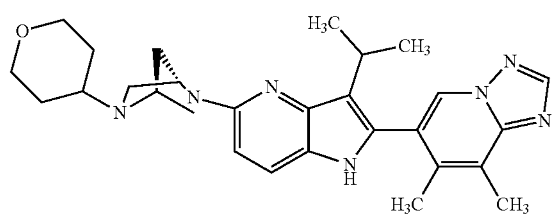 | 486.20 | 1.43 | QC-ACN-AA-XB |
| 781 | 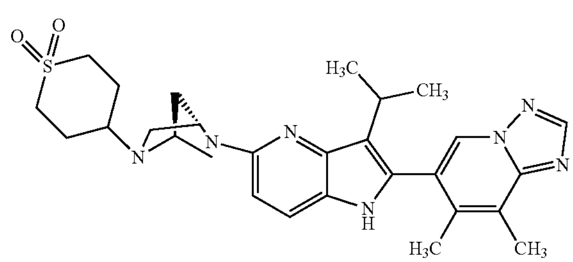 | 534.40 | 0.98 | QC-ACN-TFA-XB |
| 782 | 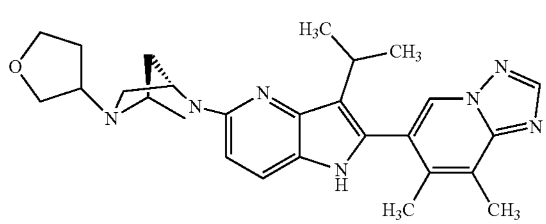 | 236.30 | 0.99 | QC-ACN-TFA-XB |

TABLE 2-continued

| Ex. No. | Structure | Obs. MS Ion | RT | QC Method |
|---|---|---|---|---|
| 783 | 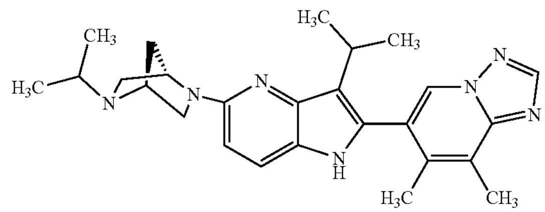 [SMILES: Cc1c(-c2[nH]c3ccc(N4C[C@@H]5C[C@H]4CN5C(C)C)nc3c2C(C)C)cn2ncnc2c1C] | 444.40 | 1.40 | QC-ACN-AA-XB |
| 784 | 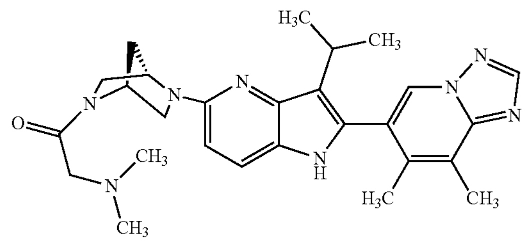 [SMILES: Cc1c(-c2[nH]c3ccc(N4C[C@@H]5C[C@H]4CN5C(=O)CN(C)C)nc3c2C(C)C)cn2ncnc2c1C] | 487.50 | 1.33 | QC-ACN-AA-XB |
| 785 | 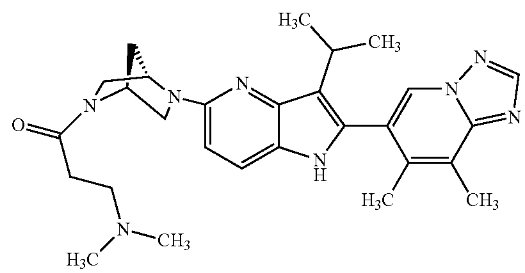 [SMILES: Cc1c(-c2[nH]c3ccc(N4C[C@@H]5C[C@H]4CN5C(=O)CCN(C)C)nc3c2C(C)C)cn2ncnc2c1C] | 501.50 | 0.82 | QC-ACN-TFA-XB |
| 786 | 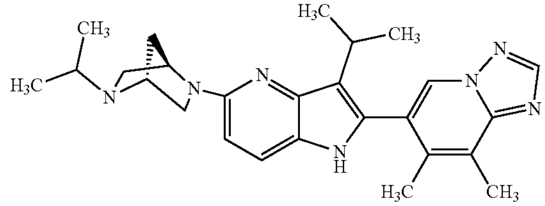 [SMILES: Cc1c(-c2[nH]c3ccc(N4C[C@H]5C[C@@H]4CN5C(C)C)nc3c2C(C)C)cn2ncnc2c1C] | 444.20 | 0.81 | QC-ACN-TFA-XB |
| 787 | 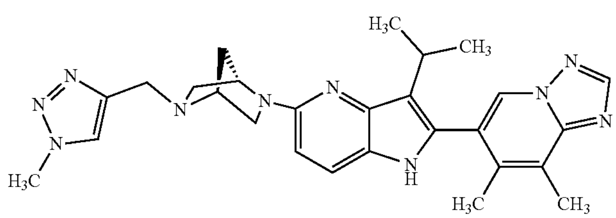 [SMILES: Cc1c(-c2[nH]c3ccc(N4C[C@@H]5C[C@H]4CN5Cc4cn(C)nn4)nc3c2C(C)C)cn2ncnc2c1C] | 497.30 | 0.80 | QC-ACN-TFA-XB |
| 788 | 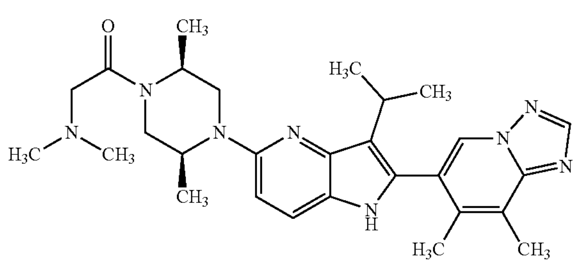 [SMILES: Cc1c(-c2[nH]c3ccc(N4C[C@H](C)N(C(=O)CN(C)C)C[C@@H]4C)nc3c2C(C)C)cn2ncnc2c1C] | 503.00 | 1.13 | QC-ACN-TFA-XB |

TABLE 2-continued

| Ex. No. | Structure | Obs. MS Ion | RT | QC Method |
|---|---|---|---|---|
| 789 | 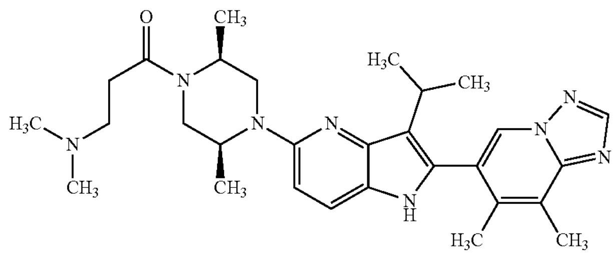 [SMILES: Cc1c(-c2[nH]c3ccc(N4C[C@H](C)N(C(=O)CCN(C)C)C[C@@H]4C)nc3c2C(C)C)cn2ncnc2c1C] | 517.40 | 0.92 | QC-ACN-TFA-XB |
| 790 | 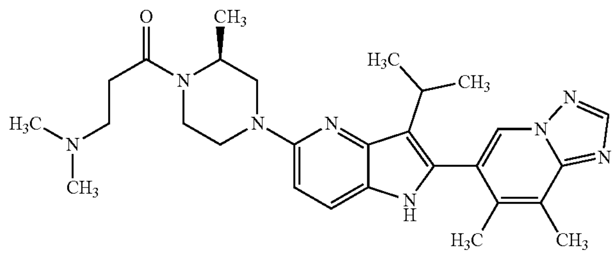 [SMILES: Cc1c(-c2[nH]c3ccc(N4CCN(C(=O)CCN(C)C)[C@@H](C)C4)nc3c2C(C)C)cn2ncnc2c1C] | 503.40 | 0.84 | QC-ACN-TFA-XB |
| 791 | 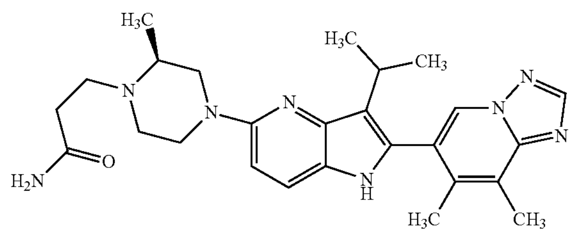 [SMILES: Cc1c(-c2[nH]c3ccc(N4CCN(CCC(N)=O)[C@@H](C)C4)nc3c2C(C)C)cn2ncnc2c1C] | 475.30 | 0.80 | QC-ACN-TFA-XB |
| 792 | 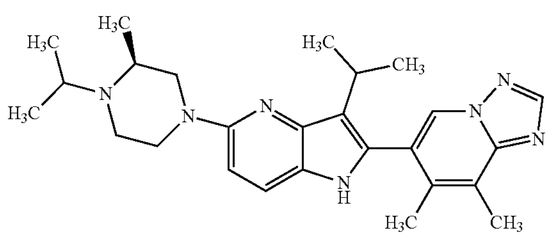 [SMILES: Cc1c(-c2[nH]c3ccc(N4CCN(C(C)C)[C@@H](C)C4)nc3c2C(C)C)cn2ncnc2c1C] | 446.20 | 1.15 | QC-ACN-TFA-XB |
| 793 | 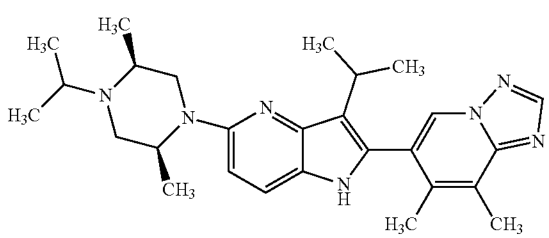 [SMILES: Cc1c(-c2[nH]c3ccc(N4C[C@H](C)N(C(C)C)C[C@@H]4C)nc3c2C(C)C)cn2ncnc2c1C] | 460.30 | 1.10 | QC-ACN-TFA-XB |
| 794 | 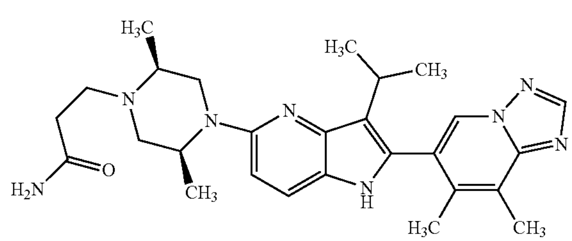 [SMILES: Cc1c(-c2[nH]c3ccc(N4C[C@H](C)N(CCC(N)=O)C[C@@H]4C)nc3c2C(C)C)cn2ncnc2c1C] | 489.30 | 0.98 | QC-ACN-TFA-XB |

TABLE 2-continued

| Ex. No. | Structure | Obs. MS Ion | RT | QC Method |
|---|---|---|---|---|
| 795 | 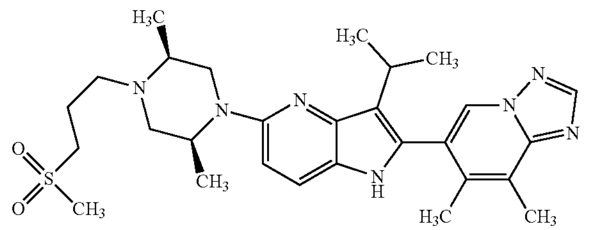 [SMILES: Cc1c(-c2[nH]c3ccc(N4C[C@H](C)N(CCCS(C)(=O)=O)C[C@@H]4C)nc3c2C(C)C)cn2ncnc2c1C] | 538.30 | 1.00 | QC-ACN-TFA-XB |
| 796 | 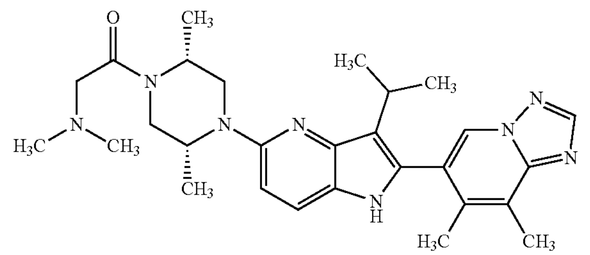 [SMILES: Cc1c(-c2[nH]c3ccc(N4C[C@@H](C)N(C(=O)CN(C)C)C[C@H]4C)nc3c2C(C)C)cn2ncnc2c1C] | 503.30 | 1.49 | QC-ACN-AA-XB |
| 797 | 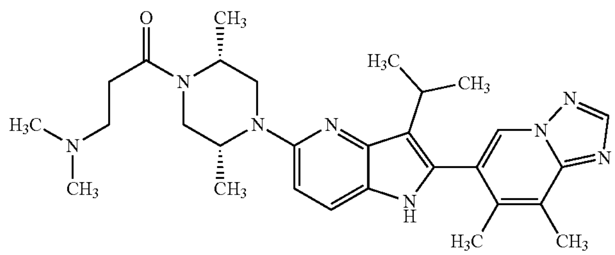 [SMILES: Cc1c(-c2[nH]c3ccc(N4C[C@@H](C)N(C(=O)CCN(C)C)C[C@H]4C)nc3c2C(C)C)cn2ncnc2c1C] | 517.40 | 0.95 | QC-ACN-TFA-XB |
| 798 | 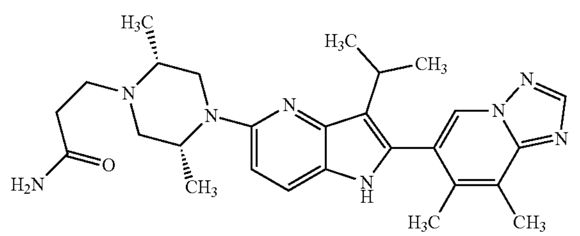 [SMILES: Cc1c(-c2[nH]c3ccc(N4C[C@@H](C)N(CCC(N)=O)C[C@H]4C)nc3c2C(C)C)cn2ncnc2c1C] | 489.00 | 0.86 | QC-ACN-TFA-XB |
| 799 | 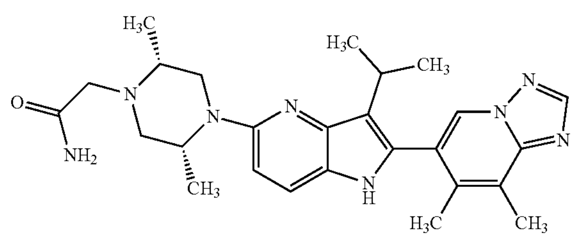 [SMILES: Cc1c(-c2[nH]c3ccc(N4C[C@@H](C)N(CC(N)=O)C[C@H]4C)nc3c2C(C)C)cn2ncnc2c1C] | 475.20 | 0.88 | QC-ACN-TFA-XB |
| 800 | 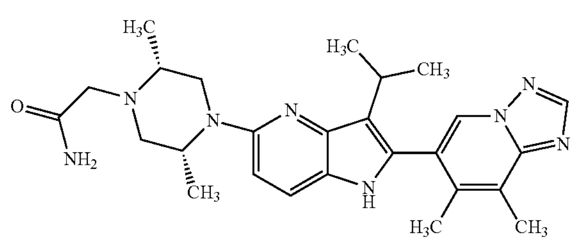 [SMILES: Cc1c(-c2[nH]c3ccc(N4C[C@@H](C)N(CC(N)=O)C[C@H]4C)nc3c2C(C)C)cn2ncnc2c1C] | 475.20 | 0.86 | QC-ACN-TFA-XB |

TABLE 2-continued

| Ex. No. | Structure | Obs. MS Ion | RT | QC Method |
|---|---|---|---|---|
| 801 | 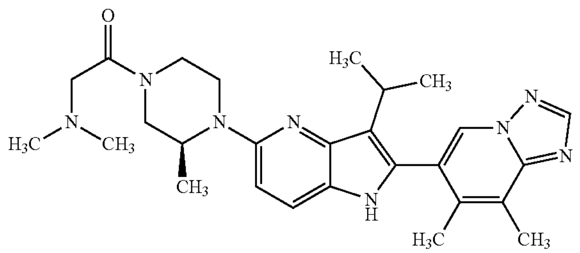 [SMILES: Cc1c(-c2[nH]c3ccc(N4CCN(C(=O)CN(C)C)C[C@@H]4C)nc3c2C(C)C)cn2ncnc2c1C] | 489.50 | 1.36 | QC-ACN-AA-XB |
| 802 | 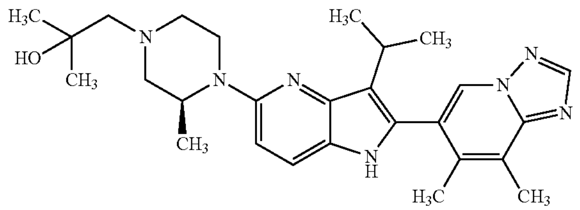 [SMILES: Cc1c(-c2[nH]c3ccc(N4CCN(CC(C)(C)O)C[C@@H]4C)nc3c2C(C)C)cn2ncnc2c1C] | 476.20 | 1.70 | QC-ACN-AA-XB |
| 803 | 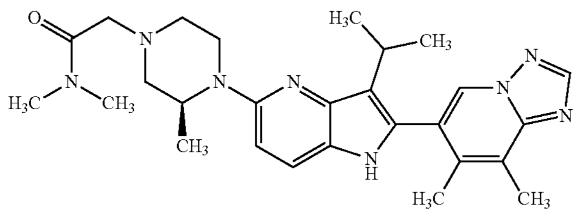 [SMILES: Cc1c(-c2[nH]c3ccc(N4CCN(CC(=O)N(C)C)C[C@@H]4C)nc3c2C(C)C)cn2ncnc2c1C] | 489.60 | 1.69 | QC-ACN-AA-XB |
| 804 | 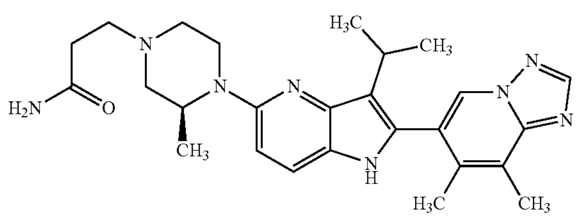 | 475.10 | 0.76 | QC-ACN-TFA-XB |
| 805 | 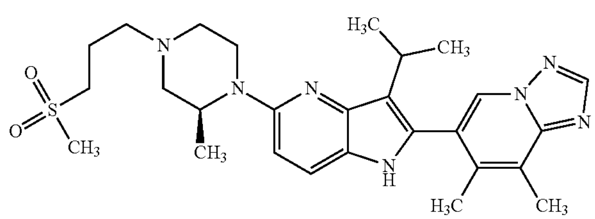 [SMILES: Cc1c(-c2[nH]c3ccc(N4CCN(CCCS(C)(=O)=O)C[C@@H]4C)nc3c2C(C)C)cn2ncnc2c1C] | 524.50 | 0.71 | QC-ACN-TFA-XB |
| 806 | 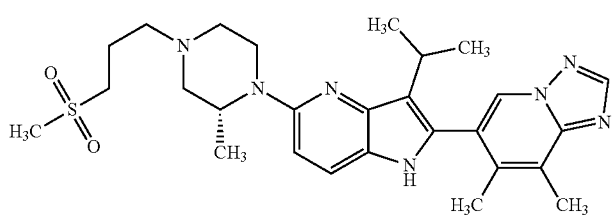 [SMILES: Cc1c(-c2[nH]c3ccc(N4CCN(CCCS(C)(=O)=O)C[C@H]4C)nc3c2C(C)C)cn2ncnc2c1C] | 524.10 | 1.05 | QC-ACN-TFA-XB |
| 807 | 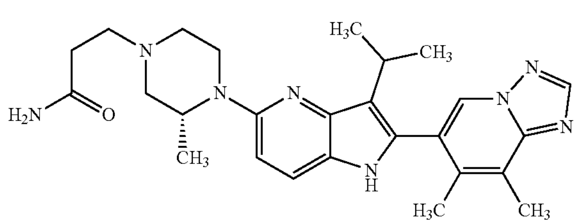 [SMILES: Cc1c(-c2[nH]c3ccc(N4CCN(CCC(N)=O)C[C@H]4C)nc3c2C(C)C)cn2ncnc2c1C] | 474.90 | 1.49 | QC-ACN-AA-XB |

TABLE 2-continued

| Ex. No. | Structure | Obs. MS Ion | RT | QC Method |
|---|---|---|---|---|
| 808 | 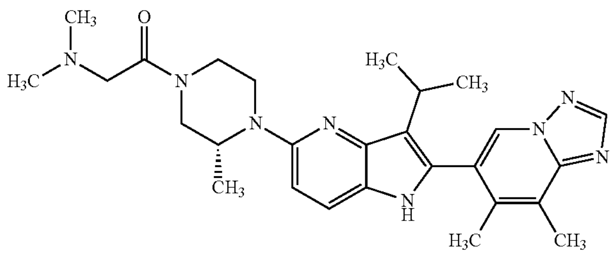 | 489.50 | 1.44 | QC-ACN-AA-XB |
| 809 | 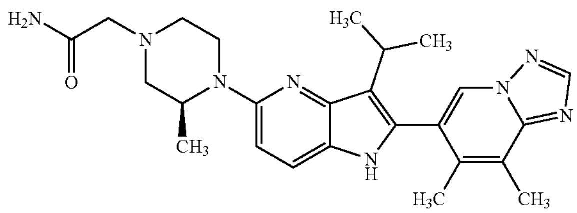 [SMILES: Cc1c(-c2[nH]c3ccc(N4CCN(CC(N)=O)C[C@@H]4C)nc3c2C(C)C)cn2ncnc2c1C] | 461.10 | 1.58 | QC-ACN-AA-XB |
| 810 | 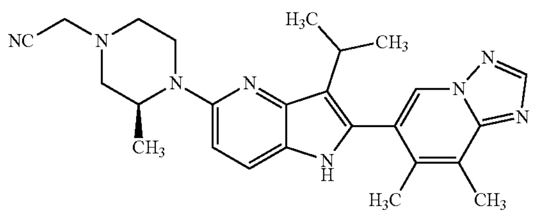 [SMILES: Cc1c(-c2[nH]c3ccc(N4CCN(CC#N)C[C@@H]4C)nc3c2C(C)C)cn2ncnc2c1C] | 443.10 | 2.02 | QC-ACN-AA-XB |
| 811 | 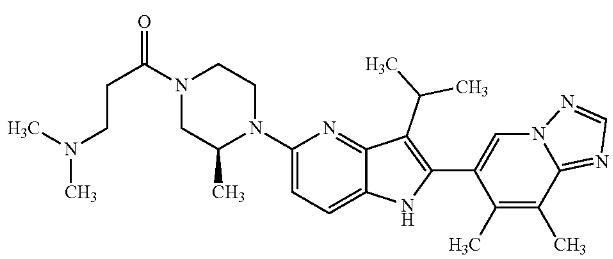 [SMILES: Cc1c(-c2[nH]c3ccc(N4CCN(C(=O)CCN(C)C)C[C@@H]4C)nc3c2C(C)C)cn2ncnc2c1C] | 502.90 | 1.45 | QC-ACN-AA-XB |
| 812 | 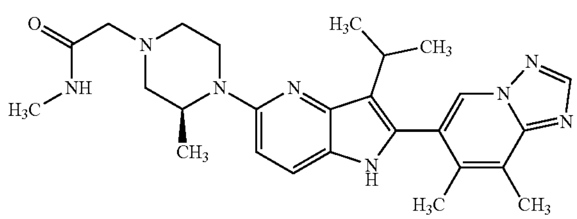 [SMILES: CNC(=O)CN1CCN(c2ccc3[nH]c(-c4cn5ncnc5c(C)c4C)c(C(C)C)c3n2)[C@@H](C)C1] | 475.10 | 1.60 | QC-ACN-AA-XB |
| 813 | 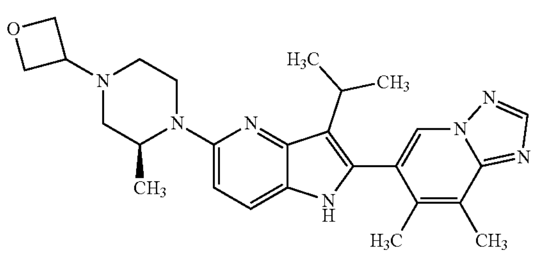 | 460.10 | 1.85 | QC-ACN-AA-XB |

TABLE 2-continued

| Ex. No. | Structure | Obs. MS Ion | RT | QC Method |
|---|---|---|---|---|
| 814 | 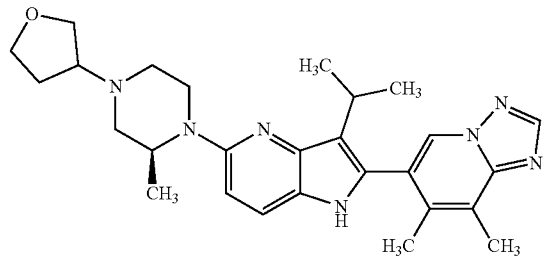 [SMILES: Cc1c(-c2[nH]c3ccc(N4CCN(C5CCOC5)C[C@@H]4C)nc3c2C(C)C)cn2ncnc2c1C] | 474.20 | 1.95 | QC-ACN-AA-XB |
| 815 | 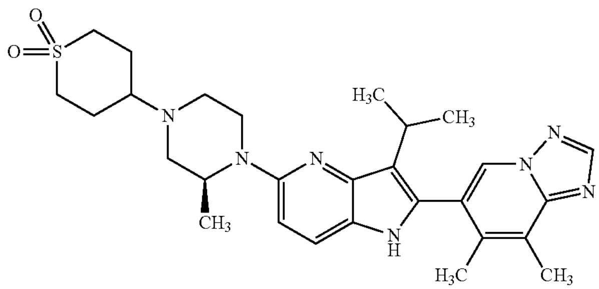 [SMILES: Cc1c(-c2[nH]c3ccc(N4CCN(C5CCS(=O)(=O)CC5)C[C@@H]4C)nc3c2C(C)C)cn2ncnc2c1C] | 536.20 | 1.80 | QC-ACN-AA-XB |
| 816 | 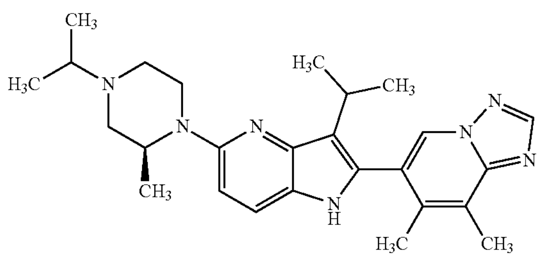 [SMILES: Cc1c(-c2[nH]c3ccc(N4CCN(C(C)C)C[C@@H]4C)nc3c2C(C)C)cn2ncnc2c1C] | 446.20 | 1.62 | QC-ACN-AA-XB |
| 817 | 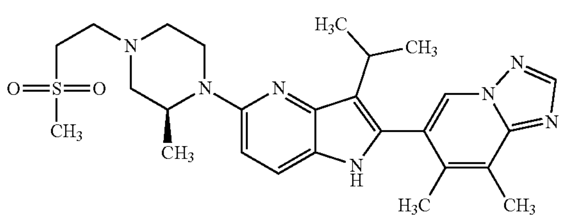 [SMILES: Cc1c(-c2[nH]c3ccc(N4CCN(CCS(C)(=O)=O)C[C@@H]4C)nc3c2C(C)C)cn2ncnc2c1C] | 510.10 | 1.66 | QC-ACN-AA-XB |
| 818 | 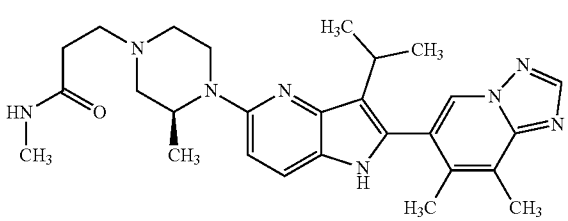 [SMILES: CNC(=O)CCN1CCN(c2ccc3[nH]c(-c4cn5ncnc5c(C)c4C)c(C(C)C)c3n2)[C@@H](C)C1] | 489.50 | 1.54 | QC-ACN-AA-XB |
| 819 | 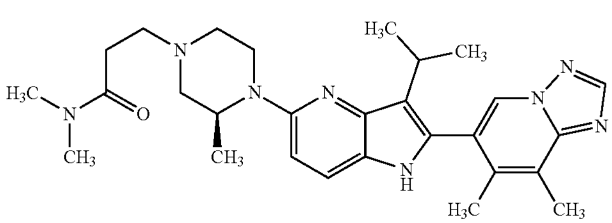 [SMILES: Cc1c(-c2[nH]c3ccc(N4CCN(CCC(=O)N(C)C)C[C@@H]4C)nc3c2C(C)C)cn2ncnc2c1C] | 525.10 | 1.70 | QC-ACN-AA-XB |

TABLE 2-continued

| Ex. No. | Structure | Obs. MS Ion | RT | QC Method |
|---|---|---|---|---|
| 820 | 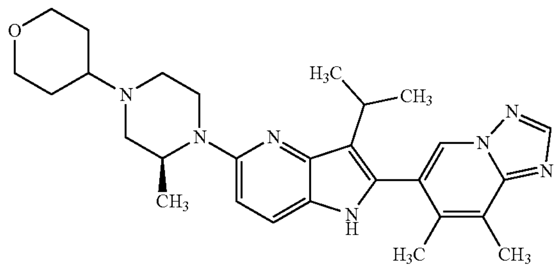 [SMILES: Cc1c(-c2[nH]c3ccc(N4CCN(C5CCOCC5)C[C@@H]4C)nc3c2C(C)C)cn2ncnc2c1C] | 487.90 | 1.94 | QC-ACN-AA-XB |
| 821 | 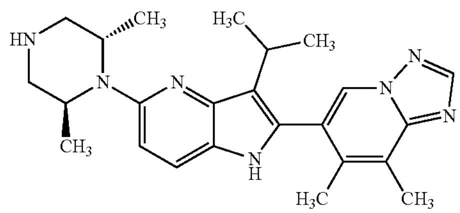 [SMILES: Cc1c(-c2[nH]c3ccc(N4[C@@H](C)CNC[C@@H]4C)nc3c2C(C)C)cn2ncnc2c1C] | 418.40 | 1.27 | QC-ACN-AA-XB |
| 822 | 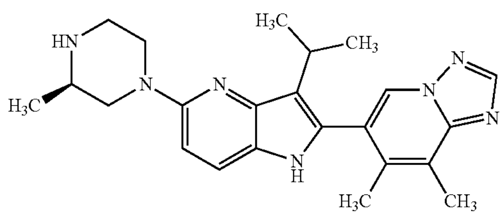 [SMILES: Cc1c(-c2[nH]c3ccc(N4CCN[C@H](C)C4)nc3c2C(C)C)cn2ncnc2c1C] | 404.40 | 1.16 | QC-ACN-AA-XB |
| 823 | 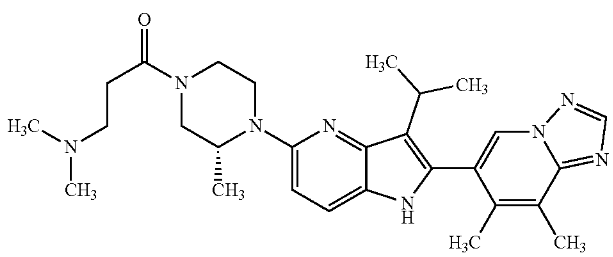 [SMILES: Cc1c(-c2[nH]c3ccc(N4CCN(C(=O)CCN(C)C)C[C@H]4C)nc3c2C(C)C)cn2ncnc2c1C] | 503.50 | 1.24 | QC-ACN-AA-XB |
| 824 | 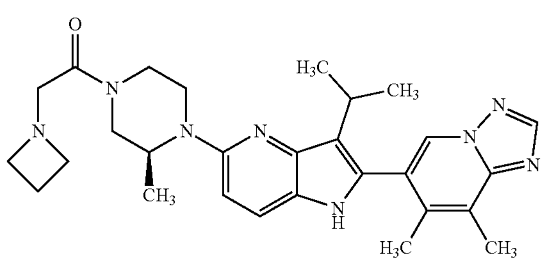 [SMILES: Cc1c(-c2[nH]c3ccc(N4CCN(C(=O)CN5CCC5)C[C@@H]4C)nc3c2C(C)C)cn2ncnc2c1C] | 501.13 | 1.08 | QC-ACN-TFA-XB |
| 825 | 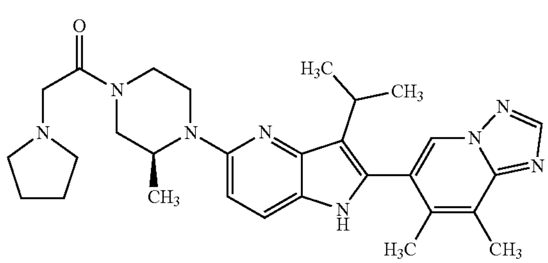 [SMILES: Cc1c(-c2[nH]c3ccc(N4CCN(C(=O)CN5CCCC5)C[C@@H]4C)nc3c2C(C)C)cn2ncnc2c1C] | 515.60 | 1.00 | QC-ACN-TFA-XB |

TABLE 2-continued

| Ex. No. | Structure | Obs. MS Ion | RT | QC Method |
|---|---|---|---|---|
| 826 | 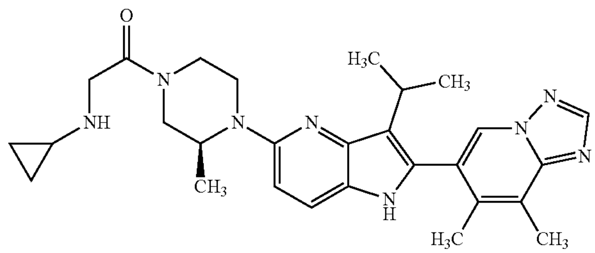 [SMILES: Cc1c(-c2[nH]c3ccc(N4CCN(C(=O)CNC5CC5)C[C@@H]4C)nc3c2C(C)C)cn2ncnc2c1C] | 500.90 | 1.13 | QC-ACN-TFA-XB |
| 827 | 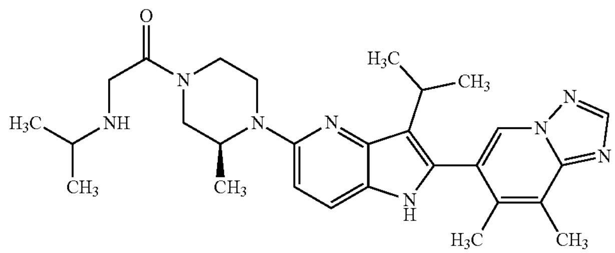 [SMILES: Cc1c(-c2[nH]c3ccc(N4CCN(C(=O)CNC(C)C)C[C@@H]4C)nc3c2C(C)C)cn2ncnc2c1C] | 502.90 | 1.15 | QC-ACN-TFA-XB |
| 828 | 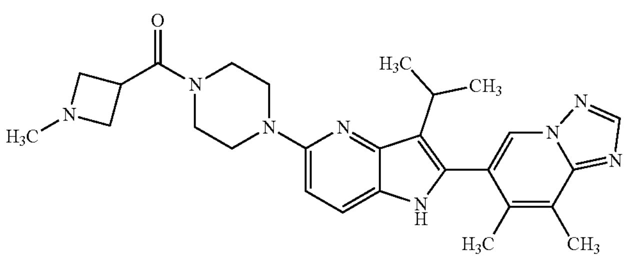 [SMILES: Cc1c(-c2[nH]c3ccc(N4CCN(C(=O)C5CN(C)C5)CC4)nc3c2C(C)C)cn2ncnc2c1C] | 487.30 | 1.35 | QC-ACN-AA-XB |
| 829 | 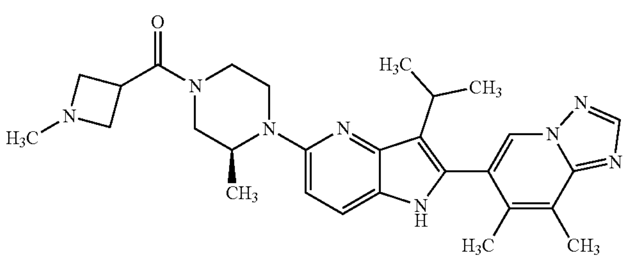 [SMILES: Cc1c(-c2[nH]c3ccc(N4CCN(C(=O)C5CN(C)C5)C[C@@H]4C)nc3c2C(C)C)cn2ncnc2c1C] | 501.30 | 1.41 | QC-ACN-AA-XB |
| 830 | 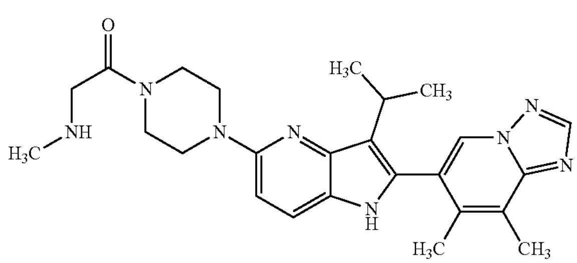 [SMILES: CNCC(=O)N1CCN(c2ccc3[nH]c(-c4cn5ncnc5c(C)c4C)c(C(C)C)c3n2)CC1] | 460.90 | 0.98 | QC-ACN-TFA-XB |
| 831 | 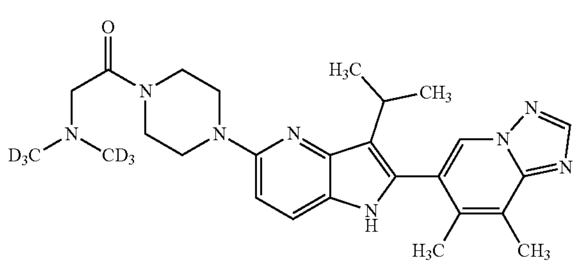 [SMILES: [2H]C([2H])([2H])N(CC(=O)N1CCN(c2ccc3[nH]c(-c4cn5ncnc5c(C)c4C)c(C(C)C)c3n2)CC1)C([2H])([2H])[2H]] | 481.60 | 1.30 | QC-ACN-AA-XB |

TABLE 2-continued

| Ex. No. | Structure | Obs. MS Ion | RT | QC Method |
|---|---|---|---|---|
| 832 | 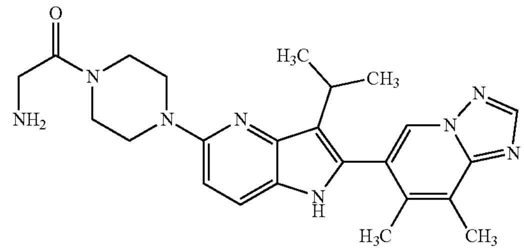 [SMILES: Cc1c(-c2[nH]c3ccc(N4CCN(C(=O)CN)CC4)nc3c2C(C)C)cn2ncnc2c1C] | 447.10 | 1.26 | QC-ACN-AA-XB |
| 833 | 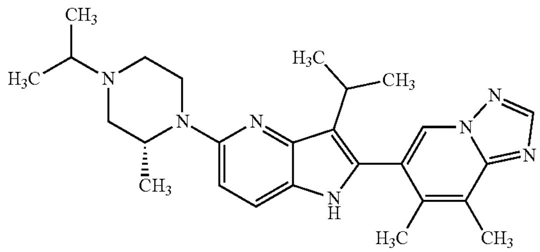 [SMILES: Cc1c(-c2[nH]c3ccc(N4CCN(C(C)C)C[C@H]4C)nc3c2C(C)C)cn2ncnc2c1C] | 446.50 | 1.02 | QC-ACN-TFA-XB |
| 834 | 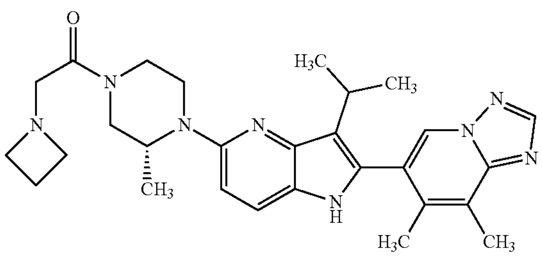 [SMILES: Cc1c(-c2[nH]c3ccc(N4CCN(C(=O)CN5CCC5)C[C@H]4C)nc3c2C(C)C)cn2ncnc2c1C] | 501.20 | 1.42 | QC-ACN-AA-XB |
| 835 | 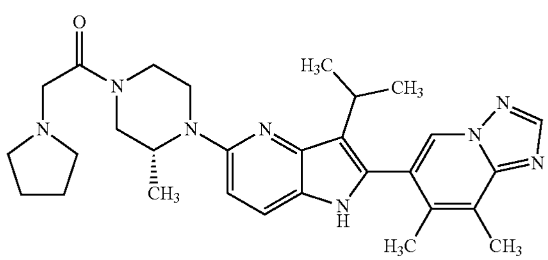 [SMILES: Cc1c(-c2[nH]c3ccc(N4CCN(C(=O)CN5CCCC5)C[C@H]4C)nc3c2C(C)C)cn2ncnc2c1C] | 515.40 | 1.57 | QC-ACN-AA-XB |
| 836 | 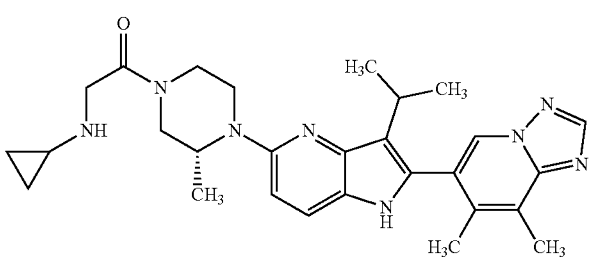 [SMILES: Cc1c(-c2[nH]c3ccc(N4CCN(C(=O)CNC5CC5)C[C@H]4C)nc3c2C(C)C)cn2ncnc2c1C] | 501.10 | 1.00 | QC-ACN-TFA-XB |
| 837 | 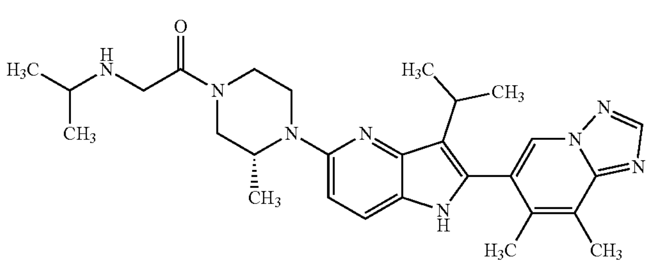 [SMILES: Cc1c(-c2[nH]c3ccc(N4CCN(C(=O)CNC(C)C)C[C@H]4C)nc3c2C(C)C)cn2ncnc2c1C] | 503.20 | 1.57 | QC-ACN-AA-XB |

TABLE 2-continued

| Ex. No. | Structure | Obs. MS Ion | RT | QC Method |
|---|---|---|---|---|
| 838 | 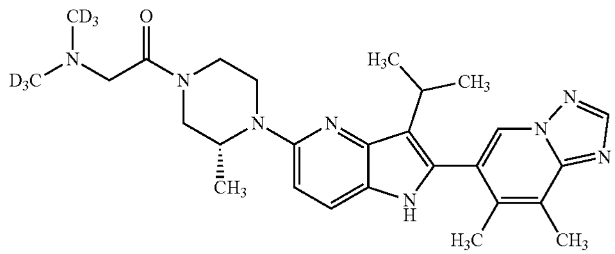 [SMILES: [2H]C([2H])([2H])N(CC(=O)N1CCN(c2ccc3[nH]c(-c4cn5ncnc5c(C)c4C)c(C(C)C)c3n2)[C@H](C)C1)C([2H])([2H])[2H]] | 495.20 | 1.53 | QC-ACN-AA-XB |
| 839 | 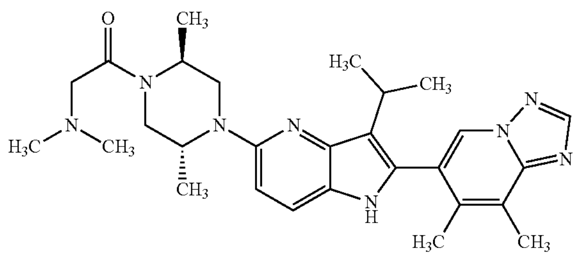 [SMILES: Cc1c(-c2[nH]c3ccc(N4C[C@H](C)N(C(=O)CN(C)C)C[C@H]4C)nc3c2C(C)C)cn2ncnc2c1C] | 503.00 | 1.64 | QC-ACN-AA-XB |
| 840 | 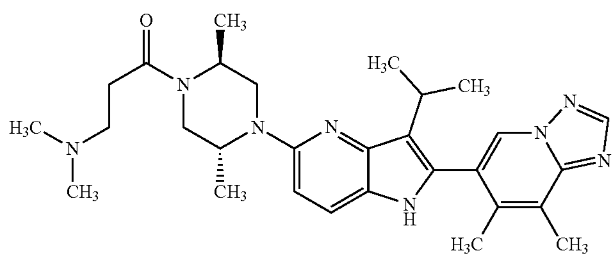 | 517.70 | 0.98 | QC-ACN-TFA-XB |
| 841 | 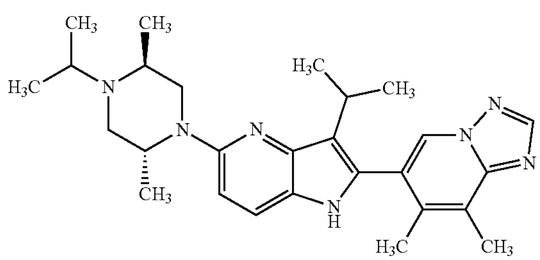 [SMILES: Cc1c(-c2[nH]c3ccc(N4C[C@H](C)N(C(C)C)C[C@H]4C)nc3c2C(C)C)cn2ncnc2c1C] | 460.40 | 1.01 | QC-ACN-TFA-XB |
| 842 | 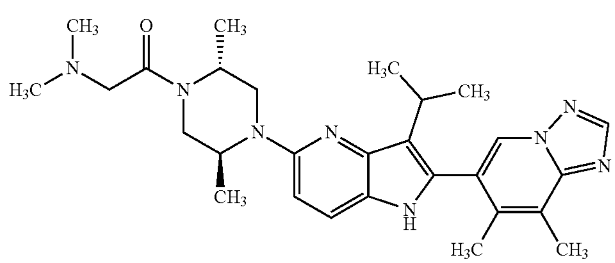 [SMILES: Cc1c(-c2[nH]c3ccc(N4C[C@@H](C)N(C(=O)CN(C)C)C[C@@H]4C)nc3c2C(C)C)cn2ncnc2c1C] | 503.40 | 1.52 | QC-ACN-AA-XB |
| 843 | 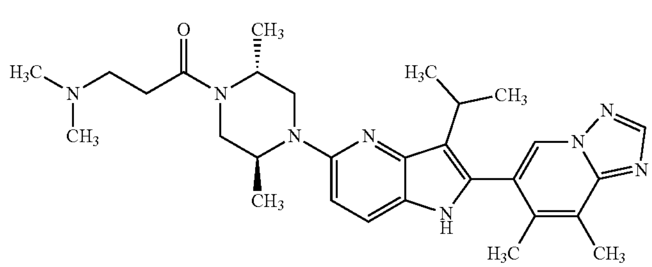 [SMILES: Cc1c(-c2[nH]c3ccc(N4C[C@@H](C)N(C(=O)CCN(C)C)C[C@@H]4C)nc3c2C(C)C)cn2ncnc2c1C] | 517.00 | 1.51 | QC-ACN-AA-XB |

TABLE 2-continued

| Ex. No. | Structure | Obs. MS Ion | RT | QC Method |
|---|---|---|---|---|
| 844 | 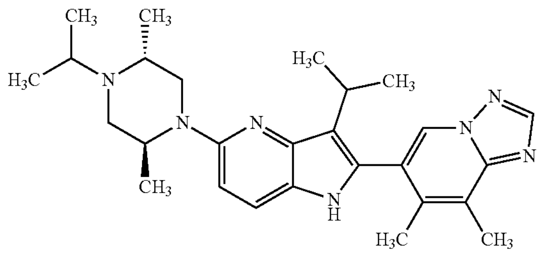 [SMILES: Cc1c(-c2[nH]c3ccc(N4C[C@@H](C)N(C(C)C)C[C@@H]4C)nc3c2C(C)C)cn2ncnc2c1C] | 460.40 | 1.59 | QC-ACN-AA-XB |
| 845 | 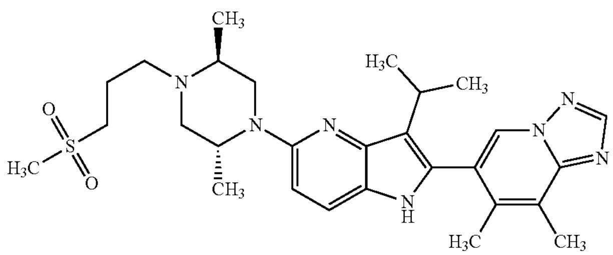 [SMILES: Cc1c(-c2[nH]c3ccc(N4C[C@H](C)N(CCCS(C)(=O)=O)C[C@H]4C)nc3c2C(C)C)cn2ncnc2c1C] | 538.30 | 1.66 | QC-ACN-AA-XB |
| 846 | 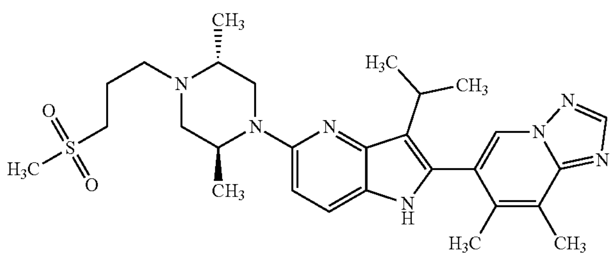 [SMILES: Cc1c(-c2[nH]c3ccc(N4C[C@@H](C)N(CCCS(C)(=O)=O)C[C@@H]4C)nc3c2C(C)C)cn2ncnc2c1C] | 538.30 | 0.95 | QC-ACN-TFA-XB |
| 847 | 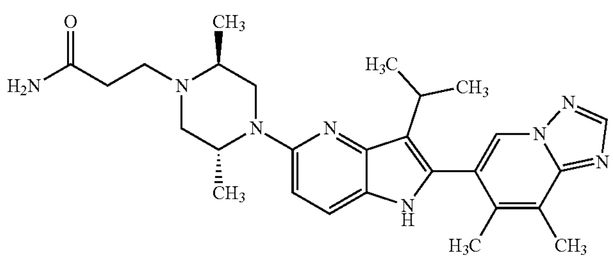 [SMILES: Cc1c(-c2[nH]c3ccc(N4C[C@H](C)N(CCC(N)=O)C[C@H]4C)nc3c2C(C)C)cn2ncnc2c1C] | 488.90 | 1.56 | QC-ACN-AA-XB |
| 848 | 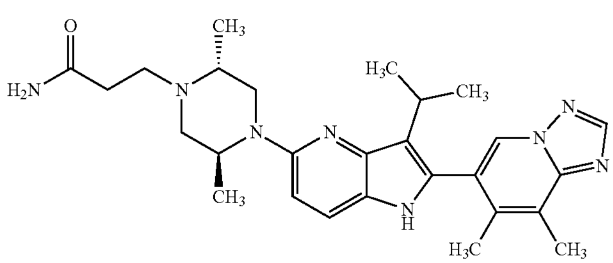 [SMILES: Cc1c(-c2[nH]c3ccc(N4C[C@@H](C)N(CCC(N)=O)C[C@@H]4C)nc3c2C(C)C)cn2ncnc2c1C] | 489.20 | 1.56 | QC-ACN-AA-XB |
| 849 | 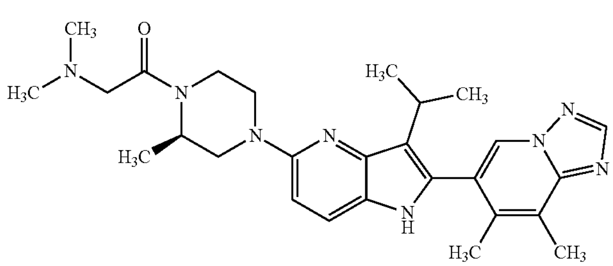 [SMILES: Cc1c(-c2[nH]c3ccc(N4CCN(C(=O)CN(C)C)[C@H](C)C4)nc3c2C(C)C)cn2ncnc2c1C] | 489.20 | 1.52 | QC-ACN-AA-XB |

TABLE 2-continued

| Ex. No. | Structure | Obs. MS Ion | RT | QC Method |
|---|---|---|---|---|
| 850 | 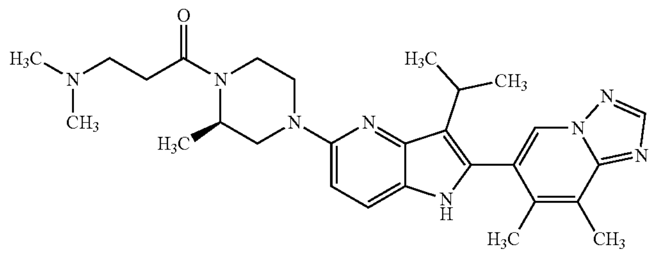 [SMILES: Cc1c(-c2[nH]c3ccc(N4CCN(C(=O)CCN(C)C)[C@H](C)C4)nc3c2C(C)C)cn2ncnc2c1C] | 503.20 | 1.41 | QC-ACN-AA-XB |
| 851 | 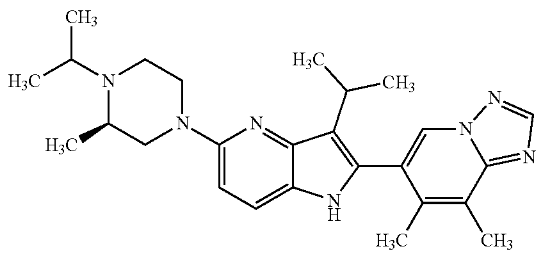 [SMILES: Cc1c(-c2[nH]c3ccc(N4CCN(C(C)C)[C@H](C)C4)nc3c2C(C)C)cn2ncnc2c1C] | 446.00 | 0.92 | QC-ACN-TFA-XB |
| 852 | 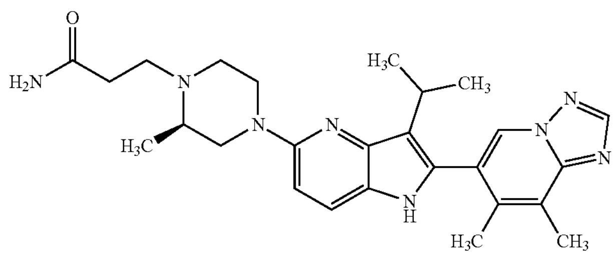 [SMILES: Cc1c(-c2[nH]c3ccc(N4CCN(CCC(N)=O)[C@H](C)C4)nc3c2C(C)C)cn2ncnc2c1C] | 474.90 | 1.45 | QC-ACN-AA-XB |
| 853 | 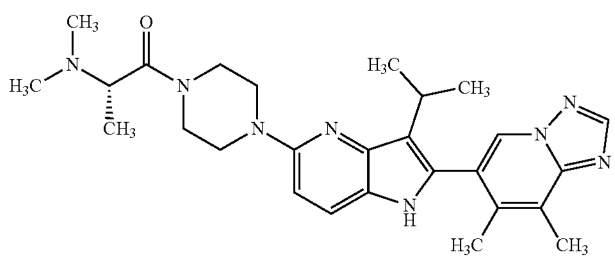 [SMILES: Cc1c(-c2[nH]c3ccc(N4CCN(C(=O)[C@H](C)N(C)C)CC4)nc3c2C(C)C)cn2ncnc2c1C] | 489.30 | 0.92 | QC-ACN-TFA-XB |
| 854 | 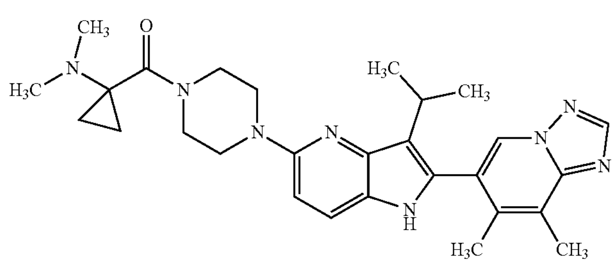 [SMILES: Cc1c(-c2[nH]c3ccc(N4CCN(C(=O)C5(N(C)C)CC5)CC4)nc3c2C(C)C)cn2ncnc2c1C] | 501.10 | 1.69 | QC-ACN-AA-XB |
| 855 | 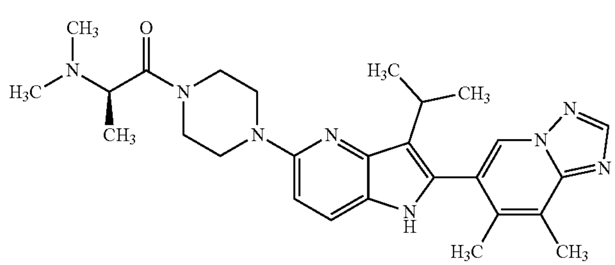 [SMILES: Cc1c(-c2[nH]c3ccc(N4CCN(C(=O)[C@@H](C)N(C)C)CC4)nc3c2C(C)C)cn2ncnc2c1C] | 245.30 | 1.02 | QC-ACN-TFA-XB |

TABLE 2-continued

| Ex. No. | Structure | Obs. MS Ion | RT | QC Method |
|---|---|---|---|---|
| 856 | 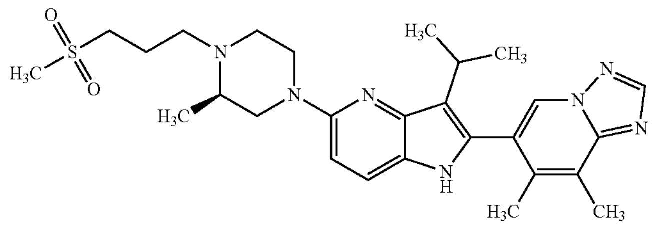 [SMILES: Cc1c(-c2[nH]c3ccc(N4CCN(CCCS(C)(=O)=O)[C@H](C)C4)nc3c2C(C)C)cn2ncnc2c1C] | 524.30 | 0.88 | QC-ACN-TFA-XB |
| 857 | 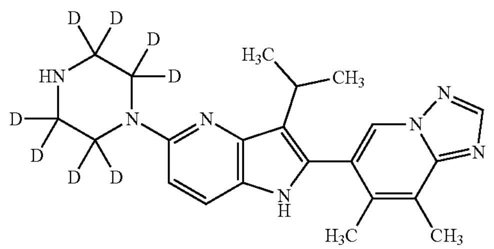 [SMILES: [2H]C1([2H])NC([2H])([2H])C([2H])([2H])N(c2ccc3[nH]c(-c4cn5ncnc5c(C)c4C)c(C(C)C)c3n2)C1([2H])[2H]] | 398.20 | 1.12 | QC-ACN-AA-XB |
| 858 | 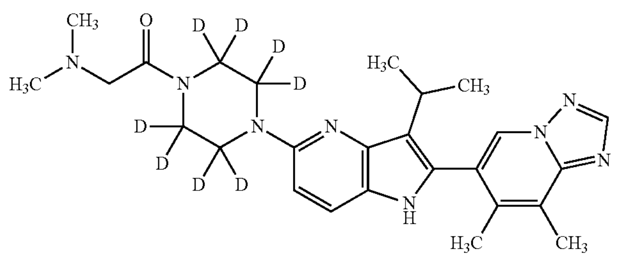 [SMILES: [2H]C1([2H])N(C(=O)CN(C)C)C([2H])([2H])C([2H])([2H])N(c2ccc3[nH]c(-c4cn5ncnc5c(C)c4C)c(C(C)C)c3n2)C1([2H])[2H]] | 483.10 | 0.78 | QC-ACN-TFA-XB |
| 859 | 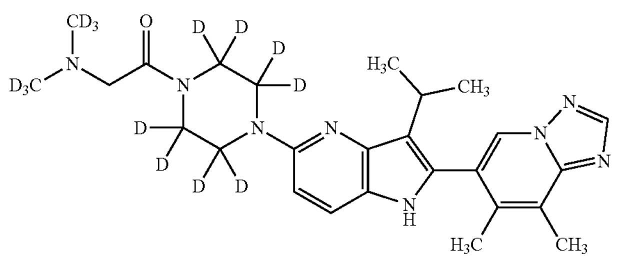 [SMILES: [2H]C([2H])([2H])N(CC(=O)N1C([2H])([2H])C([2H])([2H])N(c2ccc3[nH]c(-c4cn5ncnc5c(C)c4C)c(C(C)C)c3n2)C([2H])([2H])C1([2H])[2H])C([2H])([2H])[2H]] | 489.20 | 0.78 | QC-ACN-TFA-XB |
| 860 | 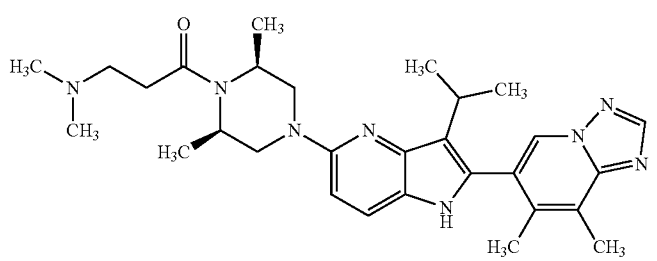 [SMILES: Cc1c(-c2[nH]c3ccc(N4C[C@@H](C)N(C(=O)CCN(C)C)[C@@H](C)C4)nc3c2C(C)C)cn2ncnc2c1C] | 517.00 | 1.60 | QC-ACN-AA-XB |
| 861 | 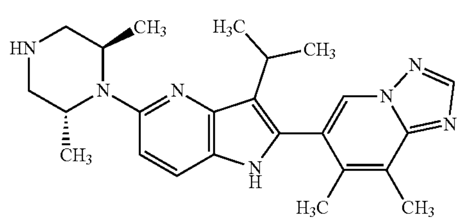 [SMILES: Cc1c(-c2[nH]c3ccc(N4[C@H](C)CNC[C@H]4C)nc3c2C(C)C)cn2ncnc2c1C] | 418.20 | 0.82 | QC-ACN-TFA-XB |

TABLE 2-continued

| Ex. No. | Structure | Obs. MS Ion | RT | QC Method |
|---|---|---|---|---|
| 862 | 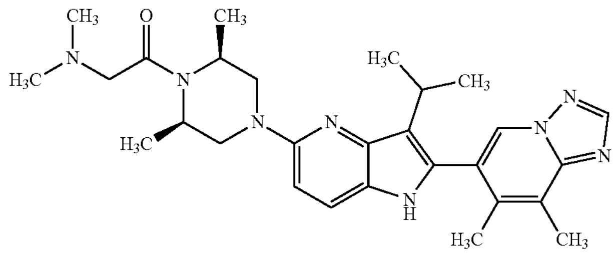 [SMILES: Cc1c(-c2[nH]c3ccc(N4C[C@@H](C)N(C(=O)CN(C)C)[C@@H](C)C4)nc3c2C(C)C)cn2ncnc2c1C] | 503.30 | 1.52 | QC-ACN-AA-XB |
| 863 | 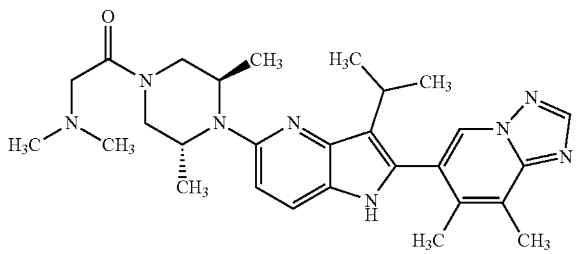 [SMILES: Cc1c(-c2[nH]c3ccc(N4[C@H](C)CN(C(=O)CN(C)C)C[C@H]4C)nc3c2C(C)C)cn2ncnc2c1C] | 503.20 | 1.38 | QC-ACN-AA-XB |
| 864 | 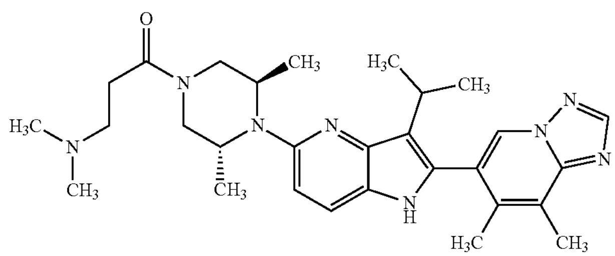 [SMILES: Cc1c(-c2[nH]c3ccc(N4[C@H](C)CN(C(=O)CCN(C)C)C[C@H]4C)nc3c2C(C)C)cn2ncnc2c1C] | 517.40 | 1.33 | QC-ACN-AA-XB |
| 865 | 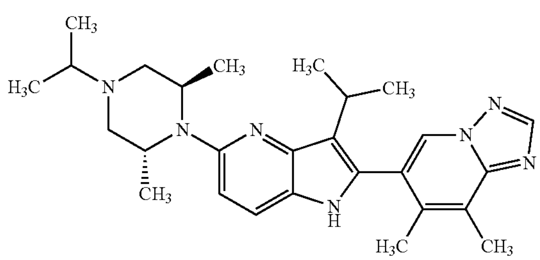 [SMILES: Cc1c(-c2[nH]c3ccc(N4[C@H](C)CN(C(C)C)C[C@H]4C)nc3c2C(C)C)cn2ncnc2c1C] | 460.40 | 1.66 | QC-ACN-AA-XB |
| 866 | 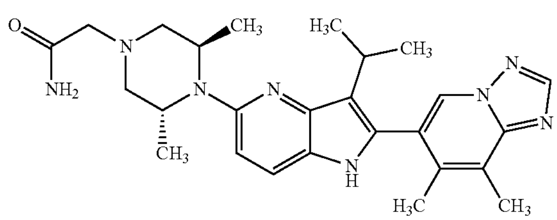 [SMILES: Cc1c(-c2[nH]c3ccc(N4[C@H](C)CN(CC(N)=O)C[C@H]4C)nc3c2C(C)C)cn2ncnc2c1C] | 475.10 | 0.84 | QC-ACN-TFA-XB |
| 867 | 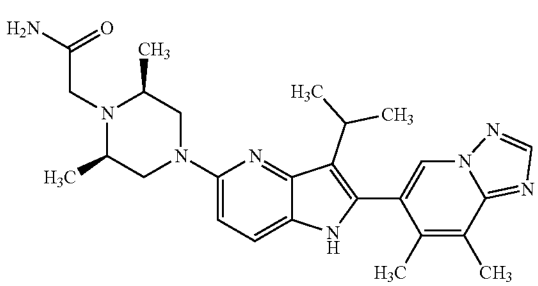 [SMILES: Cc1c(-c2[nH]c3ccc(N4C[C@@H](C)N(CC(N)=O)[C@@H](C)C4)nc3c2C(C)C)cn2ncnc2c1C] | 475.10 | 1.56 | QC-ACN-AA-XB |

TABLE 2-continued

| Ex. No. | Structure | Obs. MS Ion | RT | QC Method |
|---|---|---|---|---|
| 868 | 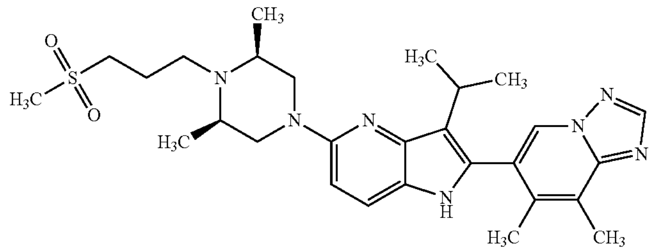 [SMILES: Cc1c(-c2[nH]c3ccc(N4C[C@@H](C)N(CCCS(C)(=O)=O)[C@@H](C)C4)nc3c2C(C)C)cn2ncnc2c1C] | 538.20 | 0.93 | QC-ACN-TFA-XB |
| 869 | 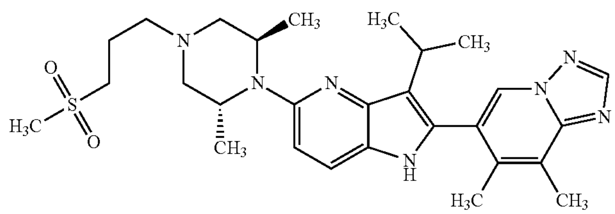 [SMILES: Cc1c(-c2[nH]c3ccc(N4[C@H](C)CN(CCCS(C)(=O)=O)C[C@H]4C)nc3c2C(C)C)cn2ncnc2c1C] | 538.10 | 1.64 | QC-ACN-AA-XB |
| 870 | 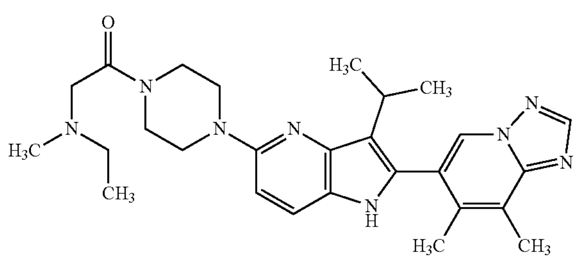 | 489.00 | 1.38 | QC-ACN-AA-XB |
| 871 | 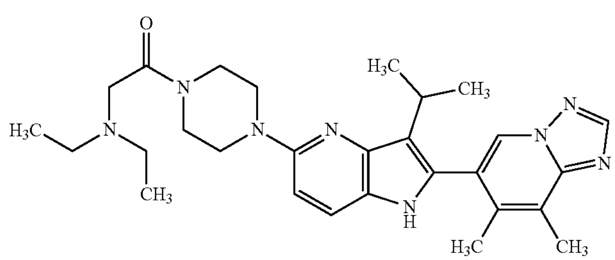 [SMILES: CCN(CC)CC(=O)N1CCN(c2ccc3[nH]c(-c4cn5ncnc5c(C)c4C)c(C(C)C)c3n2)CC1] | 503.40 | 1.42 | QC-ACN-AA-XB |
| 872 | 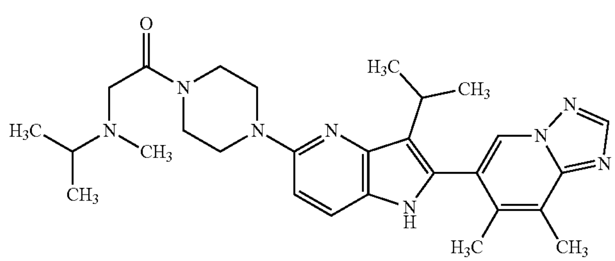 [SMILES: Cc1c(-c2[nH]c3ccc(N4CCN(C(=O)CN(C)C(C)C)CC4)nc3c2C(C)C)cn2ncnc2c1C] | 503.40 | 1.42 | QC-ACN-AA-XB |
| 873 | 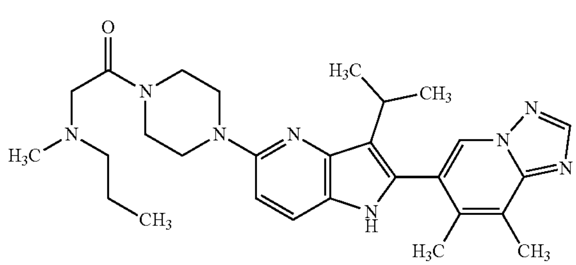 [SMILES: CCCN(C)CC(=O)N1CCN(c2ccc3[nH]c(-c4cn5ncnc5c(C)c4C)c(C(C)C)c3n2)CC1] | 503.40 | 0.87 | QC-ACN-TFA-XB |

TABLE 2-continued

| Ex. No. | Structure | Obs. MS Ion | RT | QC Method |
|---|---|---|---|---|
| 874 | 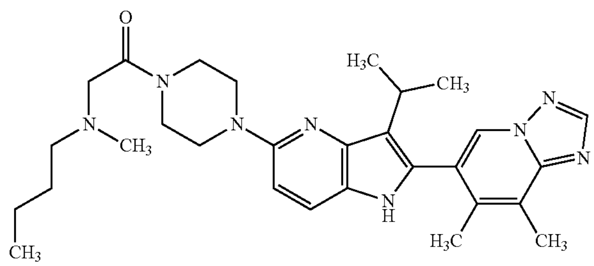 [SMILES: CCCCN(C)CC(=O)N1CCN(c2ccc3[nH]c(-c4cn5ncnc5c(C)c4C)c(C(C)C)c3n2)CC1] | 517.10 | 1.10 | QC-ACN-TFA-XB |
| 875 | 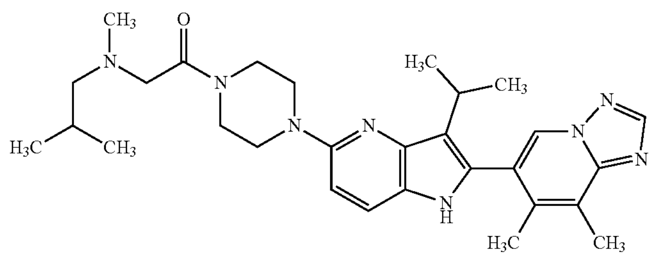 [SMILES: Cc1c(-c2[nH]c3ccc(N4CCN(C(=O)CN(C)CC(C)C)CC4)nc3c2C(C)C)cn2ncnc2c1C] | 517.00 | 2.03 | QC-ACN-AA-XB |
| 876 | 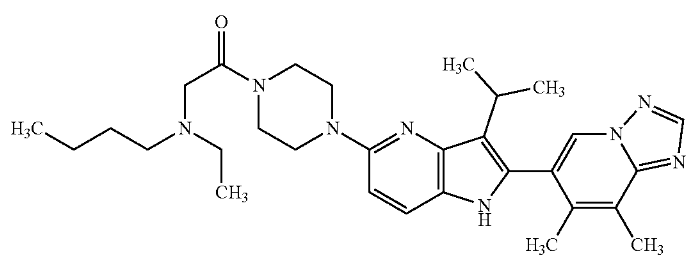 [SMILES: CCCCN(CC)CC(=O)N1CCN(c2ccc3[nH]c(-c4cn5ncnc5c(C)c4C)c(C(C)C)c3n2)CC1] | 531.40 | 1.74 | QC-ACN-AA-XB |
| 877 | 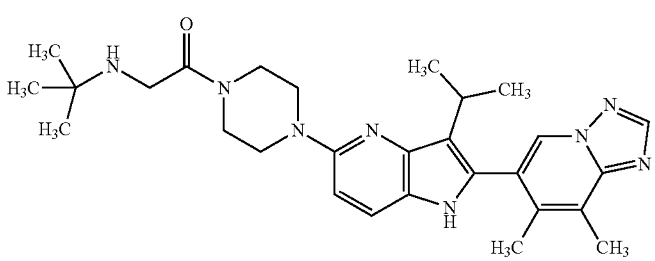 [SMILES: Cc1c(-c2[nH]c3ccc(N4CCN(C(=O)CNC(C)(C)C)CC4)nc3c2C(C)C)cn2ncnc2c1C] | 503.00 | 1.10 | QC-ACN-TFA-XB |
| 878 | 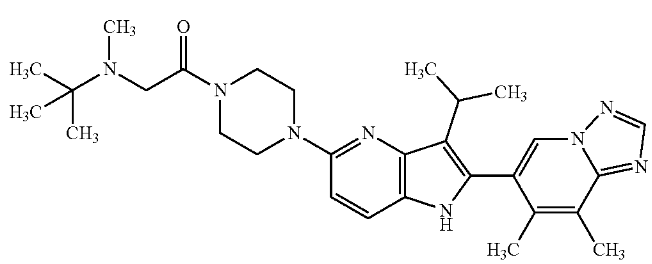 [SMILES: Cc1c(-c2[nH]c3ccc(N4CCN(C(=O)CN(C)C(C)(C)C)CC4)nc3c2C(C)C)cn2ncnc2c1C] | 517.50 | 1.48 | QC-ACN-AA-XB |

TABLE 2-continued

| Ex. No. | Structure | Obs. MS Ion | RT | QC Method |
|---|---|---|---|---|
| 879 | 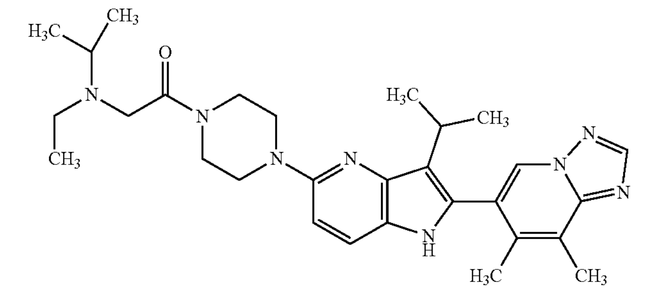 [SMILES: CCN(CC(=O)N1CCN(c2ccc3[nH]c(-c4cn5ncnc5c(C)c4C)c(C(C)C)c3n2)CC1)C(C)C] | 517.40 | 1.40 | QC-ACN-AA-XB |
| 880 | 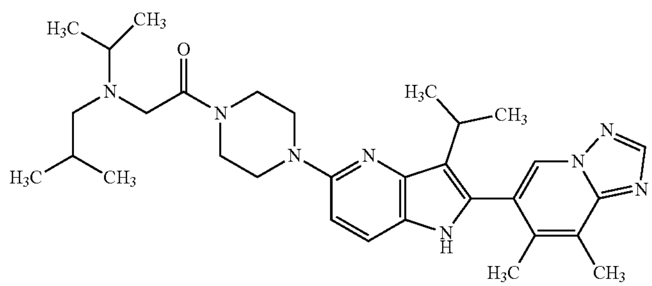 [SMILES: Cc1c(-c2[nH]c3ccc(N4CCN(C(=O)CN(CC(C)C)C(C)C)CC4)nc3c2C(C)C)cn2ncnc2c1C] | 545.40 | 2.02 | QC-ACN-AA-XB |
| 881 | 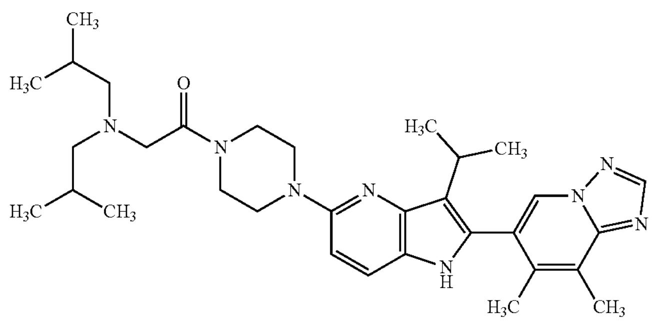 [SMILES: Cc1c(-c2[nH]c3ccc(N4CCN(C(=O)CN(CC(C)C)CC(C)C)CC4)nc3c2C(C)C)cn2ncnc2c1C] | 559.50 | 2.53 | QC-ACN-AA-XB |
| 882 | 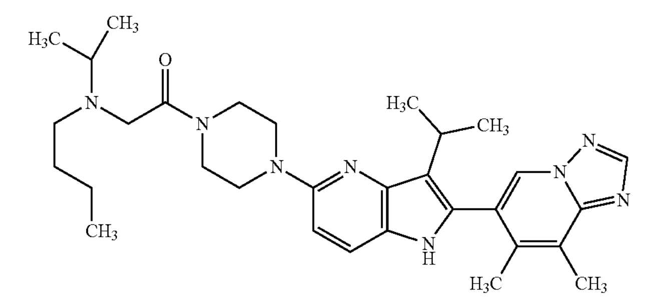 [SMILES: CCCCN(CC(=O)N1CCN(c2ccc3[nH]c(-c4cn5ncnc5c(C)c4C)c(C(C)C)c3n2)CC1)C(C)C] | 545.20 | 1.85 | QC-ACN-AA-XB |
| 883 | 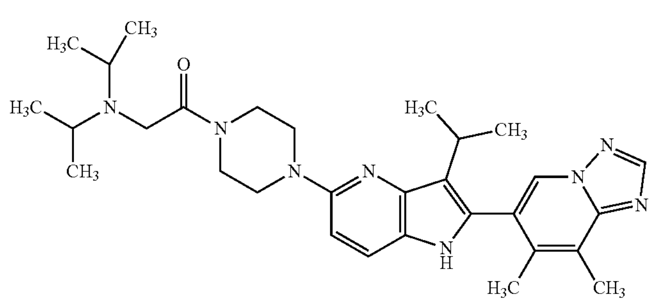 [SMILES: Cc1c(-c2[nH]c3ccc(N4CCN(C(=O)CN(C(C)C)C(C)C)CC4)nc3c2C(C)C)cn2ncnc2c1C] | 531.20 | 1.51 | QC-ACN-AA-XB |

TABLE 2-continued

| Ex. No. | Structure | Obs. MS Ion | RT | QC Method |
|---|---|---|---|---|
| 884 | 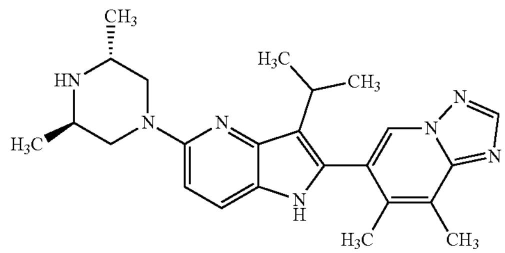 [SMILES: Cc1c(-c2[nH]c3ccc(N4C[C@@H](C)N[C@H](C)C4)nc3c2C(C)C)cn2ncnc2c1C] | 418.30 | 1.23 | QC-ACN-AA-XB |
| 885 | 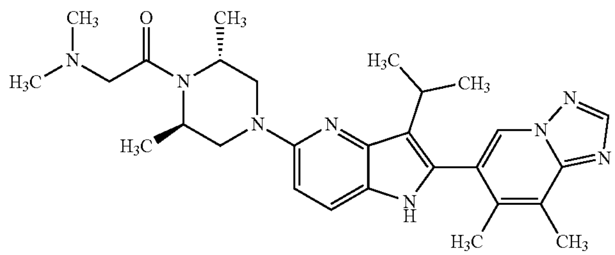 [SMILES: Cc1c(-c2[nH]c3ccc(N4C[C@@H](C)N(C(=O)CN(C)C)[C@H](C)C4)nc3c2C(C)C)cn2ncnc2c1C] | 503.10 | 1.43 | QC-ACN-AA-XB |
| 886 | 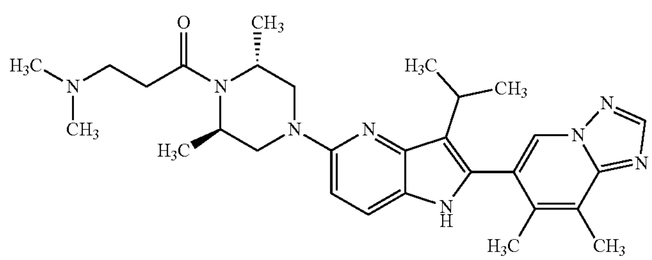 [SMILES: Cc1c(-c2[nH]c3ccc(N4C[C@@H](C)N(C(=O)CCN(C)C)[C@H](C)C4)nc3c2C(C)C)cn2ncnc2c1C] | 517.00 | 1.02 | QC-ACN-TFA-XB |
| 887 | 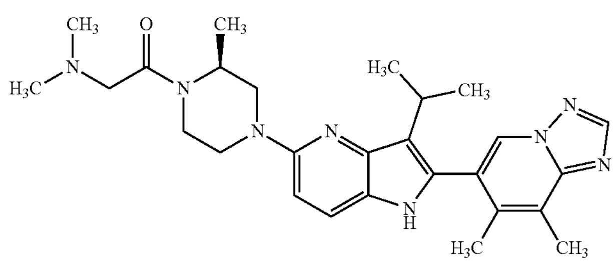 [SMILES: Cc1c(-c2[nH]c3ccc(N4CCN(C(=O)CN(C)C)[C@@H](C)C4)nc3c2C(C)C)cn2ncnc2c1C] | 489.40 | 0.85 | QC-ACN-TFA-XB |
| 888 | 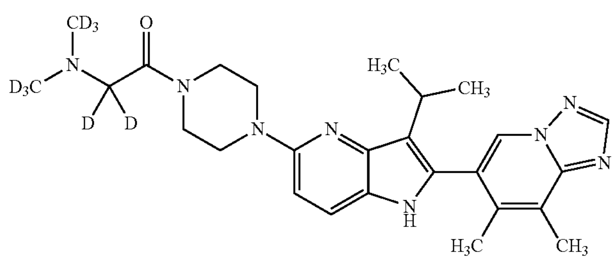 [SMILES: [2H]C([2H])([2H])N(C([2H])([2H])[2H])C([2H])([2H])C(=O)N1CCN(c2ccc3[nH]c(-c4cn5ncnc5c(C)c4C)c(C(C)C)c3n2)CC1] | 483.00 | 1.26 | QC-ACN-AA-XB |
| 889 | 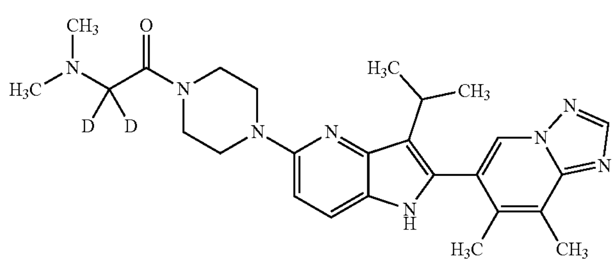 | 477.00 | 1.02 | QC-ACN-TFA-XB |

TABLE 2-continued

| Ex. No. | Structure | Obs. MS Ion | RT | QC Method |
|---|---|---|---|---|
| 890 | 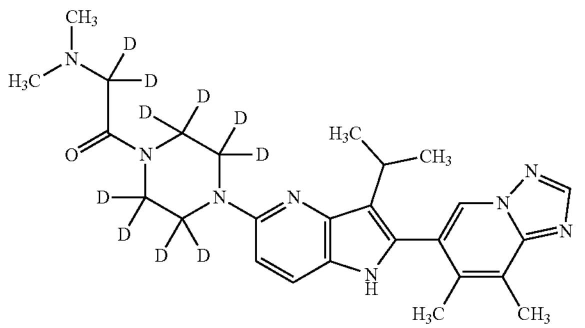 [SMILES: [2H]C([2H])([2H])N(C([2H])([2H])[2H])C([2H])([2H])C(=O)N1C([2H])([2H])C([2H])([2H])N(c2ccc3[nH]c(-c4cn5ncnc5c(C)c4C)c(C(C)C)c3n2)C([2H])([2H])C1([2H])[2H]] | 485.40 | 1.25 | QC-ACN-AA-XB |
| 891 | 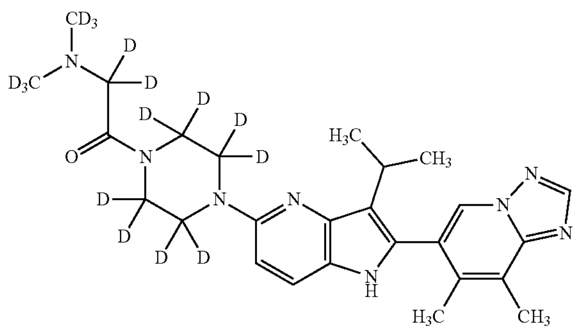 | 491.30 | 0.76 | QC-ACN-TFA-XB |
| 892 | 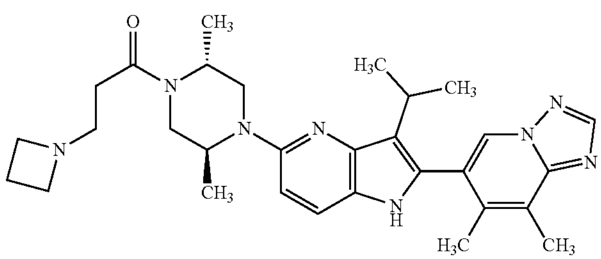 [SMILES: Cc1c(-c2[nH]c3ccc(N4C[C@@H](C)N(C(=O)CCN5CCC5)C[C@@H]4C)nc3c2C(C)C)cn2ncnc2c1C] | 529.50 | 1.39 | QC-ACN-AA-XB |
| 893 | 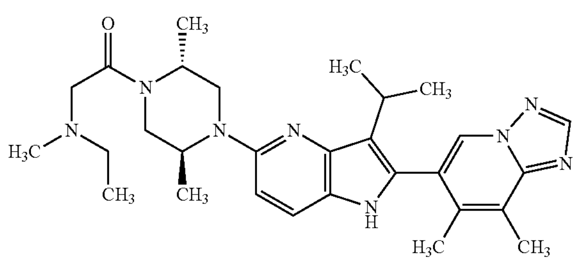 [SMILES: CCN(C)CC(=O)N1C[C@H](C)N(c2ccc3[nH]c(-c4cn5ncnc5c(C)c4C)c(C(C)C)c3n2)C[C@H]1C] | 517.50 | 1.48 | QC-ACN-AA-XB |
| 894 | 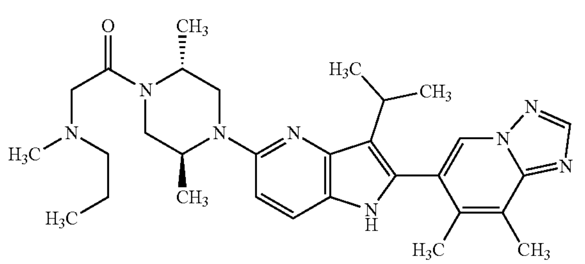 [SMILES: CCCN(C)CC(=O)N1C[C@H](C)N(c2ccc3[nH]c(-c4cn5ncnc5c(C)c4C)c(C(C)C)c3n2)C[C@H]1C] | 531.50 | 1.00 | QC-ACN-TFA-XB |

TABLE 2-continued

| Ex. No. | Structure | Obs. MS Ion | RT | QC Method |
|---|---|---|---|---|
| 895 | 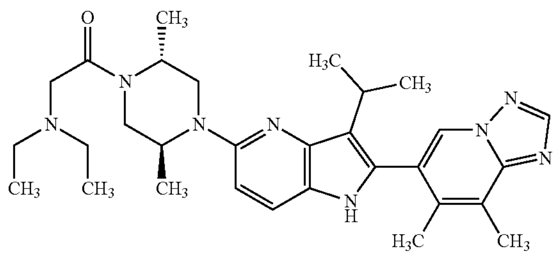 [SMILES: CCN(CC)CC(=O)N1C[C@H](C)N(c2ccc3[nH]c(-c4cn5ncnc5c(C)c4C)c(C(C)C)c3n2)C[C@H]1C] | 531.00 | 1.72 | QC-ACN-AA-XB |
| 896 | 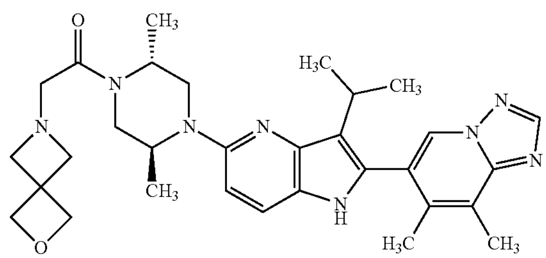 [SMILES: Cc1c(-c2[nH]c3ccc(N4C[C@@H](C)N(C(=O)CN5CC6(COC6)C5)C[C@@H]4C)nc3c2C(C)C)cn2ncnc2c1C] | 557.00 | 1.62 | QC-ACN-AA-XB |
| 897 | 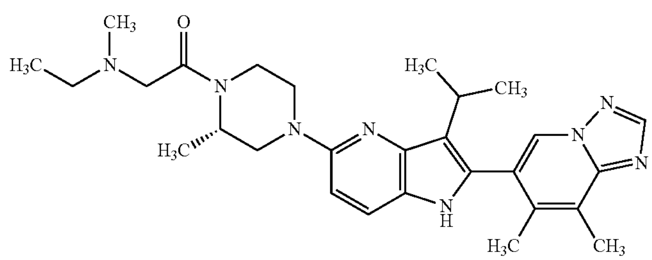 [SMILES: CCN(C)CC(=O)N1CCN(c2ccc3[nH]c(-c4cn5ncnc5c(C)c4C)c(C(C)C)c3n2)C[C@@H]1C] | 503.30 | 0.86 | QC-ACN-TFA-XB |
| 898 | 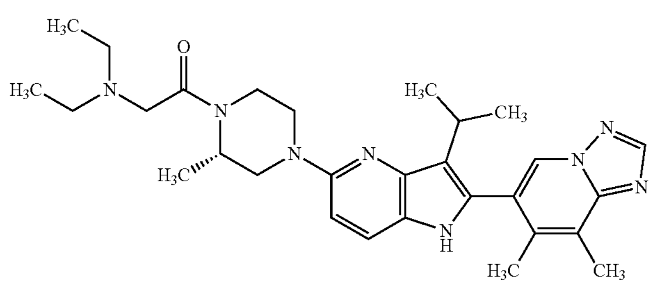 [SMILES: CCN(CC)CC(=O)N1CCN(c2ccc3[nH]c(-c4cn5ncnc5c(C)c4C)c(C(C)C)c3n2)C[C@@H]1C] | 517.30 | 1.46 | QC-ACN-AA-XB |
| 899 | 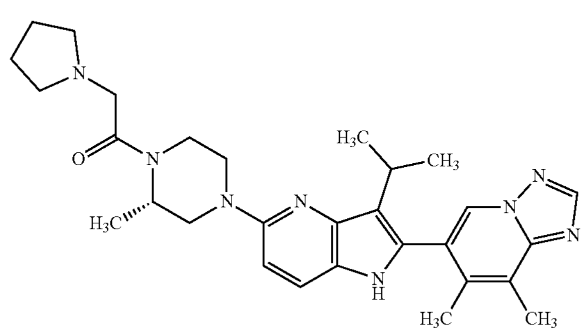 [SMILES: Cc1c(-c2[nH]c3ccc(N4CCN(C(=O)CN5CCCC5)[C@@H](C)C4)nc3c2C(C)C)cn2ncnc2c1C] | 515.30 | 0.85 | QC-ACN-TFA-XB |

TABLE 2-continued
| Ex. No. | Structure | Obs. MS Ion | RT | QC Method |
|---|---|---|---|---|
| 900 | 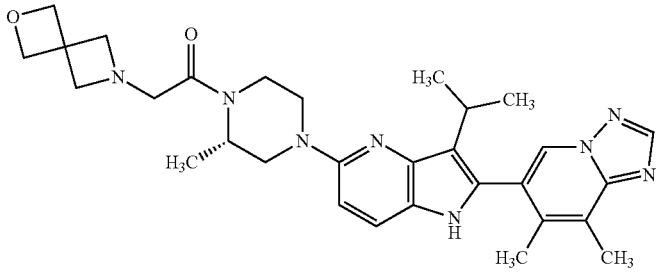 [SMILES: Cc1c(-c2[nH]c3ccc(N4CCN(C(=O)CN5CC6(COC6)C5)[C@@H](C)C4)nc3c2C(C)C)cn2ncnc2c1C] | 543.40 | 0.87 | QC-ACN-TFA-XB |
| 901 | 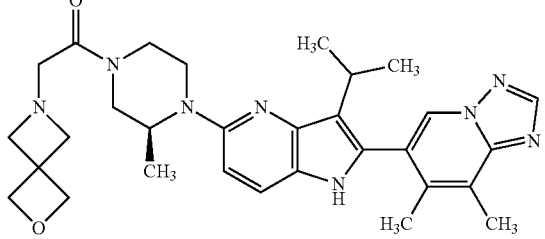 | 543.40 | 1.35 | QC-ACN-AA-XB |
| 902 | 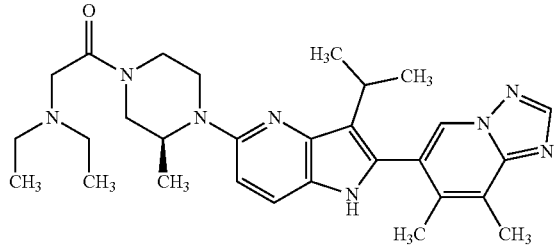 [SMILES: CCN(CC)CC(=O)N1CCN(c2ccc3[nH]c(-c4cn5ncnc5c(C)c4C)c(C(C)C)c3n2)[C@@H](C)C1] | 517.30 | 1.37 | QC-ACN-AA-XB |
| 903 | 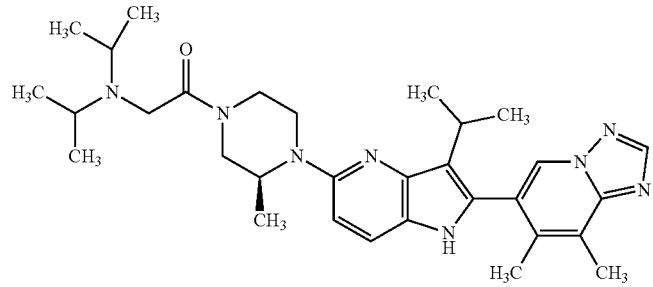 [SMILES: Cc1c(-c2[nH]c3ccc(N4CCN(C(=O)CN(C(C)C)C(C)C)C[C@@H]4C)nc3c2C(C)C)cn2ncnc2c1C] | 545.40 | 1.15 | QC-ACN-TFA-XB |
| 904 | 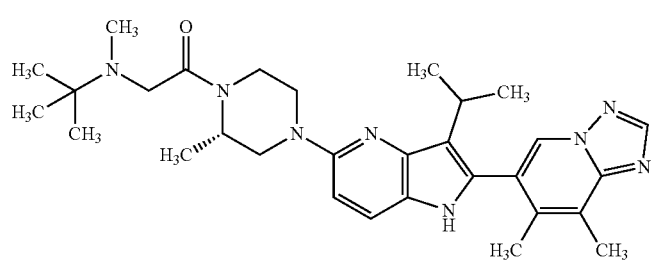 [SMILES: Cc1c(-c2[nH]c3ccc(N4CCN(C(=O)CN(C)C(C)(C)C)[C@@H](C)C4)nc3c2C(C)C)cn2ncnc2c1C] | 531.50 | 1.53 | QC-ACN-AA-XB |

TABLE 2-continued

| Ex. No. | Structure | Obs. MS Ion | RT | QC Method |
|---|---|---|---|---|
| 905 | 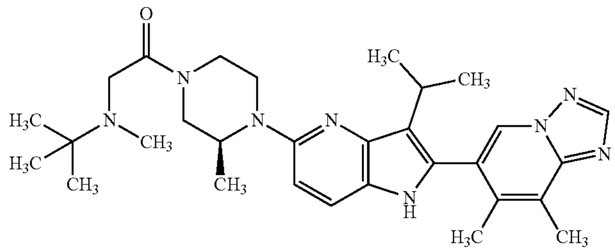 [SMILES: Cc1c(-c2[nH]c3ccc(N4CCN(C(=O)CN(C)C(C)(C)C)C[C@@H]4C)nc3c2C(C)C)cn2ncnc2c1C] | 531.40 | 1.59 | QC-ACN-AA-XB |
| 906 | 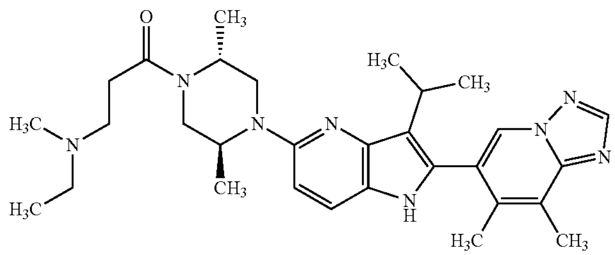 [SMILES: CCN(C)CCC(=O)N1C[C@H](C)N(c2ccc3[nH]c(-c4cn5ncnc5c(C)c4C)c(C(C)C)c3n2)C[C@H]1C] | 531.00 | 1.59 | QC-ACN-AA-XB |
| 907 | 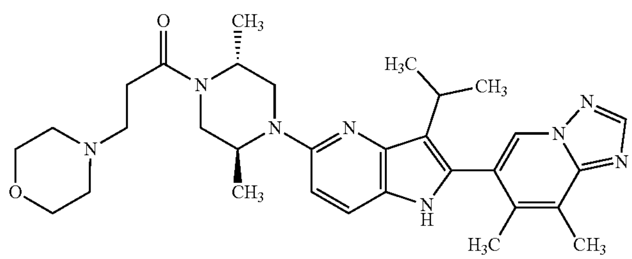 [SMILES: Cc1c(-c2[nH]c3ccc(N4C[C@@H](C)N(C(=O)CCN5CCOCC5)C[C@@H]4C)nc3c2C(C)C)cn2ncnc2c1C] | 559.00 | 1.75 | QC-ACN-AA-XB |
| 908 | 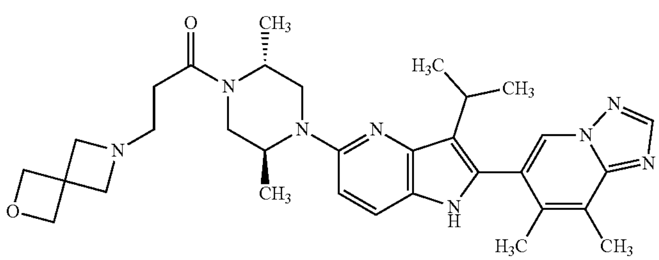 [SMILES: Cc1c(-c2[nH]c3ccc(N4C[C@@H](C)N(C(=O)CCN5CC6(COC6)C5)C[C@@H]4C)nc3c2C(C)C)cn2ncnc2c1C] | 571.40 | 0.91 | QC-ACN-TFA-XB |
| 909 | 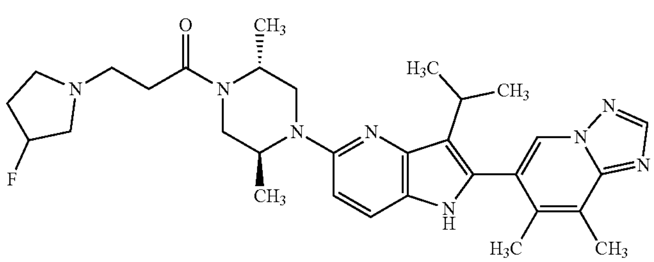 | 561.00 | 1.79 | QC-ACN-AA-XB |

TABLE 2-continued

| Ex. No. | Structure | Obs. MS Ion | RT | QC Method |
|---|---|---|---|---|
| 910 | 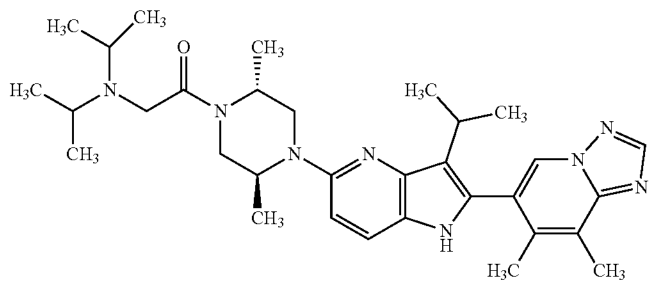 [SMILES: Cc1c(-c2[nH]c3ccc(N4C[C@@H](C)N(C(=O)CN(C(C)C)C(C)C)C[C@@H]4C)nc3c2C(C)C)cn2ncnc2c1C] | 559.50 | 1.64 | QC-ACN-AA-XB |
| 911 | 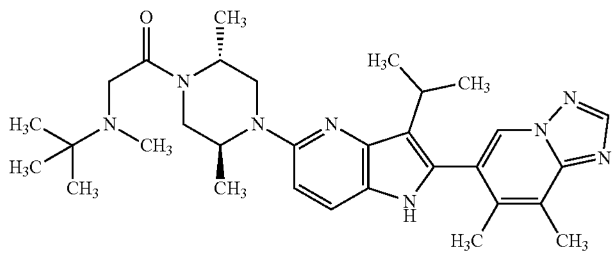 [SMILES: Cc1c(-c2[nH]c3ccc(N4C[C@@H](C)N(C(=O)CN(C)C(C)(C)C)C[C@@H]4C)nc3c2C(C)C)cn2ncnc2c1C] | 545.50 | 1.60 | QC-ACN-AA-XB |
| 912 | 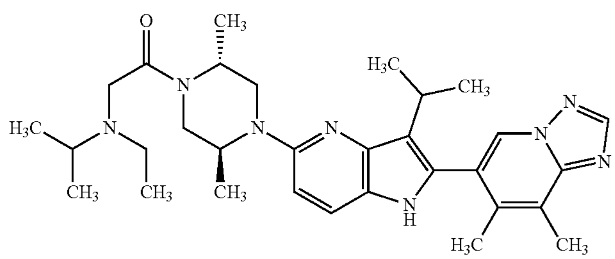 [SMILES: CCN(CC(=O)N1C[C@H](C)N(c2ccc3[nH]c(-c4cn5ncnc5c(C)c4C)c(C(C)C)c3n2)C[C@H]1C)C(C)C] | 545.50 | 1.04 | QC-ACN-TFA-XB |
| 913 | 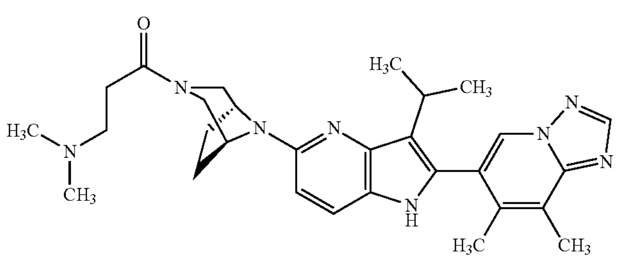 [SMILES: Cc1c(-c2[nH]c3ccc(N4[C@@H]5CC[C@H]4CN(C(=O)CCN(C)C)C5)nc3c2C(C)C)cn2ncnc2c1C] | 515.40 | 0.90 | QC-ACN-TFA-XB |
| 914 | 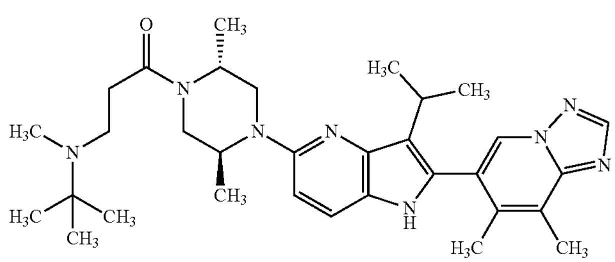 [SMILES: Cc1c(-c2[nH]c3ccc(N4C[C@@H](C)N(C(=O)CCN(C)C(C)(C)C)C[C@@H]4C)nc3c2C(C)C)cn2ncnc2c1C] | 559.50 | 1.52 | QC-ACN-AA-XB |

TABLE 2-continued

| Ex. No. | Structure | Obs. MS Ion | RT | QC Method |
|---|---|---|---|---|
| 915 | 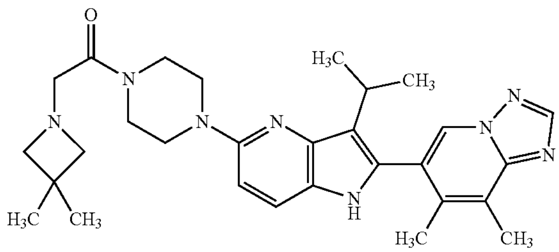 [SMILES: Cc1c(-c2[nH]c3ccc(N4CCN(C(=O)CN5CC(C)(C)C5)CC4)nc3c2C(C)C)cn2ncnc2c1C] | 515.30 | 1.38 | QC-ACN-AA-XB |
| 916 | 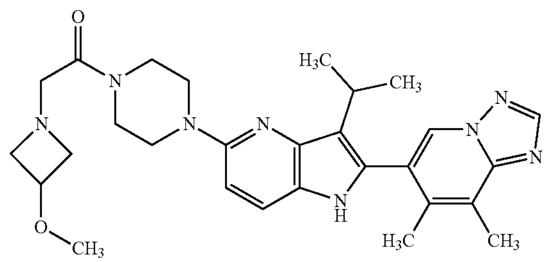 [SMILES: COC1CN(CC(=O)N2CCN(c3ccc4[nH]c(-c5cn6ncnc6c(C)c5C)c(C(C)C)c4n3)CC2)C1] | 517.30 | 0.81 | QC-ACN-TFA-XB |
| 917 | 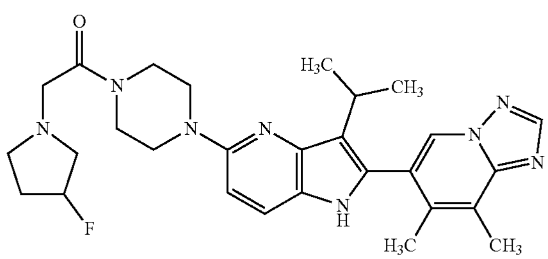 [SMILES: Cc1c(-c2[nH]c3ccc(N4CCN(C(=O)CN5CCC(F)C5)CC4)nc3c2C(C)C)cn2ncnc2c1C] | 519.20 | 1.51 | QC-ACN-AA-XB |
| 918 | 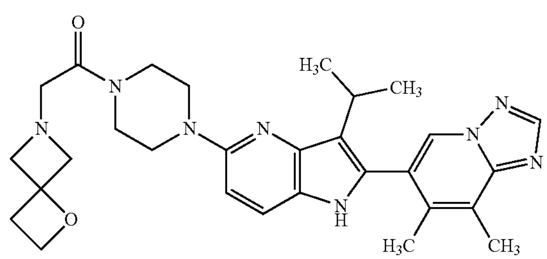 | 529.20 | 1.60 | QC-ACN-AA-XB |
| 919 | 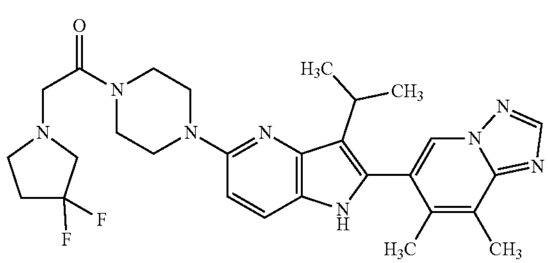 [SMILES: Cc1c(-c2[nH]c3ccc(N4CCN(C(=O)CN5CCC(F)(F)C5)CC4)nc3c2C(C)C)cn2ncnc2c1C] | 537.40 | 0.90 | QC-ACN-TFA-XB |
| 920 | 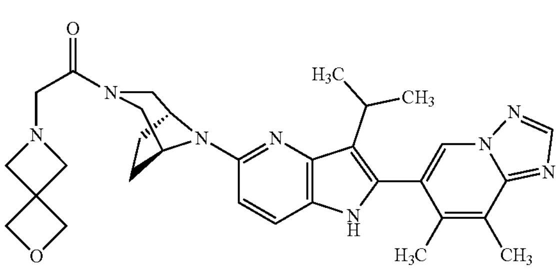 [SMILES: Cc1c(-c2[nH]c3ccc(N4[C@@H]5CC[C@H]4CN(C(=O)CN4CC6(COC6)C4)C5)nc3c2C(C)C)cn2ncnc2c1C] | 555.40 | 1.36 | QC-ACN-AA-XB |

TABLE 2-continued

| Ex. No. | Structure | Obs. MS Ion | RT | QC Method |
|---|---|---|---|---|
| 921 | 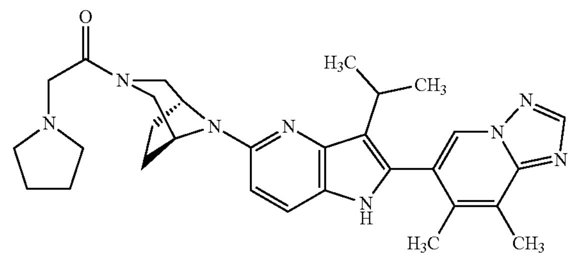 [SMILES: Cc1c(-c2[nH]c3ccc(N4[C@@H]5CC[C@H]4CN(C(=O)CN4CCCC4)C5)nc3c2C(C)C)cn2ncnc2c1C] | 527.20 | 1.49 | QC-ACN-AA-XB |
| 922 | 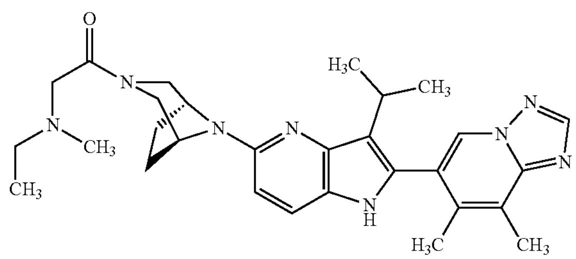 [SMILES: CCN(C)CC(=O)N1C[C@H]2CC[C@@H](C1)N2c1ccc2[nH]c(-c3cn4ncnc4c(C)c3C)c(C(C)C)c2n1] | 515.20 | 0.93 | QC-ACN-TFA-XB |
| 923 | 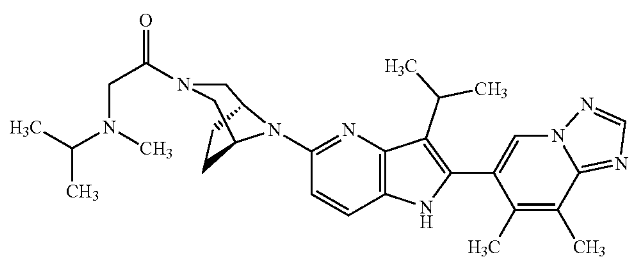 [SMILES: Cc1c(-c2[nH]c3ccc(N4[C@@H]5CC[C@H]4CN(C(=O)CN(C)C(C)C)C5)nc3c2C(C)C)cn2ncnc2c1C] | 529.40 | 0.96 | QC-ACN-TFA-XB |
| 924 | 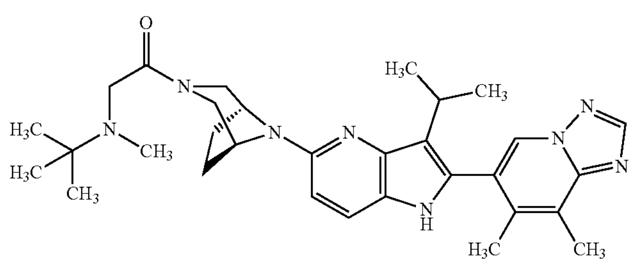 [SMILES: Cc1c(-c2[nH]c3ccc(N4[C@@H]5CC[C@H]4CN(C(=O)CN(C)C(C)(C)C)C5)nc3c2C(C)C)cn2ncnc2c1C] | 543.40 | 1.00 | QC-ACN-TFA-XB |
| 925 | 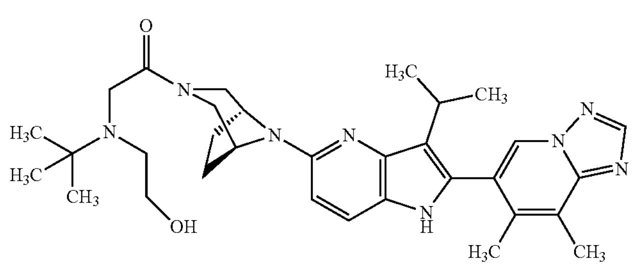 [SMILES: Cc1c(-c2[nH]c3ccc(N4[C@@H]5CC[C@H]4CN(C(=O)CN(CCO)C(C)(C)C)C5)nc3c2C(C)C)cn2ncnc2c1C] | 573.50 | 1.49 | QC-ACN-AA-XB |

TABLE 2-continued

| Ex. No. | Structure | Obs. MS Ion | RT | QC Method |
|---|---|---|---|---|
| 926 | 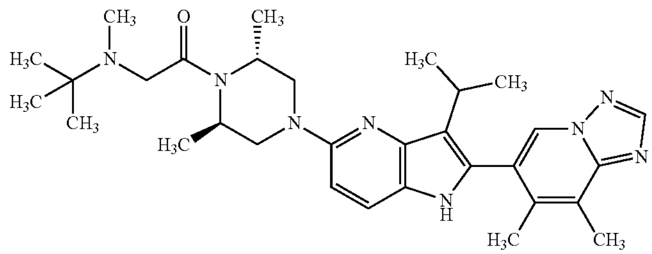 [SMILES: Cc1c(-c2[nH]c3ccc(N4C[C@@H](C)N(C(=O)CN(C)C(C)(C)C)[C@H](C)C4)nc3c2C(C)C)cn2ncnc2c1C] | 545.50 | 1.59 | QC-ACN-AA-XB |
| 927 | 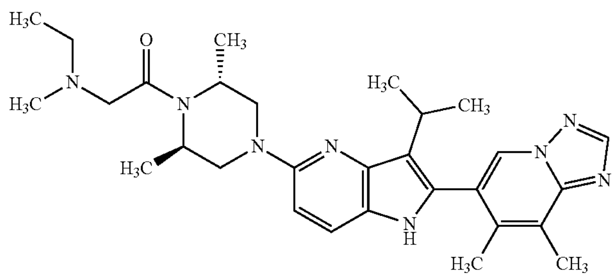 [SMILES: CCN(C)CC(=O)N1[C@H](C)CN(c2ccc3[nH]c(-c4cn5ncnc5c(C)c4C)c(C(C)C)c3n2)C[C@H]1C] | 517.20 | 0.84 | QC-ACN-TFA-XB |
| 928 | 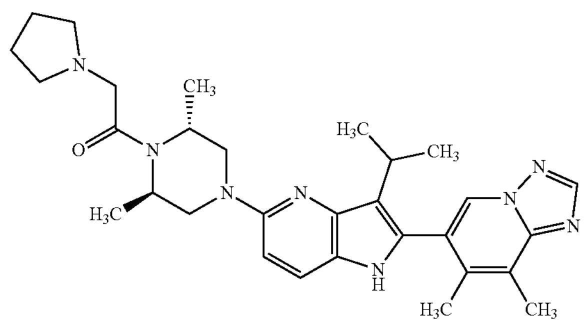 [SMILES: Cc1c(-c2[nH]c3ccc(N4C[C@@H](C)N(C(=O)CN5CCCC5)[C@H](C)C4)nc3c2C(C)C)cn2ncnc2c1C] | 529.30 | 1.51 | QC-ACN-AA-XB |
| 929 | 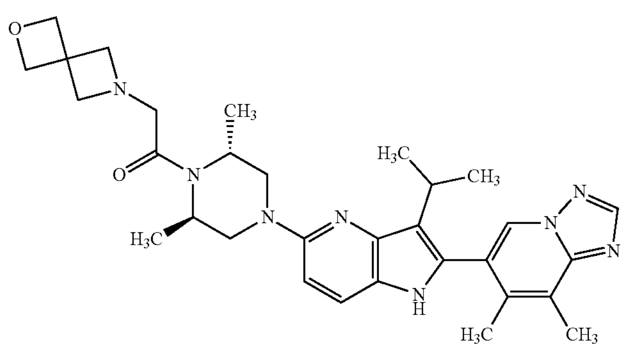 [SMILES: Cc1c(-c2[nH]c3ccc(N4C[C@@H](C)N(C(=O)CN5CC6(COC6)C5)[C@H](C)C4)nc3c2C(C)C)cn2ncnc2c1C] | 557.40 | 1.40 | QC-ACN-AA-XB |
| 930 | 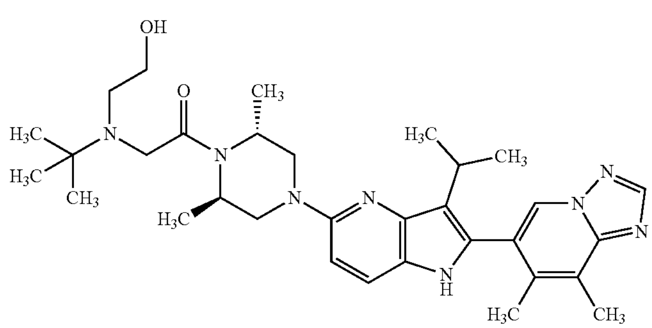 [SMILES: Cc1c(-c2[nH]c3ccc(N4C[C@@H](C)N(C(=O)CN(CCO)C(C)(C)C)[C@H](C)C4)nc3c2C(C)C)cn2ncnc2c1C] | 575.00 | 1.75 | QC-ACN-AA-XB |

TABLE 2-continued

| Ex. No. | Structure | Obs. MS Ion | RT | QC Method |
|---|---|---|---|---|
| 931 | 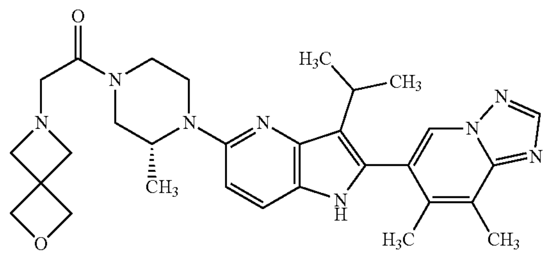 [SMILES: Cc1c(-c2[nH]c3ccc(N4CCN(C(=O)CN5CC6(COC6)C5)C[C@H]4C)nc3c2C(C)C)cn2ncnc2c1C] | 543.00 | 1.03 | QC-ACN-TFA-XB |
| 932 | 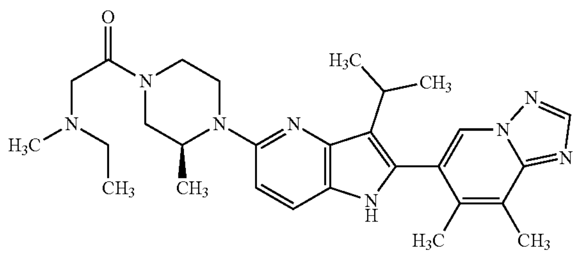 [SMILES: CCN(C)CC(=O)N1CCN(c2ccc3[nH]c(-c4cn5ncnc5c(C)c4C)c(C(C)C)c3n2)[C@@H](C)C1] | 503.50 | 1.41 | QC-ACN-AA-XB |
| 933 | 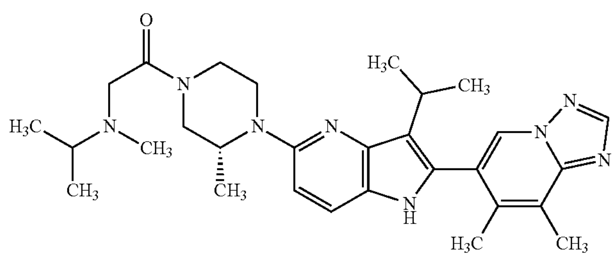 [SMILES: Cc1c(-c2[nH]c3ccc(N4CCN(C(=O)CN(C)C(C)C)C[C@H]4C)nc3c2C(C)C)cn2ncnc2c1C] | 517.20 | 1.48 | QC-ACN-AA-XB |
| 934 | 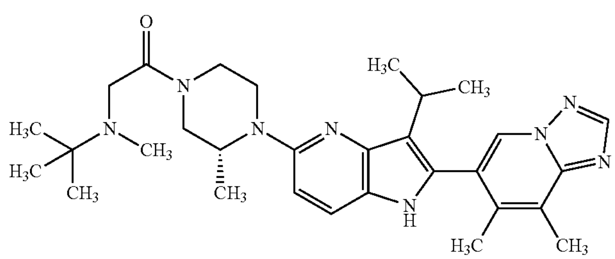 [SMILES: Cc1c(-c2[nH]c3ccc(N4CCN(C(=O)CN(C)C(C)(C)C)C[C@H]4C)nc3c2C(C)C)cn2ncnc2c1C] | 531.50 | 0.96 | QC-ACN-TFA-XB |
| 935 | 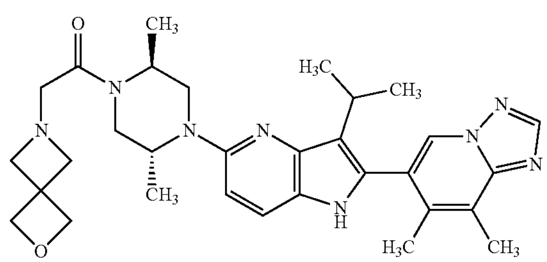 [SMILES: Cc1c(-c2[nH]c3ccc(N4C[C@H](C)N(C(=O)CN5CC6(COC6)C5)C[C@H]4C)nc3c2C(C)C)cn2ncnc2c1C] | 557.40 | 1.47 | QC-ACN-AA-XB |
| 936 | 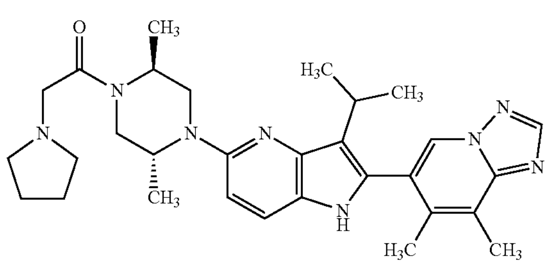 [SMILES: Cc1c(-c2[nH]c3ccc(N4C[C@H](C)N(C(=O)CN5CCCC5)C[C@H]4C)nc3c2C(C)C)cn2ncnc2c1C] | 529.50 | 1.44 | QC-ACN-AA-XB |

TABLE 2-continued

| Ex. No. | Structure | Obs. MS Ion | RT | QC Method |
|---|---|---|---|---|
| 937 | 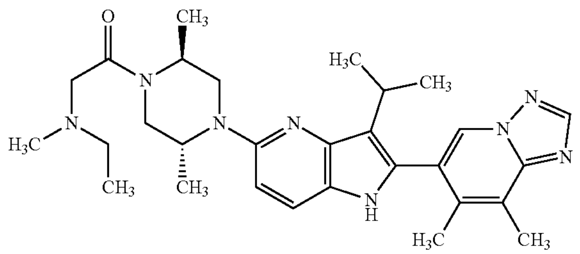 [SMILES: CCN(C)CC(=O)N1C[C@@H](C)N(c2ccc3[nH]c(-c4cn5ncnc5c(C)c4C)c(C(C)C)c3n2)C[C@@H]1C] | 517.30 | 1.10 | QC-ACN-TFA-XB |
| 938 | 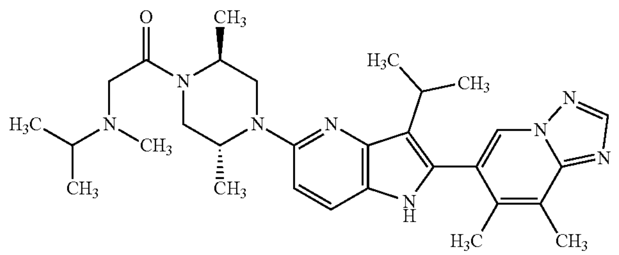 [SMILES: Cc1c(-c2[nH]c3ccc(N4C[C@H](C)N(C(=O)CN(C)C(C)C)C[C@H]4C)nc3c2C(C)C)cn2ncnc2c1C] | 531.50 | 1.53 | QC-ACN-AA-XB |
| 939 | 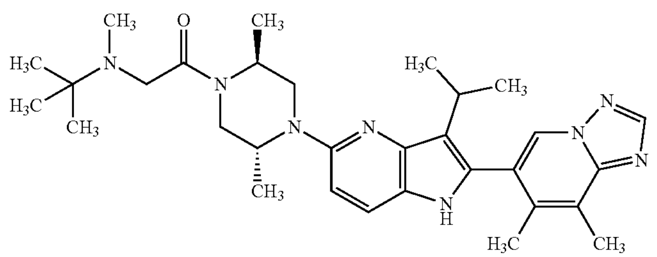 [SMILES: Cc1c(-c2[nH]c3ccc(N4C[C@H](C)N(C(=O)CN(C)C(C)(C)C)C[C@H]4C)nc3c2C(C)C)cn2ncnc2c1C] | 545.10 | 1.73 | QC-ACN-AA-XB |
| 940 | 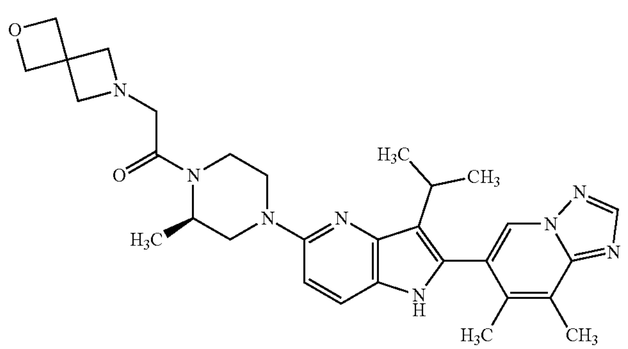 [SMILES: Cc1c(-c2[nH]c3ccc(N4CCN(C(=O)CN5CC6(COC6)C5)[C@H](C)C4)nc3c2C(C)C)cn2ncnc2c1C] | 543.20 | 1.52 | QC-ACN-AA-XB |
| 941 | 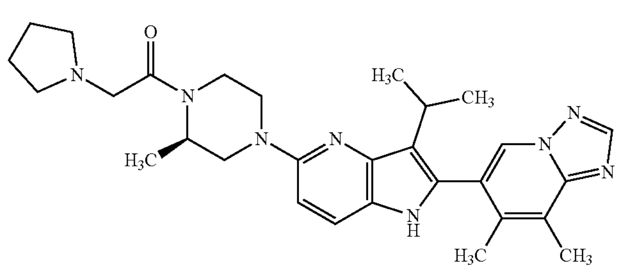 [SMILES: Cc1c(-c2[nH]c3ccc(N4CCN(C(=O)CN5CCCC5)[C@H](C)C4)nc3c2C(C)C)cn2ncnc2c1C] | 515.30 | 1.50 | QC-ACN-AA-XB |

TABLE 2-continued

| Ex. No. | Structure | Obs. MS Ion | RT | QC Method |
|---|---|---|---|---|
| 942 | 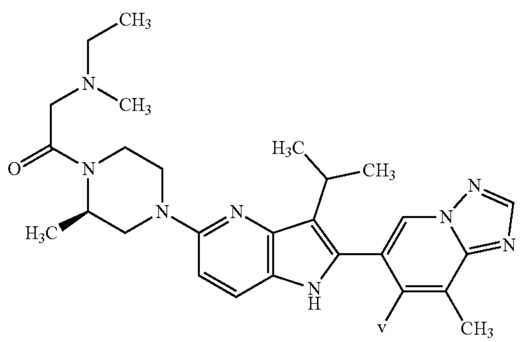 | 503.20 | 1.44 | QC-ACN-AA-XB |
| 943 | 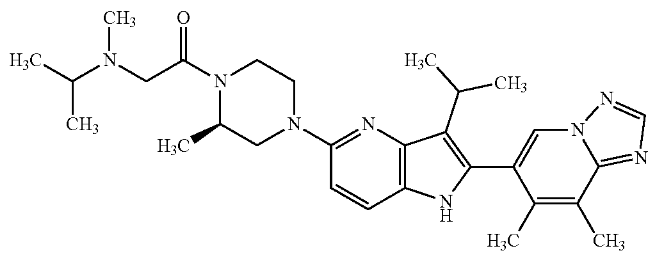 [SMILES: Cc1c(-c2[nH]c3ccc(N4CCN(C(=O)CN(C)C(C)C)[C@H](C)C4)nc3c2C(C)C)cn2ncnc2c1C] | 517.00 | 1.07 | QC-ACN-TFA-XB |
| 944 | 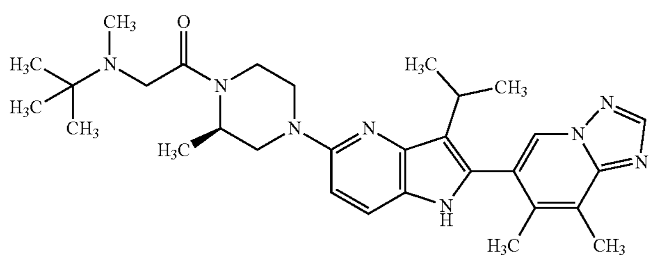 [SMILES: Cc1c(-c2[nH]c3ccc(N4CCN(C(=O)CN(C)C(C)(C)C)[C@H](C)C4)nc3c2C(C)C)cn2ncnc2c1C] | 531.30 | 1.59 | QC-ACN-AA-XB |
| 945 | 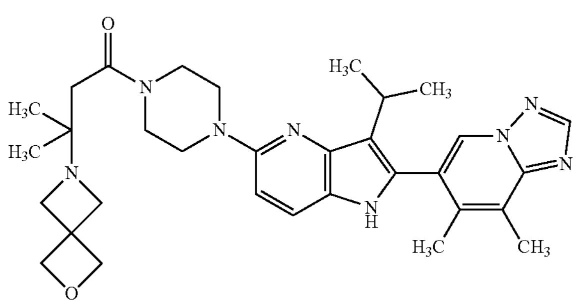 [SMILES: Cc1c(-c2[nH]c3ccc(N4CCN(C(=O)CC(C)(C)N5CC6(COC6)C5)CC4)nc3c2C(C)C)cn2ncnc2c1C] | 571.30 | 0.85 | QC-ACN-TFA-XB |
| 946 | 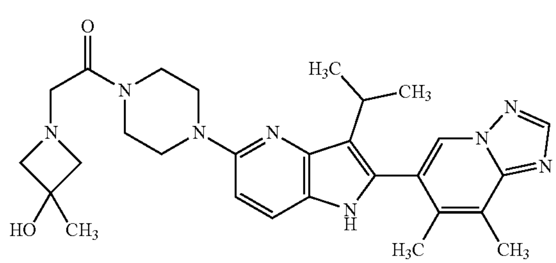 [SMILES: Cc1c(-c2[nH]c3ccc(N4CCN(C(=O)CN5CC(C)(O)C5)CC4)nc3c2C(C)C)cn2ncnc2c1C] | 517.30 | 1.00 | QC-ACN-TFA-XB |

TABLE 2-continued

| Ex. No. | Structure | Obs. MS Ion | RT | QC Method |
|---|---|---|---|---|
| 947 | 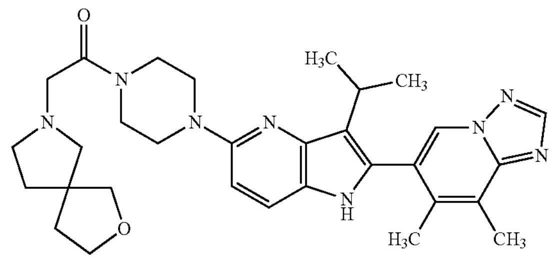 [SMILES: Cc1c(-c2[nH]c3ccc(N4CCN(C(=O)CN5CCC6(CCOC6)C5)CC4)nc3c2C(C)C)cn2ncnc2c1C] | 557.00 | 1.03 | QC-ACN-TFA-XB |
| 948 | 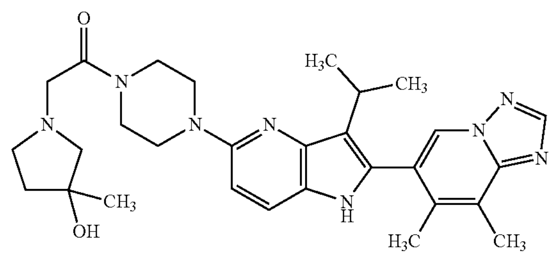 [SMILES: Cc1c(-c2[nH]c3ccc(N4CCN(C(=O)CN5CCC(C)(O)C5)CC4)nc3c2C(C)C)cn2ncnc2c1C] | 531.00 | 1.01 | QC-ACN-TFA-XB |
| 949 | 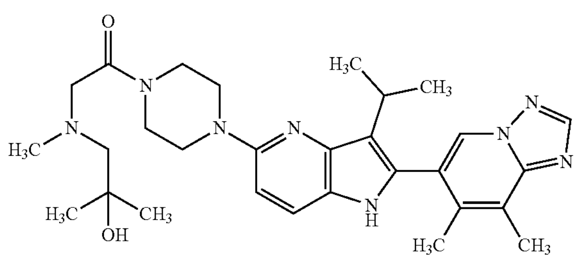 [SMILES: Cc1c(-c2[nH]c3ccc(N4CCN(C(=O)CN(C)CC(C)(C)O)CC4)nc3c2C(C)C)cn2ncnc2c1C] | 533.30 | 1.04 | QC-ACN-TFA-XB |
| 950 | 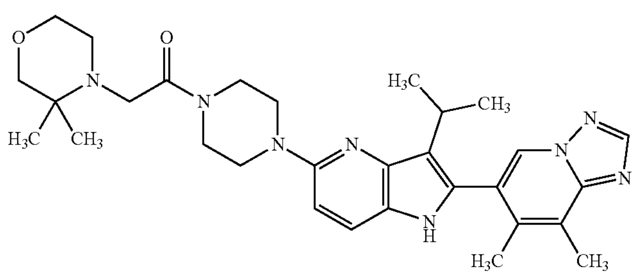 [SMILES: Cc1c(-c2[nH]c3ccc(N4CCN(C(=O)CN5CCOCC5(C)C)CC4)nc3c2C(C)C)cn2ncnc2c1C] | 545.00 | 1.81 | QC-ACN-AA-XB |
| 951 | 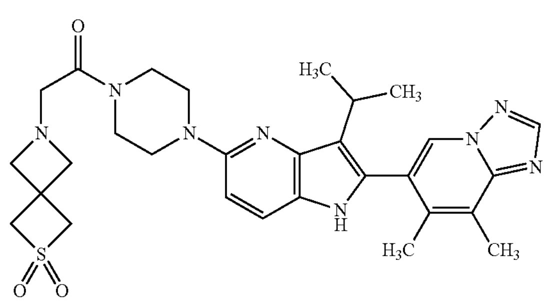 [SMILES: Cc1c(-c2[nH]c3ccc(N4CCN(C(=O)CN5CC6(C5)CS(=O)(=O)C6)CC4)nc3c2C(C)C)cn2ncnc2c1C] | 577.20 | 1.01 | QC-ACN-TFA-XB |

TABLE 2-continued
| Ex. No. | Structure | Obs. MS Ion | RT | QC Method |
|---|---|---|---|---|
| 952 | 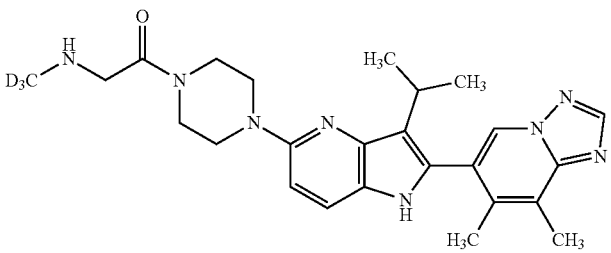 [SMILES: [2H]C([2H])([2H])NCC(=O)N1CCN(c2ccc3[nH]c(-c4cn5ncnc5c(C)c4C)c(C(C)C)c3n2)CC1] | 464.00 | 0.98 | QC-ACN-TFA-XB |
| 953 | 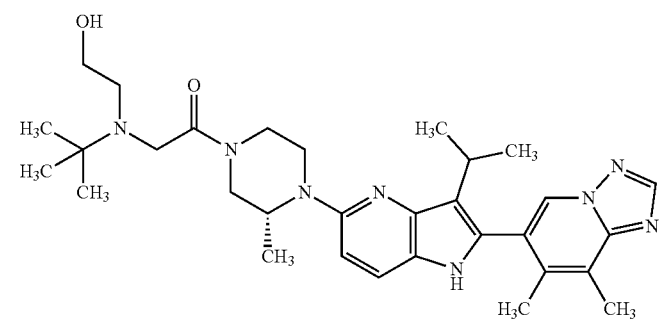 [SMILES: Cc1c(-c2[nH]c3ccc(N4CCN(C(=O)CN(CCO)C(C)(C)C)C[C@H]4C)nc3c2C(C)C)cn2ncnc2c1C] | 561.20 | 1.65 | QC-ACN-AA-XB |
| 954 | 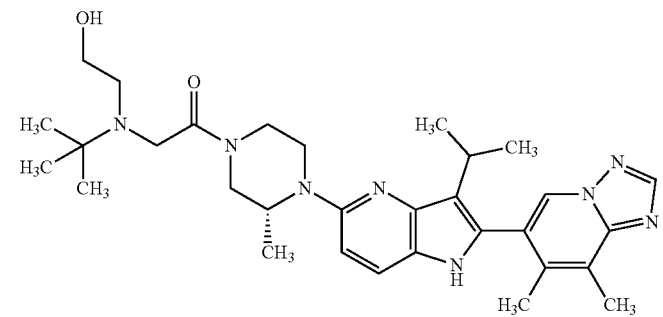 [SMILES: Cc1c(-c2[nH]c3ccc(N4CCN(C(=O)CN(CCO)C(C)(C)C)C[C@H]4C)nc3c2C(C)C)cn2ncnc2c1C] | 575.50 | 0.98 | QC-ACN-TFA-XB |
| 955 | 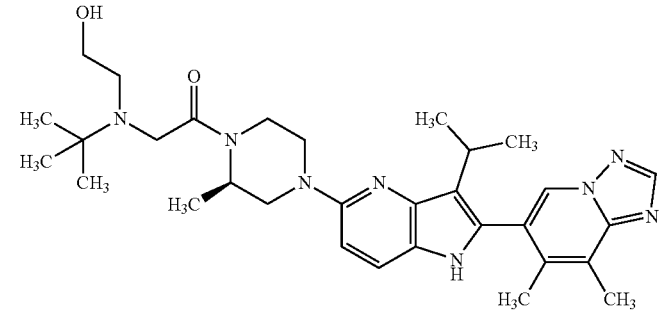 [SMILES: Cc1c(-c2[nH]c3ccc(N4CCN(C(=O)CN(CCO)C(C)(C)C)[C@H](C)C4)nc3c2C(C)C)cn2ncnc2c1C] | 561.50 | 1.55 | QC-ACN-AA-XB |
| 956 | 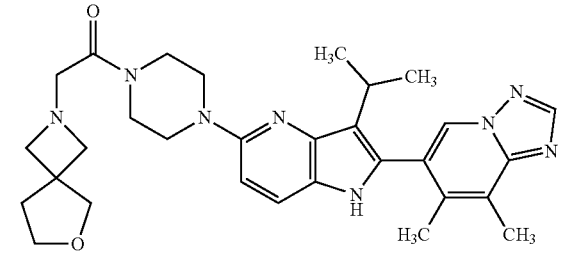 [SMILES: Cc1c(-c2[nH]c3ccc(N4CCN(C(=O)CN5CC6(CCOC6)C5)CC4)nc3c2C(C)C)cn2ncnc2c1C] | 543.40 | 1.35 | QC-ACN-AA-XB |

TABLE 2-continued

| Ex. No. | Structure | Obs. MS Ion | RT | QC Method |
|---|---|---|---|---|
| 957 | 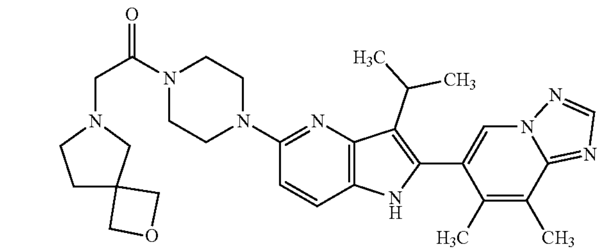 [SMILES: Cc1c(-c2[nH]c3ccc(N4CCN(C(=O)CN5CCC6(COC6)C5)CC4)nc3c2C(C)C)cn2ncnc2c1C] | 543.50 | 1.37 | QC-ACN-AA-XB |
| 958 | 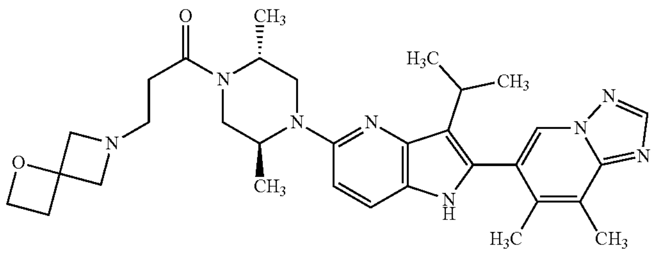 [SMILES: Cc1c(-c2[nH]c3ccc(N4C[C@@H](C)N(C(=O)CCN5CC6(CCO6)C5)C[C@@H]4C)nc3c2C(C)C)cn2ncnc2c1C] | 571.20 | 1.55 | QC-ACN-AA-XB |
| 959 | 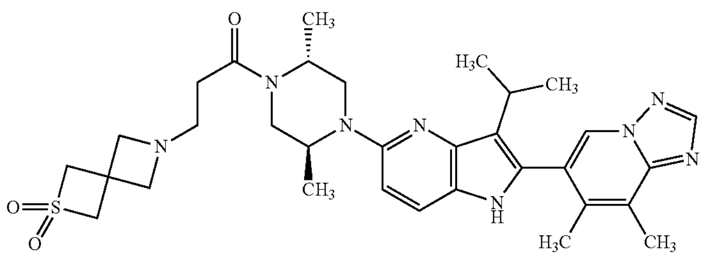 [SMILES: Cc1c(-c2[nH]c3ccc(N4C[C@@H](C)N(C(=O)CCN5CC6(C5)CS(=O)(=O)C6)C[C@@H]4C)nc3c2C(C)C)cn2ncnc2c1C] | 619.30 | 1.08 | QC-ACN-TFA-XB |
| 960 | 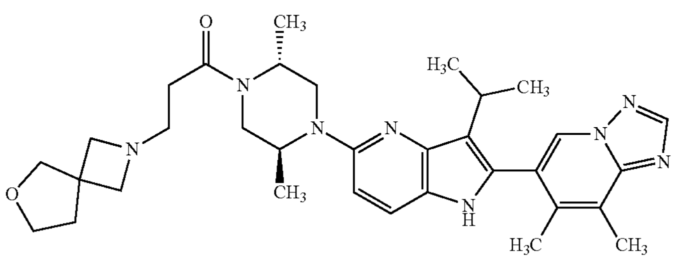 [SMILES: Cc1c(-c2[nH]c3ccc(N4C[C@@H](C)N(C(=O)CCN5CC6(CCOC6)C5)C[C@@H]4C)nc3c2C(C)C)cn2ncnc2c1C] | 585.50 | 1.42 | QC-ACN-AA-XB |
| 961 | 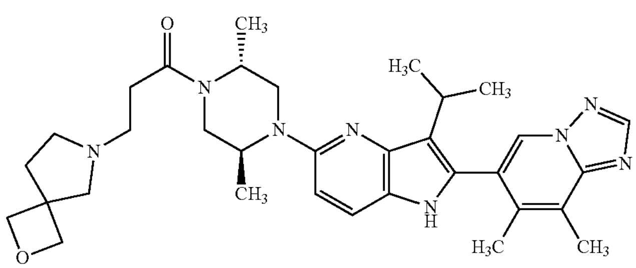 [SMILES: Cc1c(-c2[nH]c3ccc(N4C[C@@H](C)N(C(=O)CCN5CCC6(COC6)C5)C[C@@H]4C)nc3c2C(C)C)cn2ncnc2c1C] | 585.30 | 1.09 | QC-ACN-TFA-XB |
| 962 | 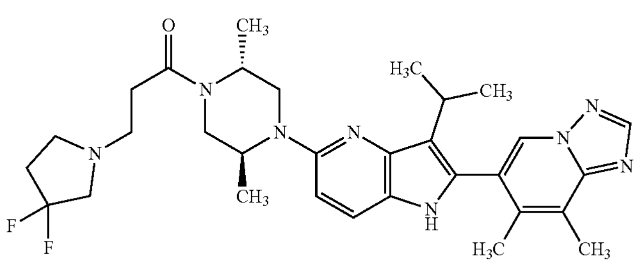 [SMILES: Cc1c(-c2[nH]c3ccc(N4C[C@@H](C)N(C(=O)CCN5CCC(F)(F)C5)C[C@@H]4C)nc3c2C(C)C)cn2ncnc2c1C] | 579.30 | 1.92 | QC-ACN-AA-XB |

TABLE 2-continued

| Ex. No. | Structure | Obs. MS Ion | RT | QC Method |
|---|---|---|---|---|
| 963 | 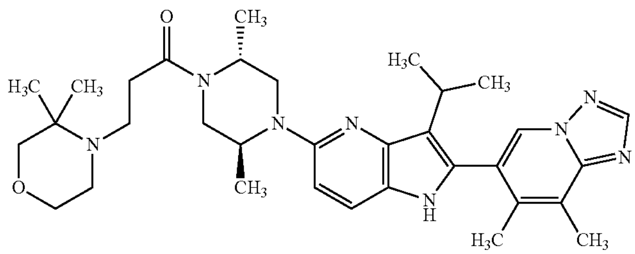 [SMILES: Cc1c(-c2[nH]c3ccc(N4C[C@@H](C)N(C(=O)CCN5CCOCC5(C)C)C[C@@H]4C)nc3c2C(C)C)cn2ncnc2c1C] | 587.20 | 1.85 | QC-ACN-AA-XB |
| 964 | 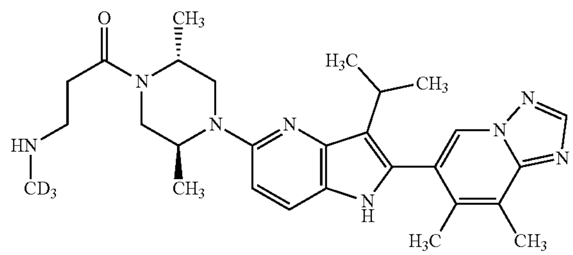 | 506.30 | 1.54 | QC-ACN-AA-XB |
| 965 | 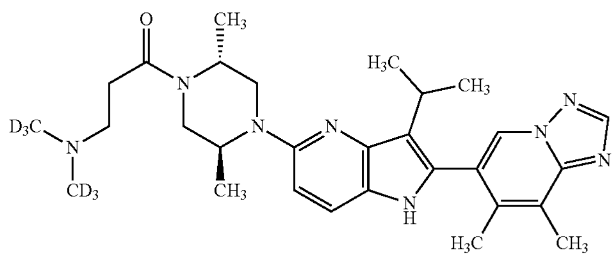 [SMILES: [2H]C([2H])([2H])N(CCC(=O)N1C[C@H](C)N(c2ccc3[nH]c(-c4cn5ncnc5c(C)c4C)c(C(C)C)c3n2)C[C@H]1C)C([2H])([2H])[2H]] | 523.40 | 1.46 | QC-ACN-AA-XB |
| 966 | 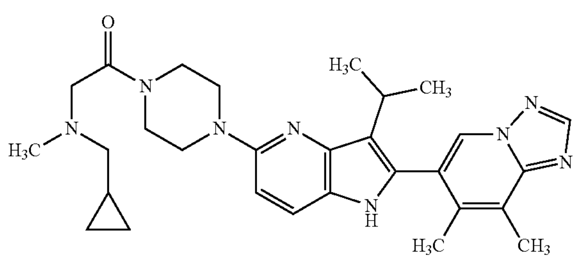 [SMILES: Cc1c(-c2[nH]c3ccc(N4CCN(C(=O)CN(C)CC5CC5)CC4)nc3c2C(C)C)cn2ncnc2c1C] | 515.60 | 1.01 | QC-ACN-TFA-XB |
| 967 | 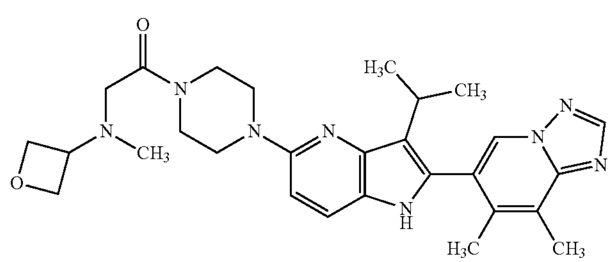 [SMILES: Cc1c(-c2[nH]c3ccc(N4CCN(C(=O)CN(C)C5COC5)CC4)nc3c2C(C)C)cn2ncnc2c1C] | 517.60 | 0.91 | QC-ACN-TFA-XB |
| 968 | 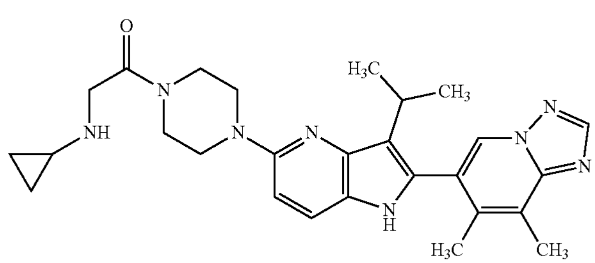 [SMILES: Cc1c(-c2[nH]c3ccc(N4CCN(C(=O)CNC5CC5)CC4)nc3c2C(C)C)cn2ncnc2c1C] | 487.20 | 1.46 | QC-ACN-AA-XB |

TABLE 2-continued

| Ex. No. | Structure | Obs. MS Ion | RT | QC Method |
|---|---|---|---|---|
| 969 | 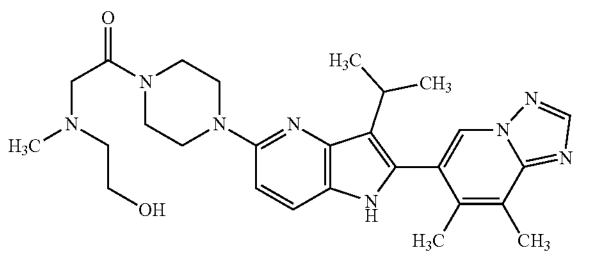 | 505.20 | 1.24 | QC-ACN-AA-XB |
| 970 | 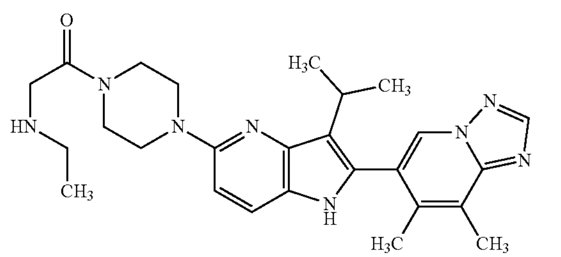 | 475.50 | 0.92 | QC-ACN-TFA-XB |
| 971 | 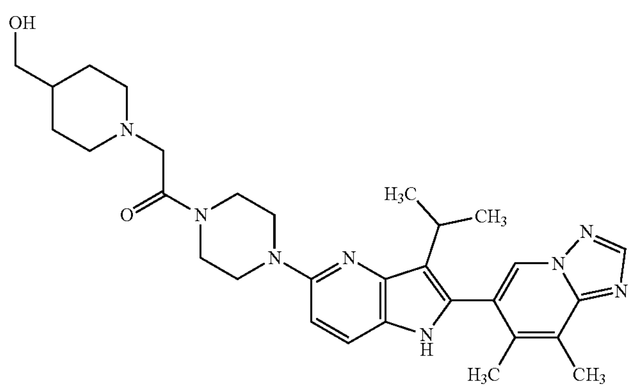 [SMILES: Cc1c(-c2[nH]c3ccc(N4CCN(C(=O)CN5CCC(CO)CC5)CC4)nc3c2C(C)C)cn2ncnc2c1C] | 545.40 | 1.25 | QC-ACN-AA-XB |
| 972 | 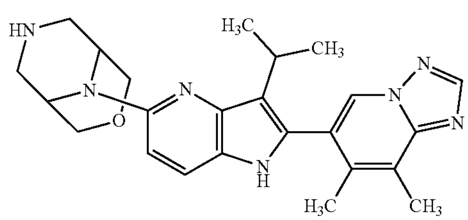 [SMILES: Cc1c(-c2[nH]c3ccc(N4C5CNCC4COC5)nc3c2C(C)C)cn2ncnc2c1C] | 432.10 | 1.25 | QC-ACN-AA-XB |
| 973 | 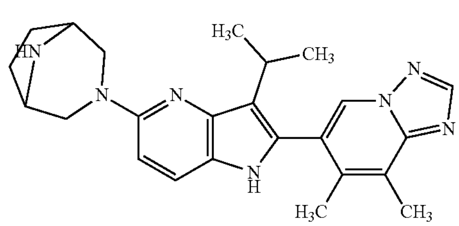 [SMILES: Cc1c(-c2[nH]c3ccc(N4CC5CCC(C4)N5)nc3c2C(C)C)cn2ncnc2c1C] | 416.10 | 1.29 | QC-ACN-AA-XB |

TABLE 2-continued

| Ex. No. | Structure | Obs. MS Ion | RT | QC Method |
|---|---|---|---|---|
| 974 | 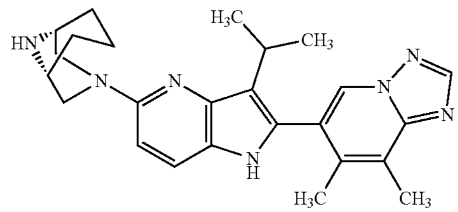 [SMILES: Cc1c(-c2[nH]c3ccc(N4C[C@H]5CCC[C@H](C4)N5)nc3c2C(C)C)cn2ncnc2c1C] | 430.00 | 1.44 | QC-ACN-AA-XB |
| 975 | 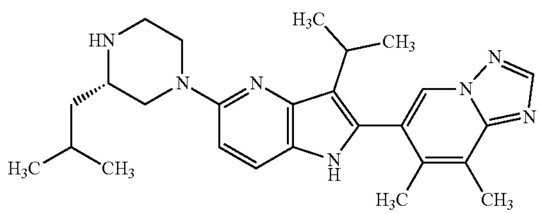 [SMILES: Cc1c(-c2[nH]c3ccc(N4CCN[C@@H](CC(C)C)C4)nc3c2C(C)C)cn2ncnc2c1C] | 223.90 | 1.28 | QC-ACN-TFA-XB |
| 976 | 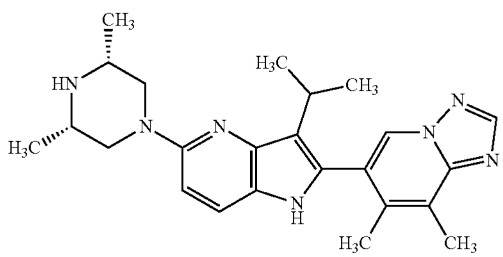 [SMILES: Cc1c(-c2[nH]c3ccc(N4C[C@@H](C)N[C@@H](C)C4)nc3c2C(C)C)cn2ncnc2c1C] | 418.10 | 1.07 | QC-ACN-TFA-XB |
| 977 | 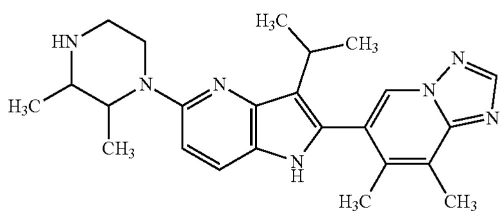 [SMILES: Cc1c(-c2[nH]c3ccc(N4CCNC(C)C4C)nc3c2C(C)C)cn2ncnc2c1C] | 418.10 | 1.08 | QC-ACN-TFA-XB |
| 978 | 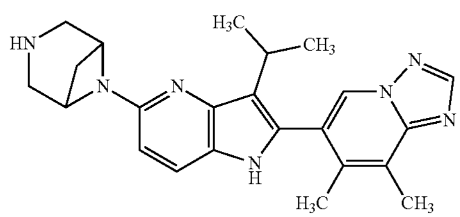 [SMILES: Cc1c(-c2[nH]c3ccc(N4C5CNCC4C5)nc3c2C(C)C)cn2ncnc2c1C] | 402.10 | 1.01 | QC-ACN-TFA-XB |
| 979 | 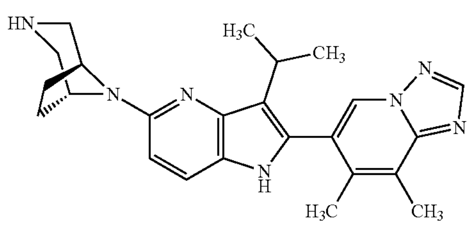 [SMILES: Cc1c(-c2[nH]c3ccc(N4[C@@H]5CC[C@H]4CNC5)nc3c2C(C)C)cn2ncnc2c1C] | 416.10 | 1.31 | QC-ACN-AA-XB |
| 980 | 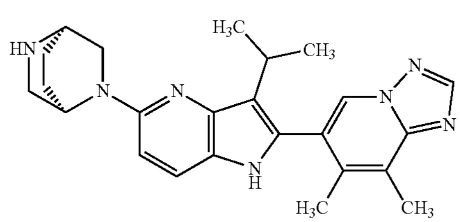 [SMILES: Cc1c(-c2[nH]c3ccc(N4C[C@H]5CC[C@@H]4CN5)nc3c2C(C)C)cn2ncnc2c1C] | 416.10 | 1.02 | QC-ACN-TFA-XB |

TABLE 2-continued

| Ex. No. | Structure | Obs. MS Ion | RT | QC Method |
|---|---|---|---|---|
| 981 | 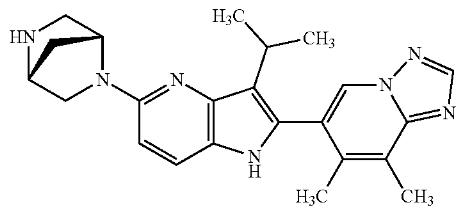 [SMILES: Cc1c(-c2[nH]c3ccc(N4C[C@H]5C[C@@H]4CN5)nc3c2C(C)C)cn2ncnc2c1C] | 402.10 | 0.99 | QC-ACN-TFA-XB |
| 982 | 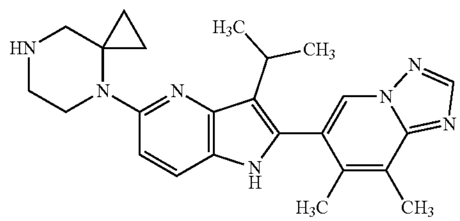 [SMILES: Cc1c(-c2[nH]c3ccc(N4CCNCC45CC5)nc3c2C(C)C)cn2ncnc2c1C] | 416.20 | 1.31 | QC-ACN-AA-XB |
| 983 | 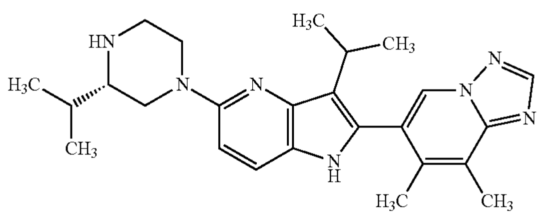 [SMILES: Cc1c(-c2[nH]c3ccc(N4CCN[C@@H](C(C)C)C4)nc3c2C(C)C)cn2ncnc2c1C] | 432.10 | 1.19 | QC-ACN-TFA-XB |
| 984 | 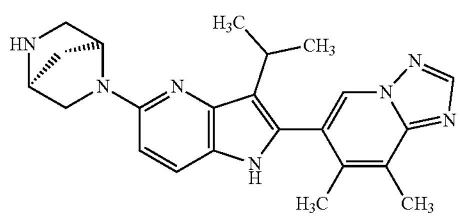 | 402.10 | 1.01 | QC-ACN-TFA-XB |
| 985 | 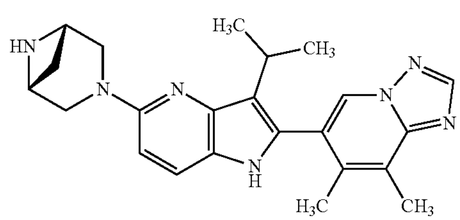 [SMILES: Cc1c(-c2[nH]c3ccc(N4C[C@H]5C[C@@H](C4)N5)nc3c2C(C)C)cn2ncnc2c1C] | 402.10 | 1.32 | QC-ACN-AA-XB |
| 986 | 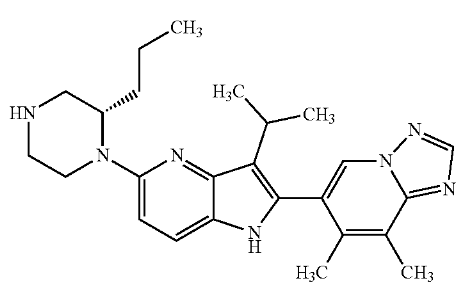 [SMILES: CCC[C@H]1CNCCN1c1ccc2[nH]c(-c3cn4ncnc4c(C)c3C)c(C(C)C)c2n1] | 432.40 | 1.45 | QC-ACN-AA-XB |

TABLE 2-continued

| Ex. No. | Structure | Obs. MS Ion | RT | QC Method |
|---|---|---|---|---|
| 987 | 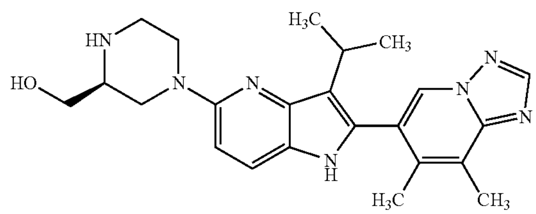 [SMILES: Cc1c(-c2[nH]c3ccc(N4CCN[C@H](CO)C4)nc3c2C(C)C)cn2ncnc2c1C] | 420.00 | 1.27 | QC-ACN-AA-XB |
| 988 | 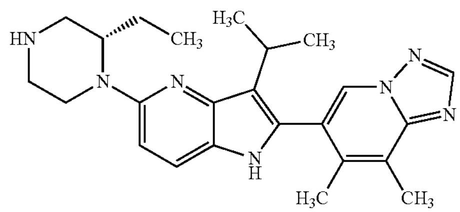 [SMILES: CC[C@H]1CNCCN1c1ccc2[nH]c(-c3cn4ncnc4c(C)c3C)c(C(C)C)c2n1] | 418.40 | 1.36 | QC-ACN-AA-XB |
| 989 | 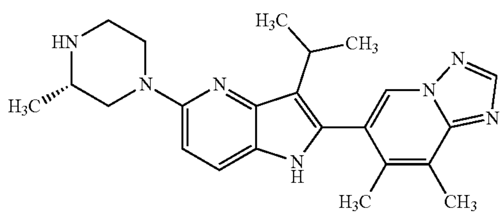 [SMILES: Cc1c(-c2[nH]c3ccc(N4CCN[C@@H](C)C4)nc3c2C(C)C)cn2ncnc2c1C] | 404.40 | 1.25 | QC-ACN-AA-XB |
| 990 | 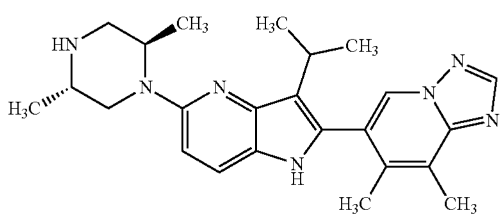 [SMILES: Cc1c(-c2[nH]c3ccc(N4C[C@H](C)NC[C@H]4C)nc3c2C(C)C)cn2ncnc2c1C] | 418.40 | 1.26 | QC-ACN-AA-XB |
| 991 | 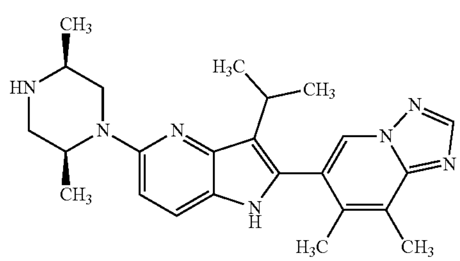 [SMILES: Cc1c(-c2[nH]c3ccc(N4C[C@H](C)NC[C@@H]4C)nc3c2C(C)C)cn2ncnc2c1C] | 418.20 | 1.50 | QC-ACN-AA-XB |
| 992 | 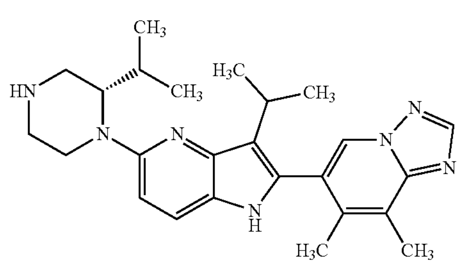 [SMILES: Cc1c(-c2[nH]c3ccc(N4CCNC[C@@H]4C(C)C)nc3c2C(C)C)cn2ncnc2c1C] | 432.30 | 0.94 | QC-ACN-TFA-XB |

TABLE 2-continued

| Ex. No. | Structure | Obs. MS Ion | RT | QC Method |
|---|---|---|---|---|
| 993 | 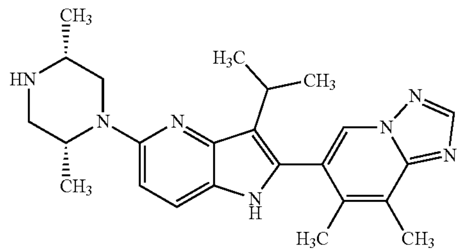 [SMILES: Cc1c(-c2[nH]c3ccc(N4C[C@@H](C)NC[C@H]4C)nc3c2C(C)C)cn2ncnc2c1C] | 418.50 | 1.37 | QC-ACN-AA-XB |
| 994 | 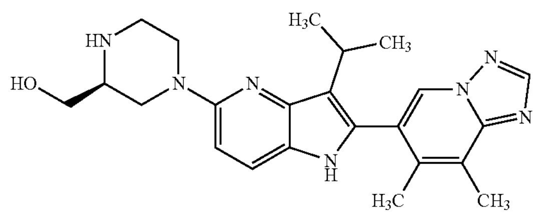 [SMILES: Cc1c(-c2[nH]c3ccc(N4CCN[C@H](CO)C4)nc3c2C(C)C)cn2ncnc2c1C] | 420.00 | 1.20 | QC-ACN-AA-XB |
| 995 | 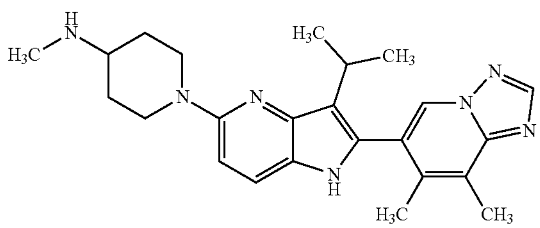 [SMILES: CNC1CCN(c2ccc3[nH]c(-c4cn5ncnc5c(C)c4C)c(C(C)C)c3n2)CC1] | 418.10 | 1.15 | QC-ACN-AA-XB |
| 996 | 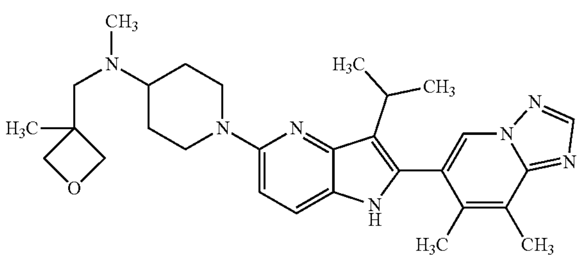 [SMILES: Cc1c(-c2[nH]c3ccc(N4CCC(N(C)CC5(C)COC5)CC4)nc3c2C(C)C)cn2ncnc2c1C] | 502.30 | 0.81 | QC-ACN-TFA-XB |
| 997 | 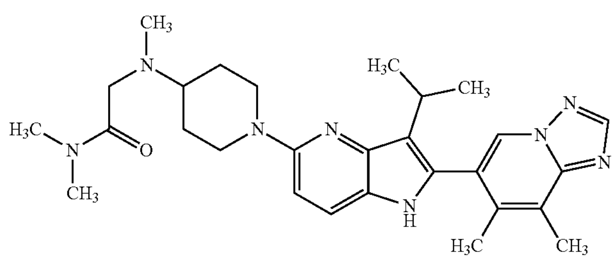 | 503.30 | 0.81 | QC-ACN-TFA-XB |
| 998 | 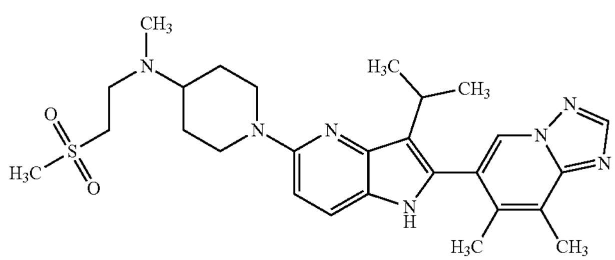 [SMILES: Cc1c(-c2[nH]c3ccc(N4CCC(N(C)CCS(C)(=O)=O)CC4)nc3c2C(C)C)cn2ncnc2c1C] | 524.20 | 0.82 | QC-ACN-TFA-XB |

TABLE 2-continued

| Ex. No. | Structure | Obs. MS Ion | RT | QC Method |
|---|---|---|---|---|
| 999 | 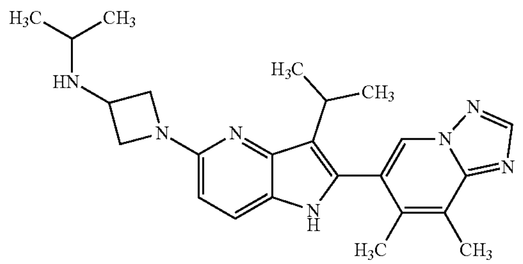 [SMILES: Cc1c(-c2[nH]c3ccc(N4CC(NC(C)C)C4)nc3c2C(C)C)cn2ncnc2c1C] | 418.10 | 1.00 | QC-ACN-TFA-XB |
| 1000 | 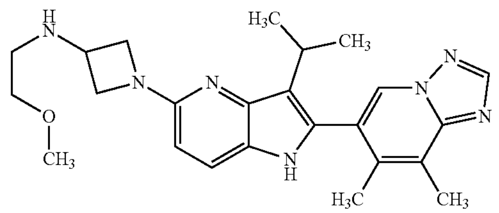 [SMILES: COCCNC1CN(c2ccc3[nH]c(-c4cn5ncnc5c(C)c4C)c(C(C)C)c3n2)C1] | 434.30 | 1.00 | QC-ACN-TFA-XB |
| 1001 | 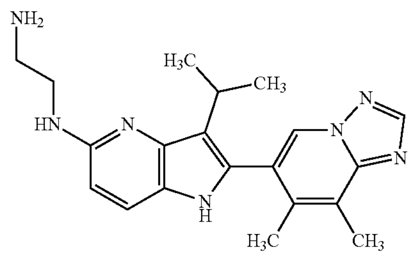 [SMILES: Cc1c(-c2[nH]c3ccc(NCCN)nc3c2C(C)C)cn2ncnc2c1C] | 364.00 | 1.09 | QC-ACN-AA-XB |
| 1002 | 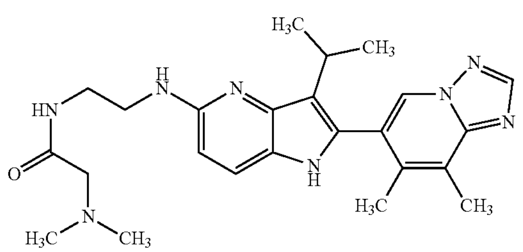 [SMILES: Cc1c(-c2[nH]c3ccc(NCCNC(=O)CN(C)C)nc3c2C(C)C)cn2ncnc2c1C] | 449.10 | 0.79 | QC-ACN-TFA-XB |
| 1003 | 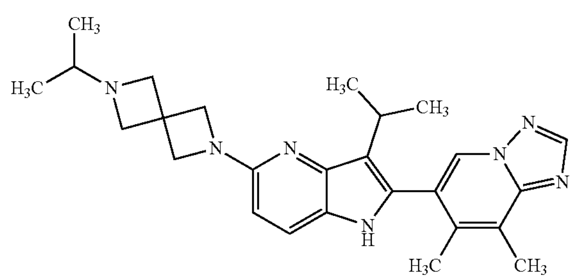 [SMILES: Cc1c(-c2[nH]c3ccc(N4CC5(C4)CN(C(C)C)C5)nc3c2C(C)C)cn2ncnc2c1C] | 444.30 | 0.81 | QC-ACN-TFA-XB |
| 1004 | 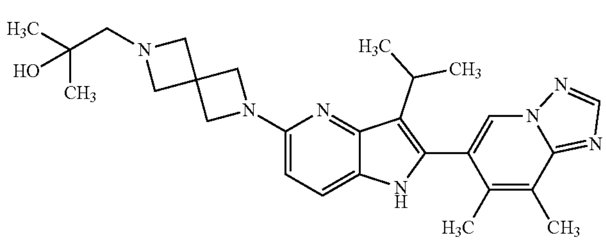 [SMILES: Cc1c(-c2[nH]c3ccc(N4CC5(CN(CC(C)(C)O)C5)C4)nc3c2C(C)C)cn2ncnc2c1C] | 473.90 | 0.99 | QC-ACN-TFA-XB |

TABLE 2-continued

| Ex. No. | Structure | Obs. MS Ion | RT | QC Method |
|---|---|---|---|---|
| 1005 | 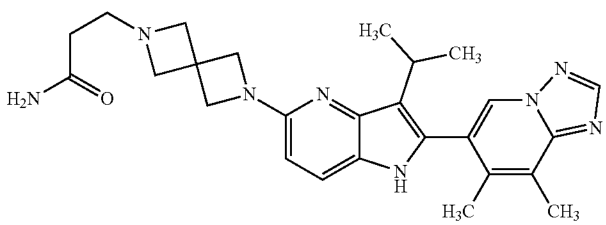 [SMILES: Cc1c(-c2[nH]c3ccc(N4CC5(CN(CCC(N)=O)C5)C4)nc3c2C(C)C)cn2ncnc2c1C] | 473.50 | 1.07 | QC-ACN-AA-XB |
| 1006 | 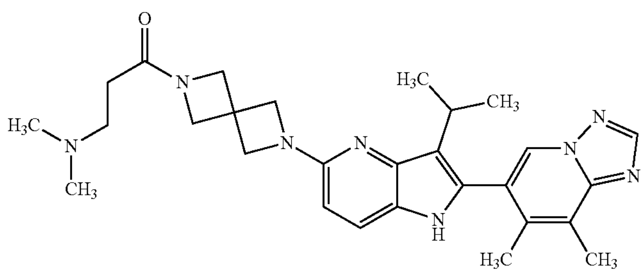 | 500.90 | 1.32 | QC-ACN-AA-XB |
| 1007 | 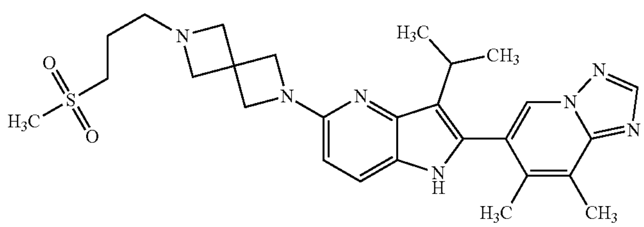 [SMILES: Cc1c(-c2[nH]c3ccc(N4CC5(CN(CCCS(C)(=O)=O)C5)C4)nc3c2C(C)C)cn2ncnc2c1C] | 522.10 | 1.44 | QC-ACN-AA-XB |
| 1008 | 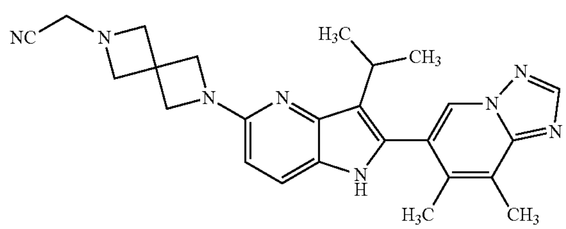 [SMILES: Cc1c(-c2[nH]c3ccc(N4CC5(CN(CC#N)C5)C4)nc3c2C(C)C)cn2ncnc2c1C] | 440.90 | 1.57 | QC-ACN-AA-XB |
| 1009 | 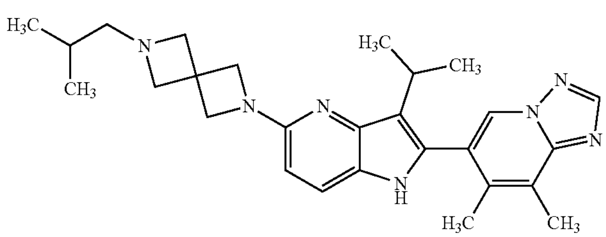 [SMILES: Cc1c(-c2[nH]c3ccc(N4CC5(CN(CC(C)C)C5)C4)nc3c2C(C)C)cn2ncnc2c1C] | 458.20 | 1.36 | QC-ACN-AA-XB |
| 1010 | 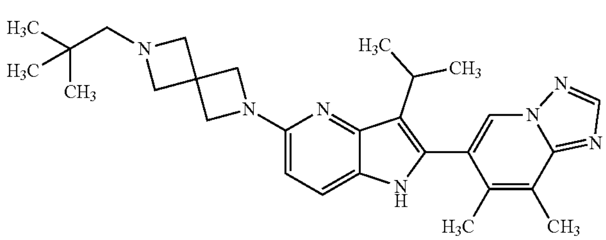 [SMILES: Cc1c(-c2[nH]c3ccc(N4CC5(CN(CC(C)(C)C)C5)C4)nc3c2C(C)C)cn2ncnc2c1C] | 472.20 | 1.53 | QC-ACN-AA-XB |

TABLE 2-continued

| Ex. No. | Structure | Obs. MS Ion | RT | QC Method |
|---|---|---|---|---|
| 1011 | 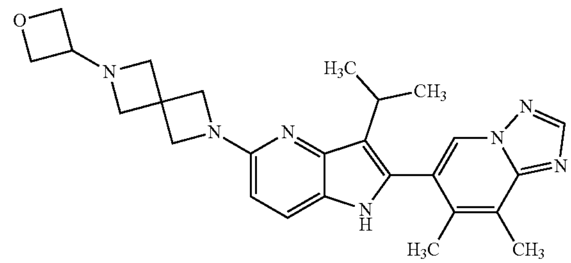 [SMILES: Cc1c(-c2[nH]c3ccc(N4CC5(C4)CN(C4COC4)C5)nc3c2C(C)C)cn2ncnc2c1C] | 458.20 | 0.76 | QC-ACN-TFA-XB |
| 1012 | 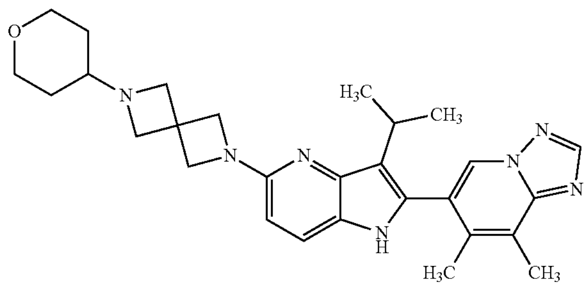 [SMILES: Cc1c(-c2[nH]c3ccc(N4CC5(C4)CN(C4CCOCC4)C5)nc3c2C(C)C)cn2ncnc2c1C] | 486.20 | 0.79 | QC-ACN-TFA-XB |
| 1013 | 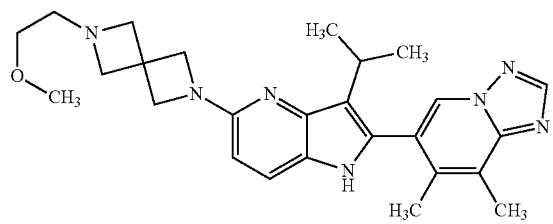 [SMILES: COCCN1CC2(C1)CN(c1ccc3[nH]c(-c4cn5ncnc5c(C)c4C)c(C(C)C)c3n1)C2] | 460.20 | 1.02 | QC-ACN-TFA-XB |
| 1014 | 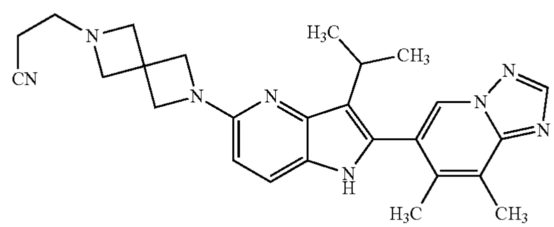 | 455.10 | 1.44 | QC-ACN-AA-XB |
| 1015 | 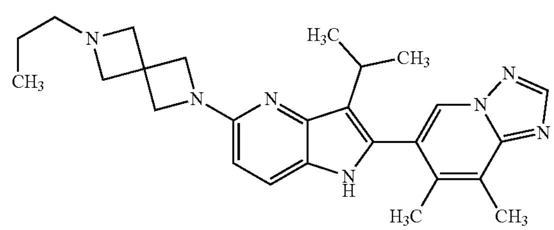 [SMILES: Cc1c(-c2[nH]c3ccc(N4CC5(CN(CCC#N)C5)C4)nc3c2C(C)C)cn2ncnc2c1C] | 444.20 | 0.83 | QC-ACN-TFA-XB |
| 1016 | 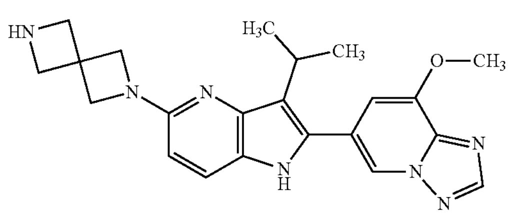 [SMILES: COc1cc(-c2[nH]c3ccc(N4CC5(CNC5)C4)nc3c2C(C)C)cn2ncnc12] | 404.20 | 1.06 | QC-ACN-AA-XB |

TABLE 2-continued

| Ex. No. | Structure | Obs. MS Ion | RT | QC Method |
|---|---|---|---|---|
| 1017 | 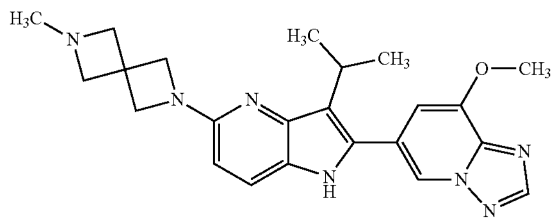 [SMILES: COc1cc(-c2[nH]c3ccc(N4CC5(CN(C)C5)C4)nc3c2C(C)C)cn2ncnc12] | 418.20 | 1.13 | QC-ACN-AA-XB |
| 1018 | 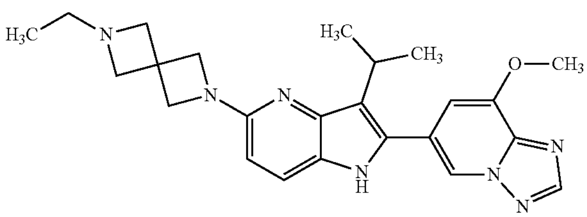 [SMILES: CCN1CC2(C1)CN(c1ccc3[nH]c(-c4cc(OC)c5ncnn5c4)c(C(C)C)c3n1)C2] | 432.10 | 1.00 | QC-ACN-TFA-XB |
| 1019 | 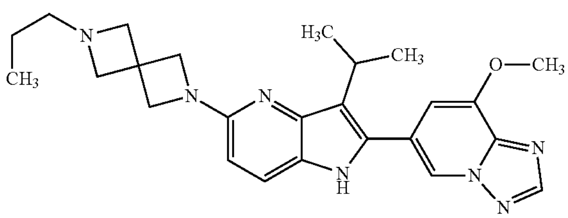 [SMILES: CCCN1CC2(C1)CN(c1ccc3[nH]c(-c4cc(OC)c5ncnn5c4)c(C(C)C)c3n1)C2] | 446.20 | 1.32 | QC-ACN-AA-XB |
| 1020 | 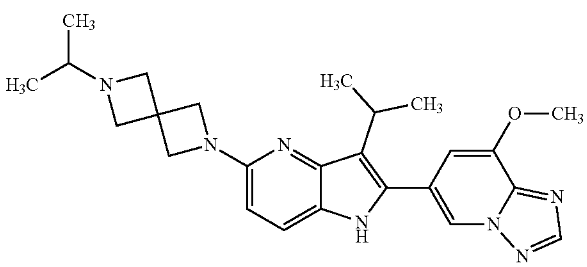 [SMILES: COc1cc(-c2[nH]c3ccc(N4CC5(C4)CN(C(C)C)C5)nc3c2C(C)C)cn2ncnc12] | 446.20 | 1.27 | QC-ACN-AA-XB |
| 1021 | 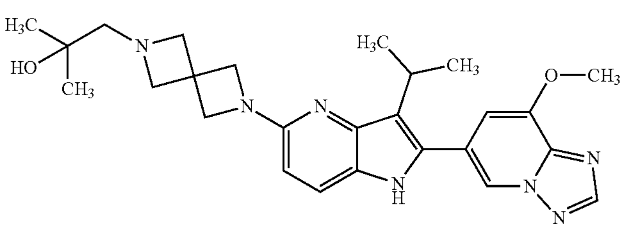 [SMILES: COc1cc(-c2[nH]c3ccc(N4CC5(CN(CC(C)(C)O)C5)C4)nc3c2C(C)C)cn2ncnc12] | 476.20 | 1.23 | QC-ACN-AA-XB |
| 1022 | 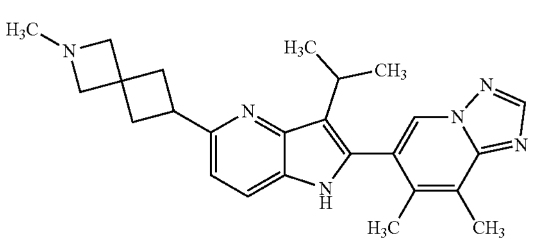 | 415.10 | 1.35 | QC-ACN-AA-XB |

TABLE 2-continued
| Ex. No. | Structure | Obs. MS Ion | RT | QC Method |
|---|---|---|---|---|
| 1023 | 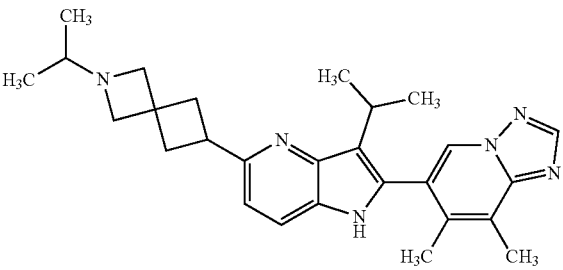 | 443.20 | 1.46 | QC-ACN-AA-XB |
| 1024 | 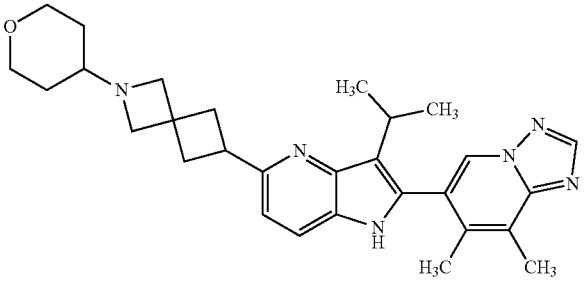 | 485.20 | 1.44 | QC-ACN-AA-XB |
| 1025 | 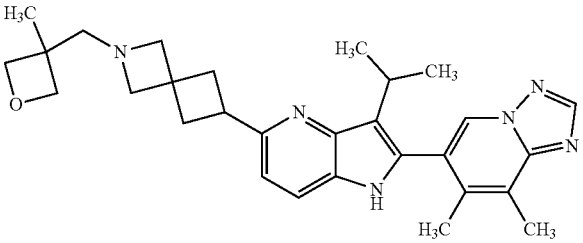 [SMILES: Cc1c(-c2[nH]c3ccc(C4CC5(C4)CN(CC4(C)COC4)C5)nc3c2C(C)C)cn2ncnc2c1C] | 485.20 | 1.37 | QC-ACN-AA-XB |
| 1026 | 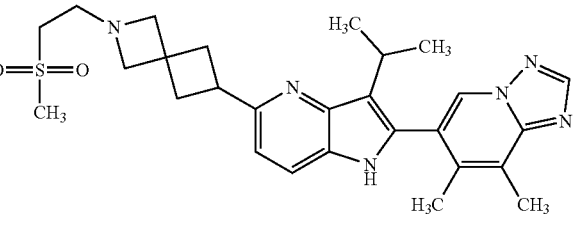 | 507.30 | 1.46 | QC-ACN-AA-XB |
| 1027 | 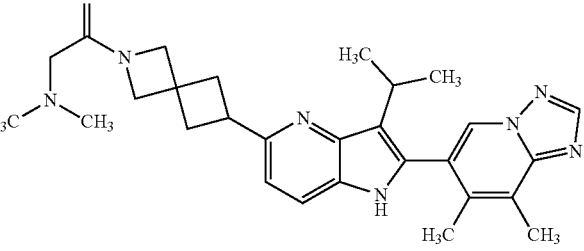 | 971.40 | 1.51 | QC-ACN-AA-XB |
| 1028 | 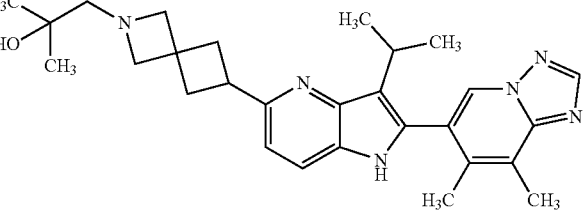 | 473.10 | 1.34 | QC-ACN-AA-XB |

TABLE 2-continued

| Ex. No. | Structure | Obs. MS Ion | RT | QC Method |
|---|---|---|---|---|
| 1029 | 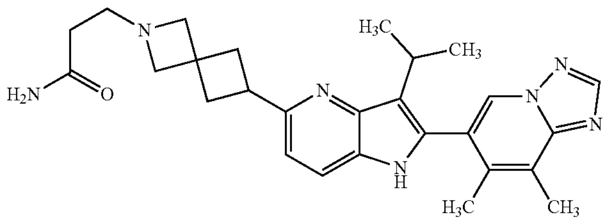 [SMILES: Cc1c(-c2[nH]c3ccc(C4CC5(C4)CN(CCC(N)=O)C5)nc3c2C(C)C)cn2ncnc2c1C] | 472.30 | 0.93 | QC-ACN-TFA-XB |
| 1030 | 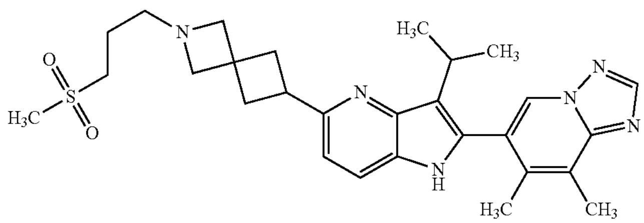 | 521.30 | 1.31 | QC-ACN-AA-XB |
| 1031 | 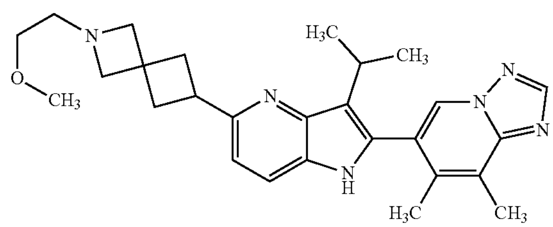 | 459.30 | 0.82 | QC-ACN-TFA-XB |
| 1032 | 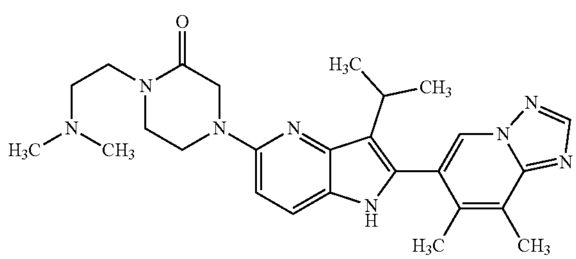 [SMILES: Cc1c(-c2[nH]c3ccc(N4CCN(CCN(C)C)C(=O)C4)nc3c2C(C)C)cn2ncnc2c1C] | 475.30 | 1.45 | QC-ACN-AA-XB |
| 1033 | 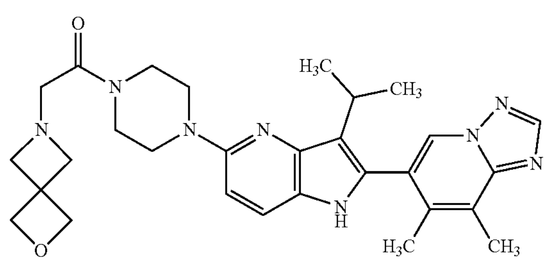 [SMILES: Cc1c(-c2[nH]c3ccc(N4CCN(C(=O)CN5CC6(COC6)C5)CC4)nc3c2C(C)C)cn2ncnc2c1C] | 529.40 | 1.27 | QC-ACN-AA-XB |
| 1034 | 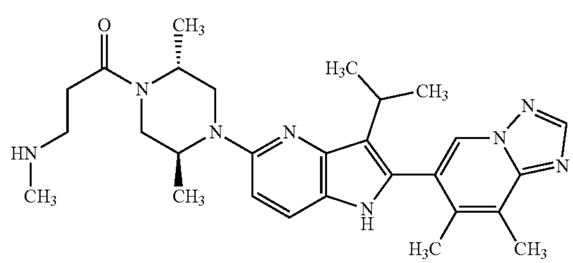 [SMILES: CNCCC(=O)N1C[C@H](C)N(c2ccc3[nH]c(-c4cn5ncnc5c(C)c4C)c(C(C)C)c3n2)C[C@H]1C] | 503.00 | 1.43 | QC-ACN-AA-XB |

Example 1035

1-(aminomethyl)₀₋₄-(2-(7,8-dimethyl-[1,2,4]triazolo[1,5-a]pyridin-6-yl)-3-isopropyl-1H-pyrrolo[3,2-b]pyridin-5-yl)cyclohexan-1-ol (1035)

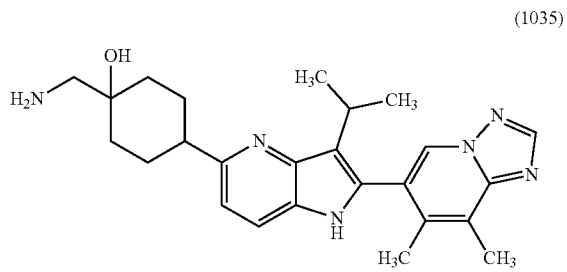 [SMILES: Cc1c(-c2[nH]c3ccc(C4CCC(O)(CN)CC4)nc3c2C(C)C)cn2ncnc2c1C]

Intermediate 1035A: 4-(2-(7,8-dimethyl-[1,2,4]triazolo[1,5-a]pyridin-6-yl)-3-isopropyl-1H-pyrrolo[3,2-b]pyridin-5-yl)-1-(nitromethyl)cyclohexanol (1035A)

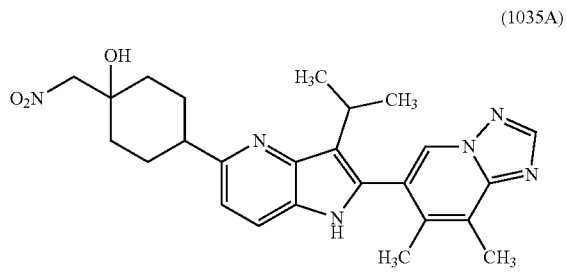 [SMILES: Cc1c(-c2[nH]c3ccc(C4CCC(O)(C[N+](=O)[O-])CC4)nc3c2C(C)C)cn2ncnc2c1C]

To a 2 dram vial were added 4-(2-(7,8-dimethyl-[1,2,4]triazolo[1,5-a]pyridin-6-yl)-3-isopropyl-1H-pyrrolo[3,2-b]pyridin-5-yl)cyclohexan-1-one (0.200 g, 0.498 mmol), MeOH (5 mL), diethylamine (0.052 mL, 0.498 mmol) and nitromethane (0.269 mL, 4.98 mmol). Next, 20 µL of water was added and the reaction mixture was stirred for 5 days at 25° C. The reaction mixture was concentrated under a stream of nitrogen gas, diluted with water and stirred for 30 minutes. The white precipitate was filtered off and washed with water and dried through air to afford 4-(2-(7,8-dimethyl-[1,2,4]triazolo[1,5-a]pyridin-6-yl)-3-isopropyl-1H-pyrrolo[3,2-b]pyridin-5-yl)-1-(nitromethyl)cyclohexanol (0.200 g, 0.552 mmol, 100% yield) as a white solid. LCMS retention time 0.64 min [Method A]. MS m/z: 363.2 (M+H).

Example 1035

To a Parr bottle were added 4-(2-(7,8-dimethyl-[1,2,4]triazolo[1,5-a]pyridin-6-yl)-3-isopropyl-1H-pyrrolo[3,2-b]pyridin-5-yl)-1-(nitromethyl)cyclohexanol, and 1:1 ethyl acetate:MeOH (7 mL). The vessel was purged with nitrogen gas and 10% Pd—C (0.053 g, 0.050 mmol) was added. The bottle was placed on the Parr apparatus and pump/purged with nitrogen gas three times and back-filled with hydrogen gas. The reaction vessel was set to shake for 6 hours at 40 psi. The reaction mixture was diluted with MeOH and then filtered through a pad of Celite and concentrated. The residue was suspended in DMF (2 mL), filtered through a 0.45 micron nylon syringe filter. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 6% B, 6-42% B over 28 minutes, then a 6-minute hold at 100% B; Flow Rate: 20 mL/min; Column Temperature: 25° C. Fractions containing the product were combined and dried via centrifugal evaporation to afford 1-(aminomethyl)-4-(2-(7,8-dimethyl-[1,2,4]triazolo[1,5-a] pyridin-6-yl)-3-isopropyl-1H-pyrrolo[3,2-b]pyridin-5-yl)cyclohexan-1-ol (0.8 mg, 0.00185 mmol, 0.4% yield), m/z (432.9, M+H). Retention time, 1.253 min using LCMS Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM. $^1$H NMR (500 MHz, DMSO-$d_6$) δ 11.15-10.98 (m, 1H), 8.79 (s, 1H), 8.47 (s, 1H), 7.60 (br d, J=8.5 Hz, 1H), 7.08-6.93 (m, 1H), 4.80-4.80 (m, 1H), 3.33-3.19 (m, 1H), 2.91 (br d, J=7.0 Hz, 2H), 2.68 (br d, J=7.0 Hz, 3H), 2.17 (s, 3H), 2.06-1.93 (m, 2H), 1.89 (s, 3H), 1.70 (br t, J=15.9 Hz, 4H), 1.40 (br d, J=6.4 Hz, 8H).

The following examples were prepared according to the general procedures described in the above examples.

TABLE 3

| Ex. No. | Structure | Obs. MS Ion | RT | QC Method |
|---|---|---|---|---|
| 1035 | ![structure] | 433.10 | 1.24 | QC-ACN-AA-XB |

TABLE 3-continued

| Ex. No. | Structure | Obs. MS Ion | RT | QC Method |
|---|---|---|---|---|
| 1036 | 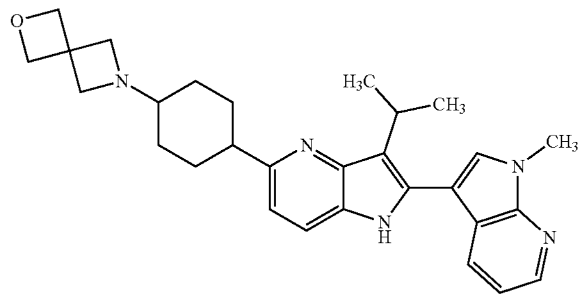 [SMILES: CC(C)c1c(-c2cn(C)c3ncccc23)[nH]c2ccc(C3CCC(N4CC5(COC5)C4)CC3)nc12] | 470.30 | 1.27 | QC-ACN-AA-XB |
| 1037 | 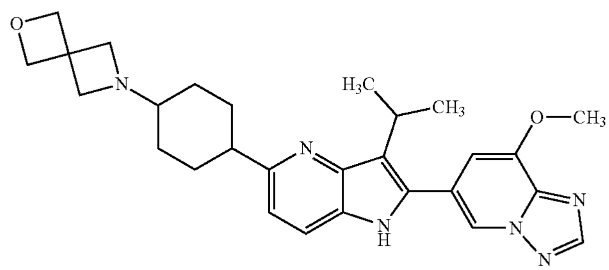 [SMILES: COc1cc(-c2[nH]c3ccc(C4CCC(N5CC6(COC6)C5)CC4)nc3c2C(C)C)cn2ncnc12] | 487.30 | 0.75 | QC-ACN-TFA-XB |
| 1038 | 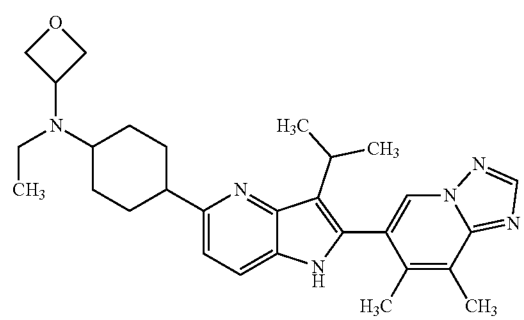 [SMILES: CCN(C1CCC(c2ccc3[nH]c(-c4cn5ncnc5c(C)c4C)c(C(C)C)c3n2)CC1)C1COC1] | 487.40 | 0.82 | QC-ACN-TFA-XB |
| 1039 | 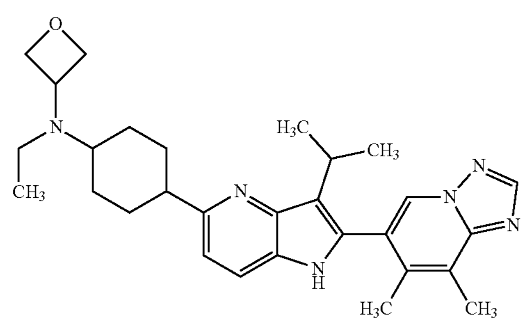 [SMILES: CCN(C1CCC(c2ccc3[nH]c(-c4cn5ncnc5c(C)c4C)c(C(C)C)c3n2)CC1)C1COC1] | 487.40 | 0.82 | QC-ACN-TFA-XB |
| 1040 | 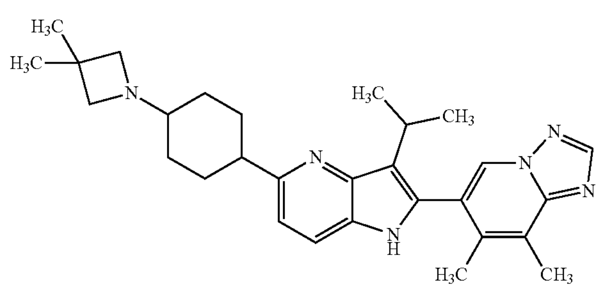 [SMILES: Cc1c(-c2[nH]c3ccc(C4CCC(N5CC(C)(C)C5)CC4)nc3c2C(C)C)cn2ncnc2c1C] | 471.40 | 1.00 | QC-ACN-TFA-XB |

TABLE 3-continued
| Ex. No. | Structure | Obs. MS Ion | RT | QC Method |
|---|---|---|---|---|
| 1041 | 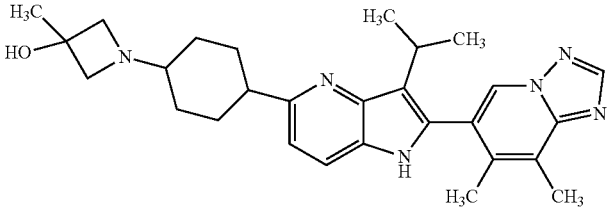 [SMILES: Cc1c(-c2[nH]c3ccc(C4CCC(N5CC(C)(O)C5)CC4)nc3c2C(C)C)cn2ncnc2c1C] | 473.20 | 1.38 | QC-ACN-AA-XB |
| 1042 | 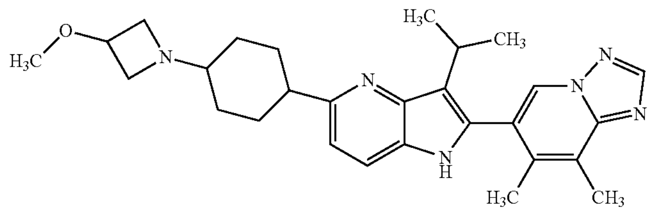 [SMILES: COC1CN(C2CCC(c3ccc4[nH]c(-c5cn6ncnc6c(C)c5C)c(C(C)C)c4n3)CC2)C1] | 473.40 | 1.39 | QC-ACN-AA-XB |
| 1043 | 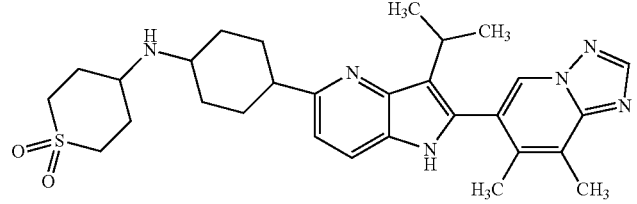 [SMILES: Cc1c(-c2[nH]c3ccc(C4CCC(NC5CCS(=O)(=O)CC5)CC4)nc3c2C(C)C)cn2ncnc2c1C] | 535.10 | 0.99 | QC-ACN-TFA-XB |
| 1044 | 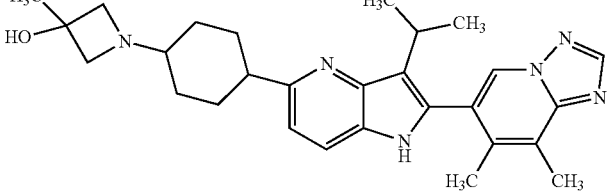 | 473.30 | 0.84 | QC-ACN-TFA-XB |
| 1045 | 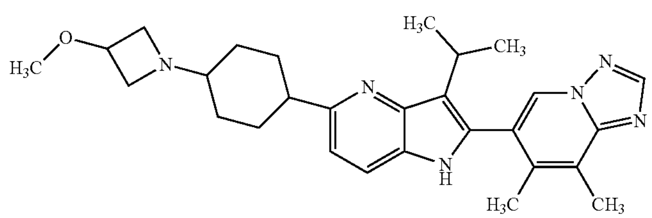 [SMILES: COC1CN(C2CCC(c3ccc4[nH]c(-c5cn6ncnc6c(C)c5C)c(C(C)C)c4n3)CC2)C1] | 473.30 | 1.01 | QC-ACN-TFA-XB |
| 1046 | 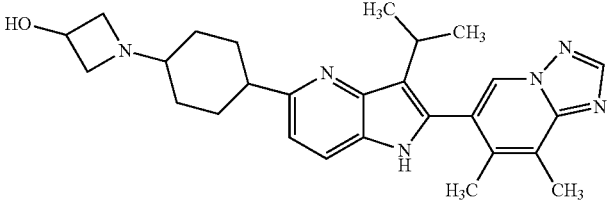 | 459.30 | 0.81 | QC-ACN-TFA-XB |
| 1047 | 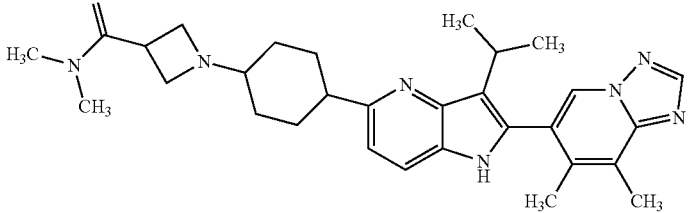 | 514.40 | 1.22 | QC-ACN-AA-XB |

TABLE 3-continued

| Ex. No. | Structure | Obs. MS Ion | RT | QC Method |
|---|---|---|---|---|
| 1048 | 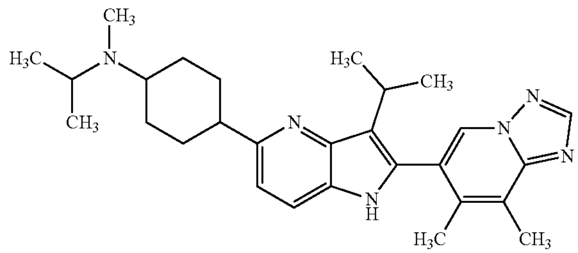 [SMILES: Cc1c(-c2[nH]c3ccc(C4CCC(N(C)C(C)C)CC4)nc3c2C(C)C)cn2ncnc2c1C] | 459.00 | 1.08 | QC-ACN-TFA-XB |
| 1049 | 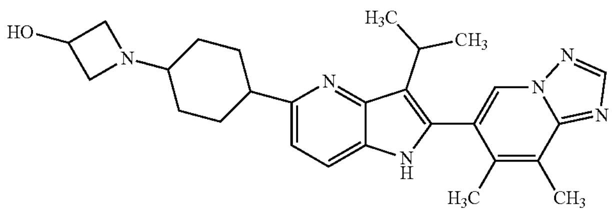 [SMILES: Cc1c(-c2[nH]c3ccc(C4CCC(N5CC(O)C5)CC4)nc3c2C(C)C)cn2ncnc2c1C] | 459.10 | 0.75 | QC-ACN-TFA-XB |
| 1050 | 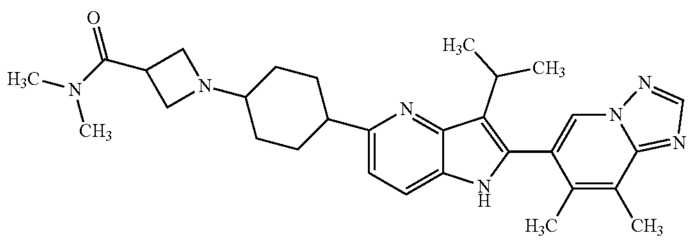 [SMILES: Cc1c(-c2[nH]c3ccc(C4CCC(N5CC(C(=O)N(C)C)C5)CC4)nc3c2C(C)C)cn2ncnc2c1C] | 514.40 | 0.87 | QC-ACN-TFA-XB |
| 1051 | 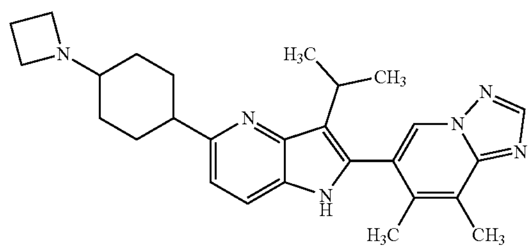 [SMILES: Cc1c(-c2[nH]c3ccc(C4CCC(N5CCC5)CC4)nc3c2C(C)C)cn2ncnc2c1C] | 443.10 | 1.45 | QC-ACN-AA-XB |
| 1052 | 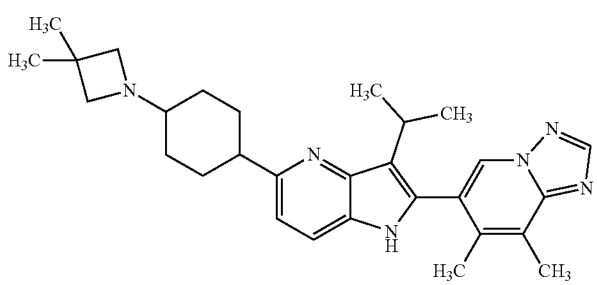 [SMILES: Cc1c(-c2[nH]c3ccc(C4CCC(N5CC(C)(C)C5)CC4)nc3c2C(C)C)cn2ncnc2c1C] | 471.10 | 1.04 | QC-ACN-TFA-XB |
| 1053 | 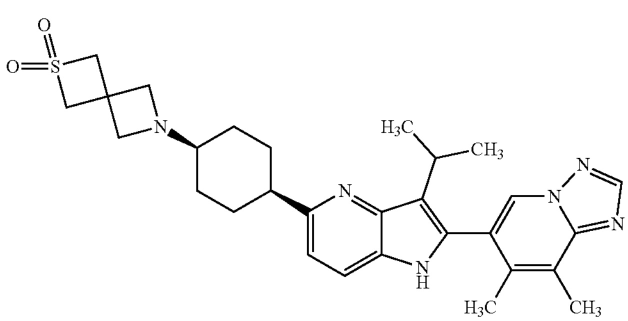 [SMILES: Cc1c(-c2[nH]c3ccc([C@H]4CC[C@@H](N5CC6(C5)CS(=O)(=O)C6)CC4)nc3c2C(C)C)cn2ncnc2c1C] | 533.50 | 0.56 | A1 |

TABLE 3-continued

| Ex. No. | Structure | Obs. MS Ion | RT | QC Method |
|---|---|---|---|---|
| 1054 | 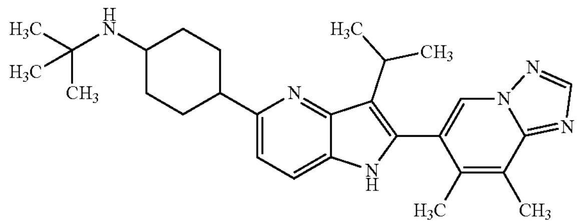 [SMILES: Cc1c(-c2[nH]c3ccc(C4CCC(NC(C)(C)C)CC4)nc3c2C(C)C)cn2ncnc2c1C] | 459.50 | 1.54 | QC-ACN-AA-XB |
| 1055 | 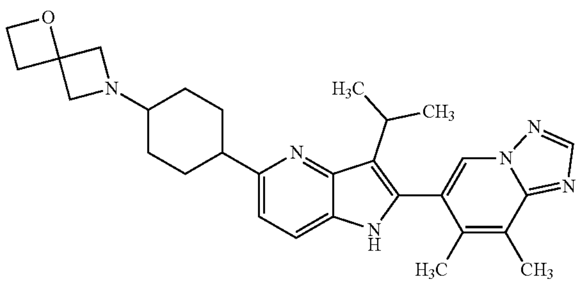 [SMILES: Cc1c(-c2[nH]c3ccc(C4CCC(N5CC6(CCO6)C5)CC4)nc3c2C(C)C)cn2ncnc2c1C] | 485.50 | 1.45 | QC-ACN-AA-XB |
| 1056 | 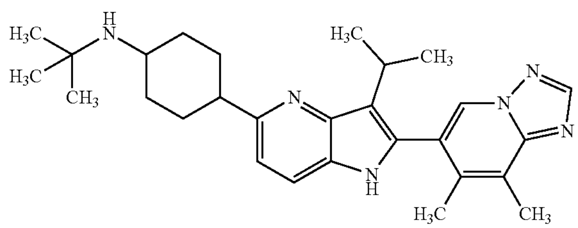 [SMILES: Cc1c(-c2[nH]c3ccc(C4CCC(NC(C)(C)C)CC4)nc3c2C(C)C)cn2ncnc2c1C] | 459.10 | 1.48 | QC-ACN-AA-XB |
| 1057 | 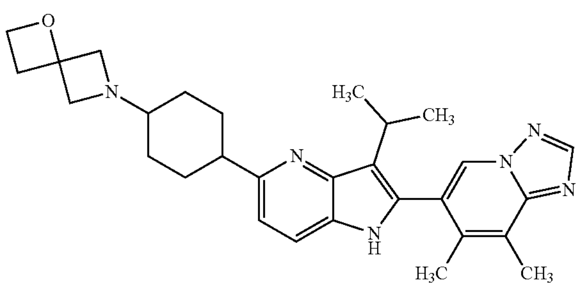 [SMILES: Cc1c(-c2[nH]c3ccc(C4CCC(N5CC6(CCO6)C5)CC4)nc3c2C(C)C)cn2ncnc2c1C] | 485.20 | 0.81 | QC-ACN-TFA-XB |
| 1058 | 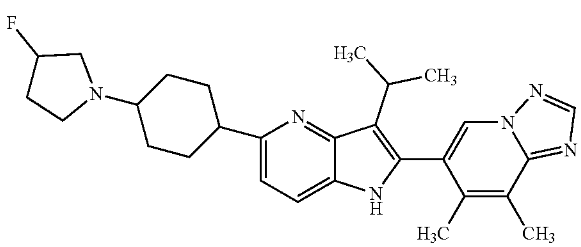 [SMILES: Cc1c(-c2[nH]c3ccc(C4CCC(N5CCC(F)C5)CC4)nc3c2C(C)C)cn2ncnc2c1C] | 475.00 | 1.59 | QC-ACN-AA-XB |
| 1059 | 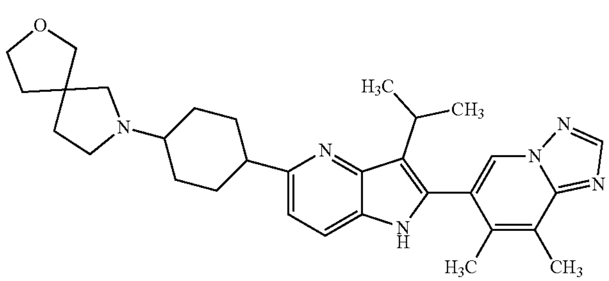 [SMILES: Cc1c(-c2[nH]c3ccc(C4CCC(N5CCC6(CCOC6)C5)CC4)nc3c2C(C)C)cn2ncnc2c1C] | 513.40 | 0.85 | QC-ACN-TFA-XB |

TABLE 3-continued

| Ex. No. | Structure | Obs. MS Ion | RT | QC Method |
|---|---|---|---|---|
| 1060 | 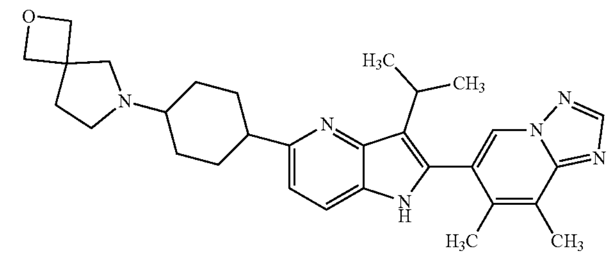 [SMILES: Cc1c(-c2[nH]c3ccc(C4CCC(N5CCC6(COC6)C5)CC4)nc3c2C(C)C)cn2ncnc2c1C] | 499.10 | 1.41 | QC-ACN-AA-XB |
| 1061 | 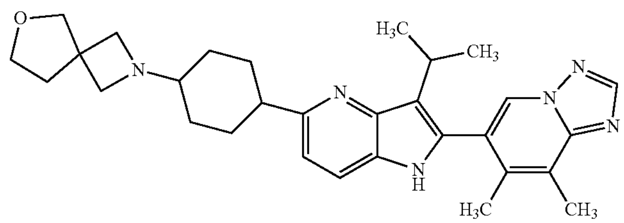 [SMILES: Cc1c(-c2[nH]c3ccc(C4CCC(N5CC6(CCOC6)C5)CC4)nc3c2C(C)C)cn2ncnc2c1C] | 499.40 | 0.83 | QC-ACN-TFA-XB |
| 1062 | 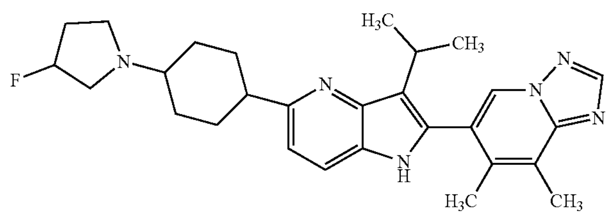 [SMILES: Cc1c(-c2[nH]c3ccc(C4CCC(N5CCC(F)C5)CC4)nc3c2C(C)C)cn2ncnc2c1C] | 475.00 | 1.80 | QC-ACN-AA-XB |
| 1063 | 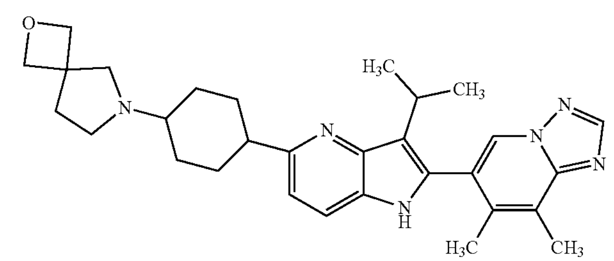 [SMILES: Cc1c(-c2[nH]c3ccc(C4CCC(N5CCC6(COC6)C5)CC4)nc3c2C(C)C)cn2ncnc2c1C] | 499.40 | 1.02 | QC-ACN-TFA-XB |
| 1064 | 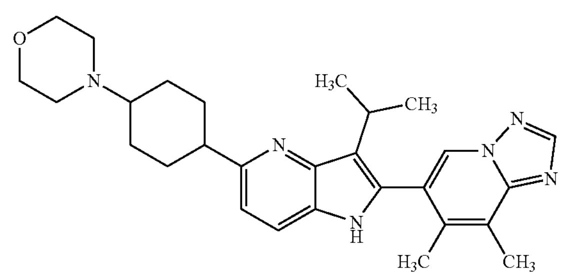 [SMILES: Cc1c(-c2[nH]c3ccc(C4CCC(N5CCOCC5)CC4)nc3c2C(C)C)cn2ncnc2c1C] | 473.00 | 1.82 | QC-ACN-AA-XB |
| 1065 | 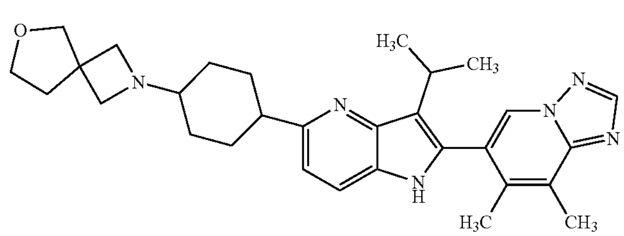 [SMILES: Cc1c(-c2[nH]c3ccc(C4CCC(N5CC6(CCOC6)C5)CC4)nc3c2C(C)C)cn2ncnc2c1C] | 499.20 | 1.61 | QC-ACN-AA-XB |

TABLE 3-continued

| Ex. No. | Structure | Obs. MS Ion | RT | QC Method |
|---|---|---|---|---|
| 1066 | 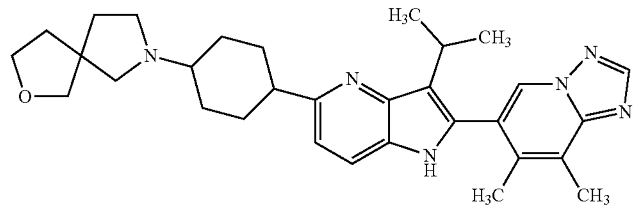 [SMILES: Cc1c(-c2[nH]c3ccc(C4CCC(N5CCC6(CCOC6)C5)CC4)nc3c2C(C)C)cn2ncnc2c1C] | 513.50 | 0.85 | QC-ACN-TFA-XB |
| 1067 | 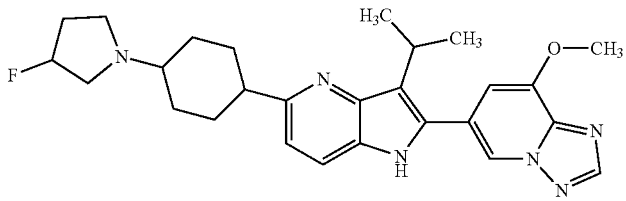 [SMILES: COc1cc(-c2[nH]c3ccc(C4CCC(N5CCC(F)C5)CC4)nc3c2C(C)C)cn2ncnc12] | 477.20 | 0.77 | QC-ACN-TFA-XB |
| 1068 | 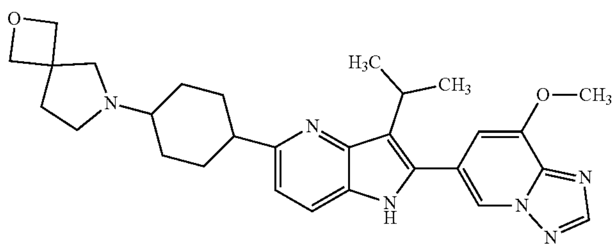 [SMILES: COc1cc(-c2[nH]c3ccc(C4CCC(N5CCC6(COC6)C5)CC4)nc3c2C(C)C)cn2ncnc12] | 501.30 | 0.78 | QC-ACN-TFA-XB |
| 1069 | 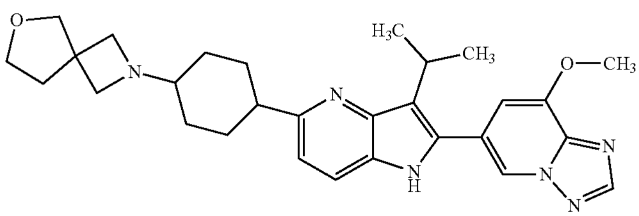 [SMILES: COc1cc(-c2[nH]c3ccc(C4CCC(N5CC6(CCOC6)C5)CC4)nc3c2C(C)C)cn2ncnc12] | 501.00 | 0.99 | QC-ACN-TFA-XB |
| 1070 | 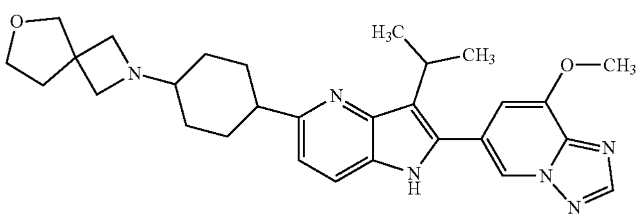 [SMILES: COc1cc(-c2[nH]c3ccc(C4CCC(N5CC6(CCOC6)C5)CC4)nc3c2C(C)C)cn2ncnc12] | 501.00 | 1.00 | QC-ACN-TFA-XB |
| 1071 | 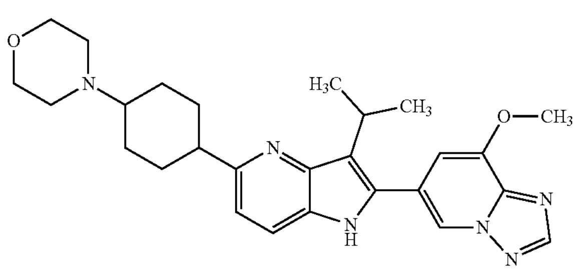 [SMILES: COc1cc(-c2[nH]c3ccc(C4CCC(N5CCOCC5)CC4)nc3c2C(C)C)cn2ncnc12] | 475.30 | 1.52 | QC-ACN-AA-XB |
| 1072 | 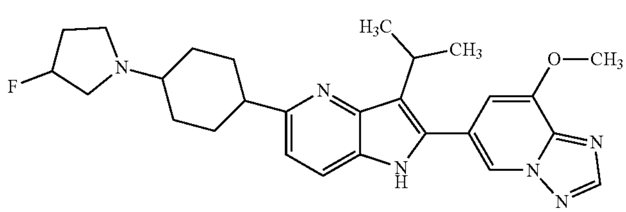 [SMILES: COc1cc(-c2[nH]c3ccc(C4CCC(N5CCC(F)C5)CC4)nc3c2C(C)C)cn2ncnc12] | 477.40 | 0.81 | QC-ACN-TFA-XB |

TABLE 3-continued

| Ex. No. | Structure | Obs. MS Ion | RT | QC Method |
|---|---|---|---|---|
| 1073 | 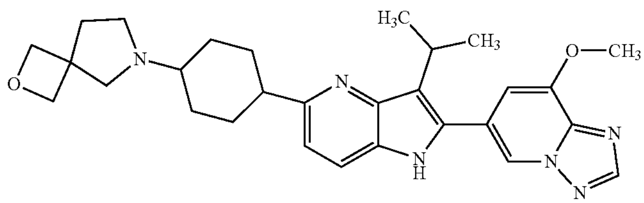 [SMILES: COc1cc(-c2[nH]c3ccc(C4CCC(N5CCC6(COC6)C5)CC4)nc3c2C(C)C)cn2ncnc12] | 501.30 | 0.79 | QC-ACN-TFA-XB |
| 1074 | 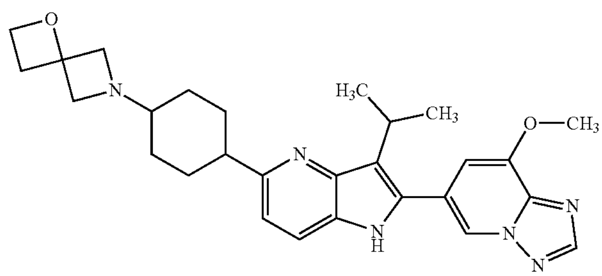 [SMILES: COc1cc(-c2[nH]c3ccc(C4CCC(N5CC6(CCO6)C5)CC4)nc3c2C(C)C)cn2ncnc12] | 487.00 | 1.45 | QC-ACN-AA-XB |
| 1075 | 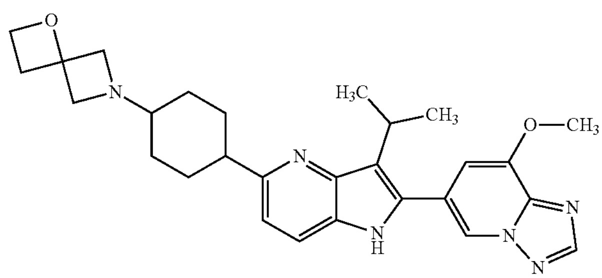 [SMILES: COc1cc(-c2[nH]c3ccc(C4CCC(N5CC6(CCO6)C5)CC4)nc3c2C(C)C)cn2ncnc12] | 486.90 | 1.59 | QC-ACN-AA-XB |
| 1076 | 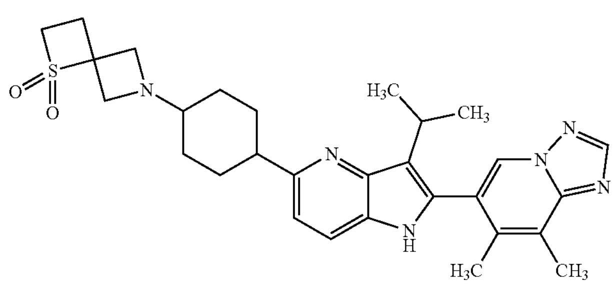 [SMILES: Cc1c(-c2[nH]c3ccc(C4CCC(N5CC6(CCS6(=O)=O)C5)CC4)nc3c2C(C)C)cn2ncnc2c1C] | 533.30 | 1.70 | QC-ACN-AA-XB |
| 1077 | 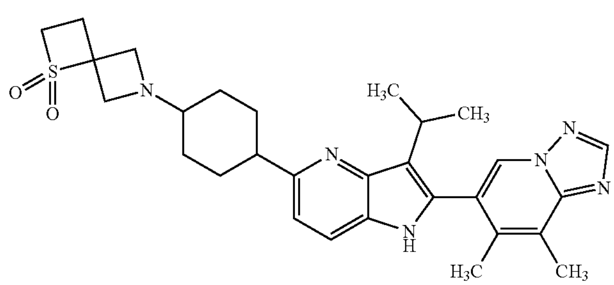 [SMILES: Cc1c(-c2[nH]c3ccc(C4CCC(N5CC6(CCS6(=O)=O)C5)CC4)nc3c2C(C)C)cn2ncnc2c1C] | 533.10 | 0.80 | QC-ACN-TFA-XB |

TABLE 3-continued

| Ex. No. | Structure | Obs. MS Ion | RT | QC Method |
|---|---|---|---|---|
| 1078 | 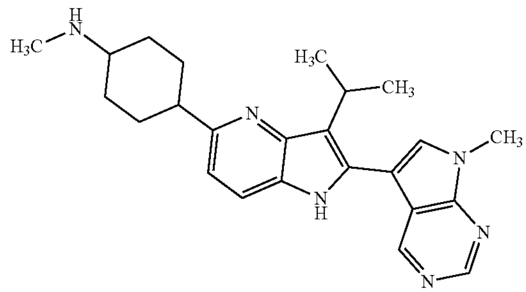 | 403.10 | 1.43 | QC-ACN-AA-XB |

BIOLOGICAL ASSAYS

The pharmacological properties of the compounds of this invention may be confirmed by a number of biological assays. The exemplified biological assays, which follow, have been carried out with compounds of the invention.

TLR7/8/9 Inhibition Reporter Assays

HEK-Blue™-cells (Invivogen) overexpressing human TLR7, TLR8 or TLR9 receptors were used for screening inhibitors of these receptors using an inducible SEAP (secreted embryonic alkaline phosphatase) reporter gene under the control of the IFN-β minimal promoter fused to five NF-κB and AP-1-binding sites. Briefly, cells are seeded into Greiner 384 well plates (15000 cells per well for TLR7, 20,000 for TLR8 and 25,000 for TLR9) and then treated with test compounds in DMSO to yield a final dose response concentration range of 0.05 nM-50 µM. After a 30 minute compound pre-treatment at room temperature, the cells are then stimulated with a TLR7 ligand (gardiquimod at a final concentration of 7.5 µM), TLR8 ligand (R848 at a final concentration of 15.9 µM) or TLR9 ligand (ODN2006 at a final concentration of 5 nM) to activate NF-κB and AP-1 which induce the production of SEAP. After a 22 hour incubation at 37° C., 5% $CO_2$, SEAP levels are determined with the addition of HEK-Blue™ Detection reagent (Invivogen), a cell culture medium that allows for detection of SEAP, according to manufacturer's specifications. The percent inhibition is determined as the % reduction in the HEK-Blue signal present in wells treated with agonist plus DMSO alone compared to wells treated with a known inhibitor.

TABLE 4

TLR7/8/9 Reporter Assay Data
(NT = not tested)

| Ex. No. | TLR7 $IC_{50}$ (nM) | TLR8 $IC_{50}$ (nM) | TLR9 $IC_{50}$ (nM) |
|---|---|---|---|
| 1 | 20 | 3.8 | 7734 |
| 2 | 1.7 | 0.27 | 7325 |
| 3 | 0.93 | 1.1 | 8542 |
| 4 | 0.60 | 0.71 | 1072 |
| 5 | 471 | 4063 | 37 |
| 6 | 0.30 | 3.2 | 625 |
| 7 | 4.4 | 52 | 8124 |
| 8 | 4.7 | 21 | 8554 |
| 9 | 1.7 | 8.2 | 2248 |
| 10 | 0.42 | 5.3 | 1053 |
| 11 | 1.7 | 21 | 6794 |
| 12 | 10 | 1.6 | 10102 |
| 13 | 3.2 | 1.9 | 5020 |
| 14 | 11 | 4.2 | 4331 |
| 15 | 7.3 | 4.3 | 1940 |
| 16 | 0.60 | 2.1 | 635 |
| 17 | 3.7 | 7.7 | 1097 |
| 18 | 14 | 14 | 1494 |
| 19 | 125 | 73 | 6023 |
| 20 | 2.7 | 1.3 | 614 |
| 21 | 91 | 46 | >50000 |
| 22 | 56 | 12 | 21148 |
| 23 | >3125 | >3125 | >50000 |
| 24 | 40 | 2.7 | 13976 |
| 25 | 181 | 117 | 11662 |
| 26 | 1769 | 2131 | >50000 |
| 27 | >3125 | >3125 | >50000 |
| 28 | 263 | 1496 | >50000 |
| 29 | 4.6 | 2.7 | 2832 |
| 30 | 70 | 43 | 22593 |
| 31 | 13 | 19 | 6059 |
| 32 | 7.3 | 6.9 | 1883 |
| 33 | 6.5 | 1.9 | 1915 |
| 34 | 17 | 6.0 | 1218 |
| 35 | 589 | 282 | 13783 |
| 36 | >3125 | >3125 | 22084 |
| 37 | 1269 | 465 | >50000 |
| 38 | 21 | 5.2 | 44362 |
| 39 | 40 | 4.8 | NT |
| 40 | 24 | 1.7 | 7956 |
| 41 | 264 | 177 | >50000 |
| 42 | 178 | 57 | >50000 |
| 43 | 2.0 | 7.8 | 560 |
| 44 | 12 | 15 | 3374 |
| 45 | 22 | 20 | 7280 |
| 46 | 4.3 | 4.9 | 1682 |
| 47 | NT | NT | NT |
| 48 | 7.4 | 9.3 | 31274 |
| 49 | 1.0 | 0.62 | 2673 |
| 50 | 0.49 | 0.39 | 2839 |
| 51 | 5.1 | 7.0 | 16309 |
| 52 | 7.9 | 20 | NT |
| 53 | 0.62 | 0.23 | 1988 |
| 54 | 2.9 | 2.8 | 10376 |
| 55 | 2.1 | 0.39 | 3340 |
| 56 | 2.0 | 1.1 | 6340 |
| 57 | 7.4 | 1.3 | 5070 |
| 58 | 1.3 | 0.72 | 1969 |
| 59 | 1.3 | 1.1 | 2376 |
| 60 | 5.6 | 5.9 | 20242 |
| 61 | 4.4 | 1.8 | 2411 |
| 62 | 3.8 | 1.5 | 11497 |

TABLE 4-continued

TLR7/8/9 Reporter Assay Data
(NT = not tested)

| Ex. No. | TLR7 IC$_{50}$ (nM) | TLR8 IC$_{50}$ (nM) | TLR9 IC$_{50}$ (nM) |
|---|---|---|---|
| 63 | 7.4 | 4.0 | 42357 |
| 64 | 3.8 | 1.6 | 5084 |
| 65 | 1.9 | 1.3 | 25112 |
| 66 | 1.4 | 0.98 | 3870 |
| 67 | 0.98 | 0.42 | 963 |
| 68 | 1.4 | 0.79 | 6300 |
| 69 | 1310 | 1314 | 25816 |
| 70 | 2.3 | 1.2 | 2967 |
| 71 | 99 | 31 | 3897 |
| 72 | 2.9 | 0.90 | 3416 |
| 73 | 29 | 5.7 | 24942 |
| 74 | 2468 | 2562 | >50000 |
| 75 | 18 | 9.8 | >50000 |
| 76 | 34 | 15 | >50000 |
| 77 | 4.8 | 2.0 | 11648 |
| 78 | 3.7 | 10 | 3171 |
| 79 | 373 | 355 | 9724 |
| 80 | 1.3 | 1.6 | 4558 |
| 81 | 1.3 | 0.95 | 20099 |
| 82 | 0.77 | 0.41 | 6376 |
| 83 | 3.6 | 6.9 | 5445 |
| 84 | 2196 | >3125 | >50000 |
| 85 | 1.8 | 5.8 | 5178 |
| 86 | 7.5 | 2.9 | >50000 |
| 87 | 3.5 | 0.58 | >50000 |
| 88 | 68 | 91 | 3595 |
| 89 | 0.51 | 0.59 | 3258 |
| 90 | 0.57 | 4.2 | 4999 |
| 91 | 0.68 | 0.53 | 6311 |
| 92 | 0.87 | 0.78 | 3992 |
| 93 | 5.3 | 7.2 | 35043 |
| 94 | 1.0 | 1.4 | 9352 |
| 95 | 4.9 | 3.6 | >50000 |
| 96 | 1.5 | 0.28 | 9430 |
| 97 | 28 | 4.1 | >50000 |
| 98 | 0.74 | 0.72 | 5226 |
| 99 | 0.51 | 2.9 | 4303 |
| 100 | 3.2 | 0.55 | 6146 |
| 101 | 3.7 | 0.25 | 6402 |
| 102 | 12 | 5.1 | >50000 |
| 103 | 7.3 | 2.6 | NT |
| 104 | 2.3 | 0.75 | 4161 |
| 105 | 3.9 | 0.15 | 9237 |
| 106 | 2.2 | 0.28 | 7779 |
| 107 | 2.2 | 0.37 | 5627 |
| 108 | 2.5 | 0.99 | 3512 |
| 109 | 3.6 | 1.3 | 8014 |
| 110 | 1.9 | 0.76 | 4544 |
| 111 | NT | NT | NT |
| 112 | 2.2 | 1.2 | 6009 |
| 113 | 1.4 | 0.95 | 3363 |
| 114 | 4.7 | 1.8 | 7590 |
| 115 | 1.2 | 0.49 | 3482 |
| 116 | 9.7 | 5.0 | 35642 |
| 117 | 1.4 | 0.81 | 5643 |
| 118 | 1.8 | 0.86 | 5581 |
| 119 | 1.8 | 0.96 | 14141 |
| 120 | 2.3 | 0.60 | 5487 |
| 121 | 3.4 | 0.80 | 6348 |
| 122 | 1.7 | 1.1 | 7251 |
| 123 | 1.9 | 6.3 | 8648 |
| 124 | 1.2 | 4.7 | 5786 |
| 125 | 2.6 | 0.66 | 6544 |
| 126 | 5.9 | 1.5 | 6117 |
| 127 | 4.6 | 0.48 | 5898 |
| 128 | 5.4 | 2.6 | 35374 |
| 129 | 6.7 | 1.3 | 22827 |
| 130 | 4.3 | 4.7 | >50000 |
| 131 | 3.3 | 0.63 | 8572 |
| 132 | 2.8 | 0.51 | 7393 |
| 133 | 4.3 | 1.4 | >50000 |
| 134 | 3.7 | 1.1 | 26146 |
| 135 | 4.7 | 1.6 | 13167 |
| 136 | 5.7 | 0.79 | 8223 |
| 137 | 5.6 | 1.3 | 8446 |
| 138 | 11 | 4.6 | >50000 |
| 139 | 37 | 14 | >50000 |
| 140 | 127 | 186 | >50000 |
| 141 | 134 | 148 | >50000 |
| 142 | 107 | 45 | >50000 |
| 143 | 7.8 | 4.5 | >50000 |
| 144 | 8.4 | 1.2 | >50000 |
| 145 | 1.5 | 0.49 | 8201 |
| 146 | 5.6 | 2.5 | 12892 |
| 147 | 5.0 | 0.26 | 18656 |
| 148 | 97 | 16 | >50000 |
| 149 | 9.3 | 0.40 | 19497 |
| 150 | 12 | 2.7 | >50000 |
| 151 | 1.2 | 1.2 | 11995 |
| 152 | 2.7 | 1.6 | 5877 |
| 153 | 0.87 | 1.6 | 7150 |
| 154 | 1919 | 600 | >50000 |
| 155 | 401 | 56 | >50000 |
| 156 | 1.5 | 0.79 | 6752 |
| 157 | 2.2 | 1.2 | 8844 |
| 158 | 2.3 | 0.96 | 8256 |
| 159 | 2.4 | 1.0 | 7735 |
| 160 | 1.8 | 1.2 | 10645 |
| 161 | 1.4 | 0.92 | 5918 |
| 162 | 2.8 | 2.8 | 23098 |
| 163 | 9.7 | 5.0 | 24797 |
| 164 | 33 | 2.0 | 19767 |
| 165 | 11 | 0.68 | 22656 |
| 166 | 1.5 | 18 | 2189 |
| 167 | 0.43 | 1.7 | 156 |
| 168 | 0.89 | 3.4 | 658 |
| 169 | 3.1 | 21 | 1224 |
| 170 | 2.0 | 17 | 1411 |
| 171 | 0.45 | 1.8 | 560 |
| 172 | 1.9 | 13 | 1792 |
| 173 | 2.0 | 10 | 578 |
| 174 | 4.3 | 37 | 1468 |
| 175 | 0.35 | 2.0 | 926 |
| 176 | 5.2 | 84 | 16006 |
| 177 | 0.28 | 2.5 | 148 |
| 178 | 0.48 | 1.8 | 895 |
| 179 | 0.92 | 7.0 | 1741 |
| 180 | 2.8 | 11 | 1871 |
| 181 | 1.7 | 13 | 561 |
| 182 | 0.48 | 1.1 | 301 |
| 183 | 5.6 | 15 | 1031 |
| 184 | 8.8 | 18 | 2054 |
| 185 | 38 | 110 | 10316 |
| 186 | 2.2 | 9.3 | 1011 |
| 187 | 2.1 | 20 | 4221 |
| 188 | 0.29 | 2.5 | 158 |
| 189 | 1.6 | 6.7 | 313 |
| 190 | 0.80 | 2.8 | 353 |
| 191 | 0.90 | 2.7 | 202 |
| 192 | 3.1 | 19 | 1106 |
| 193 | 1.5 | 6.0 | 648 |
| 194 | 8.6 | 47 | 3594 |
| 195 | 0.80 | 4.3 | 530 |
| 196 | 1.7 | 10 | 712 |
| 197 | 0.34 | 1.7 | 134 |
| 198 | 1.0 | 7.8 | 1142 |
| 199 | 0.16 | 6.4 | 1189 |
| 200 | 1.8 | 8.5 | 773 |
| 201 | 1.5 | 6.0 | 570 |
| 202 | 3.8 | 28 | 2030 |
| 203 | 2.0 | 7.9 | 537 |
| 204 | 0.98 | 2.9 | 1332 |
| 205 | 0.42 | 1.0 | 134 |
| 206 | 9.5 | 22 | 2389 |
| 207 | 1.9 | 4.4 | 253 |
| 208 | 2.2 | 16 | 1350 |

TABLE 4-continued

TLR7/8/9 Reporter Assay Data
(NT = not tested)

| Ex. No. | TLR7 IC$_{50}$ (nM) | TLR8 IC$_{50}$ (nM) | TLR9 IC$_{50}$ (nM) |
|---|---|---|---|
| 209 | 0.71 | 4.0 | 641 |
| 210 | >3125 | >3125 | >50000 |
| 211 | 1.1 | 6.8 | 585 |
| 212 | 3.4 | 6.8 | 1192 |
| 213 | 9.5 | 17 | 706 |
| 214 | 3.9 | 6.3 | 833 |
| 215 | 6.0 | 7.6 | 2254 |
| 216 | 5.1 | 18 | 416 |
| 217 | 5.0 | 8.6 | 522 |
| 218 | 8.5 | 20 | 389 |
| 219 | 3.9 | 8.0 | 2484 |
| 220 | 6.7 | 6.1 | 1020 |
| 221 | 3.7 | 13 | 435 |
| 222 | 5.8 | 21 | 657 |
| 223 | 0.60 | 1.4 | 485 |
| 224 | 1.5 | 4.2 | 718 |
| 225 | 4.0 | 35 | 3360 |
| 226 | 2.7 | 14 | 1790 |
| 227 | 2.0 | 7.7 | 926 |
| 228 | 3.3 | 23 | 2387 |
| 229 | 19 | 18 | 1709 |
| 230 | 38 | 33 | 2460 |
| 231 | 0.61 | 3.0 | 365 |
| 232 | 3.0 | 9.8 | 484 |
| 233 | 11 | 24 | 2662 |
| 234 | 1.6 | 5.0 | 435 |
| 235 | 1.0 | 2.0 | 929 |
| 236 | 3.9 | 2.8 | 376 |
| 237 | 20 | 19 | 18183 |
| 238 | 0.71 | 0.97 | 297 |
| 239 | 106 | 181 | >50000 |
| 240 | 5.4 | 16 | 5076 |
| 241 | 2.0 | 2.9 | 1754 |
| 242 | 1.5 | 15 | 2407 |
| 243 | 7.6 | 9.5 | 999 |
| 244 | 1.6 | 8.2 | 2349 |
| 245 | 2.7 | 4.7 | 343 |
| 246 | 1.9 | 2.6 | 4283 |
| 247 | 1.2 | 1.2 | 825 |
| 248 | 1.5 | 13 | 1785 |
| 249 | 25 | 7.3 | 5978 |
| 250 | 26 | 57 | 13721 |
| 251 | 8.6 | 13 | 1754 |
| 252 | 8.0 | 10 | 7255 |
| 253 | 0.65 | 0.72 | 1149 |
| 254 | 72 | 27 | 8734 |
| 255 | 0.60 | 0.25 | 218 |
| 256 | 1.2 | 3.7 | 335 |
| 257 | 35 | 25 | 175 |
| 258 | 13 | 3.5 | 100 |
| 259 | 19 | 7.1 | 321 |
| 260 | 527 | 173 | 10867 |
| 261 | 262 | 90 | 381 |
| 262 | 170 | 19 | 354 |
| 263 | 6.2 | 7.6 | 338 |
| 264 | 55 | 42 | 255 |
| 265 | 0.59 | 0.91 | 392 |
| 266 | 45 | 13 | 322 |
| 267 | 1.9 | 2.6 | 453 |
| 268 | 94 | 32 | 578 |
| 269 | 223 | 88 | 670 |
| 270 | 38 | 28 | 322 |
| 271 | 120 | 40 | 228 |
| 272 | 76 | 50 | 398 |
| 273 | 75 | 66 | 1114 |
| 274 | 8.5 | 3.7 | 474 |
| 275 | 14 | 8.5 | 684 |
| 276 | 8.9 | 9.0 | 309 |
| 277 | 0.40 | 1.6 | 1378 |
| 278 | 1.5 | 1.2 | 837 |
| 279 | 0.31 | 1.4 | 1817 |
| 280 | 1.1 | 7.2 | 1268 |
| 281 | 0.48 | 1.7 | 880 |
| 282 | 0.32 | 0.91 | 661 |
| 283 | 0.92 | 1.4 | 298 |
| 284 | 3.0 | 15 | 4038 |
| 285 | 3.6 | 5.5 | 2310 |
| 286 | 5.2 | 9.2 | 1566 |
| 287 | 25 | 33 | 2361 |
| 288 | 28 | 114 | 6454 |
| 289 | 3.5 | 11 | 967 |
| 290 | 2.1 | 6.3 | 425 |
| 291 | 2.6 | 11 | 735 |
| 292 | 99 | 127 | 1615 |
| 293 | 75 | 208 | 5641 |
| 294 | 85 | 174 | 2270 |
| 295 | 11 | 11 | 883 |
| 296 | 0.59 | 6.8 | 600 |
| 297 | 8.4 | 15 | 885 |
| 299 | 10 | 6.0 | 680 |
| 300 | 48 | 286 | 9048 |
| 301 | 2.0 | 42 | 4089 |
| 302 | 0.74 | 4.9 | 739 |
| 303 | 0.55 | 6.9 | 1233 |
| 304 | 0.53 | 1.8 | 1068 |
| 305 | 4.0 | 16 | 8237 |
| 306 | 13 | 61 | 10058 |
| 307 | 0.86 | 2.7 | 2978 |
| 308 | 11 | 11 | 3965 |
| 309 | 0.31 | 4.6 | 268 |
| 310 | 0.39 | 4.1 | 1782 |
| 311 | 2.8 | 44 | 2017 |
| 312 | 0.26 | 1.6 | 577 |
| 313 | 0.21 | 7.0 | 1200 |
| 314 | 2.4 | 47 | 5508 |
| 315 | 1.8 | 29 | 5223 |
| 316 | 1.4 | 41 | 3018 |
| 317 | 4.8 | 94 | 3611 |
| 318 | 0.17 | 2.1 | 1060 |
| 319 | 0.44 | 4.1 | 1690 |
| 320 | 1.0 | 22 | 1480 |
| 321 | NT | 3.0 | 1041 |
| 322 | 1.7 | 19 | 7409 |
| 323 | 1.1 | 31 | 1357 |
| 324 | 6.6 | 240 | 20509 |
| 325 | 1.5 | 38 | 3110 |
| 326 | 0.13 | 3.7 | 988 |
| 327 | >3125 | >3125 | >50000 |
| 328 | 0.08 | 1.1 | 576 |
| 329 | 1.6 | 23 | 2066 |
| 330 | 0.14 | 4.8 | 2970 |
| 331 | 1.7 | 34 | 1914 |
| 332 | 1.3 | 88 | 2663 |
| 333 | 0.60 | 12 | 1456 |
| 334 | 4.6 | 127 | 2400 |
| 335 | NT | 4.0 | 1927 |
| 336 | 2.8 | 48 | 3439 |
| 337 | 21 | 350 | >50000 |
| 338 | 81 | 1170 | >50000 |
| 339 | 0.20 | 7.1 | 5888 |
| 340 | 1.4 | 51 | 1869 |
| 341 | 0.12 | 0.32 | 2643 |
| 342 | 0.98 | 3.9 | 1906 |
| 343 | 0.19 | 0.54 | 1251 |
| 344 | 0.72 | 4.8 | 2789 |
| 345 | 0.21 | 0.68 | 1675 |
| 346 | 0.32 | 6.0 | 6294 |
| 347 | 0.27 | 1.0 | 2466 |
| 348 | 0.82 | 8.3 | 6961 |
| 349 | 7.7 | 63 | >50000 |
| 350 | 0.72 | 1.0 | 1155 |
| 351 | 2.3 | 4.3 | 1688 |
| 352 | 5.4 | 9.2 | 2321 |
| 353 | 0.64 | 0.96 | 940 |
| 354 | 1.0 | 2.3 | 790 |
| 355 | 2.6 | 10 | 4497 |

TABLE 4-continued

TLR7/8/9 Reporter Assay Data
(NT = not tested)

| Ex. No. | TLR7 IC$_{50}$ (nM) | TLR8 IC$_{50}$ (nM) | TLR9 IC$_{50}$ (nM) |
|---|---|---|---|
| 356 | 2.8 | 5.1 | 2865 |
| 357 | 3.9 | 4.4 | 1050 |
| 358 | 0.95 | 2.8 | 1325 |
| 359 | 9.1 | 29 | 4870 |
| 360 | 1.3 | 3.4 | 1414 |
| 361 | 0.79 | 1.0 | 1251 |
| 362 | 1.6 | 5.1 | 1634 |
| 363 | 3.3 | 6.6 | 1476 |
| 364 | 1.5 | 9.6 | 2523 |
| 365 | 4.2 | 7.9 | 3197 |
| 366 | 5.3 | 15 | 4693 |
| 367 | 1.5 | 3.5 | 838 |
| 368 | 1.5 | 2.5 | 1612 |
| 369 | 0.46 | 1.3 | 402 |
| 370 | 8.6 | 23 | >50000 |
| 371 | 6.0 | 14 | 4358 |
| 372 | 3.2 | 7.6 | 1464 |
| 373 | 8.6 | 8.3 | 1956 |
| 374 | 36 | 187 | 21615 |
| 375 | 0.87 | 4.4 | 2716 |
| 376 | 0.71 | 1.2 | 1027 |
| 377 | 2.1 | 2.2 | 767 |
| 378 | 1.6 | 4.6 | 1636 |
| 379 | 2.6 | 4.7 | 909 |
| 380 | 1.4 | 1.6 | 1878 |
| 381 | 3.7 | 5.5 | 8062 |
| 382 | 7.8 | 22 | >50000 |
| 383 | 33 | 167 | >50000 |
| 384 | 13 | 25 | 1526 |
| 385 | 22 | 46 | 11236 |
| 386 | 1.5 | 4.2 | 1440 |
| 387 | 7.2 | 19 | 5513 |
| 388 | 0.87 | 2.2 | 891 |
| 389 | 0.45 | 1.6 | 923 |
| 390 | 1.6 | 7.6 | 3094 |
| 391 | 2.6 | 14 | 2451 |
| 392 | 3.2 | 6.1 | 1746 |
| 393 | 0.47 | 1.3 | 360 |
| 394 | 1.4 | 1.5 | 1412 |
| 395 | 7.4 | 10 | 1621 |
| 396 | 1.7 | 17 | 1531 |
| 397 | 6.3 | 10 | 2402 |
| 398 | 3.8 | 17 | 4119 |
| 399 | 0.83 | 1.8 | 988 |
| 400 | 0.74 | 2.9 | 1549 |
| 401 | 5.7 | 6.4 | 5719 |
| 402 | 31 | 43 | 5146 |
| 403 | 7.7 | 44 | 4281 |
| 404 | 3.8 | 9.3 | 1544 |
| 405 | 3.6 | 2.5 | 1425 |
| 406 | 1.4 | 3.0 | 1466 |
| 407 | 7.2 | 8.5 | 2457 |
| 408 | 18 | 43 | 6440 |
| 409 | 1.7 | 1.6 | 550 |
| 410 | 5.0 | 6.5 | 4925 |
| 411 | 6.3 | 8.0 | 2297 |
| 412 | 2.2 | 2.1 | 727 |
| 413 | 17 | 18 | 4737 |
| 414 | 5.1 | 12 | 1756 |
| 415 | 2.5 | 3.5 | 1240 |
| 416 | 0.85 | 1.2 | 1622 |
| 417 | 5.2 | 7.1 | 9504 |
| 418 | NT | 3.9 | 2865 |
| 419 | 4.1 | 2.5 | 1744 |
| 420 | 1.2 | 2.8 | 3530 |
| 421 | 1.6 | 1.8 | 2058 |
| 422 | 15 | 35 | 6239 |
| 423 | 175 | 83 | >50000 |
| 424 | 0.89 | 0.74 | 1531 |
| 425 | 0.87 | 0.50 | 2915 |
| 426 | 2.5 | 2.6 | 1398 |
| 427 | 2.4 | 7.6 | 4904 |
| 428 | 7.4 | 6.4 | 9858 |
| 429 | 3.4 | 5.2 | 7002 |
| 430 | 13 | 14 | 15105 |
| 431 | 16 | 11 | 4657 |
| 432 | 0.37 | 0.55 | 584 |
| 433 | 42 | 60 | >50000 |
| 434 | 1.5 | 2.4 | 7432 |
| 435 | 2.7 | 5.5 | 2176 |
| 436 | 8.9 | 27 | 8941 |
| 437 | 5.1 | 11 | 3752 |
| 438 | 0.77 | 0.39 | 1458 |
| 439 | 3.5 | 32 | 24228 |
| 440 | 6.4 | 14 | >50000 |
| 441 | 0.79 | 0.63 | 1660 |
| 442 | 3.7 | 3.5 | 18317 |
| 443 | 15 | 57 | NT |
| 444 | 16 | 5.2 | 39175 |
| 445 | 1.5 | 3.6 | 4887 |
| 446 | 0.91 | 0.91 | 364 |
| 447 | 1.7 | 2.3 | 1637 |
| 448 | 7.5 | 24 | 7692 |
| 449 | 323 | 165 | 17986 |
| 450 | 0.61 | 0.71 | 1193 |
| 451 | 0.48 | 0.63 | 1045 |
| 452 | 2.7 | 4.4 | 3091 |
| 453 | 4.0 | 3.3 | 1440 |
| 454 | 1.2 | 0.68 | 2393 |
| 455 | 14 | 12 | 9203 |
| 456 | 2.6 | 8.1 | 7726 |
| 457 | 0.32 | 0.30 | 622 |
| 458 | 5.0 | 10 | 9840 |
| 459 | 6.2 | 4.3 | 2790 |
| 460 | 0.88 | 0.79 | 2063 |
| 461 | 2.6 | 1.7 | 8471 |
| 462 | 6.9 | 8.4 | 4538 |
| 463 | 7.4 | 24 | 16002 |
| 464 | 0.68 | 0.85 | 1774 |
| 465 | 1.1 | 1.9 | 5660 |
| 466 | 59 | 204 | 5796 |
| 467 | 1.2 | 3.5 | 413 |
| 468 | 46 | 99 | NT |
| 469 | 0.98 | 2.9 | 1709 |
| 470 | 1.3 | 6.0 | 7422 |
| 471 | 2.8 | 3.2 | 4706 |
| 472 | 0.34 | 1.1 | 2511 |
| 473 | 7.1 | 9.6 | 7373 |
| 474 | 0.46 | 0.43 | 1450 |
| 475 | 1.4 | 2.2 | 3504 |
| 476 | 0.81 | 2.6 | 9749 |
| 477 | 8.3 | 6.0 | 6162 |
| 478 | 13 | 15 | 24545 |
| 479 | 2.9 | 10 | 23712 |
| 480 | 2.0 | 14 | 11749 |
| 481 | 0.82 | 3.9 | 13037 |
| 482 | 96 | 238 | >50000 |
| 483 | 0.94 | 1.2 | 5126 |
| 484 | 6.1 | 11 | 7071 |
| 485 | 1.1 | 2.2 | 2516 |
| 486 | 1.2 | 1.9 | 2367 |
| 487 | 0.75 | 0.49 | 2289 |
| 488 | 11 | 8.4 | 5364 |
| 489 | 20 | 20 | 6674 |
| 490 | 1.2 | 3.4 | 2127 |
| 491 | 0.89 | 8.0 | 677 |
| 492 | 1.4 | 1.9 | 1478 |
| 493 | 1755 | 3791 | >50000 |
| 494 | 5.2 | 2.8 | 14070 |
| 495 | 3.3 | 1.3 | 3603 |
| 496 | 7.5 | 2.1 | 2615 |
| 497 | 52 | 67 | >50000 |
| 498 | NT | NT | NT |
| 499 | 607 | 833 | >50000 |
| 500 | 19 | 39 | >50000 |
| 501 | 6.3 | 16 | 9553 |

TABLE 4-continued

TLR7/8/9 Reporter Assay Data
(NT = not tested)

| Ex. No. | TLR7 IC$_{50}$ (nM) | TLR8 IC$_{50}$ (nM) | TLR9 IC$_{50}$ (nM) |
|---|---|---|---|
| 502 | 0.79 | 5.1 | 2897 |
| 503 | 1.4 | 9.2 | 2503 |
| 504 | 0.55 | 0.64 | 3743 |
| 505 | 3.5 | 4.9 | 7601 |
| 506 | 0.41 | 0.42 | 3183 |
| 507 | 1.1 | 2.4 | 8492 |
| 508 | 1.1 | 3.3 | 6846 |
| 509 | 17 | 30 | 9105 |
| 510 | 5.9 | 28 | >50000 |
| 511 | 5.8 | 4.8 | >50000 |
| 512 | 1.1 | 5.6 | 304 |
| 513 | 319 | 307 | 545 |
| 514 | 38 | 44 | 7111 |
| 515 | 7.9 | 21 | 223 |
| 516 | 0.22 | 1.9 | 155 |
| 517 | 1.1 | 6.0 | 150 |
| 518 | 1.6 | 32 | 721 |
| 519 | 8.3 | 12 | 362 |
| 520 | 0.80 | 7.0 | 285 |
| 521 | 0.62 | 1.3 | 238 |
| 522 | 2.6 | 495 | 144 |
| 523 | 1.2 | 147 | 1470 |
| 524 | 0.88 | 6.7 | 407 |
| 525 | 0.18 | 48 | 771 |
| 526 | 8.8 | 14 | 666 |
| 527 | 7.3 | 3.0 | 1157 |
| 528 | NT | 23 | 5701 |
| 529 | 2.9 | 12 | 1833 |
| 530 | 7.1 | 8.8 | 4764 |
| 531 | 19 | 21 | 1289 |
| 532 | 0.58 | 4.4 | 3594 |
| 533 | 0.50 | 3.3 | 1459 |
| 534 | 1.2 | 8.0 | 4276 |
| 535 | 2.0 | 8.6 | 5717 |
| 536 | 0.66 | 4.1 | 2659 |
| 537 | 2.1 | 7.1 | 2853 |
| 538 | 2.0 | 3.3 | 8184 |
| 539 | 0.47 | 0.82 | 3322 |
| — | — | — | — |
| 540 | 1.1 | 1.4 | 1951 |
| 541 | 1.2 | 0.36 | 1429 |
| 542 | 24 | 17 | 9235 |
| 543 | 14 | 5.3 | 2279 |
| 544 | 11 | 6.4 | 5660 |
| 545 | 22 | 7.5 | 2464 |
| 546 | 9.5 | 1.6 | 1379 |
| 547 | 0.27 | 0.55 | 789 |
| 548 | 0.71 | 0.98 | 1090 |
| 549 | 1.8 | 18 | 401 |
| 550 | 0.87 | 15 | 796 |
| 551 | 0.94 | 5.5 | 582 |
| 552 | 0.83 | 2.1 | 4099 |
| 553 | 0.63 | 3.2 | 537 |
| 554 | 1.5 | 2.5 | 2861 |
| 555 | 0.85 | 3.0 | 341 |
| 556 | 1.7 | 1.1 | 5079 |
| 557 | 0.66 | 1.2 | 440 |
| 558 | 1.2 | 5.6 | 3427 |
| 559 | 0.72 | 4.6 | 4923 |
| 560 | 1.2 | 1.0 | 3821 |
| 561 | 0.64 | 3.0 | 5653 |
| 562 | 1.9 | 1.1 | 6484 |
| 563 | 0.83 | 2.4 | 4257 |
| 564 | 7.9 | 4.2 | 1764 |
| 565 | 8.8 | 6.9 | 3224 |
| 566 | 24 | 18 | 18988 |
| 567 | 18 | 18 | 2325 |
| 568 | 6.0 | 3.8 | 2081 |
| 569 | 11 | 3.0 | 2183 |
| 570 | 10 | 57 | 143 |
| 571 | 7.5 | 2.1 | 813 |
| 572 | 4.6 | 25 | 1197 |
| 573 | 0.99 | 9.1 | 3234 |
| 574 | 3.0 | 47 | 11936 |
| 575 | 0.44 | 121 | 1352 |
| 576 | NT | NT | NT |
| 577 | 0.69 | 7.4 | 1881 |
| 578 | 0.53 | 287 | 4190 |
| 579 | 0.39 | 79 | 1838 |
| 580 | 0.41 | 8.7 | 1789 |
| 581 | 0.30 | 79 | 4920 |
| 582 | 0.99 | 12 | 7463 |
| 583 | 0.32 | 5.1 | 1552 |
| 584 | 0.24 | 29 | 2006 |
| 585 | 0.46 | 8.6 | 1839 |
| 586 | 0.75 | 98 | 2897 |
| 587 | 0.31 | 27 | 1408 |
| 588 | 2.3 | 42 | 16107 |
| 589 | 0.25 | 62 | 1062 |
| 590 | 3.0 | 4.7 | 3549 |
| 591 | 4.8 | 7.7 | 2852 |
| 592 | 2.9 | 7.4 | 2244 |
| 593 | 1.4 | 2.6 | 974 |
| 594 | 3.9 | 16 | 7906 |
| 595 | 122 | >3125 | 10867 |
| 596 | 13 | 67 | 3204 |
| 597 | 1.3 | 1.2 | 918 |
| 598 | 0.81 | 3.1 | 949 |
| 599 | 2.7 | 4.8 | 3047 |
| 600 | 0.75 | 6.2 | 2051 |
| 601 | 46 | 46 | >50000 |
| 602 | 1.2 | 6.8 | 1430 |
| 603 | 1.5 | 5.2 | 1190 |
| 604 | 2.8 | 2.5 | 5914 |
| 605 | 13 | 17 | 4244 |
| 606 | 2.3 | 3.9 | 1711 |
| 607 | 2.1 | 2.6 | 1142 |
| 608 | 1.1 | 6.1 | 1713 |
| 609 | 2.6 | 23 | 2718 |
| 610 | 1.5 | 14 | 1771 |
| 611 | 8.4 | 17 | 1933 |
| 612 | 13 | 56 | 3927 |
| 613 | 2.0 | 3.2 | 1243 |
| 614 | 1.9 | 13 | 1014 |
| 615 | 2.4 | 7.9 | 1958 |
| 616 | 3.6 | 1.5 | 1282 |
| 617 | 2219 | 1325 | 20509 |
| 618 | 4.8 | 4.6 | 3699 |
| 619 | 0.43 | 3.0 | 865 |
| 620 | 0.73 | 2.4 | 223 |
| 621 | 7.0 | 7.5 | 14661 |
| 622 | 30 | 14 | 5071 |
| 623 | 1.6 | 2.0 | 3127 |
| 624 | 3.0 | 2.0 | 2568 |
| 625 | 0.72 | 10 | 978 |
| 626 | 29 | 8.0 | 13454 |
| 627 | 7.9 | 18 | 4504 |
| 628 | 2.1 | 3.3 | 343 |
| 629 | 2.6 | 6.5 | 1920 |
| 630 | 1.9 | 14 | 1284 |
| 631 | 4.0 | 1.9 | 3067 |
| 632 | 3.1 | 2.2 | 439 |
| 633 | 40 | 33 | 25537 |
| 634 | 2.0 | 3.0 | 2374 |
| 635 | 5.7 | 1.1 | 1785 |
| 636 | 46 | 28 | 21593 |
| 637 | 3.8 | 0.53 | 1359 |
| 638 | 2.9 | 7.3 | 1272 |
| 639 | 0.98 | 1.9 | 1472 |
| 640 | 4.9 | 4.9 | 13508 |
| 641 | 9.2 | 3.5 | 3344 |
| 642 | 14 | 26 | 18090 |
| 643 | 5.4 | 5.3 | 3170 |
| 644 | 2.7 | 4.5 | 2690 |
| 645 | 21 | 303 | 4087 |
| 646 | 2.1 | 11 | 4140 |

TABLE 4-continued

TLR7/8/9 Reporter Assay Data
(NT = not tested)

| Ex. No. | TLR7 IC$_{50}$ (nM) | TLR8 IC$_{50}$ (nM) | TLR9 IC$_{50}$ (nM) |
|---|---|---|---|
| 647 | 2.3 | 26 | 5888 |
| 648 | 2.1 | 40 | 2073 |
| 649 | 6.2 | 10 | 3283 |
| 650 | 6.7 | 18 | 3125 |
| 651 | 1.7 | 24 | 687 |
| 652 | 3.0 | 22 | 1600 |
| 653 | 5.5 | 13 | 13221 |
| 654 | 6.4 | 9.6 | 4917 |
| 655 | 1.4 | 11 | 2069 |
| 656 | 1.4 | 4.7 | 1853 |
| 657 | 2.1 | 10 | 842 |
| 658 | 3.8 | 8.2 | 13603 |
| 659 | 12 | 24 | 8538 |
| 660 | 3.3 | 15 | 14410 |
| 661 | 2.3 | 5.5 | 13871 |
| 662 | 1.8 | 1.0 | 9030 |
| 663 | 3.5 | 9.9 | 21144 |
| 664 | 22 | 14 | 38509 |
| 665 | 34 | 17 | >50000 |
| 666 | 0.73 | 1.6 | 6563 |
| 667 | 145 | 711 | >50000 |
| 668 | 1.7 | 22 | 17531 |
| 669 | 7.4 | 5.6 | 31553 |
| 670 | 56 | 58 | >50000 |
| 671 | 1.4 | 2.1 | 4480 |
| 672 | 4.7 | 90 | 6244 |
| 673 | 5.2 | 6.9 | 14419 |
| 674 | 32 | 48 | >50000 |
| 675 | 9.7 | 4.6 | 14462 |
| 676 | 1.0 | 2.5 | 5718 |
| 677 | 17 | 53 | >50000 |
| 678 | 36 | 29 | >50000 |
| 679 | 16 | 5.8 | 20652 |
| 680 | 12 | 5.2 | 1058 |
| 681 | 104 | 199 | 4236 |
| 682 | 16 | 24 | 1052 |
| 683 | 12 | 13 | 322 |
| 684 | 14 | 13 | 365 |
| 685 | 32 | 39 | 1576 |
| 686 | >3125 | >3125 | >50000 |
| 687 | 39 | 16 | 5774 |
| 688 | 8.4 | 23 | 177 |
| 689 | 11 | 42 | 433 |
| 690 | 15 | 31 | 288 |
| 691 | 11 | 9.2 | 315 |
| 692 | 43 | 58 | 1528 |
| 693 | 6.5 | 15 | 437 |
| 694 | 2309 | 2850 | 14611 |
| 695 | 42 | 20 | 3952 |
| 696 | 75 | 36 | 1311 |
| 697 | 20 | 111 | 919 |
| 698 | 12 | 28 | 1004 |
| 699 | 12 | 46 | 430 |
| 700 | 26 | 43 | 2328 |
| 701 | 49 | 15 | 1748 |
| 702 | 41 | 14 | 2228 |
| 703 | 8.9 | 16 | 326 |
| 704 | 11 | 13 | 166 |
| 705 | 18 | 15 | 655 |
| 706 | 8.5 | 18 | 1020 |
| 707 | 1.5 | 5.3 | 1412 |
| 708 | 12 | 280 | >50000 |
| 709 | 2330 | >3125 | >50000 |
| 710 | 2.0 | 3.2 | 4665 |
| 711 | 2.0 | 2.9 | 1699 |
| 712 | 1.9 | 11 | 3145 |
| 713 | 6.2 | 28 | 4878 |
| 714 | 1.8 | 9.3 | 203 |
| 715 | 1.7 | 11 | 8707 |
| 716 | 0.74 | 6.7 | 2526 |
| 717 | 1062 | 1101 | 2525 |
| 718 | 9.6 | 3.6 | 6211 |
| 719 | 2.8 | 7.0 | 2596 |
| 720 | 13 | 94 | 20336 |
| 721 | 0.41 | 0.53 | 982 |
| 722 | 6.5 | 46 | 18477 |
| 723 | 0.99 | 2.4 | 4391 |
| 724 | 0.63 | 2.0 | 2194 |
| 725 | 0.62 | 1.9 | 2059 |
| 726 | 1357 | 2090 | 39366 |
| 727 | 3.6 | 3.2 | 3352 |
| 728 | 0.74 | 0.67 | 3538 |
| 729 | 1.1 | 1.3 | 1941 |
| 730 | 3.3 | 23 | 10526 |
| 731 | 4.6 | 15 | 1640 |
| 732 | 10 | 70 | 4834 |
| 733 | 53 | 1014 | >50000 |
| 734 | 26 | 252 | >50000 |
| 735 | 25 | 61 | 262 |
| 736 | 631 | 269 | >50000 |
| 737 | 0.59 | 0.55 | 7774 |
| 738 | 0.46 | 0.89 | 6226 |
| 739 | 0.85 | 1.6 | 5324 |
| 740 | 2.2 | 5.1 | 623 |
| 741 | 1.9 | 6.5 | 3034 |
| 742 | 2.9 | 3.1 | 4580 |
| 743 | 3.6 | 8.4 | 1881 |
| 744 | 2.0 | 7.1 | 3058 |
| 745 | 2.2 | 5.8 | 2446 |
| 746 | 1.1 | 10 | 3106 |
| 747 | 0.59 | 4.1 | 7379 |
| 748 | 7.5 | 15 | 37886 |
| 749 | 2.9 | 2.6 | 14893 |
| 750 | 1.2 | 3.7 | 6145 |
| 751 | 13 | 7.3 | 26035 |
| 752 | 0.38 | 0.53 | 10266 |
| 753 | 3.8 | 12 | 27862 |
| 754 | 5.2 | 1.7 | 5432 |
| 755 | 2.8 | 6.2 | 3734 |
| 756 | 3.9 | 6.0 | 9055 |
| 757 | 0.70 | 1.9 | 5215 |
| 758 | 0.89 | 1.7 | 18200 |
| 759 | 3.8 | 14 | 38197 |
| 760 | 4.2 | 27 | 7629 |
| 761 | 9.0 | 14 | 8170 |
| 762 | 3.8 | 8.6 | 18318 |
| 763 | 3.8 | 2.6 | 4579 |
| 764 | 1.9 | 2.8 | 14428 |
| 765 | 5.6 | 3.5 | 10263 |
| 766 | 0.86 | 1.2 | 3512 |
| 767 | 5.4 | 2.9 | 8300 |
| 768 | 6.4 | 9.6 | 20957 |
| 769 | 1.3 | 4.5 | 5569 |
| 770 | 11 | 24 | 18183 |
| 771 | 4.3 | 9.2 | 9843 |
| 772 | 3.2 | 10 | 4713 |
| 773 | 3.0 | 4.6 | 2706 |
| 774 | 3.7 | 5.7 | 18596 |
| 775 | 3.8 | 4.4 | 8447 |
| 776 | 6.0 | 5.3 | 13088 |
| 777 | 9.2 | 7.4 | 14795 |
| 778 | 2.7 | 2.3 | 7908 |
| 779 | 7.3 | 11 | 34519 |
| 780 | 1.9 | 5.4 | 5225 |
| 781 | 11 | 18 | 14380 |
| 782 | 1.3 | 4.7 | 5736 |
| 783 | 1.8 | 3.9 | 8377 |
| 784 | 2.9 | 9.4 | 4527 |
| 785 | 8.0 | 13 | 4684 |
| 786 | 7.7 | 12 | 14676 |
| 787 | 9.4 | 4.9 | 12254 |
| 788 | 2.1 | 3.2 | 8302 |
| 789 | 3.2 | 3.7 | 13321 |
| 790 | 0.42 | 0.85 | 8810 |
| 791 | 5.3 | 1.1 | 18146 |
| 792 | 4.0 | 1.0 | 8555 |

TABLE 4-continued

TLR7/8/9 Reporter Assay Data
(NT = not tested)

| Ex. No. | TLR7 IC$_{50}$ (nM) | TLR8 IC$_{50}$ (nM) | TLR9 IC$_{50}$ (nM) |
|---|---|---|---|
| 793 | 1.4 | 1.4 | 7829 |
| 794 | 1.4 | 1.5 | 18048 |
| 795 | 12 | 8.1 | >50000 |
| 796 | 6.0 | 15 | 11322 |
| 797 | 10 | 14 | 17578 |
| 798 | 4.2 | 5.7 | 22334 |
| 799 | 5.0 | 21 | >50000 |
| 800 | 20 | 26 | >50000 |
| 801 | 0.57 | 0.56 | 10960 |
| 802 | 3.0 | 0.65 | 17918 |
| 803 | 4.3 | 4.0 | 39663 |
| 804 | 1.2 | 0.56 | 18116 |
| 805 | 2.1 | 0.57 | 24156 |
| 806 | 1.1 | 1.1 | 29426 |
| 807 | 0.95 | 1.3 | 16263 |
| 808 | 0.19 | 1.4 | 8946 |
| 809 | 2.2 | 3.1 | 35999 |
| 810 | 0.64 | 0.63 | 7355 |
| 811 | 0.36 | 0.59 | 5596 |
| 812 | 2.2 | 3.6 | >50000 |
| 813 | 3.7 | 9.1 | >50000 |
| 814 | 1.9 | 2.3 | >50000 |
| 815 | 1.8 | 1.4 | >50000 |
| 816 | 1.7 | 1.7 | 8723 |
| 817 | 2.1 | 2.9 | >50000 |
| 818 | 0.78 | 0.43 | 12846 |
| 819 | 2.2 | 0.58 | 21064 |
| 820 | 2.7 | 2.0 | 9396 |
| 821 | 1.3 | 1.3 | 6694 |
| 822 | 1.1 | 0.24 | 6914 |
| 823 | 0.49 | 1.2 | 6932 |
| 824 | 1.6 | 2.1 | 5791 |
| 825 | 0.53 | 1.1 | 6277 |
| 826 | 0.70 | 1.0 | 15739 |
| 827 | 0.46 | 0.34 | 4852 |
| 828 | 0.88 | 1.4 | 7157 |
| 829 | 3.7 | 12 | 17264 |
| 830 | 0.62 | 0.63 | 7443 |
| 831 | 1.5 | 2.3 | 8550 |
| 832 | 4.0 | 2.3 | 16779 |
| 833 | 1.9 | 4.9 | 9782 |
| 834 | 0.46 | 2.5 | 4367 |
| 835 | 0.70 | 4.1 | 5560 |
| 836 | 2.4 | 4.1 | 16449 |
| 837 | 0.70 | 1.6 | 7822 |
| 838 | 0.60 | 3.5 | 9891 |
| 839 | 0.37 | 3.2 | 7869 |
| 840 | 0.38 | 1.5 | 7401 |
| 841 | 5.6 | 28 | 14253 |
| 842 | 0.38 | 0.47 | 6919 |
| 843 | 0.52 | 1.4 | 5479 |
| 844 | 2.0 | 11 | 8817 |
| 845 | 7.2 | 14 | 21276 |
| 846 | 0.55 | 1.2 | 22620 |
| 847 | 4.9 | 8.3 | 22521 |
| 848 | 1.2 | 2.2 | 17494 |
| 849 | 0.53 | 1.6 | 8120 |
| 850 | 0.72 | 1.6 | 6540 |
| 851 | 5.9 | 2.2 | 9978 |
| 852 | 5.2 | 0.82 | 16163 |
| 853 | 0.51 | 0.66 | 9571 |
| 854 | 11 | 5.0 | 32272 |
| 855 | 2.4 | 4.6 | 14322 |
| 856 | 7.3 | 0.46 | 27144 |
| 857 | 0.65 | 0.40 | 4396 |
| 858 | 1.1 | 1.3 | 7132 |
| 859 | 0.97 | 1.5 | 7308 |
| 860 | 0.30 | 0.62 | 5062 |
| 861 | 0.31 | 4.2 | 5010 |
| 862 | 0.29 | 2.2 | 7037 |
| 863 | 0.52 | 17 | 6065 |
| 864 | 1.5 | 12 | 5693 |
| 865 | 1.3 | 72 | 8891 |
| 866 | 3.2 | 74 | 47596 |
| 867 | 4.5 | 11 | >50000 |
| 868 | 12 | 6.1 | >50000 |
| 869 | 1.9 | 34 | 40301 |
| 870 | 0.56 | 3.3 | 14448 |
| 871 | 1.6 | 5.1 | 12728 |
| 872 | 0.97 | 3.8 | 9539 |
| 873 | 3.1 | 1.8 | 12788 |
| 874 | 1.2 | 5.3 | 15548 |
| 875 | 6.6 | 3.2 | 40475 |
| 876 | 644 | 517 | 13255 |
| 877 | 1.5 | 1.6 | 12556 |
| 878 | 0.48 | 2.2 | 9042 |
| 879 | 1.0 | 3.4 | 7546 |
| 880 | 6.4 | 30 | 19328 |
| 881 | 25 | 68 | 43465 |
| 882 | 3.3 | 11 | 7764 |
| 883 | 7.4 | 2.3 | 12546 |
| 884 | 0.90 | 0.17 | 6501 |
| 885 | 1.6 | 3.8 | 7846 |
| 886 | 2.8 | 1.7 | 2568 |
| 887 | 0.50 | 0.68 | 8121 |
| 888 | 1.2 | 0.59 | 12211 |
| 889 | 1.5 | 0.76 | 9839 |
| 890 | 1.8 | 1.4 | 14745 |
| 891 | 0.64 | 0.93 | 17965 |
| 892 | 0.62 | 1.4 | 3285 |
| 893 | 0.34 | 0.74 | 7440 |
| 894 | 0.37 | 0.89 | 10763 |
| 895 | 0.74 | 1.1 | 7926 |
| 896 | 0.69 | 0.37 | 8435 |
| 897 | 0.86 | 1.5 | 11982 |
| 898 | 2.1 | 3.2 | 17320 |
| 899 | 1.0 | 1.7 | 9780 |
| 900 | 1.1 | 1.4 | 15593 |
| 901 | 0.72 | 0.15 | 13255 |
| 902 | 1.1 | 1.4 | 15789 |
| 903 | 3.0 | 4.1 | 35228 |
| 904 | 1.0 | 4.2 | 14798 |
| 905 | 0.51 | 0.82 | 12016 |
| 906 | 0.39 | 0.67 | 7799 |
| 907 | 0.76 | 0.45 | >50000 |
| 908 | 0.89 | 0.26 | 6457 |
| 909 | 0.54 | 0.91 | 6707 |
| 910 | 0.68 | 0.86 | 5398 |
| 911 | 0.68 | 1.5 | 7016 |
| 912 | 0.98 | 2.2 | 9330 |
| 913 | 1.0 | 1.8 | 8845 |
| 914 | 0.73 | 0.94 | 6046 |
| 915 | 2.3 | 1.0 | 11137 |
| 916 | 18 | 11 | 14537 |
| 917 | 5.2 | 2.9 | 43171 |
| 918 | 3.2 | 6.3 | 20583 |
| 919 | 23 | 1.0 | 13895 |
| 920 | 2.6 | 5.9 | 12088 |
| 921 | 0.61 | 3.4 | 5267 |
| 922 | 0.55 | 2.1 | 9372 |
| 923 | 1.2 | 3.6 | 6556 |
| 924 | 1.7 | 4.9 | 7234 |
| 925 | 0.79 | 9.2 | 10082 |
| 926 | 3.3 | 3.0 | 3040 |
| 927 | 2.9 | 3.7 | 4357 |
| 928 | 1.5 | 6.9 | 3640 |
| 929 | 2.6 | 3.9 | 5086 |
| 930 | 22 | 7.4 | 24293 |
| 931 | 2.5 | 3.9 | 14927 |
| 932 | 0.66 | 10 | 14343 |
| 933 | 0.63 | 18 | 18442 |
| 934 | 0.86 | 8.6 | 9746 |
| 935 | 0.48 | 2.9 | 5613 |
| 936 | 0.56 | 3.5 | 4638 |
| 937 | 0.52 | 14 | 14243 |
| 938 | 2.6 | 4.9 | 8560 |

TABLE 4-continued

TLR7/8/9 Reporter Assay Data
(NT = not tested)

| Ex. No. | TLR7 IC$_{50}$ (nM) | TLR8 IC$_{50}$ (nM) | TLR9 IC$_{50}$ (nM) |
|---|---|---|---|
| 939 | 1.5 | 9.8 | 11863 |
| 940 | 1.7 | 0.66 | 8343 |
| 941 | 0.66 | 0.66 | 7198 |
| 942 | 0.50 | 3.4 | 12005 |
| 943 | 1.1 | 1.1 | 10046 |
| 944 | 3.1 | 4.9 | 17114 |
| 945 | 4.8 | 0.94 | 7846 |
| 946 | 1.4 | 1.8 | 8950 |
| 947 | 1.9 | 0.66 | 8773 |
| 948 | 2.8 | 1.4 | 12817 |
| 949 | 2.6 | 1.6 | 31028 |
| 950 | 7.2 | 4.9 | 36119 |
| 951 | 6.5 | 1.5 | >50000 |
| 952 | 1.8 | 0.70 | 7862 |
| 953 | 0.92 | 5.3 | 12031 |
| 954 | 1.9 | 36 | 20896 |
| 955 | 0.76 | 2.0 | 20450 |
| 956 | 1.0 | 1.9 | 9650 |
| 957 | 0.92 | 2.9 | 24415 |
| 958 | 0.27 | 2.3 | 11244 |
| 959 | 1.4 | 0.29 | 7681 |
| 960 | 0.77 | 0.32 | 3166 |
| 961 | 0.35 | 0.80 | 8337 |
| 962 | 3.7 | 17 | >50000 |
| 963 | 0.84 | 1.9 | 35268 |
| 964 | 0.53 | 0.25 | 3095 |
| 965 | 0.39 | 1.1 | 6483 |
| 966 | 2.4 | 1.3 | 6022 |
| 967 | 7.9 | 1.2 | 38697 |
| 968 | 1.9 | 0.69 | 16436 |
| 969 | 1.3 | 0.12 | 7175 |
| 970 | 3.1 | 0.92 | 10709 |
| 971 | 3.0 | 0.85 | 9246 |
| 972 | 3.3 | 3.1 | 6915 |
| 973 | 6.7 | 1.7 | 15804 |
| 974 | 1.1 | 0.71 | 3918 |
| 975 | 12 | 0.61 | 6463 |
| 976 | 2.5 | 0.96 | 13425 |
| 977 | 1.4 | 2.1 | 8600 |
| 978 | 11 | 1.8 | 11451 |
| 979 | 1.1 | 0.80 | 4291 |
| 980 | 2.2 | 2.3 | 6271 |
| 981 | 0.95 | 0.51 | 3066 |
| 982 | 9.8 | 20 | 32827 |
| 983 | 0.82 | 0.12 | 6525 |
| 984 | 1.0 | 0.85 | 3427 |
| 985 | 1.6 | 1.1 | 3897 |
| 986 | 0.63 | 0.38 | 2821 |
| 987 | 2.9 | 0.50 | 11253 |
| 988 | 0.36 | 0.23 | 3767 |
| 989 | 0.69 | 0.31 | 7098 |
| 990 | 0.80 | 4.0 | 6024 |
| 991 | 0.27 | 0.32 | 5986 |
| 992 | 0.66 | 0.72 | 6311 |
| 993 | 0.82 | 1.5 | 7230 |
| 994 | 13 | 3.4 | 11830 |
| 995 | 0.56 | 0.48 | 7020 |
| 996 | 1.3 | 0.40 | 11011 |
| 997 | 2.4 | 2.4 | 13578 |
| 998 | 1.9 | 0.44 | 20008 |
| 999 | 7.5 | 2.1 | 10466 |
| 1000 | 18 | 3.2 | 6438 |
| 1001 | 70 | 40 | 11739 |
| 1002 | 10 | 4.6 | 1099 |
| 1003 | 1.8 | 3.7 | 3164 |
| 1004 | 2.1 | 1.3 | 2794 |
| 1005 | 4.4 | 7.4 | 1659 |
| 1006 | 3.6 | 9.6 | 339 |
| 1007 | 3.2 | 4.0 | 2337 |
| 1008 | 15 | 32 | 13326 |
| 1009 | 4.5 | 7.7 | 2657 |
| 1010 | 3.6 | 4.7 | 2431 |
| 1011 | 11 | 22 | 23736 |
| 1012 | 0.59 | 1.4 | 1686 |
| 1013 | 11 | 9.2 | 7677 |
| 1014 | 21 | 26 | 21927 |
| 1015 | 1.3 | 7.8 | 2384 |
| 1016 | 2.9 | 38 | 641 |
| 1017 | 1.3 | 16 | 3302 |
| 1018 | 1.7 | 8.9 | 2782 |
| 1019 | 1.7 | 16 | 3278 |
| 1020 | 1.8 | 17 | 3863 |
| 1021 | 4.3 | 11 | 5329 |
| 1022 | 0.91 | 1.9 | 3650 |
| 1023 | 10 | 3.6 | 6939 |
| 1024 | 1.8 | 1.2 | 4538 |
| 1025 | 3.0 | 0.86 | 5861 |
| 1026 | 4.5 | 6.3 | 14488 |
| 1027 | 0.60 | 9.2 | 3003 |
| 1028 | 7.6 | 2.1 | 16992 |
| 1029 | 1.4 | 5.0 | 8378 |
| 1030 | 3.1 | 1.9 | 6278 |
| 1031 | 18 | 2.0 | 12671 |
| 1032 | 1206 | 196 | 25365 |
| 1033 | 1086 | 974 | 22372 |
| 1034 | 1398 | >3125 | 26595 |
| 1035 | 1.7 | 21 | 3666 |
| 1036 | 1.3 | 2.7 | 1931 |
| 1037 | 3.1 | 6.2 | 1609 |
| 1038 | 0.98 | 1.3 | 1910 |
| 1039 | 7.2 | 6.4 | 3068 |
| 1040 | 0.17 | 0.66 | 1106 |
| 1041 | 0.49 | 0.85 | 2424 |
| 1042 | 2.2 | 3.3 | 3316 |
| 1043 | 2.1 | 1.6 | 1749 |
| 1044 | 4.1 | 9.2 | 3595 |
| 1045 | 4.8 | 3.6 | 3236 |
| 1046 | 0.64 | 2.4 | 2502 |
| 1047 | 1.3 | 3.5 | 4493 |
| 1048 | 4.4 | 13 | 9827 |
| 1049 | 1.6 | 5.4 | 2599 |
| 1050 | 2.8 | 4.8 | 2657 |
| 1051 | 0.41 | 1.5 | 1908 |
| 1052 | 8.9 | 17 | 5920 |
| 1053 | 2.5 | 4.8 | 4807 |
| 1054 | 5.4 | 1.7 | 1692 |
| 1055 | 4.3 | 8.3 | 5471 |
| 1056 | 2.1 | 1.2 | 2992 |
| 1057 | 0.81 | 1.7 | 2698 |
| 1058 | 1.9 | 3.5 | 5275 |
| 1059 | 1.6 | 1.4 | 2247 |
| 1060 | 0.50 | 0.50 | 2598 |
| 1061 | 2.7 | 4.8 | 3175 |
| 1062 | 13 | 25 | 10182 |
| 1063 | 10 | 18 | 8057 |
| 1064 | 0.34 | 0.96 | 2455 |
| 1065 | 1.1 | 1.1 | 2796 |
| 1066 | 9.0 | 11 | 4291 |
| 1067 | 1.0 | 4.5 | 5396 |
| 1068 | 0.88 | 1.8 | 2957 |
| 1069 | 0.09 | 0.17 | 735 |
| 1070 | 0.54 | 0.72 | 845 |
| 1071 | 3.7 | 25 | 5951 |
| 1072 | 2.9 | 35 | 5841 |
| 1073 | 4.6 | 28 | 5832 |
| 1074 | 0.59 | 1.9 | 2126 |
| 1075 | 1.8 | 11 | 3354 |
| 1076 | 1.6 | 1.8 | 10583 |
| 1077 | 18 | 38 | 21801 |
| 1078 | 9.8 | 216 | >50000 |

In Vivo Mouse TLR7 PD Model:

Adult male $C_{5-7}BL/6$ mice were used for the experiments. Mice (7 to 10 per group) were randomized into different treatment groups based on body weight. Mice from the respective treatment groups were administered orally with vehicle or test compound. Thirty min after the oral administration of vehicle or test compound, mice were challenged with intraperitoneal injection of gardiquimod for TLR7 PD model. Ninety minutes after gardiquimod injection, mice were bled under isoflurane anaesthesia and plasma IL-6 and IFN-alpha levels were estimated by using commercially available ELISA kit (BD Biosciences, PBL Life Sciences). At the end of experiment, mean cytokine data was plotted and one way ANOVA with Dunnett's test was performed to calculate the significance of test compound treated group vs. vehicle control group. Percent inhibition of cytokine induction was calculated for test compound treated group vs vehicle control group. Data from multiple studies with different test compounds is shown in Table 5.

TABLE 5

Percent inhibition of IL-6 and IFN-alpha in mouse TLR7 PD model
TLR7 PD model

| Ex. No. | Dose (mg/kg) | % inhibition of IL6 | % inhibition of IFN-alpha |
|---|---|---|---|
| 3 | 0.005 | 0 | 29 |
|   | 0.01 | 24 | 37 |
|   | 0.05 | 75 | 94 |
|   | 0.25 | 90 | 99 |
|   | 0.5 | 91 | 100 |
| 4 | 0.0015 | 0 | 0 |
|   | 0.003 | 23 | 33 |
|   | 0.015 | 75 | 74 |
|   | 0.075 | 76 | 93 |
|   | 0.15 | 95 | 99 |
| 438 | 0.003 | 25 | 36 |
|   | 0.006 | 41 | 57 |
|   | 0.03 | 56 | 67 |
|   | 0.15 | 78 | 96 |
|   | 0.3 | 82 | 98 |

MRL/Lpr Model of SLE:

Male MRL/lpr mice of 12-14 weeks age were screened and randomized based on the titres of anti-dsDNA antibodies and urinary NGAL (Neutrophil Gelatinase Associated Lipocalin). Mice were treated orally, once daily for 8 weeks with vehicle or test compound. The effect of test compound on disease severity was assessed by measuring end points including proteinuria, urinary-NGAL, urinary TIMP1, blood urea nitrogen (BUN), anti-dsDNA Ab, anti-smRNP Ab titer, and plasma levels of IL10 and IL12p40. At the end of experiment, all mice were euthanized by $CO_2$ asphyxiation and kidney samples were subjected for histology. To calculate the significance of test compound treated group vs. vehicle control group, one way ANOVA with Dunnett's test was performed. Percent reduction in disease severity was calculated for each parameter, for test compound treated group vs vehicle control group. Data from a study with test compound is shown in Table 6.

TABLE 6

Inhibition of disease development by TLR7/8
inhibitors in MRL/lpr model of lupus

| Ex. No. | Dose (mg/kg) | Protein-uria | Urinary NGAL | Urinary TIMP1 | Anti-SmRNP Ab titer | Anti-dsDNA Ab titer | IL-12p40 | IL-10 |
|---|---|---|---|---|---|---|---|---|
| 438 | 0.1 | 31 | 34 | 0 | 23 | 0 | 16 | 0 |
|  | 0.3 | 80 | 58 | 42 | 44 | 28 | 33 | 18 |

TABLE 6-continued

Inhibition of disease development by TLR7/8
inhibitors in MRL/lpr model of lupus

| Ex. No. | Dose (mg/kg) | Protein-uria | Urinary NGAL | Urinary TIMP1 | Anti-SmRNP Ab titer | Anti-dsDNA Ab titer | IL-12p40 | IL-10 |
|---|---|---|---|---|---|---|---|---|
| 1 |  | 73 | 63 | 54 | 49 | 39 | 26 | 19 |
| 3 |  | 82 | 67 | 56 | 43 | 44 | 28 | 21 |
| 10 |  | 84 | 67 | 79 | 51 | 37 | 41 | 22 |

What is claimed is:
1. A compound of Formula (I)

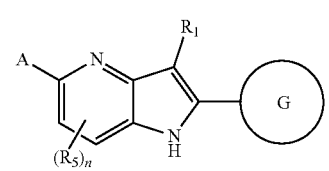

N-oxide, or a salt thereof, wherein:
G is:

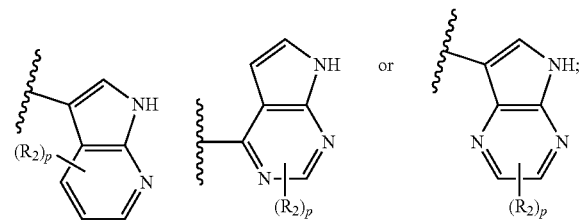

A is $-CR_xR_{12}R_{13}$, wherein $R_{12}$ and $R_{13}$ together with the carbon atom to which they are attached form a cyclohexyl group substituted with zero to 4 $R_{12a}$;

$R_1$ is H, $C_{1-3}$ alkyl, $C_{1-2}$ fluoroalkyl, $C_{1-2}$ hydroxyalkyl, or $C_{1-3}$ hydroxy-fluoroalkyl;

each $R_2$ is independently F, Cl, —CN, —OH, $C_{1-2}$ alkyl, $C_{1-2}$ fluoroalkyl, $C_{1-2}$ cyanoalkyl, $C_{1-2}$ hydroxyalkyl, —$(CH_2)_{0-2}O(C_{1-2}$ alkyl), or —$(CH_2)_{1-2}S(O)_2(C_{1-2}$ alkyl);

each $R_5$ is independently F, —CN, $C_{1-2}$ alkyl, $C_{1-2}$ fluoroalkyl, or —$OCH_3$;

each $R_{12a}$ is independently F, Cl, —OH, —$CH_2NH_2$, —$NH_2$, —$NH(CH_3)$, —$NH(CH(CH_3)_2)$, —$NH(C(CH_3)_3)$, —$N(CH_3)_2$, —$N(CH_3)CH_2CH_3$, —$N(CH_3)CH(CH_3)_2$, —$N(CH_3)CH_2C(CH_3)_3$, —$N(CH_2CH_3)_2$, —$NH(CH_2CHF_2)$, —$NH(CH_2CH_2CHF_2)$, —$NH(CH_2CN)$, —$NH(CH_2CH_2CN)$, —$N(CH_3)CH_2CH_2CN$, —$NH(CH2CH2OH)$, —$NH(CH_2C(CH_3)_2OH)$, —$NH(CH_2C(CH_3)_2OH)$, —$N(CH_3)CH_2CH_2OH$, —$NHCH_2C(O)N(CH_3)_2$, —$NHCH_2C(O)NH(C(CH_3)_3)$, —$N(CH_3)CH_2C(O)NH_2$, —$N(CH_3)CH_2C(O)NH(CH_3)$, —$N(CH_2CH_2OH)(CH_2C(O)N(CH_3)_2)$, —$N(CH_2CH_2OH)(CH_2CH_2S(O)_2CH_3)$, —$N(CH_2CH_3)(CH_2C(O)N(CH_3)_2)$, —$N(CH_2CH_3)(CH_2CH_2S(O)_2CH_3)$, —$N(CH_2CN)(CH_2C(O)N(CH_3)_2$, —$N(CH_2CN)(CH_2C(O)N(CH_3)_2)$, —$N(CH_2CN)(CH_2CH_2S(O)_2CH_3)$, —$N(CH_3)(CH_2CH_2OCH_3)$, —$N(CH_3)C(O)CH_2N(CH_3)_2$, —$N(CH_3)C(O)CH_3$, —$N(CH_3)CH_2CH_2OCH_3$, —$NH(C(CH_3)_2C(O)N(CH_3)_2)$, —$NH(C(CH_3)_2C(O)NH$ (CH$_3$), —NH(CH$_2$C(O)N(CH$_3$)CH$_2$CH$_2$OCH$_3$), —NH(CH$_2$CH$_2$OCH$_3$), —N(CH$_3$)CH$_2$C(O)NH$_2$, —N(CH$_3$)CH$_2$C(O)N(CH$_3$)$_2$, —NH(CH$_2$CH$_2$S(O)$_2$NH$_2$), —NHCH$_2$CH$_2$S(O)$_2$CH$_3$, —NHCH$_2$C(CH)$_2$S(O)$_2$CH$_3$, or —NHCH$_2$CH$_2$S(O)$_2$CF$_3$; or two R$_{12a}$ and the carbon atom to which they are attached form C=O;

each R$_x$ is independently H or —CH$_3$;

n is zero, 1, or 2; and p is zero, 1, 2, 3, or 4.

2. The compound according to claim 1, N-oxide, or a salt thereof, wherein:

R$_1$ is —CH(CH$_3$)$_2$;

each R$_2$ is independently —CH$_3$, —CH$_2$CH$_3$, —CH$_2$CN, —CH$_2$OH, —CH$_2$CH$_2$OH, —OCH$_3$, —CH$_2$OCH$_3$, or —CH$_2$CH$_2$S(O)$_2$CH$_3$;

each R$_5$ is independently F or —CH$_3$;

each R$_{12a}$ is independently —OH, —CH$_2$NH$_2$, —NH$_2$, —NH(CH$_3$), —NH(CH(CH$_3$)$_2$), —NH(C(CH$_3$)$_3$), —N(CH$_3$)$_2$, —N(CH$_3$)CH$_2$CH$_3$, —N(CH$_3$)CH(CH$_3$)$_2$, —N(CH$_3$)CH$_2$C(CH$_3$)$_3$, —N(CH$_2$CH$_3$)$_2$, —NH(CH$_2$CHF$_2$), —NH(CH$_2$CH$_2$CHF$_2$), —NH(CH$_2$CN), —NH(CH$_2$CH$_2$CN), —N(CH$_3$)CH$_2$CH$_2$CN, —NH(CH$_2$CH$_2$OH), —NH(CH$_2$C(CH$_3$)$_2$OH), —NH(CH$_2$C(CH$_3$)$_2$OH), —N(CH$_3$)CH$_2$CH$_2$OH, —NHCH$_2$C(O)N(CH$_3$)$_2$, —NHCH$_2$C(O)NH(C(CH$_3$)$_3$), —N(CH$_3$)CH$_2$C(O)NH$_2$, —N(CH$_3$)CH$_2$C(O)NH(CH$_3$), —N(CH$_2$CH$_2$OH)(CH$_2$C(O)N(CH$_3$)$_2$), —N(CH$_2$CH$_2$OH)(CH$_2$CH$_2$S(O)$_2$CH$_3$), —N(CH$_2$CH$_3$)(CH$_2$C(O)N(CH$_3$)$_2$), —N(CH$_2$CH$_3$)(CH$_2$CH$_2$S(O)$_2$CH$_3$), —N(CH$_2$CN)(CH$_2$C(O)N(CH$_3$)$_2$), —N(CH$_2$CN)(CH$_2$C(O)N(CH$_3$)$_2$), —N(CH$_2$CN)(CH$_2$CH$_2$S(O)$_2$CH$_3$), —N(CH$_3$)(CH$_2$CH$_2$OCH$_3$), —N(CH$_3$)C(O)CH$_2$N(CH$_3$)$_2$, —N(CH$_3$)C(O)CH$_3$, —N(CH$_3$)CH$_2$CH$_2$OCH$_3$, —NH(C(CH$_3$)$_2$C(O)N(CH$_3$)$_2$), —NH(C(CH$_3$)$_2$C(O)NH(CH$_3$), —NH(CH$_2$C(O)N(CH$_3$)CH$_2$CH$_2$OCH$_3$), —NH(CH$_2$CH$_2$OCH$_3$), —N(CH$_3$)CH$_2$C(O)NH$_2$, —N(CH$_3$)CH$_2$C(O)N(CH$_3$)$_2$, —NH(CH$_2$CH$_2$S(O)$_2$NH$_2$), —NHCH$_2$CH$_2$S(O)$_2$CH$_3$, —NHCH$_2$C(CH)$_2$S(O)$_2$CH$_3$, or —NHCH$_2$CH$_2$S(O)$_2$CF$_3$; or two R$_{12a}$ and the carbon atom to which they are attached form C=O;

each R$_x$ is independently H or —CH$_3$;

n is zero or 1; and p is zero, 1, or 2.

3. The compound according to claim 1 or a salt thereof, wherein each R$_{12a}$ is independently —NH$_2$, —NH(CH$_3$), —NH(CH(CH$_3$)$_2$), —NH(C(CH$_3$)$_3$), —N(CH$_3$)$_2$, —N(CH$_3$)CH$_2$CH$_3$, —N(CH$_3$)CH(CH$_3$)$_2$, —N(CH$_3$)CH$_2$C(CH$_3$)$_3$, —N(CH$_2$CH$_3$)$_2$, —NH(CH$_2$CHF$_2$), —NH(CH$_2$CH$_2$CHF$_2$), —NH(CH$_2$CN), —NH(CH$_2$CH$_2$CN), —N(CH$_3$)CH$_2$CH$_2$CN, —NH(CH$_2$CH$_2$OH), —NH(CH$_2$C(CH$_3$)$_2$OH), —NH(CH$_2$C(CH$_3$)$_2$OH), or —N(CH$_3$)CH$_2$CH$_2$OH; or two R$_{12a}$ and the carbon atom to which they are attached form C=O.

4. The compound according to claim 1 or a salt thereof, wherein each R$_{12a}$ is independently —NHCH$_2$C(O)N(CH$_3$)$_2$, —NHCH$_2$C(O)NH(C(CH$_3$)$_3$), —N(CH$_3$)CH$_2$C(O)NH$_2$, —N(CH$_3$)CH$_2$C(O)NH(CH$_3$), —N(CH$_2$CH$_2$OH)(CH$_2$C(O)N(CH$_3$)$_2$), —N(CH$_2$CH$_2$OH)(CH$_2$CH$_2$S(O)$_2$CH$_3$), —N(CH$_2$CH$_3$)(CH$_2$C(O)N(CH$_3$)$_2$), —N(CH$_2$CH$_3$)(CH$_2$CH$_2$S(O)$_2$CH$_3$), —N(CH$_2$CN)(CH$_2$C(O)N(CH$_3$)$_2$), —N(CH$_2$CN)(CH$_2$C(O)N(CH$_3$)$_2$), —N(CH$_2$CN)(CH$_2$CH$_2$S(O)$_2$CH$_3$), —N(CH$_3$)(CH$_2$CH$_2$OCH$_3$), —N(CH$_3$)C(O)CH$_2$N(CH$_3$)$_2$, —N(CH$_3$)C(O)CH$_3$, —N(CH$_3$)CH$_2$CH$_2$OCH$_3$, —NH(C(CH$_3$)$_2$C(O)N(CH$_3$)$_2$), —NH(C(CH$_3$)$_2$C(O)NH(CH$_3$), —NH(CH$_2$C(O)N(CH$_3$)CH$_2$CH$_2$OCH$_3$), —NH(CH$_2$CH$_2$OCH$_3$), —N(CH$_3$)CH$_2$C(O)NH$_2$, —N(CH$_3$)CH$_2$C(O)N(CH$_3$)$_2$, —NH(CH$_2$CH$_2$S(O)$_2$NH$_2$), —NHCH$_2$CH$_2$S(O)$_2$CH$_3$, —NHCH$_2$C(CH)$_2$S(O)$_2$CH$_3$, or —NHCH$_2$CH$_2$S(O)$_2$CF$_3$; or two R$_{12a}$ and the carbon atom to which they are attached form C=O.

5. A pharmaceutical composition comprising a compound according to claim 1 or a pharmaceutically-acceptable salt thereof, and a pharmaceutically acceptable carrier.

6. A method for treating a disease comprising administrating to a subject in need thereof, a therapeutically-effective amount of at least one compound according to claim 1 or a pharmaceutically-acceptable salt thereof, wherein the disease is an autoimmune disease or a chronic inflammatory disease.

7. The method according to claim 6 or a pharmaceutically-acceptable salt thereof, wherein said autoimmune disease or chronic inflammatory disease is selected from systemic lupus erythematosus (SLE), rheumatoid arthritis, multiple sclerosis (MS), and Sjögren's syndrome.

* * * * *

UNITED STATES PATENT AND TRADEMARK OFFICE
CERTIFICATE OF CORRECTION

PATENT NO. : 11,053,244 B1
APPLICATION NO. : 16/910101
DATED : July 6, 2021
INVENTOR(S) : Dyckman et al.

Page 1 of 1

It is certified that error appears in the above-identified patent and that said Letters Patent is hereby corrected as shown below:

In the Claims

In Claim 1, Column 574, Line 55, delete "-NH(CH2CH2OH)," and insert -- -NH(CH$_2$CH$_2$OH), --, therefor.

In Claim 1, Column 574, Line 62-63, delete "-N(CH$_2$CN)(CH$_2$C(O)N(CH$_3$)$_2$," and insert -- -N(CH$_2$CN)(CH$_2$C(O)N(CH$_3$)$_2$), --, therefor.

In Claim 1, Column 574, Line 67 to Column 575, Line 1, delete "-NH(C(CH$_3$)$_2$C(O)NH(CH$_3$)," and insert -- -NH(C(CH$_3$)$_2$C(O)NH(CH$_3$)), --, therefor.

In Claim 2, Column 575, Line 32-33, delete "-N(CH$_2$CN)(CH$_2$C(O)N(CH$_3$)$_2$," and insert -- -N(CH$_2$CN)(CH$_2$C(O)N(CH$_3$)$_2$), --, therefor.

In Claim 2, Column 575, Line 38-39, delete "-NH(C(CH$_3$)$_2$C(O)NH(CH$_3$)," and insert -- -NH(C(CH$_3$)$_2$C(O)NH(CH$_3$)), --, therefor.

In Claim 4, Column 576, Line 19-20, delete "-N(CH$_2$CN)(CH$_2$C(O)N(CH$_3$)$_2$," and insert -- -N(CH$_2$CN)(CH$_2$C(O)N(CH$_3$)$_2$), --, therefor.

In Claim 4, Column 576, Line 24, delete "-NH(C(CH$_3$)$_2$C(O)NH(CH$_3$)," and insert -- -NH(C(CH$_3$)$_2$C(O)NH(CH$_3$)), --, therefor.

In Claim 5, Column 576, Line 32 (Approx.), delete "thereof," and insert -- thereof; --, therefor.

Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*